(12) United States Patent
Ogawa et al.

(10) Patent No.: US 11,124,486 B2
(45) Date of Patent: Sep. 21, 2021

(54) 6-MEMBERED HETEROCYCLIC DERIVATIVES AND PHARMACEUTICAL COMPOSITION COMPRISING THE SAME

(71) Applicant: Shionogi & Co., Ltd., Osaka (JP)

(72) Inventors: Tomoyuki Ogawa, Osaka (JP); Hiroyuki Kai, Osaka (JP); Keiichiro Hirai, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 16/851,419

(22) Filed: Apr. 17, 2020

(65) Prior Publication Data

US 2020/0262796 A1 Aug. 20, 2020

Related U.S. Application Data

(63) Continuation of application No. 15/568,822, filed as application No. PCT/JP2016/062759 on Apr. 22, 2016, now Pat. No. 10,774,051.

(30) Foreign Application Priority Data

Apr. 24, 2015 (JP) ................................. 2015-089431
Jun. 25, 2015 (JP) ................................. 2015-127214

(51) Int. Cl.
*C07D 239/52* (2006.01)
*C07D 403/12* (2006.01)
(Continued)

(52) U.S. Cl.
CPC ........ *C07D 239/52* (2013.01); *A61K 31/4412* (2013.01); *A61K 31/505* (2013.01);
(Continued)

(58) Field of Classification Search
CPC .............. A61K 31/4412; A61K 31/505; A61K 31/5377; A61K 31/506; A61K 31/53;
(Continued)

(56) References Cited

U.S. PATENT DOCUMENTS 6,417,192 B1 7/2002 Hickey
2009/0281107 A1 11/2009 Congy et al.
(Continued)

FOREIGN PATENT DOCUMENTS

EP 2 399 910 12/2011
KR 10-2012-0089074 8/2012
(Continued)

OTHER PUBLICATIONS

Cecil Textbook of Medicine, 20th edition (1996), vol. 2, pp. 2050-2057.*

Cecil Textbook of Medicine, 20th edition (1996), vol. 2, pp. 1992-1996.*

FDA mulls drug to slow late-stage Alzheimer's [online], [retrieved on Sep. 23, 2003], Retrieved from the internet, URL;http;//www.cnn/com/2003/HEALTH/conditions/09/24/alzheimers.drug.ap/index.html>.*

International Search Report dated Jul. 26, 2016 in International Application No. PCT/JP2016/062759.
(Continued)

*Primary Examiner* — Rebecca L Anderson
(74) *Attorney, Agent, or Firm* — Wenderoth, Lind & Ponack, L.L.P.

(57) ABSTRACT

A compound represented by Formula (I):

Chemical Formula 1

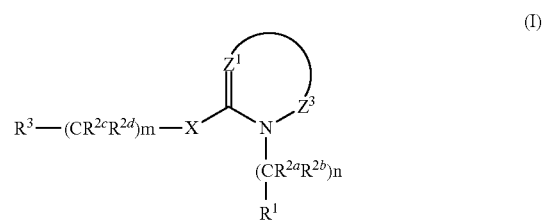

(I)

wherein

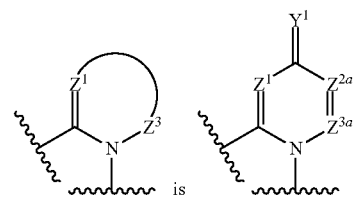 is or the like,
$Y^1$ is O or the like; $Z^1$ is $C(R^4)$ or N; $Z^{2a}$ is $C(R^{5a})$ or the like; $Z^{3a}$ is $C(R^6)$ or the like; $R^4$, $R^{5a}$ and $R^6$ are each independently a hydrogen atom or the like; $R^1$ is substituted or unsubstituted aromatic carbocyclyl or the like; $R^{2a}$, $R^{2b}$, $R^{2c}$ and $R^{2d}$ are each independently a hydrogen atom or the like; X is $N(R^{7a})$ or the like; $R^{7a}$ is a hydrogen atom or the like; $R^3$ is

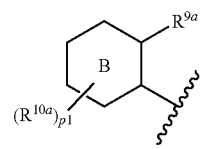

or the like,
Ring B is a 6-membered aromatic carbocycle or the like; $R^{9a}$ and $R^{10a}$ are each independently halogen or the like; n is an integer from 1 to 5; m is an integer from 0 to 4; and p1 is an integer from 0 to 3,
or a pharmaceutically acceptable salt thereof.

6 Claims, No Drawings

(51) Int. Cl.

| | | |
|---|---|---|
| C07D 401/12 | (2006.01) | |
| C07D 405/12 | (2006.01) | |
| C07D 239/47 | (2006.01) | |
| C07D 239/48 | (2006.01) | |
| C07D 409/12 | (2006.01) | |
| C07D 413/12 | (2006.01) | |
| C07D 417/12 | (2006.01) | |
| C07D 487/04 | (2006.01) | |
| C07D 498/04 | (2006.01) | |
| C07D 239/54 | (2006.01) | |
| C07D 253/06 | (2006.01) | |
| C07D 213/69 | (2006.01) | |
| C07D 401/06 | (2006.01) | |
| C07D 239/60 | (2006.01) | |
| C07D 409/06 | (2006.01) | |
| C07D 471/04 | (2006.01) | |
| C07D 213/74 | (2006.01) | |
| C07D 239/545 | (2006.01) | |
| C07D 253/075 | (2006.01) | |
| A61K 31/5377 | (2006.01) | |
| A61K 31/53 | (2006.01) | |
| A61K 31/505 | (2006.01) | |
| A61K 31/4412 | (2006.01) | |
| A61K 31/506 | (2006.01) | |

(52) U.S. Cl.
CPC ............ *A61K 31/506* (2013.01); *A61K 31/53* (2013.01); *A61K 31/5377* (2013.01); *C07D 213/69* (2013.01); *C07D 213/74* (2013.01); *C07D 239/47* (2013.01); *C07D 239/48* (2013.01); *C07D 239/54* (2013.01); *C07D 239/545* (2013.01); *C07D 239/60* (2013.01); *C07D 253/06* (2013.01); *C07D 253/075* (2013.01); *C07D 401/06* (2013.01); *C07D 401/12* (2013.01); *C07D 403/12* (2013.01); *C07D 405/12* (2013.01); *C07D 409/06* (2013.01); *C07D 409/12* (2013.01); *C07D 413/12* (2013.01); *C07D 417/12* (2013.01); *C07D 471/04* (2013.01); *C07D 487/04* (2013.01); *C07D 498/04* (2013.01)

(58) Field of Classification Search
CPC .. C07D 239/52; C07D 213/69; C07D 213/74; C07D 239/47; C07D 239/48; C07D 239/54; C07D 239/545; C07D 239/60; C07D 253/06; C07D 253/075; C07D 401/06; C07D 401/12; C07D 403/12; C07D 405/12; C07D 409/06; C07D 409/12; C07D 413/12; C07D 417/04; C07D 487/04; C07D 498/04
See application file for complete search history.

(56) References Cited

U.S. PATENT DOCUMENTS

| | | |
|---|---|---|
| 2011/0319400 A1 | 12/2011 | Flores et al. |
| 2011/0319418 A1 | 12/2011 | Flores et al. |
| 2013/0172317 A1 | 7/2013 | Kai et al. |
| 2013/0225596 A1 | 8/2013 | Kai et al. |
| 2016/0024072 A1 | 1/2016 | Kai et al. |
| 2016/0052892 A1 | 2/2016 | Kai et al. |
| 2016/0115151 A1 | 4/2016 | Kai |
| 2016/0318916 A1 | 11/2016 | Tanaka et al. |

FOREIGN PATENT DOCUMENTS

| | | |
|---|---|---|
| WO | 90/01477 | 2/1990 |
| WO | 99/24420 | 5/1999 |
| WO | 03/042190 | 5/2003 |
| WO | 03/042191 | 5/2003 |
| WO | 03/099211 | 12/2003 |
| WO | 2004/058270 | 7/2004 |
| WO | 2004/058731 | 7/2004 |
| WO | 2004/099146 | 11/2004 |
| WO | 2006/003500 | 1/2006 |
| WO | 2006/003513 | 1/2006 |
| WO | 2006/003517 | 1/2006 |
| WO | 2006/086229 | 8/2006 |
| WO | 2006/102112 | 9/2006 |
| WO | 2006/104713 | 10/2006 |
| WO | 2006/104715 | 10/2006 |
| WO | 2007/079163 | 7/2007 |
| WO | 2007/079214 | 7/2007 |
| WO | 2008/066789 | 6/2008 |
| WO | 2008/124153 | 10/2008 |
| WO | 2009/002423 | 12/2008 |
| WO | 2009/057827 | 5/2009 |
| WO | 2009/058653 | 5/2009 |
| WO | 2010/126104 | 4/2010 |
| WO | 2010/072597 | 7/2010 |
| WO | 2010/072599 | 7/2010 |
| WO | 2010/072605 | 7/2010 |
| WO | 2010/072607 | 7/2010 |
| WO | 2010/072647 | 7/2010 |
| WO | 2010/125101 | 11/2010 |
| WO | 2010/125102 | 11/2010 |
| WO | 2010/133973 | 11/2010 |
| WO | 2011/012592 | 2/2011 |
| WO | 2011/033055 | 3/2011 |
| WO | 2011/047323 | 4/2011 |
| WO | 2011/079000 | 6/2011 |
| WO | 2011/109254 | 9/2011 |
| WO | 2012/036193 | 3/2012 |
| WO | 2013/089212 | 6/2013 |
| WO | 2013/118855 | 8/2013 |
| WO | 2014/023691 | 2/2014 |
| WO | 2014/152537 | 9/2014 |
| WO | 2014/152604 | 9/2014 |
| WO | 2014/152621 | 9/2014 |
| WO | 2014/154896 | 10/2014 |
| WO | 2016/019228 | 2/2016 |
| WO | 2016/039983 | 3/2016 |
| WO | 2016/084922 | 6/2016 |
| WO | 2016/088838 | 6/2016 |
| WO | 2017/104691 | 6/2017 |
| WO | 2017/204316 | 11/2017 |
| WO | 2017/204318 | 11/2017 |
| WO | 2017/209265 | 12/2017 |
| WO | 2017/209267 | 12/2017 |
| WO | 2018/074390 | 4/2018 |
| WO | 2018/074565 | 4/2018 |

OTHER PUBLICATIONS

Geoffrey Burnstock, "Purinergic mechanosensory transduction and visceral pain", Molecular Pain, 2009, 5:69.
Alberto Baroja-Mazo et al., "The participation of plasma membrane hemichannels to purinergic signaling", Biochimica et Biophysica Acta 1828 (2013), 79-93.
Amanda MacKenzie et al., "Rapid Secretion on Interleukin-1β by Microvesicle Shedding", Immunity, vol. 8, 825-835, Nov. 2001.
Iain P. Chessell et al., "Disruption of the P2X7 purinoceptor gene abolishes chronic inflammatory and neuropathic pain", Pain 114 (2005) 386-396.
Robert E. Sorge et al., "Genetically determined P2X7 receptor pore formation regulates variability in chronic pain sensitivity", Nature Medicine, 2012, 18, 595-599.
Stephen D. Skaper et al., "The $P2X_7$ purinergic receptor: from physiology to neurological disorders", The FASEB Journal, 2010, vol. 24, No. 2, 337-345.
Takato Takenouchi et al., "P2X7 Receptor Signaling Pathway as a Therapeutic Target for Neurodegenerative Diseases", Arch. Immunol. Ther. Exp. (2010) 58:91-96.
Scott A. Friedle et al., "Recent Patents on Novel $P2X_7$ Receptor Antagonists and their Potential for Reducing Central Nervous System Inflammation", Recent Patents on CNS Drug Discovery, 2010, 5, 35-45.

(56) References Cited

OTHER PUBLICATIONS

Jamal El Bakali et al, "4-Oxo-1,4-dihydropyridines as Selective $CB_2$ Cannabinoid Receptor Ligands: Structural Insights into the Design of a Novel Inverse Agonist Series", Journal of Medicinal Chemistry 2010, 53, 7918-7931.
E. Wyrzykiewicz, Rapid Communications in Mass Spectrometry 2005; 19: 580-584.
Elżieta Wyrzykiewicz et al., "Thio Analogs of Pyrimidine Bases: Synthesis and EIMS Study of New ortho-(meta- and para-)Brombenzyl S-Mono and S-N-1-Disubstituted 5-Morpholinomethyl(5-piperidinomethyl)-2-thiouracils", Journal of Heterocyclic Chemistry, 2007, 44(1), pp. 55-61.
Tomasz Pospieszny et al., "A practical synthesis of new S,N-disubstituted derivatives of 5-(4-methylpiperidino)methyl-2-thiouracil", Tetrahedron Letters 49 (2008) 5319-5321.
E. Wyrzykiewicz, Rapid Communications in Mass Spectrometry 2006; 20: 713-718.
Tomasz Pospieszny et al., "Differentation of the isomeric o(m- and p-) nitro-(chloro- and bromo-)benzyl-2,4-(and 2,1-) disubstituted 2-thiocytosinium halides by electron impact ionisation and fast atom bombardment mass spectrometry", European Journal of Mass Spectrometry, 15, 497-506 (2009).
Mazurizio Botta et al., "Research on Antiviral Agents. 5. Lithiation of 6-Methyluracil as a New and Efficient Entry to C(6)-Substituted Uracils", Heterocycles, vol. 43, No. 8, 1996, 1687-1697.
Elżhietz Wyrzykiewicz et al., "Syntheses, EMIS and $^{13}C$ NMR Study of 1,2-DI-Substituted Derivatives of 2-thio-6-aminouracil", Phosphorus, Sulfur, and Silicon and Related Elements, 2003, 178(10), pp. 2263-2278.
Elżhietz Wyrzykiewica et al., "Syntheses, EIMS, $^1H$ NMR, and $^{13}C$ NMR Study of 2-Mono, 1,2-Di, and 2,4-Di Substituted Derivatives of 2-Thiocytosine", Phosphorus, Sulfur and Silicon, 180:2051-2070, 2005.
STN International, File Registry [online], ED Entered STN: Jul. 7, 2006, retrieval date: Jul. 6, 2016, CAS Registry No. 890950-70-6, 890950-18-2, 890949-51-6.
STN International, File Registry [online], Entered STN: Jul. 3, 2006, retrieval date: Jul. 6, 2016, CAS Registry No. 890300-01-3.
STN International, File Registry [online], Entered STN: Apr. 20, 2006, retrieval date: Jul. 6, 2016, CAS Registry No. 881277-99-2, 881277-91-4.
STN International, File Registry [online], Entered STN: Apr. 20, 2006, retrieval date: Jul. 6, 2016, CAS Registry No. 881277-75-4, 881277-67-4, 881275-43-0, 881275-27-0, 881270-51-5.
STN International, File Registry [online], Entered STN: Apr. 20, 2006, retrieval date: Jul. 6, 2016, CAS Registry No. 881275-35-0, 881275-19-0, 881270-83-3, 881270-75-3, 881270-67-3, 881270-59-3, 881270-35-5.
STN International, File Registry [online], Entered STN: Mar. 15, 2005, retrieval date: Jul. 6, 2016, CAS Registry No. 845662-16-0.
STN International, File Registry [online], Entered STN: Sep. 13, 2004, retrieval date: Jul. 6, 2016, CAS Registry No. 743418-95-3.
STN International, File Registry [online], Entered STN: Sep. 9, 2011, retrieval date: Jul. 6, 2016, CAS Registry No. 1330248-96-8, 1330247-61-4, 1330192-65-8, 1330099-66-5, 1330098-81-1, 1330098-14-0, 1330096-77-9, 1330093-54-3, 1329833-00-2, 1329792-28-0, 1329791-26-5, 1329767-45-4, 1329765-15-2, 1329537-97-4, 1329532-85-5, 1329437-21-9, 1327140-78-2.
STN International, File Registry [online], Entered STN: Sep. 14, 1990, retrieval date: Jul. 6, 2016, CAS Registry No. 129351-60-6.
Allen J. Duplantier, et al., "Optimization of the physicochemical and pharmacokinetic attributes in a 6-azauracil series of $P2X_7$ receptor antagonists leading to the discovery of the clinical candidate CE-224,535", Bioorganic & Medicinal Chemistry Letters 21 (2011) 3708-3711.
Chakrapaini Subramanyam et al., "Discovery, synthesis and SAR of azinyl- and azolylbenzamides antagonists of the $P2X_7$ receptor", Bioorganic & Medicinal Chemistry Letters 21 (2011) 5475-5479.

Francisco Lopez-Tapia et al., "Novel Series of Dihydropyridinone P2X7 Receptor Antagonists", Journal of Medicinal Chemistry, 2015, 58, 8413-8426.
Jin-Hee Park et al. "P2X7 receptor antagonists: a patent review (2010-2015)", Expert Opinion on Therapeutic Patents, 27:3, 257-267 (2017).
Nathalie Azaroual et al., "NMR studies of interactions of new $CB_2$ cannabinoid receptor ligands with cyclodextrins hosts. Correlation with micellar electrokinetic chromatography and reversed phase high performance liquid chromatography", Journal of Inclusion Phenomena and Macrocyclic Chemistry, 2014, 78, pp. 265-274.
STN International, File Registry [online], Entered STN: Apr. 20, 2006, retrieval date: Jul. 6, 2016, CAS Registry No. 881270-27-5.
International Preliminary Report on Patentability dated Nov. 2, 2017 in International Application No. PCT/JP2016/062759.
Xiangyang Chen, et al., "Discovery of 2-chloro-N-((4,4-difluoro-1-hydroxycyclohexyl)methyl)-5-(5-fluoropyrimidin-2-yl)benzamide as a potent and CNS penetrable $P2_{X7}$ receptor antagonist", Bioorganic & Medicinal Chemistry Letters (2010), 20(10), 3107-3111.
Xiaohai Wang et al., "P2X7 receptor inhibition improves recovery after spinal cord injury", Nature Medicine, 2004, 10, 8, 821-827.
Michael A. Letavic et al., "Synthesis and Pharmacological Characterization of Two Novel, Brain Penetrating $P2X_7$ Antagonists", J. Med. Chem. Lett., 2013, 4, 419-422.
Derek W. Nelson et al., "Structure—Activity Relationship Studies on a Series of Novel, Substituted 1-Benzyl-5-phenyltetrazole $P2X_7$ Antagonists", J. Med. Chem., 2006, 49, 3659-3666.
Official Action dated Dec. 28, 2017 in U.S. Appl. No. 15/108,089.
Extended European Search Report dated Aug. 24, 2018 in European Application No. 16783270.8.
Database PubChem Compound [Online] Mar. 17, 2015, retrieved from NCBI Database accession No. 91562890.
Database PubChem Compound [Online] Feb. 12, 2015, retrieved from NCBI Database accession No. 87636489.
Database PubChem Compound [Online] Dec. 4, 2011, retrieved from NCBI Database accession No. 53945740.
Database PubChem Compound [Online] Dec. 4, 2011, retrieved from NCBI Database accession No. 53935711.
Swanson et al., "Identification of (R)-(2-Chloro-3-(trifluoromethyl)phenyl)(1-(5-fluoropyridin-2-yl)-4-methyl-6,7-dihydro-1H-imidazo[4,5-c]pyridin-5(4H)-yl)methanone (JNJ 54166060), a Small Molecule Antagonist of the P2X7 receptor", Journal of Medicinal Chemistry, vol. 59, pp. 8535-8548, 2016.
Letavic et al., "4-Methyl-6,7-dihydro-4H-triazolo[4,5-c]pyridine-Based P2X7 Receptor Antagonists: Optimization of Pharmacokinetic Properties Leading to the Identification of a Clinical Candidate", Journal of Medicinal Chemistry, vol. 60, pp. 4559-4572, 2017.
Chrovian et al., "A Dipolar Cycloaddition Reaction to Access 6-Methyl-4,5,6,7-tetrahydro-1H-[1,2,3]triazolo[4,5-c]pyridines Enables the Discovery Synthesis and Preclinical Profiling of a P2X7 Antagonist Clinical Candidate", Journal of Medicinal Chemistry, vol. 61, pp. 207-223, 2018.
Savall et al., "Synthesis, SAR, and Pharmacological Characterization of Brain Penetrant P2X7 Receptor Antagonists", ACS Medicinal Chemistry Letters, vol. 6, pp. 671-676, 2015.
Bhattacharya et al., "Neuropsychopharmacology of JNJ-55308942: evaluation of a clinical candidate targeting P2X7 ion channels in animal models of neuroinflammation and anhedonia", Neuropsychopharmacology, vol. 43, pp. 2586-2596, 2018.
Communication pursuant to Article 94(3) EPC dated Oct. 23, 2019 in corresponding European Patent Application No. 16783270.8.
Malik et al., "Unique chlorine effect in regioselective one-pot synthesis of 1-alkyl/ally1-3-(o-chlorobenzyl) uracils: anti-HIV activity of selected uracil derivatives", Tetrahedron, vol. 62, No. 25 (2006), pp. 5944-5951.

\* cited by examiner

6-MEMBERED HETEROCYCLIC DERIVATIVES AND PHARMACEUTICAL COMPOSITION COMPRISING THE SAME

TECHNICAL FIELD

The invention relates to a compound useful for the treatment of diseases or conditions associated with the P2X7 receptor and a pharmaceutical composition containing thereof.

BACKGROUND ART

Adenosine triphosphate (ATP) is known to serve as a source of energy in cells and a substrate of phosphorylation, as well as an extracellular messenger. It is known that ATP is released from a cell by various stimulation such as cellular injury, inflammation, nociceptive stimulus, reduced blood oxygen level, and also known to be released together with another messenger from a primary sensory nerve terminal. (Non-Patent Document 1) ATP thus released mediates various extracellular signal transductions through an ATP receptor.

ATP receptor is categorized into ionotropic P2X family and G protein-coupled P2Y family. For P2X family, seven subtypes have been reported, and a member of this family forms a homo-trimeric structure or a hetero-trimeric structure together with another member of this subtype and functions as a non-specific cation channel.

The P2X7 receptor, a non-selective cation channel, belongs to the P2X family, and forms a homo-trimeric structure. Activation of P2X7 by extracellular ATP allows for the passage of cations across the plasma membrane. Prolonged or repeated ATP stimulation leads to the pore formation of pannexin hemichannel, and induces the cellular activation following the release of small molecule such as ATP. (Non-Patent Document 2) It is reported that the activation of P2X7 is involved in inflammation, immune and pain by the maturation and secretion of proinflammatory cytokines such as interleukin-1 beta and interleukin-18. (Non-Patent Document 3) Thus, it is known that the P2X7 receptor is involved in pain, central nervous system disease, immune disease and inflammatory disease. (Non-Patent Document 7-8, and Patent Document 1)

P2X7 is distributed in macrophages, mast cells, microglia, and astrocytes. It is known that disruption of the P2X7 receptor gone abolishes chronic inflammatory and neuropathic pain. (Non-Patent Document 4) It is reported that the P451L mutation of the mouse P2X7 gene has impaired pore formation and shows less mechanical sensitivity of neuropathic pain model mice. (Non-Patent Document 5) Additionally, an association between lower pain intensity in chronic pain patients and the hypofunctional allele of P2X7 has been reported, suggesting that P2X7 antagonist is useful in the treatment of chronic pain such as rheumatoid arthritis, osteoarthritis and neuropathic pain.

Additionally, it has been reported that P2X7 may be involved in multiple sclerosis, spinal cord injury, stroke, Alzheimer's disease, and depression (Non-Patent Document 6), suggesting that P2X7 antagonist is useful in the treatment of these central nervous system disease.

The compounds having an analgesic effect are described in Patent Documents 2-5 and 8-11. However, the compounds have different chemical structures from the compounds of the present invention, and there is neither disclosure nor suggestion about an antagonistic activity for the P2X7 receptor.

The compounds having similar chemical structures to the compounds of the present invention and having an analgesic activity are described in Patent Documents 6, 7, and 12-15. However, there is neither disclosure nor suggestion about an antagonistic activity for the P2X7 receptor.

The compounds having an antagonistic activity for the P2X7 receptor are described in Patent Document 16. However, the compounds have different chemical structures from the compounds of the present invention.

PRIOR ART REFERENCES

Patent Document

[Patent Document 1] International Publication WO 2012/036193A
[Patent Document 2] International Publication WO 2014/200078A
[Patent Document 3] International Publication WO 2013/089212A
[Patent Document 4] International Publication WO 2012/020749A
[Patent Document 5] International Publication WO 2010/092966A
[Patent Document 6] International Publication WO 2013/118855A
[Patent Document 7] International Publication WO 2012/020742A
[Patent Document 8] US Publication No. 2011/0319418A
[Patent Document 9] International Publication WO 2006/104715A
[Patent Document 10] International Publication WO 2006/104713A
[Patent Document 11] International Publication WO 2006/102112A
[Patent Document 12] US Publication No. 2011/0319400A
[Patent Document 13] International Publication WO 2009/058653A
[Patent Document 14] International Publication WO 2007/079214A
[Patent Document 15] International Publication WO 2007/079163A
[Patent Document 16] International Publication WO 2015/099107A

Non-Patent Document

[Non-patent Document 1] Burnstock G., Mol Pain. 2009, 5, 69
[Non-patent Document 2] Baroja-Mazo A et al., Biochim Biophys Acta. 201.3, 1828, 79-93
[Non-patent Document 3] MacKenzie A et al., Immunity. 2001, 15, 825-835
[Non-patent Document 4] Chessell I P et al., Pain. 2005, 114, 386-396
[Non-patent Document 5] Sorge R E et al., Nature Med. 2012, 18, 595-599
[Non-patent Document 6] Skaper S D et al., FASER J. 2010, 24, 337-345
[Non-patent Document 7] Takenouchi T et al., Arch Immunol Ther Exp (Warsz). 2010 April; 58(2): 91-6
[Non-patent Document 8] Friedle S A et al., Recent Pat CNS Drug Discov. 2010 January; 5(1): 35-45
[Non-patent Document 9] Journal of Medicinal Chemistry 2010, 53(22), 7918-7931

SUMMARY OF THE INVENTION

Problems to be Solved by the Invention

The objective of the present invention is to provide novel compounds having an antagonistic activity for the P2X7 receptor and a pharmaceutical composition having an antagonistic activity for the P2X7 receptor.

Means for Solving the Problem

The present invention relates to the following (1), (1α), (1a'), (2) to (96) and (1001) to (1.007):

(1)
A compound represented by Formula (I):

[Chemical Formula 1]

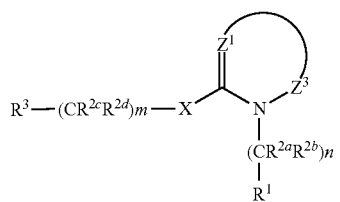
(I)

wherein

[Chemical Formula 2]

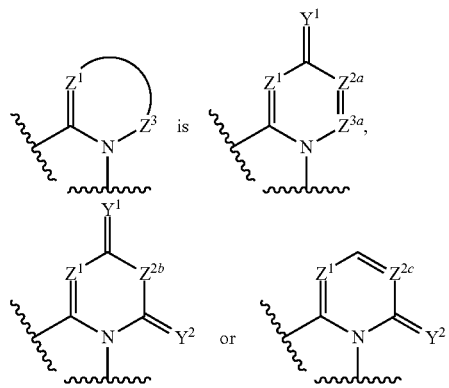 is $Y^1$ and $Y^2$ are each independently $N(R^Y)$, O or S:
Z is $C(R^4)$ or N;
$Z^{2a}$ is $C(R^{5a})$ or N;
$Z^{2b}$ is $C(R^{5a})(R^{5a'})$ or $N(R^{5b})$;
$Z^{2c}$ is $C(R^{5a})$ or N;
$Z^{3a}$ is $C(R^6)$ or N;
provided that when $Z^1$ is N, then each of $Z^{2a}$, $Z^{2b}$ and $Z^{2c}$ is $C(R^{5a})$:
when $Z^1$ is $C(R^4)$, then $Z^{2e}$ is N; and
when $Z^{2a}$ is N, then $Z^{3a}$ is $C(R^6)$;
  $R^Y$ is each independently a hydrogen atom, hydroxy, cyano, carboxy, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
  $R^4$ and $R^6$ are each independently a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, or substituted or unsubstituted alkynylamino;
  $R^{5a}$ and $R^{5a'}$ are each independently a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic hoterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic hetorocyclylsulfonyloxy, substituted or unsubstituted non-aromatic heterocyclylsulfonyloxy, substituted or unsubstituted aromatic carbocyclyloxyaulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic hetorocyclylcarbamoyl, substituted or unsubstituted non-aromatic hetorocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic hctorocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic hoterocyclyloxycarbonylamino, or substituted or unsubstituted non aromatic heterocyclyloxycarbonyl amino;

$R^{5b}$ is a hydrogen atom, carboxy, carbamoyl, sulfamoyl, sulfo, cyano, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarhonyl, substituted or unsubstituted non-aromatic heterocyclyloxycarbonyl, substituted or unsubstituted aromatic carbocyclylcarbamoyl, substituted or unsubstituted non-aromatic; carbocyclylcarbamoyl, substituted or unsubstituted aromatic heterocyclylcarbamoyl, or substituted or unsubstituted non-aromatic heterocyclylcarbamoyl;

$R^1$ is substituted or unsubstituted aromatic carbocyclyl, substituted or unsubstituted non-aromatic carbocyclyl, substituted or unsubstituted aromatic heterocyclyl, or substituted or unsubstituted non-aromatic heLerocyclyl;

$R^{2a}$ is each independently a hydrogen atom, halogen, hydroxy, substituted or unsubstituted alkyl, or substituted or unsubstituted alkyloxy;

$R^{2b}$ is each independently a hydrogen atom, halogen, hydroxy, substituted or unsubstituted alkyl, or substituted or unsubstituted alkyloxy;

$R^{2a}$ and $R^{2b}$ which are attached to the same carbon atom may be taken together to form oxo;

X is $N(R^{7a})$, $C(R^{8a})(R^{8b})$, O or S;

$R^{7a}$ is a hydrogen atom, substituted or unsubstituted alkyl, or substituted or unsubstituted alkylcarbonyl;

$R^{8a}$ and $R^{8b}$ are each independently a hydrogen atom, halogen, hydroxy, substituted or unsubstituted alkyl, or substituted or unsubstituted alkyloxy;

$R^{2c}$ is each independently a hydrogen atom, halogen, hydroxy, substituted or unsubstituted alkyl, or substituted or unsubstituted alkyloxy;

$R^{2d}$ is each independently a hydrogen atom, halogen, hydroxy, substituted or unsubstituted alkyl, or substituted or unsubstituted alkyloxy;

$R^{2c}$ and $R^{2d}$ which are attached to the same carbon atom may be taken together to form a substituted or unsubstituted non-aromatic carbocycle, or two $R^{2c}$ may be taken together to form a substituted or unsubstituted non-aromatic carbocycle;

R³ is a group represented by the Formula:

[Chemical Formula 3]

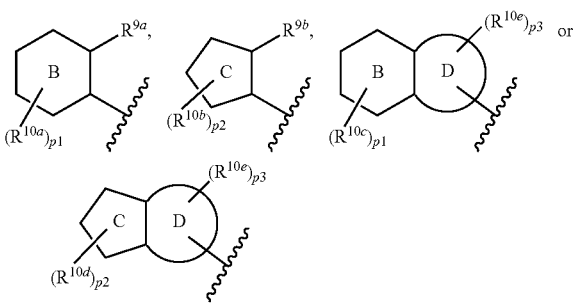

wherein
- Ring B is a 6-membered aromatic carbocycle, a 6-membered non-aromatic carbocycle, a 6-membered aromatic heterocycle, or a 6-membered non-aromatic heterocycle;
- Ring C is a 5-membered non-aromatic carbocycle, a 5-membered aromatic heterocycle, or a 5-membered non-aromatic heterocycle;
- Ring D is a 5-membered non-aromatic carbocycle, or a 6-membered non-aromatic carbocycle;
- $R^{9a}$ and $R^{10a}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted or alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarhonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

$R^{10a}$, $R^{10b}$, $R^{10c}$ and $R^{10d}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic hotorocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic hoterocyclyloxycarbonylamino, or substituted or unsubstituted non-aromatic heterocyclyloxycarbonylamino;

$R^{9a}$, $R^{9b}$, $R^{10a}$ and $R^{10b}$ may be any of the following a) to c):

a) $R^{9a}$ and $R^{10a}$, or $R^{9b}$ and $R^{10b}$ are taken together to form a (C1-C3) bridge, wherein one of the carbon atoms constituting the bridge may be replaced with an oxygen atom or a nitrogen atom;

b) $R^{9a}$ and $R^{10a}$ which are attached to the adjacent atoms, or $R^{9b}$ and $R^{10b}$ which are attached to the adjacent atoms are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle; and c) two $R^{10a}$ which are attached to the adjacent atom, or two $R^{10b}$ which are attached to the adjacent atom are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle; and $R^{10e}$ is each independently halogen, hydroxy, substituted or unsubstituted alkyl, or substituted or unsubstituted alkyloxy;

n is an integer from 1 to 5;

m is an integer from 0 to 4;

p1 is an integer from 0 to 3;

p2 is an integer from 0 to 2;

p3 is an integer from 0 to 2;

provided that i) when X is $C(R^{7a})(R^{7b})$, O or S and one of $R^{5a}$ and $R^{5b'}$ is hydrogen, then the other of $R^{5a}$ and $R^{5a'}$ is not a hydrogen atom, hydroxy, methyl substituted with a substituted or unsubstituted 6-membered cyclic group, octadecyloxy, or ethyloxycarbonyl, i') when X is $C(R^{7a})(R^{7b})$, O or S, then $R^{5b}$ is not a hydrogen atom or methyl substituted with a substituted or unsubstituted 6-membered cyclic group; and ii) when X is O, n is 1, and

[Chemical Formula 4]

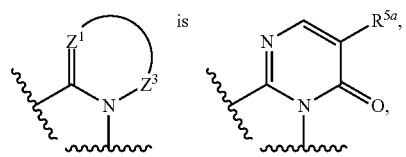

then $R^{2a}$ and $R^{2b}$ are not taken together to form oxo, provided that the following compounds are excluded:

[Chemical Formula 5]

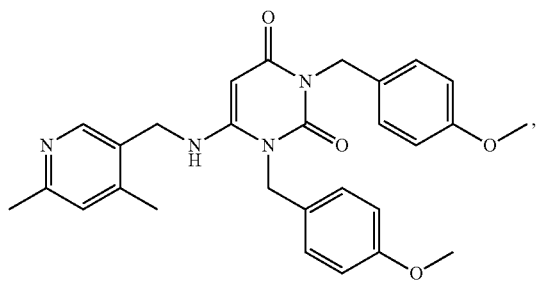

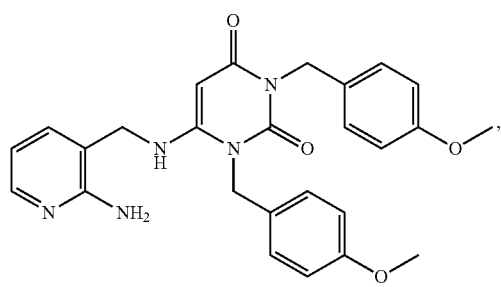

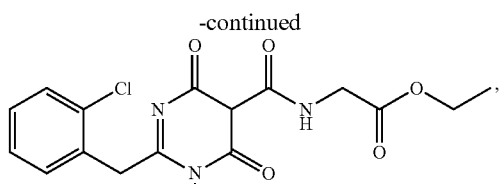

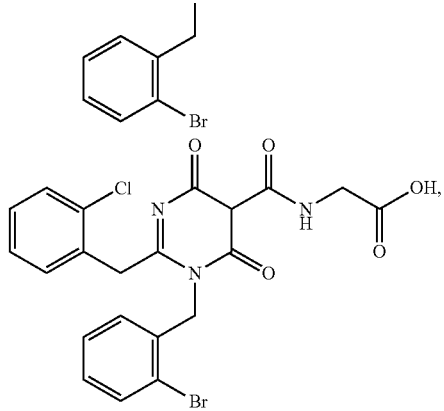

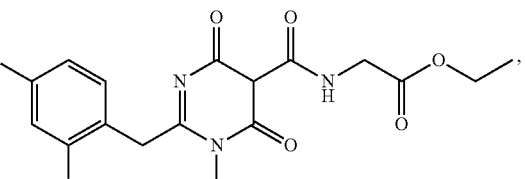

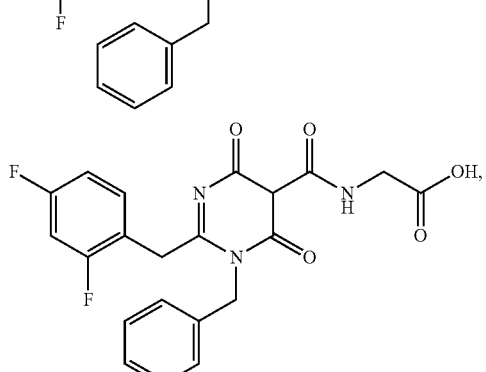

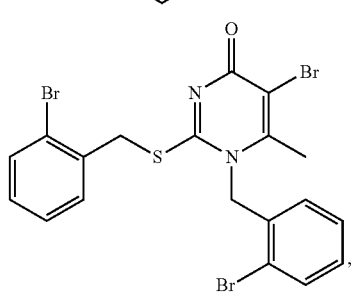

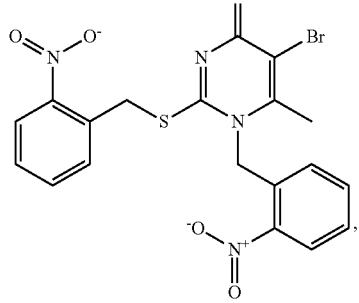

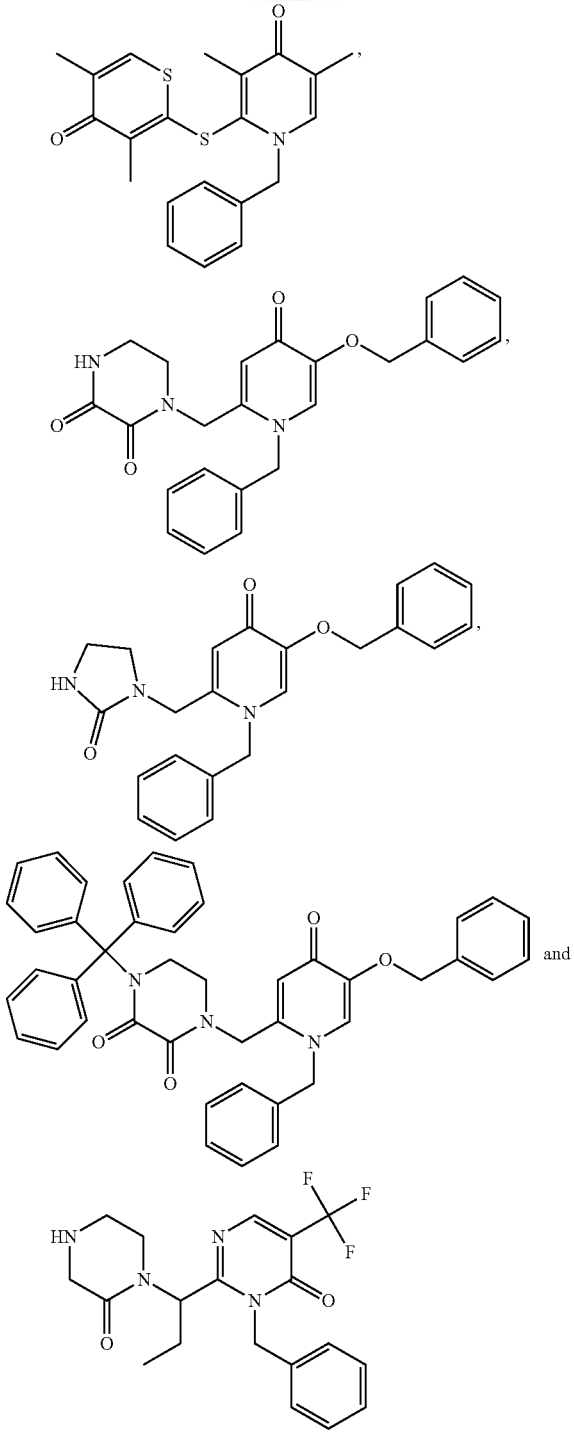

or a pharmaceutically acceptable salt thereof.

The above definition of $R^3$ means that $R^{10e}$ is a substituent on Ring D, $R^{10c}$ is a substituent on Ring B, and $R^{10d}$ is a substituent on Ring C.

(1α)

The compound according to the above (1), wherein
$Y^1$ and $Y^2$ are each independently O or S; and
$Z^{2b}$ is CH($R^{5a}$) or N($R^{5b}$).

or a pharmaceutically acceptable salt thereof.

(1α')

A compound represented by Formula (I):

[Chemical Formula 6]

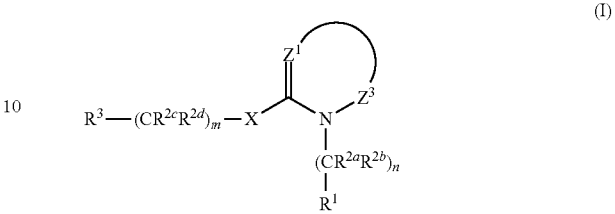

wherein

[Chemical Formula 7]

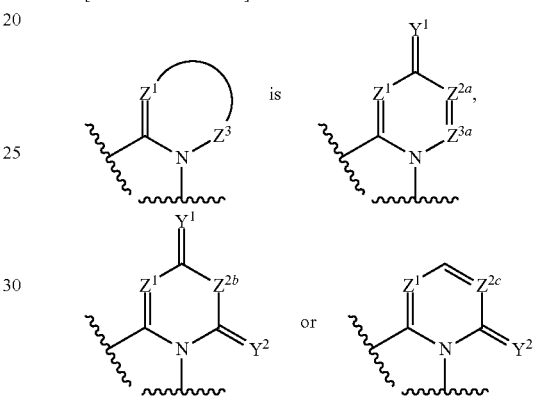

$Y^1$ and $Y^2$ are each independently O or S;
$Z^1$ is C($R^4$) or N;
$Z^{2a}$ is C($R^{5a}$) or N;
$Z^{2b}$ is CH($R^{5a}$) or N($R^{5b}$);
$Z^{2c}$ is C($R^{5a}$) or N;
$Z^{3a}$ is C($R^5$) or N;
provided that when $Z^1$ is N, then each of $Z^{2a}$, $Z^{2b}$ and $Z^{2c}$ is C($R^{5a}$);
when $Z^1$ is C($R^4$), then $Z^{2c}$ is N; and
when $Z^{2a}$ is N, then $Z^{8a}$ is C($R^6$):

$R^4$ and $R^6$ are each independently a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkonylsulfanyl, substituted or unsubstituted alkynylsulfanyl, substituted or unsubstituted alkylamino, substituted or unsubstituted alkenylamino, or substituted or unsubstituted alkynylamino;

$R^{5a}$ is a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkonyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

$R^{5b}$ is a hydrogen atom, carboxy, carbamoyl, sulfamoyl, sulfo, cyano, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, or substituted or unsubstituted non-aromatic heterocyclylcarbamoyl;

$R^1$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{2a}$ is each independently a hydrogen atom, halogen, hydroxy, substituted or unsubstituted alkyl, or substituted or unsubstituted alkyloxy;

$R^{2b}$ is each independently a hydrogen atom, halogen, hydroxy, substituted or unsubstituted alkyl, or substituted or unsubstituted alkyloxy;

$R^{2a}$ and $R^{2b}$ which are attached to the same carbon atom may be taken together to form oxo;

X is $N(R^{7a})$, $C(R^{8a})(R^{8b})$, O or S;

$R^{7a}$ is a hydrogen atom, substituted or unsubstituted alkyl, or substituted or unsubstituted alkylcarbonyl;

$R^{8a}$ and $R^{8b}$ are each independently a hydrogen atom, halogen, hydroxy, substituted or unsubstituted alkyl, or substituted or unsubstituted alkyloxy;

$R^{2c}$ is each independently a hydrogen atom, halogen, hydroxy, substituted or unsubstituted alkyl, or substituted or unsubstituted alkyloxy;

$R^{2d}$ is each independently a hydrogen atom, halogen, hydroxy, substituted or unsubstituted alkyl, or substituted or unsubstituted alkyloxy;

$R^{2c}$ and $R^{2d}$ which are attached to the same carbon atom may be taken together to form a substituted or unsubstituted non-aromatic carbocycle, or two $R^{2c}$ may be taken together to form a substituted or unsubstituted non-aromatic carbocycle;

$R^3$ is a group represented by the Formula:

[Chemical Formula 8]

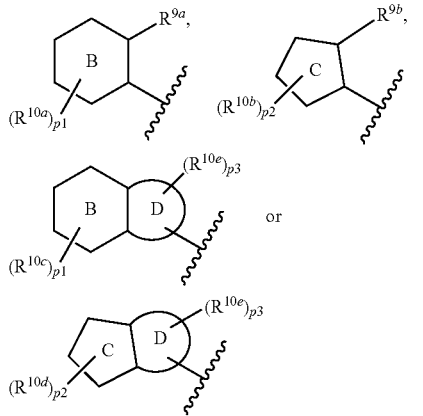

wherein
Ring R is a 6-membered aromatic carbocycle, a 6-membered non-aromatic carbocycle, a 6-membered aromatic heterocycle, or a 6-membered non-aromatic heterocycle;

Ring C is a 5-membered non-aromatic carbocycle, a 5-membered aromatic heterocycle, or a 5-membered non-aromatic heterocycle;

Ring D is a 5-membered non-aromatic carbocycle, or a 6-membered non-aromatic carbocycle;

$R^{9a}$ and $R^{9b}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

$R^{10a}$, $R^{10b}$, $R^{10c}$ and $R^{10d}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

$R^{9a}$, $R^{9b}$, $R^{10a}$ and $R^{10b}$ may be any of the following a) to c):

a) $R^{9a}$ and $R^{10a}$, or $R^{9b}$ and $R^{10b}$ are taken together to form a (C1-C3) bridge, wherein one of the carbon atoms constituting the bridge may be replaced with an oxygen atom or a nitrogen atom;

b) $R^{9a}$ and $R^{10a}$ which are attached to the adjacent atoms, or $R^{9b}$ and $R^{10b}$ which are attached to the adjacent atoms are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle; and c) two $R^{10a}$ which are attached to the adjacent atom, or two $R^{10b}$ which are attached to the adjacent atom are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle; and $R^{10e}$ is each independently halogen, hydroxy, substituted or unsubstituted alkyl, or substituted or unsubstituted alkyloxy;

n is an integer from 1 to 5;
m is an integer from 0 to 4;
p1 is an integer from 0 to 3;
p2 is an integer from 0 to 2;
p3 is an integer from 0 to 2;

provided that i) when X is $C(R^{7a})(R^{7b})$, O or S, then $R^{5a}$ is not a hydrogen atom, hydroxy, methyl substituted with a substituted or unsubstituted 6-membered cyclic group, octadecyloxy, or ethyloxycarbonyl, and i') when X is $C(R^{7a})(R^{7b})$, O or S, then $R^{5b}$ is not a hydrogen atom or methyl substituted with a substituted or unsubstituted 6-membered cyclic group; and ii) when X is O, n is 1, and

[Chemical Formula 9]

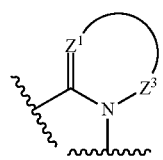 is 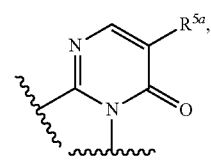

then $R^{2a}$ and $R^{2b}$ are not taken together to form oxo, provided that the following compounds are excluded:

[Chemical Formula 10]

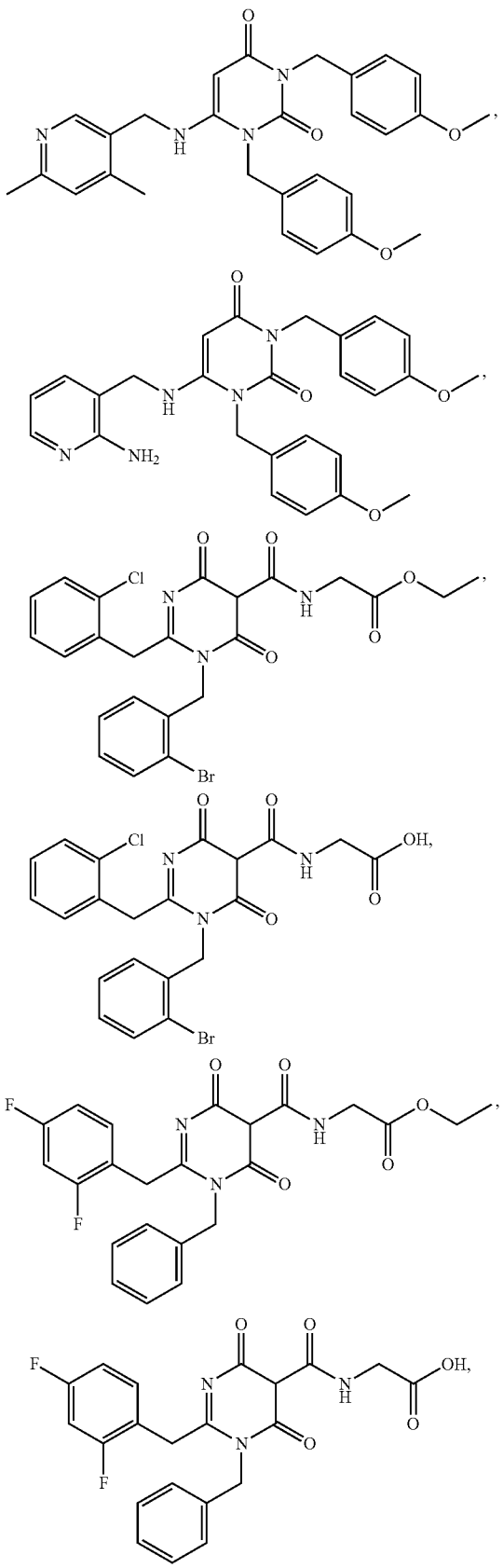

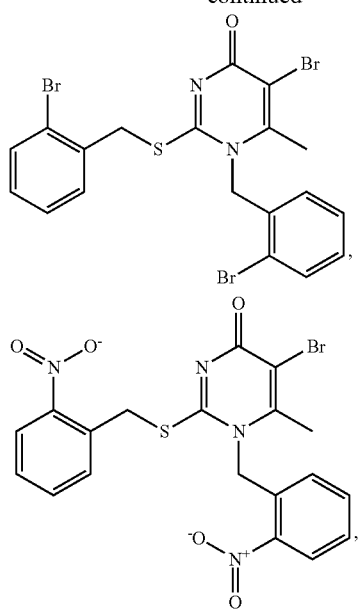

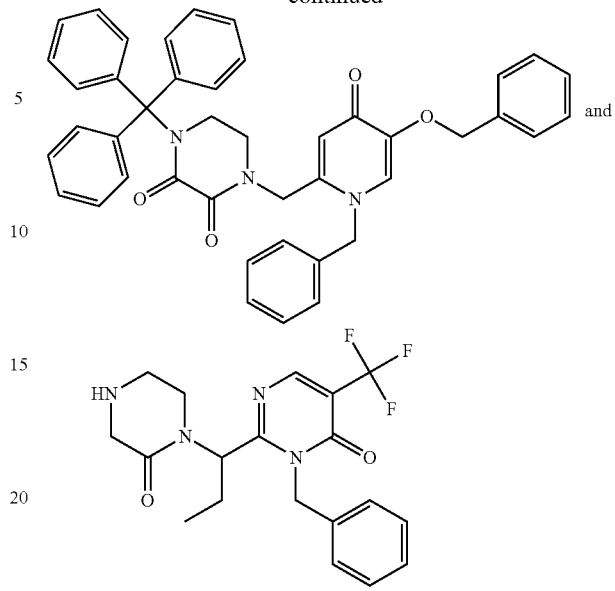

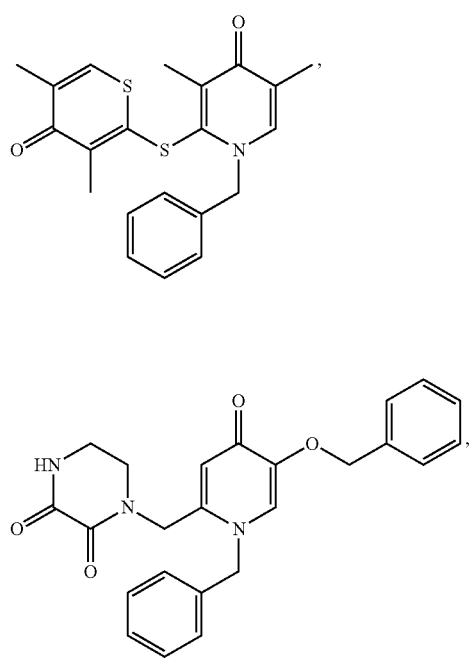

or a pharmaceutically acceptable salt thereof.

(2)

The compound according to the above (1), (1α), or (1α'), wherein

X is N(R$^{7a}$) or O.

or a pharmaceutically acceptable salt thereof.

(3)

The compound according to the above (0.1), (1α) or (1α'), wherein

X is N(R$^{7a}$), or a pharmaceutically acceptable salt thereof.

(4)

The compound according to any one of the above (1), (1α), (1α') and (2) to (3), wherein R$^{7a}$ is a hydrogen atom or substituted or unsubstituted alkyl, or a pharmaceutically acceptable salt thereof.

(5)

The compound according to any one of the above (1), (1α), (1α') and (2) to (3), wherein R$^{7a}$ is a hydrogen atom, or a pharmaceutically acceptable salt thereof.

(6)

The compound according to any one of the above (1), (1α), (1α') and (2) to (5), wherein

[Chemical Formula 11]

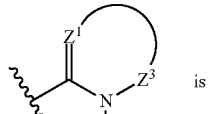 is

[Chemical Formula 12]

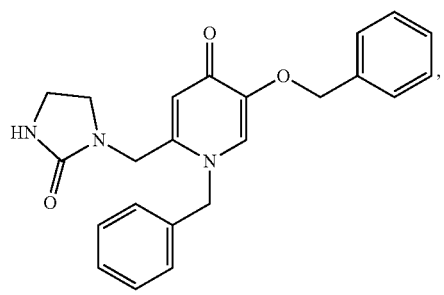

-continued

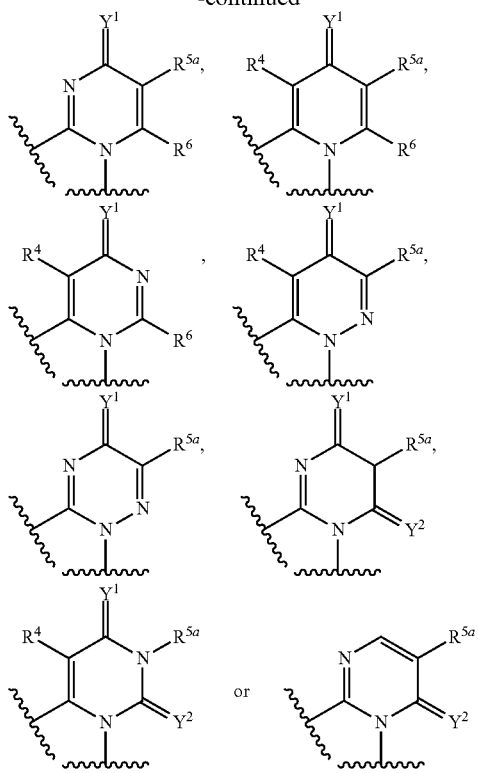

or a pharmaceutically acceptable salt thereof.

(7) The compound according to any one of the above (1), (1α), (1α') and (2) to (5), wherein

[Chemical Formula 13]

is

[Chemical Formula 14]

or a pharmaceutically acceptable salt thereof.

(8) The compound according to any one of the above (1), (1α), (1α') and (2) to (5), wherein

[Chemical Formula 15]

is or a pharmaceutically acceptable salt thereof.

(9) The compound according to any one of the above (1), (1α), (1α') and (2) to (5), wherein is or a pharmaceutically acceptable salt thereof.

(10) The compound according to any one of the above (1), (1α), (1α') and (2) to (9), wherein $R^1$ is substituted or unsubstituted 6- to 10-membered aromatic carbocyclyl, substituted or unsubstituted 3- to 10-membered non-aromatic carbocyclyl, substituted or unsubstituted 5- to 10-membered aromatic heterocyclyl, or substituted or unsubstituted 3- to 10-membered non-aromatic heterocyclyl, or a pharmaceutically acceptable salt thereof.

(11) The compound according to any one of the above (1), (1α), (1α') and (2) to (9), wherein $R^1$ is substituted or unsubstituted 6-membered aromatic carbocyclyl, substituted or unsubstituted 3- to 6-membered non-aromatic carbocyclyl, substituted or unsubstituted 5- to 6-membered aromatic heterocyclyl, or substituted or unsubstituted 5- to 6-membered non-aromatic heterocyclyl, or a pharmaceutically acceptable salt thereof.

(12) The compound according to any one of the above (1), (1α), (1α') and (2) to (9), wherein $R^1$ is substituted or unsubstituted 6-membered aromatic carbocyclyl, or substituted or unsubstituted 5- to 6-membered aromatic heterocyclyl, or a pharmaceutically acceptable salt thereof.

(13) The compound according to any one of the above (1), (1α), (1α') and (2) to (9), wherein R[1] is 6-membered aromatic carbocyclyl substituted with one or more halogen atom(s) and optionally substituted with one or more and same or different substituent(s), 3- to 6-membered non-aromatic carbocyclyl substituted with one or more halogen atom(s) and optionally substituted with one or more and same or different substituent(s), 5- to 6-membered aromatic heterocyclyl substituted with one or more halogen atom(s) and optionally substituted with one or more and same or different substituent(s), or 5- to 6-membered non-aromatic heterocyclyl substituted with one or more halogen atom(s) and optionally substituted with one or more and same or different substituent(s),
or a pharmaceutically acceptable salt thereof.

(14)
The compound according to any one of the above (1), (1α), (1α') and (2) to (9), wherein
R[1] is 6-membered aromatic carbocyclyl substituted with one or more halogen atom(s) and optionally substituted with one or more and same or different substituent(s), or 5- to 6-membered aromatic heterocyclyl substituted with one or more halogen atom(s) and optionally substituted with one or more and same or different, substituent(s),
or a pharmaceutically acceptable salt thereof.

(15)
The compound according to any one of the above (1), (1α), (1α') and (2) to (9), wherein
R[3] is

[Chemical Formula 16]

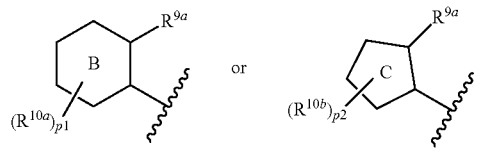

or a pharmaceutically acceptable salt thereof.

(16)
The compound according to any one of the above (1), (1α), (1α') and (2) to (15), wherein
$R^{9a}$ and $R^{9b}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfinyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted aryloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocycyloxycarbonylamino, substituted or unsubstituted aromatic heterocyclyloxycarbonylamino, or substituted or unsubstituted non-aromatic heterocyclyloxycarbonylamino
or a pharmaceutically acceptable salt, thereof.

(17)
The compound according to any one of the above (1), (1α), (1α') and (2) to (15), wherein
$R^{9a}$ and $R^{9b}$ are each independently halogen, hydroxy, amino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfonyl, substituted or unsubstituted alkynylsulfinyl, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy,
or a pharmaceutically acceptable salt thereof.

(18)
The compound according to any one of the above (1), (1α), (1α') and (2) to (15), wherein
$R^{9a}$ and $R^{9b}$ are each independently halogen, hydroxy, amino, substituted or unsubstituted alkyl, substituted or unsubstituted alkyloxy, substituted or unsubstituted alkylsulfanyl, substituted or unsubstituted alkylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy,
or a pharmaceutically acceptable salt thereof.

(19)
The compound according to any one of the above (1), (1α), (1α') and (2) to (15), wherein
$R^{9a}$ and $R^{9b}$ are each independently halogen, substituted or unsubstituted alkyl, substituted or unsubstituted alkonyl, substituted or unsubstituted alkynyl, substituted or unsubstituted alkylsulfanyl, substituted or unsubstituted alkenylsulfanyl, or substituted or unsubstituted alkynylsulfanyl,
or a pharmaceutically acceptable salt thereof.

(20)
The compound according to any one of the above (1), (1α), (1α') and (2) to (15), wherein
$R^{9a}$ and $R^{9b}$ are each independently halogen, substituted or unsubstituted alkyl, substituted or unsubstituted alkenyl, or substituted or unsubstituted alkynyl,
or a pharmaceutically acceptable salt thereof.

(21)
The compound according to any one of the above (1), (1α), (1α') and (2) to (21), wherein
$R^{9a}$ and $R^{9b}$ are each independently substituted or unsubstituted alkyl,
or a pharmaceutically acceptable salt thereof.

(22)
The compound according to any one of the above (1), (1α), (1α') and (2) to (21), wherein
$R^{10a}$ and $R^{10b}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfinyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted aryloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynyl carbonyl amino, substituted or unsubstituted alkylsulfonylamino, substituted or unsubstituted alkenylsulfonylamino, substituted or unsubstituted alkynylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclyl amino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonyl amino, substituted or unsubstituted non-aromatic, heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino, or a pharmaceutically acceptable salt thereof.

(23)

The compound according to any one of the above (1), (1α), (1α') and (2) to (21), wherein $R^{10a}$ and $R^{10b}$ are each independently halogen, hydroxy, amino, carbamoyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynyl sulfonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfamoyl, substituted or unsubstituted non-aromatic carbocyclylsulfamoyl, substituted or unsubstituted aromatic heterocyclylsulfamoyl, or substituted or unsubstituted non-aromatic heterocyclylsulfamoyl, or a pharmaceutically acceptable salt, thereof.

(24)

The compound according to any one of the above (1), (1α), (1α') and (2) to (21), wherein $R^{10a}$ and $R^{10b}$ are each independently halogen, hydroxy, amino, carbamoyl, cyano, substituted or unsubstituted alkyl, substituted or unsubstituted alkenyl, substituted or unsubstituted alkyloxy, substituted or unsubstituted alkylsulfanyl, substituted or unsubstituted alkylamino, substituted or unsubstituted alkylcarbonyl, substituted or unsubstituted alkylsulfonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfamoyl, substituted or unsubstituted non-aromatic carbocyclylsulfamoyl, substituted or unsubstituted aromatic heterocyclylsulfamoyl, or substituted or unsubstituted non-aromatic heterocyclylsulfamoyl, or a pharmaceutically acceptable salt thereof.

(25)

The compound according to any one of the above (1), (1α), (1α') and (2) to (21), wherein $R^{10a}$ and $R^{10b}$ are each independently halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or a pharmaceutically acceptable salt thereof.

(26)

The compound according to any one of the above (1), (1α), (1α') and (2) to (21), wherein $R^{10a}$ and $R^{10b}$ are each independently halogen, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or a pharmaceutically acceptable salt thereof.

(27)

The compound according to any one of the above (1), (1α), (1α') and (2) to (26), wherein p1 is 1 or 2, or a pharmaceutically acceptable salt thereof.

(28)

The compound according to any one of the above (1), (1α), (1α') and (2) to (27), wherein
p2 is 1.
or a pharmaceutically acceptable salt thereof.

(29)

The compound according to any one of the above (1), (1α), (1α') and (2) to (28), wherein
$R^3$ is

[Chemical Formula 17]

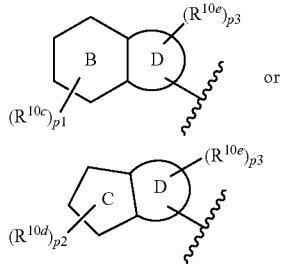

or a pharmaceutically acceptable salt thereof.

(30)

The compound according to any one of the above (1), (1α), (1α') and (2) to (29), wherein
$R^{10c}$ and $R^{10d}$ are each independently halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy,
or a pharmaceutically acceptable salt thereof.

(31)

The compound according to any one of the above (1), (1α), (1α') and (2) to (29), wherein
$R^{10c}$ and $R^{10d}$ are each independently halogen, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy,
or a pharmaceutically acceptable salt thereof.

(32)

The compound according to any one of the above (1), (1α), (1α') and (2) to (29), wherein
$R^{10c}$ and $R^{10d}$ are each independently halogen, substituted or unsubstituted alkyl, or substituted or unsubstituted alkyloxy,
or a pharmaceutically acceptable salt thereof.

(33)

The compound according to any one of the above (1), (1α), (1α') and (2) to (32), wherein
$R^{10e}$ is each independently halogen, or substituted or unsubstituted alkyl,
or a pharmaceutically acceptable salt thereof.

(34)

The compound according to any one of the above (1), (1α), (1α') and (2) to (33), wherein
p3 is 0,
or a pharmaceutically acceptable salt thereof.

(35)

The compound according to any one of the above (1), (1α), (1α') and (2) to (28), wherein
$R^3$ is a group represented by the formula:

[Chemical Formula 18]

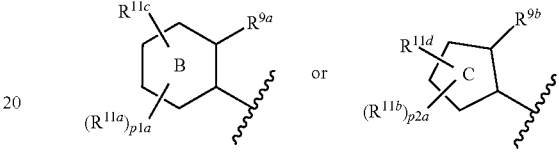

wherein
$R^{11a}$ and $R^{11b}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxy carbonyl, substituted or unsubstituted alkylsulfonyloxy, substituted or unsubstituted alkenylsulfonyloxy, substituted or unsubstituted alkynylsulfonyloxy, substituted or unsubstituted aryloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic, heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclyl sulfonyloxy, substituted or unsubstituted aromatic heterocyclylsulfonyloxy, substituted or unsubstituted non-aromatic heterocyclyl sulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic, heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonyl amino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino.

$R^{11c}$
is taken together with $R^{9a}$ which is attached to the adjacent atom to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle;
is taken together with $R^{11a}$ which is attached to the adjacent atom to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle; or
is taken together with $R^{11a}$ which is attached to a non-adjacent atom to form a (C1-C3) bridge, wherein one of the carbon atoms constituting the bridge may be replaced with an oxygen atom or a nitrogen atom:

$R^{11d}$
it taken together with $R^{9b}$ which is attached to the adjacent atom to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle;
is taken together with $R^{11b}$ which is attached to the adjacent atom to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle; or
is taken together with $R^{11b}$ which is attached to a non-adjacent atom to form a (C1-C3) bridge, wherein one of the carbon atoms constituting the bridge may be replaced with an oxygen atom or a nitrogen atom;
   p1a is an integer from 0 to 2; and
   p2a is 0 or 1,
or a pharmaceutically acceptable salt thereof.

(36)
   The compound according to the above (35), wherein
   $R^{11c}$ is taken together with $R^{9b}$ which is attached to the adjacent atom to form a substituted or unsubstituted 5- to 6-membered non-aromatic carbocycle, a substituted or unsubstituted 5- to 6-membered aromatic heterocycle, or a substituted or unsubstituted 5- to 6-membered non-aromatic heterocycle,
or a pharmaceutically acceptable salt thereof.

(37)
   The compound according to the above (35), wherein
   $R^{11d}$ is token together with $R^{9b}$ which is attached to the adjacent atom to form a substituted or unsubstituted 6-membered aromatic carbocycle, or a substituted or unsubstituted 6-membered aromatic heterocycle,
or a pharmaceutically acceptable salt thereof.

(38)
   The compound according to the above (35), wherein
   $R^{11c}$ is taken together with $R^{11a}$ which is attached to the adjacent atom to form a substituted or unsubstituted 5- to 6-membered non-aromatic carbocycle, a substituted or unsubstituted 5- to 6-membered aromatic heterocycle, or a substituted or unsubstituted 5- to 6-membered non-aromatic heterocycle,
or a pharmaceutically acceptable salt thereof.

(39)
   The compound according to the above (35), wherein
   $R^{11d}$ is taken together with $R^{11b}$ which is attached to the adjacent atom to form a substituted or unsubstituted 6-membered aromatic carbocycle, or a substituted or unsubstituted 6-membered aromatic heterocycle,
or a pharmaceutically acceptable salt thereof.

(40)
   The compound according to the above (35), wherein
   Ring B is a 6-membered non-aromatic carbocycle, or a 6-membered non-aromatic heterocycle; and
   $R^{11c}$ is taken together with $R^{11a}$ which is attached to a non-adjacent atom to form a (C1-C3) bridge consisting of carbon,
or a pharmaceutically acceptable salt thereof.

(41)

The compound according to the above (35), wherein
Ring C is a 5-membered non-aromatic carbocycle, or a 5-membered non-aromatic heterocycle; and
$R^{11d}$ is taken together with $R^{11b}$ which is attached to a nonadjacent atom to form a (C1-C3) bridge consisting of carbon,
or a pharmaceutically acceptable salt thereof.

(42)

The compound according to any one of the above (35) to (41), wherein
$R^{11a}$ and $R^{11b}$ are each independently halogen, hydroxy, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfonyl, substituted or unsubstituted alkynylsulfanyl, substituted or unsubstituted alkylamino, substituted or unsubstituted alkenylamino, or substituted or unsubstituted alkynylamino,
or a pharmaceutically acceptable salt thereof.

(43)

The compound according to any one of the above (35) to (41), wherein
$R^{11a}$ and $R^{11b}$ are each independently halogen, hydroxy, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy,
or a pharmaceutically acceptable salt thereof.

(41)

The compound according to any one of the above (35) to (41), wherein
$R^{11a}$ and $R^{11b}$ are each independently halogen, or substituted or unsubstituted alkyl,
or a pharmaceutically acceptable salt thereof.

(45)

The compound according to any one of the above (35) to (44), wherein
p1a is 0 or 1,
or a pharmaceutically acceptable salt thereof.

(46)

The compound according to any one of the above (35) to (45), wherein
p2a is 0,
or a pharmaceutically acceptable salt thereof.

(47)

The compound according to any one of the above (1), (1α), (1α') and (2) to (46), wherein
Ring B is a 6-membered aromatic carbocycle or a 6-membered aromatic heterocycle,
or a pharmaceutically acceptable salt thereof.

(48)

The compound according to any one of the above (1), (1α), (1α') and (2) to (46), wherein
Ring C is a 5-membered aromatic heterocycle,
or a pharmaceutically acceptable salt thereof.

(49)

The compound according to any one of the above (1), (1α), (1α') and (2) to (48), wherein
$R^{5a}$ is a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylsulfanyl, substituted or unsubstituted alkenyl sulfanyl, substituted or unsubstituted alkynylsulfanyl, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkynylcarbonylamino, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.

(50)

The compound according to any one of the above (1), (1α), (1α') and (2) to (48), wherein
$R^{5a}$ is a hydrogen atom, halogen, hydroxy, carboxy, amino, carbamoyl, cyano, substituted or unsubstituted alkyl, substituted or unsubstituted alkyloxy, substituted or unsubstituted alkyloxycarbonyl, substituted or unsubstituted alkylcarbamoyl, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.
or a pharmaceutically acceptable salt thereof.

(51)

The compound according to any one of the above (1), (1α), (1α') and (2) to (48), wherein
$R^{5a}$ is a hydrogen atom, halogen, amino, carbamoyl, cyano, substituted or unsubstituted alkyl, substituted or unsubstituted alkyloxy, substituted or unsubstituted alkylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.

(52)

The compound according to any one of the above (1), (1α), (1α') and (2) to (48), wherein
$R^{5a}$ is a hydrogen atom, halogen, substituted or unsubstituted alkyl, or substituted or unsubstituted alkyloxy,
or a pharmaceutically acceptable salt thereof.

(53)

The compound according to any one of the above (1), (1α), (1α') and (2) to (52), wherein
$R^{5b}$ is a hydrogen atom, carboxy, carbamoyl, cyano, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.

(54)

The compound according to any one of the above (1), (1α), (1α') and (2) to (52), wherein

(55) The compound according to any one of the above (1), (1α), (1α') and (2) to (52), wherein
$R^{5b}$ is substituted or unsubstituted alkyl,
or a pharmaceutically acceptable salt thereof.

(56) The compound according to any one of the above (1), (1α), (1α') and (2) to (55), wherein
n is an integer from 1 to 3,
or a pharmaceutically acceptable salt thereof.

(57) The compound according to any one of the above (1), (1α), (1α') and (2) to (55), wherein
n is 1.
or a pharmaceutically acceptable salt thereof.

(58) The compound according to any one of the above (1), (1α), (1α') and (2) to (57), wherein
$R^{3a}$ is each independently a hydrogen atom, halogen, or substituted or unsubstituted alkyl, or $R^{2a}$ and $R^{2b}$ which are attached to the same carbon atom are taken together to form oxo,
or a pharmaceutically acceptable salt thereof.

(59) The compound according to any one of the above (1), (1α), (1α') and (2) to (57), wherein
$R^{2a}$ is each independently a hydrogen atom, halogen, or substituted or unsubstituted alkyl,
or a pharmaceutically acceptable salt thereof.

(60) The compound according to any one of the above (1), (1α), (1α') and (2) to (57), wherein
$R^{2a}$ in a hydrogen atom,
or a pharmaceutically acceptable salt thereof.

(61) The compound according to any one of the above (1), (1α), (1α') and (2) to (60), wherein
$R^{2b}$ is each independently a hydrogen atom, halogen, or substituted or unsubstituted alkyl, or $R^{2a}$ and $R^{2b}$ which are attached to the same carbon atom are taken together to form oxo,
or a pharmaceutically acceptable salt thereof.

(62) The compound according to any one of the above (1), (1α), (1α') and (2) to (60), wherein
$R^{2b}$ is each independently a hydrogen atom, halogen, or substituted or unsubstituted alkyl,
or a pharmaceutically acceptable salt thereof.

(63) The compound according to any one of the above (1), (1α), (1α') and (2) to (60), wherein
$R^{2b}$ is a hydrogen atom,
or a pharmaceutically acceptable salt, thereof.

(64) The compound according to any one of the above (1), (1α), (1α') and (2) to (63), wherein
m is an integer from 0 to 2,
or a pharmaceutically acceptable salt thereof.

(65) The compound according to any one of the above (1), (1α), (1α') and (2) to (63), wherein
m is 0,
or a pharmaceutically acceptable salt thereof.

(66) The compound according to any one of the above (1), (1α), (1α') and (2) to (65), wherein
$R^{2c}$ is each independently a hydrogen atom, halogen, or substituted or unsubstituted alkyl,
or a pharmaceutically acceptable salt thereof.

(67) The compound according to any one of the above (1), (1α), (1α') and (2) to (65), wherein
$R^{2c}$ is a hydrogen atom,
or a pharmaceutically acceptable salt thereof.

(68) The compound according to any one of the above (1), (1α), (1α') and (2) to (67), wherein
$R^{2d}$ is each independently a hydrogen atom, halogen, or substituted or unsubstituted alkyl.
or a pharmaceutically acceptable salt thereof.

(69) The compound according to any one of the above (1), (1α), (1α') and (2) to (67), wherein
$R^{2d}$ is a hydrogen atom,
or a pharmaceutically acceptable salt thereof.

(70) The compound according to any one of the above (1), (1α), (1α') and (2) to (69), wherein
$Y^1$ is O,
or a pharmaceutically acceptable salt thereof.

(71) The compound according to any one of the above (1), (1α), (1α') and (2) to (70), wherein
$Y^2$ is O,
or a pharmaceutically acceptable salt thereof.

(72) The compound according to any one of the above (1), (1α), (1α') and (2) to (71), wherein
$R^4$ is a hydrogen atom, halogen, or substituted or unsubstituted alkyl,
or a pharmaceutically acceptable salt, thereof.

(73) The compound according to any one of the above (1), (1α), (1α') and (2) to (71), wherein
$R^4$ is a hydrogen atom.
or a pharmaceutically acceptable salt thereof.

(71) The compound according to any one of the above (1), (1α), (1α') and (2) to (73), wherein
$R^6$ is a hydrogen atom, halogen, or substituted or unsubstituted alkyl,
or a pharmaceutically acceptable salt thereof.

(75) The compound according to any one of the above (1), (1α), (1α') and (2) to (73), wherein
$R^6$ is a hydrogen atom,
or a pharmaceutically acceptable salt thereof.

(76) The compound according to any one of the above (1), (1α), (1α') and (2) to (75), wherein
$R^{3a'}$ is a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylsulfanyl, substituted or unsubstituted alkenylsulfanyl, substituted or unsubstituted alkynylsulfanyl, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkynylcarbonylamino, substituted or unsubstituted alkyloxycarbonylamino, substituted or unsubstituted alkenyloxycarbonyl amino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

(77)

The compound according to any one of the above (1), (1α), (1α') and (2) to (75), wherein $R^{5a'}$ is a hydrogen atom, halogen, hydroxy, carboxy, amino, carbamoyl, cyano, substituted or unsubstituted alkyl, substituted or unsubstituted alkyloxy, substituted or unsubstituted alkyloxycarbonyl, substituted or unsubstituted alkylcarbamoyl, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt, thereof.

(78)

The compound according to any one of the above (1), (1α), (1α') and (2) to (75), wherein $R^{5a'}$ is a hydrogen atom, halogen, amino, carbamoyl, cyano, substituted or unsubstituted alkyl, substituted or unsubstituted alkyloxy, substituted or unsubstituted alkylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

(79)

The compound according to any one of the above (1), (1α), (1α') and (2) to (75), wherein $R^{5a'}$ is a hydrogen atom, halogen, substituted or unsubstituted alkyl, or substituted or unsubstituted alkyloxy, or a pharmaceutically acceptable salt thereof.

(80)

The compound according to any one of the above (1), (1α), (1α') and (2) to (75), wherein $R^{5a'}$ is a hydrogen atom, or a pharmaceutically acceptable salt, thereof.

(81)

The compound according to any one of the above (1), (1α), (1α') and (2) to (80), wherein $R^Y$ is each independently a hydrogen atom, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

(82)

The compound according to any one of the above (1), (1α), (1α') and (2) to (80), wherein $R^Y$ is each independently a hydrogen atom, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy, or a pharmaceutically acceptable salt thereof.

(83)

The compound according to any one of the above (1), (1α), (1α') and (2) to (80), wherein $R^Y$ is each independently a hydrogen atom, hydroxy, cyano, substituted or unsubstituted alkyl, or substituted or unsubstituted alkyloxy, or a pharmaceutically acceptable salt thereof.

(84)

The compound according to the above (1), (1α) or (1α'), wherein

[Chemical Formula 19]

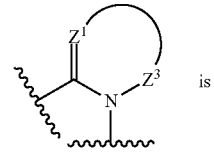

is

[Chemical Formula 20]

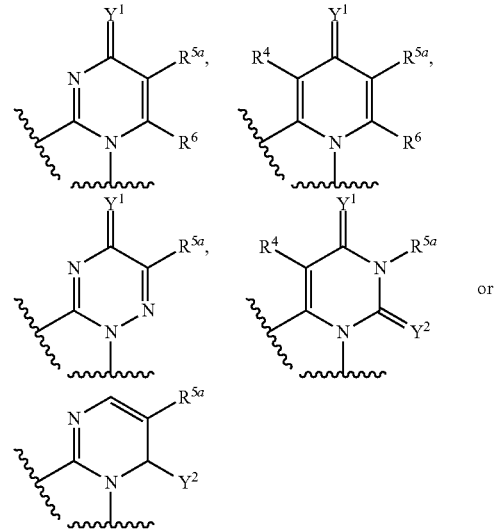

each of $Y^1$ and $Y^2$ is O;

each of $R^4$ and $R^6$ is a hydrogen atom;

$R^{5a}$ is a hydrogen atom, halogen, hydroxy, carboxy, amino, carbamoyl, cyano, substituted or unsubstituted alkyl, substituted or unsubstituted alkyloxy, substituted or unsubstituted alkyloxycarbonyl, substituted or unsubstituted alkylcarbamoyl, or substituted or unsubstituted alkyloxycarbonylamino;

$R^{5b}$ is a hydrogen atom, carboxy, carbamoyl, cyano, substituted or unsubstituted alkyl, or substituted or unsubstituted alkylcarbonyl;

X is N(H);

$R^1$ is substituted or unsubstituted 6-membered aromatic carbocyclyl, or substituted or unsubstituted 5- to 6-membered aromatic heterocyclyl;

each of $R^{2a}$ and $R^{2b}$ is a hydrogen atom;

$R^3$ is

[Chemical Formula 21]

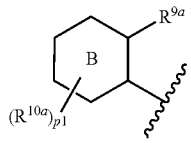

$R^{9a}$ is halogen, or substituted or unsubstituted alkyl;

$R^{10a}$ is halogen, hydroxy, amino, carbamoyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfinyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfamoyl, substituted or unsubstituted non-aromatic carbocyclylsulfamoyl, substituted or unsubstituted aromatic heterocyclyl sulfamoyl, or substituted or unsubstituted non-aromatic heterocyclylsulfamoyl;

m is 0;

n is 1; and p1 is an integer from 0 to 2, or a pharmaceutically acceptable salt thereof.

(85) The compound according to the above (84), wherein

[Chemical Formula 22]

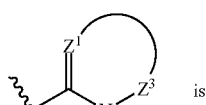

[Chemical Formula 23]

is

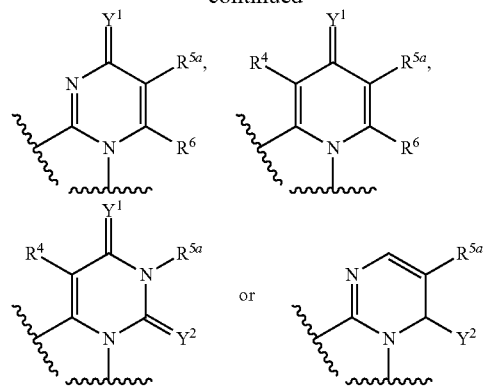

or a pharmaceutically acceptable salt thereof.

(86) The compound according to the above (84), wherein

[Chemical Formula 24]

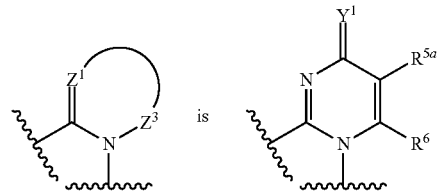

or a pharmaceutically acceptable salt thereof.

(87) The compound according to the above (84), wherein

[Chemical Formula 25]

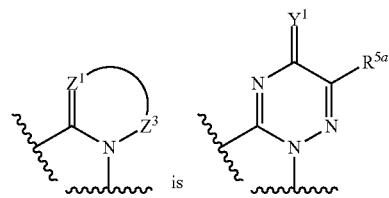

or a pharmaceutically acceptable salt thereof.

(88) The compound according to the above (1), (1α) or (1α'), wherein the compound is Compound I-0005, Compound I-0006, Compound I-0354, Compound I-0365, Compound I-0372. Compound I-0702, Compound I-0707, Compound I-0842, Compound I-0910, or Compound I-1040, or a pharmaceutically acceptable salt thereof.

(89) The compound according to the above (1), (1α) or (1α'), wherein the compound is Compound I-1041. Compound I-1050, Compound I-1066, Compound I-1108, Compound I-1232, Compound I-1261, Compound I-1281, Compound I-1295, Compound I-1296, or Compound I-1297, or a pharmaceutically acceptable salt thereof.

(90)
The compound according to the above (1), (1α) or (1α'), wherein
the compound is
[Chemical Formula 26]
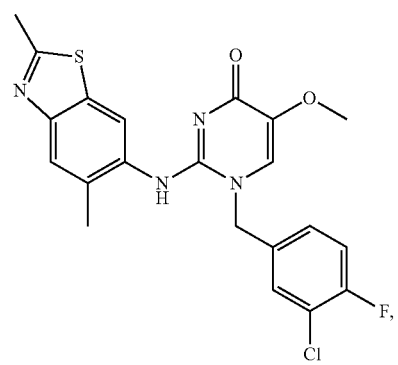
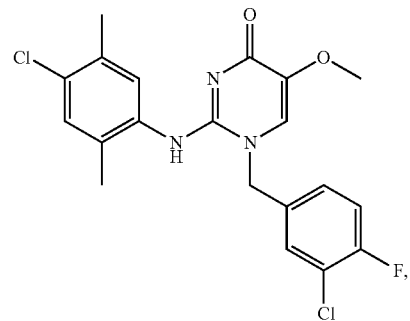
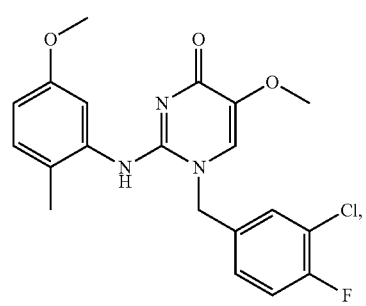
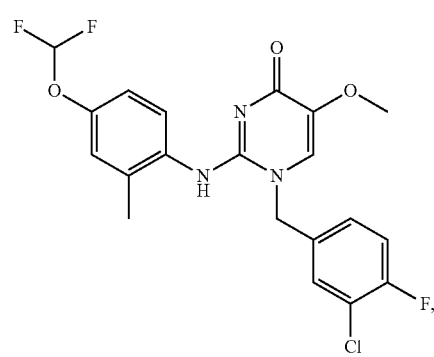
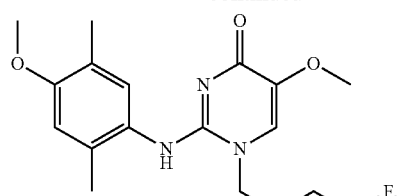
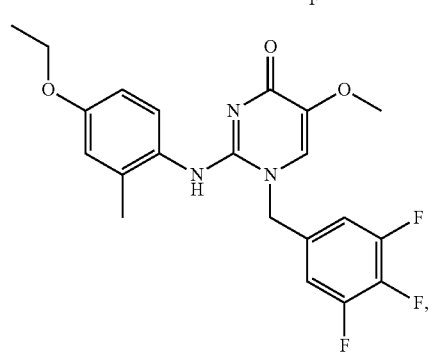
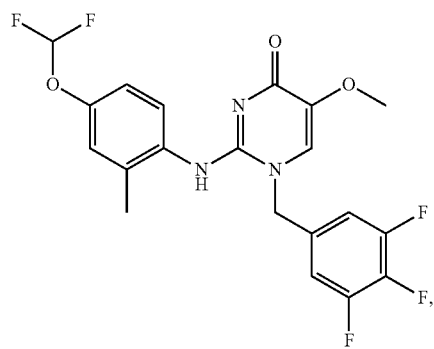
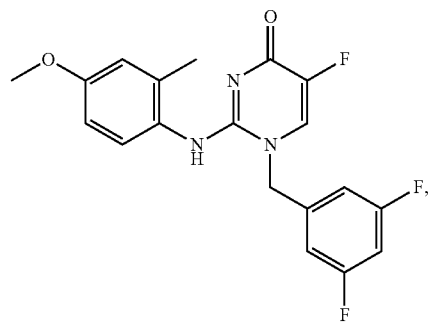
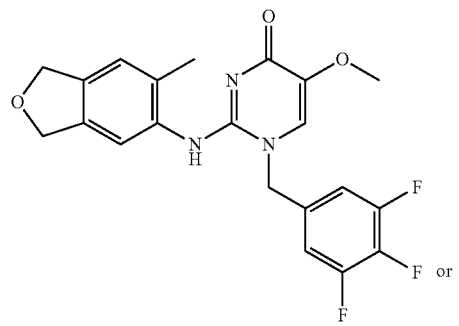

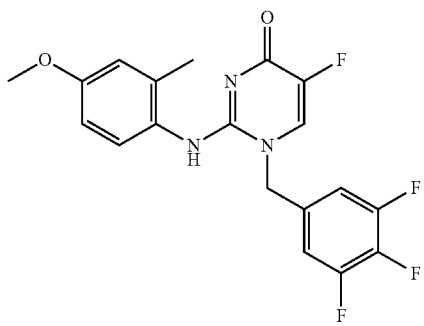
or a pharmaceutically acceptable salt thereof.
(91)
The compound according to the above (1). (1α) or (1α'), wherein
the compound is
[Chemical Formula 27]
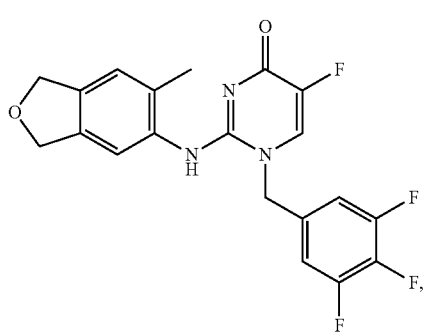
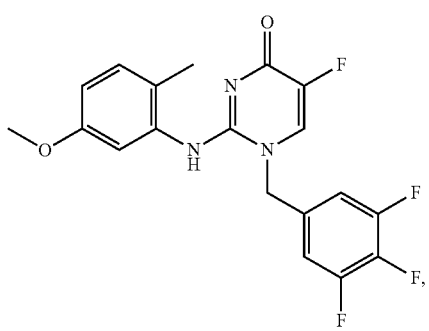
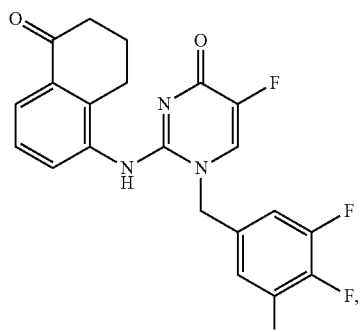
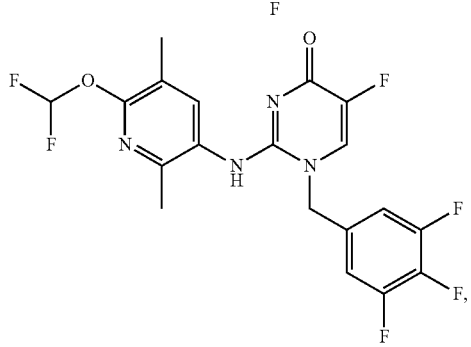
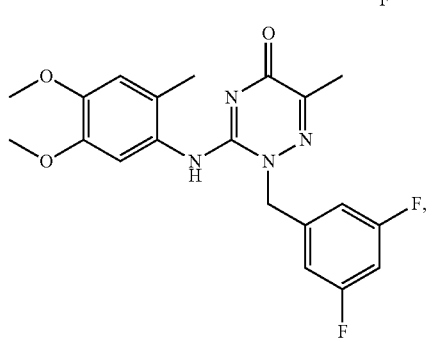
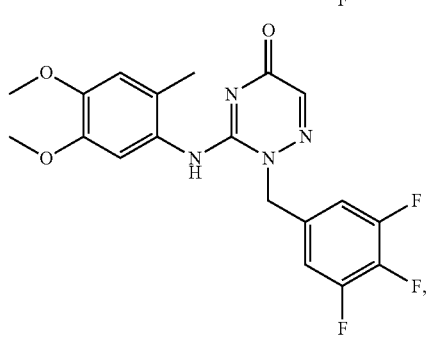

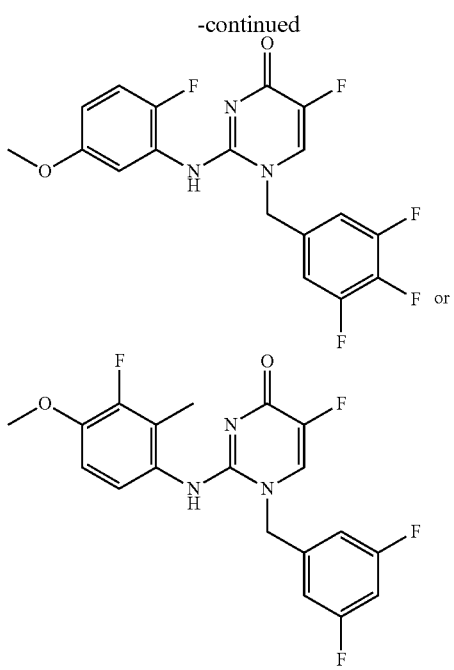

or a pharmaceutically acceptable salt thereof.

(92)
A pharmaceutical composition comprising the compound according to any one of the above (1) to (91), or a pharmaceutically acceptable salt thereof.

(93)
The pharmaceutical composition according to the above (92) having an antagonistic activity for the P2X7 receptor.

(94)
The compound according to any one of the above (1) to (91), or a pharmaceutically acceptable salt thereof for use in treating and/or preventing a disease associated with the P2X7 receptor.

(95)
A method for treating and/or preventing a disease associated with the P2X7 receptor characterized by administering the compound according to any one of the above (1) to (91), or a pharmaceutically acceptable salt thereof.

(96)
Use of the compound according to any one of the above (1) to (91), or a pharmaceutically acceptable salt thereof for manufacture of a medicament for treating and/or preventing a disease associated with the P2X7 receptor.

(1001) A pharmaceutical composition comprising the compound according to any one of the above (1) to (91), or a pharmaceutically acceptable salt thereof, for oral administration.

(1002) The pharmaceutical composition according to (1001), which is a tablet, powder, granule, capsule, pill, film, suspension, emulsion, elixir, syrup, lemonade, spirit, aromatic water, extract, decoction or tincture.

(1003) The pharmaceutical composition according to (1002), which is a sugar-coated tablet, film-coated tablet, enteric-coated tablet, sustained-release tablet, troche tablet, sublingual tablet, buccal tablet, chewable tablet, orally dispersing tablet, dry syrup, soft capsule, micro capsule or sustained-release capsule.

(1004) A pharmaceutical composition comprising the compound according to any one of the above (1) to (91), or a pharmaceutically acceptable salt thereof, for parenteral administration.

(1005) The pharmaceutical composition according to (1004), for dermal, subcutaneous, intravenous, intraarterial, intramuscular, intraperitoneal, transmucosal, inhalation, transnasal, ophthalmic, inner ear or vaginal administration.

(1006) The pharmaceutical composition according to (1004) or (1.005), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

(1007) A pharmaceutical composition comprising the compound according to any one of the above (1) to (91), or a pharmaceutically acceptable salt thereof, for a pediatric or geriatric patient.

Effect of the Invention

The compounds of the present invention have an antagonistic activity for the P2X7 receptor, and are useful as a therapeutic and/or preventive agent for diseases or conditions associated with the P2X7 receptor.

MODE FOR CARRYING OUT THE INVENTION

Terms used in this description are explained below. Each term, unless otherwise indicated, has the same meaning when it is used alone or together with other terms.

The term "consist of" means having only a component.

The term "comprise" means that an element that is not described is not excluded without limitations to a component.

"Halogen" includes a fluorine atom, a chlorine atom, a bromine atom and an iodine atom. A fluorine atom and a chlorine atom are preferable.

"Alkyl" includes a C1 to C15, preferably C1 to C10, more preferably C1 to C6 and further preferably C1 to C4 linear or branched hydrocarbon group. For example, it includes methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

"Alkenyl" includes a C2 to C15, preferably C2 to C10, more preferably C2 to C6 and further preferably C2 to C4 linear or branched hydrocarbon group having one or more double bond(s) at any position(s). For example, it includes vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.

"Alkynyl" includes a C2 to C10, preferably C2 to C8, more preferably C2 to <16 and further preferably C2 to C4 linear or branched hydrocarbon group having one or more triple bond(s) at any position(s). For example, it includes ethynyl, propynyl, butynyl, pentynyl, hexynyl, heptynyl, octynyl, nonynyl, decynyl and the like. Furthermore, it may have double bond(s) at any position(s).

A preferred embodiment of "alkynyl" is ethynyl, propynyl, butynyl or pentynyl.

"Aromatic carbocycle" means a cyclic aromatic hydrocarbon ring which is monocyclic or polycyclic having two or more rings. For example, it includes benzene, naphthalene, anthracene, phenanthrene and the like.

A preferred embodiment, of "aromatic carbocycle" is benzene.

"Aromatic carbocyclyl" means a cyclic aromatic hydrocarbon group which is monocyclic or polycyclic having two or more rings. For example, it includes phenyl, naphthyl, anthryl, phenanthryl and the like.

A preferred embodiment of "aromatic carbocyclyl" is phenyl.

"Non-aromatic carbocycle" means a cyclic saturated hydrocarbon ring or a cyclic unsaturated non-aromatic hydrocarbon ring, which is monocyclic or polycyclic having two or more rings. "Non-aromatic carbocycle", which is polycyclic having two or more rings, includes a fused ring wherein a non-aromatic carbocycle, which is monocyclic or polycyclic having two or more rings, is fused with a ring of the above "aromatic carbocycle".

In addition, the "non-aromatic carbocycle" also includes a ring having a bridge or a ring to form a spiro ring as follows.

[Chemical Formula 28]

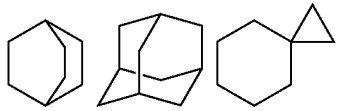

A non-aromatic carbocycle which is monocyclic is preferably C3 to C16, more preferably C3 to C12 and further preferably C4 to C8 carbocycle. For example, it includes cyclopropane, cyclobutane, cyclopentane, cyclohexane, cycloheptane, cyclooctane, cyclononane, cyclodecane, cyclopropane, cyclobutene, cyclopentene, cyclohexene, cycloheptene, cyclohexadiene and the like.

A non-aromatic carbocycle which is polycyclic having two or more rings includes, for example, indane, indene, acenaphthalene, tetrahydronaphthalene, fluorene and the like.

"Non-aromatic carbocyclyl" means a cyclic saturated hydrocarbon group or a cyclic unsaturated non-aromatic hydrocarbon group, which is monocyclic or polycyclic having two or more rings. "Non-aromatic carbocyclyl", which is polycyclic having two or more rings, includes a fused ring group wherein a non-aromatic carbocyclyl, which is monocyclic or polycyclic having two or more rings, is fused with a ring of the above "aromatic carbocyclyl".

In addition, the "non-aromatic carbocyclyl" also includes a group having a bridge or a group to form a spiro ring as follows:

[Chemical Formula 29]

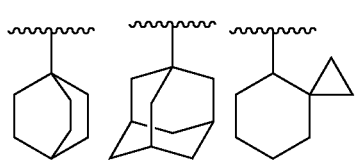

A non-aromatic carbocyclyl which is monocyclic is preferably C3 to C10, more preferably C3 to C12 and further preferably C4 to C8 carbocyclyl. For example, it includes cyclopropyl, cyclobutyl, cyclopentyl, cyclohexyl, cyclohep-tyl, cyclooctyl, cyclononyl, cyclodecyl, cyclopropenyl, cyclobutenyl, cyclopentenyl, cyclohexenyl, cycloheptenyl, cyclohexadienyl and the like.

A non-aromatic carbocyclyl which is polycyclic having two or more rings includes, for example, indanyl, indenyl, acenaphthyl, tetrahydronaphthyl, fluorenyl and the like.

"Aromatic heterocyclo" means an aromatic ring, which is monocyclic or polycyclic having two or more rings, containing one or more and same or different of heteroatom(s) selected independently from O, S and N.

"Aromatic heterocyclo", which is polycyclic having two or more rings, includes a fused ring wherein an aromatic heterocycle, which is monocyclic or polycyclic having two or more rings, is fused with a ring of the above "aromatic carbocycle".

An aromatic heterocycle which is monocyclic is preferably a 5- to 8-membered and more preferably 5- to 6-membered ring. For example, it includes pyrrole, imidazole, pyrazole, pyridine, pyridazine, pyrimidine, pyrazine, triazole, triazine, tetrazole, furan, thiophene, isoxazole, oxazole, oxadiazole, isothiazole, thiazole, thiadiazole and the like.

An aromatic heterocycle which is bicyclic includes, for example, indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, thiazolopyridine and the like.

An aromatic heterocycle which is polycyclic having three or more rings includes, for example, carbazole, acridine, xanthene, phenothiazine, phenoxathiine, phenoxazine, dibenzofuran and the like.

"Aromatic heterocyclyl" means an aromatic cyclyl, which is monocyclic or polycyclic having two or more rings, containing one or more and same or different of heteroatom (s) selected independently from O, S and N.

"Aromatic heterocyclyl", which is polycyclic having two or more rings, includes a fused ring group wherein an aromatic heterocyclyl, which is monocyclic or polycyclic having two or more rings, is fused with a ring of the above "aromatic carbocyclyl".

An aromatic heterocyclyl which is monocyclic is preferably a 5- to 8-membered and more preferably 5- to 6-membered ring. For example, it includes pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like.

An aromatic heterocyclyl which is bicyclic includes, for example, indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like.

An aromatic heterocyclyl which is polycyclic having three or more rings includes, for example, carbazolyl, acridinyl, xanthenyl, phenothiazinyl, phenoxathiinyl, phenoxazinyl, dibenzofuryl and the like.

"Non-aromatic heterocycle" means a non-aromatic ring, which is monocyclic or polycyclic having two or more rings, containing one or more and same or different of heteroatom (s) selected independently from O, S and N.

"Non-aromatic heterocycle", which is polycyclic having two or more rings, includes a fused ring wherein a non-aromatic heterocycle, which is monocyclic or polycyclic having two or more ring(s), is fused with a ring of the above "aromatic carbocycle", "non-aromatic carbocycle" and/or "aromatic heterocycle". The non-aromatic heterocycle, which is polycyclic having two or more rings, further includes a fused ring wherein an aromatic heterocycle, which is monocyclic or polycyclic having two or more rings, is fused with a ring of the above "non-aromatic carbocycle".

In addition, the "non-aromatic heterocycle" also includes a ring having a bridge or a ring to form a spiro ring as follows.

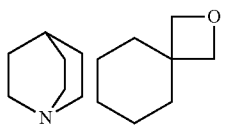

[Chemical Formula 30]

A non-aromatic heterocycle which is monocyclic is preferably a 3- to 8-membered and more preferably 5- to 6-membered ring. For example, it includes dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridino, tetrahydrofuran, tetrahydropyrane, dihydrothiazole, tetrahydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxoline, oxepane, thiolane, thiine, thiazine and the like.

A non-aromatic heterocycle which is polycyclic having two or more rings includes, for example, indoline, isoindolinel, chromane, isochromane and the like.

"Non-aromatic heterocyclyl" means a non-aromatic cyclyl, which is monocyclic or polycyclic having two or more rings, containing one or more and same or different of heteroatom(s) selected independently from O, S and N.

"Non-aromatic heterocyclyl", which is polycyclic having two or more rings, includes a fused ring group wherein a non-aromatic heterocycle, which is monocyclic or polycyclic having two or more ring(s), is fused with a ring of the above "aromatic carbocyclyl", "non-aromatic carbocyclyl" and/or "aromatic heterocyclyl". The non-aromatic heterocyclyl, which is polycyclic having two or more rings, further includes a fused ring wherein an aromatic heterocyclyl, which is monocyclic or polycyclic having two or more rings, is fused with a ring of the above "non-aromatic carbocyclyl".

In addition, the "non-aromatic heterocyclyl" also includes a group having a bridge or a group to form a spiro ring as follows:

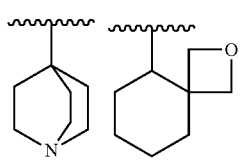

[Chemical Formula 31]

A non-aromatic heterocyclyl which is monocyclic is preferably a 3- to 8-membered and more preferably 5- to 6-membered ring. For example, it includes dioxanyl, thiiranyl, oxiranyl, oxetanyl, oxathiolanyl, azetidinyl, thienyl, thiazolidinyl, pyrrolidinyl, pyrrolinyl, imidazolidinyl, imidazolinyl, pyrazolidinyl, pyrazolinyl, piperidinyl, piperazinyl, morpholinyl, morpholino, thiomorpholinyl, thiomorpholino, dihydropyridinyl, tetrahydropyridinyl, tetrahydrofuryl, tetrahydropyranyl, dihydrothiazolinyl, totrahydrothiazolinyl, tetrahydroisothiazolinyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like.

A non-aromatic heterocyclyl which is polycyclic having two or more rings includes, for example, indolinyl, isoindolinyl, chromanyl, isochromanyl and the like.

"Alkyloxy" means a group wherein the above "alkyl" is bonded to an oxygen atom. For example, it includes methyloxy, ethyloxy, n-propyloxy, isopropyloxy, n-butyloxy, tert-butyloxy, isobutyloxy, sec-butyloxy, pentyloxy, isopentyloxy, hexyloxy and the like.

A preferred embodiment of "alkyloxy" is methyloxy, ethyloxy, n-propyloxy, isopropyloxy or tert-butyloxy.

"Alkenyloxy" means a group wherein the above "alkenyl" is bonded to an oxygen atom. For example, it includes vinyloxy, allyloxy, 1-propenyloxy, 2-butenyloxy, 2-pentenyloxy, 2-hexenyloxy, 2-heptenyloxy, 2-octenyloxy and the like.

"Alkynyloxy" means a group wherein the above "alkynyl" is bonded to an oxygen atom. For example, it includes ethynyloxy, 1-propynyloxy, 2-propynyloxy, 2-butynyloxy, 2-pentynyloxy. 2-hexynyloxy, 2-heptynyloxy, 2-octynyloxy and the like.

"Alkylsulfanyl" means a group wherein a hydrogen atom bonded to a sulfur atom of a sulfanyl group is replaced with the above "alkyl". For example, it includes methylsulfanyl, ethylsulfanyl, n-propylsulfanyl, isopropylsulfanyl and the like.

"Alkenylsulfonyl" means a group wherein a hydrogen atom bonded to a sulfur atom of a sulfanyl group is replaced with the above "alkenyl". For example, it includes ethylenylsulfanyl, propenylsulfanyl and the like.

"Alkynylsulfanyl" means a group wherein a hydrogen atom bonded to a sulfur atom of a sulfanyl group is replaced with the above "alkynyl". For example, it includes ethynylsulfanyl, propynylsulfanyl and the like.

"Alkylamino" means a group wherein a hydrogen atom attached to a nitrogen atom of an amino group is replaced with the above "alkyl". For example, it includes methylamino, ethylamino, isopropylamino and the like. Another hydrogen atom attached to the nitrogen atom of the amino group may be replaced with the above "alkyl".

A preferred embodiment of "alkylamino" is methylamino or ethylamino.

"Alkenylamino" means a group wherein a hydrogen atom attached to a nitrogen atom of an amino group is replaced with the above "alkenyl". For example, it includes ethylenylamino, propenylamino and the like. Another hydrogen atom attached to the nitrogen atom of the amino group may be replaced with the above "alkyl".

"Alkynylamino" means a group wherein a hydrogen atom attached to a nitrogen atom of an amino group is replaced with the above "alkynyl". For example, it includes ethynylamino, propynylamino and the like. Another hydrogen atom attached to the nitrogen atom of the amino group may be replaced with the above "alkyl".

"Alkylcarbonyl" means a group wherein the above "alkyl" is bonded to a carbonyl group. For example, it includes methylcarbonyl, ethylcarbonyl, propylcarbonyl, isopropylcarbonyl, tert-butylcarbonyl, isobutylcarbonyl, sec-butylcarbonyl, pentylcarbonyl, isopenthylcarbonyl, hexylcarbonyl and the like.

A preferred embodiment of "alkylcarbonyl" is methylcarbonyl, ethylcarbonyl or n-propylcarbonyl.

"Alkenylcarbonyl" means a group wherein the above "alkenyl" is bonded to a carbonyl group. For example, it includes ethylenylcarbonyl, propenylcarbonyl and the like.

"Alkynylcarbonyl" means a group wherein the above "alkynyl" is bonded to a carbonyl group. For example, it includes ethynylcarbonyl, propynylcarbonyl and the like.

"Alkylsulfonyl" means a group wherein the above "alkyl" is bonded to a sulfonyl group. For example, it includes methylsulfonyl, ethylsulfonyl, propylsulfonyl, isopropylsulfonyl, tert-butylsulfonyl, isobutylsulfonyl, see-butylsulfonyl and the like.

A preferred embodiment, of "alkylsulfonyl" is methylsulfonyl or ethylsulfonyl.

"Alkenylsulfonyl" means a group wherein the above "alkenyl" is bonded to a sulfonyl group. For example, it includes ethylenylsulfonyl, propenylsulfonyl and the like.

"Alkynylsulfinyl" means a group wherein the above "alkynyl" is bonded to a sulfonyl group. For example, it includes ethynyl sulfonyl, propynylsulfonyl and the like.

"Alkylcarbonyloxy" means a group wherein the above "alkylcarbonyl" is bonded to an oxygen atom. For example, it includes methylcarbonyloxy, ethylcarbonyloxy, propylcarbonyloxy, isopropylcarbonyloxy, tert-butylcarbonyloxy, isobutylcarbonyloxy, sec-butylcarbonyloxy and the like.

A preferred embodiment of "alkylcarbonyloxy" is methylcarbonyloxy or ethylcarbonyloxy.

"Alkenylcarbonyloxy" means a group wherein the above "alkenylcarbonyl" is bonded to an oxygen atom. For example, it includes ethylenylcarbonyloxy, propenylcarbonyloxy and the like.

"Alkynylcarbonyloxy" means a group wherein the above "alkynylcarbonyl" is bonded to an oxygen atom. For example, it includes ethynylcarbonyloxy, propenylcarbonyloxy and the like.

"Alkyloxycarbonyl" means a group wherein the above "alkyloxy" is bonded to a carbonyl group. For example, it includes methyloxycarbonyl, ethyloxycarbonyl, propyloxycarbonyl, isopropyloxycarbonyl, tert-butyloxycarbonyl, isobutyloxycarbonyl, sec-butyloxycarbonyl, penthyloxycarbonyl, isopenthyloxycarbonyl, hexyloxycarbonyl and the like.

A preferred embodiment of "alkyloxycarbonyl" is methyloxycarbonyl, ethyloxycarbonyl or propyloxycarbonyl.

"Alkenyloxycarbonyl" means a group wherein the above "alkenyloxy" is bonded to a carbonyl group. For example, it includes ethylenyloxycarbonyl, propenyloxycarbonyl and the like.

"Alkynyloxycarbonyl" means a group wherein the above "alkynyloxy" is bonded to a carbonyl group. For example, it includes ethynyloxycarbonyl, propynyloxycarbonyl and the like.

"Alkylsulfonyloxy" means a group wherein the above "alkylsulfonyl" is bonded to an oxygen atom. For example, it includes methylsulfonyloxy, arylsulfonyloxy, propylsulfonyloxy, isopropylsulfonyloxy, tert-butylsulfonyloxy, isobutyl sulfonyloxy, sec-butylsulfonyloxy and the like.

A preferred embodiment of "alkylsulfonyloxy" is methylsulfonyloxy or ethylsulfonyloxy.

"Alkenylsulfonyloxy" means a group wherein the above "alkenylsulfonyl" is bonded to an oxygen atom. For example, it includes ethylenylsulfonyloxy, propenylsulfonyloxy and the like.

"Alkynylsulfonyloxy" means a group wherein the above "alkynylsulfonyl" is bonded to an oxygen atom. For example, it includes ethynylsulfonyloxy, propynylsulfonyloxy and the like.

"Alkyloxysulfonyl" means a group wherein the above "alkyloxy" is bonded to a sulfonyl group. For example, it includes methyloxysulfonyl, ethyloxysulfonyl, propyloxysulfonyl, isopropyloxysulfonyl, tert-butyloxysulfonyl, isobutyloxysulfonyl, sec-butyloxysulfonyl, pentyloxysulfonyl, isopentyloxysulfonyl, hexyloxysulfenyl and the like.

A preferred embodiment of "alkyloxysulfonyl" is methyloxysulfonyl, ethyloxysulfonyl, or propyloxysulfonyl.

"Alkenyloxysulfonyl" means a group wherein the above "alkenyloxy" is bonded to a sulfonyl group. For example, it includes ethylenyloxysulfonyl, propenyloxysulfonyl and the like.

"Alkynyloxysulfonyl" means a group wherein the above "alkynyloxy" is bonded to a sulfonyl group. For example, it includes ethynyloxysulfonyl, propynyloxysulfonyl and the like.

"Alkylcarbamoyl" means a group wherein a hydrogen atom bonded to a nitrogen atom of a carbamoyl group is replaced with the above "alkyl". For example, it includes methylcarbamoyl, ethylcarbamoyl and the like. Another hydrogen atom bonded to the nitrogen atom of the carbamoyl group may be replaced with the above "alkyl".

"Alkenylcarbamoyl" means a group wherein a hydrogen atom bonded to a nitrogen atom of a carbamoyl group is replaced with the above "alkenyl". For example, it includes ethylenylcarbamoyl, propenylcarbamoyl and the like. Another hydrogen atom bonded to the nitrogen atom of the carbamoyl group may be replaced with the above "alkyl".

"Alkynylcarbamoyl" means a group wherein a hydrogen atom bonded to a nitrogen atom of a carbamoyl group is replaced with the above "alkynyl". For example, it includes ethynylcarbamoyl, propynyl carbamoyl and the like. Another hydrogen atom bonded to the nitrogen atom of the carbamoyl group may be replaced with the above "alkyl".

"Alkylsulfamoyl" means a group wherein a hydrogen atom bonded to a nitrogen atom of a sulfamoyl group is replaced with the above "alkyl". For example, it includes methylsulfamoyl, dimethylsulfamoyl and the like. Another hydrogen atom bonded to the nitrogen atom of the sulfamoyl group may be replaced with the above "alkyl".

"Alkenylsulfamoyl" means a group wherein a hydrogen atom bonded to a nitrogen atom of a sulfamoyl group is replaced with the above "alkenyl". For example, it includes ethylenylsulfamoyl, propenylsulfamoyl and the like. Another hydrogen atom bonded to the nitrogen atom of the carbamoyl group may be replaced with the above "alkyl".

"Alkynylsulfamoyl" means a group wherein a hydrogen atom bonded to a nitrogen atom of a sulfamoyl group is replaced with the above "alkynyl". For example, it includes ethynylsulfamoyl, propynylsulfamoyl and the like. Another hydrogen atom bonded to the nitrogen atom of the carbamoyl group may be replaced with the above "alkyl".

"Alkylcarbonylamino" means a group wherein a hydrogen atom bonded to a nitrogen atom of an amino group is replaced with the above "alkylcarbonyl". For example, it includes methylcarbonylamino, ethylcarbonylamino, propylcarbonylamino, isopropylcarbonylamino, tert-butylcarbonylamino, isobutylcarbonylamino, sec-butylcarbonylamino and the like. Another hydrogen atom bonded to the nitrogen atom of the amino group may be replaced with the above "alkyl".

A preferred embodiment of "alkylcarbonylamino" is methylcarbonylamino or ethylcarbonylamino.

"Alkenylcarbonylamino" means a group wherein a hydrogen atom bonded to a nitrogen atom of an amino group is replaced with the above "alkenylcarbonyl". For example, it includes ethylenylcarbonylamino, propenylcarbonylamino and the like. Another hydrogen atom bonded to the nitrogen atom of the amino group may be replaced with the above "alkyl".

"Alkynylcarbonylamino" means a group wherein a hydrogen atom bonded to a nitrogen atom of an amino group is replaced with the above "alkynylcarbonyl". For example, it includes ethynylcarbonylamino, propynylcarbonylamino and the like. Another hydrogen atom bonded to the nitrogen atom of the amino group may be replaced with the above "alkyl".

"Alkylsulfonylamino" means a group wherein a hydrogen atom bonded to a nitrogen atom of an amino group is replaced with the above "alkylsulfonyl". For example, it includes methylsulfonylamino, ethylsulfonylamino, propylsulfonylamino, isopropylsulfonylamino, tert-butylsulfonylamino, isobutylsulfonylamino, sec-butylsulfonylamino and the like. Another hydrogen atom bonded to the nitrogen atom of the amino group may be replaced with the above "alkyl".

A preferred embodiment, of "alkylsulfonylamino" is methylsulfonylamino or ethylsulfonylamino.

"Alkonylsulfonylamino" means a group wherein a hydrogen atom bonded to a nitrogen atom of an amino group is replaced with the above "alkenylsulfonyl". For example, it includes ethylenylsulfonylamino, propenylsulfonylamino and the like. Another hydrogen atom bonded to the nitrogen atom of the amino group may be replaced with the above "alkyl".

"Alkynylsulfonylamino" means a group wherein a hydrogen atom bonded to a nitrogen atom of an amino group is replaced with the above "alkynylsulfonyl". For example, it includes ethynylsulfonylamino, propynylsulfonylamino and the like. Another hydrogen atom bonded to the nitrogen atom of the amino group may be replaced with the above "alkyl".

"Alkyloxycarbonylamino" means a group wherein a hydrogen atom bonded to a nitrogen atom of an amino group is replaced with the above "alkyloxycarbonyl". For example, it includes methyloxycarbonylamino, ethyloxycarbonylamino, propyloxycarbonyl amino, isopropyloxycarbonyl amino, tert-butyloxycarbonylamino, isobutyloxycarbonylamino, sec-butyloxycarbonylamino, pentyloxycarbonylamino, isopentyloxycarbonylamino, hexyloxycarbonylamino and the like. Another hydrogen atom bonded to the nitrogen atom of the amino group may be replaced with the above "alkyl".

A preferred embodiment of "alkyloxycarbonyl" is methyloxycarbonylamino, ethyloxycarbonylamino, propyloxycarbonylamino and the like.

"Alkenyloxycarbonylamino" means a group wherein a hydrogen atom bonded to a nitrogen atom of an amino group is replaced with the above "alkenyloxycarbonyl". For example, it includes ethylenyloxycarbonylamino, propenyloxycarbonylamino and the like. Another hydrogen atom bonded to the nitrogen atom of the amino group may be replaced with the above "alkyl".

"Alkynyloxycarbonylamino" means a group wherein a hydrogen atom bonded to a nitrogen atom of an amino group is replaced with the above "alkynyloxycarbonyl". For example, it includes ethynyloxycarbonylamino, propynyloxycarbonylamino and the like. Another hydrogen atom bonded to the nitrogen atom of the amino group may be replaced with the above "alkyl".

"Haloalkyl" moans a group wherein one or more "halogen" described above is bonded to the above "alkyl". For example, it includes monofluoromethyl, monofluoroethyl, monofluoropropyl, 2,2,3,3,3-pentafluoropropyl, monochloromethyl, trifluoromethyl, trichloromethyl. 2,2,2-trifluoroethyl, 2,2,2-trichloroethyl, 1,2-dibromoethyl, 1,1,1-trifluoropropan-2-yl and the like.

A preferred embodiment, of "haloalkyl" is trifluoromethyl or trichloromethyl.

"Haloalkyloxy" means a group wherein the above "haloalkyl" is bonded to an oxygen atom. For example, it includes monofluoromethoxy, monofluoroethoxy, trifluoromethoxy, trichloromethoxy, trifluoroethoxy, trichloroethoxy and the like.

A preferred embodiment of "haloalkyloxy" is trifluoromethoxy or trichloromethoxy.

"Haloalkylamino" means a group wherein a hydrogen atom bonded to a nitrogen atom of on amino group is replaced with the above "haloalkyl". For example, it includes monofluoromethyl amino, monofluoroethylamino, trifluoromethylamine, trichloromethylamino, trifluoroethylamino, trichloroethylamine and the like. Another hydrogen atom bonded to the nitrogen atom of the amino group may be replaced with the above "alkyl" or the above "haloalkyl".

A preferred embodiment of "haloalkylamino" is trifluoromethylamine or trichloromethylamino.

"Haloalkylsulfanyl" means a group wherein the above "haloalkyl" is bonded to a sulfanyl group. For example, it includes monofluoromethylsulfanyl, monofluoroethylsulfanyl, trifluoromethylsulfanyl, trichloromethyl sulfanyl, trifluoroethylsulfonyl, trichloroethylsulfanyl and the like.

A preferred embodiment of "haloalkylsulfanyl" is trifluoromethylsulfanyl or trichloromethylsulfonyl.

"Haloalkylcarbonyl" means a group wherein the above "haloalkyl" is bonded to a carbonyl group. For example, it includes monofluoromothylcarbonyl, monofluoroethylcarbonyl, trifluoromethylcarbonyl, trichloromethylcarbonyl, trifluoroethylcarbonyl, trichloroethylcarbonyl and the like.

A preferred embodiment of "haloalkylcarbonyl" is trifluoromethylcarbonyl or trichloromethylcarbonyl.

"Haloalkylsulfonyl" means a group wherein the above "haloalkyl" is bonded to a sulfonyl group. For example, it includes monofluoromethylsulfonyl, monofluoroethylsulfonyl, trifluoromethylsulfonyl, trichloromethylsulfonyl, trifluoroethylsulfonyl, trichloroethylsulfonyl and the like.

A preferred embodiment of "haloalkylsulfonyl" is trifluoromethylsulfonyl or trichloromethylsulfonyl.

"Haloalkylcarbamoyl" means a group wherein a hydrogen atom bonded to a nitrogen atom of a carbamoyl group is replaced with the above "haloalkyl". For example, it includes monofluoromethylcarbamoyl, monofluoroethylcarbamoyl, trifluoromethylcarbamoyl, trichloromethylcarbamoyl, trifluoroethylcarbamoyl, trichloroethylcorbamoyl and the like. Another hydrogen atom bonded to the nitrogen atom of the carbamoyl group may be replaced with the above "alkyl" or the above "haloalkyl".

A preferred embodiment, of "haloalkylcarbamoyl" is trifluoromethylcarbamoyl or trichloromethylcarbamoyl.

"Haloalkylsulfamoyl" means a group wherein a hydrogen atom bonded to a nitrogen atom of a sulfamoyl group is replaced with the above "haloalkyl". For example, it includes monofluoromethylsulfamoyl, monofluoroethylsulfamoyl, trifluoromethylsulfainoyl, trichloromethylsulfamoyl, trifluo methylsulfamoyl, trichloroethylsulfamoyl and the like. Another hydrogen atom bonded to the nitrogen atom of the sulfamoyl group may be replaced with the above "alkyl" or the above "haloalkyl".

A preferred embodiment of "haloalkylsulfamoyl" is trifluoromethylsulfamoyl or trichloromethylsulfamoyl.

"Haloalkylcarbonylamino" means a group wherein a hydrogen atom bonded to a nitrogen atom of an amino group is replaced with the above "haloalkylcarbonyl". For example, it includes monofluoromethylcarbonylamino, monofluoroethylcarbonylamino, trifluoromethylcarbonylamino, trichloromethylcarbonylamino, trifluoroethylcarbonylamino, trichloroethylcarbonylamino and the like. Another hydrogen atom bonded to the nitrogen atom of the amino group may be replaced with the above "alkyl" or the above "haloalkyl".

A preferred embodiment of "haloalkylcarbonylamino" is trifluoromethylcarbonylamino or trichloromethylcarbonylamino.

"Haloalkylsulfonylamino" means a group wherein a hydrogen atom bonded to a nitrogen atom of an amino group is replaced with the above "haloalkylsulfonyl". For example, it includes monofluoromethylsulfonylamino, monofluoroethyl sulfonyl amino, trifluoromethylsulfonylamino, trichloromethylsulfonylamino, trifluoroethylsulfonylamino, trichloroethylsulfonylamino and the like. Another hydrogen atom bonded to the nitrogen atom of the amino group may be replaced with the above "alkyl" or the above "haloalkyl".

A preferred embodiment of "haloalkylsulfonylamino" is trifluoromethylsulfonylamino or trichloromethylsulfonylamino.

The "aromatic carbocycle" part of "aromatic carbocyclyloxy", "aromatic carbocyclylamino", "aromatic carbocyclylsulfanyl", "aromatic carbocyclylcarbonyl", "aromatic carbocyclylsulfonyl", "aromatic carbocyclylcarbonyloxy", "aromatic carbocyclylsulfonyloxy", "aromatic carbocyclyloxycarbonyl", "aromatic carbocyclyloxysulfonyl", "aromatic carbocyclylcarbamoyl", "aromatic carbocyclylsulfamoyl", "aromatic carbocyclylcarbonylamino", "aromatic carbocyclylsulfonylamino", and "aromatic carbocyclyloxycarbonylamino" is the same as the above "aromatic carbocyclyl".

"Aromatic carbocyclyloxy" means a group wherein "aromatic carbocycle" is bonded to an oxygen atom. For example, it includes phenyloxy, naphthyloxy and the like.

"Aromatic carbocyclylamino" means a group wherein a hydrogen atom attached to a nitrogen atom of an amino group is replaced with the "aromatic carbocycle". For example, it includes phenylamino, naphthylamino and the like. Another hydrogen atom bonded to the nitrogen atom of the amino group may be replaced with the above "alkyl".

"Aromatic carbocyclylsulfanyl" means a group wherein a hydrogen atom bonded to a sulfur atom of a sulfanyl group is replaced with "aromatic carbocycle". For example, it includes phenylsulfanyl, naphthylsulfanyl and the like.

"Aromatic carbocyclylcarbonyl" means a group wherein "aromatic carbocycle" is bonded to a carbonyl group. For example, it includes phenylcarbonyl, naphthylcarbonyl and the like.

"Aromatic carbocyclylsulfonyl" means a group wherein "aromatic carbocycle" is bonded to a sulfonyl group. For example, it, includes phenylsulfonyl, naphthylsulfonyl and the like.

"Aromatic carbocyclylcarbonyloxy" means a group wherein the above "aromatic carbocyclylcarbonyl" is bonded to an oxygen atom. For example, it includes phenylcarbonyloxy, naphthylcarbonyloxy and the like.

"Aromatic carbocyclylsulfonyloxy" means a group wherein the above "aromatic carbocyclylsulfonyl" is bonded to an oxygen atom. For example, it includes phenylsulfonyloxy, naphthylsulfonyloxy and the like.

"Aromatic carbocyclyloxycarbonyl" means a group wherein the above "aromatic carbocyclyloxy" is bonded to a carbonyl group. For example, it includes phenyloxycarbonyl, naphthyloxycarbonyl and the like.

"Aromatic carbocycyloxysulfonyl" means a group wherein the above "aromatic carbocyclyloxy" is bonded to a sulfonyl group. For example, it includes phenyloxysulfonyl, naphthyloxysulfonyl and the like.

"Aromatic carbocyclylcarbamoyl" means a group wherein a hydrogen atom bonded to a nitrogen atom of a carbamoyl group is replaced with the "aromatic carbocycle". For example, it includes phenylcarbamoyl, naphthylcarbamoyl and the like. Another hydrogen atom bonded to the nitrogen atom of the carbamoyl group may be replaced with the above "alkyl".

"Aromatic carbocyclylsulfamoyl" means a group wherein a hydrogen atom bonded to a nitrogen atom of a sulfamoyl group is replaced with the "aromatic carbocycle". For example, it includes phenylsulfamoyl, naphthylsulfoniyl and the like. Another hydrogen atom bonded to the nitrogen atom of the sulfamoyl group may be replaced with the above "alkyl".

"Aromatic carbocyclylcarbonylamino" means a group wherein a hydrogen atom attached to a nitrogen atom of an amino group is replaced with the above "aromatic carbocyclylcarbonyl". For example, it includes phenylcarbonylamino, naphthylcarbonylamino and the like. Another hydrogen atom bonded to the nitrogen atom of the amino group may be replaced with the above "alkyl".

"Aromatic carbocyclylsulfonylamino" means a group wherein a hydrogen atom bonded to a nitrogen atom of an amino group is replaced with the above "aromatic carbocyclylsulfonyl". For example, it includes phenylsulfonylamino, naphthylsulfonylamino and the like. Another hydrogen atom bonded to the nitrogen atom of the amino group may be replaced with the above "alkyl".

"Aromatic carbocyclyloxycarbonylamino" means a group wherein a hydrogen atom bonded to a nitrogen atom of an amino group is replaced with the above "aromatic carbocyclyloxycarbonyl". For example, it includes phenyloxycarbonylamino, naphthyloxycarbonylamino and the like. Another hydrogen atom bonded to the nitrogen atom of the amino group may be replaced with the above "alkyl".

The "non-aromatic carbocycle" part of "non-aromatic carbocyclyloxy", "non-aromatic carbocyclylamino", "non-aromatic carbocyclylsulfanyl", "non-aromatic carbocyclylcarbonyl", "non-aromatic carbocyclylsulfonyl", "non-aromatic carbocyclylcarbonyloxy", "non-aromatic carbocyclylsulfonyloxy", "non-aromatic carbocyclyloxycarbonyl", "non-aromatic carbocyclyloxysulfonyl", "non-aromatic carbocyclylcarbamoyl", "non-aromatic carbocyclylsulfamoyl", "non-aromatic carbocyclylcarbonylamino", "non-aromatic carbocyclylsulfonylamino", and "non-aromatic carbocyclyloxycarbonylamino" is the same as the above "non-aromatic carbocyclyl".

"Non-aromatic carbocyclyloxy" means a group wherein "non-aromatic carbocycle" is bonded to an oxygen atom. For example, it includes cyclopropyloxy, cyclohexyloxy, cyclohexenyloxy and the like.

"Non-aromatic carbocyclylamino" means a group wherein a hydrogen atom attached to a nitrogen atom of an amino group is replaced with the "non-aromatic carbocycle". For example, it includes cyclopropylamino, cyclohexylamino, cyclohexenylamino and the like. Another hydrogen atom bonded to the nitrogen atom of the amino group may be replaced with the above "alkyl".

"Non-aromatic carbocyclylsulfanyl" means a group wherein a hydrogen atom bonded to a sulfur atom of a sulfanyl group is replaced with "non-aromatic carbocycle". For example, it includes cyclopropylsulfanyl, cyclohexylsulfanyl, cyclohexenylsulfanyl and the like.

"Non-aromatic carbocyclylcarbonyl" means a group wherein "non-aromatic carbocycle" is bonded to a carbonyl group. For example, it includes cyclopropylcarbonyl, cyclohexylcarbonyl, cyclohexenylcarbonyl and the like.

"Non-aromatic carbocyclylsulfonyl" means a group wherein "non-aromatic carbocycle" is bonded to a sulfonyl group. For example, it includes cyclopropylsulfonyl, cyclohexylsulfonyl, cyclohexenylsulfonyl and the like.

"Non-aromatic carbocyclylcarbonyloxy" means a group wherein the above "non-aromatic carbocyclylcarbonyl" is bonded to an oxygen atom. For example, it includes cyclopropylcarbonyloxy, cyclohexylcarbonyloxy, cyclohexenylcarbonyloxy and the like.

"Non-aromatic carbocyctylsulfonyloxy" means a group wherein the above "non-aromatic carbocyclylsulfonyl" is bonded to an oxygen atom. For example, it includes cyclopropylsulfonyloxy, cyclohexylsulfonyloxy, cyclohexenylsulfonyloxy and the like.

"Non-aromatic carbocyclyloxycarbonyl" means a group wherein the above "non-aromatic carbocyclyloxy" is bonded to a carbonyl group. For example, it includes cyclopropyloxycarbonyl, cyclohexyloxycarbonyl, cyclohexenyloxycarbonyl and the like.

"Non-aromatic carbocyclyloxyaulfonyl" means a group wherein the above "non-aromatic carbocyclyloxy" is bonded to a sulfonyl group. For example, it includes cyclopropyloxysulfonyl, cyclohexyloxysulfonyl, cyclohexenyloxysulfonyl and the like.

"Non-aromatic carbocyclylcarbamoyl" means a group wherein a hydrogen atom bonded to a nitrogen atom of a carbamoyl group is replaced with the "non-aromatic carbocycle". For example, it includes cyclopropylcarbamoyl, cyclohexylcarbamoyl, cyclohexenylcarbamoyl and the like. Another hydrogen atom bonded to the nitrogen atom of the carbamoyl group may be replaced with the above "alkyl".

"Non-aromatic carbocyclylsulfamoyl" means a group wherein a hydrogen atom bonded to a nitrogen atom of a sulfamoyl group is replaced with the "non-aromatic carbocycle". For example, it includes cyclopropylsulfamoyl, cyclohexylsulfamoyl, cyclohexenylsulfamoyl and the like. Another hydrogen atom bonded to the nitrogen atom of the sulfamoyl group may be replaced with the above "alkyl".

"Non-aromatic carbocyclylcarbonylamino" means a group wherein a hydrogen atom attached to a nitrogen atom of an amino group is replaced with the above "non-aromatic carbocyclylcarbonyl". For example, it includes cyclopropylcarbonyl amino, cyclohexylcarbonylamino, cyclohexenylcarbonylamino and the like. Another hydrogen atom bonded to the nitrogen atom of the amino group may be replaced with the above "alkyl".

"Non-aromatic carbocyclylsulfonylamino" means a group wherein a hydrogen atom bonded to a nitrogen atom of an amino group is replaced with the above "non-aromatic carbocyclylsulfonyl". For example, it includes cyclopropylsulfonylamino, cyclo hexylsulfonyl amino, cyclohexenylsulfonylamino and the like. Another hydrogen atom bonded to the nitrogen atom of the amino group may be replaced with the above "alkyl".

"Non-aromatic carbocyclyloxycarbonylamino" means a group wherein a hydrogen atom attached to a nitrogen atom of an amino group is replaced with the above "non-aromatic carbocyclyloxycarbonyl". For example, it includes cyclopropyloxycarbonylamino, cyclohexyloxycarbonylamino, cyclohexanyloxycarbonyl amino and the like. Another hydrogen atom bonded to the nitrogen atom of the amino group may be replaced with the above "alkyl".

The "aromatic heterocycle" part of "aromatic heterocyclyloxy", "aromatic heterocyclylamino", "aromatic heterocyclylsulfanyl", "aromatic heterocyclylcarbonyl", "aromatic heterocyclylsulfonyl", "aromatic heterocyclylcarbonyloxy", "aromatic heterocyclylsulfonyloxy", "aromatic heterocyclyloxycarbonyl", "aromatic heterocyclyloxysulfonyl", "aromatic heterocyclylcarbamoyl", "aromatic heterocyclylsulfamoyl", "aromatic heterocyclylcarbonylamino", "aromatic heterocyclylsulfonylamino", and "aromatic hoterocycyloxycarbonylamino" is the same as the above "aromatic heterocyclyl".

"Aromatic heterocyclyloxy" means a group wherein "aromatic heterocycle" is bonded to an oxygen atom. For example, it includes pyridyloxy, oxazolyloxy and the like.

"Aromatic heterocyclylamino" means a group wherein a hydrogen atom attached to a nitrogen atom of an amino group is replaced with the "aromatic heterocycle". For example, it includes pyridylamino, oxazolylamino and the like. Another hydrogen atom bonded to the nitrogen atom of the amino group may be replaced with the above "alkyl".

"Aromatic heterocyclylsulfanyl" means a group wherein a hydrogen atom bonded to a sulfur atom of a sulfanyl group is replaced with "aromatic heterocycle". For example, it includes pyridylsulfanyl, oxazol ylsulfanyl and the like.

"Aromatic heterocyclylcarbonyl" means a group wherein "aromatic heterocycle" is bonded to a carbonyl group. For example, it includes pyridylcarbonyl, oxazolylcarbonyl and the like.

"Aromatic heterocyclylsulfonyl" means a group wherein "aromatic heterocycle" is bonded to a sulfonyl group. For example, it includes pyridylsulfonyl, oxazolylsulfonyl and the like.

"Aromatic heterocyclylcarbonyloxy" means a group wherein the above "aromatic heterocyclylcarbonyl" is bonded to an oxygen atom. For example, it includes pyridylcarbonyloxy, oxazolylcarbonyloxy and the like.

"Aromatic hoterocyclylsulfonyloxy" means a group wherein the above "aromatic heterocyclylsulfonyl" is bonded to an oxygen atom. For example, it includes pyridylsulfonyloxy, oxazolyloxysulfonyloxy and the like.

"Aromatic heterocyclyloxycarbonyl" means a group wherein the above "aromatic heterocyclyloxy" is bonded to a carbonyl group. For example, it includes pyridyloxycarbonyl, oxazolyloxycarbonyl and the like.

"Aromatic heterocyclyloxysulfonyl" means a group wherein the above "aromatic heterocyclyloxy" is bonded to a sulfonyl group. For example, it includes pyridyloxysulfonyl, oxazolyloxysulfonyl and the like.

"Aromatic heterocyclylcarbamoyl" means a group wherein a hydrogen atom bonded to a nitrogen atom of a carbamoyl group is replaced with the "aromatic heterocycle". For example, it includes pyridylcarbamoyl, oxazol ylcarbamoyl and the like. Another hydrogen atom bonded to the nitrogen atom of the carbamoyl group may be replaced with the above "alkyl".

"Aromatic heterocycylsulfamoyl" means a group wherein a hydrogen atom bonded to a nitrogen atom of a sulfamoyl group is replaced with the "aromatic heterocycle". For example, it includes pyridylsulfamoyl, oxazolylsulfamoyl and the like. Another hydrogen atom bonded to the nitrogen atom of the sulfamoyl group may be replaced with the above "alkyl".

"Aromatic heterocyclylcarbonyl amino" means a group wherein a hydrogen atom attached to a nitrogen atom of an amino group is replaced with the above "aromatic heterocyclylcarbonyl". For example, it includes pyridylcarbonylamino, oxazolylcarbonylamino and the like. Another hydrogen atom bonded to the nitrogen atom of the amino group may be replaced with the above "alkyl".

"Aromatic heterocyclylsulfonylamino" means a group wherein a hydrogen atom bonded to a nitrogen atom of an amino group is replaced with the above "aromatic heterocyclylsulfonyl". For example, it includes pyridylsulfonylamino, oxazolylsulfonylamino and the like. Another hydrogen atom bonded to the nitrogen atom of the amino group may be replaced with the above "alkyl".

"Aromatic heterocyclyloxycarbonylamino" means a group wherein a hydrogen atom attached to a nitrogen atom of an amino group is replaced with the above "aromatic heterocyclyloxycarbonyl". For example, it includes pyridyloxycarbonylamino, oxazolyloxycarbonylamino and the like. Another hydrogen atom bonded to the nitrogen atom of the amino group may be replaced with the above "alkyl".

The "non-aromatic heterocycle" part of "non-aromatic heterocyclyloxy", "non-aromatic heterocyclylamino", "non-aromatic heterocyclyl sulfanyl", "non-aromatic heterocyclylcarbonyl", "non-aromatic heterocyclylsulfonyl", "non-aromatic heterocyclylcarbonyloxy", "non-aromatic heterocyclylsulfonyloxy", "non-aromatic heterocyclyloxycarbonyl", "non-aromatic heterocyclyloxysulfonyl", "non-aromatic heterocyclylcarbamoyl", "non-aromatic heterocyclylsulfamoyl", "non-aromatic heterocyclylcarbonylamino", "non-aromatic heterocyclylsulfonylamino", and "non-aromatic heterocyclyloxycarbonylamino" is the same as the above "non-aromatic heterocyclyl".

"Non-aromatic heterocyclyloxy" means a group wherein "non-aromatic heterocycle" is bonded to an oxygen atom. For example, it includes piperidinyloxy, tetrahydrofuryloxy and the like.

"Non-aromatic heterocyclylamino" means a group wherein a hydrogen atom attached to a nitrogen atom of an amino group is replaced with the "non-aromatic heterocycle". For example, it includes piperidinylamino, tetrahydrofurylamino and the like. Another hydrogen atom bonded to the nitrogen atom of the amino group may be replaced with the above "alkyl".

"Non-aromatic heterocyclylsulfanyl" means a group wherein a hydrogen atom bonded to a sulfur atom of a sulfanyl group is replaced with "non-aromatic heterocycle". For example, it includes piperidinylsulfonyl, tetrahydrofurylsulfanyl and the like.

"Non-aromatic heterocyclylcarbonyl" means a group wherein "non-aromatic heterocycle" is bonded to a carbonyl group. For example, it includes piperidinylcarbonyl, tetrahydrofurylcarbonyl and the like.

"Non-aromatic heterocyclylsulfonyl" means a group wherein "non-aromatic heterocycle" is bonded to a sulfonyl group. For example, it includes piperidinylsulfonyl, tetrahydrofurylsulfonyl and the like.

"Non-aromatic heterocyclylcarbonyloxy" moans a group wherein the above "non-aromatic heterocyclylcarbonyl" is bonded to an oxygen atom. For example, it includes piperidinylcarbonyloxy, tetrahydrofurylcarbonyloxy and the like.

"Non-aromatic heterocyclylsulfonyloxy" moans a group wherein the above "non-aromatic heterocyclylsulfonyl" is bonded to an oxygen atom. For example, it includes piperidinylsulfonyloxy, tetrahydrofuryl sulfonyloxy and the like.

"Non-aromatic heterocyclyloxycarbonyl" means a group wherein the above "non-aromatic heterocyclyloxy" is bonded to a carbonyl group. For example, it includes piperidinyloxycarbonyl, tetrahydrofuryloxycarbonyl and the like.

"Non-aromatic heterocyclyloxysulfonyl" means a group wherein the above "non-aromatic heterocyclyloxy" is bonded to a sulfonyl group. For example, it includes piperidinyloxysulfonyl, tetrahydrofuryloxysulfonyl and the like.

"Non-aromatic heterocyclylcarbamoyl" means a group wherein a hydrogen atom bonded to a nitrogen atom of a carbamoyl group is replaced with the "non-aromatic heterocycle". For example, it includes piperidinylcarbamoyl, tetrahydrofurylcarbamoyl and the like. Another hydrogen atom bonded to the nitrogen atom of the carbamoyl group may be replaced with the above "alkyl".

"Non-aromatic heterocyclylsulfamoyl" means a group wherein a hydrogen atom bonded to a nitrogen atom of a sulfamoyl group is replaced with the "non-aromatic heterocycle". For example, it includes piperidinylsulfamoyl, tetrahydrofurylsulfamoyl and the like. Another hydrogen atom bonded to the nitrogen atom of the sulfamoyl group may be replaced with the above "alkyl".

"Non-aromatic heterocyclylcarbonylamino" means a group wherein a hydrogen atom attached to a nitrogen atom of an amino group is replaced with the above "non-aromatic heterocyclylcarbonyl". For example, it includes piperidinylcarbonylamino, tetrahydrofurylcarbonylamiuo and the like. Another hydrogen atom bonded to the nitrogen atom of the amino group may be replaced with the above "alkyl".

"Non-aromatic heterocyclylsulfonylamino" means a group wherein a hydrogen atom bonded to a nitrogen atom of an amino group is replaced with the above "non-aromatic heterocyclylsulfonyl". For example, it includes piperidinylsulfonylamino, tetrahydrofurylsulfonylamino and the like. Another hydrogen atom bonded to the nitrogen atom of the amino group may be replaced with the above "alkyl".

"Non-aromatic heterocyclyloxycarbonyl amino" means a group wherein a hydrogen atom attached to a nitrogen atom of an amino group is replaced with the above "non-aromatic heterocyclyloxycarbonyl". For example, it includes piperidinyloxycarbonylamino, tetrahydrofuryloxycarbonylamino and the like. Another hydrogen atom bonded to the nitrogen atom of the amino group may be replaced with the above "alkyl".

"Haloalkyl" means a group wherein one or more "halogen" described above is bonded to the above "alkyl". For example, it includes monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl and the like.

A preferred embodiment of "haloalkyl" is trifluoromethyl or trichloromethyl.

"Haloalkyloxy" means a group wherein the above "haloalkyl" is bonded to an oxygen atom. For example, it includes monofluoromethoxy, Monofluoroethoxy, trifluoromethoxy, trichloromethoxy, trifluoroethoxy, trichloroethoxy and the like.

A preferred embodiment of "halonlkyloxy" is trifluoromethoxy or trichloromethoxy.

"Haloalkylamino" moans a group wherein a hydrogen atom bonded to a nitrogen atom of an amino group is replaced with the above "haloalkyl", For example, it includes monofluoromethylamino, monofluoroethylamino, trifluoromethylamine, trichloromethylamino, trifluoroethylamino, trichloroethylamine and the like. Another hydrogen atom bonded to the nitrogen atom of the amino group may be replaced with the above "alkyl" or the above "haloalkyl".

A preferred embodiment of "haloalkylamino" is trifluoromethyl amino or trichloromethylamino.

"Haloalkylsulfonyl" means a group wherein the above "haloalkyl" is bonded to a sulfanyl group. For example, it includes monofluoromethyl sulfanyl, monofluoroethylsulfanyl, trifluoromethylsulfanyl, trichloromethylsulfonyl, trifluoroethylsulfonyl, trichloroethylsulfanyl and the like.

A preferred embodiment of "haloalkylsulfanyl" is trifluoromethylsulfanyl or trichloromethylsulfanyl.

"Haloalkylcarbonyl" means a group wherein the above "haloalkyl" is bonded to a carbonyl group. For example, it includes monofluoromethylcarbonyl, monofluoroethylcarbonyl, trifluoromethylcarbonyl, trichloromethylcarbonyl, trifluoroethylcarbonyl, trichloroethylcarbonyl and the like.

A preferred embodiment of "haloalkylcarbonyl" is trifluoromethylcarbonyl or trichloromethylcarbonyl.

"Haloalkylsulfonyl" means a group wherein the above "haloalkyl" is bonded to a sulfonyl group. For example, it includes monofluoromethylsulfonyl, monofluoroethylsulfonyl, trifluoromethylsulfonyl, trichloromethylsulfonyl, trifluoroethylsulfonyl, trichloroethyl sulfonyl and the like.

A preferred embodiment of "haloalkylsulfonyl" is trifluoromethylsulfonyl or trichloromethylsulfonyl.

"Haloalkylcorbamoyl" means a group wherein a hydrogen atom bonded to a nitrogen atom of a carbamoyl group is replaced with the above "haloalkyl". For example, it includes monofluoromethylcarbamoyl, monofluoroethylcarbamoyl, trifluoromethylcarbamoyl, trichloromethylcarbamoyl, trifluoroethylcarbamoyl, trichloroethylcarbamoyl and the like. Another hydrogen atom bonded to the nitrogen atom of the carbamoyl group may be replaced with the above "alkyl" or the above "haloalkyl".

A preferred embodiment of "haloalkylcarbamoyl" is trifluoromethylcarbamoyl or trichloromethylcarbamoyl.

"Haloalkylsulfamoyl" means a group wherein a hydrogen atom bonded to a nitrogen atom of a sulfamoyl group is replaced with the above "haloalkyl". For example, it includes monofluoromethylsulfamoyl, monofluoroethylsulfamoyl, trifluoromethylsulfamoyl, trichloromethylsulfamoyl, trifluoroethylsulfamoyl, trichloroethylsulfamoyl and the like. Another hydrogen atom bonded to the nitrogen atom of the sulfamoyl group may be replaced with the above "alkyl" or the above "haloalkyl".

A preferred embodiment of "haloalkylsulfamoyl" is trifluoromethylsulfamoyl or trichloromethylsulfamoyl.

"Haloalkylcarbonylamino" means a group wherein a hydrogen atom bonded to a nitrogen atom of an amino group is replaced with the above "haloalkylcarbonyl". For example, it includes monofluoromethylcarbonylamino, monofluoroethylcarbonylamino, trifluoromethylcarbonylamino, trichloromethylcarbonylamino, trifluoroethylcarbonylamino, trichloroethylcarbonylamino and the like. Another hydrogen atom bonded to the nitrogen atom of the amino group may be replaced with the above "alkyl" or the above "haloalkyl".

A preferred embodiment of "haloalkylcarbonylamino" is trifluoromethylcarbonylamino or trichloromethylcarbonylamino.

"Haloalkylsulfonylamino" means a group wherein a hydrogen atom bonded to a nitrogen atom of an amino group is replaced with the above "haloalkylsulfonyl". For example, it includes monofluoromethylsulfonylamino, monofluoroethylsulfonylamino, trifluoromethylsulfonylamino, trichloromethylsulfonylamino, trifluoroethylsulfonylamino, trichloroethylsulfonylamino and the like. Another hydrogen atom bonded to the nitrogen atom of the amino group may be replaced with the above "alkyl" or the above "haloalkyl".

A preferred embodiment of "haloalkylsulfonylamino" is trifluoromethylsulfonylamino or trichloromethylsulfonylamino.

"Haloalkylcarbonyloxy" means a group wherein the above "haloalkylcarbonyl" is bonded to an oxygen atom. For example, it includes monofluoromethylcarbonyloxy, monofluoroethylcarbonyloxy, trifluoromethylcarbonyloxy, (trichloromethylcarbonyloxy, trifluoroethylcarbonyloxy, trichloroethylcarbonyloxy and the like.

A preferred embodiment of "haloalkylcarbonyloxy" is trifluoromethylcarbonyloxy or trichloromethylcarbonyloxy.

"Haloalkylsulfonyloxy" means a group wherein the above "haloalkylsulfonyl" is bonded to an oxygen atom. For example, it includes monofluoromethylsulfonyloxy, monofluoroetliylsulfonyloxy, trifluoromethylsulfonyloxy, trichloromethyl sulfonyloxy, trifluoroethylsulfonyloxy, trichloroethylsulfonyloxy and the like.

A preferred embodiment of "haloalkylsulfonyloxy" is trifluoromethylsulfonyloxy or trichloromethylsulfonyloxy.

"Haloalkyloxycarbonyl" means a group wherein the above "haloaryloxy" is bonded to a carbonyl group. For example, it includes monofluoromethyl oxycarbonyl, monofluoroethyloxycarbonyl, trifluoromethyloxycarbonyl, trichloromethyloxycarbonyl, trifluoroethyloxycarbonyl, trichloroethyloxycarbonyl and the like.

A preferred embodiment of "haloalkyloxycarbonyl" is trifluoromethyloxycarbonyl or trichloromethyloxycarbonyl.

"Haloalkyloxysulfonyl" means a group wherein the above "haloaryloxy" is bonded to a sulfonyl group. For example, it includes monofluoromethyloxysulfonyl, monofluoroethyloxysulfonyl, trifluoromethyl oxysulfonyl, trichloromethyloxy sulfonyl, trifluoroethyloxysulfonyl, trichloroethyloxysulfonyl and the like.

A preferred embodiment of "haloalkyloxysulfonyl" is trifluoromethyl oxysulfonyl or trichloromethyloxysulfonyl.

The substituents of "substituted or unsubstituted alkyl" include the substituent group A. A carbon atom at any position(s) may be bonded to one or more group(s) selected from the substituent group A.

The substituent group A: halogen, hydroxy, carboxy, amino, carbamoyl, sulfamoyl, sulfo, cyano, alkyloxy optionally substituted with one or more group(s) selected from the substituent group C, alkylamino optionally substituted with one or more group(s) selected from the substituent group C, alkylsulfanyl optionally substituted with one or more group (s) selected from the substituent group C, alkylcarbonyl optionally substituted with one or more group(s) selected from the substituent, group C, alkylsulfonyl optionally substituted with one or more group(s) selected from the substituent group C, alkylcarbonylamino optionally substituted with one or more group(s) selected from the substituent, group C, alkylsulfonylamino optionally substituted with one or more group(s) selected from the substituent group C, alkylcarbamoyl optionally substituted with one or more group(s) selected from the substituent group C, alkylsulfamoyl optionally substituted with one or more group(s) selected from the substituent group C, alkylcarbonyloxy optionally substituted with one or more group(s) selected from the substituent group C, alkyloxycarbonyl optionally substituted with one or more group(s) selected from the substituent group C, alkylsulfonyloxy optionally substituted with one or more group(s) selected from the substituent group C, aryloxysulfonyl optionally substituted with one or more group(s) selected from the substituent group C, aromatic carbocyclyl optionally substituted with one or more group(s) selected from the substituent group E, non-aromatic carbocyclyl optionally substituted with one or more group(s) selected from the substituent group E, aromatic heterocyclyl optionally substituted with one or more group(s) selected from the substituent group E, non-aromatic heterocyclyl optionally substituted with one or more group(s) selected from the substituent group E, aromatic carbocyclyloxy optionally substituted with one or more group(s) selected from the substituent group E, non-aromatic carbocyclyloxy optionally substituted with one or more group(s) selected from the substituent group E, aromatic heterocyclyloxy optionally substituted with one or more group(s) selected from the substituent group E, non-aromatic heterocyclyloxy optionally substituted with one or more group(s) selected from the substituent group E, aromatic carbocyclylsulfanyl optionally substituted with one or more group(s) selected from the substituent, group E, non-aromatic carbocyclylsulfanyl optionally substituted with one or more group (s) selected from the substituent group E, aromatic heterocyclylsulfanyl optionally substituted with one or more group (s) selected from the substituent group E, non-aromatic heterocyclylsulfanyl optionally substituted with one or more group(s) selected from the substituent group E, aromatic carbocyclylamino optionally substituted with one or more group(s) selected from the substituent group E, non-aromatic carbocyclylamino optionally substituted with one or more group(s) selected from the substituent group E, aromatic heterocyclylamino optionally substituted with one or more group(s) selected from the substituent group E, non-aromatic heterocyclylamino optionally substituted with one or more group(s) selected from the substituent group E, aromatic carbocyclylcarbonyl optionally substituted with one or more group(s) selected from the substituent group E, non-aromatic carbocyclylcarbonyl optionally substituted with one or more group(s) selected from the substituent group E, aromatic heterocyclylcarbonyl optionally substituted with one or more group(s) selected from the substituent group E, non-aromatic heterocyclylcarbonyl optionally substituted with one or more group(s) selected from the substituent group E, aromatic carbocyclylsulfonyl optionally substituted with one or more group(s) selected from the substituent group E, non-aromatic carbocyclylsulfonyl optionally substituted with one or more group(s) selected from the substituent group E, aromatic heterocyclylsulfonyl optionally substituted with one or more group(s) selected from the substituent group E, non-aromatic heterocyclylsulfonyl optionally substituted with one or more group (s) selected from the substituent group E, aromatic carbocyclylcarbonylamino optionally substituted with one or more group(s) selected from the substituent group E, non-aromatic carbocyclylcarbonylamino optionally substituted with one or more group(s) selected from the substituent group E, aromatic heterocyclylcarbonylamino optionally substituted with one or more group(s) selected from the substituent group E, non-aromatic heterocyclylcarbonylamino optionally substituted with one or more group(s) selected from the substituent group E, aromatic carbocyclylsulfonylamino optionally substituted with one or more group(s) selected from the substituent group E, non-aromatic carbocyclylsulfonylamino optionally substituted with one or more groups) selected from the substituent group E, aromatic heterocyclylsulfonylamino optionally substituted with one or more group(s) selected from the substituent group E, non-aromatic heterocyclylsulfonylamino optionally substituted with one or more group(s) selected from the substituent group E, aromatic carbocyclylcarbamoyl optionally substituted with one or more group(s) selected from the substituent group E, non-aromatic carbocyclylcarbamoyl optionally substituted with one or more group(s) selected from the substituent group E, aromatic heterocyclylcarbamoyl optionally substituted with one or more group(s) selected from the substituent group E, non-aromatic heterocyclylcarbamoyl optionally substituted with one or more group(s) selected from the substituent group E, aromatic carbocyclylsulfamoyl optionally substituted with one or more group (s) selected from the substituent group E, non-aromatic carbocyclylsulfamoyl optionally substituted with one or more group(s) selected from the substituent group E, aromatic heterocyclylsulfamoyl optionally substituted with one or more group(s) selected from the substituent group E, non-aromatic heterocyclylsulfamoyl optionally substituted with one or more group(s) selected from the substituent group E, aromatic carbocycyloxycarbonyl optionally substituted with one or more group(s) selected from the substituent group E, non-aromatic carbocycyloxycarbonyl optionally substituted with one or more group(s) selected from the substituent, group E, aromatic heterocyclyloxycarbonyl optionally substituted with one or more group(s) selected from the substituent group E, non-aromatic heterocyclyloxycarbonyl optionally substituted with one or more group(s) selected from the substituent group E, aromatic carbocycyloxysulfonyl optionally substituted with one or more group (s) selected from the substituent group E, non-aromatic carbocycyloxysulfonyl optionally substituted with one or more group(s) selected from the substituent group E, aromatic heterocyclyloxysulfonyl optionally substituted with one or more group(s) selected from the substituent group E, non-aromatic heterocyclyloxysulfonyl optionally substituted with one or more group(s) selected from the substituent group E, aromatic carbocyclylcarbonyloxy optionally substituted with one or more group(s) selected from the substituent group E, non-aromatic carbocyclylcarbonyloxy optionally substituted with one or more group(s) selected from the substituent group E, aromatic heterocyclylcarbonyloxy optionally substituted with one or more group(s) selected from the substituent group E, non-aromatic heterocyclylcarbonyloxy optionally substituted with one or more group(s) selected from the substituent group E, aromatic carbocyclylsulfonyloxy optionally substituted with one or more group(s) selected from the substituent group E, non-aromatic carbocyclylsulfonyloxy optionally substituted with one or more group(s) selected from the substituent group E, aromatic heterocyclylsulfonyloxy optionally substituted with one or more group(s) selected from the substituent, group E, and non-aromatic heterocyclylsulfonyloxy optionally substituted with one or more group(s) selected from the substituent group E.

The substituents of "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfonyl", "substituted or unsubstituted alkynylsulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted aryloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted nonylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonylamino" include the substituent group B. A carbon atom at arty position(s) may be bonded to one or more group(s) selected from the substituent group B.

The substituent group B: halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group B, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group (a) selected from the substituent group D, alkylcarbonyloxy optionally substituted with one or more group(s) selected from the substituent group D, alkyloxycarbonyl optionally substituted with one or more group(s) selected from the substituent group D, alkylsulfonyloxy optionally substituted with one or more group(s) selected from the substituent group D, aryloxysulfonyl optionally substituted with one or more group(s) selected from the substituent group D, aromatic carbocyclyl optionally substituted with one or more group(s) selected from the substituent group E, non-aromatic carbocyclyl optionally substituted with one or more group(s) selected from the substituent group E, aromatic heterocyclyl optionally substituted with one or more group (s) selected from the substituent group E, non-aromatic heterocyclyl optionally substituted with one or more group (s) selected from the substituent, group E, aromatic carbocyclyloxy optionally substituted with one or more group(s) selected from the substituent group E, non-aromatic carbocyclyloxy optionally substituted with one or more group(s) selected from the substituent, group E, aromatic heterocyclyloxy optionally substituted with one or more group(s) selected from the substituent group E, non-aromatic heterocyclyloxy optionally substituted with one or more group(s) selected from the substituent group E, aromatic carbocyclylsulfanyl optionally substituted with one or more group(s) selected from the substituent group E, non-aromatic carbocyclylsulfanyl optionally substituted with one or more group (s) selected from the substituent group E, aromatic heterocyclylsulfanyl optionally substituted with one or more group (s) selected from the substituent group E, non-aromatic heterocyclylsulfanyl optionally substituted with one or more group(s) selected from the substituent group E, aromatic carbocyclylamino optionally substituted with one or more group(s) selected from the substituent group E, non-aromatic carbocyclylamino optionally substituted with one or more group(s) selected from the substituent group E, aromatic heterocyclylamino optionally substituted with one or more group(s) selected from the substituent group E, non-aromatic heterocyclylamino optionally substituted with one or more group(s) selected from the substituent group E, aromatic carbocyclylcarbonyl optionally substituted with one or more group (a) selected from the substituent group E, non-aromatic carbocyclylcarbonyl optionally substituted with one or more group(s) selected from the substituent group E, aromatic heterocyclylcarbonyl optionally substituted with one or more group(s) selected from the substituent group E, non-aromatic heterocyclylcarbonyl optionally substituted with one or more group(s) selected from the substituent group E, aromatic carbocyclyl sulfonyl optionally substituted with one or more group(s) selected from the substituent group E, non-aromatic carbocyclylsulfonyl optionally substituted with one or more group(s) selected from the substituent group E, aromatic heterocyclylsulfonyl optionally substituted with one or more group(s) selected from the substituent group E, non-aromatic heterocyclylsulfonyl optionally substituted with one or more group (s) selected from the substituent group E, aromatic carbocyclylcarbonylamino optionally substituted with one or more group(s) selected from the substituent, group E, non-aromatic carbocyclylcarbonylamino optionally substituted with one or more group(s) selected from the substituent group E, aromatic heterocyclylcarbonylamino optionally substituted with one or more group(s) selected from the substituent group E, non-aromatic heterocyclylcarbonylamino optionally substituted with one or more group(s) selected from the substituent group E, aromatic carbocyclylsulfonylamino optionally substituted with one or more group(s) selected from the substituent group E, non-aromatic carbocyclylsulfonylamino optionally substituted with one or more group(s) selected from the substituent group E, aromatic heterocyclylsulfonylamino optionally substituted with one or more group(s) selected from the substituent group E, non-aromatic heterocyclylsulfonylamino optionally substituted with one or more group(s) selected from the substituent group E, aromatic carbocyclylcarbamoyl optionally substituted with one or more group(s) selected from the substituent, group E, non-aromatic carbocyclylcarbamoyl optionally substituted with one or more group(s) selected from the substituent group E, aromatic heterocyclylcarbamoyl optionally substituted with one or more group(s) selected from the substituent group E, non-aromatic heterocyclylcarbamoyl optionally substituted with one or more group(s) selected from the substituent group E, aromatic carbocyclylsulfamoyl optionally substituted with one or more group (s) selected from the substituent group E, non-aromatic carbocyclylsulfamoyl optionally substituted with one or more group(s) selected from the substituent group E, aromatic heterocyclylsulfamoyl optionally substituted with one or more group(s) selected from the substituent group E, non-aromatic heterocyclylsulfamoyl optionally substituted with one or more group(s) selected from the substituent group E, aromatic carbocyclyloxycarbonyl optionally substituted with one or more group(s) selected from the substituent group E, non-aromatic carbocyclyloxycarbonyl optionally substituted with one or more group(s) selected from the substituent group E, aromatic heterocyclyloxycarbonyl optionally substituted with one or more group(s) selected from the substituent group E, non-aromatic heterocyclyloxycarbonyl optionally substituted with one or more group(s) selected from the substituent group E, aromatic carbocyclyloxysulfonyl optionally substituted with one or more group(s) selected from the substituent group E, non-aromatic carbocyclyloxysulfonyl optionally substituted with one or more group(s) selected from the substituent group E, aromatic heterocyclyloxysulfonyl optionally substituted with one or more group(s) selected from the substituent group E, non-aromatic heterocyclyloxysulfonyl optionally substituted with one or more group(s) selected from the substituent group E, aromatic carbocyclylcarbonyloxy optionally substituted with one or more group(s) selected from the substituent group E, non-aromatic carbocyclylcarbonyloxy optionally substituted with one or more group(s) selected from the substituent group E, aromatic heterocyclyl carbonyloxy optionally substituted with one or more group (s) selected from the substituent group E, non-aromatic heterocyclylcarbonyloxy optionally substituted with one or more group(s) selected from the substituent group E, aromatic carbocyclyl sulfonyloxy optionally substituted with one or more group(s) selected from the substituent group E, non-aromatic carbocyclylsulfonyloxy optionally substituted with one or more group(s) selected from the substituent group E, aromatic heterocyclylsulfonyloxy optionally substituted with one or more group(s) selected from the substituent group E, and non-aromatic heterocyclylsulfonyloxy optionally substituted with one or more group(s) selected from the substituent group E.

The substituents on the rings of "aromatic carbocycle", "non-aromatic carbocycle", "aromatic heterocycle", and "non-aromatic heterocycle" of "substituted or unsubstituted aromatic carbocycle", "substituted or unsubstituted non-aromatic carbocycle", "substituted or unsubstituted aromatic heterocycle", and "substituted or unsubstituted non-aromatic heterocycle", "substituted or unsubstituted 6-membered aromatic carbocycle", "substituted or unsubstituted 5- to 6-membered non-aromatic carbocycle", "substituted or unsubstituted 5- to 6-membered aromatic heterocycle", and "substituted or unsubstituted 5- to 6-membered non-aromatic heterocycle".

"substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl", "substituted or unsubstituted 6- to 10-membered aromatic carbocyclyl", "substituted or unsubstituted 3- to 10-membered non-aromatic carbocyclyl", "substituted or unsubstituted 5- to 10-membered aromatic heterocyclyl", and "substituted or unsubstituted 3- to 10-membered non-aromatic heterocyclyl", "substituted or unsubstituted 6-membered aromatic carbocyclyl", "substituted or unsubstituted 3- to 6-membered non-aromatic carbocyclyl", "substituted or unsubstituted 5- to 6-membered aromatic heterocyclyl", and "substituted or unsubstituted 5- to 6-membered non-aromatic heterocyclyl", "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", and "substituted or unsubstituted non-aromatic heterocyclylamino", "substituted or unsubstituted aromatic carbocyclylsulfanyl", "substituted or unsubstituted non-aromatic carbocyclylsulfanyl", "substituted or unsubstituted aromatic heterocyclylsulfanyl", and "substituted or unsubstituted non-aromatic heterocyclyl sulfanyl", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl", "substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl", "substituted or unsubstituted aromatic carbocyclylcarbonyloxy", "substituted or unsubstituted non-aromatic carbocyclylcarbonyloxy", "substituted or unsubstituted aromatic heterocyclylcarbonyloxy", and "substituted or unsubstituted non-aromatic heterocyclylcarbonyloxy", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfonyloxy", "substituted or unsubstituted non-aromatic carbocyclylsulfonyloxy", "substituted or unsubstituted aromatic heterocyclylsulfonyloxy", and "substituted or unsubstituted non-aromatic haterocyclylsulfonyloxy", "substituted or unsubstituted aromatic carbocyclyloxysulfonyl", "substituted or unsubstituted non-aromatic carbocyclyloxy sulfonyl", "substituted or unsubstituted aromatic heterocyclyloxysulfonyl", and "substituted or unsubstituted non-aromatic heterocyclyloxysulfonyl", "substituted or unsubstituted aromatic carbocyclylcarbamoyl", "substituted or unsubstituted non-aromatic carbocyclylcarbamoyl", "substituted or unsubstituted aromatic heterocyclylcarbamoyl", and "substituted or unsubstituted non-aromatic heterocyclylcarbamoyl", "substituted or unsubstituted aromatic carbocyclylsulfamoyl", "substituted or unsubstituted non-aromatic carbocyclylsulfamoyl", "substituted or unsubstituted aromatic heterocyclylsulfamoyl", and "substituted or unsubstituted non-aromatic heterocyclylsulfamoyl", "substituted or unsubstituted aromatic carbocyclylcarbonylamino", "substituted or unsubstituted non-aromatic carbocyclylcarbonylamino", "substituted or unsubstituted aromatic heterocyclylcarbonylamino", and "substituted or unsubstituted non-aromatic heterocyclylcarbonylamino", "substituted or unsubstituted aromatic carbocyclylsulfonylamino", "substituted or unsubstituted non-aromatic carbocyclylsulfonylamino", "substituted or unsubstituted aromatic heterocyclylsulfonylamino", and "substituted or unsubstituted non-aromatic heterocyclylsulfonylamino", and "substituted or unsubstituted aromatic carbocyclyloxycarbonylamino", "substituted or unsubstituted non-aromatic carbocyclyloxycarbonylamino", "substituted or unsubstituted aromatic heterocyclyloxycarbonylamino", and "substituted or unsubstituted non-aromatic heterocyclyloxycarbonylamino" include the substituent group D. An atom at any position(s) on the ring may be bonded to one or more group(s) selected from the substituent group G.

The substituent group C: halogen, hydroxy, carboxy, amino, carbamoyl, sulfamoyl, sulfo, cyano, alkyl optionally substituted with one or more group(s) selected from the substituent group D, alkenyl optionally substituted with one or more group(s) selected from the substituent group D, alkynyl optionally substituted with one or more group(s) selected from the substituent group D, alkyloxy optionally substituted with one or more group(s) selected from the substituent group D, alkenyloxy optionally substituted with one or more group(s) selected from the substituent, group D, alkynyloxy optionally substituted with one or more group(s) selected from the substituent group D, alkylamino optionally substituted with one or more group(s) selected from the substituent group D, alkenylamino optionally substituted with one or more group(s) selected from the substituent group D, alkynylamino optionally substituted with one or more group(s) selected from the substituent group U, alkylsulfanyl optionally substituted with one or more group (s) selected from the substituent group D, alkenylsulfanyl optionally substituted with one or more group(s) selected from the substituent group D, alkynylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, alkylcarbonyloxy optionally substituted with one or more group(s) selected from the substituent group D, alkyloxycarbonyl optionally substituted with one or more group(s) selected from the substituent group D, alkylsulfonyloxy optionally substituted with one or more group(s) selected from the substituent group D, aryloxysulfonyl optionally substituted with one or more group(s) selected from the substituent group D, aromatic carbocyclyl optionally substituted with one or more group(s) selected from the substituent group E, non-aromatic carbocyclyl optionally substituted with one or more group(s) selected from the substituent group E, aromatic heterocyclyl optionally substituted with one or more group (s) selected from the substituent group E, non-aromatic heterocyclyl optionally substituted with one or more group(s) selected from the substituent group E, aromatic, carbocyclyloxy optionally substituted with one or more group(s) selected from the substituent group E, non-aromatic carbocyclyloxy optionally substituted with one or more group(s) selected from the substituent group E, aromatic heterocyclyloxy optionally substituted with one or more group(s) selected from the substituent group E, non-aromatic heterocyclyloxy optionally substituted with one or more group(s) selected from the substituent group E, aromatic carbocyclylsulfanyl optionally substituted with one or more group(s) selected from the substituent group E, non-aromatic carbocyclylsulfanyl optionally substituted with one or more group(s) selected from the substituent group E, aromatic heterocyclylsulfanyl optionally substituted with one or more group(s) selected from the substituent group E, non-aromatic heterocyclylsulfanyl optionally substituted with one or more group(s) selected from the substituent group E, aromatic carbocyclyl amino optionally substituted with one or more group(s) selected from the substituent group E, non-aromatic carbocyclylamino optionally substituted with one or more group (s) selected from the substituent group E, aromatic heterocyclylamino optionally substituted with one or more group (s) selected from the substituent group E, non-aromatic heterocyclylamino optionally substituted with one or more group(s) selected from the substituent group E, aromatic carbocyclylcarbonyl optionally substituted with one or more group(s) selected from the substituent group E, non-aromatic carbocyclylcarbonyl optionally substituted with one or more group(s) selected from the substituent group E, aromatic heterocyclylcarbonyl optionally substituted with one or more group(s) selected from the substituent group E, non-aromatic heterocyclylcarbonyl optionally substituted with one or more group(s) selected from the substituent group E, aromatic carbocyclyl sulfonyl optionally substituted with one or more group(s) selected from the substituent group E, non-aromatic carbocyclylsulfonyl optionally substituted with one or more group(s) selected from the substituent group E, aromatic heterocyclylsulfonyl optionally substituted with one or more group(s) selected from the substituent group E, non-aromatic heterocyclylsulfonyl optionally substituted with one or more group(s) selected from the substituent group E, aromatic carbocyclylcarbonylamino optionally substituted with one or more group(s) selected from the substituent group E, non-aromatic carbocyclylcarbonylamino optionally substituted with one or more group(s) selected from the substituent group E, aromatic heterocyclylcarbonylamino optionally substituted with one or more group(s) selected from the substituent group E, non-aromatic heterocyclylcarbonylamino optionally substituted with one or more group(s) selected from the substituent group E, aromatic carbocyclylsulfonylamino optionally substituted with one or more group(s) selected from the substituent group E, non-aromatic carbocyclylsulfonylamino optionally substituted with one or more group(s) selected from the substituent group E, aromatic heterocyclylsulfonylamino optionally substituted with one or more group(s) selected from the substituent group E, non-aromatic heterocyclylsulfonylamino optionally substituted with one or more group(s) selected from the substituent group E, aromatic carbocyclylcarbamoyl optionally substituted with one or more group(s) selected from the substituent group E, non-aromatic carbocyclylcarbamoyl optionally substituted with one or more group(s) selected from the substituent group E, aromatic heterocyclylcarbamoyl optionally substituted with one or more group(s) selected from the substituent, group E, non-aromatic heterocyclylcarbamoyl optionally substituted with one or more group(s) selected from the substituent group E, aromatic carbocyclylsulfamoyl optionally substituted with one or more group (s) selected from the substituent group E, non-aromatic carbocyclylsulfamoyl optionally substituted with one or more group(s) selected from the substituent group E, aromatic heterocyclylsulfamoyl optionally substituted with one or more group(s) selected from the substituent, group E, non-aromatic heterocyclylsulfamoyl optionally substituted with one or more group(s) selected from the substituent group E, aromatic carbocyclyloxycarbonyl optionally substituted with one or more group(s) selected from the substituent group E, non-aromatic carbocyclyloxycarbonyl optionally substituted with one or more group(s) selected from the substituent group E, aromatic heterocyclyloxycarbonyl optionally substituted with one or more group(s) selected from the substituent group E, non-aromatic heterocyclyloxycarbonyl optionally substituted with one or more group(s) selected from the substituent group E, aromatic carbocyclyloxysulfonyl optionally substituted with one or more group(s) selected from the substituent group E, non-aromatic carbocyclyloxysulfonyl optionally substituted with one or more group(s) selected from the substituent group E, aromatic heterocyclyloxysulfonyl optionally substituted with one or more group(s) selected from the substituent group E, non-aromatic heterocyclyloxysulfonyl optionally substituted with one or more group(s) selected from the substituent group E, aromatic carbocyclylcarbonyloxy optionally substituted with one or more group(s) selected from the substituent group E, non-aromatic carbocyclylcarbonyloxy optionally substituted with one or more group(s) selected from the substituent group E, aromatic heterocyclylcarbonyloxy optionally substituted with one or more group(s) selected from the substituent group E, non-aromatic heterocyclylcarbonyloxy optionally substituted with one or more group(s) selected from the substituent group E, aromatic, carbocyclyl sulfonyloxy optionally substituted with one or more group(s) selected from the substituent group E, non-aromatic carbocyclyl sulfon yloxy optionally substituted with one or more group(s) selected from the substituent group E, aromatic heterocyclylsulfonyloxy optionally substituted with one or more group(s) selected from the substituent group E, and non-aromatic heterocyclylsulfonyloxy optionally substituted with one or more group(s) selected from the substituent group E.

The substituent group C: halogen, hydroxy, carboxy, amino, carbamoyl, sulfamoyl, sulfo, cyano, alkyloxy, haloalkyloxy, alkylamino, haloalkylamino, alkylsulfanyl, haloalkylsulfanyl, and aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent, group F, and non-aromatic heterocyclyl optionally substituted with one or more group(s) selected from the substituent group F.

The substituent group D: halogen, hydroxy, carboxy, amino, carbamoyl, sulfamoyl, sulfo, and cyano.

The substituent group E: halogen, hydroxy, carboxy, amino, carbamoyl, sulfamoyl, sulfo, and cyano, and alkyl optionally substituted with one or more group(s) selected from the substituent group D, alkyloxy optionally substituted with one or more group(s) selected from the substituent group D, alkylamino optionally substituted with one or more group (a) selected from the substituent group D, alkylsulfanyl optionally substituted with one or more group (s) selected from the substituent group D, alkylcarbonyl optionally substituted with one or more group(s) selected from the substituent, group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, alkylcarbonyloxy optionally substituted with one or more group(s) selected from the substituent group D, alkyloxycarbonyl optionally substituted with one or more group(s) selected from the substituent group D, alkylsulfonyloxy optionally substituted with one or more group(s) selected from the substituent group D, and aryloxysulfonyl optionally substituted with one or more group(s) selected from the substituent group D.

The substituent group F: halogen, hydroxy, carboxy, amino, carbamoyl, sulfamoyl, sulfo, cyano, alkyl, haloalkyl, alkyloxy, haloaryloxy, alkylamino, haloalkylamino, alkylsulfanyl, haloalkylsulfanyl, alkylcarbonyl, haloalkylcarbonyl, alkylsulfonyl, haloalkylsulfonyl, alkylcarbonylamino, haloalkylcarbonylamino, alkylsulfonylamino, haloalkylsulfonylamino, alkylcarbamoyl, haloalkylcarbamoyl, alkylsulfamoyl, and haloalkylsulfamoyl.

"Substituted or unsubstituted non-aromatic carbocyclyl" and "substituted or unsubstituted non-aromatic heterocyclyl" may be optionally substituted with one or more group (s) selected from "oxo". In this case, it means a group wherein two hydrogen atoms on a carbon atom are replaced as below.

[Chemical Formula 32]

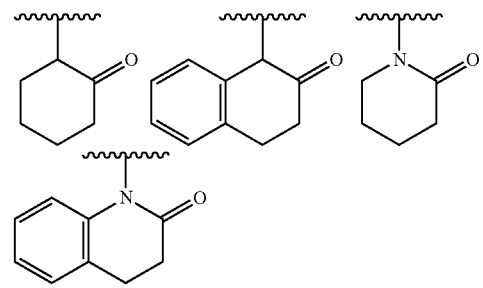

The non-aromatic carbocycle or non-aromatic heterocycle part of the above "non-aromatic carbocyclyloxy", "non-aromatic carbocyclylamino", "non-aromatic carbocyclylsulfanyl", "non-aromatic carbocyclylcarbonyl", "non-aromatic carbocyclylsulfonyl", "non-aromatic carbocyclylcarbonyloxy", "non-aromatic carbocyclylsulfonyloxy", "non-aromatic carbocyclyloxycarbonyl", "non-aromatic carbocycly-loxysulfonyl", "non-aromatic carbocyclylcarbamoyl", "non-aromatic carbocyclylsulfamoyl", "non-aromatic carbocyclylcarbonylamino", "non-aromatic carbocyclylsulfonylamino", "non-aromatic carbocyclyloxycarbonylamino", "non-aromatic heterocyclyloxy", "non-aromatic heterocyclylamino", "non-aromatic heterocyclylsulfanyl", "non-aromatic heterocyclyl carbonyl", "non-aromatic heterocyclylsulfonyl", "non-aromatic heterocyclylcarbonyloxy", "non-aromatic heterocyclylsulfonyloxy", "non-aromatic heterocyclyloxycarbonyl", "non-aromatic heterocyclyloxysulfonyl", "non aromatic heterocyclylcarbamoyl", "non-aromatic heterocyclylsulfamoyl", "non-aromatic heterocyclylcarbonylamino", "non-aromatic heterocyclylsulfonylamino", and "non-aromatic heterocyclyloxycarbonylamino" may be optionally substituted with one or more group(s) selected from "oxo" as above.

The substituents on the rings of "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted 5- to 10-membered aromatic carbocyclyl", "substituted or unsubstituted 3- to 10-membered non-aromatic carbocyclyl", "substituted or unsubstituted 5- to 10-membered aromatic heterocyclyl", "substituted or unsubstituted 3- to 10-membered non-aromatic heterocyclyl", "substituted or unsubstituted 6-membered aromatic carbocyclyl", "substituted or unsubstituted 3- to 6-membered non-aromatic carbocyclyl", "substituted or unsubstituted 5- to 6-membered aromatic heterocyclyl", and "substituted or unsubstituted 5- to 6-membered non-aromatic heterocyclyl" in $R^1$ include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment, is, for example, halogen, hydroxy, carboxy, amino, carbamoyl, sulfamoyl, sulfo, cyano, alkyl, haloalkyl, alkyloxy, haloaryloxy, alkylamino, haloalkylamino, alkylsulfanyl, haloalkylsulfanyl, alkylcarbonyl, haloalkylcarbonyl, alkylsulfonyl, haloalkylsulfonyl, alkylcarbonylamino, haloalkylcarbonylamino, alkylsulfonylamino, haloalkylsulfonylamino, alkylcarbamoyl, haloalkylcarbamoyl, alkylsulfamoyl, haloalkylsulfamoyl, or the like.

One embodiment is, for example, halogen, hydroxy, cyano, alkyl optionally substituted with one or more group(s) selected from the substituent, group D, alkyloxy optionally substituted with one or more group(s) selected from the substituent group D, alkylamino optionally substituted with one or more group(s) selected from the substituent group D, alkylsulfanyl optionally substituted with one or more group Os) selected from the substituent group D or the like.

One embodiment is, for example, halogen, alkyl, haloalkyl, alkyloxy, haloaryloxy, alkylamino, haloalkylamino, alkylsulfanyl, haloalkylsulfanyl or the like.

One embodiment is, for example, halogen, alkyl optionally substituted with one or more group(s) selected from the substituent group D, alkyloxy optionally substituted with one or more group(s) selected from the substituent group D or the like.

One embodiment is, for example, halogen, alkyl, haloalkyl, alkyloxy, haloalkyloxy or the like.

One embodiment is, for example, halogen, alkyl, haloalkyl or the like.

One embodiment is, for example, halogen.

One embodiment is, for example, halogen, cyano, alkyl optionally substituted with one or more group(s) selected from the substituent group D, alkyloxy optionally substituted with one or more group(s) selected from the substituent group D or the like.

One embodiment is, for example, halogen, cyano, alkyl, haloalkyl, alkyloxy, haloalkyloxy or the like.

The substituents of "substituted or unsubstituted alkyl", and "substituted or unsubstituted alkyloxy" in $R^{2a}$, $R^{2b}$, $R^{2c}$, $R^{2d}$, $R^{8a}$ and $R^{8b}$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F and the like.

One embodiment is, for example, halogen, hydroxy, carboxy, amino, carbamoyl, sulfamoyl, sulfo, cyano or the like.

One embodiment is, for example, halogen, hydroxy, cyano or the like.

One embodiment is, for example, halogen or the like.

The substituents of "substituted or unsubstituted alkyl", and "substituted or unsubstituted alkylcarbonyl" in $R^{7a}$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent, group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, aromatic carbocyclyl optionally substituted with one or more group(s) selected from the substituent, group F, non-aromatic carbocyclyl optionally substituted with one or more group(s) selected from the substituent group F, aromatic heterocyclyl optionally substituted with one or more group(s) selected from the substituent, group F, non-aromatic heterocyclyl optionally substituted with one or more group(s) selected from the substituent group F and the like.

One embodiment is, for example, halogen, hydroxy, carboxy, amino, carbamoyl, sulfamoyl, sulfo, cyano or the like.

One embodiment is, for example, halogen, hydroxy, cyano or the like.

One embodiment is, for example, halogen or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl". "substituted or unsubstituted alkylamino", "substituted or unsubstituted alkenylamino", and "substituted or unsubstituted alkynylamino" in $R^4$ and $R^6$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent, group F, non-aromatic heterocyclyl optionally substituted with one or more group(s) selected from the substituent group F and the like.

One embodiment is, for example, halogen, hydroxy, carboxy, amino, carbamoyl, sulfamoyl, sulfo, cyano or the like.

One embodiment is, for example, halogen, hydroxy, cyano or the like.

One embodiment is, for example, halogen.

The substituents of "substituted or unsubstituted alkyl" in $R^{5a}$, $R^{5a'}$ and $R^{5b}$ include halogen, hydroxy, carboxy, amino, carbamoyl, sulfamoyl, sulfo, cyano, alkyloxy optionally substituted with one or more group(s) selected from the substituent group C, alkylamino optionally substituted with one or more group(s) selected from the substituent group C, alkylsulfanyl optionally substituted with one or more group (s) selected from the substituent group C, alkylcarbonyl optionally substituted with one or more group(s) selected from the substituent group C, alkylsulfonyl optionally substituted with one or more group(s) selected from the substituent group C, alkylcarbonylamino optionally substituted with one or more group(s) selected from the substituent group C, alkylsulfonylamino optionally substituted with one or more group(s) selected from the substituent group C, alkylcarbamoyl optionally substituted with one or more group(s) selected from the substituent group C, alkylsulfamoyl optionally substituted with one or more group(s) selected from the substituent group C, aromatic carbocyclyl optionally substituted with one or more group(s) selected from the substituent group E, non-aromatic carbocyclyl optionally substituted with one or more group(s) selected from the substituent group E, aromatic heterocyclyl optionally substituted with one or more group(s) selected from the substituent group E, non aromatic heterocyclyl optionally substituted with one or more group(s) selected from the substituent, group E, aromatic carbocyclyloxy optionally substituted with one or more group(s) selected from the substituent group E, non-aromatic carbocyclyloxy optionally substituted with one or more group(s) selected from the substituent group E, aromatic heterocyclyloxy optionally substituted with one or more group(s) selected from the substituent group E, non-aromatic heterocyclyloxy optionally substituted with one or more group(s) selected from the substituent group E, aromatic carbocyclylsulfanyl optionally substituted with one or more group(s) selected from the substituent, group E, non-aromatic carbocyclylsulfanyl optionally substituted with one or more group(s) selected from the substituent group E, aromatic heterocyclylsulfanyl optionally substituted with one or more group(s) selected from the substituent group E, non-aromatic heterocyclylsulfanyl optionally substituted with one or more group(s) selected from the substituent group E, aromatic carbocyclyl amino optionally substituted with one or more group(s) selected from the substituent group E, non-aromatic carbocyclylamino optionally substituted with one or more group (s) selected from the substituent group E, aromatic heterocyclylamino optionally substituted with one or more group (s) selected from the substituent, group E, non-aromatic heterocyclylamino optionally substituted with one or more group(s) selected from the substituent group E, aromatic carbocyclylcarbonyl optionally substituted with one or more group(s) selected from the substituent group E, non-aromatic carbocyclylcarbonyl optionally substituted with one or more group(s) selected from the substituent group E, aromatic heterocyclylcarbonyl optionally substituted with one or more group(s) selected from the substituent group E, non-aromatic heterocyclylcarbonyl optionally substituted with one or more group(s) selected from the substituent group E, aromatic carbocyclyl sulfonyl optionally substituted with one or more group(s) selected from the substituent group E, non-aromatic carbocyclylsulfonyl optionally substituted with one or more group(s) selected from the substituent group E, aromatic heterocyclylsulfonyl optionally substituted with one or more group(s) selected from the substituent group E, non-aromatic heterocyclylsulfonyl optionally substituted with one or more group(s) selected from the substituent group E, aromatic carbocyclylcarbonylamino optionally substituted with one or more group(s) selected from the substituent group E, non-aromatic carbocyclylcarbonylamino optionally substituted with one or more group(s) selected from the substituent group E, aromatic heterocyclylcarbonylamino optionally substituted with one or more group(s) selected from the substituent group E, non-aromatic heterocyclylcarbonylamino optionally substituted with one or more group(s) selected from the substituent group E, aromatic carbocyclylsulfonylamino optionally substituted with one or more group(s) selected from the substituent group E, non-aromatic carbocyclylsulfonylamino optionally substituted with one or more group(s) selected from the substituent group E, aromatic heterocyclylsulfonylamino optionally substituted with one or more group(s) selected from the substituent group E, non-aromatic heterocyclylsulfonylamino optionally substituted with one or more group(s) selected from the substituent group E, aromatic carbocyclylcarbamoyl optionally substituted with one or more group(s) selected from the substituent group E, non-aromatic carbocyclylcarbamoyl optionally substituted with one or more group(s) selected from the substituent group E, aromatic heterocyclylcarbamoyl optionally substituted with one or more group(s) selected from the substituent, group E, non-aromatic heterocyclylcarbamoyl optionally substituted with one or more group(s) selected from the substituent group E, aromatic carbocyclylsulfamoyl optionally substituted with one or more group (s) selected from the substituent group E, non-aromatic carbocyclylsulfamoyl optionally substituted with one or more group(s) selected from the substituent group E, aromatic heterocyclylsulfamoyl optionally substituted with one or more group(s) selected from the substituent, group E, non-aromatic heterocyclylsulfamoyl optionally substituted with one or more group(s) selected from the substituent group E and the like.

One embodiment is, for example, halogen, hydroxy, carboxy, amino, carbamoyl, sulfamoyl, sulfo, cyano, alkylcarbonyl optionally substituted with one or more group(s) selected from the substituent group C, alkylcarbonylamino optionally substituted with one or more group(s) selected from the substituent group C, alkylcarbamoyl optionally substituted with one or more group(s) selected from the substituent group C, aromatic carbocyclylcarbonyl optionally substituted with one or more group(s) selected from the substituent group F, non-aromatic carbocyclylcarbonyl optionally substituted with one or more group(s) selected from the substituent group F, aromatic heterocyclylcarbonyl optionally substituted with one or more group(s) selected from the substituent group F, non-aromatic heterocyclylcarbonyl optionally substituted with one or more group(s) selected from the substituent, group F, aromatic carbocyclylcarbonylamino optionally substituted with one or more group(s) selected from the substituent group F, non-aromatic carbocyclylcarbonylamino optionally substituted with one or more group(s) selected from the substituent group F, aromatic heterocyclylcarbonyl amino optionally substituted with one or more group(s) selected from the substituent group F, non-aromatic heterocyclylcarbonyl amino optionally substituted with one or more group(s) selected from the substituent group F, aromatic carbocyclylcarbamoyl optionally substituted with one or more group(s) selected from the substituent group F, non-aromatic carbocyclylcarbamoyl optionally substituted with one or more group(s) selected from the substituent group F, aromatic heterocyclylcarbamoyl optionally substituted with one or more group(s) selected from the substituent group F, non-aromatic heterocyclylcarbamoyl optionally substituted with one or more group(s) selected from the substituent group F or the like.

One embodiment is, for example, halogen, hydroxy, carboxy, carbamoyl, cyano, alkylcarbamoyl optionally substituted with one or more group(s) selected from the substituent group C, aromatic carbocyclylcarbonyl optionally substituted with one or more group(s) selected from the substituent group F, non-aromatic carbocyclylcarbonyl optionally substituted with one or more group(s) selected from the substituent group F, aromatic heterocyclylcarbonyl optionally substituted with one or more group(s) selected from the substituent group F, non-aromatic heterocyclylcarbonyl optionally substituted with one or more group(s) selected from the substituent, group F, aromatic carbocyclylcarbamoyl optionally substituted with one or more group (s) selected from the substituent group F, non-aromatic carbocyclylcarbamoyl optionally substituted with one or mom group(s) selected from the substituent group F, aromatic heterocyclylcarbamoyl optionally substituted with one or more group(s) selected from the substituent-group F, non-aromatic heterocyclylcarbamoyl optionally substituted with one or more group(s) selected from the substituent group F or the like.

One embodiment is, for example, halogen, hydroxy, carboxy, carbamoyl, alkylcarbamoyl optionally substituted with one or mom group(s) selected from (hydroxy, cyano and alkyloxy), non-aromatic heterocyclylcarbonyl, aromatic carbocyclylcarbamoyl optionally substituted with one or more group(s) selected from (halogen and alkyl), non-aromatic heterocyclylcarbamoyl, or the like.

The substituents of "substituted or unsubstituted alkylcarbamoyl" in $R^{6a}$, $R^{5a'}$ and $R^{5b}$ include halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or mom group (s) selected from the substituent, group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group (s) selected from the substituent group F, aromatic carbocyclyloxy optionally substituted with one or more group(s) selected from the substituent group F, non-aromatic carbocyclyloxy optionally substituted with one or more group(s) selected from the substituent group F, aromatic heterocyclyloxy optionally substituted with one or more group(s) selected from the substituent group F, non-aromatic heterocyclyloxy optionally substituted with one or more group(s) selected from the substituent group F, aromatic carbocyclylsulfanyl optionally substituted with one or more group(s) selected from the substituent group F, non-aromatic carbocyclylsulfanyl optionally substituted with one or more group (s) selected from the substituent group F, aromatic heterocyclylsulfanyl optionally substituted with one or more group (s) selected from the substituent group F, non-aromatic heterocyclylsulfanyl optionally substituted with one or more group(s) selected from the substituent group F, aromatic carbocyclylamino optionally substituted with one or more group(s) selected from the substituent group F, non-aromatic carbocyclylamino optionally substituted with one or more group(s) selected from the substituent group F, aromatic heterocyclylamino optionally substituted with one or more group(s) selected from the substituent group F, non-aromatic heterocyclylamino optionally substituted with one or more group(s) selected from the substituent group F and the like.

One embodiment is, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent, group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, aromatic carbocyclyl optionally substituted with one or more group(s) selected from the substituent group F, non-aromatic carbocyclyl optionally substituted with one or more group (s) selected from the substituent group F, aromatic heterocyclyl optionally substituted with one or more group(s) selected from the substituent group F, non-aromatic heterocyclyl optionally substituted with one or more group(s) selected from the substituent group F or the like.

One embodiment, is, for example, halogen, hydroxy, cyano, alkyloxy optionally substituted with one or more group(s) selected from the substituent group D, alkylcarbonyl optionally substituted with one or more group(s) selected from the substituent, group D, alkylsulfonyl optionally substituted with one or more group(s) selected from the substituent group D, alkylcarbamoyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F or the like.

One embodiment is, for example, halogen, cyano, alkyloxy, alkylcarbonyl, alkylsulfonyl, alkylcarbamoyl, aromatic carbocyclyl or the like.

The substituents of "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynyl sulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfinyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted alkyloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonyl amino", and "substituted or unsubstituted alkynyloxycarbonylamino" in $R^{5a}$, ligand $R^{5b}$ include halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent, group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F, aromatic carbocyclyloxy optionally substituted with one or more group(s) selected from the substituent group F, non-aromatic carbocyclyloxy optionally substituted with one or more group (a) selected from the substituent group F, aromatic heterocyclyloxy optionally substituted with one or more group(s) selected from the substituent group F, non-aromatic heterocyclyloxy optionally substituted with one or more group(s) selected from the substituent group F, aromatic carbocyclylsulfanyl optionally substituted with one or more group(s) selected from the substituent group F, non-aromatic carbocyclylsulfanyl optionally substituted with one or more group (s) selected from the substituent group F, aromatic heterocyclylsulfanyl optionally substituted with one or more group(s) selected from the substituent group F, non-aromatic heterocyclylsulfanyl optionally substituted with one or more group(s) selected from the substituent group F, aromatic carbocyclyl amino optionally substituted with one or more group(s) selected from the substituent group F, non-aromatic carbocyclylamino optionally substituted with one or more group(s) selected from the substituent group F, aromatic heterocyclylamino optionally substituted with one or more group(s) selected from the substituent group F, and non-aromatic heterocyclylamino optionally substituted with one or more group(s) selected from the substituent group F and the like.

One embodiment is, for example, halogen, hydroxy, carboxy, amino, carbamoyl, sulfamoyl, sulfo, cyano, alkyloxy optionally substituted with one or more group (s) selected from the substituent group D, alkylamino optionally substituted with one or more group(s) selected from the substituent, group D, alkylsulfanyl optionally substituted with one or more group(s) selected from the substituent, group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F or the like.

One embodiment is, for example, halogen, hydroxy, cyano, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group (s) selected from the substituent group F or the like.

One embodiment is, for example, halogen, aromatic carbocyclyl or the like.

One embodiment is, for example, halogen or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfonyl", "substituted or unsubstituted alkynyl sulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted aryloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonylamino" in $R^{9a}$ and $R^{9b}$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group (a) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F, aromatic carbocyclyloxy optionally substituted with one or more group(s) selected from the substituent group F, non-aromatic carbocyclyloxy optionally substituted with one or more group(s) selected from the substituent group F, aromatic heterocyclyloxy optionally substituted with one or more group(s) selected from the substituent group F, non-aromatic heterocyclyloxy optionally substituted with one or more group(s) selected from the substituent group F, aromatic carbocyclyl sulfanyl optionally substituted with one or more group(s) selected from the substituent group F, non-aromatic carbocyclylsulfanyl optionally substituted with one or more group(s) selected from the substituent group F, aromatic heterocyclylsulfanyl optionally substituted with one or more group(s) selected from the substituent group F, non-aromatic heterocyclylsulfanyl optionally substituted with one or more group(s) selected from the substituent group F, aromatic carbocyclylamino optionally substituted with one or more group(s) selected from the substituent, group F, non-aromatic carbocyclylamino optionally substituted with one or more group (s) selected from the substituent group F, aromatic heterocyclylamino optionally substituted with one or more group (s) selected from the substituent group F, and non-aromatic heterocyclylamino optionally substituted with one or more group(s) selected from the substituent group F and the like.

One embodiment is, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group (a) selected from the substituent group D, alkylsulfanyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F or the like.

One embodiment is, for example, halogen, alkyloxy optionally substituted with one or more group(s) selected from the substituent group D, aromatic carbocyclyl optionally substituted with one or more group(s) selected from the substituent group F, nonaromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F or the like.

One embodiment is, for example, halogen, aromatic carbocyclyl optionally substituted with one or more group(s) selected from the substituent group F, non-aromatic carbocyclyl optionally substituted with one or more group(s) selected from the substituent, group F, aromatic heterocyclyl optionally substituted with one or more group(s) selected from the substituent group F, non-aromatic heterocyclyl optionally substituted with one or more group(s) selected from the substituent group F or the like.

One embodiment is, for example, halogen, aromatic carbocyclyl, aromatic heterocyclyl or the like.

One embodiment is, for example, halogen or the like.

The substituents on the rings of "aromatic carbocycle", "non-aromatic carbocycle", "aromatic heterocycle", and "non-aromatic heterocycle" of
"substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl".

"substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", and "substituted or unsubstituted non-aromatic heterocyclylamino", "substituted or unsubstituted aromatic carbocyclylsulfanyl", "substituted or unsubstituted non-aromatic carbocyclylsulfanyl", "substituted or unsubstituted aromatic heterocyclyl sulfanyl", and "substituted or unsubstituted non-aromatic heterocyclylsulfanyl", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl", "substituted or unsubstituted aromatic carbocyclylsulfonyl", "substituted or unsubstituted non-aromatic carbocyclylsulfonyl", "substituted or unsubstituted aromatic heterocyclylsulfanyl", and "substituted or unsubstituted non-aromatic heterocyclylsulfonyl", "substituted or unsubstituted aromatic carbocyclylcarbonyloxy", "substituted or unsubstituted non-aromatic carbocyclylcarbonyloxy", "substituted or unsubstituted aromatic heterocyclylcarbonyloxy", and "substituted or unsubstituted non-aromatic heterocyclylcarbonyloxy", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfonyloxy", "substituted or unsubstituted non-aromatic carbocyclylsulfonyloxy", "substituted or unsubstituted aromatic heterocyclylsulfonyloxy", and "substituted or unsubstituted non aromatic heterocyclylsulfonyloxy", "substituted or unsubstituted aromatic carbocyclyloxysulfonyl", "substituted or unsubstituted non-aromatic carbocyclyloxysulfonyl", "substituted or unsubstituted aromatic heterocyclyloxysulfonyl", and "substituted or unsubstituted non-aromatic heterocyclyloxysulfonyl", "substituted or unsubstituted aromatic carbocyclylcarbamoyl", "substituted or unsubstituted non-aromatic carbocyclylcarbamoyl", "substituted or unsubstituted aromatic heterocyclylcarbamoyl", and "substituted or unsubstituted non-aromatic heterocyclylcarbamoyl", "substituted or unsubstituted aromatic carbocyclylsulfamoyl", "substituted or unsubstituted non-aromatic carbocyclylsulfamoyl", "substituted or unsubstituted aromatic heterocyclylsulfamoyl", and "substituted or unsubstituted non-aromatic heterocyclylsulfamoyl", "substituted or unsubstituted aromatic carbocyclylcarbonylamino", "substituted or unsubstituted non-aromatic carbocyclylcarbonylamino", "substituted or unsubstituted aromatic heterocyclylcarbonylamino", and "substituted or unsubstituted non-aromatic heterocyclylcarbonylamino", "substituted or unsubstituted aromatic carbocyclylsulfonylamino", "substituted or unsubstituted non-aromatic carbocyclylsulfonylamino", "substituted or unsubstituted aromatic heterocyclylsulfonylamino", and "substituted or unsubstituted non-aromatic heterocyclyl sulfonyl amino", and "substituted or unsubstituted aromatic carbocyclyloxycarbonylamino", "substituted or unsubstituted non-aromatic carbocyclyloxycarbonylamino", "substituted or unsubstituted aromatic heterocyclyloxycarbonylamino", and "substituted or unsubstituted non-aromatic heterocyclyloxycarbonylamino" in $R^{9a}$ and $R^{9b}$ include, for example, halogen, hydroxy, carboxy, amino, carbamoyl, sulfamoyl, sulfo, cyano, alkyl optionally substituted with one or more group (s) selected from the substituent, group D, alkyloxy optionally substituted with one or more group(s) selected from the substituent group D, alkylamino optionally substituted with one or more group (s) selected from the substituent group D, alkylsulfanyl optionally substituted with one or more group (s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, cyano, alkyl optionally substituted with one or more group (s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group (s) selected from the substituent group D or the like.

One embodiment, is, for example, halogen, alkyl optionally substituted with one or more group(s) selected from the substituent group D, alkyloxy optionally substituted with one or more group(s) selected from the substituent group D or the like.

One embodiment is, for example, halogen, alkyl, haloalkyl, alkyloxy, haloalkyloxy or the like.

One embodiment is, for example, halogen or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfinyl", "substituted or unsubstituted alkynylsulfanyl". "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfinyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted aryloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkyloxycarbonylamino" in $R^{10a}$, $R^{10aa}$, $R^{10ab}$, $R^{10ac}$, $R^{10b}$, $R^{10c}$ and $R^{10d}$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, aromatic carbocyclyl optionally substituted with one or more group(s) selected from the substituent, group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F, aromatic carbocyclyloxy optionally substituted with one or more group(s) selected from the substituent group F, non-aromatic carbocyclyloxy optionally substituted with one or more group(s) selected from the substituent group F, aromatic heterocyclyloxy optionally substituted with one or more group(s) selected from the substituent group F, non-aromatic heterocyclyloxy optionally substituted with one or more group(s) selected from the substituent group F, aromatic carbocyclylsulfanyl optionally substituted with one or more group(s) selected from the substituent group F, non-aromatic carbocyclylsulfanyl optionally substituted with one or more group(s) selected from the substituent group F, aromatic heterocyclylsulfanyl optionally substituted with one or more group(s) selected from the substituent group F, non-aromatic heterocyclylsulfanyl optionally substituted with one or more group(s) selected from the substituent group F, aromatic carbocyclylamino optionally substituted with one or more group(s) selected from the substituent group F, non-aromatic carbocyclylamino optionally substituted with one or more group (s) selected from the substituent group F, aromatic heterocyclylamino optionally substituted with one or more group (s) selected from the substituent group F, and non-aromatic heterocyclylamino optionally substituted with one or more group(s) selected from the substituent group F and the like.

One embodiment is, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, aromatic carbocyclyl optionally substituted with one or more group(s) selected from the substituent, group F, non-aromatic carbocyclyl optionally substituted with one or more group (s) selected from the substituent, group F, aromatic heterocyclyl optionally substituted with one or more group (s) selected from the substituent, group F, non-aromatic heterocyclyl optionally substituted with one or more group (s) selected from the substituent group F or the like.

One embodiment, is, for example, halogen, hydroxy, cyano, alkyloxy optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent, group F, non-aromatic heterocyclyl optionally substituted with one or more group(s) selected from the substituent group F or the like.

One embodiment is, for example, halogen, hydroxy, alkyloxy, haloalkyloxy, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent, group F or the like.

One embodiment is, for example, halogen, hydroxy, alkyloxy optionally substituted with one or more group(s) selected from the substituent group D, non-aromatic heterocyclyl optionally substituted with one or more group(s) selected from the substituent group F or the like.

One embodiment is, for example, halogen, hydroxy, alkyloxy, haloalkyloxy, aromatic carbocyclyl, non-aromatic carbocyclyl, aromatic heterocyclyl, non-aromatic heterocyclyl or the like.

One embodiment is, for example, halogen, hydroxy, alkyloxy, non-aromatic heterocyclyl or the like.

One embodiment is, for example, halogen, hydroxy, alkyloxy or the like.

The substituents on the rings of "aromatic carbocycle", "non-aromatic carbocycle", "aromatic heterocycle", and "non-aromatic heterocycle" of "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", and "substituted or unsubstituted non-aromatic heterocyclylamino", "substituted or unsubstituted aromatic carbocyclylsulfanyl", "substituted or unsubstituted non-aromatic carbocyclylsulfanyl", "substituted or unsubstituted aromatic heterocyclyl sulfanyl", and "substituted or unsubstituted non-aromatic heterocyclylsulfanyl", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl", "substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl", "substituted or unsubstituted aromatic carbocyclylcarbonyloxy", "substituted or unsubstituted non-aromatic carbocyclylcarbonyloxy", "substituted or unsubstituted aromatic heterocyclylcarbonyloxy", and "substituted or unsubstituted non-aromatic heterocyclylcarbonyloxy", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfonyloxy", "substituted or unsubstituted non-aromatic carbocyclylsulfonyloxy", "substituted or unsubstituted aromatic heterocyclylsulfonyloxy", and "substituted or unsubstituted non-aromatic heterocyclylsulfonyloxy", "substituted or unsubstituted aromatic carbocyclyloxysulfonyl", "substituted or unsubstituted non-aromatic carbocyclyloxysulfonyl", "substituted or unsubstituted aromatic heterocyclyloxysulfonyl", and "substituted or unsubstituted non-aromatic heterocyclyloxysulfonyl", "substituted or unsubstituted aromatic carbocyclylcarbamoyl", "substituted or unsubstituted non-aromatic carbocyclylcarbamoyl", "substituted or unsubstituted aromatic heterocyenylcarbamoyl", and "substituted or unsubstituted non-aromatic heterocyclylcarbamoyl".

"substituted or unsubstituted aromatic carbocyclylsulfamoyl", "substituted or unsubstituted non-aromatic carbocyclylsulfamoyl", "substituted or unsubstituted aromatic heterocyclylsulfamoyl", and "substituted or unsubstituted non-aromatic heterocyclylsulfamoyl", "substituted or unsubstituted aromatic carbocyclylcarbonylamino", "substituted or unsubstituted non-aromatic carbocyclylcarbonylamino", "substituted or unsubstituted aromatic heterocyclylcarbonylamino", and "substituted or unsubstituted non-aromatic heterocyclylcarbonylamino", "substituted or unsubstituted aromatic carbocyclylsulfonylamino", "substituted or unsubstituted non-aromatic carbocyclylsulfonylamino", "substituted or unsubstituted aromatic heterocyclylsulfonylamino", and "substituted or unsubstituted non-aromatic heterocyclylsulfonylamino", and "substituted or unsubstituted aromatic carbocyclyloxycarbonylamino", "substituted or unsubstituted non-aromatic carbocyclyloxycarbonylamino", "substituted or unsubstituted aromatic heterocyclyloxycarbonyl amino", and "substituted or unsubstituted non-aromatic heterocyclyloxycarbonylamino" in $R^{10a}$, $R^{10aa}$, $R^{10ab}$, $R^{10ac}$, $R^{10b}$, $R^{10c}$ and $R^{10d}$ include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent, group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent, group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

One embodiment, is, for example, halogen, alkyl, haloalkyl, alkyloxy, haloalkyloxy or the like.

One embodiment is, for example, halogen, alkyl, haloalkyl or the like.

One embodiment is, for example, halogen, alkyl or the like.

The substituents of "substituted or unsubstituted alkyl", and "substituted or unsubstituted alkyloxy" in $R^{10c}$ include, for example, halogen, hydroxy, carboxy, amino, carbamoyl, sulfamoyl, sulfo, cyano and the like.

One embodiment is, for example, halogen, hydroxy, cyano or the like.

One embodiment is, for example, halogen or the like.

The substituents on the rings of "substituted or unsubstituted aromatic carbocycle", "substituted or unsubstituted non-aromatic carbocycle", "substituted or unsubstituted aromatic heterocycle", and "substituted or unsubstituted non-aromatic heterocycle" when "$R^{9a}$ and $R^{10a}$ which an; attached to the adjacent atoms, or $R^{9b}$ and $R^{10b}$ which are attached to the adjacent atoms are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle", "$R^{11c}$ is taken together with $R^{9a}$ which is attached to the adjacent atom to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle", and "$R^{11c}$ is taken together with $R^{9a}$ which is attached to the adjacent atoms to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle, and the substituents on the rings of "substituted or unsubstituted 5-membered non-aromatic carbocycle", "substituted or unsubstituted 5-membered aromatic heterocycle", "substituted or unsubstituted 5-membered non-aromatic heterocycle", "substituted or unsubstituted 6-membered aromatic carbocycle", "substituted or unsubstituted 6-membered non-aromatic carbocycle", "substituted or unsubstituted 6-membered aromatic heterocycle" and "substituted or unsubstituted 6-membered non-aromatic heterocycle" in Ring F3, Ring G3, and Ring H2 include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent, group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent, group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, alkylcarbonyloxy optionally substituted with one or more group(s) selected from the substituent group D, alkyloxycarbonyl optionally substituted with one or more group(s) selected from the substituent, group D, alkylsulfonyloxy optionally substituted with one or more group(s) selected from the substituent group D, aryloxysulfonyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group (s) selected from the substituent group F or the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group (s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

One embodiment is, for example, halogen, alkyl, haloalkyl, alkyloxy, haloalkyloxy or the like.

One embodiment is, for example, halogen, alkyl or the like.

One embodiment is, for example, halogen, hydroxy, alkyl optionally substituted with one or more group(s) selected from the substituent group D, alkyloxy optionally substituted with one or more group(s) selected from the substituent group D, alkyloxycarbonyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group (s) selected from the substituent group F or the like.

One embodiment is, for example, halogen, hydroxy, alkyl optionally substituted with one or more group(s) selected from the substituent group D, alkyloxycarbonyl optionally substituted with one or more group(s) selected from the substituent group D, aromatic carbocyclyl optionally substituted with one or more group(s) selected from the substituent group F or the like.

One embodiment is, for example, halogen, hydroxy, alkyl, alkyloxyoxycarbonyl, aromatic carbocyclyl or the like.

The substituents on the rings of "substituted or unsubstituted aromatic carbocycle", "substituted or unsubstituted non-aromatic carbocycle", "substituted or unsubstituted aromatic heterocycle", and "substituted or unsubstituted non-aromatic heterocycle" when "two $R^{10a}$ which are attached to the adjacent atoms, or two $R^{10b}$ which are attached to the adjacent atoms are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle", "$R^{11c}$ is taken together with which is attached to the adjacent atom to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle", and "$R^{11d}$ is taken together with $R^{11bb}$ which is attached to the adjacent atoms to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle", and the substituents on the rings of "substituted or unsubstituted 5-membered non-aromatic carbocycle", "substituted or unsubstituted 5-membered aromatic heterocycle", "substituted or unsubstituted 5-membered non-aromatic, heterocycle", "substituted or unsubstituted 6-membered aromatic carbocycle", "substituted or unsubstituted 6-membered non-aromatic carbocycle", "substituted or unsubstituted 6-membered aromatic heterocycle" and "substituted or unsubstituted 6-membered non-aromatic heterocycle" in Ring F1, Ring F2, Ring G1, Ring G2, and Ring H1 include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group (s) selected from the substituent, group D, alkylcarbonylamino optionally substituted with one or more group(s) selected from the substituent group D, alkylsulfonylamino optionally-substituted with one or more group(s) selected from the substituent group D, alkylcarbamoyl optionally substituted with one or more group(s) selected from the substituent, group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent, group D, alkylamino optionally substituted with one or more group(s) selected from the substituent group D, alkylsulfanyl optionally substituted with one or more group (s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

One embodiment is, for example, halogen, alkyl, haloalkyl, alkyloxy, haloalkyloxy or the like.

One embodiment is, for example, halogen, alkyl, haloalkyl, alkyloxy or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynyl sulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted aryloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonylamino" in $R^{11a}$ and $R^{11b}$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent, group F, aromatic carbocyclyloxy optionally substituted with one or more group(s) selected from the substituent group F, non-aromatic carbocyclyloxy optionally substituted with one or more group(s) selected from the substituent group F, aromatic heterocyclyloxy optionally substituted with one or more group(s) selected from the substituent group F, non-aromatic heterocyclyloxy optionally substituted with one or more group(s) selected from the substituent group F, aromatic carbocyclylsulfanyl optionally substituted with one or more group(s) selected from the substituent group F, non-aromatic carbocyclylsulfanyl optionally substituted with one or more group(s) selected from the substituent group F, aromatic heterocyclylsulfanyl optionally substituted with one or more group(s) selected from the substituent group F, non-aromatic heterocyclylsulfanyl optionally substituted with one or more group(s) selected from the substituent group F, aromatic carbocyclylamino optionally substituted with one or more group(s) selected from the substituent group F, non-aromatic carbocyclylamino optionally substituted with one or more group (s) selected from the substituent group F, aromatic heterocyclylamino optionally substituted with one or more group (s) selected from the substituent group F, and non-aromatic heterocyclylamino optionally substituted with one or more group(s) selected from the substituent group F and the like.

One embodiment is, for example, halogen, hydroxy, carboxy, amino, carbamoyl, sulfamoyl, sulfo, cyano, alkyloxy optionally substituted with one or more group(s) selected from the substituent, group D, alkylamino optionally substituted with one or more group(s) selected from the substituent group D, alkylsulfanyl optionally substituted with one or more group(s) selected from the substituent, group D or the like.

One embodiment is, for example, halogen, hydroxy, cyano or the like.

One embodiment is, for example, halogen or the like.

The substituents on the rings of "aromatic carbocycle", "non-aromatic carbocycle", "aromatic heterocycle", and "non-aromatic heterocycle" of "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic, heterocyclyloxy", and "substituted or unsubstituted non-aromatic, heterocyclyloxy", "substituted or unsubstituted aromatic carbocyclylamino", "substituted or unsubstituted non-aromatic carbocyclylamino", "substituted or unsubstituted aromatic heterocyclylamino", and "substituted or unsubstituted non-aromatic heterocyclylamino", "substituted or unsubstituted aromatic carbocyclylsulfanyl", "substituted or unsubstituted non-aromatic carbocyclylsulfanyl", "substituted or unsubstituted aromatic heterocyclylsulfanyl", and "substituted or unsubstituted non-aromatic heterocyclylsulfanyl", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl", "substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl", "substituted or unsubstituted aromatic carbocyclylcarbonyloxy", "substituted or unsubstituted non-aromatic carbocyclylcarbonyloxy", "substituted or unsubstituted aromatic heterocyclylcarbonyloxy", and "substituted or unsubstituted non-aromatic heterocyclylcarbonyloxy", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfonyloxy", "substituted or unsubstituted non-aromatic carbocyclylsulfonyloxy", "substituted or unsubstituted aromatic heterocyclylsulfonyloxy", and "substituted or unsubstituted non-aromatic heterocyclylsulfonyloxy", "substituted or unsubstituted aromatic carbocyclyloxysulfonyl", "substituted or unsubstituted non-aromatic carbocyclyloxysulfonyl", "substituted or unsubstituted aromatic heterocyclyloxysulfonyl", and "substituted or unsubstituted non-aromatic heterocyclyloxysulfonyl".

"substituted or unsubstituted aromatic carbocyclylcarbamoyl", "substituted or unsubstituted non-aromatic carbocyclylcarbamoyl", "substituted or unsubstituted aromatic heterocyclylcarbamoyl", and "substituted or unsubstituted non-aromatic heterocyclylcarbamoyl", "substituted or unsubstituted aromatic carbocyclylsulfamoyl", "substituted or unsubstituted non-aromatic carbocyclylsulfamoyl", "substituted or unsubstituted aromatic heterocycylsulfamoyl", and "substituted or unsubstituted non-aromatic heterocyclylsulfamoyl", "substituted or unsubstituted aromatic carbocyclylcarbonylamino", "substituted or unsubstituted non-aromatic carbocyclylcarbonylamino", "substituted or unsubstituted aromatic heterocyclylcarbonylamino", and "substituted or unsubstituted non-aromatic heterocyclylcarbonyl amino", "substituted or unsubstituted aromatic carbocyclylsulfonylamino", "substituted or unsubstituted non-aromatic carbocyclylsulfonylamino", "substituted or unsubstituted aromatic heterocyclylsulfonylamino", and "substituted or unsubstituted non-aromatic heterocyclylsulfonylamino", and "substituted or unsubstituted aromatic carbocyclyloxycarbonyl amino", "substituted or unsubstituted non-aromatic carbocyclyloxycarbonylamino", "substituted or unsubstituted aromatic heterocyclyloxycarbonylamino", and "substituted or unsubstituted non-aromatic heterocyclyloxycarbonylamino" in $R^{10a1}$, $R^{10a2}$, $R^{10b1}$, $R^{11a}$ and $R^{11b}$ include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent, group D, alkylcarbonyl optionally substituted with one or more group(s) selected from the substituent group D, alkylsulfonyl optionally substituted with one or more group (s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group (s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

One embodiment is, for example, halogen, alkyl, haloalkyl, alkyloxy, haloalkyloxy or the like.

One embodiment is, for example, halogen, alkyl, haloalkyl or the like.

One embodiment is, for example, halogen or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", and "substituted or unsubstituted alkynyloxy" in $R^Y$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s)

selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F and the like.

One embodiment is, for example, halogen, hydroxy, carboxy, amino, carbamoyl, sulfamoyl, sulfo, cyano or the like.

One embodiment, is, for example, halogen, hydroxy, cyano or the like.

One embodiment is, for example, halogen.

The substituents on the rings of "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl" in $R^Y$ include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent, group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent, group D, alkyloxy optionally substituted with one or more group(s) selected from the substituent group D, alkylamino optionally substituted with one or more group(s) selected from the substituent group D, alkylsulfanyl optionally substituted with one or more group (s) selected from the substituent group D or the like.

One embodiment is, for example, halogen, alkyl optionally substituted with one or more group(s) selected from the substituent group D, alkyloxy optionally substituted with one or more group(s) selected from the substituent, group D or the like.

One embodiment is, for example, halogen, alkyl, haloalkyl, alkyloxy, haloalkyloxy or the like.

One embodiment is, for example, halogen, alkyl, haloalkyl or the like.

One embodiment is, for example, halogen or the like.

One aspect of the present invention is illustrated below.

Specific examples of each substituent in the compound represented by Formula (I) or pharmaceutically acceptable salt thereof are shown below. All combinations of these specific examples are illustrated for the compound represented by Formula (I).

(a)

A compound according to any one of the following (a-1) to (a-3) or a pharmaceutically acceptable salt thereof.

(a-1) The compound represented by formula (I) wherein X is $N(R^{7a})$ or O, or pharmaceutically acceptable salt thereof.

(a-2) The compound represented by formula (I) wherein X is $N(R^{7a})$, or pharmaceutically acceptable salt thereof.

(a-3) The compound represented by formula (I) wherein X is O, or pharmaceutically acceptable salt thereof, (b) A compound according to any one of the following (b-1) to (b-3) or a pharmaceutically acceptable salt thereof.

(b-1) The compound of formula (I) or the above (a), wherein $R^{7a}$ is a hydrogen atom, or substituted or unsubstituted alkyl, or pharmaceutically acceptable salt thereof.

(b-2) The compound of formula (I) or the above (a), wherein $R^{7a}$ is a hydrogen atom, alkyl, or haloalkyl, or pharmaceutically acceptable salt thereof.

(b-3) The compound of formula (I) or the above (a), wherein $R^{7a}$ is a hydrogen atom, or pharmaceutically acceptable salt thereof.

(e) A compound according to any one of the following (c-1) to (c-4) or a pharmaceutically acceptable salt thereof.

(c-1) The compound of formula (I) or the above (a) or (b), wherein $R^{8a}$ and $R^{8b}$ are each independently a hydrogen atom, halogen or substituted or unsubstituted alkyl, or pharmaceutically acceptable salt thereof.

(c-2) The compound of formula (I) or the above (a) or (b), wherein $R^{8a}$ and $R^{8b}$ are each independently a hydrogen atom, halogen, alkyl, or haloalkyl, or pharmaceutically acceptable salt thereof.

(c-3) The compound of formula (I) or the above (a) or (b) wherein $R^{8a}$ and $R^{8b}$ are each independently a hydrogen atom, or halogen, or pharmaceutically acceptable salt thereof.

(c-4) The compound of formula (I) or the above (a) or (b) wherein each of $R^{8a}$ and $R^{8b}$ is a hydrogen atom, or pharmaceutically acceptable salt thereof.

(d) A compound according to any one of the following (d-1) to (d-7) or a pharmaceutically acceptable salt thereof.

(d-1) The compound of any one of formula (I) and the above (a) to (c), wherein

[Chemical Formula 33]

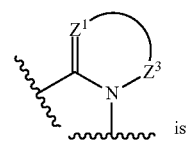

is

[Chemical Formula 34]

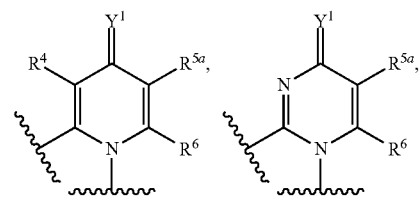

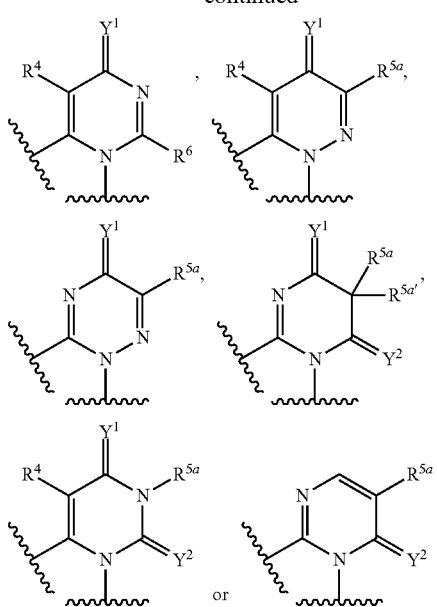

or pharmaceutically acceptable salt thereof.

(d-2) The compound of any one of formula (I) and the above (a) to (c), wherein

[Chemical Formula 35]

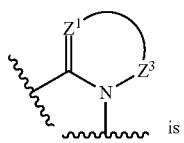 is

[Chemical Formula 36]

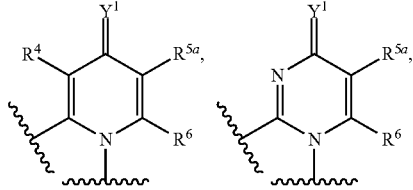

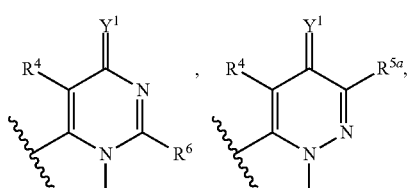

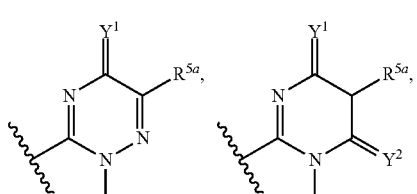

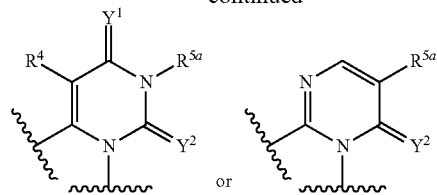

or or pharmaceutically acceptable salt thereof.

(d-3) The compound of any one of formula (I) and the above (a) to (c), wherein

[Chemical Formula 37]

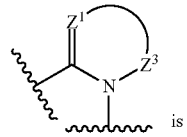 is

[Chemical Formula 38]

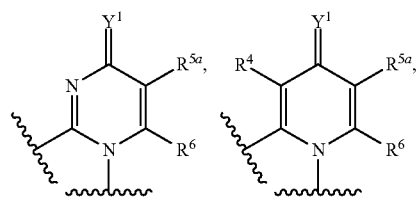

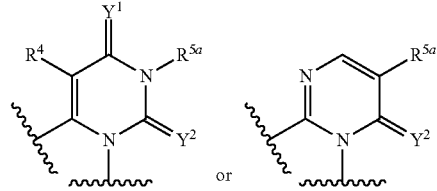

or or pharmaceutically acceptable salt thereof.

(d-4) The compound of any one of formula (I) and the above (a) to (c), wherein

[Chemical Formula 39]

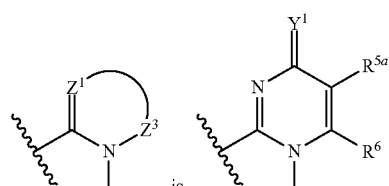 is or pharmaceutically acceptable salt thereof.

(d-5) The compound of any one of formula (I) and the above (a) to (c), wherein

[Chemical Formula 40]

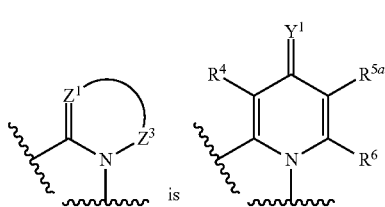

is or pharmaceutically acceptable salt thereof.
(d-6) The compound of any one of formula (I) and the above (a) to (c), wherein

[Chemical Formula 41]

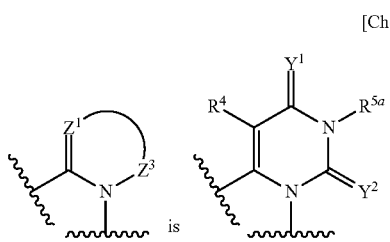

is or pharmaceutically acceptable salt thereof.
(d-7) The compound of any one of formula (I) and the above (a) to (c), wherein

[Chemical Formula 42]

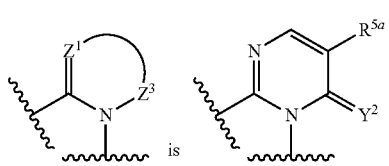

is or pharmaceutically acceptable salt thereof.
(e) A compound according to any one of the following (e-1) to (e-37) or a pharmaceutically acceptable salt thereof.
(e-1) The compound of any one of formula (I) and the above (a) to (d), wherein $R^1$ is substituted or unsubstituted 6- to 10-membered aromatic carbocyclyl, substituted or unsubstituted 3- to 10-membered non-aromatic carbocyclyl, substituted or unsubstituted 5- to 10-membered aromatic heterocyclyl, or substituted or unsubstituted 3- to 10-membered non-aromatic heterocyclyl, or pharmaceutically acceptable salt thereof.
(e-2) The compound of any one of formula (I) and the above (a) to (d), wherein $R^1$ is substituted or unsubstituted 6-membered aromatic carbocyclyl, substituted or unsubstituted 3- to 6-membered non-aromatic carbocyclyl, substituted or unsubstituted 5- to 6-membered aromatic heterocyclyl, or substituted or unsubstituted 5- to 6-membered non-aromatic heterocyclyl, or pharmaceutically acceptable salt thereof.
(e-3) The compound of any one of formula (I) and the above (a) to (d), wherein $R^1$ is substituted or unsubstituted 6-membered aromatic carbocyclyl, or substituted or unsubstituted 5- to 6-membered aromatic heterocyclyl, or pharmaceutically acceptable salt thereof.
(e-4) The compound of any one of formula (I) and the above (a) to (d), wherein $R^1$ is substituted or unsubstituted phenyl, or substituted or unsubstituted thienyl, or pharmaceutically acceptable salt thereof.
(e-5) The compound of any one of formula (I) and the above (a) to (d), wherein $R^1$ is 6-membered aromatic carbocyclyl substituted with one or more halogen atom(s) and optionally substituted with one or more and same or different substituent(s), 3- to 6-membered non-aromatic carbocyclyl substituted with one or more halogen atom(s) and optionally substituted with one or more and same or different substituent(s), 5- to 6-membered aromatic heterocyclyl substituted with one or more halogen atom(s) and optionally substituted with one or more and same or different substituent(s), or 5- to 6-membered non-aromatic heterocyclyl substituted with one or more halogen atom(s) and optionally substituted with one or more and same or different substituent(s), or pharmaceutically acceptable salt thereof.
(e-6) The compound of any one of formula (I) and the above (a) to (d), wherein $R^1$ is 6-membered aromatic carbocyclyl substituted with one or more halogen atom(s) and optionally substituted with one or more and same or different substituent(s), or 5' to 6-membered aromatic heterocyclyl substituted with one or more halogen atom(s) and optionally substituted with one or more and same or different substituent(s), or pharmaceutically acceptable salt thereof.
(e-7) The compound of any one of formula (I) and the above (a) to (d), wherein $R^1$ is phenyl substituted with one or more halogen atom(s) and optionally substituted with one or more and same or different substituent(s), or thienyl substituted with one or more halogen atom(s) and optionally substituted with one or more and same or different substituent(s), or pharmaceutically acceptable salt thereof.
(e-8) The compound of any one of formula (I) and the above (a) to (d), wherein $R^1$ is phenyl substituted with one or more halogen atom(s) and optionally substituted with one or more group(s) selected from halogen, alkyl, haloalkyl, alkyloxy, and haloaryloxy, or thienyl substituted with one or more halogen atom(s) and optionally substituted with one or more group(s) selected from halogen, alkyl, haloalkyl, alkyloxy, and haloaryloxy, or pharmaceutically acceptable salt thereof.
(e-9) The compound of any one of formula (I) and the above (a) to (d), wherein $R^1$ is phenyl substituted with one or more halogen atom(s) and optionally substituted with one or more group(s) selected from halogen, alkyl, and haloalkyl, or pharmaceutically acceptable salt thereof.
(e-10) The compound of any one of formula (I) and the above (a) to (d), wherein $R^1$ is a group represented by the formula:

[Chemical Formula 43]

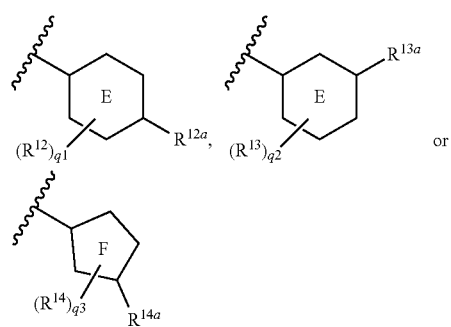

wherein
Ring E is a 6-membered aromatic carbocycle, a 6-membered non-aromatic carbocycle, a 6-membered aromatic heterocycle, or a 6-membered non-aromatic heterocycle;
Ring F is a 5-membered non-aromatic carbocycle, a 5-membered aromatic heterocycle, or a 5-membered non-aromatic heterocycle;
$R^{12a}$, $R^{13a}$, and $R^{14a}$ are each independently halogen;
$R^{12}$, $R^{13}$, and $R^{14}$ are each independently a group selected from the substituent group C;
q1 is an integer from 0 to 2;
q2 is an integer from 0 to 2; and
q3 is 0 or 1,
or pharmaceutically acceptable salt thereof.
(e-11) The compound of any one of formula (I) and the above (a) to (d), wherein $R^1$ is a group represented by the formula:

[Chemical Formula 44]

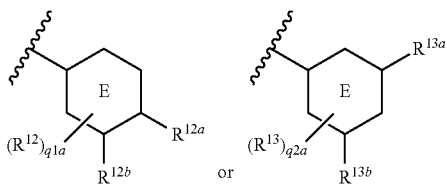

wherein
$R^{12}$ and $R^{13}$ are each independently a group selected from the substituent group C;
$R^{12a}$ and $R^{13a}$ are each independently halogen;
$R^{12b}$ and $R^{13b}$ are each independently halogen, alkyl optionally substituted with one or more group(s) selected from the substituent group D, or alkyloxy optionally substituted with one or more group(s) selected from the substituent group D;
q1a is 0 or 1; and
q2a is 0 or 1,
or pharmaceutically acceptable salt thereof.
(e-12) The compound of any one of formula (I) and the above (a) to (d), wherein $R^1$ is a group represented by the formula:

[Chemical Formula 45]

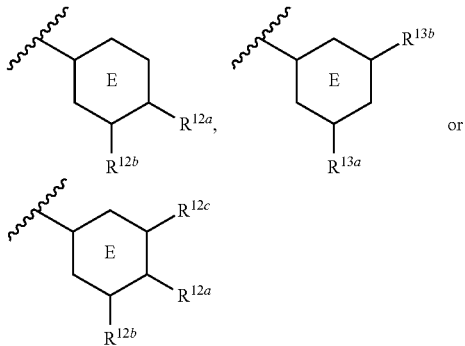

wherein
$R^{12a}$ and $R^{13a}$ are each independently halogen; and
each of $R^{12b}$, $R^{12c}$, and $R^{13b}$ is halogen, alkyl optionally substituted with one or more group(s) selected from the substituent group D, or alkyloxy optionally substituted with one or more group(s) selected from the substituent group D, or pharmaceutically acceptable salt thereof.

(e-13) The compound of any one of the above (e-10) to (e-12), wherein $R^{12a}$, $R^{13a}$ and $R^{14a}$ are each independently a fluorine atom, or a chlorine atom, or pharmaceutically acceptable salt thereof.

(e-14) The compound of any one of the above (e-10) to (e-12), wherein each of $R^{12a}$, $R^{13a}$ and $R^{14a}$ is a fluorine atom, or pharmaceutically acceptable salt thereof.

(e-15) The compound of any one of the above (e-10) to (e-14), wherein $R^{12b}$, $R^{12c}$ and $R^{13b}$ are each independently halogen, or alkyl optionally substituted with one or more group(s) selected from the substituent group D, or pharmaceutically acceptable salt thereof.

(e-16) The compound of any one of the above (e-10) to (e-14), wherein $R^{12b}$, $R^{12c}$ and $R^{13b}$ are each independently halogen, alkyl, or haloalkyl, or pharmaceutically acceptable salt thereof.

(e-17) The compound of any one of the above (e-10) to (e-14), wherein $R^{12b}$, $R^{12c}$ and $R^{31b}$ are each independently halogen, methyl, or halomethyl, or pharmaceutically acceptable salt thereof.

(e-18) The compound of any one of the above (e-10) to (e-14), wherein $R^{12b}$, $R^{12c}$ and $R^{13b}$ are each independently a fluorine atom, or a chlorine atom, or pharmaceutically acceptable salt thereof.

(e-19) The compound of any one of the above (e-10) to (e-14), wherein each of $R^{12b}$, $R^{12c}$ anil $R^{13b}$ is a fluorine atom, or pharmaceutically acceptable salt thereof.

(e-20) The compound of any one of the above (e-10) to (e-19), wherein $R^{12}$, $R^{13}$, and $R^{14}$ are each independently halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent, group D, alkylamino optionally substituted with one or more group(s) selected from the substituent group D, or alkylsulfanyl optionally substituted with one or more group(s) selected from the substituent, group D, or pharmaceutically acceptable salt thereof.

(e-21) The compound of any one of the above (e-10) to (e-19), wherein $R^{12}$, $R^{13}$, and $R^{14}$ are each independently halogen, cyano, alkyl optionally substituted with one or more group(s) selected from the substituent group D, or alkyloxy optionally substituted with one or more group(s) selected from the substituent group D, or pharmaceutically acceptable salt thereof.

(e-22) The compound of any one of the above (e-10) to (e-19), wherein $R^{12}$, $R^{13}$, and $R^{14}$ are each independently halogen, alkyl, or haloalkyl, or pharmaceutically acceptable salt thereof.

(e-23) The compound of any one of the above (e-10) to (e-19), wherein $R^{12}$, $R^{13}$, and $R^{14}$ are each independently halogen, methyl, or halomethyl, or pharmaceutically acceptable salt thereof.

(e-24) The compound of any one of the above (e-10) to (e-19), wherein $R^{12}$, $R^{13}$, and $R^{14}$ are each independently a fluorine atom, or a chlorine atom, or pharmaceutically acceptable salt thereof.

(e-25) The compound of any one of the above (e-10) to (e-19), wherein each of $R^{12}$, $R^{13}$, and $R^{14}$ is a fluorine atom, or pharmaceutically acceptable salt thereof.

(e-26) The compound of any one of the above (e-10) to (e-25), wherein each of q1, q2, and q3 is 0, or pharmaceutically acceptable salt thereof.

(e-27) The compound of any one of the above (e-10) to (e-25), wherein each of q1, q2, and q3 is 1, or pharmaceutically acceptable salt thereof.

(e-28) The compound of any one of the above (e-10) to (e-25), wherein each of q1 and q2 is 2, or pharmaceutically acceptable salt, thereof.

(e-29) The compound of any one of the above (e-10) to (e-25), wherein each of q1a and q2a is 0, or pharmaceutically acceptable salt thereof.

(e-30) The compound of any one of the above (e-10) to (e-25), wherein each of q1a and q2a is 1, or pharmaceutically acceptable salt thereof.

(e-31) The compound of any one of the above (e-10) to (e-30), wherein Ring E is cyclohexene, benzene or a 0-membered aromatic heterocycle, or pharmaceutically acceptable salt thereof.

(e-32) The compound of any one of the above (e-10) to (e-30), wherein Ring E is benzene, or a 6-membered aromatic heterocycle, or pharmaceutically acceptable salt thereof.

(e-33) The compound of any one of the above (e-10) to (e-30), wherein Ring E is benzene, pyridine, pyrimidine, or pyrazine, or pharmaceutically acceptable salt thereof.

(e-31) The compound of any one of the above (e-10) to (e-30), wherein Ring E is benzene, or pyridine, or pharmaceutically acceptable salt thereof.

(e-35) The compound of any one of the above (e-10) to (e-30), wherein Ring E is benzene, or pharmaceutically acceptable salt thereof.

(e-36) The compound of any one of the above (e-10) to (e-35), wherein Ring F is a 5-membered aromatic heterocycle, or pharmaceutically acceptable salt thereof.

(e-37) The compound of any one of the above (e-10) to (e-35), wherein Ring F is thiophene, or pharmaceutically acceptable salt thereof.

(f) A compound according to any one of the following (f-1) to (f-21) or a pharmaceutically acceptable salt thereof.

(f-1) The compound of any one of formula (I) and the above (a) to (e), wherein $R^8$ is a group represented by the Formula:

[Chemical Formula 46]

wherein $R^{9a}$ and $R^{9b}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted aryloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonyl amino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxy carbonylamino:

$R^{10a}$ and $R^{10b}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfinyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted aryloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclyl amino, substituted or unsubstituted non-aromatic carbocyclylmino, substituted or unsubstituted aromatic heterocyclylamino, substituted or unsubstituted non-aromatic heterocyclylamino, substituted or unsubstituted aromatic carbocyclyl sulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclyl sulfonyl, substituted or unsubstituted aromatic heterocyclyl sulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonyl amino, substituted or unsubstituted aromatic heterocyclylcarbonyl amino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino:

p1 is an integer from 0 to 3; and
p2 is an integer from 0 to 2,
or pharmaceutically acceptable salt thereof.

(f-2) The compound of the above (f-1), wherein $R^3$ is

[Chemical Formula 47]

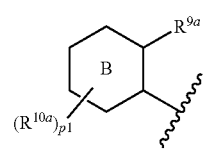

or pharmaceutically acceptable salt thereof.

(f-3) The compound of the above (f-1), wherein $R^3$ is

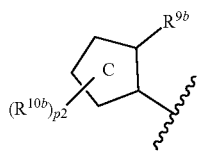

or pharmaceutically acceptable salt thereof.

(f-4) The compound of any one of the above (f-1) to (f-3), wherein $R^{10a}$ and $R^{10b}$ are each independently halogen, hydroxy, amino, carbamoyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynyl sulfonyl, substituted or unsubstituted alkyloxycarbonyl, substituted or unsubstituted alkenyloxycarbonyl, substituted or unsubstituted alkynyloxycarbonyl, substituted or unsubstituted aryloxysulfonyl, substituted or unsubstituted alkenyloxysulfonyl, substituted or unsubstituted alkynyloxysulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl, or pharmaceutically acceptable salt thereof.

(f-5) The compound of any one of the above (f-1) to (f-3), wherein $R^{10a}$ and $R^{10b}$ are each independently halogen, hydroxy, amino, carbamoyl, cyano, substituted or unsubstituted alkyl, substituted or unsubstituted alkenyl, substituted or unsubstituted alkyloxy, substituted or unsubstituted alkylsulfanyl, substituted or unsubstituted alkylamino, substituted or unsubstituted alkylcarbonyl, substituted or unsubstituted alkylsulfonyl, substituted or unsubstituted alkyloxycarbonyl, substituted or unsubstituted aryloxysulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic, carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl, or pharmaceutically acceptable salt thereof.

(f-6) The compound of any one of the above (f-1) to (f-3), wherein $R^{10a}$ and $R^{10b}$ are each independently halogen, hydroxy, amino, carbamoyl, cyano, substituted or unsubstituted alkyl, substituted or unsubstituted alkenyl, substituted or unsubstituted alkynyl, substituted or unsubstituted alkyloxy, substituted or unsubstituted alkylsulfanyl, substituted or unsubstituted alkylamino, substituted or unsubstituted alkylcarbonyl, substituted or unsubstituted alkylsulfonyl, substituted or unsubstituted alkyloxycarbonyl, substituted or unsubstituted aryloxysulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.

(f-7) The compound of any one of the above (f-1) to (f-3), wherein $R^{10a}$ and $R^{10b}$ are each independently halogen, hydroxy, carbamoyl, cyano, substituted or unsubstituted alkyl, substituted or unsubstituted alkenyl, substituted or unsubstituted alkynyl, substituted or unsubstituted alkyloxy, substituted or unsubstituted alkylsulfanyl, substituted or unsubstituted alkylamino, substituted or unsubstituted alkylcarbonyl, substituted or unsubstituted alkylsulfonyl, substituted or unsubstituted alkyloxycarbonyl, substituted or unsubstituted aromatic heterocyclyl, substituted or unsubstituted non-aromatic heterocyclyl, substituted or unsubstituted aromatic carbocyclyloxy, or substituted or unsubstituted aromatic heterocyclyloxy, or pharmaceutically acceptable salt thereof.

(f-8) The compound of any one of the above (f-1) to (f-3), wherein $R^{10a}$ and $R^{10b}$ are each independently halogen; hydroxy; carbamoyl; cyano;

alkyl substituted with one or more group(s) selected from halogen, hydroxy, alkyloxy, and a non-aromatic heterocycle; unsubstituted alkyl;

alkenyl substituted with one or more group(s) selected from halogen, hydroxy, alkyloxy, and a non-aromatic heterocycle; unsubstituted alkenyl;

alkynyl substituted with one or more group(s) selected from halogen, hydroxy, alkyloxy, and a non-aromatic heterocycle; unsubstituted alkynyl;

alkyloxy substituted with one or more group(s) selected from halogen, hydroxy, alkyloxy, and a non-aromatic heterocycle; unsubstituted alkyloxy;

alkylsulfanyl substituted with one or more group(s) selected from halogen, hydroxy, alkyloxy, and a non-aromatic heterocycle; unsubstituted alkylsulfanyl;

alkylamino substituted with one or more group(s) selected from halogen, hydroxy, alkyloxy, and a non-aromatic heterocyclo; unsubstituted alkylamino;

alkylcarbonyl substituted with one or more group(s) selected from halogen, hydroxy, alkyloxy, and a non-aromatic heterocycle; unsubstituted alkylcarbonyl;
alkylsulfonyl substituted with one or more group(s) selected from halogen, hydroxy, alkyloxy, and a non-aromatic heterocycle; unsubstituted alkylsulfonyl;
alkyloxycarbonyl substituted with one or more group(s) selected from halogen, hydroxy, alkyloxy, and a non-aromatic heterocycle; unsubstituted alkyloxycarbonyl;
aromatic heterocyclyl substituted with one or more group(s) selected from halogen, alkyl, alkyloxy, and alkyloxycarbonyl; unsubstituted aromatic heterocyclyl;
non-aromatic heterocyclyl substituted with one or more group(s) selected from halogen, alkyl, alkyloxy, and alkyloxycarbonyl; unsubstituted non-aromatic heterocyclyl;
aromatic carbocyclyloxy substituted with one or more group(s) selected from halogen, alkyl, alkyloxy, and alkyloxycarbonyl; unsubstituted aromatic carbocyclyloxy; aromatic heterocyclyloxy substituted with one or more group(s) selected from halogen, alkyl, alkyloxy, and alkyloxycarbonyl; or unsubstituted aromatic heterocyclyloxy, or pharmaceutically acceptable salt thereof.
(f-9) The compound of any one of the above (f-1) to (f-3), wherein $R^{10a}$ and $R^{10b}$ are each independently halogen; hydroxy; carbamoyl; cyano;
alkyl substituted with one or more group(s) selected from halogen, hydroxy, alkyloxy, and a non-aromatic heterocycle; unsubstituted alkyl;
unsubstituted alkenyl; unsubstituted alkynyl;
alkyloxy substituted with one or more group(s) selected from halogen; unsubstituted alkyloxy;
alkylsulfanyl substituted with one or more group(s) selected from halogen; unsubstituted alkylsulfanyl;
unsubstituted alkylamino; unsubstituted alkylcarbonyl; unsubstituted alkylsulfonyl; unsubstituted alkyloxycarbonyl;
aromatic heterocyclyl substituted with one or more group(s) selected from alkyl and alkyloxy; unsubstituted aromatic heterocyclyl;
non-aromatic heterocyclyl substituted with one or more group(s) selected from alkyl and alkyloxycarbonyl; unsubstituted non-aromatic heterocyclyl; unsubstituted aromatic carbocyclyloxy;
aromatic heterocyclyloxy substituted with one or more group(s) selected from halogen; or
unsubstituted aromatic heterocyclyloxy, or pharmaceutically acceptable salt thereof.
(f10) The compound of any one of the above (f-1) to (f-3), wherein $R^{10a}$ and $R^{10b}$ are each independently halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.
(f-11) The compound of any one of the above (f-1) to (f-3), wherein $R^{10a}$ and $R^{10b}$ are each independently halogen, substituted or unsubstituted alkyl, substituted or unsubstituted alkyloxy, substituted or unsubstituted alkylsulfanyl, substituted or unsubstituted alkylamino, substituted or unsubstituted alkylcarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclyl sulfanyl, or pharmaceutically acceptable salt thereof.
(f-12) The compound of any one of the above (f-1) to (f-3), wherein $R^{10a}$ and $R^{10b}$ are each independently halogen, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted noil-aromatic heterocyclyl, substituted or unsubstituted aromatic carboey cl yloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.
(f-13) The compound of any one of the above (f-1) to (f-3), wherein $R^{10a}$ and $R^{0b}$ are each independently halogen, substituted or unsubstituted alkyl, substituted or unsubstituted alkyloxy, substituted or unsubstituted alkylsulfanyl, substituted or unsubstituted alkylamino, substituted or unsubstituted aromatic heterocyclyl, substituted or unsubstituted non-aromatic heterocyclyl, substituted or unsubstituted aromatic heterocyclyloxy, substituted or unsubstituted non-aromatic heterocyclyloxy, substituted or unsubstituted aromatic heterocyclylamino, substituted or unsubstituted non-aromatic heterocyclylamino, substituted or unsubstituted aromatic heterocyclylsulfanyl, or substituted or unsubstituted non-aromatic heterocyclylsulfanyl, or pharmaceutically acceptable salt thereof.
(f-14) The compound of any one of the above (f-1) to (f-3), wherein $R^{10a}$ and $R^{10b}$ are each independently halogen, substituted or unsubstituted alkyl, substituted or unsubstituted alkyloxy, substituted or unsubstituted aromatic heterocyclyl, substituted or unsubstituted non-aromatic heterocyclyl, substituted or unsubstituted aromatic heterocyclyloxy, or substituted or unsubstituted non-aromatic heterocyclyloxy, or pharmaceutically acceptable salt thereof.
(f-15) The compound of any one of the above (f-1) to (f-3), wherein $R^{10a}$ and $R^{10b}$ are each independently halogen; alkyl; haloalkyl; alkyloxy; haloalkyloxy; aromatic heterocyclyl substituted with one or more group(s) selected from halogen, alkyl, haloalkyl, alkyloxy, and haloalkyloxy; unsubstituted aromatic heterocyclyl; non-aromatic heterocyclyl substituted with one or more group(s) selected from halogen, alkyl, haloalkyl, alkyloxy, and haloalkyloxy; unsubstituted non-aromatic heterocyclyl;
aromatic heterocyclyloxy substituted with one or more group(s) selected from halogen, alkyl, haloalkyl, alkyloxy, and haloalkyloxy; or unsubstituted aromatic heterocyclyloxy, or pharmaceutically acceptable salt thereof.

(f-16) The compound of any one of the above (f-1) to (f-1.5), wherein p1 is 1 or 2, or pharmaceutically acceptable salt thereof.

(f-17) The compound of any one of the above (f-1) to (f-15), wherein p1 is 2, or pharmaceutically acceptable salt thereof.

(f-18) The compound of any one of the above (f-1) to (f-15), wherein p1 is 1, or pharmaceutically acceptable salt thereof.

(f-19) The compound of any one of the above (f-1) to (f-1.5), wherein p1 is 0, or pharmaceutically acceptable salt thereof.

(f-20) The compound of any one of the above (f-1) to (f-9), wherein p2 is 1, or pharmaceutically acceptable salt thereof.

(f-21) The compound of any one of the above (f-1) to (f-19), wherein p2 is 0, or pharmaceutically acceptable salt thereof.

(g) A compound according to any one of the following (g-1) to (g-51) or a pharmaceutically acceptable salt thereof.

(g-1) The compound of any one of Formula (I) and the above (a) to (f), wherein $R^3$ is a group represented by the Formula:

[Chemical Formula 49]

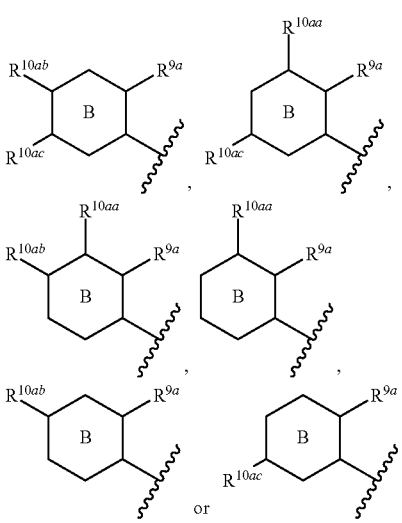

wherein $R^{10aa}$, $R^{10ab}$, and $R^{10ac}$ are each independently the same as $R^{10a}$ of the above (f-1),
or pharmaceutically acceptable salt thereof.

(g-2) The compound of any one of Formula (I) and the above (a) to (f), wherein $R^3$ is

[Chemical Formula 50]

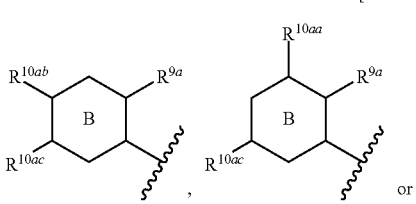

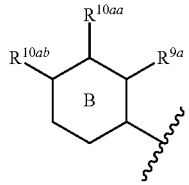

or pharmaceutically acceptable salt thereof.

(g-3) The compound of any one of Formula (I) and the above (a) to (f), wherein $R^3$ is

[Chemical Formula 51]

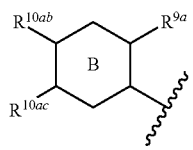

or pharmaceutically acceptable salt thereof.

(g-4) The compound of any one of Formula (I) and the above (a) to (f), wherein $R^3$ is

[Chemical Fromula 52]

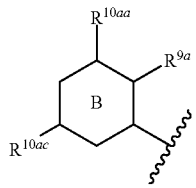

or pharmaceutically acceptable salt thereof.

(g-5) The compound of any one of Formula (I) and the above (a) to (f), wherein $R^3$ is

[Chemical Formula 53]

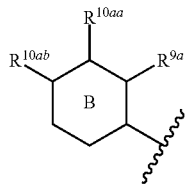

or pharmaceutically acceptable salt thereof.

(g-6) The compound of any one of Formula (I) and the above (a) to (f), wherein $R^3$ is

[Chemical Formula 54]

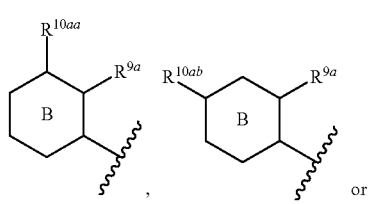

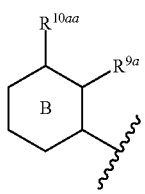

or pharmaceutically acceptable salt thereof.
(g-7) The compound of any one of Formula (I) and the above (a) to (f), wherein $R^3$ is

[Chemical Formula 55]

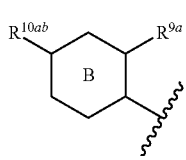

or pharmaceutically acceptable salt thereof.
(g-8) The compound of any one of Formula (I) and the above (a) to (f), wherein $R^3$ is

[Chemical Formula 56]

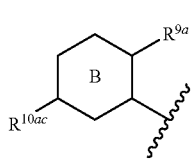

or pharmaceutically acceptable salt thereof.
(g-9) The compound of any one of Formula (I) and the above (a) to (f), wherein $R^3$ is

[Chemical Formula 57]

or pharmaceutically acceptable salt thereof.
(g-10) The compound of any one of the above (g-1) to (g-9), wherein $R^{10aa}$ is halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfonyl, substituted or unsubstituted alkynylsulfanyl, substituted or unsubstituted alkylamino, substituted or unsubstituted alkenylamino, substituted or unsubstituted alkynylamino, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.

(g-11) The compound of any one of the above (g-1) to (g-9), wherein $R^{10aa}$ is halogen, substituted or unsubstituted alkyl, substituted or unsubstituted alkyloxy, substituted or unsubstituted alkylsulfanyl, substituted or unsubstituted alkylamino, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.

(g-12) The compound of any one of the above (g-1) to (g-9), wherein $R^{10aa}$ is halogen, substituted or unsubstituted alkyl, substituted or unsubstituted alkyloxy, substituted or unsubstituted alkylsulfanyl, substituted or unsubstituted alkylamino, substituted or unsubstituted alkyloxycarbonyl, substituted or unsubstituted aromatic heterocyclyl, or substituted or unsubstituted aromatic carbocyclyloxy, or pharmaceutically acceptable salt thereof.

(g-13) The compound of any one of the above (g-1) to (g-9), wherein $R^{10aa}$ is halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, or substituted or unsubstituted alkynylamino, or pharmaceutically acceptable salt thereof.

(g-14) The compound of any one of the above (g-1) to (g-9), wherein $R^{10aa}$ is halogen, substituted or unsubstituted alkyl, substituted or unsubstituted alkyloxy, substituted or unsubstituted alkylsulfanyl, or substituted or unsubstituted alkylamino, or pharmaceutically acceptable salt thereof.

(g-15) The compound of any one of the above (g-1) to (g-9), wherein $R^{10aa}$ is halogen, substituted or unsubstituted alkyl, or substituted or unsubstituted alkyloxy, or pharmaceutically acceptable salt thereof.

(g-16) The compound of any one of the above (g-1) to (g-9), wherein $R^{10aa}$ is halogen, alkyl, haloalkyl, alkyloxy, or haloalkyloxy, or pharmaceutically acceptable salt thereof.

(g-17) The compound of any one of the above (g-1) to (g-9), wherein $R^{10aa}$ is alkyl substituted with one or more group (s) selected from halogen, hydroxy, and alkyloxy; unsubstituted alkyl;
alkyloxy substituted with one or more group(s) selected from halogen, hydroxy, and alkyloxy; unsubstituted alkyloxy;
alkylamino substituted with one or more group(s) selected from halogen, hydroxy, and alkyloxy; unsubstituted alkylamino;
alkylsulfanyl substituted with one or more group(s) selected from halogen, hydroxy, and alkyloxy; unsubstituted alkylsulfanyl;
alkyloxycarbonyl substituted with one or more group(s) selected from halogen, hydroxy, and alkyloxy; unsubstituted alkyloxycarbonyl;

unsubstituted aromatic heterocyclyl; or unsubstituted aromatic carbocyclyloxy, or pharmaceutically acceptable salt thereof.

(g-18) The compound of any one of the above (g-1) to (g-9), wherein $R^{10aa}$ is alkyl substituted with one or more group(s) selected from halogen, hydroxy, and alkyloxy; unsubstituted alkyl;
alkyloxy substituted with one or more group(s) selected from halogen; unsubstituted alkyloxy:
unsubstituted alkylamino;
unsubstituted alkylsulfanyl;
unsubstituted alkyloxycarbonyl;
unsubstituted aromatic heterocyclyl; or
unsubstituted aromatic carbocyclyloxy,
or pharmaceutically acceptable salt thereof.

(g-19) The compound of any one of the above (g-1) to (g-9), wherein $R^{10aa}$ is halogen, or pharmaceutically acceptable salt thereof.

(g-20) The compound of any one of the above (g-1) to (g-19), wherein $R^{10ab}$ is halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt, thereof.

(g-21) The compound of any one of the above (g-1) to (g-19), wherein $R^{10ab}$ is halogen, hydroxy, cyano, substituted or unsubstituted alkyl, substituted or unsubstituted alkyloxy, substituted or unsubstituted alkylsulfanyl, substituted or unsubstituted alkylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.

(g-22) The compound of any one of the above (g-1) to (g-19), wherein $R^{10ab}$ is halogen, cyano, substituted or unsubstituted alkyl, substituted or unsubstituted alkyloxy, substituted or unsubstituted non-aromatic heterocyclyl, or substituted or unsubstituted aromatic heterocyclyloxy, or pharmaceutically acceptable salt thereof.

(g-23) The compound of any one of the above (g-1) to (g-19), wherein $R^{10ab}$ is halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, or substituted or unsubstituted alkynylamino, or pharmaceutically acceptable salt thereof.

(g-24) The compound of any one of the above (g-1) to (g-19), wherein $R^{10ab}$ is halogen, substituted or unsubstituted alkyl, substituted or unsubstituted alkyloxy, substituted or unsubstituted alkylsulfanyl, or substituted or unsubstituted alkylamino, or pharmaceutically acceptable salt thereof.

(g-25) The compound of any one of the above (g-1) to (g-19), wherein $R^{10ab}$ is halogen, substituted or unsubstituted alkyl, or substituted or unsubstituted alkyloxy, or pharmaceutically acceptable salt, thereof.

(g-26) The compound of any one of the above (g-1) to (g-19), wherein $R^{10ab}$ is halogen, alkyl, haloalkyl, alkyloxy, or haloalkyloxy, or pharmaceutically acceptable salt thereof.

(g-27) The compound of any one of the above (g-1) to (g-19), wherein $R^{10ab}$ is halogen; cyano;
alkyl substituted with one or more group(s) selected from halogen; unsubstituted alkyl;
alkyloxy substituted with one or more group(s) selected from halogen; unsubstituted alkyloxy;
alkylamino substituted with one or more group(s) selected from halogen; unsubstituted alkyloxy;
non-aromatic heterocyclyl substituted with one or more group(s) selected from halogen; unsubstituted non-aromatic heterocyclyl;
aromatic heterocyclyloxy substituted with one or more group(s) selected from halogen; or unsubstituted aromatic heterocyclyloxy,
or pharmaceutically acceptable salt thereof.

(g-28) The compound of any one of the above (g-1) to (g-19), wherein $R^{10ab}$ is halogen; cyano;
unsubstituted alkyl;
alkyloxy substituted with one or more groups(s) selected from halogen; unsubstituted alkyloxy;
unsubstituted alkylamino;
unsubstituted non-aromatic heterocyclyl; or
aromatic heterocyclyloxy substituted with one or more group(s) selected from halogen,
or pharmaceutically acceptable salt thereof.

(g-29) The compound of any one of the above (g-1) to (g-19), wherein $R^{10ab}$ is halogen or pharmaceutically acceptable salt thereof.

(g-30) The compound of any one of the above (g-1) to (g-19), wherein $R^{10ab}$ is a fluorine atom or a chlorine atom, or pharmaceutically acceptable salt thereof.

(g-31) The compound of any one of the above (g-1) to (g-19), wherein $R^{10ab}$ is substituted or unsubstituted alkyl, or pharmaceutically acceptable salt thereof.

(g-32) The compound of any one of the above (g-1) to (g-19), wherein $R^{10ab}$ is alkyl or haloalkyl, or pharmaceutically acceptable salt thereof.

(g-33) The compound of any one of the above (g-1) to (g-19), wherein $R^{10ab}$ is substituted or unsubstituted alkyloxy, or pharmaceutically acceptable salt thereof.

(g-34) The compound of any one of the above (g-1) to (g-19), wherein $R^{10ab}$ is alkyloxy or haloalkyloxy, or pharmaceutically acceptable salt thereof.

(g-35) The compound of any one of the above (g-1) to (g-34), wherein $R^{10ac}$ is halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfonyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfinyl, substituted or unsubstituted alkyloxycarbonyl, substituted or unsubstituted alkenyloxycarbonyl, substituted or unsubstituted alkynyloxycarbonyl, substituted or unsubstituted aryloxysulfonyl, substituted or unsubstituted alkenyloxysulfonyl, substituted or unsubstituted alkynyloxysulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclyl amino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclyl sulfanyl, or pharmaceutically acceptable salt thereof.

(g-36) The compound of any one of the above (g-1) to (g-34), wherein $R^{10ac}$ is halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkylsulfanyl, substituted or unsubstituted alkylamino, substituted or unsubstituted alkylcarbonyl, substituted or unsubstituted alkylsulfonyl, substituted or unsubstituted alkyloxycarbonyl, substituted or unsubstituted aryloxysulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl, or pharmaceutically acceptable salt thereof.

(g-37) The compound of any one of the above (g-1) to (g-34), wherein $R^{10ac}$ is halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkylsulfanyl, substituted or unsubstituted alkylamino, substituted or unsubstituted alkylcarbonyl, substituted or unsubstituted alkylsulfonyl, substituted or unsubstituted alkyloxycarbonyl, substituted or unsubstituted alkyloxysulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.

(g-38) The compound of any one of the above (g-1) to (g-34), wherein $R^{10ac}$ is substituted or unsubstituted alkyl, substituted or unsubstituted alkenyl, substituted or unsubstituted alkynyl, substituted or unsubstituted alkyloxy, substituted or unsubstituted alkylsulfanyl, substituted or unsubstituted alkylsulfonyl, substituted or unsubstituted alkyloxycarbonyl, substituted or unsubstituted aromatic carbocyclyl, substituted or unsubstituted aromatic heterocyclyl, substituted or unsubstituted non-aromatic heterocyclyl, substituted or unsubstituted non-aromatic carbocyclyloxy, or substituted or unsubstituted aromatic heterocyclyloxy, or pharmaceutically acceptable salt thereof.

(g-39) The compound of any one of the above (g-11 to (g-34), wherein $R^{10ac}$ is alkyl substituted with one or more group(s) selected from halogen, hydroxy, and non-aromatic heterocyclyl; unsubstituted alkyl;
alkyl substituted with one or more group(s) selected from halogen, hydroxy, and non-aromatic heterocyclyl;
unsubstituted alkenyl;
alkyl substituted with one or more group(s) selected from halogen, hydroxy, and non-aromatic heterocyclyl;
unsubstituted alkynyl:
unsubstituted alkynyl;
alkyloxy substituted with one or more group(s) selected from halogen, hydroxy, and non-aromatic heterocyclyl; unsubstituted alkyloxy:
alkylsulfanyl substituted with one or more group(s) selected from halogen, hydroxy, and non-aromatic heterocyclyl; unsubstituted alkylsulfanyl;
alkylsulfonyl substituted with one or more group(s) selected from halogen, hydroxy, and non-aromatic heterocyclyl; unsubstituted alkylsulfonyl:
alkyloxycarbonyl substituted with one or more group(s) selected from halogen, hydroxy, and non-aromatic heterocyclyl; unsubstituted alkyloxycarbonyl;
aromatic carbocyclyl substituted with one or more group (a) selected from alkyl, alkyloxy, and alkyloxycarbonyl; unsubstituted aromatic carbocyclyl:
aromatic heterocyclyl substituted with one or more group(s) selected from alkyl, alkyloxy, and alkyloxycarbonyl; unsubstituted aromatic heterocyclyl;
non-aromatic heterocyclyl substituted with one or more group(s) selected from alkyl, alkyloxy, and alkyloxycarbonyl; unsubstituted non-aromatic heterocyclyl;
non-aromatic carbocyclyloxy substituted with one or more group(s) selected from alkyl, alkyloxy, and alkyloxycarbonyl; unsubstituted non-aromatic carbocyclyloxy;
aromatic heterocyclyloxy substituted with one or more group(s) selected from alkyl, alkyloxy, and alkyloxycarbonyl; or unsubstituted aromatic heterocyclyloxy, or pharmaceutically acceptable salt thereof.

(g-40) The compound of any one of the above (g-1) to (g-34), wherein $R^{10ac}$ is alkyl substituted with one or more group(s) selected from halogen, hydroxy, and non-aromatic heterocyclyl; unsubstituted alkyl;

unsubstituted alkenyl;
unsubstituted alkynyl;
alkyloxy substituted with one or more group(s) selected from halogen; unsubstituted alkyloxy;
alkylsulfanyl substituted with one or more group(s) selected from halogen; unsubstituted alkylsulfonyl;
unsubstituted alkyloxycarbonyl:
unsubstituted aromatic carbocyclyl;
aromatic heterocyclyl substituted with one or more group(s) selected from alkyl and alkyloxy; unsubstituted aromatic heterocyclyl;
non-aromatic heterocyclyl substituted with one or more group(s) selected from alkyl and alkyloxycarbonyl; unsubstituted non-aromatic heterocyclyl; unsubstituted non-aromatic carbocyclyloxy:
or unsubstituted aromatic heterocyclyloxy,
or pharmaceutically acceptable salt thereof.
(g-41) The compound of any one of the above (g-1) to (g-34), wherein R is halogen, substituted or unsubstituted alkyl, substituted or unsubstituted alkyloxy, substituted or unsubstituted alkylsulfanyl, substituted or unsubstituted alkylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.
(g-42) The compound of any one of the above (g-1) to (g-34), wherein $R^{10ac}$ is halogen, substituted or unsubstituted alkyl, substituted or unsubstituted alkyloxy, substituted or unsubstituted aromatic heterocyclyl, substituted or unsubstituted non-aromatic heterocyclyl, substituted or unsubstituted aromatic heterocyclyloxy, or substituted or unsubstituted non-aromatic heterocyclyloxy, or pharmaceutically acceptable salt, thereof.
(g-43) The compound of any one of the above (g-1) to (g-34), wherein $R^{10ac}$ is halogen; alkyl; haloalkyl; alkyloxy; haloaryloxy;
aromatic heterocyclyl substituted with one or more group(s) selected from halogen, alkyl, haloalkyl, alkyloxy, and haloaryloxy; unsubstituted aromatic heterocyclyl; non-aromatic heterocyclyl substituted with one or more group (s) selected from halogen, alkyl, haloalkyl, alkyloxy, and haloaryloxy; unsubstituted non-aromatic heterocyclyl;
aromatic heterocyclyloxy substituted with one or more group(s) selected from halogen, alkyl, haloalkyl, alkyloxy, and haloaryloxy; or unsubstituted aromatic heterocyclyloxy, or pharmaceutically acceptable salt thereof.
(g-44) The compound of any one of the above (g-1) to (g-34), wherein $R^{10ac}$ is halogen, or pharmaceutically acceptable salt thereof.
(g-45) The compound of any one of the above (g-1) to (g-34), wherein $R^{10ac}$ is a fluorine atom or a chlorine atom, or pharmaceutically acceptable salt thereof.
(g-46) The compound of any one of the above (g-1) to (g-34), wherein $R^{10ac}$ is substituted or unsubstituted alkyl, or pharmaceutically acceptable salt thereof.
(g-47) The compound of any one of the above (g-1) to (g-34), wherein $R^{10ac}$ is alkyl or haloalkyl, or pharmaceutically acceptable salt thereof.
(g-48) The compound of any one of the above (g-1) to (g-34), wherein $R^{10ac}$ is substituted or unsubstituted alkyloxy, or pharmaceutically acceptable salt thereof.
(g-49) The compound of any one of the above (g-1) to (g-34), wherein $R^{10ac}$ is alkyloxy or haloaryloxy, or pharmaceutically acceptable salt thereof.
(g-50) The compound of any one of the above (g-1) to (g-34), wherein $R^{10ac}$ is substituted or unsubstituted aromatic heterocyclyl or substituted or unsubstituted nonaromatic heterocyclyl, or pharmaceutically acceptable salt thereof.
(g-51) The compound of any one of the above (g-1) to (g-34), wherein $R^{10ac}$ is substituted or unsubstituted aromatic heterocyclyloxy or substituted or unsubstituted non-aromatic heterocyclyloxy, or pharmaceutically acceptable salt thereof.
(h) A compound according to any one of the following (h-1) to (h-34) or a pharmaceutically acceptable salt thereof.
(h-1) The compound of any one of Formula (I) and the above (a) to (e), wherein $R^3$ is a group represented by the formula:

[Chemical Formula 58]

wherein Ring F1 and Ring F2 are each independently a substituted or unsubstituted 5-membered non-aromatic carbocycle, a substituted or unsubstituted 5-membered aromatic heterocycle, or a substituted or unsubstituted 5-membered non-aromatic heterocycle;
Ring G1 and Ring G2 are each independently a substituted or unsubstituted 6-membered aromatic carbocycle, a substituted or unsubstituted 6-membered non-aromatic carbocycle, a substituted or unsubstituted 6-membered aromatic heterocycle, or a substituted or unsubstituted 6-membered non-aromatic heterocycle:
Ring H1 is a substituted or unsubstituted 6-membered aromatic carbocycle, a substituted or unsubstituted 6-membered non-aromatic carbocycle, a substituted or unsubstituted 6-membered aromatic heterocycle, or a substituted or unsubstituted 6-membered non-aromatic heterocycle:
p1b and p1c are each independently 0 or 1;
$R^{9a}$ and $R^{9b}$ are the same as the above (f-1); and
$R^{10a1}$ is the same as $R^{10a}$ of the above (f-1),
or pharmaceutically acceptable salt thereof.
The above definition of $R^3$ means that $R^{10a1}$ is a substituent on Ring B.

(h-2) The compound of any one of Formula (I) and the above (a) to (e), wherein $R^3$ is

[Chemical Formula 59]

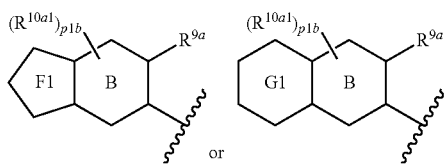

or pharmaceutically acceptable salt thereof.

(h-3) The compound of any one of Formula (I) and the above (a) to (e), wherein $R^3$ is

[Chemical Formula 60]

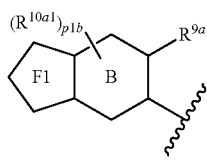

or pharmaceutically acceptable salt thereof.

(h-4) The compound of any one of Formula (I) and the above (a) to (e), wherein $R^3$ is

[Chemical Formula 61]

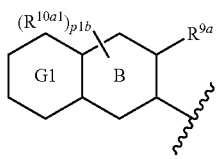

or pharmaceutically acceptable salt thereof.

(h-5) The compound of any one of Formula (I) and the above (a) to (e), wherein $R^3$ is

[Chemical Formula 62]

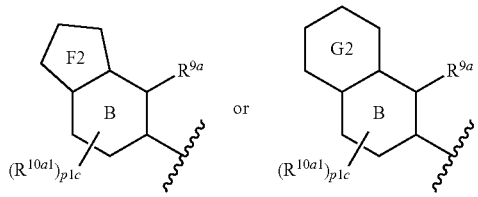

or pharmaceutically acceptable salt thereof.

(h-6) The compound of any one of Formula (I) and the above (a) to (e), wherein $R^3$ is

[Chemical Formula 63]

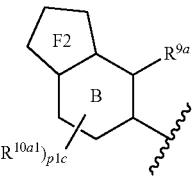

or pharmaceutically acceptable salt thereof.

(h-7) The compound of any one of Formula (I) and the above (a) to (e), wherein $R^3$ is

[Chemical Formula 64]

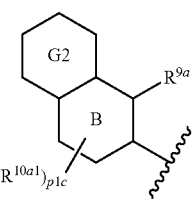

or pharmaceutically acceptable salt, thereof.

(h-8) The compound of any one of the above (h-1) to (h-7), wherein Ring F1 is substituted or unsubstituted cyclopentane, substituted or unsubstituted furan, substituted or unsubstituted thiophene, substituted or unsubstituted pyrrole, substituted or unsubstituted pyrazole, substituted or unsubstituted imidazole, substituted or unsubstituted thiazole, substituted or unsubstituted oxazole, substituted or unsubstituted dihydrofuran, substituted or unsubstituted dihydrothiophene, substituted or unsubstituted dihydropyrrole, or substituted or unsubstituted dioxolo, or pharmaceutically acceptable salt thereof.

(h-9) The compound of any one of the above (h-1) to (h-7), wherein Ring F1 is substituted or unsubstituted cyclopentane, substituted or unsubstituted furan, substituted or unsubstituted pyrrole, substituted or unsubstituted pyrazole, substituted or unsubstituted thiazole, substituted or unsubstituted oxazole, substituted or unsubstituted dihydrofuran, or substituted or unsubstituted dioxole, or pharmaceutically acceptable salt thereof.

(h-10) The compound of any one of the above (h-1) to (h-7), wherein Ring F1 is cyclopentane substituted with one or more group(s) selected from halogen and alkyl; unsubstituted cyclopentane;
furan substituted with one or more group(s) selected from halogen and alkyl; unsubstituted furan;
pyrrole substituted with one or more group(s) selected from halogen and alkyl; unsubstituted pyrrole;
pyrazole substituted with one or more group(s) selected from halogen and alkyl; unsubstituted pyrazole;
thiazole substituted with one or more group(s) selected from halogen and alkyl; unsubstituted thiazole;
oxazole substituted with one or more group(s) selected from halogen and alkyl; unsubstituted oxazole;
dihydrofuran substituted with one or more group(s) selected from halogen and alkyl; unsubstituted dihydrofuran;
dioxole substituted with one or more group(s) selected from halogen and alkyl; or unsubstituted dioxole, or pharmaceutically acceptable salt thereof.

(b-11) The compound of any one of the above (h-1) to (h-7), wherein Ring F1 is unsubstituted cyclopentane; furan substituted with one or more group(s) selected from alkyl;

unsubstituted pyrrole; unsubstituted pyrazole; thiazole substituted with one or more group(s) selected from alkyl; unsubstituted oxazole; unsubstituted dihydrofuran; dioxole substituted with one or more group(s) selected from halogen; or unsubstituted dioxole, or pharmaceutically acceptable salt thereof.

(h-12) The compound of any one of the above (h-1) to (h-7), wherein Ring F2 is substituted or unsubstituted cyclopentane, substituted or unsubstituted furan, substituted or unsubstituted thiophene, substituted or unsubstituted pyrrole, substituted or unsubstituted pyrazole, substituted or unsubstituted imidazole, substituted or unsubstituted thiazole, substituted or unsubstituted oxazole, substituted or unsubstituted dihydrofuran, substituted or unsubstituted dihydrothiophene, or substituted or unsubstituted dihydropyrrole, or pharmaceutically acceptable salt thereof.

(h-13) The compound of any one of the above (h-1) to (h-7), wherein Ring F2 is substituted or unsubstituted furan, substituted or unsubstituted pyrrole, substituted or unsubstituted thiazole, or substituted or unsubstituted dihydrofuran, or pharmaceutically acceptable salt, thereof.

(h-4) The compound of any one of the above (h-1) to (h-7), wherein Ring F2 is furan substituted with one or more group(s) selected from alkyl and alkyloxy; unsubstituted furan;
pyrrole substituted with one or more group(s) selected from alkyl and alkyloxy; unsubstituted pyrrole;
thiazole substituted with one or more group(s) selected from alkyl and alkyloxy; unsubstituted thiazole;
dihydrofuran substituted with one or more group(s) selected from alkyl and alkyloxy; or unsubstituted dihydrofuran, or pharmaceutically acceptable salt thereof.

(h-15) The compound of any one of the above (h-1) to (h-7), wherein Ring F2 is furan substituted with one or more group(s) selected from alkyl; unsubstituted furan; unsubstituted pyrrole; thiazole substituted with one or more group(s) selected from alkyl and alkyloxy; unsubstituted thiazole; or unsubstituted dihydrofuran, or pharmaceutically acceptable salt thereof.

(h-16) The compound of any one of the above (h-1) to (e-15), wherein Ring G1, and Ring G2 are each independently substituted or unsubstituted benzene, substituted or unsubstituted cyclohexane, substituted or unsubstituted pyridine, substituted or unsubstituted pyrazine, substituted or unsubstituted pyrimidine, substituted or unsubstituted pyran, substituted or unsubstituted dihydropyran, substituted or unsubstituted dihydropyridine, substituted or unsubstituted tetrahydropyridine, substituted or unsubstituted dihydropyrazine, substituted or unsubstituted tetrahydropyrazine, substituted or unsubstituted oxazine, substituted or unsubstituted dihydrooxazine, substituted or unsubstituted dioxin, or substituted or unsubstituted dihydrodioxin, or pharmaceutically acceptable salt thereof.

(h-17) The compound of any one of the above (h-1) to (h-15), wherein Ring G1 and Ring G2 are each independently substituted or unsubstituted pyridine, substituted or unsubstituted pyrazine, substituted or unsubstituted pyrimidine, substituted or unsubstituted pyran, substituted or unsubstituted dihydropyran, or substituted or unsubstituted dihydrodioxin, or pharmaceutically acceptable salt thereof.

(h-18) The compound of any one of the above (h-1) to (h-15), wherein Ring G1 and Ring (12 are each independently substituted or unsubstituted pyridine, substituted or unsubstituted pyran, substituted or unsubstituted dihydropyran, or substituted or unsubstituted dihydrodioxin, or pharmaceutically acceptable salt thereof.

(h-19) The compound of any one of the above (h-1) to (h-15), wherein Ring G1 and Ring G2 are each independently
pyridine substituted with one or more group(s) selected from halogen; unsubstituted pyridine:
pyran substituted with one or more group(s) selected from halogen; unsubstituted pyran;
dihydropyran substituted with one or more group(s) selected from halogen; unsubstituted dihydropyran;
dihydrodioxin substituted with one or more group(s) selected from halogen; or unsubstituted dihydrodioxin, or pharmaceutically acceptable salt thereof.

(h-20) The compound of any one of the above (h-1) to (h-15), wherein Ring G1 and Ring G2 are each independently unsubstituted pyridine; unsubstituted pyran; unsubstituted dihydropyran; dihydrodioxin substituted with one or more group(s) selected from halogen; or unsubstituted dihydrodioxin, or pharmaceutically acceptable salt thereof.

(h-21) The compound of any one of the above (h-1) to (h-20), wherein Ring H1 is substituted or unsubstituted benzene, substituted or unsubstituted cyclohexane, substituted or unsubstituted pyridine, substituted or unsubstituted pyrazine, substituted or unsubstituted pyrimidine, or pharmaceutically acceptable salt thereof.

(h-22) The compound of any one of the above (h-1) to (h-20), wherein Ring H1 is each independently substituted or unsubstituted benzene, or pharmaceutically acceptable salt thereof.

(h-23) The compound of any one of the above (h-1) to (h-20), wherein Ring H1 is benzene substituted with one or more group(s) selected from halogen, or pharmaceutically acceptable salt thereof.

(h-24) The compound of any one of the above (h-1) to (h-20), wherein Ring H1 is unsubstituted benzene, or pharmaceutically acceptable salt thereof.

(h-25) The compound of any one of the above (h-1) to (h-24), wherein p1b is 0, or pharmaceutically acceptable salt thereof.

(h-26) The compound of any one of the above (h-1) to (h-24), wherein p1b is 1, or pharmaceutically acceptable salt thereof.

(h-27) The compound of any one of the above (h-1) to (h-26), wherein p1c is 0, or pharmaceutically acceptable salt thereof.

(h-28) The compound of any one of the above (h-1) to (h-26), wherein p1c is 1, or pharmaceutically acceptable salt thereof.

(h-29) The compound of any one of the above (h-1) to (h-28), wherein $R^{10a1}$ is halogen, hydroxy, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfonyl, substituted or unsubstituted alkynylsulfanyl, substituted or unsubstituted alkylamino, substituted or unsubstituted alkenylamino, or substituted or unsubstituted alkynylamino, or pharmaceutically acceptable salt thereof.

(h-80) The compound of any one of the above (h-1) to (h-28), wherein $R^{10a1}$ is halogen, substituted or unsubstituted alkyl, substituted or unsubstituted alkyloxy, substituted or unsubstituted alkylsulfanyl, or substituted or unsubstituted alkylamino, or pharmaceutically acceptable salt thereof.

(h-31) The compound of any one of the above (h-1) to (h-28), wherein $R^{10a}$ halogen, substituted or unsubstituted alkyl, or substituted or unsubstituted alkyloxy, or pharmaceutically acceptable salt thereof.

(h-32) The compound of any one of the above (h-1) to (h-28), wherein $R^{10a1}$ is halogen, alkyl, haloalkyl, alkyloxy, or haloalkyloxy, or pharmaceutically acceptable salt thereof.

(h-33) The compound of any one of the above (h-1) to (h-28), wherein $R^{10a1}$ is unsubstituted or unsubstituted alkyl, or pharmaceutically acceptable salt thereof.

(h-34) The compound of any one of the above (h-1) to (h-28), wherein $R^{10a1}$ is unsubstituted alkyl, or pharmaceutically acceptable salt thereof.

(i) A compound according to any one of the following (i-1) to (i-16) or a pharmaceutically acceptable salt thereof.

(i-1) The compound of any one of Formula (I) and the above (a) to (h), wherein $R^{9a}$ and $R^{9b}$ are each independently halogen, hydroxy, amino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted nr unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.

(i-2) The compound of any one of Formula (I) and the above (a) to (h), wherein $R^{9a}$ and $R^{9b}$ are each independently halogen, hydroxy, amino, substituted or unsubstituted alkyl, substituted or unsubstituted alkyloxy, substituted or unsubstituted alkylsulfanyl, substituted or unsubstituted alkylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.

(i-3) The compound of any one of Formula (I) and the above (a) to (h), wherein $R^{9a}$ and $R^{9b}$ are each independently halogen, substituted or unsubstituted alkyl, substituted or unsubstituted alkyloxy, substituted or unsubstituted alkylsulfanyl, substituted or unsubstituted alkylamino, substituted or unsubstituted aromatic carbocyclyl, or substituted or unsubstituted aromatic carbocyclyloxy, or pharmaceutically acceptable salt thereof.

(i-4) The compound of any one of Formula (I) and the above (a) to (h), wherein $R^{9a}$ and $R^{9b}$ are each independently halogen;

alkyl substituted with one or more group(s) selected from halogen, alkyloxy, aromatic carbocyclyl, and aromatic heterocyclyl; unsubstituted alkyl;

alkyloxy substituted with one or more group(s) selected from halogen, alkyloxy, aromatic carbocyclyl, and aromatic heterocyclyl; unsubstituted alkyloxy;

alkylsulfanyl substituted with one or more group (a) selected from halogen, alkyloxy, aromatic carbocyclyl, and aromatic heterocyclyl; unsubstituted alkylsulfanyl;

alkylamino substituted with one or more group(s) selected from halogen, alkyloxy, aromatic carbocyclyl, and aromatic heterocyclyl; unsubstituted alkylamino;

aromatic carbocyclyl substituted with one or more group(s) selected from halogen, alkyl, and alkyloxy; unsubstituted aromatic carbocyclyl;

aromatic carbocyclyloxy substituted with one or more group (s) selected from halogen, alkyl, and alkyloxy; or unsubstituted aromatic carbocyclyloxy, or pharmaceutically acceptable salt thereof.

(i-5) The compound of any one of Formula (I) and the above (a) to (h), wherein $R^{9a}$ and $R^{9b}$ are each independently halogen;

alkyl substituted with one or more group(s) selected from halogen, alkyloxy, aromatic carbocyclyl, and aromatic heterocyclyl; unsubstituted alkyl; alkyloxy substituted with one or more group(s) selected from halogen; unsubstituted alkyloxy;

unsubstituted alkylsulfanyl;

unsubstituted alkylamino;

unsubstituted aromatic carbocyclyl:

aromatic carbocyclyloxy substituted with one or more group (s) selected from alkyl; or unsubstituted aromatic carbocyclyloxy, or pharmaceutically acceptable salt thereof.

(i-6) The compound of any one of Formula U) and the above (a) to (h), wherein $R^{9a}$ and $R^{9b}$ are each independently halogen;

alkyl substituted with one or more group(s) selected from halogen, alkyloxy, aromatic carbocyclyl, and aromatic heterocyclyl; or unsubstituted alkyl, or pharmaceutically acceptable salt thereof.

(i-7) The compound of any one of Formula (I) and the above (a) to (h), wherein $R^{9a}$ and $R^{9b}$ are each independently halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfonyl, substituted or unsubstituted alkynylsulfanyl, substituted or unsubstituted alkylamino, substituted or unsubstituted alkenylamino, or substituted or unsubstituted alkynylamino, or pharmaceutically acceptable salt thereof.

(i-8) The compound of any one of Formula (L) and the above (a) to (h), wherein $R^{9a}$ and $R^{9b}$ are each independently halogen, substituted or unsubstituted alkyl, substituted or unsubstituted alkyloxy, substituted or unsubstituted alkylsulfanyl, or substituted or unsubstituted alkylamino, or pharmaceutically acceptable salt thereof.

(i-9) The compound of any one of Formula (I) and the above (a) to (h), wherein $R^{9a}$ and $R^{9b}$ are each independently halogen, substituted or unsubstituted alkyl, substituted or unsubstituted alkylsulfanyl, or pharmaceutically acceptable salt thereof.

(i-10) The compound of any one of Formula (I) and the above (a) to (h), wherein $R^{9a}$ and $R^{9b}$ are each independently halogen, substituted or unsubstituted alkyl, substituted or unsubstituted alkenyl, or substituted or unsubstituted alkynyl, or pharmaceutically acceptable salt thereof.

(i-11) The compound of any one of Formula (I) and the above (a) to (h), wherein $R^{9a}$ and $R^{9b}$ are each independently halogen, or substituted or unsubstituted alkyl, or pharmaceutically acceptable salt thereof.

(i-12) The compound of any one of Formula (I) and the above (a) to (h), wherein $R^{9a}$ and $R^{9b}$ are each independently halogen, or substituted or unsubstituted alkyl, or pharmaceutically acceptable salt thereof.

(i-13) The compound of any one of Formula (I) and the above (a) to (h), wherein $R^{9a}$ and $R^{9b}$ are each independently halogen, alkyl, or haloalkyl, or pharmaceutically acceptable salt thereof.

(i-14) The compound of any one of Formula (I) and the above (a) to (h), wherein $R^{9a}$ and $R^{9b}$ are each independently substituted or unsubstituted C1 to C3 alkyl, or pharmaceutically acceptable salt thereof.

(i-1.5) The compound of any one of Formula (I) and the above (a) to (h), wherein $R^{9a}$ and $R^{9b}$ are each independently unsubstituted C1 to C3 alkyl, or pharmaceutically acceptable salt thereof.

(i-16) The compound of any one of Formula (I) and the above (a) to (h), wherein $R^{9a}$ and $R^{9b}$ are each independently unsubstituted methyl or unsubstituted ethyl, or pharmaceutically acceptable salt, thereof.

(j) A compound according to any one of the following (j-1) to (j-30) or a pharmaceutically acceptable salt thereof.

(j-1) The compound of any one of Formula (I) and the above (a) to (e), wherein $R^3$ is a group represented by the Formula:

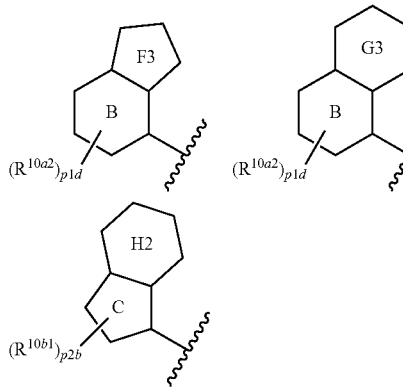

[Chemical Formula 65]

wherein Ring F3 is a substituted or unsubstituted 5-membered non-aromatic carbocycle, a substituted or unsubstituted 5-membered aromatic heterocycle, or a substituted or unsubstituted 5-membered non-aromatic heterocycle:

Ring G3 is a substituted or unsubstituted 6-membered aromatic carbocycle, a substituted or unsubstituted 6-membered non-aromatic carbocycle, a substituted or unsubstituted 6-membered aromatic heterocycle, or a substituted or unsubstituted (i-membered non-aromatic heterocycle-.

Ring H2 is a substituted or unsubstituted 6-membered aromatic carbocycle, a substituted or unsubstituted 6-membered non-aromatic carbocycle, a substituted or unsubstituted 6-membered aromatic heterocycle, or a substituted or unsubstituted 6-membered non-aromatic heterocycle;

p1d and p2b are each independently 0 or 1; and $R^{10a2}$ and $R^{10b1}$ are the same as $R^{10a}$ and $R^{10b}$ of the above (f-1), or pharmaceutically acceptable salt thereof.

(j-2) The compound of any one of Formula (I) and the above (a) to (e), wherein $R^3$ is

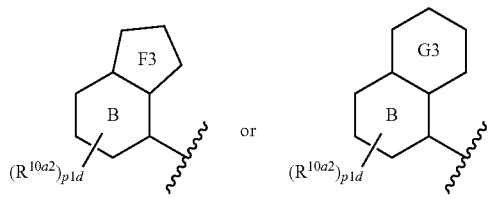

[Chemical Formula 66]

or pharmaceutically acceptable salt thereof.

(j-3) The compound of any one of Formula (I) and the above (a) to (e), wherein $R^3$ is

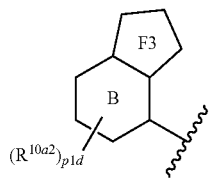

[Chemical Formula 67]

or pharmaceutically acceptable salt thereof.

(j-4) The compound of any one of Formula (I) and the above (a) to (e), wherein $R^3$ is

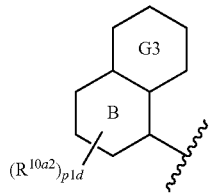

[Chemical Formula 68]

or pharmaceutically acceptable salt thereof.

(j-5) The compound of any one of the above (j-1) to (j-4), wherein Ring F3 is substituted or unsubstituted cyclopentane, substituted or unsubstituted furan, substituted or unsubstituted thiophene, substituted or unsubstituted pyrrole, substituted or unsubstituted pyrazole, substituted or unsubstituted imidazole, substituted or unsubstituted thiazole, substituted or unsubstituted oxazole, substituted or unsubstituted dihydrofuran, substituted or unsubstituted dihydrothiophene, substituted or unsubstituted dihydropyrrole, or substituted or unsubstituted dioxole, or pharmaceutically acceptable salt thereof.

(j-6) The compound of any one of the above (j-1) to (j-4), wherein Ring F3 is cyclopentane substituted with one or more group(s) selected from alkyl; unsubstituted cyclopentane;

furan substituted with one or more group(s) selected from alkyl; unsubstituted furan; thiophene substituted with one or more group(s) selected from alkyl; unsubstituted thiophene;

pyrrole substituted with one or more group(s) selected from alkyl; unsubstituted pyrrole:
imidazole substituted with one or more group(s) selected from alkyl; unsubstituted imidazole;
thiazole substituted with one or more group(s) selected from alkyl; unsubstituted thiazole:
oxazole substituted with one or more group(s) selected from alkyl; unsubstituted oxazole;
dihydrofuran substituted with one or more group(s) selected from alkyl; unsubstituted dihydrofuran;
dioxole substituted with one or more group(s) selected from alkyl; or unsubstituted dioxole,
or pharmaceutically acceptable salt thereof.

(j-7) The compound of any one of the above (j-1) to (j-4), wherein Ring F3 is unsubstituted cyclopentane;
unsubstituted furan:
unsubstituted thiophene;
pyrrole substituted with one or more group(s) selected from alkyl and an aromatic carbocycle; unsubstituted pyrrole;
unsubstituted imidazole;
unsubstituted thiazole;
unsubstituted oxazole;
unsubstituted dihydrofuran;
or unsubstituted dioxole, or pharmaceutically acceptable salt thereof.

(j-8) The compound of any one of the above (j-1) to (j-4), wherein Ring F3 is substituted or unsubstituted cyclopentane, substituted or unsubstituted furan, substituted or unsubstituted thiophene, substituted or unsubstituted pyrrole, or substituted or unsubstituted dihydrofuran, or pharmaceutically acceptable salt thereof.

(j-9) The compound of any one of the above (j-1) to (j-4), wherein Ring F3 is substituted or unsubstituted furan, substituted or unsubstituted thiophene, or substituted or unsubstituted pyrrole, or pharmaceutically acceptable salt thereof.

(j-10) The compound of any one of the above (j-1) to (j-4), wherein Ring F3 is furan substituted with one or more group(s) selected from alkyl; unsubstituted furan; thiophene substituted with one or more group(s) selected from alkyl; unsubstituted thiophene:
pyrrole substituted with one or more group(s) selected from alkyl; or unsubstituted pyrrole, or pharmaceutically acceptable salt thereof.

(j-11) The compound of any one of the above (j-1) to (j-4), wherein Ring F3 is substituted furan:
unsubstituted thiophene;
pyrrole substituted with one or more group(s) selected from alkyl; or unsubstituted pyrrole, or pharmaceutically acceptable salt thereof.

(j-12) The compound of any one of the above (j-1) to (j-11), wherein Ring G3 is substituted or unsubstituted benzene, substituted or unsubstituted cyclohexane, substituted or unsubstituted pyridine, substituted or unsubstituted pyrazine, substituted or unsubstituted pyrimidine, substituted or unsubstituted pyran, substituted or unsubstituted dihydropyran, substituted or unsubstituted dihydropyridine, substituted or unsubstituted tetrahydropyridine, substituted or unsubstituted dihydropyrazine, substituted or unsubstituted tetrahydropyrazine, substituted or unsubstituted oxazine, substituted or unsubstituted dihydrooxazine, substituted or unsubstituted dioxin, or substituted or unsubstituted dihydrodioxin, or pharmaceutically acceptable salt thereof.

(j-13) The compound of any one of the above (j-1) to (j-11), wherein Ring G3 is substituted or unsubstituted cyclohexane, substituted or unsubstituted dihydropyridine, substituted or unsubstituted tetrahydropyridine, or substituted or unsubstituted dihydrodioxin, or pharmaceutically acceptable salt thereof.

(j-14) The compound of any one of the above (j-1) to (j-11), wherein Ring G3 is cyclohexane substituted with one or more group(s) selected from alkyl; unsubstituted cyclohexane;
dihydropyridine substituted with one or more group(s) selected from alkyl;
unsubstituted dihydropyridine;
tetrahydropyridine substituted with one or more group(s) selected from alkyl; unsubstituted tetrahydropyridine:
dihydrodioxin substituted with one or more group(s) selected from alkyl; or unsubstituted dihydrodioxin, or pharmaceutically acceptable salt thereof.

(j-15) The compound of any one of the above (j-1) to (j-11), wherein Ring (<3 is unsubstituted cyclohexane;
dihydropyridine substituted with one or more group(s) selected from alkyl; unsubstituted dihydropyridine;
unsubstituted tetrahydropyridine,
or unsubstituted dihydrodioxin, or pharmaceutically acceptable salt thereof.

(j-16) The compound of any one of the above (j-1) to (j-11), wherein Ring G3 is unsubstituted cyclohexane;
dihydropyridine substituted with one or more group(s) selected from alkyl; or unsubstituted dihydropyridine, or pharmaceutically acceptable salt thereof.

(j-17) The compound of any one of the above (j-1) to (j-16), wherein Ring H2 is substituted or unsubstituted benzene, substituted or unsubstituted cyclohexane, substituted or unsubstituted pyridine, substituted or unsubstituted pyrazine, substituted or unsubstituted pyrimidine, or pharmaceutically acceptable salt, thereof.

(j-18) The compound of any one of the above (j-1) to (j-16), wherein Ring H2 is each independently substituted or unsubstituted benzene, or pharmaceutically acceptable salt thereof.

(j-19) The compound of any one of the above (j-1) to (j-16), wherein Ring H2 is benzene substituted with one or more group(s) selected from halogen, or pharmaceutically acceptable salt, thereof.

(j-20) The compound of any one of the above (j-1) to (j-16), wherein Ring H2 is unsubstituted benzene, or pharmaceutically acceptable salt thereof.

(j-21) The compound of any one of the above (j-1) to (j-20), wherein p1d is 0, or pharmaceutically acceptable salt thereof.

(j-22) The compound of any one of the above (j-1) to (j-20), wherein p1d is 1, or pharmaceutically acceptable salt thereof.

(j-23) The compound of any one of the above (j-1) to (j-22), wherein p2b is 0, or pharmaceutically acceptable salt thereof.

(j-24) The compound of any one of the above (j-1) to (j-22), wherein p2b is 1, or pharmaceutically acceptable salt thereof.

(j-25) The compound of any one of the above (j-1) to (j-21), wherein $R^{10a2}$ and $R^{10b1}$ are each independently halogen, hydroxy, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, or substituted or unsubstituted alkynylamino, or pharmaceutically acceptable salt thereof.

(j-26) The compound of any one of the above (j-1) to (j-24), wherein $R^{10a2}$ and $R^{10b1}$ are each independently halogen, substituted or unsubstituted alkyl, substituted or unsubstituted alkyloxy, substituted or unsubstituted alkylsulfanyl, or substituted or unsubstituted alkylamino, or pharmaceutically acceptable salt thereof.

(j-27) The compound of any one of the above (j-1) to (j-24), wherein $R^{10a1}$ and $R^{10b1}$ are each independently halogen, substituted or unsubstituted alkyl, or substituted or unsubstituted alkyloxy, or pharmaceutically acceptable salt thereof.

(j-28) The compound of any one of the above (j-1) to (j-24), wherein $R^{10a2}$ and $R^{10b1}$ are each independently halogen, alkyl, haloalkyl, alkyloxy, or haloaryloxy, or pharmaceutically acceptable salt thereof.

(j-29) The compound of any one of the above (j-1) to (j-24), wherein $R^{10a2}$ and $R^{10b1}$ are each independently halogen or unsubstituted or unsubstituted alkyl, or pharmaceutically acceptable salt thereof.

(j-30) The compound of any one of the above (j-1) to (j-24), wherein $R^{10a2}$ and $R^{10b1}$ are each independently halogen or unsubstituted alkyl, or pharmaceutically acceptable salt thereof.

(k) A compound according to any one of the following (k-1) to (k-11) or a pharmaceutically acceptable salt thereof.

(k 1) The compound of any one of Formula (I) and the above (a) to (e), wherein $R^3$ is

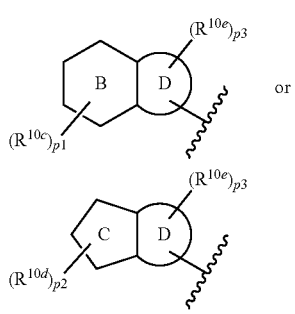

[Chemical Formula 69]

or or pharmaceutically acceptable salt thereof.

The above definition of $R^3$ means that $R^{10c}$ is a substituent, on Ring B, and $R^{10e}$ is a substituent on Ring D.

(k-2) The compound of any one of Formula (I) and the above (a) to (e), wherein $R^3$ is

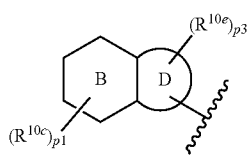

[Chemical Formula 70]

or pharmaceutically acceptable salt thereof.

(k-3) The compound of the above (k-1) or (k-2), wherein $R^{10c}$ and $R^{10d}$ are each independently halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.

(k-4) The compound of the above (k-1) or (k-2), wherein $R^{10c}$ and $R^{10d}$ are each independently halogen, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.

(k-5) The compound of the above (k-1) or (k-2), wherein $R^{10c}$ and $R^{10d}$ are each independently halogen, substituted or unsubstituted alkyl, substituted or unsubstituted alkyloxy, or pharmaceutically acceptable salt thereof.

(k-6) The compound of the above (k-1) or (k-2), wherein $R^{10c}$ and $R^{10d}$ are each independently halogen, alkyl, haloalkyl, alkyloxy, haloalkyloxy, or pharmaceutically acceptable salt thereof.

(k-7) The compound of the above (k-1) or (k-2), wherein $R^{10c}$ and $R^{10d}$ are each independently halogen, or pharmaceutically acceptable salt thereof.

(k-8) The compound of any one of the above (k-1) to (k-7), wherein $R^{10e}$ is each independently halogen, or substituted or unsubstituted alkyl, or pharmaceutically acceptable salt thereof.

(k-9) The compound of any one of the above (k-1) to (k-7), wherein $R^{10e}$ is each independently halogen, alkyl, or haloalkyl, or pharmaceutically acceptable salt thereof.

(k-10) The compound of any one of the above (k-1) to (k-7), wherein $R^{10e}$ is each independently halogen, or pharmaceutically acceptable salt thereof.

(k-11) The compound of any one of the above (k-1) to (k-10), wherein p3 is 0, or pharmaceutically acceptable salt thereof.

(l) A compound according to any one of the following (l-1) to (l-6) or a pharmaceutically acceptable salt thereof.

(l-1) The compound of any one of Formula (I) and the above (a) to (k), wherein Ring B is benzene, cyclohexene, or a 6-membered aromatic heterocycle, or pharmaceutically acceptable salt thereof.

(l-2) The compound of any one of Formula (I) and the above (a) to (k), wherein Ring B is benzene, or a 6-membered aromatic heterocycle, or pharmaceutically acceptable salt thereof.

(l-3) The compound of any one of Formula (I) and the above (a) to (k), wherein Ring B is benzene, cyclohexene, pyridine, pyrimidine, or pyrazine, or pharmaceutically acceptable salt, thereof.

(l-4) The compound of any one of Formula (I) and the above (a) to (k), wherein Ring B is benzene, pyridine, pyrimidine, or pyrazine, or pharmaceutically acceptable salt thereof.

(l-5) The compound of any one of Formula (I) and the above (a) to (k), wherein Ring B is benzene, or pyridine, or pharmaceutically acceptable salt thereof.

(l-6) The compound of any one of Formula (I) and the above (a) to (k), wherein Ring B is benzene, or pharmaceutically acceptable salt thereof.

(m) A compound according to any one of the following (m-1) to (m-4) or a pharmaceutically acceptable salt thereof.

(m-1) The compound of any one of Formula (I) and the above (a) to (l), wherein Ring C is cyclopentane, or a 5-membered aromatic heterocycle, or pharmaceutically acceptable; salt thereof.

(m-2) The compound of any one of Formula (I) and the above (a) to (l), wherein Ring C is a 5-membered aromatic heterocycle, or pharmaceutically acceptable salt thereof.

(m-3) The compound of any one of Formula (I) and the above (a) to (l), wherein Ring C is cyclopentane, pyrrole, imidazole, pyrazole, furan, thiophene, isoxazole, oxazole, isothiazole, or thiazole, or pharmaceutically acceptable salt thereof.

(m-4) The compound of any one of Formula (I) and the above (a) to (l), wherein Ring C is thiophene, or pharmaceutically acceptable salt thereof.

(n) A compound according to any one of the following (n-1) to (n-19) or a pharmaceutically acceptable salt thereof.

(n-1) The compound of any one of Formula (I) and the above (a) to (m), wherein $R^{5a}$ is a hydrogen atom, halogen, hydroxy, carboxy, amino, carbamoyl, sulfamoyl, sulfo, cyano, substituted or unsubstituted alkyl, substituted or unsubstituted alkyloxy, substituted or unsubstituted alkylsulfanyl, substituted or unsubstituted alkylamino, substituted or unsubstituted alkylcarbonyl, substituted or unsubstituted alkylsulfonyl, substituted or unsubstituted alkylcarbamoyl, substituted or unsubstituted alkylsulfamoyl, substituted or unsubstituted alkylcarbonylamino, substituted or unsubstituted alkylsulfonylamino, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsxdistituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonyl amino, substituted or unsubstituted aromatic carbocyclylsulfonylamino, substituted or unsubstituted non-aromatic carbocyclylsulfonylamino, substituted or unsubstituted aromatic heterocyclylsulfonylamino, or substituted or unsubstituted non-aromatic heterocyclylsulfonylamino, or pharmaceutically acceptable salt thereof.

(n-2) The compound of any one of Formula (I) and the above (a) to (m), wherein $R^{5a}$ is a hydrogen atom, halogen, hydroxy, amino, carbamoyl, cyano, substituted or unsubstituted alkyl, substituted or unsubstituted alkyloxy, substituted or unsubstituted alkylamino, substituted or unsubstituted alkylcarbonyl, substituted or unsubstituted alkylcarbamoyl, substituted or unsubstituted alkylcarbonylamino, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, or substituted or unsubstituted non-aromatic heterocyclylcarbonylamino, or pharmaceutically acceptable salt thereof.

(n-8) The compound of any one of Formula (I) and the above (a) to (m), wherein $R^{5a}$ is a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylsulfanyl, substituted or unsubstituted alkenylsulfonyl, substituted or unsubstituted alkynylsulfanyl, substituted or unsubstituted alkyloxycarbonyl, substituted or unsubstituted alkenyloxycarbonyl, substituted or unsubstituted alkynyl oxycarbonyl, substituted or unsubstituted alkylcarbamoyl, substituted or unsubstituted alkenylcarbamoyl, substituted or unsubstituted alky ylcarbamoyl, substituted or unsubstituted alkylcarbonylamino, substituted or unsubstituted alkenylcarbonylamino, substituted or unsubstituted alkynylcarbonylamino, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(n-4) The compound of any one of Formula (I) and the above (a) to (m), wherein $R^{5a}$ is a hydrogen atom, halogen, hydroxy, carboxy, amino, carbamoyl, sulfamoyl, sulfo, cyano, substituted or unsubstituted alkyl, substituted or unsubstituted alkyloxy, substituted or unsubstituted alkylamino, substituted or unsubstituted alkyloxycarbonyl, substituted or unsubstituted alkylcarbamoyl, substituted or unsubstituted alkylcarbonylamino, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(n-5) The compound of any one of Formula (I) and the above (a) to (m), wherein $R^{5a}$ is a hydrogen atom, halogen, hydroxy, carboxy, amino, carbamoyl, cyano, substituted or unsubstituted alkyl, substituted or unsubstituted alkyloxy, substituted or unsubstituted alkyloxycarbonyl, substituted or unsubstituted alkylcarbamoyl, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(n-6) The compound of any one of Formula (I) and the above (a) to (m), wherein $R^{5a}$ is a hydrogen atom, halogen, hydroxy, carboxy, amino, carbamoyl, cyano, substituted or unsubstituted alkyl, substituted or unsubstituted alkyloxy, substituted or unsubstituted alkyloxycarbonyl, substituted or unsubstituted alkylcarbamoyl, substituted or unsubstituted alkyloxycarbonylamino, or substituted or unsubstituted aromatic carbocyclyl, or pharmaceutically acceptable salt, thereof.

(n-7) The compound of any one of Formula (I) and the above (a) to (m), wherein $R^{5a}$ is a hydrogen atom;
halogen;
hydroxy;
carboxy;
amino;
carbamoyl;
cyano;
alkyl substituted with one or more group(s) selected from halogen, hydroxy, carboxy, carbamoyl, alkylcarbamoyl optionally substituted with one or more group(s) selected from (hydroxy, cyano and alkyloxy), non-aromatic heterocyclylcarbonyl, aromatic carbocyclylcarbamoyl optionally substituted with one or more group(s) selected from (halogen and alkyl), and non-aromatic heterocyclyl carbamoyl; unsubstituted alkyl; alkyloxy substituted with one or more group(s) selected from halogen and an aromatic carbocycle; unsubstituted alkyloxy;
unsubstituted alkyloxycarbonyl;
alkylcarbamoyl substituted with one or more group(s) selected from halogen, cyano, alkyloxy, alkylcarbonyl, alkylsulfonyl, alkylcarbamoyl, and aromatic carbocyclyl; unsubstituted alkylcarbamoyl;
unsubstituted alkyloxycarbonylamino; or
unsubstituted aromatic carbocyclyl,
or pharmaceutically acceptable salt thereof.

(N-8) The compound of any one of Formula (I) and the above (a) to (m), wherein $R^{5A}$ is a hydrogen atom;
halogen;
alkyl substituted with one or more group(s) selected from halogen, hydroxy, carboxy, carbamoyl, alkylcarbamoyl optionally substituted with one or more group(s) selected from (hydroxy, cyano and alkyloxy), non-aromatic heterocyclylcarbonyl, aromatic carbocyclylcarbamoyl optionally substituted with one or more group(s) selected from (halogen and alkyl), and non-aromatic heterocyclyl carbamoyl;
unsubstituted alkyl;
alkyloxy substituted with one or more group(s) selected from halogen and an aromatic carbocycle; or
unsubstituted alkyloxy,
or pharmaceutically acceptable salt, thereof.

(n-9) The compound of any one of Formula (I) and the above (a) to (m), wherein $R^{5a}$ is a hydrogen atom, halogen, amino, carbamoyl, cyano, substituted or unsubstituted alkyl, substituted or unsubstituted alkyloxy, substituted or unsubstituted alkylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(n-10) The compound of any one of Formula (I) and the above (a) to (m), wherein $R^{5a}$ is a hydrogen atom, halogen, amino, carbamoyl, cyano, alkyl, haloalkyl, alkyloxy, haloaryloxy, alkylamino, haloalkylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(n-11) The compound of any one of Formula (I) and the above (a) to (m), wherein $R^{5a}$ is a hydrogen atom, halogen, substituted or unsubstituted alkyl, or substituted or unsubstituted alkyloxy, or pharmaceutically acceptable salt thereof.

(n-12) The compound of any one of Formula (I) and the above (a) to (m), wherein $R^{5a}$ is a hydrogen atom, halogen, alkyl, haloalkyl, alkyloxy, or haloalkyloxy, or pharmaceutically acceptable salt thereof.

(n-13) The compound of any one of Formula (I) and the above (a) to (m), wherein $R^{5a}$ is substituted or unsubstituted alkyloxy, or pharmaceutically acceptable salt thereof.

(n-14) The compound of any one of Formula (I) and the above (a) to (m), wherein $R^{5a}$ is alkyloxy or haloalkyloxy, or pharmaceutically acceptable salt thereof.

(n-15) The compound of any one of Formula (I) and the above (a) to (m), wherein $R^{5a}$ is substituted or unsubstituted alkyl, or pharmaceutically acceptable salt thereof.

(n-10) The compound of any one of Formula (I) and the above (a) to (m), wherein $R^{5a}$ is alkyl or haloalkyl, or pharmaceutically acceptable salt thereof.

(n-17) The compound of any one of Formula (I) and the above (a) to (m), wherein $R^{5a}$ is halogen, or pharmaceutically acceptable salt thereof.

(n-18) The compound of any one of Formula (I) and the above (a) to (m), wherein $R^{5a}$ is a fluorine atom or a chlorine atom, or pharmaceutically acceptable salt thereof.

(n-19) The compound of any one of Formula (I) and the above (a) to (m), wherein $R^{5a}$ is a fluorine atom, or pharmaceutically acceptable salt thereof.

(o) A compound according to any one of the following (o-1) to (o-9) or a pharmaceutically acceptable salt thereof.

(o-1) The compound of any one of Formula (I) and the above (a) to (n), wherein $R^{5b}$ is a hydrogen atom, carboxy, carbamoyl, sulfamoyl, sulfo, cyano, substituted or unsubstituted alkyl, substituted or unsubstituted alkylcarbonyl, substituted or unsubstituted alkyloxycarbonyl, substituted or unsubstituted alkylcarbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, or substituted or unsubstituted non-aromatic heterocyclylcarbamoyl, or pharmaceutically acceptable salt thereof.

(o-2) The compound of any one of Formula (I) and the above (a) to (n), wherein $R^{5b}$ is a hydrogen atom, carboxy, carbamoyl, cyano, substituted or unsubstituted alkyl, substituted or unsubstituted alkylcarbonyl, substituted or unsubstituted alkyloxycarbonyl, substituted or unsubstituted alkylcarbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, or substituted or unsubstituted non-aromatic heterocyclylcarbamoyl, or pharmaceutically acceptable salt thereof.

(o-3) The compound of any one of Formula (I) and the above (a) to (n), wherein $R^{5b}$ is a hydrogen atom, carboxy, carbamoyl, cyano, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(o-4) The compound of any one of Formula (L) and the above (a) to (n), wherein $R^{5b}$ is a hydrogen atom, substituted or unsubstituted alkyl, substituted or unsubstituted alkylcarbonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(o-5) The compound of any one of Formula (I) and the above (a) to (n), wherein $R^{5b}$ is a hydrogen atom, or substituted or unsubstituted alkyl, or pharmaceutically acceptable salt thereof.

(o-6) The compound of any one of Formula (I) and the above (a) to (n), wherein $R^{5b}$ is a hydrogen atom, alkyl, or haloalkyl, or pharmaceutically acceptable salt thereof.

(o-7) The compound of any one of Formula (I) and the above (a) to (n), wherein $R^{5b}$ is unsubstituted alkyl, or pharmaceutically acceptable salt thereof.

(o-8) The compound of any one of Formula (L) and the above (a) to (n), wherein $R^{5b}$ is a hydrogen atom;

carboxyl carbamoyl;

cyano;

alkyl substituted with one or more group(s) selected from halogen, hydroxy, carboxy, carbamoyl, alkylcarbamoyl optionally substituted with one or more group(s) selected from (hydroxy, cyano and alkyloxy), non-aromatic heterocyclylcarbonyl, aromatic carbocyclylcarbamoyl optionally substituted with one or more group(s) selected from (halogen and alkyl), and non-aromatic heterocyclylcarbamoyl;

unsubstituted alkyl;

unsubstituted alkyloxycarbonyl;

alkylcarbamoyl substituted with one or more group(s) selected from halogen, cyano, alkyloxy, alkylcarbonyl, alkylsulfonyl, alkylcarbamoyl, and aromatic carbocyclyl;

unsubstituted alkylcarbamoyl; or unsubstituted aromatic carbocyclyl, or pharmaceutically acceptable salt thereof.

(o-9) The compound of any one of Formula ft) and the above (a) to (n), wherein $R^{5b}$ is a hydrogen atom;

halogen;

alkyl substituted with one or more group (a) selected from halogen, hydroxy, carboxy, carbamoyl, alkylcarbamoyl optionally substituted with one or more group(s) selected from (hydroxy, cyano and alkyloxy), non-aromatic heterocyclylcarbonyl, aromatic carbocyclylcarbamoyl optionally substituted with one or more group(s) selected from (halogen and alkyl), and non-aromatic heterocyclylcarbamoyl;

or unsubstituted alkyl, or pharmaceutically acceptable salt thereof.

(p) A compound of any one of the following (p-1) to (p-3) or a pharmaceutically acceptable salt thereof.

(p-1) The compound of any one of Formula (I) and the above (a) to (o), wherein n is an integer from 1 to 3, or pharmaceutically acceptable salt thereof.

(p-2) The compound of any one of Formula (I) and the above (a) to (o), wherein n is 1 or 2, or pharmaceutically acceptable salt thereof.

(p-3) The compound of any one of Formula (I) and the above (a) to (o), wherein n is 1, or pharmaceutically acceptable salt thereof.

(q) A compound according to any one of the following (q-1) to (q-7) or a pharmaceutically acceptable salt thereof.

(q-1) The compound of any one of Formula (I) and the above (a) to (p), wherein $R^{2a}$ is a hydrogen atom, halogen, or substituted or unsubstituted alkyl, or $R^{2a}$ and $R^{2b}$ which are attached to the same carbon atom are taken together to form oxo, or pharmaceutically acceptable salt thereof.

(q-2) The compound of any one of Formula (I) and the above (a) to (p), wherein $R^{2a}$ is a hydrogen atom, or halogen, or $R^{2a}$ and $R^{2b}$ which are attached to the same carbon atom are taken together to form oxo, or pharmaceutically acceptable salt thereof.

(q-3) The compound of any one of Formula (I) and the above (a) to (p), wherein $R^{2a}$ is a hydrogen atom, or $R^{2a}$ and $R^{2b}$ which are attached to the same carbon atom are taken together to form oxo, or pharmaceutically acceptable salt thereof.

(q-4) The compound of any one of Formula (I) and the above (a) to (p), wherein $R^{2a}$ is a hydrogen atom, halogen, or substituted or unsubstituted alkyl, or pharmaceutically acceptable salt thereof.

(q-5) The compound of any one of Formula (I) and the above (a) to (p), wherein $R^{2a}$ is a hydrogen atom, halogen, alkyl, or haloalkyl, or pharmaceutically acceptable salt thereof.

(q-6) The compound of any one of Formula (I) and the above (a) to (p), wherein $R^{2a}$ is a hydrogen atom, or halogen, or pharmaceutically acceptable salt thereof.

(q-7) The compound of any one of Formula (I) and the above (a) to (p), wherein $R^{2a}$ is a hydrogen atom, or pharmaceutically acceptable salt thereof.

(r) A compound according to any one of the following (r-1) to (r-7) or a pharmaceutically acceptable salt thereof.

(r-1) The compound of any one of Formula (I) and the above (a) to (q), wherein $R^{2b}$ is a hydrogen atom, halogen, or substituted or unsubstituted alkyl, or $R^{2a}$ and $R^{2b}$ which are attached to the same carbon atom are taken together to form oxo, or pharmaceutically acceptable salt thereof.

(r-2) The compound of any one of Formula (I) and the above (a) to (q), wherein $R^{2b}$ is a hydrogen atom, or halogen, or $R^{2a}$ and $R^{2b}$ which are attached to the same carbon atom are taken together to form oxo, or pharmaceutically acceptable salt thereof.

(r-3) The compound of any one of Formula (I) and the above (a) to (q), wherein $R^{2b}$ is a hydrogen atom, or $R^{2a}$ and $R^{2b}$ which are attached to the same carbon atom are taken together to form oxo, or pharmaceutically acceptable salt thereof.

(r-4) The compound of any one of Formula (I) and the above (a) to (q), wherein $R^{2b}$ is a hydrogen atom, halogen, or substituted or unsubstituted alkyl, or pharmaceutically acceptable salt thereof.

(r-5) The compound of any one of Formula (I) and the above (a) to (q), wherein $R^{2b}$ is a hydrogen atom, halogen, alkyl, or haloalkyl, or pharmaceutically acceptable salt, thereof.

(r-6) The compound of any one of Formula (I) and the above (a) to (q), wherein $R^{2b}$ is a hydrogen atom, or halogen, or pharmaceutically acceptable salt thereof.

(r-7) The compound of any one of Formula (I) and the above (a) to (q), wherein $R^{2b}$ is a hydrogen atom, or pharmaceutically acceptable salt thereof.

(s) A compound according to any one of the following (s-1) to (s-3) or a pharmaceutically acceptable salt thereof.

(s-1) The compound of any one of Formula (I) and the above (a) to (r), wherein m is an integer from 0 to 2, or pharmaceutically acceptable salt thereof.

(s-2) The compound of any one of Formula (I) and the above (a) to (r), wherein m is 0 or 1, or pharmaceutically acceptable salt thereof.

(a-3) The compound of any one of Formula (I) and the above (a) to (r), wherein m is 0, or pharmaceutically acceptable salt thereof.

(t) A compound according to any one of the following (t-1) to (t-4) or a pharmaceutically acceptable salt, thereof.

(t-1) The compound of any one of Formula (I) and the above (a) to (s), wherein $R^{2c}$ is a hydrogen atom, halogen, or substituted or unsubstituted alkyl, or pharmaceutically acceptable salt thereof.

(t-2) The compound of any one of Formula (I) and the above (a) to (s), wherein $R^{2c}$ is a hydrogen atom, halogen, alkyl, or haloalkyl, or pharmaceutically acceptable salt thereof.

(t-3) The compound of any one of Formula (I) and the above (a) to (s), wherein $R^{2c}$ is a hydrogen atom, or halogen, or pharmaceutically acceptable salt thereof.

(t-4) The compound of any one of Formula (I) and the above (a) to (s), wherein $R^{2c}$ is a hydrogen atom, or pharmaceutically acceptable salt thereof.

(u) A compound according to any one of the following (u-1) to (u-4) or a pharmaceutically acceptable salt thereof.

(u-1) The compound of any one of Formula (I) and the above (a) to (t), wherein $R^{2d}$ is a hydrogen atom, halogen, or substituted or unsubstituted alkyl, or pharmaceutically acceptable salt thereof.

(u-2) The compound of any one of Formula (I) and the above (a) to (t), wherein $R^{2d}$ is a hydrogen atom, halogen, alkyl, or haloalkyl, or pharmaceutically acceptable salt thereof.

(u-3) The compound of any one of Formula (I) and the above (a) to (t), wherein $R^{2d}$ is a hydrogen atom, or halogen, or pharmaceutically acceptable salt thereof.

(u-4) The compound of any one of Formula (I) and the above (a) to (t), wherein $R^{2d}$ is a hydrogen atom, or pharmaceutically acceptable salt thereof.

(v) A compound according to any one of the following (v-1) to (v-4) or a pharmaceutically acceptable salt thereof.

(v-1) The compound of any one of Formula (I) and the above (a) to (u), wherein $Y^1$ is O, or pharmaceutically acceptable salt thereof.

(v-2) The compound of any one of Formula (I) and the above (a) to (u), wherein $Y^2$ is O, or pharmaceutically acceptable salt thereof.

(v-3) The compound of any one of Formula (I) and the above (a) to (u), wherein each of $Y^1$ and $Y^2$ is O, or pharmaceutically acceptable salt thereof.

(v-4) The compound of any one of Formula (I) and the above (a) to (u), wherein $Y^1$ and $Y^2$ are each independently O or S, or pharmaceutically acceptable salt, thereof.

(w) A compound according to any one of the following (w-1) to (w-4) or a pharmaceutically acceptable salt thereof.

(w-1) The compound of any one of Formula (I) and the above (a) to (v), wherein $R^4$ is a hydrogen atom, halogen, or substituted or unsubstituted alkyl, or pharmaceutically acceptable salt thereof.

(w-2) The compound of any one of Formula (I) and the above (a) to (v), wherein $R^4$ is a hydrogen atom, halogen, alkyl, or haloalkyl, or pharmaceutically acceptable salt thereof.

(w-3) The compound of any one of Formula (I) and the above (a) to (v), wherein $R^4$ is a hydrogen atom, or halogen, or pharmaceutically acceptable salt thereof.

(w-4) The compound of any one of Formula (I) and the above (a) to (v), wherein $R^4$ is a hydrogen atom, or pharmaceutically acceptable salt thereof.

(x) A compound according to any one of the following (x-1) to (x-4) or a pharmaceutically acceptable salt thereof.

(x-1) The compound of any one of Formula (I) and the above (a) to (w), wherein $R^6$ is a hydrogen atom, halogen, or substituted or unsubstituted alkyl, or pharmaceutically acceptable salt thereof.

(x-2) The compound of any one of Formula (I) and the above (a) to (w), wherein $R^6$ is a hydrogen atom, halogen, alkyl, or haloalkyl, or pharmaceutically acceptable salt thereof.

(x-3) The compound of any one of Formula (I) and the above (a) to (w), wherein $R^6$ is a hydrogen atom, or halogen, or pharmaceutically acceptable salt thereof.

(x-4) The compound of any one of Formula (I) and the above (a) to (w), wherein $R^6$ is a hydrogen atom, or pharmaceutically acceptable salt thereof.

(y) A compound according to any one of the following (y-1) to (y-8) or a pharmaceutically acceptable salt thereof.

(y-1) The compound of any one of Formula (I) and the above (a) to (x), wherein $R^{5a'}$ is a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted alkylsulfanyl, substituted or unsubstituted alkenylsulfonyl, substituted or unsubstituted alkynylsulfanyl, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted alkylcarbonylamino, substituted or unsubstituted alkenylcarbonylamino, substituted or unsubstituted alkynylcarbonylamino, substituted or unsubstituted alkyloxycarbonylamino, substituted or unsubstituted alkenyloxycarbonylamino, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(y-2) The compound of any one of Formula (I) and the above (a) to (x), wherein $R^{5a'}$ is a hydrogen atom, halogen, hydroxy, carboxy, amino, carbamoyl, cyano, substituted or unsubstituted alkyl, substituted or unsubstituted alkyloxy, substituted or unsubstituted alkyloxycarbonyl, substituted or unsubstituted alkylcarbamoyl, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(y-3) The compound of any one of Formula (I) and the above (a) to (x), wherein $R^{5a'}$ is a hydrogen atom, halogen, amino, carbamoyl, cyano, substituted or unsubstituted alkyl, substituted or unsubstituted alkyloxy, substituted or unsubstituted alkylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(y-4) The compound of any one of Formula (I) and the above (a) to (x), wherein $R^{5a'}$ is a hydrogen atom, halogen, substituted or unsubstituted alkyl, or substituted or unsubstituted alkyloxy, or pharmaceutically acceptable salt thereof.

(y-5) The compound of any one of Formula (I) and the above (a) to (x), wherein $R^{5a'}$ is a hydrogen atom, halogen, alkyl, haloalkyl, alkyloxy, or haloaryloxy, or pharmaceutically acceptable salt thereof.

(y-6) The compound of any one of Formula (I) and the above (a) to (x), wherein $R^{5a'}$ is a hydrogen atom, halogen, alkyl, or haloalkyl, or pharmaceutically acceptable salt thereof.

(y-7) The compound of any one of Formula (I) and the above (a) to (x), wherein $R^{5a'}$ is a hydrogen atom, or halogen, or pharmaceutically acceptable salt thereof.

(y-8) The compound of any one of Formula (I) and the above (a) to (x), wherein $R^{5a'}$ is a hydrogen atom, or pharmaceutically acceptable salt thereof.

(z) A compound according to any one of the following (z-1) to (z-4) or a pharmaceutically acceptable salt thereof.

(z-1) The compound of any one of Formula (I) and the above (a) to (y), wherein $R^Y$ is each independently a hydrogen atom, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or pharmaceutically acceptable salt thereof.

(z-2) The compound of any one of Formula (I) and the above (a) to (y), wherein $R^Y$ is each independently a hydrogen atom, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy, or pharmaceutically acceptable salt thereof.

(z-3) The compound of any one of Formula (I) and the above (a) to (y), wherein $R^Y$ is each independently a hydrogen atom, hydroxy, cyano, substituted or unsubstituted alkyl, or substituted or unsubstituted alkyloxy, or pharmaceutically acceptable salt thereof.

(z-4) The compound of any one of Formula (I) and the above (a) to (y), wherein $R^Y$ is each independently a hydrogen atom, hydroxy, cyano, alkyl, haloalkyl, alkyloxy, or haloaryloxy, or pharmaceutically acceptable salt thereof.

The compounds represented by Formula (I) are not limited to specific isomers but include all possible isomers (e.g., keto-enol isomers, imine-enamine isomers, diastereoisomers, enantiomers, rotamers or the like), racemates or mixtures thereof.

For example, a compound represented by Formula (I) wherein $R^{7a}$ is a hydrogen atom includes the following tautomer.

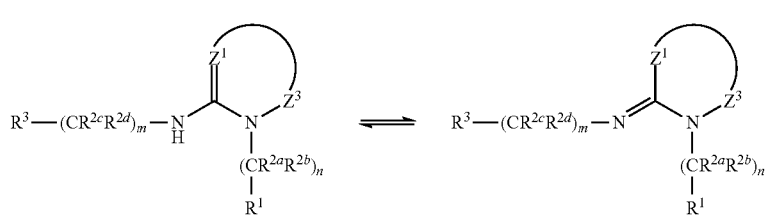

[Chemical Formula 71]

Likewise, a tautomer of the ring represented by the Formula:

[Chemical Formula 72]

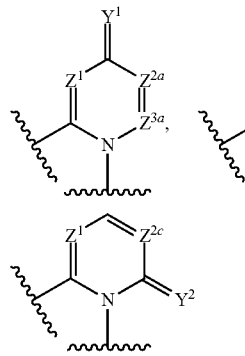

is included.

In the present specification, in a group represented by the Formula:

[Chemical Formula 73]

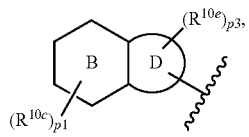

p1 hydrogen atom(s) which is attached to a ring-constituting atom on Ring B can be replaced with $R^{10a}$ and $R^{10c}$.

In the present specification, in a group represented by the Formula:

[Chemical Formula 74]

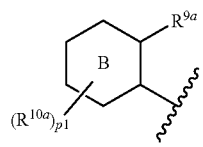

p2 hydrogen atom(s) which is attached to a ring-constituting atom on Ring C can be replaced with $R^{10b}$ and $R^{10d}$.

In the present, specification, in a group represented by the Formula:

[Chemical Formula 75]

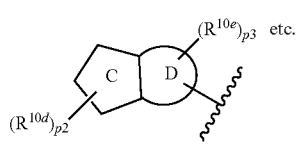

p3 hydrogen atom(s) which is attached to a ring-constituting atom on Ring 1) can be replaced with $R^{10e}$.

In the present specification, in a group represented by the formula:

[Chemical Formula 76]

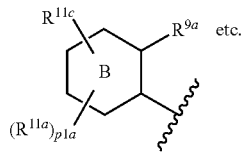

p1a hydrogen atom(s) which is attached to a ring-constituting atom on Ring B can be replaced with $R^{11a}$. Also, any hydrogen atom which is attached to a ring-constituting atom on Ring B can be replaced with $R^{11c}$.

In the present specification, in a group represented by the Formula:

[Chemical Formula 77]

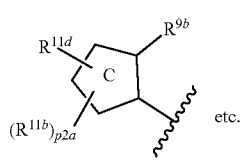

p2a hydrogen atom(s) which is attached to a ring-constituting atom on Ring C can be replaced with $R^{11b}$. Also, any hydrogen atom which is attached to a ring-constituting atom on Ring C can be replaced with $R^{11a}$.

In the present specification, in a group represented by the Formula:

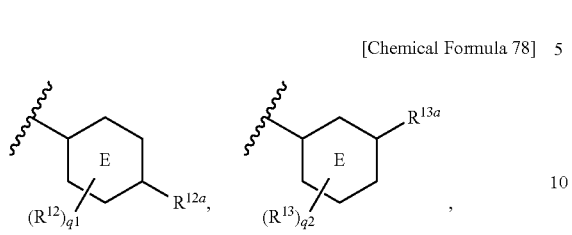

[Chemical Formula 78]

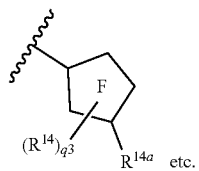

etc.

q1 hydrogen atom(s) which is attached to a ring-constituting atom on Ring E can be replaced with $R^{12}$. q2 hydrogen atom(s) which is attached to a ring-constituting atom on Ring E can be replaced with $R^{13}$. q3 hydrogen atom(s) which is attached to a ring-constituting atom on Ring F can be replaced with $R^{14}$.

In the present specification, in a group represented by the Formula:

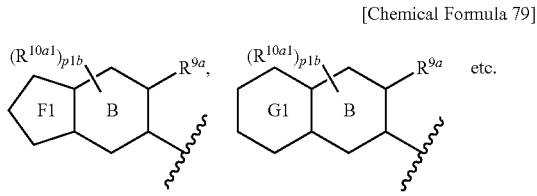

[Chemical Formula 79]

etc.

p1b hydrogen atom(s) which is attached to a ring-constituting atom on Ring B can be replaced with $R^{10a1}$.

In the present, specification, in a group represented by the Formula:

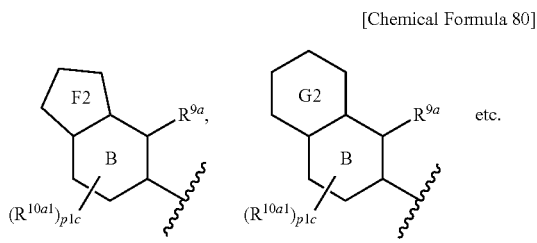

[Chemical Formula 80]

etc.

p1c hydrogen atom(s) which is attached to a ring constituting atom on Ring B can be replaced with $R^{10a1}$.

In the present specification, in a group represented by the Formula:

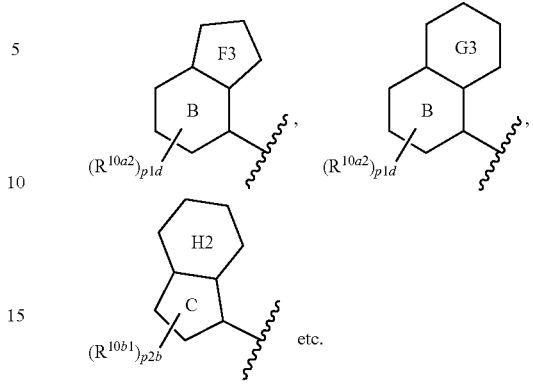

[Chemical Formula 81]

etc.

p1d hydrogen atom(s) which is attached to a ring-constituting atom on Ring B can be replaced with $R^{10a2}$. p2b hydrogen atom(s) which is attached to a ring-constituting atom on Ring C can be replaced with $R^{10b1}$.

One or more hydrogen, carbon and/or other atoms in the compounds represented by Formula (I) may be replaced with isotopes of hydrogen, carbon and/or other atoms respectively. Example s of isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds represented by Formula (I) include the compounds replaced with these isotopes. The compounds replaced with the above isotopes are useful as medicines and include all of radiolabeled compounds of the compound of Formula (I). A "method of radiolabeling" in the manufacture of the "radiolabeled compounds" is encompassed by the present, invention, and the "radiolabeled compounds" are useful for studies on metabolized drug pharmacokinetics, studies on binding assay and/or diagnostic tools.

A radiolabeled compound of the compounds represented by Formula (I) can be prepared using well-known methods in the art. For example, a tritium-labeled compound represented by Formula (I) can be prepared by introducing a tritium to a certain compound represented by Formula (I), through a catalytic dehalogenation reaction using a tritium. This method comprises reacting with an appropriately-halogenated precursor of the compound represented by Formula (I) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds represented by Formula (D include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric, acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds represented by Formula (I) of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds represented by Formula (I). When the compounds represented by Formula (I) or pharmaceutically acceptable salts thereof are allowed to stand in the atmosphere, the compounds may absorb water, resulting in attachment of adsorbed water or formation of hydrates. Recrystallization of the compounds represented by Formula (I) or pharmaceutically acceptable salts thereof may produce crystal polymorphs.

The compounds represented by Formula (I) of the present, invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds represented by Formula (I) through enzymatic oxidation, reduction, hydrolysis or the like under physiological conditions in vivo, compounds that are converted to the compounds represented by Formula (I) through hydrolysis by gastric acid etc., and the like. Methods for selecting and preparing suitable prodrug derivatives are described in, for example, "Design of Prodrugs, Elsevier. Amsrdam, 1985". Prodrugs themselves may have some activity.

When the compounds represented by Formula (I) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chlorido, suitable sulfonyl anhydride and mixed anhydride, or with a condensing agent. For example, they include $CH_3COO-$, $C_2H_5COO-$, tert-BuCOO-, $C_{15}H_{31}COO-$, PhCOO-, (m-NaOOCPh)COO-, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3O$-$PhSO_3-$, $PhSO_3-$ and p-$CH_3PhSO_3-$.

The compounds of the present invention have an antagonistic activity for the P2X7 receptor, and therefore, are useful as a therapeutic and/or preventive agent for diseases associated with the P2X7 receptor. As the diseases associated with the P2X7 receptor, pain, central nervous system diseases, immune diseases and inflammatory diseases and the like, preferably pain are exemplified (Non-patent Document 7-8 and Patent Document 1 etc.).

As pain, pain associated with zoster, postherpetic neuralgia, trigeminal neuralgia, thalamic pain, cancer pain, postoperative pain, menstrual pain, labor pain, chest pain, abdominal pain, colic pain, lumbar backache, headache, migraine, sciatica, sore muscle, orofacial pain, toothache, glossagra, shoulder pain, nociceptive pain, pain associated with deafferentation, psychogenic pain and the like; pain associated with the disease such as entrapment neuropathy, carpal canal syndrome, diabetes, Guillain-Barre syndrome, myofascial pain syndrome, fibromyalgia syndrome, complex regional pain syndrome, causalgia, Hansen's disease, spinal cord injury, stroke, multiple sclerosis, Parkinson's disease, endometriosis, hernia of intervertebral disk, arthritis, rheumatoid arthritis, osteoarthritis, cervical spondylosis deformans, spinal canal stenosis, thoracic outlet syndrome, traumatic brachial plexus injury syndrome, shoulder-hand syndrome, whiplash injury, cholelithiasis, pancreatitis, cystitis, urethritis, urinary calculosis, prostatitis, ulcerative colitis, Crohn's disease, irritable bowel syndrome, bone fracture, osteoporosis, gout, cauda equina syndrome, ankylosing spondylitis, painful spasm, ABC syndrome, skin disease, arteriosclerosis obliterans, Buerger's disease, Raynaud's phenomenon, gangrene, temporomandibular arthrosis, somatoform disorder, somatization disorder, depression and the like;

pain associated with drug therapy, and pain associated with radiation therapy are exemplified.

Additionally, effects for opioid tolerance can be expected.

As central nervous system diseases, Alzheimer's disease, Cerebral amyloid angiopathy, Parkinson's disease, Creutzfeldt-Jakob disease, Huntington's chorea, depression, schizophrenia, attention deficit hyperactivity disorder, sleep disorder, autism spectrum disorder, epilepsy, stroke, multiple sclerosis, spinal cord injury, amyotrophic lateral sclerosis, opioid dependence, cocaine dependence, nicotine dependence and the like are exemplified.

Preferably, as central nervous system diseases, Alzheimer's disease, Cerebral amyloid angiopathy, Parkinson's disease, depression, schizophrenia, attention deficit hyperactivity disorder, sleep disorder, autism spectrum disorder, epilepsy, stroke, multiple sclerosis, spinal cord injury, amyotrophic lateral sclerosis, opioid dependence, cocaine dependence, nicotine dependence and the like are exemplified.

As immune diseases and inflammatory diseases, rheumatoid arthritis, osteoarthritis, asthma, bronchitis, chronic obstructive pulmonary disease, pulmonary emphysema, septic shock, hepatitis, hepatic fibrosis, hepatic cirrhosis, cholecystitis, glomerulonephritis, nephrotic syndrome, pancreatitis, cystitis, urethritis, prostatitis, ulcerative colitis, Crohn's disease, irritable bowel syndrome, psoriasis, atopic dermatitis, contact dermatitis, eczematous dermatitis, delayed-type hypersensitivity reaction, conjunctivitis, uveitis, growth and metastasis of malignant cell (prostate cancer, breast, cancer, lung cancer, uterine cancer, pancreatic cancer, colorectal cancer etc.), leukemia, meningitis, burn injury, glossitis, gingivitis, periodontal disease, esophagitis and the like are exemplified. It is possible that rejection associated with allograft or blood transfusion is involved in the P2X7 receptor. As the other diseases associated with the P2X7 receptor, circulatory diseases such as atherosclerosis, ischemic heart disease, diabetes and the like, bone diseases such as osteoporosis, bone Paget's disease, osteonecrosis, temporomandibular arthrosis and the like, and urologic diseases such as overactive bladder, stress urinary incontinence, prostatomegaly and the like are exemplified.

Preferably, as immune diseases and inflammatory diseases, rheumatoid arthritis, arthritis, osteoarthritis, asthma, bronchitis, chronic obstructive pulmonary disease, cystitis, ulcerative colitis, Crohn's disease and the like are exemplified.

(Synthetic Procedures for the Compound of the Present Invention)

For example, the compounds represented by Formula (I) of the present invention can be prepared by the general procedures described below. The starting materials and reaction reagents used in such synthesis are commercially available or can be synthesized according to methods well known in the art using the compounds commercially available. The methods for extraction, purification and the like may be carried out by using the usual method for the experiments of organic chemistry.

The compounds of the present invention can be synthesized by referring to the known methods in the art.

In all the following steps, when a substituent which interferes with the reaction, e.g. hydroxy, mercapto, amino, formyl, carbonyl, carboxy, is possessed, the substituent is protected by the method such as those described in Protective Groups in Organic Synthesis, Theodora W Greene (John Wiley & Sons) in advance, and the protective group may be removed at a desirable step.

During all the following steps, the order of the steps to be performed may be appropriately changed. In each step, an intermediate may be isolated and then used in the next step.

In this description, meanings of each abbreviation are as follows:
DIEA: N,N-diisopropylethylamine
DMF: N,N-dimethylformamide
DMSO: Dimethyl sulfoxide
DPPA: Diphenylphosphoryl azide
IPE: Diisopropyl ether
NBS: N-bromosuccinimide
NMP: N-methylpyrrolidone
HATU: O-(7-azabenzotriazol-1-yl)-1,1,3,3-tetramethyluronium hexafluorophosphate
HOAt: 1-hydroxy-7-azabenzotriazole
PdCl$_2$(dppf): [1,1'-bis(diphenylphosphino)ferrocene]palladium (II) dichloride
Xantphos: 4,5'-bis(diphenylphosphino)-9,9'-dimethylxanthene

[Method A]

[Chemical Formula 82]

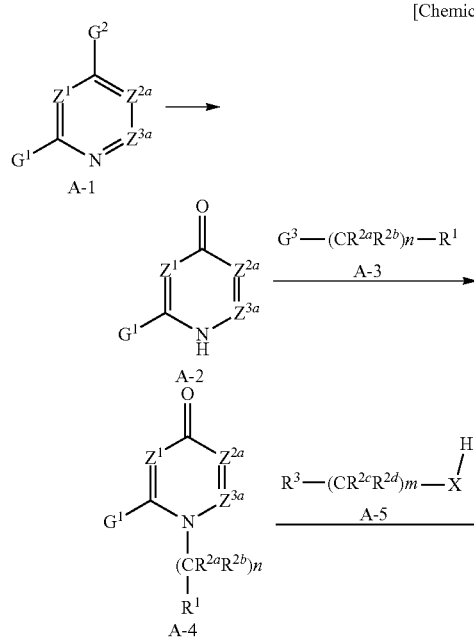

-continued

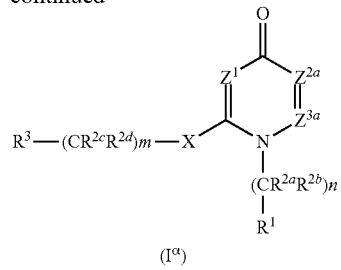

wherein $G^1$, $G^2$ and $G^3$ are each independently a leaving group such as halogen, substituted or unsubstituted alkylsulfanyl, substituted or unsubstituted alkylsulfinyl, or substituted or unsubstituted alkylsulfonyl; and the other symbols are the same as the above (1).

Step 1

A compound (A-2) can be synthesized by the reaction of a compound (A-1) with a basic aqueous solution.

As the base, for example, metal hydroxide (e.g., sodium hydroxide, potassium hydroxide, lithium hydroxide etc.), metal carbonate (e.g., sodium carbonate, potassium carbonate, cesium carbonate etc.) and the like are exemplified. 1.0 or more mole equivalent(s), preferably 1.0 to 5.0 mole equivalent(s) can be used per an equivalent of the compound (A-1).

As the reaction solvent, ethers (e.g., tetrahydrofuran, diethyl ether, dioxane, dimethoxyethane etc.), DMF, DMSO, NMP, water and a mixed solvent thereof and the like are exemplified.

The reaction temperature is 0° C. to 40° C., preferably 0° C. to 20° C.

The reaction time is 0.5 to 48 hours, preferably 1 to 16 hours.

The obtained desired compound (A-2) can be purified as necessary by the methods which are usually used (e.g., column chromatography, recrystallization etc.).

Step 2

A compound (A-4) can be synthesized by the reaction of the compound (A-2) with a compound (A-3) in the presence of a base in the appropriate solvent.

In this reaction, 1.0 or more mole equivalent(s) of the compound (A-3), preferably 1.0 to 5.0 mole equivalent(s) can be used per an equivalent of the compound (A-2).

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium carbonate, cesium carbonate etc.), metal alkoxide (e.g., sodium methoxide, sodium ethoxide, potassium tert-butoxide etc.), metal alkyl (e.g., butyllithium etc.), pyridine, triethylamine. DIEA and the like are exemplified. 1.0 or more mole equivalent(s), preferably 1.0 to 5.0 mole equivalent(s) can be used per an equivalent, of the compound (A-2).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, acetonitrile, pyridine, water and the like are exemplified. The reaction solvent may be used alone or in combination.

The reaction temperature is 0 to 200° C., under microwave irradiation as necessary, preferably 0 to 150° C.

The reaction time is 0.1 to 72 hours, preferably 0.0 hours to 18 hours.

The obtained desired compound (A-4) can be purified as necessary by the methods which are usually used (e.g., column chromatography, recrystallization etc.).

Step 3

A compound (1α) can be synthesized by the reaction of the compound (A-4) with a compound (A-5) in the presence of a palladium catalyst and a base or an acid without any solvent or in the appropriate solvent as necessary.

In this reaction, 1.0 or more mole equivalent(s) of the compound (A-5), preferably 1.0 to 5.0 mole equivalent(s) can be used per an equivalent of the compound (A-4).

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium carbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 1.0 or more mole equivalent(s), preferably 1.0 to 5.0 mole equivalent(s) can be used per an equivalent of the compound (A-4).

As the acid, for example, acetic acid, propionic acid and the like are exemplified. 1.0 or more mole equivalent(s), preferably 1.0 to 5.0 mole equivalent(s) can be used per an equivalent of the compound (A-4).

As the palladium catalyst, palladium acetate, bis(dibenzylideneacetone)palladium, tetrakistriphenylphosphinepalladium, bis(triphenylphosphine)palladium(II) dichloride, bis(tri-tert-butylphosphine)palladium, PdCl$_2$(dppf)CH$_2$Cl$_2$ and the like are exemplified. 0.001 to 0.5 mole equivalents can be used per an equivalent of the compound (A-4).

As the reaction solvent, alcohols (e.g., tert-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, acetonitrile, pyridine, water and the like are exemplified. The reaction solvent may be used alone or in combination.

The reaction temperature is 0 to 200° C., under microwave irradiation as necessary, preferably 0 to 150° C.

The reaction time is 0.1 to 72 hours, preferably 0.5 hours to 18 hours.

The obtained desired compound (1α) can be purified as necessary by the methods which are usually used (e.g., column chromatography, recrystallization etc.).

[Method B]

[Chemical Formula 83]

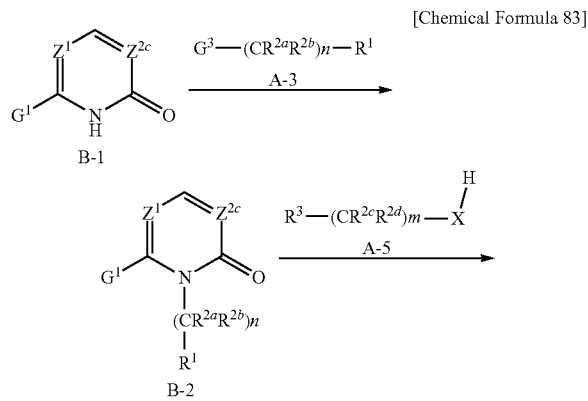

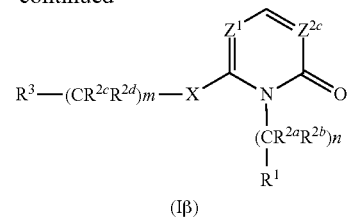

(Iβ)

wherein G$^1$ and G$^3$ are the same as the method A, and the other symbols are the same as the above (1).

Step 1

A compound (B-2) can be synthesized by the reaction of a compound (B-1) with the compound (A-3) according to the synthetic procedures described in the step 2 of the method A.

The obtained desired compound (B-2) can be purified as necessary by the methods which are usually used (e.g., column chromatography, recrystallization etc.).

Step 2

A compound (16) can be synthesized by the reaction of the compound (B-2) with the compound (A-5) according to the synthetic procedures described in the step 3 of the method A.

The obtained desired compound (IB) can be purified as necessary by the methods which are usually used (e.g., column chromatography, recrystallization etc.).

[Method C]

[Chemical Formula 84]

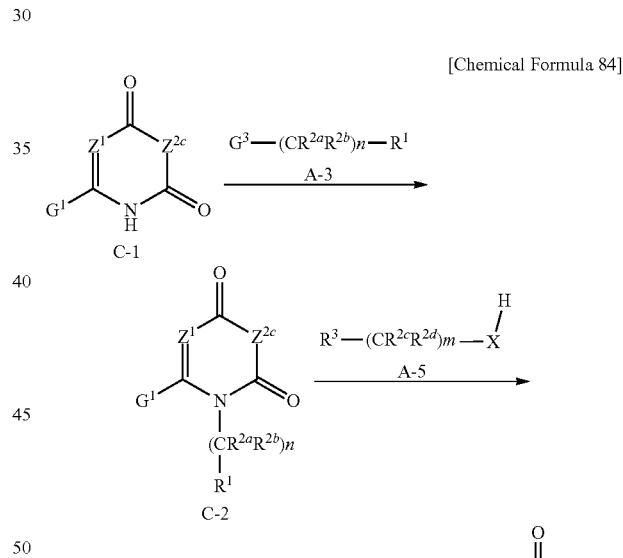

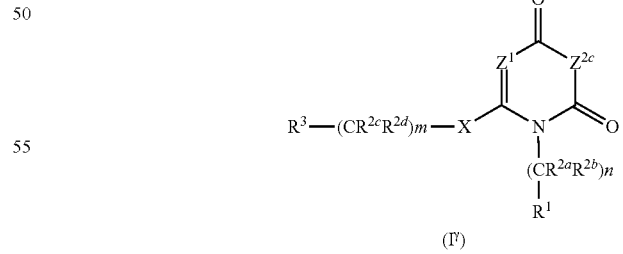

(I′)

wherein G$^1$ and G$^3$ are the same as the method A, and the other symbols are the same as the above (1).

Step 1

A compound (C-2) can be synthesized by the reaction of a compound (C-1) with the compound (A-3) according to the synthetic procedures described in the step 2 of the method A.

The obtained desired compound (C-2) can be purified as necessary by the methods which are usually used (e.g., column chromatography, recrystallization etc.).

Step 2

A compound (Iy) can be synthesized by the reaction of the compound (C-2) with the compound (A-5) according to the synthetic procedures described in the step 3 of the method A.

The obtained desired compound (Iy) can be purified as necessary by the methods which are usually used (e.g., column chromatography, recrystallization etc.).

[Method D]

[Chemical Formula 85]

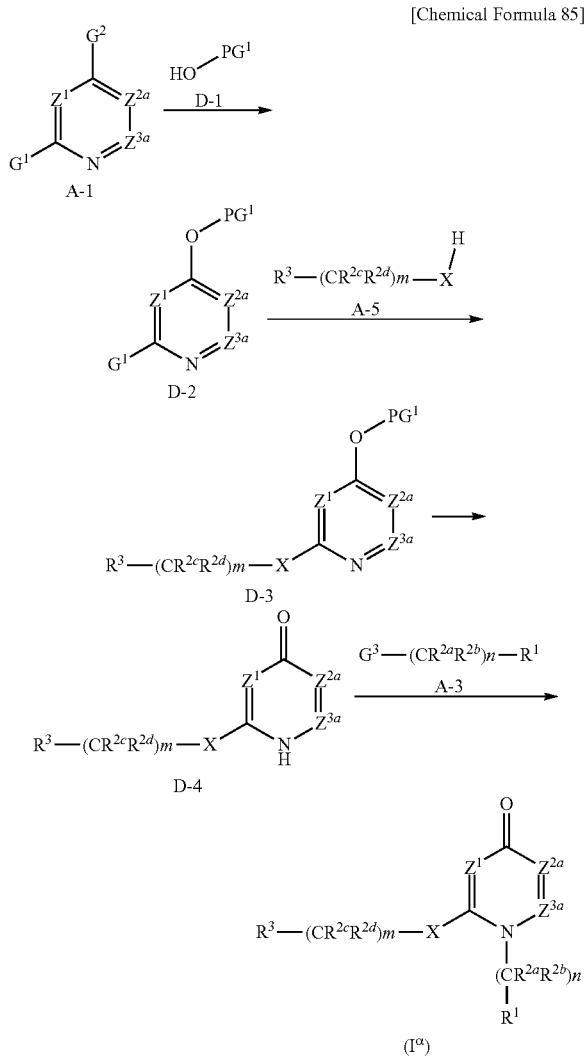

wherein $PG^1$ is an appropriate protecting group of a hydroxy group;
$G^1$ and $G^3$ are the same as the method A, and the other symbols are the same as the above (1).

Step 1

A compound (D-2) can be synthesized by the reaction of a compound (A-1) with a compound (D-1) in the presence of a base in the appropriate solvent.

In this reaction. 1.0 or more mole equivalents) of the compound (D-1), preferably 1.0 to 5.0 mole equivalent(s) can be used per an equivalent of the compound (A-1).

As the base which can be used, for example, metal hydride (e.g., sodium hydrido, lithium hydrido etc.), molal carbonato (e.g., sodium carbonato, potassium bicarbonate, cesium carbonate etc.), metal alkoxide (e.g., sodium methoxide, sodium ethoxide, potassium tert-butoxide etc.), metal alkyl (e.g., butyllithium etc.) are exemplified. 1.0 or more mole equivalents), preferably 1.0 to 1.5 mole equivalents) can be used per an equivalent of the compound (A-1).

As the reaction solvent, alcohols (e.g., tert-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, DMSO, NMP, a mixed solvent thereof and the like are exemplified.

As the reaction temperature, −20° C. to 200° C., preferably 0° C. to 30° C. are exemplified.

As the reaction time, 0.1 to 80 hours, preferably 1 to 16 hours are exemplified.

The obtained desired compound (D-2) can be purified as necessary by the methods which are usually used (e.g., column chromatography, recrystallization etc.).

Step 2

A compound (D-3) can be synthesized by the reaction of the compound (D-2) with the compound (A-5) according to the synthetic procedures described in the step 3 of the method A.

The obtained desired compound (D-3) can be purified as necessary by the methods which are usually used (e.g., column chromatography, recrystallization etc.).

Step 3

A compound (D-4) can be synthesized by the deprotection of the compound (D-3) in the presence of an acid or a Lewis acid or a base in the appropriate solvent.

As the acid, hydrochloric acid-ethyl acetate, hydrochloric acid-methanol, hydrochloric acid-dioxane, hydrobromic acid-acetic acid, hydrobromic acid, sulfuric acid, formic acid, trifluoroacetic acid and the like are exemplified. As the Lewis acid, trimethylsilyl iodide, $BBr_3$, $AlCl_3$, $BF_3.(Et_2O)$ and the like are exemplified. As the base, tetrabutyl ammonium fluoride, hydrogen fluoride-pyridine and the like are exemplified. 0.01 or more mole equivalents, preferably 0.5 to 10.0 mole equivalents can be used per an equivalent of the compound (D-3).

As the reaction solvent, alcohols (e.g., methanol, ethanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, acetonitrile, DMA, pyridine, water and the like are exemplified. The reaction solvent may be used alone or in combination.

The reaction temperature is 0 to 200° C., under microwave irradiation as necessary, preferably 0 to 150° C.

The reaction time is 0.1 to 72 hours, preferably 0.5 hours to 18 hours.

The obtained desired compound (D-4) can be purified as necessary by the methods which are usually used (e.g., column chromatography, recrystallization etc.).

Step 4

A compound (1α) can be synthesized by the reaction of the compound (D-4) with the compound (A-3) according to the synthetic procedures described in the step 2 of the method B.

The obtained desired compound (1α) can be purified as necessary by the methods which are usually used (e.g., column chromatography, recrystallization etc.).

[Method E]

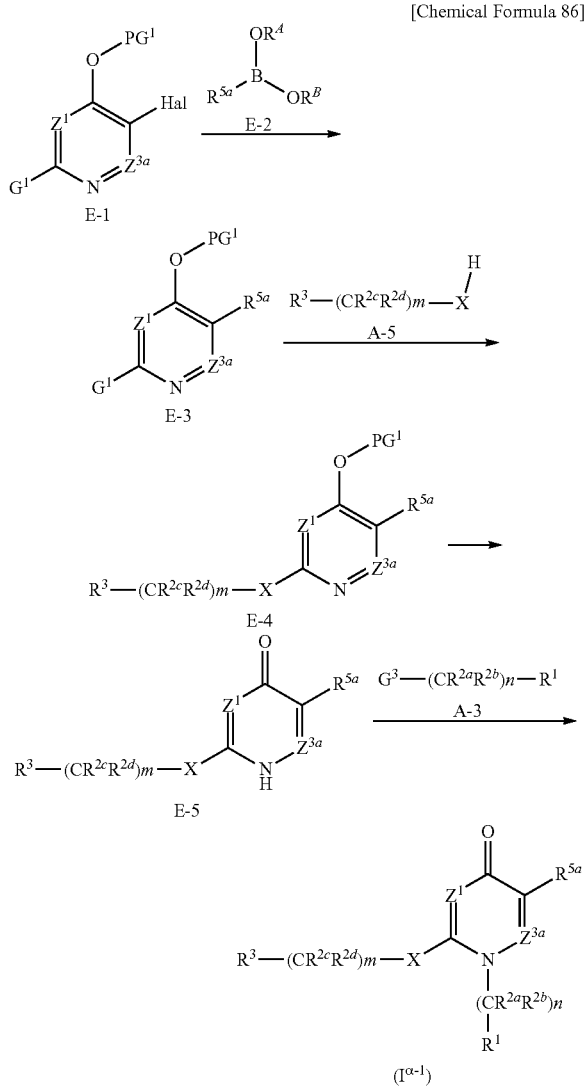

wherein $R^A$ and $R^B$ are each independently hydrogen, or substituted or unsubstituted alkyl, or are taken together to form a substituted or unsubstituted non-aromatic heterocycle)
Hal is halogen;
$PG^1$ is an appropriate protecting group of a hydroxy group)
$G^1$ and $G^3$ are the same as the method A, and the other symbols are the same as the above (1).

Step 1

A compound (E-3) can be synthesized by the reaction of the compound (E-1) with boronic acid or boronate ester (E-2) in the presence of a metal catalyst and a base in the appropriate solvent.

In this reaction, 1.0 or more mole equivalent(s) of boronic acid or boronate ester (E-2), preferably 1.0 to 5.0 mole equivalent(s) can be used per an equivalent of the compound (E-1).

As the metal catalyst, palladium (II) acetate, bis(dibenzylideneacetone)palladium, Tetrakistriphenylphosphinepalladium, bis(triphenylphosphine)palladium (II) dichloride, bis(tri-tert-butylphosphine)palladium, $PdCl_2(dppF)CH_2Cl_2$ and the like are exemplified. 0.001 to 1.0 mole equivalents) can be used per an equivalent of the compound (E-1).

As the base, lithium hydroxide, sodium hydroxide, potassium hydroxide, potassium tert-butoxide, sodium tert-butoxide, sodium carbonate, cesium carbonate, potassium bicarbonate, sodium hydrogen carbonate, sodium phosphate, sodium hydrogen phosphate, potassium phosphate, potassium hydrogen phosphate and the like can be exemplified. 1.0 to 10.0 mole equivalent(s) can be used per an equivalent of the compound (E-1).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.). DMF, DMA, NMP, DMSO, water and a mixed solvent thereof and the like are exemplified.

The reaction temperature is 20 to 250° C., under microwave irradiation as necessary, preferably 0 to 200° C.

The reaction time is 0.1 to 48 hours, preferably 0.5 to 12 hours.

The obtained desired compound (E-3) can be purified as necessary by the methods which are usually used (e.g., column chromatography, recrystallization etc.).

Step 2

A compound (E-4) can be synthesized by the reaction of the compound (E-3) with the compound (A-5) according to the synthetic procedures described in the step 2 of the method D.

The obtained desired compound (E-4) can be purified as necessary by the methods which are usually used (e.g., column chromatography, recrystallization etc.).

Step 3

A compound (E-5) can be synthesized by the deprotection of the protecting group of the hydroxy group of the compound (E-4) according to the synthetic procedures described in the step 3 of the method D.

The obtained desired compound (E-5) can be purified as necessary by the methods which are usually used (e.g., column chromatography, recrystallization etc.).

Step 4

A compound (Iα-1) can be synthesized by the reaction of the compound (E-5) with the compound (A-3) according to the synthetic procedures described in the step 2 of the method B.

The obtained desired compound (Iα-1) can be purified as necessary by the methods which are usually used (e.g., column chromatography, recrystallization etc.).

[Method F]

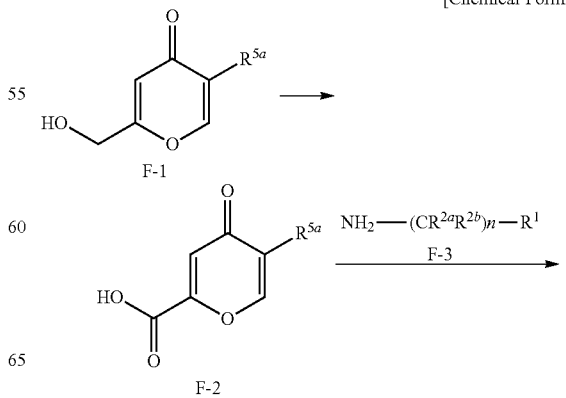

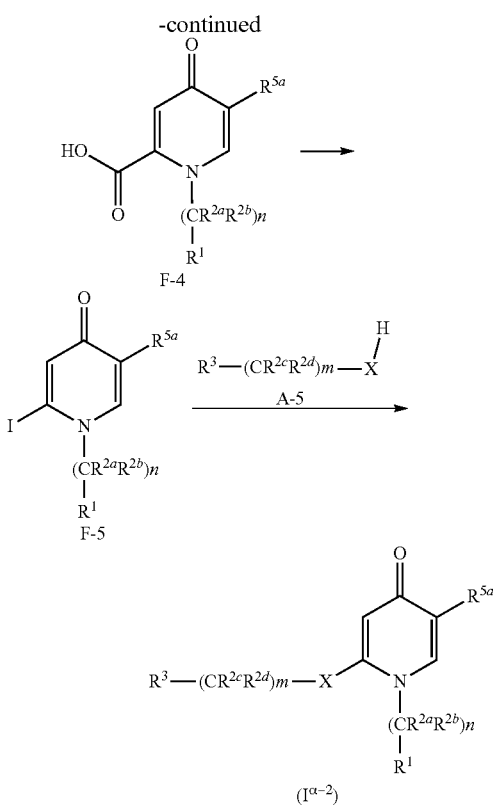

wherein each symbol is the same as the above (1).

Step 1

A compound (F-2) can be synthesized by the reaction of the compound (F-1) with 2,2,2,6-tetramethylpiperidino 1-oxyl in the presence of an oxidizing agent.

As the oxidizing agent, for example, sodium hypochlorite, iodobenzene diacetate and the like are exemplified. 1.0 or more mole equivalents), preferably 1.0 to 5.0 mole equivalent(s) can be used per an equivalent of the compound (F-1).

As the reaction solvent, ethers (e.g., tetrahydrofuran, diethyl ether, dioxane, dimethoxyethane etc.), halogenated hydrocarbons (e.g., chloroform, dichloromethane etc.), acetonitrile, water and the like are exemplified. The reaction solvent may be used alone or in combination.

The reaction temperature is 0 to 100° C., preferably 0 to 60° C.

The reaction time is 0.1 to 72 hours, preferably 0.5 hours to 18 hours.

The obtained desired compound (F-2) can be purified as necessary by the methods which are usually used (e.g., column chromatography, recrystallization etc.).

Step 2

A compound (F-1) can be synthesized by the reaction of the compound (F-2) with a compound (F-3) in the presence of a base in the appropriate solvent.

In this reaction, 1.0 or more mole equivalent(s) of the compound (F-3), preferably 1.0 to 5.0 mole equivalent(s) can be used per an equivalent of the compound (F-2).

As the base, for example, metal hydroxide (e.g., sodium hydroxide, potassium hydroxide, tripotassium phosphate etc.), metal hydride (e.g., sodium hydride, lithium hydride etc.), metal carbonato (e.g., sodium carbonato, potassium carbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 1.0 or more mole equivalent(s), preferably 1.0 to 5.0 mole equivalent(s) can be need per an equivalent of the compound (F-2).

As the reaction solvent, alcohols (e.g., tertbutanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, acetonitrile, pyridine, water and the like are exemplified. The reaction solvent may be used alone or in combination.

The reaction temperature is 0 to 200° C., under microwave irradiation as necessary, preferably 0 to 1.50° C.

The reaction time is 0.1 to 72 hours, preferably 0.5 to 18 hours.

The obtained desired compound (F-4) can lie purified as necessary by the methods which are usually used (e.g., column chromatography, recrystallization etc.).

Step 3

A compound (F-5) can be synthesized by the reaction of the compound (F-4) with iodine in a DMSO solution.

The reaction temperature is −10° C. to 200° C., preferably 0° C. to 150° C.

The reaction time is 0.1 to 72 hours, preferably 0.5 hours to 18 hours.

The obtained desired compound (F-5) can be purified as necessary by the methods which are usually used (e.g., column chromatography, recrystallization etc.).

Step 4

A compound (Iα-2) can be synthesized by the reaction of the compound (F-5) with the compound (A-5) according to the synthetic procedures described in the step 3 of the method A.

The obtained desired compound (Iα-2) can be purified os necessary by the methods which are usually used (e.g., column chromatography, recrystallization etc.).

[Method G]

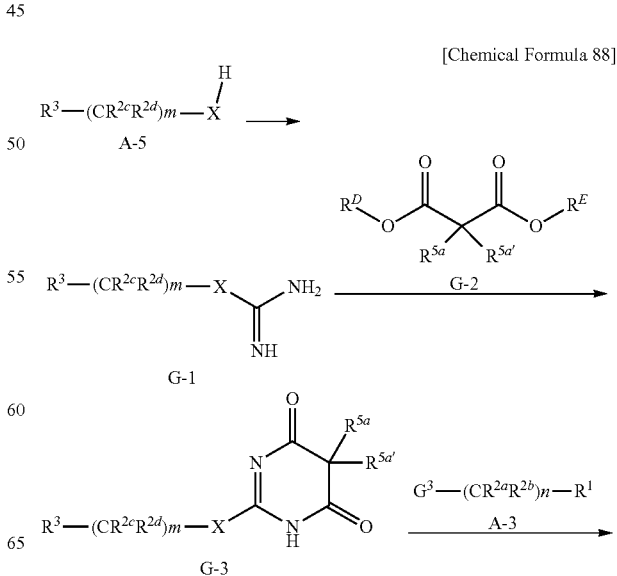

[Chemical Formula 88]

-continued

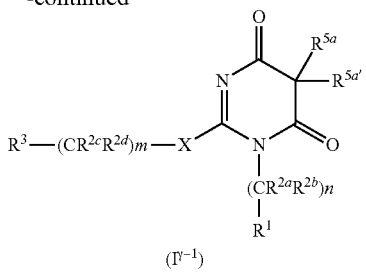

(I'−1)

wherein $R^D$ and $R^E$ are each independently substituted or unsubstituted alkyl; $G^3$ is the same as the method A, and the other symbols are the same as the above (1).

Step 1

A compound (G-1) can be synthesized by the reaction of the compound (A-5) with 1-amidinopyrazole hydrochloride.

In this reaction, 1.0 or more mole equivalent(s) of the 1-amidinopyrazole hydrochloride, preferably 1.0 to 5.0 mole equivalent(s) can be used per an equivalent of the compound (A-5).

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium bicarbonate, cesium carbonate etc.), metal alkoxide (e.g., sodium methoxide, sodium ethoxide, potassium tertbutoxide etc.), metal alkyl (e.g., butyllithium etc.), pyridine, triethylamine, DIEA and the like are exemplified. 1.0 or more mole equivalent(s), preferably 1.0 to 5.0 mole equivalent(s) can be used per an equivalent of the compound (A-5).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, acetonitrile, DMA and the like are exemplified. The reaction solvent may be used alone or in combination.

The reaction temperature is 0 to 200° C., under microwave irradiation as necessary, preferably 0 to 150° C.

The reaction time is 0.1 to 72 hours, preferably 0.5 to 18 hours.

The obtained desired compound (G-1) can be purified as necessary by the methods which ore usually used (e.g., column chromatography, recrystallization etc.).

Step 2

A compound (G-3) can be synthesized by the reaction of the compound (G-1) with a compound (G-2) in the presence of a base in the appropriate solvent.

In this reaction, 1.0 or more mole equivalent(s) of the compound (G-2), preferably 1.0 to 5.0 mole equivalent(s) can be used per an equivalent of the compound (G-1).

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium carbonate, cesium carbonate etc.), metal alkoxide (e.g., sodium methoxide, sodium ethoxide, potassium tertbutoxide etc.), metal alkyl (e.g., butyllithium etc.), triethylamine, DIEA, DBU and the like are exemplified. 1.0 or more mole equivalent(s), preferably 1.0 to 5.0 mole equivalent(s) can be used per an equivalent of the compound (G-1).

As the reaction solvent, alcohols (e.g., tertbutanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, NMP, acetonitrile. DMA and the like are exemplified. The reaction solvent can be used alone or in combination.

The reaction temperature is 0 to 200° C., under microwave irradiation as necessary, preferably 0 to 150° C.

The reaction time is 0.1 to 72 hours, preferably 0.5 hours to 18 hours.

The obtained desired compound (G-3) can be purified as necessary by the methods which are usually used (e.g., column chromatography, recrystallization etc.).

Step 3

A compound (Iγ-1) can be synthesized by the reaction of the compound (G-3) and a compound (A-3) according to the synthetic procedures described in the step 2 of the method A.

The obtained desired compound (Iγ-1) can be purified as necessary by the methods which are usually used (e.g., column chromatography, recrystallization etc.).

The synthesis methods of methods H to N shown below can be used not only in the synthesis of a compound represented by formula (Iα) but also in the synthesis of compounds represented by formula (Iβ) and formula (Iγ).

[Method H]

[Chemical Formula 89]

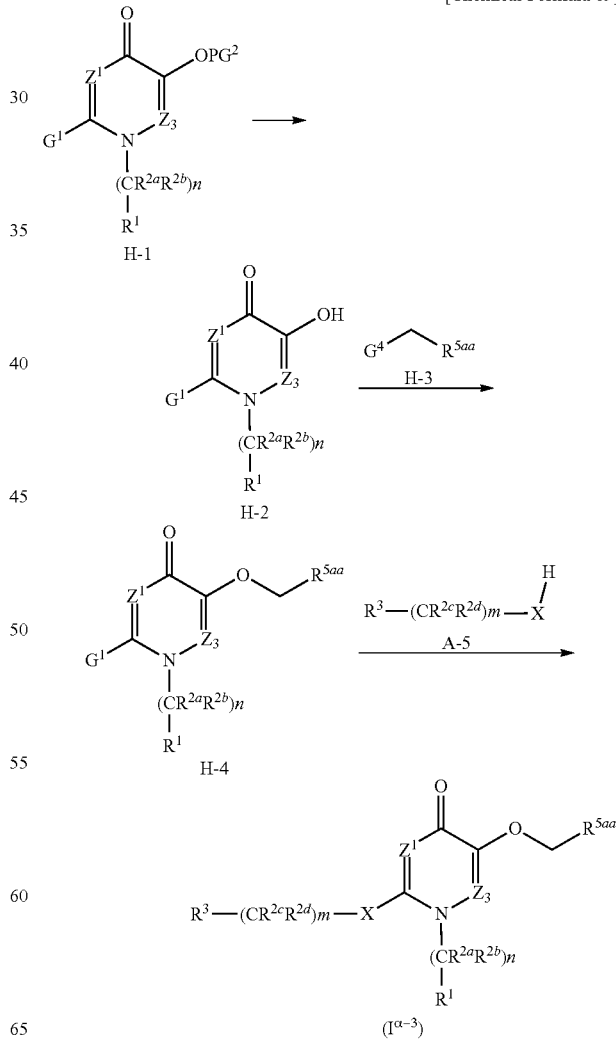

wherein PC² is an appropriate protecting group of a hydroxy group;

G¹ and G⁴ are each independently a leaving group such as halogen, substituted or unsubstituted alkylsulfanyl, substituted or unsubstituted alkylsulfinyl, or substituted or unsubstituted alkylsulfonyl;

$R^{5aa}$ is a hydrogen atom, a hydrogen atom, a substituent selected from the substituent group B, or the like; and the other symbols are the same as the above (1).

Step 1

A compound (H-2) can be synthesized by the deprotection of the protecting grovip of the hydroxy group of the compound (H-1) obtained by the method A according to the synthetic procedures described in the step 3 of the method D.

The obtained desired compound (H-2) can be purified as necessary by the methods which are usually used (e.g., column chromatography, recrystallization etc.).

Step 2

A compound (H-4) can be synthesized by the reaction of the compound (H-2) and a compound (H-3) according to the synthetic procedures described in the step 2 of the method A.

The obtained desired compound (H-4) can be purified as necessary by the methods which are usually used (e.g., column chromatography, recrystallization etc.).

Step 3

A compound represented by a compound (Iα-3) can be synthesized by the reaction of the compound (H-4) and a compound (A-5) according to the synthetic procedures described in the step 3 of the method A.

The obtained desired compound (Iα-3) can be purified as necessary by the methods which are usually used (e.g., column chromatography, recrystallization etc.).

[Method I]

[Chemical Formula 90]

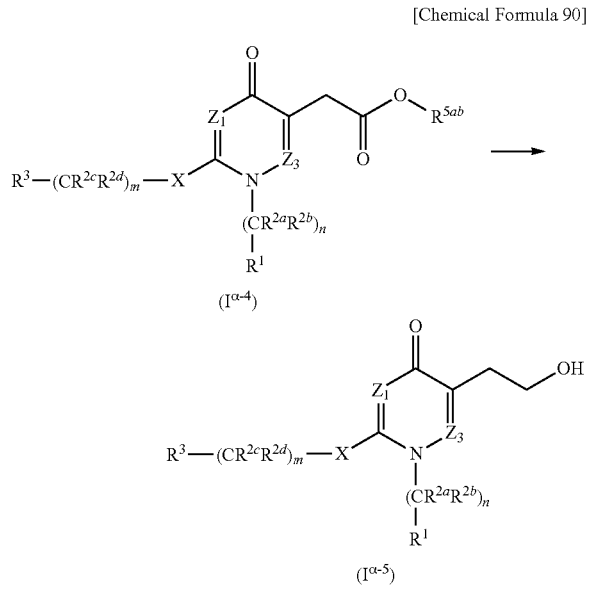

wherein $R^{5ab}$ is substituted or unsubstituted alkyl; and the other symbols are the same as the above (1>.

A compound (Iα-5) can be synthesized by reduction using the compound (Iα-4) obtained by the method A in the appropriate solvent.

As the reducing agent, sodium borohydride, lithium borohydride, lithium aluminum hydride and the like are exemplified. 1 or more mole equivalent(s), preferably 1.0 to 5.0 mole equivalent(s) can be used per an equivalent of the compound (Iα-4).

As the reaction solvent, alcohols (e.g., methanol, ethanol, isopropanol etc.), ethers (e.g., tetrahydrofuran, diethyl ether, dioxane, dimethoxyethane etc.), dichloromethane, water and the like are exemplified. The reaction solvent may be used alone or in combination.

The reaction temperature is −10 to 100° C., preferably 0 to 100° C.

The reaction time is 0.1 to 72 hours, preferably 0.5 hours to 18 hours.

The obtained desired compound (Iα-5) can be purified as necessary by the methods which are usually used (e.g., column chromatography, recrystallization etc.).

[Method J]

[Chemical Formula 91]

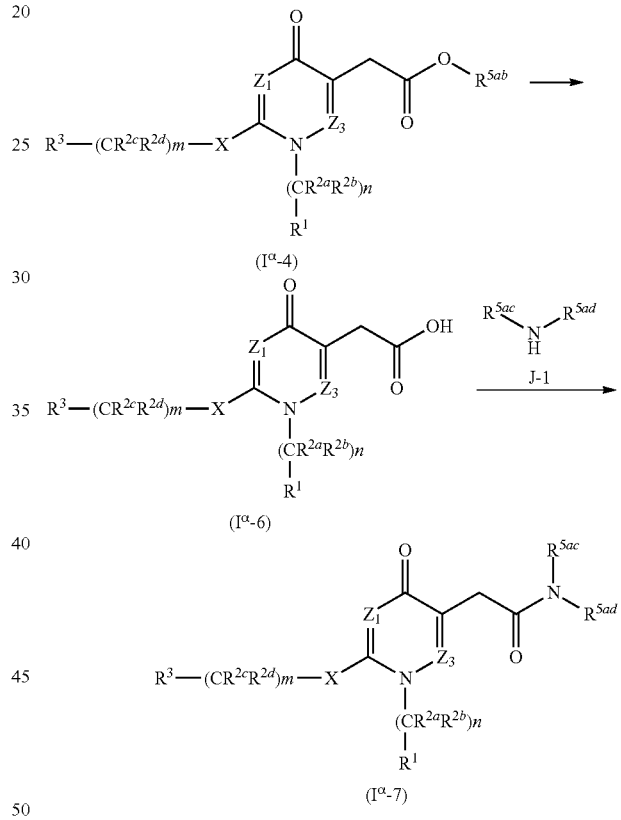

wherein $R^{5ab}$ is substituted or unsubstituted alkyl;

$R^{5ac}$ and $R^{5ad}$ are each independently a hydrogen atom, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl or the like; and the other symbols ore the same as the above (1).

Step 1

A compound (Iα-6) can be synthesized by hydrolysis using the compound (Iα-4) obtained by the method A in the presence of an acid or a base.

As the acid, hydrochloric acid, p-toluenesulfonic acid, sulfuric acid, formic acid, trifluoroacetic acid and the like are exemplified.

As the base, lithium hydroxide, sodium hydroxide, potassium hydroxide, sodium carbonate, cesium carbonate, potassium carbonate, sodium hydrogen carbonate, sodium phosphate, sodium hydrogen phosphate, potassium phosphate, potassium hydrogen phosphato, tetrabutyl ammonium fluoride and the like are exemplified.

1 or more mole equivalent(s), preferably 5 mole equivalents can be used per an equivalent of the compound (Iα-4).

As the reaction solvent, alcohols (e.g., methanol, ethanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, DMSO, NMP, acetonitrile. DMA, water and the like are exemplified. The reaction solvent may be used alone or in combination.

The reaction temperature is −10 to 200° C., preferably 0 to 150° C.

The reaction time is 0.1 to 72 hours, preferably 0.5 hours to 18 hours.

The obtained desired compound (Iα-7) can be purified as necessary by the methods which are usually used (e.g., column chromatography, recrystallization etc.).

Step 2

A compound (Iα-7) can be synthesized by the condensation of the compound (Iα-6) with the compound (J-1) in the appropriate solvent.

As the condensing agent, condensing agents such as 1-hydroxybenzotriazole, HOAt, 1-ethyl-3-(3-dimethylaminopropyl)carbodiimide hydrochloride, HATU, and (benzotriazol-1-yloxy)tripyrrolidinophosphonium hexafluorophosphate, and bases such as triethylamine and diisopropylethylamine, and the like are exemplified. 1 or more mole equivalent(s), preferably 1 to 5 mole equivalent(s) can be used per an equivalent of the compound (Iα-6).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, NMP, acetonitrile, DMA and the like are exemplified. The reaction solvent can be used alone or in combination.

The reaction temperature is −10 to 200° C., preferably 0 to 150° C.

The reaction time is 0.1 to 72 hours, preferably 0.0 hours to 18 hours.

The obtained desired compound (Iα-7) can be purified as necessary by the methods which are usually used (e.g., column chromatography, recrystallization etc.).

[Method K]

[Chemical Formula 92]

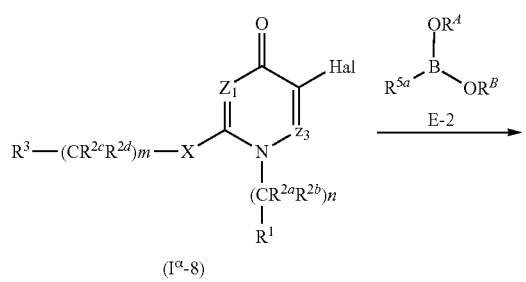

(Iα-8)

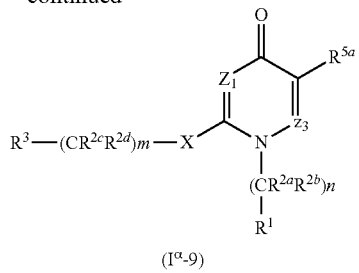

(Iα-9)

wherein Hal is halogen;
R$^A$ and R$^B$ are the same as the method E, and the other symbols are the same as the above (1).

A compound (Iα-9) can be synthesized by the reaction of the compound (Iα-8) obtained by the method A with a boronic acid or a boronic acid ester (E-2) according to the synthetic procedures described in the method E.

The obtained desired compound (Iα-9) can bo purified as necessary by the methods which are usually used (e.g., column chromatography, recrystallization etc.).

[Method L]

[Chemical Formula 93]

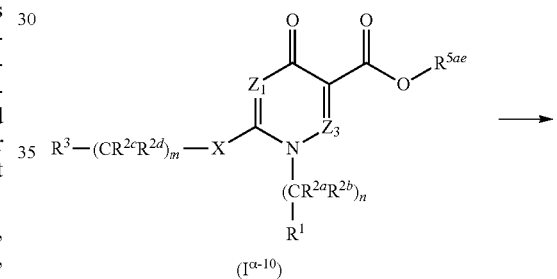

(Iα-10)

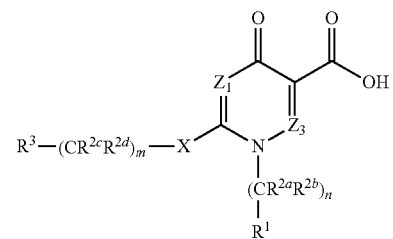

(Iα-11)

wherein R$^{5ac}$ is substituted or unsubstituted alkyl, and the other symbols are the same as the above (1).

A compound (Iα-11) can be synthesized by the hydrolysis of the compound (Iα-10) obtained by the method A according to the synthetic procedures described in the step 1 of the method J.

The obtained desired compound (Iα-11) can be purified as necessary by the methods which are usually used (e.g., column chromatography, recrystallization etc.).

[Method M]

[Chemical Formula 94]

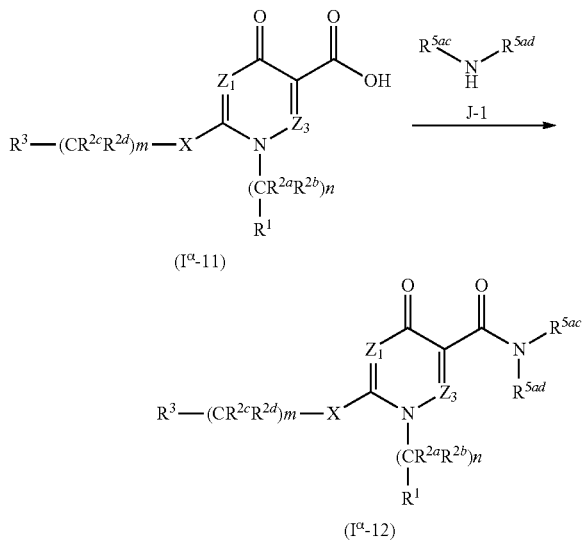

wherein $R^{5ac}$ and $R^{5ad}$ are the same as the method J, and the other symbols are the same as the above (1).

A compound (Iα-12) can be synthesized by the condensation of the compound (Iα-10) obtained by the method K with the compound (J-1) according to the synthetic procedures described in the step 2 of the method J.

The obtained desired compound (Iα-12) can be purified as necessary by the methods which are usually used (e.g., column chromatography, recrystallization etc.).

[Method N]

[Chemical Formula 95]

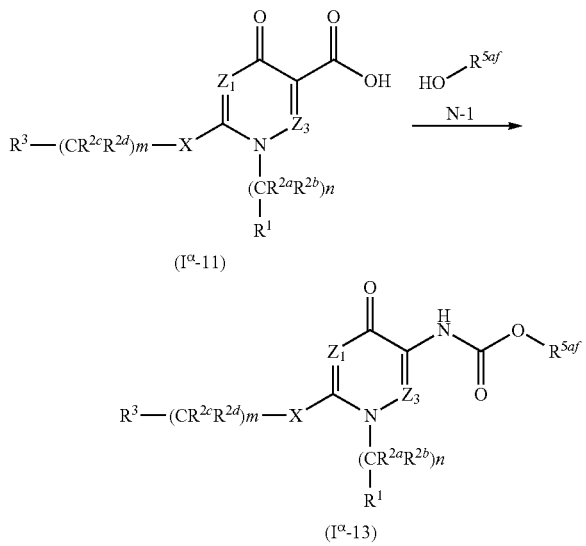

wherein $R^{5af}$ is substituted or unsubstituted alkyl, substituted or unsubstituted aromatic carbocyclyl, or substituted or unsubstituted aromatic heterocyclyl, and the other symbols are the same as the above (1).

A compound (Iα-13) can be synthesized by the reaction of the compound (Iα-11) obtained by the method K with an alcohol (N-1) in the presence of DPPA in the appropriate solvent.

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, DMSO, NMP, acetonitrile, DMA and the like are exemplified. The reaction solvent can be used alone or in combination.

The reaction temperature is −10 to 200° C., preferably 0 to 150° C.

The reaction time is 0.1 to 72 hours, preferably 0.5 hours to 18 hours.

The obtained desired compound (Iα-13) can be purified as necessary by the methods which are usually used (e.g., column chromatography, recrystallization etc.).

In the synthesis of the compound of the present invention, C=O can be appropriately converted to C=S at a desirable step on the basis of the synthesis method of method O shown below. [Method O]

[Chemical Formula 96]

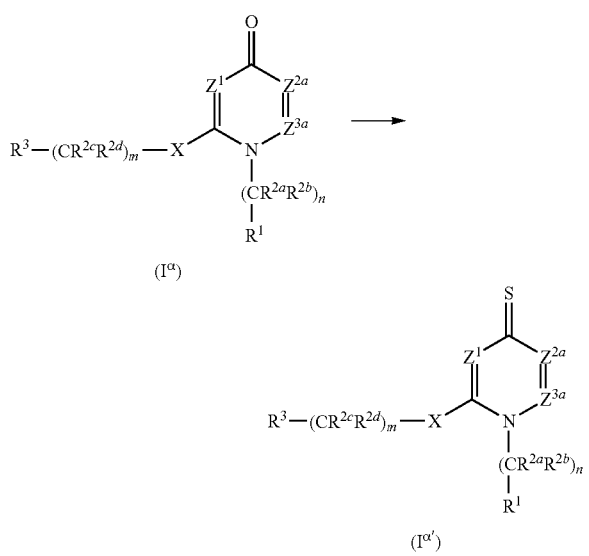

wherein each symbol is the same as the above (1).

A compound (Iα') can be synthesized by the reaction of the compound (Iα) obtained by the method A with 2,4-bis(4-methoxyphenyl)-1,3,2,4-dithiadiphosphethane-2,4-disulfide in the appropriate solvent.

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), acetonitrile and the like are exemplified. The reaction solvent can be used alone or in combination.

The reaction temperature is −10 to 110° C., preferably 0 to 80° C.

The reaction time is 0.1 to 72 hours, preferably 0.5 hours to 18 hours.

The obtained desired compound (Iα') can be purified as necessary by the methods which are usually used (e.g., column chromatography, recrystallization etc.).

[Method P]

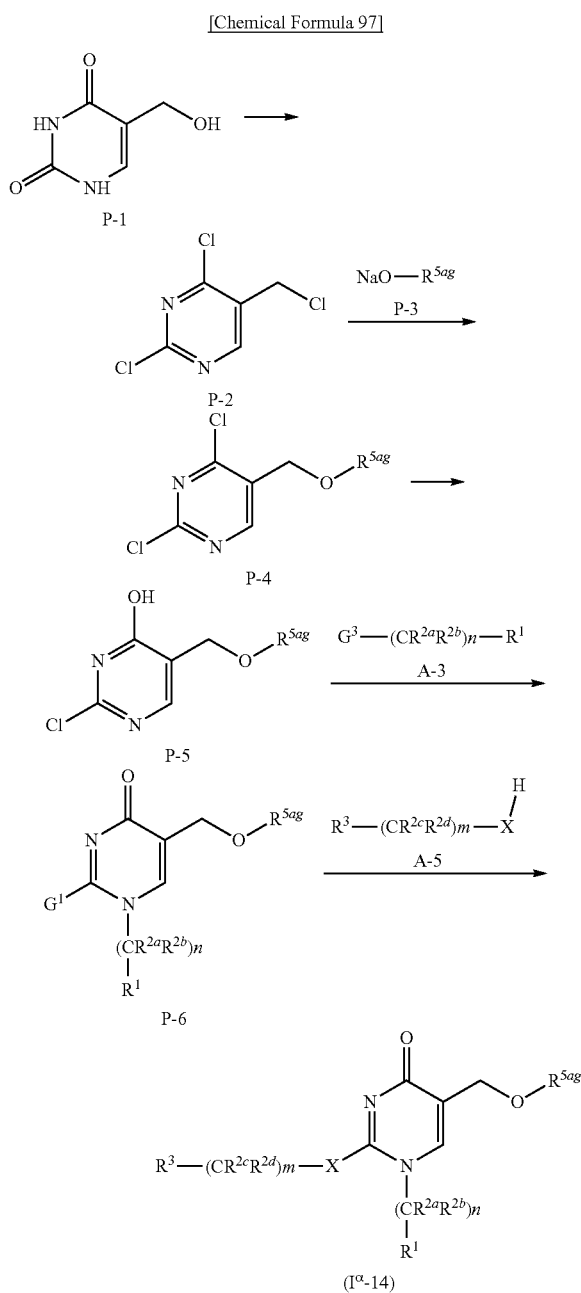

wherein $R^{5ag}$ is substituted or unsubstituted alkyl, substituted or unsubstituted aromatic carbocyclyl, or substituted or unsubstituted aromatic heterocyclyl, $G^1$ and $G^3$ are the same as the method A, and the other symbols are the same as the above (1).

Step 1

A compound (P-2) can be synthesized by the reaction of a compound (P-1) with an acid chloride in the presence of a base in the appropriate solvent.

As the acid chloride, for example, phosphoryl chloride, thionyl chloride, oxalyl chloride and the like are exemplified. 1.0 or more mole equivalent(s), preferably 1.0 to 5.0 mole equivalent(s) can be used per an equivalent of the compound (P-1).

As the base, for example, pyridine, triethylamine, DIEA and the like are exemplified.

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.) ethers (e.g., tetrahydrofuran, diethyl ether, dioxane, dimethoxyethane etc.), and a mixed solvent thereof and the like are exemplified.

The reaction temperature is 0° C. to 100° C., preferably 0° C. to 20° C.

The reaction time is 0.5 hours to 48 hours, preferably 1 hour to 12 hours.

The obtained desired compound (P-2) can be purified as necessary by the methods which are usually used (e.g., column chromatography, recrystallization etc.).

Step 2

A compound (P-4) can be synthesized by the reaction of the compound (P-2) with a compound (P-3) in the appropriate solvent.

In this reaction, 1.0 or more mole equivalent(s) of the compound (P-3), preferably 1.0 to 3.0 mole equivalent(s) can be used per an equivalent of the compound (P-2).

As the reaction solvent, alcohols (e.g., methanol, ethanol, tert-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, NMP, acetonitrile, DMA and the like are exemplified. The reaction solvent, can be used alone or in combination.

The reaction temperature is 0 to 100° C., preferably 0 to 40° C.

The reaction time is 0.5 to 48 hours, preferably 1 hour to 8 hours.

The obtained desired compound (P-4) can be purified as necessary by the methods which are usually used (e.g., column chromatography, recrystallization etc.).

Step 3

A compound (P-5) can be synthesized by the reaction of the compound (P-4) with a basic aqueous solution according to the synthetic procedures described in the step 1 of the method A.

The obtained desired compound (P-5) can be purified as necessary by the methods which are usually used (e.g., column chromatography, recrystallization etc.).

Step 4

A compound (P-6) can be synthesized by the reaction of the compound (P-5) with the compound (A-3) according to the synthetic procedures described in the step 2 of the method A.

The obtained desired compound (P-6) can be purified as necessary by the methods which are usually used (e.g., column chromatography, recrystallization etc.).

Step 5

A compound (Iα-14) can be synthesized by the reaction of the compound (P-6) with the compound (A-5) according to the synthetic procedures described in the step 3 of the method A.

The obtained desired compound (Iα-14) can be purified as necessary by the methods which are usually used (e.g., column chromatography, recrystallization etc.).

[Method Q]

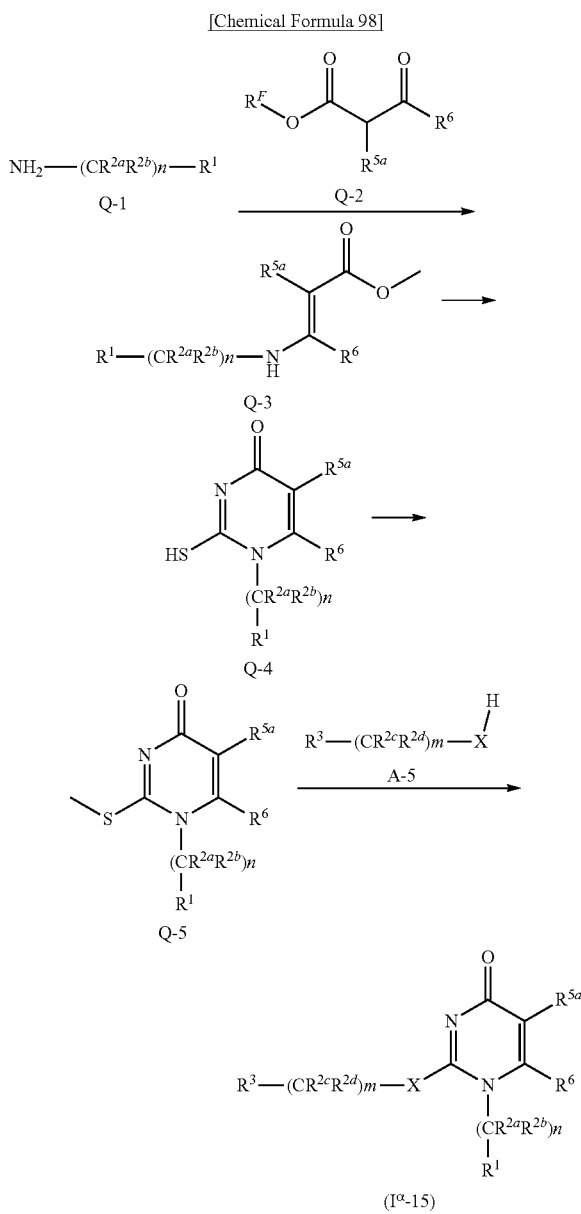

wherein $R^F$ is substituted or unsubstituted alkyl; and the other symbols are the same as the above (1).

Step 1

A compound (Q-3) can be synthesized by the reaction of a compound (Q-1) with a compound (Q-2) in the presence of an acid in the appropriate solvent.

In this reaction, 1.0 or more mole equivalent(s) of the compound (Q-2), preferably 1.0 to 2.0 mole equivalent(s) can be used per an equivalent of the compound (Q-1).

As the acid, for example, acetic acid, trifluoroacetic acid, p-toluenesulfonic acid and the like are exemplified. 0.05 or more mole equivalents, preferably 0.1 to 2.0 mole equivalents can be used per an equivalent of the compound (Q-1).

As the reaction solvent, alcohols (e.g., methanol, ethanol, tert-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, NMP, acetonitrile, DMA and the like are exemplified. The reaction solvent can be used alone or in combination.

The reaction temperature is 0° C. to 100° C., preferably 0° C. to 20° C.

The reaction time is 0.5 hours to 48 hours, preferably 1 hour to 12 hours.

The obtained desired compound (Q-3) can be purified as necessary by the methods which are usually used (e.g., column chromatography, recrystallization etc.).

Step 2

A compound (Q-4) can be synthesized by the reaction of the compound (Q-3) with trimethylsilyl isothiocyanate in the appropriate solvent or without any solvent.

As the reaction solvent, alcohols (e.g., methanol, ethanol, tort-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, NMP, acetonitrile, DMA and the like are exemplified. The reaction solvent can be used alone or in combination.

The reaction temperature is 0° C. to 200° C., preferably 40° C. to 150° C.

The reaction time is 0.5 hours to 48 hours, preferably 1 hour to 12 hours.

The obtained desired compound (Q-4) can be purified as necessary by the methods which are usually used (e.g., column chromatography, recrystallization etc.).

Step 3

A compound (Q-5) can be synthesized by the reaction of the compound (Q-4) with methyl iodide in the presence of a base in the appropriate solvent.

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium carbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 1.0 or more mole equivalent(s), preferably 1.0 to 5.0 mole equivalent(s) can be used per an equivalent of the compound (Q-4).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, NMP, acetonitrile. DMA and the like are exemplified. The reaction solvent can be used alone or in combination.

The reaction temperature is 0° C. to 100° C., preferably 0° C. to 40° C.

The reaction time is 0.5 hours to 48 hours, preferably 1 hour to 8 hours.

The obtained desired compound (Q-5) can be purified as necessary by the methods which are usually used (e.g., column chromatography, recrystallization etc.).

Step 4

A compound (Iα-15) can be synthesized by the reaction of the compound (Q-5) with the compound (A-5) according to the synthetic procedures described in the step 3 of the method A.

The obtained desired compound (Iα-15) can be purified as necessary by the methods which are usually used (e.g., column chromatography, recrystallization etc.).

In the synthesis of the compound of the present invention, C=S can be appropriately converted to C=N($R^Y$) at a desirable step on the basis of the synthesis method of method ft shown below.

[Method R]

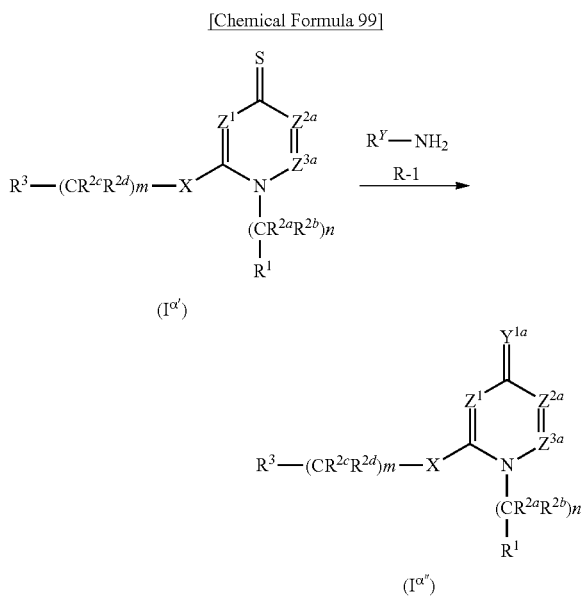

wherein $Y^{1s}$ is $C=N(R^Y)$, and the other symbols are the same as the above (1).

A compound (Iα″) can be synthesized by the reaction of the compound (Iα′) obtained by the method Q with a compound (R-1) in the presence of an acid or a base in the appropriate solvent.

In this reaction, 1.0 or more mole equivalent(s) of the compound (R-1), preferably 1.0 to 5.0 mole equivalent(s) can be used per an equivalent of the compound (Iα′).

As the acid, for example, acetic acid, trifluoroacetic acid, p-toluenesulfonic acid and the like are exemplified. 0.05 or more mole equivalents, preferably 0.1 to 2.0 mole equivalents can be used per an equivalent of the compound (1α′).

As the base, for example, pyridine, triethylamine, DIEA and the like are exemplified. 1.0 or more mole equivalent(s), preferably 1.0 to 20.0 mole equivalent(s) can be used per an equivalent of the compound (Iα′).

As the reaction solvent, alcohols (e.g., methanol, ethanol, tert-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, NMP, acetonitrile, DMA and the like are exemplified. The reaction solvent can be used alone or in combination.

The reaction temperature is 0 to 150° C., preferably 0 to 80° C.

The reaction time is 0.1 to 72 hours, preferably 0.5 hours to 18 hours.

The obtained desired compound (Iα″) can be purified as necessary by the methods which are usually used (e.g., column chromatography, recrystallization etc.).

An optically active form of the compound represented by Formula (I) can be produced by using an optically active starting material, synthesizing an optically active intermediate by asymmetric synthesis at an appropriate step, or optically resolving racemic intermediates or final products at an appropriate step. The approach for the optical resolution includes a method of resolving optical isomers using an optically active column, kinetic optical resolution using enzymatic reaction or the like, crystallization and resolution of diastereomers by salt formation using a chiral acid or a chiral base, preferential crystallization and the like.

The preferred compound of the present invention not only has an antagonistic activity for the P2X7 receptor but also is useful as a medicine and has any or all of the following superior characteristics:

a) The inhibitory activity for CYP enzymes (e.g., CYP1A2, CYP2C9, CYP2C19, CYP2D6, CYP3A4 and the like) is weak.
b) The compound demonstrates good pharmacokinetics, such as a high bioavailability, moderate clearance and the like.
c) The compound has a high metabolic stability.
d) The compound has no irreversible inhibitory effect against CYP enzymes (e.g., CYP3A4) when the concentration is within the range described in the present description as the measurement conditions.
e) The compound has no mutagenicity.
f) The compound is associated with a low cardiovascular risk.
g) The compound has a high solubility.
h) The compound has a high selectivity for the P2X7 receptor (e.g., high selectivity in the other receptors of the P2X family).
i) The compound has a high brain distribution.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may prepared according to the usual method and administered. The tablets can be sugar-coated tablets, film-coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, moistening agents, disintegrants, lubricants, diluents and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old.

The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

The present, invention will be described in more detail with reference to, hut not limited to, the following Examples, Reference Examples and Test Examples.

NMR analysis of each example was performed by 400 MHz using DMSO-$d_6$, or $CDCl_3$.

"RT" in tables means retention time in LC/MS: liquid column chromatography/mass analysis and these are measured under the conditions as below:

Condition [1]
Column: Shim-pack XR-ODS (2.2 μm, i.d. 50×3.0 mm) (Shimadzu)
Flow rate: 1.6 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 0.5 minute.

Condition [2]
Column: ACQUITY HPLC (registered trademark BEH C18 (1.7 μm
i.d.2.1×50 mm)(Waters)
Flow rate: 0.8 mL/min
UV detection wavelength: 254 nm
Mobile phases: [A] is 10 mmol/L Ammonium Carbonate solution, and [B] is acetonitrile.
Gradient: linear gradient of 5% to 100% solvent [B] for 3.5 minutes was performed, and 100% solvent [B] was maintained for 0.5 minute.

Condition [3]
Column: ACQUITY UPLC (registered trademark) BEH C18 (1.7 μm
i.d. 2.1×50 mm)(Waters)
Flow rate: 0.8 mL/min
UV detection wavelength: 254 nm
Mobile phases: [A] is 0.1% formic acid solution, and [B] is 0.1% formic acid in acetonitrile solvent.
Gradient: linear gradient of 5% to 100% solvent [B] for 3.5 minutes was performed, and 100% solvent [B] was maintained for 0.5 minute.

In the structural formulas of the compounds described in Examples, the following bonding pattern means a double bond and represents that stereoscopic information on E-Z conformation is unknown. A compound having the bond represented by the following bonding pattern is only an E form, only a Z form, or a mixture of an E form and a Z form.

[Chemical Formula 100]

Example 1

Synthesis of Compound I-0001

[Chemical Formula 101]

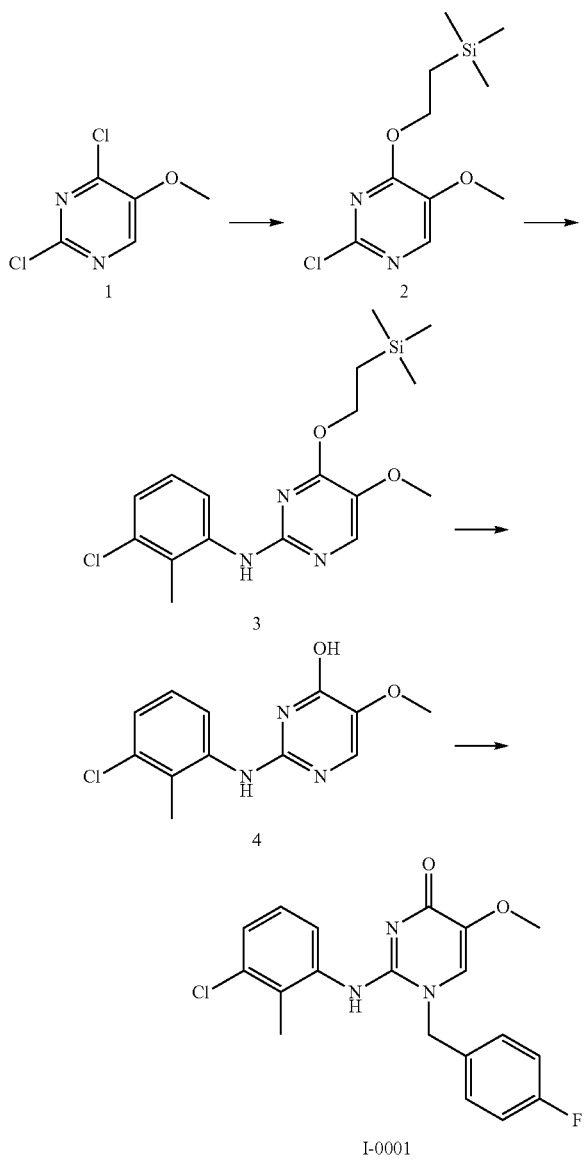

Step 1

Under nitrogen atmosphere, 2-(trimethylsilyl)ethanol (6.04 mL, 41.9 mmol) was dissolved in tetrahydrofuran (100 mL). Under ice cooling, sodium hydride (60% oil dispersion, 1.23 g, 30.7 mmol) was added to the solution. The mixture was stirred at room temperature for 30 minutes. Under ice cooling, the compound I (5.0 g, 27.9 mmol) in 50 mL of tetrahydrofuran solution was added dropwise to the mixture. The mixture was stirred at room temperature for 3 hours. 1 mol/L aqueous solution of hydrochloric acid was added to the mixture. The mixture was extracted with ethyl acetate. The organic layer was washed by the saturated aqueous solution of sodium hydrogen carbonate and brine, and dried over anhydrous sodium sulfate. The solvent was evaporated under reduced pressure. The obtained residue was purified by silica-gel column chromatography (hexane-ethyl acetate) to give the compound 2 (6.24 g, yield 85.7%).

$^1$H-NMR (CDCl$^3$) δ: 0.09 (s, 9H), 1.20 (t, J=8.0 Hz, 2H), 3.91 (s, 3H), 4.54 (t, J=8.0 Hz, 2H), 7.86 (s, 1H).

Step 2

The compound 2 (1.0 g, 3.83 mmol) was dissolved in dioxane (10 mL). 3-chloro-2-methylaniline (760 mg, 5.37 mmol), bis(dibenzylideneacetone)palladium (220 mg, 0.383 mmol), Xantphos (333 mg, 0.575 mmol) and cesium carbonate (1.75 g, 5.37 mmol) were added to the solution. The mixture was stirred under reflux for 8 hours. Water was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (hexane-ethyl acetate) to give the compound 3 (1.1.5 g, yield 82.0%).

$^1$H-NMR (CDCl$_3$) δ: 0.07 (s, 9H), 1.19 (t, J=8.1 Hz, 2H), 2.38 (s, 3H), 3.84 (e, 3H), 4.47 (t, J=8.4 Hz, 2H), 6.58 (s, 1H), 7.08-7.10 (m, 2H), 7.79 (s, 1H), 7.87-7.95 (m, 1H).

Step 3

The compound 3 (1.14 g, 3.12 mmol) was dissolved in tetrahydrofuran (5 mL). Tetrabutyl ammonium fluoride (1 mol/L tetrahydrofuran solution. 6.2 mL, 6.2 mmol) was added to the solution. The mixture was stirred at room temperature for 3 days. The solvent was evaporated under reduced pressure. The obtained residue was purified by silica-gel column chromatography (chloroform-methanol) to give the compound 4 (828 mg, yield 100%).

$^1$H-NMR (DMSO-d$_6$) δ: 2.25 (s, 3H), 3.64 (s, 3H), 7.13-7.40 (m, 3H), 7.67-7.82 (m, 1H), 7.90-8.11 (br, 1H), 11.20-11.06 (br, 1H).

Step 4

Under nitrogen atmosphere), the compound 4 (53 mg, 0.199 mmol) was dissolved in a mixed solution of DMF (0.3 mL) and dimethoxyethane (1.5 mL). Sodium hydride (60% oil dispersion, 9 mg, 0.225 mmol) was added to the solution. The mixture was stirred at room temperature for 5 minutes. Then, lithium bromide (35 mg, 0.403 mmol) was added to the mixture. The mixture was stirred for 10 minutes, p-Fluorobenzyl bromide (50 µL, 0.402 mmol) was added to the mixture. The mixture was stirred at room temperature for 2 days. A 2 mol/L aqueous solution of hydrochloric acid was added to the mixture. The mixture was extracted with ethyl acetate. The organic layer was washed by water, and dried over anhydrous sodium sulfate. The solvent was evaporated under reduced pressure. The obtained residue was purified by silica-gel column chromatography (chloroform-methanol) to give the compound I-0001 (12 mg, yield 16.0%).

$^1$H-NMR (CDCl$_3$) δ: 2.06 (s, 3H), 3.71 (s, 3H), 5.01 (s, 2H), 6.66 (d, J=6.4 Hz, 1H), 6.80 (s, 1H), 7.04-7.15 (m, 4H), 7.32-7.40 (m, 2H), 7.63-7.61 (br, 1-H).

Example 2

Synthesis of Compound I-0002

[Chemical Formula 102]

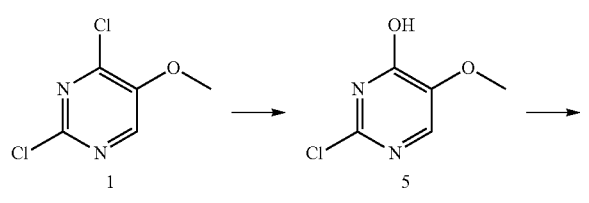

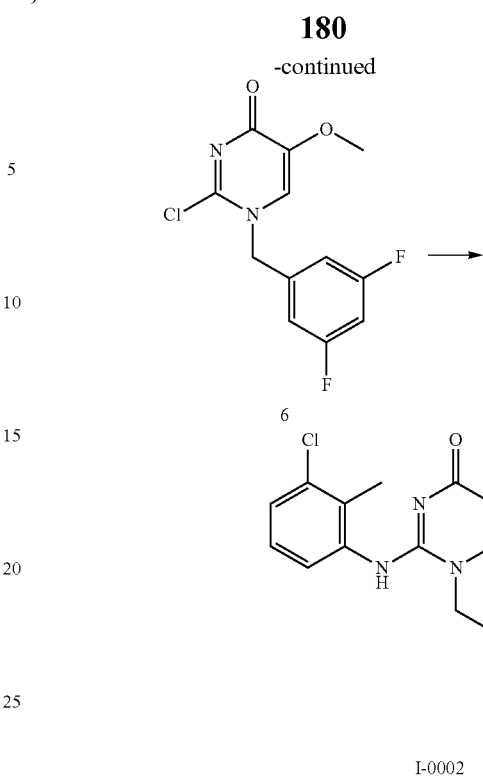

Step 1

The compound I (40.0 g, 223 mmol) was dissolved in tetrahydrofuran (80 mL). A 1 mol/L aqueous solution of sodium hydroxide (447 mL, 447 mmol) was added to the solution. The mixture was stirred at room temperature for 4 hours. The reaction mixture was washed by ethyl ether. A 2 mol/L hydrochloric acid solution (230 mL, 400 mmol) was added to the aqueous layer. The mixture was stirred. The precipitates were filtered, washed by water, and dried to give the compound 5<30.8 g. yield 86%).

$^1$H-NMR (DMSO-d$_6$) δ: 3.70 (s, 3H), 7.60 (s, 1H)

Step 2

The compound 5 (2.0 g, 12.46 mmol) was dissolved in dichloromethane (20 mL). DIEA (3.26 mL, 18.68 mmol) was added to the solution. The mixture was stirred until dissolved. Then, 3,5-difluorobenzyl bromide (1.91 mL, 14.95 mmol) was added to the mixture. The mixture was stirred at room temperature for 4 hours. After the mixture was left standing overnight, the precipited solids wore filtered, and dried to give the compound 6 (1.1 g, yield 31%).

$^1$H NMR (DMSO-d$_6$) δ: 3.70 (s, 3H), 5.30 (s, 2H), 7.05-7.13 (m, 2H), 7.82 (m, 1H)

Step 3

The compound 6 (100 mg, 0.35 mmol) was dissolved in dioxane (2 mL). 3-chloro-2-methylaniline (74 mg, 0.52 mmol) was added to the solution. The mixture was stirred under microwave irradiation at 170° C. for 10 minutes. The solvent in the reaction mixture was evaporated under reduced pressure. The obtained residue was purified by silica-gel column chromatography (ethyl acetate-n-hexane) to give the compound I-0002 (33 mg, yield 24%).

$^1$H-NMR (CDCl$_3$) δ: 2.05 (s, 3H), 3.73 (s, 3H), 5.01 (s, 2H), 6.65 (m, 1H), 6.75-6.95 (m, 4H), 7.05-7.15 (m, 2H), 7.59 (s, 1H)

Example 3

Synthesis of Compound I-0003

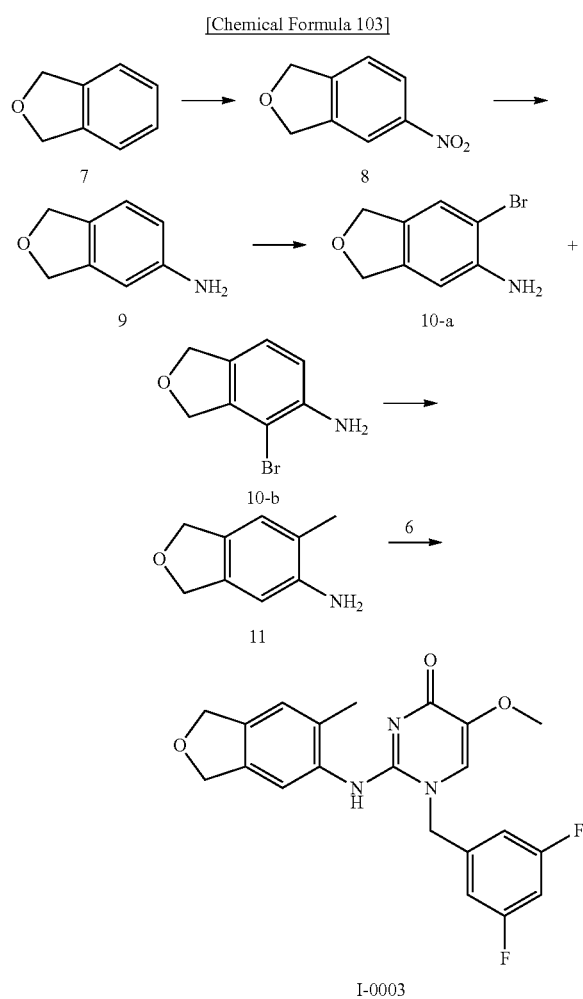

I-0003

Step 1

The compound 7 (5 g, 41.6 mmol) was dissolved in concentrated sulfuric acid (35 mL). Under ice cooling, potassium nitrate (3.82 g, 37.8 mmol) dissolved in sulfuric acid (8 mL) was added to the solution. The mixture was stirred for 80 minutes. Water and ice were added to the reaction mixture. The precipitated solids were filtered to give the compound 8 (5.68 g, yield 00%).

$^1$H-NMR (CDCl$_3$) δ: 5.18 (s, 4H), 7.89 (d, J=8.2 Hz, 1H), 8.11 (s, 1H), 8.18 (dd, J=8.3, 1.8 Hz, 1H).

Step 2

The compound 8 (5.63 g, 34.1 mmol) was dissolved in ethanol (56 mL). Tin chloride dihydrate (23.1 g, 102 mmol) was added to the solution. The mixture was stirred at 70° C. for 1 hour. After cooled to room temperature, water and 2 mol/L aqueous solution of sodium hydroxide were added to the reaction mixture to adjust the pH to 7. The reaction mixture was extracted with ethyl acetate. The organic layer was washed by brine. The solvent was evaporated under reduced pressure to give the crude product of the compound 9 (4.6 g, yield 98%).

$^1$H-NMR (CDCl$_3$) δ: 8.71 (br s, 2H), 6.02 (s, 4H), 6.57 (s, 1H), 6.60 (dd, J=7.9, 2.0 Hz, 1H), 7.01 (d, J=7.9 Hz, 1H).

Step 3

The compound 9 (7.5 g, 27.7 mmol) was dissolved in acetonitrile (90 mL). NBS (5.18 g, 29.1 mmol) was added to the solution at −10° C. The mixture was stirred at −10° C. for 30 minutes. Water was added to the reaction mixture. The mixture was extracted with ethyl acetate. The organic layer was washed by water and brine. The solvent was evaporated under reduced pressure. The obtained residue was purified by silica-gel column chromatography (hexane-ethyl acetate) to give the mixture 10 (5:1 mixture of the compound 10-a and the compound 10-b) (3.68 g, yield 62%).

$^1$H-NMR (CDCl$_3$) δ: 4.08 (s, 2H), 4.98 (dd, J=7.8, 1.3 Hz, 4H), 6.61 (s, 1H), 7.28 (s, 1H).

Step 4

The mixture 10 (3.68 g, 17.2 mmol) was dissolved in dioxane (86 mL) and water (7.2 mL). Trimethylboroxine (2.88 mL, 20.6 mmol), PdCl$_2$ (dppf) CH$_2$Cl$_2$ (1.40 g, 1.72 mmol) and potassium carbonate (7.13 g, 51.6 mmol) were added to the solution. The mixture was stirred under reflux for 3 hours. Water was added to the reaction mixture. The mixture was extracted with ethyl acetate. The organic layer was washed by water and brine. The solvent was evaporated under reduced pressure. The obtained residue was purified by silica-gel column chromatography (hexane-ethyl acetate). The obtained residue was solidified with ethyl acetate. The precipitated solids were filtered to afford the compound 11 (694 mg, yield 27%).

$^1$H-NMR (CDCl$_3$) δ: 2.18 (s, 3H), 3.62 (s, 2H), 5.01 (s, 4H), 6.56 (s, 1H), 6.92 (s, 1H).

Step 5

The compound 11 (122 mg, 0.82 mmol) was dissolved in dioxane (4 mL). The compound 6 (21.3 mg, 0.74 mmol) was added to the solution. The mixture was stirred under microwave irradiation at 150° C. for 10 minutes. Water was added to the reaction mixture. The mixture was extracted with ethyl acetate. The organic layer was washed by brine. The solvent, was evaporated. The obtained residue was purified by amino column chromatography (chloroform-methanol) to give the compound I-0003 (17 mg, yield 5%).

$^1$H-NMR (DMSO-D$_6$) δ: 3.59 (s, 3H), 4.94 (s, 4H), 5.20 (s, 2H), 7.01-7.03 (m, 3H), 7.11 (s, 1H), 7.24 (t, J=9.0 Hz, 1H), 7.34 (s, 1H), 8.36 (s, 1H).

Example 4

Synthesis of Compound I-0004

[Chemical Formula 104]

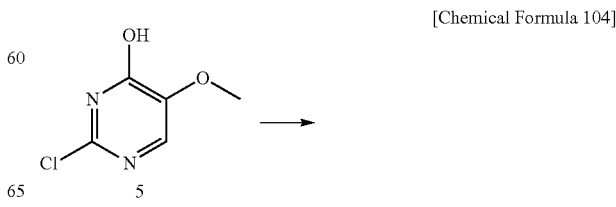

5

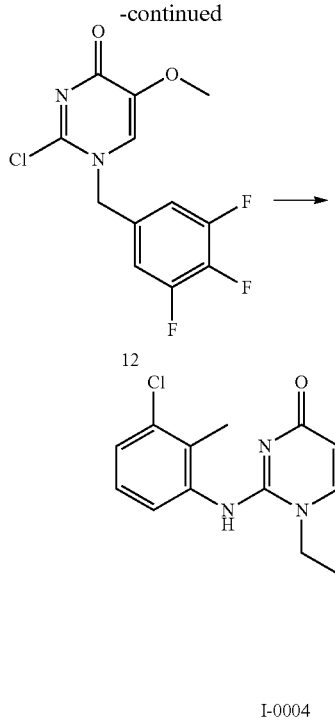

12

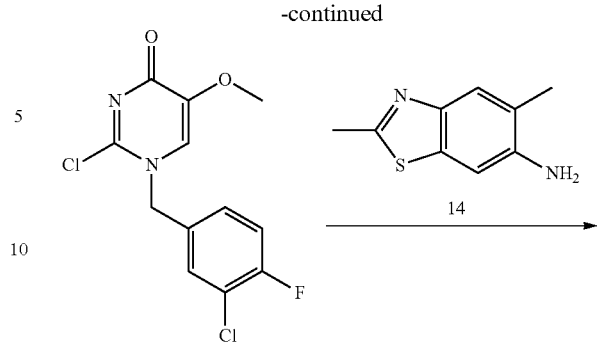

13

I-0004

Step 1

The compound 5 (0.5 g, 8.11 mmol) was dissolved in dichloromethane (5 mL). DIEA (0.82 mL, 4.67 mmol) was added to the solution. The mixture was stirred until dissolved. Then, 3,4,5-trifluorobenzyl bromide (0.50 mL, 1.67 mmol) was added to the mixture. The mixture was stirred al room temperature for 1 hour. After the mixture was left standing overnight, the precipitated solids were filtered, and dried to give, the compound 12 (0.2 g, yield 22%).

$^1$H-NMR (DMSO-d$_6$) δ: 3.70 (s, 3H), 5.26 (s, 2H), 7.33-7.43 (m, 2H), 7.79 (s, 1H)

Step 2

The compound 12 (100 mg, 0.35 mmol) was dissolved in dioxane (2 mL). 3-chloro-2-methylaniline (70 mg, 0.49 mmol) was added to the solution. The mixture was stirred under microwave irradiation at 170° C. for 10 minutes. The solvent was evaporated under reduced pressure. The obtained residue was purified by silica-gel column chromatography (ethyl acetate-n-hexane, subsequently chloroform-methanol-water) to give the compound I-0004 (47 mg, yield 35%).

$^1$H-NMR (DMSO-d$_6$) δ: 1.90 (s, 3H), 3.61 (s, 3H), 5.14 (brs, 2H), 6.90-7.60 (m, 7H)

Example 5

Synthesis of Compound I-0005

[Chemical Formula 105]

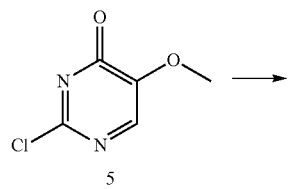

5

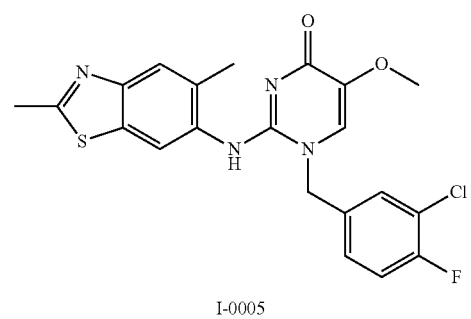

I-0005

The compound 5 (5 g, 31.1 mmol) was dissolved in dichloromethane (50 mL). DIEA (8.2 mL, 40.7 mmol) was added to the solution. The mixture was stirred until dissolved. Then, 3-chloro-4-fluorobenzyl bromide (5.03 mL, 37.4 mmol) was added to the mixture. The mixture was stirred at room temperature for 8 hours. After the mixture was left standing overnight, the precipitated solids were filtered, and dried to give the compound 13 (3.0 g, yield 32%).

$^1$H-NMR (DMSO-d$_6$) δ: 3.70 (s, 3H), 5.29 (s, 2H), 7.32-7.38 (m, 1H), 7.46 (t, 1H, J=8.9 Hz), 7.64 (1H, dd, J=7.0, 1.9 Hz), 7.84 (1H, s)

Step 2

The compound 13 (250 mg, 0.83 mmol) was dissolved in dioxane (4 mL). The compound 14 (191 mg, 1.07 mmol) was added to the solution. The mixture was stirred under microwave irradiation at 150° C. for 20 minutes. Water was added to the reaction mixture. The mixture was extracted with ethyl acetate. The organic layer was washed by brine. The solvent was evaporated under reduced pressure. The obtained residue was purified by silica-gel column chromatography (chloroform-methanol) to give the compound I-0005 (194 mg, yield 53%).

$^1$H-NMR (DMSO-D$_6$) δ: 1.95<s, 3H), 2.77 (s, 3H), 3.60 (s, 5H), 5.20 (s, 2H), 7.37 (s, 3H), 7.48 (s, 1H), 7.58 (s, 1H), 7.74 (s, 1H), 8.49 (s, 1H).

Example 6

Synthesis of Compound I-0006

[Chemical Formula 106]

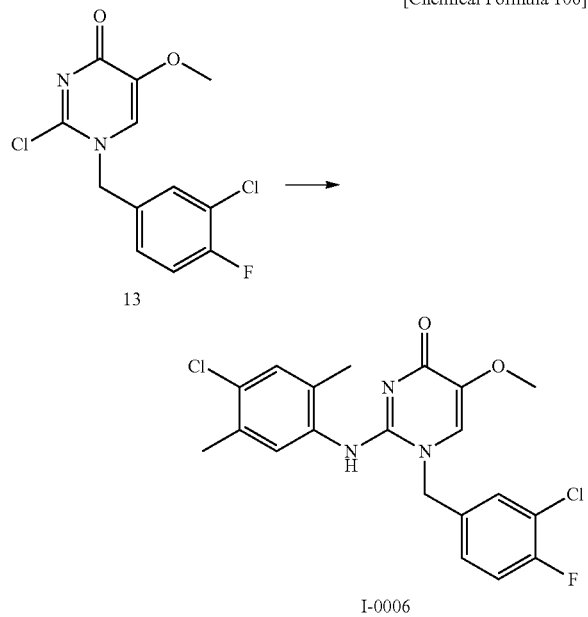

The compound 13 (100 mg, 0.330 mmol) was dissolved in dioxane (2.0 mL). 4-Chloro-2,5-dimethylaniline (103 mg, 0.660 mmol) was added to the solution. The mixture was stirred under microwave irradiation at 130° C. for 10 minutes. The solvent was evaporated under reduced pressure. The obtained residue was purified by reverse-phase silica-gel column chromatography (water-acetonitrile) to give the compound I-0006 (61.6 mg, yield 44%) as a white powder.

LC-MS (Condition [3]): RT=2.07, 422 [M+H]

1H-NMR (DMSO-D6) δ: 1.79 (3H, s), 2.26 (3H, s), 3.60 (3H, s), 5.17 (2H, br s), 6.95-7.55 (6H, m), 8.38 (1H, s).

Example 7

Synthesis of Compound I-0007

[Chemical Formula 107]

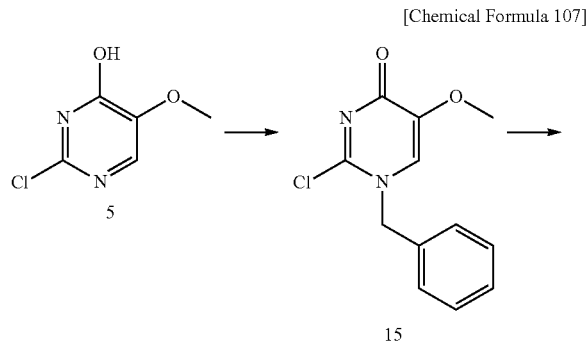

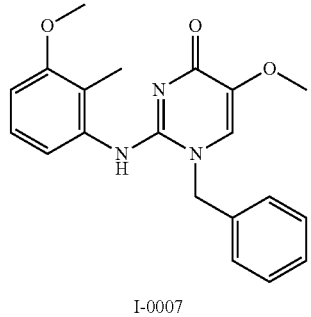

I-0007

Step 1

The compound 5 (10 g, 62.3 mmol) was dissolved in dichloromethane (100 mL). DIEA (16.32 mL, 93 mmol) was added to the solution. The mixture was stirred until dissolved. Then, benzyl bromide (8.89 mL, 74.7 mmol) was added to the mixture. The mixture was stirred at room temperature for 3 hours. After the mixture was left, standing overnight, 2 mol/L aqueous solution of hydrochloric acid was added to the reaction mixture. The mixture was extracted with chloroform. The organic layer was washed by the saturated aqueous solution of sodium hydrogen carbonate and brine, and dried over anhydrous sodium sulfate. The obtained residue was solidified with ethyl acetate. The precipitated solids were filtered, and dried to give the compound 15 (8.42 g, yield 54%).

$^1$H-NMR (DMSO-D$_6$) δ: 1.95 (s, 3H), 2.77 (s, 8H), 3.60 (s, 5H), 5.20 (s, 2H), 7.37 (s, 3H), 7.48 (s, 1H), 7.58 (s, 1H), 7.74 (s, 1H), 8.49 (s, 1H).

Step 2

Under nitrogen atmosphere, the compound 2 (80 mg, 0.319 mmol) was dissolved in dioxane (1.6 mL). 2-methyl-3-methoxyaniline (52.5 mg, 0.383 mmol), palladium acetate (2.85 mg, 0.013 mmol), Xantphos (11.04 mg, 0.019 mmol) and cesium carbonate (104 mg, 0.318 mmol) were added to the solution. The mixture was stirred under reflux for 5 hours. Water was added to the reaction mixture. The mixture was extracted with dichloromethane. The organic layer was washed by the saturated aqueous solution of ammonium chloride and brine, and dried over anhydrous sodium sulfate. The solvent was evaporated under reduced pressure. The obtained residue was purified by silica-gel column chromatography (chloroform-methanol) to give the compound I-0007 (12.5 mg, yield 11%).

LC-MS (Condition (31): RT=1.53, 352 [M+H]$^+$ $^1$H-NMR (DMSO-D$_6$) δ: 1.67 (s, 3H), 3.62 (s, 3H), 3.74 (s, 3H), 5.21 (s, 2H), 6.68 (1H, d, d=7.8 Hz), 6.84 (1H, d, J=8.3 Hz), 7.33-7.44 (m, 7H), 8.37 (s, 1H).

Example 8

Synthesis of Compound I-0008

[Chemical Formula 108]

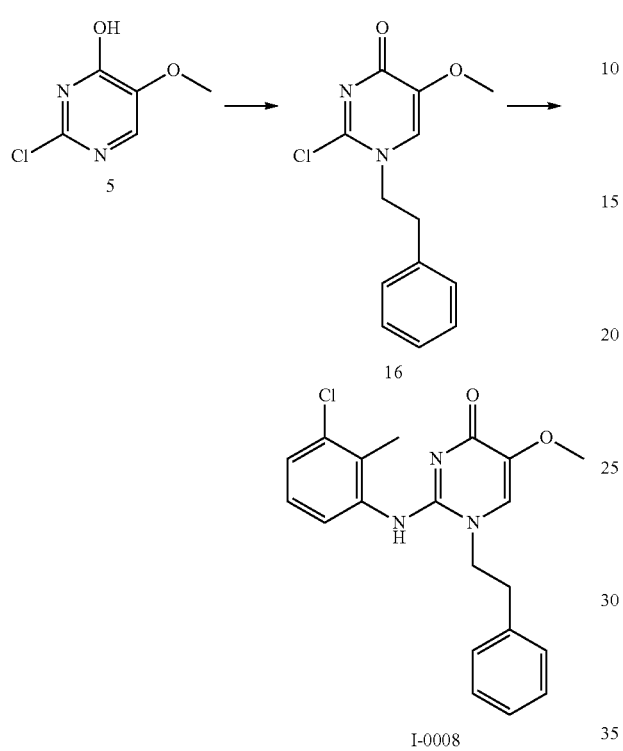

I-0008

Step 1

The compound 5 (300 mg, 1.87 mmol) was dissolved in dichloromethane (3 mL). DIEA (0.359 mL, 2.06 mmol) was added to the solution. The mixture was stirred until dissolved. Then, 2-bromoethylbenzene (380 mg, 2.06 mmol) was added to the mixture. The mixture was stirred at room temperature for 1.5 hours. After the mixture was left standing overnight, the reaction mixture was poured into water. The mixture was extracted with ethyl acetate. The organic layer was washed by brine, and dried over anhydrous sodium sulfate. The solvent was evaporated under reduced pressure. The obtained residue was purified by silica-gel column chromatography (methanol-chloroform) to give the compound 16 (15.3 mg, yield 3%).

$^1$H-NMR (CDCl3) δ: 3.11 (t, 2H), 3.19 (s, 3H), 4.25 (t, 2H), 6.36 (s, 1H), 7.12-7.14 (m, 2H), 7.28-7.35 (m, 3H)

Step 2

The compound 2 (1.5.0 mg, 0.057 mmol) was dissolved in dioxane (0.75 mL). 3-Chloro-2-methylaniline (16.0 mg, 0.113 mmol) was added to the solution. The mixture was stirred under microwave irradiation at 130° C. for 10 minutes. The solvent was evaporated under reduced pressure. The obtained residue was purified by silica-gel column chromatography (ethyl acetate-n-hexane) to give the compound I-0008 (13.1 mg, yield 63%).

$^1$H-NMR (CDCl3) δ: 3.12 (t, 2H), 2.22 (s, 3H), 3.48 (s, 3H), 4.07 (t, 2H), 6.30 (s, 1H), 6.67-6.69 (d, 2H), 7.09-7.12 (m, 2H), 7.21-7.23 (m, 2H), 7.26-7.28 (m, 1H), 7.28-7.36 (m, 2H), 7.53 (m, 1H)

Example 9

Synthesis of Compound I-0009

[Chemical Formula 109]

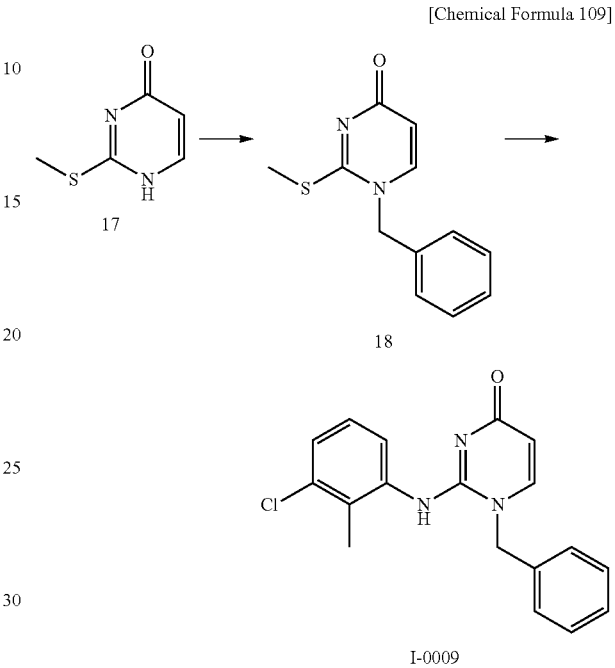

I-0009

Step 1

The compound 17 (500 mg, 3.52 mmol) was dissolved in dichloromethane (5 mL). DIEA (921 μL, 5.28 mmol) and benzyl bromide (501 μL, 4.22 mmol) were added to the solution. The mixture was stirred at room temperature for 1 day. A 2 mol/L aqueous solution of hydrochloric acid was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (chloroform-methanol) to give the compound 18 (567 mg, yield (>9.4%).

$^1$H-NMR (CDCl$_3$) δ: 2.60 (s, 3H), 5.03 (s, 2H), 6.07 (d, J=7.6 Hz, 1H), 7.16-7.29 (m, 3H), 7.35-7.49 (m, 3H).

Step 2

The compound 18 (0.100 mg, 0.430 mmol) was dissolved in tert-butanol (2 mL). Acetic acid (369 μL, 6.46 mmol) and 3-chloro-2-methylaniline (91 mg, 0.646 mmol) were added to the solution. The mixture was stirred under reflux for 33 hours. After cooled to room temperature, the mixture was diluted with ethyl acetate. The mixture was washed by the saturated aqueous solution of sodium hydrogen carbonate and brine, and dried over anhydrous sodium sulfate. The solvent was evaporated under reduced pressure. The obtained residue was purified by silica-gel column chromatography (hexane-ethyl acetate) to give the compound I-0009 (65 mg, yield 46.3%).

$^1$H NMR (CDCl$_3$) δ: 2.03 (s, 3H), 5.07 (s, 2H), 5.43 (d, J=7.6 Hz, 1H), 6.68 (d, J=6.81 Hz, 1H), 7.05-7.13 (m, 2H), 7.20 (d, J=7.6 Hz, 1H), 7.32-7.49 (m, 6H).

Example 10

Synthesis of Compound I-0010

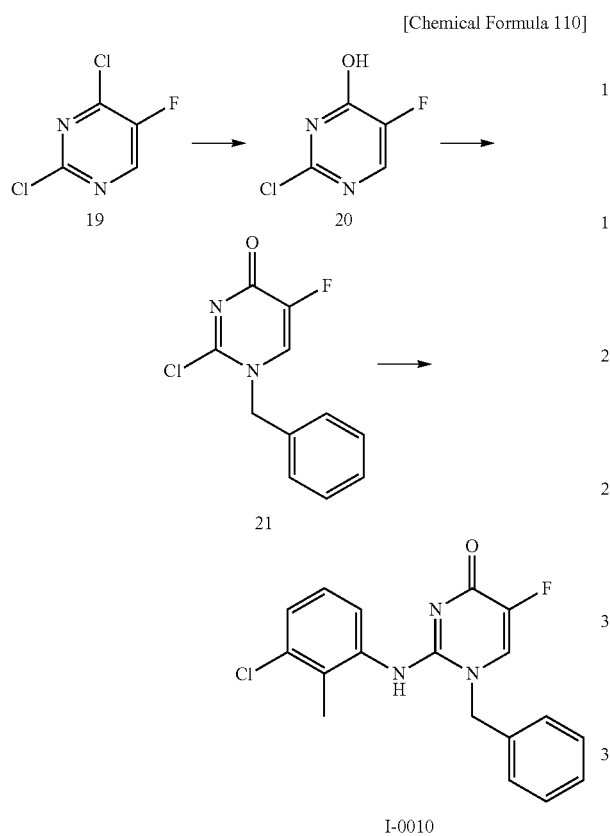

[Chemical Formula 110]

Step 1

The compound 19 (5.0 g, 29.9 mmol) was dissolved in tetrahydrofuran (10 mL). A 1 mol/L aqueous solution of sodium hydroxide (45 mL. 45.0 mmol) was added to the solution. The mixture was stirred at room temperature for 24 hours. The reaction mixture was washed by diethyl ether. Under ice cooling, 2 mol/L aqueous solution of hydrochloric acid was added to the mixture to adjust the pH to 3. The precipitated solids were filtered, and washed by cold water. The obtained solid was dried to give the compound 20 (2.5 g, yield 56.2%).

$^1$H-NMR (DMSO-$d_6$) δ: 8.15 (s, 1H).

Step 2

The compound 20 (500 mg, 3.37 mmol) was dissolved in dichloromethane (5 mL). DIEA (882 μL, 5.05 mmol) and benzyl bromide (480 μL, 4.04 mmol) were added to the solution. The mixture was stirred at room temperature for 2 days. A 2 mol/L aqueous solution of hydrochloric acid was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (chloroform-methanol) to afford the compound 21 (331 mg, yield 41.2%).

$^1$H-NMR (CDCl$_3$) δ: 5.22 (s, 2H), 7.22-7.30 (m, 2H), 7.38-7.50 (m, 3H).

Step 3

The compound 21 (100 mg, 0.419 mmol) was dissolved in dioxane (3 mL). 3-Chloro-2-methylaniline (71 mg, 0.501 mmol), palladium acetate (9 mg, 0.04 mmol), Xantphos (36 mg, 0.062 mmol) and cesium carbonate (191 mg, 0.587 mmol) were added to the solution. The mixture was stirred under microwave irradiation at 1.30° C. for 90 minutes. Water was added to the reaction mixture. The mixture was extracted with ethyl acetate. The organic layer was washed by brine, and dried over anhydrous sodium sulfate. The solvent was evaporated under reduced pressure. The obtained residue was purified by silica-gel column chromatography (chloroform-methanol) to give the compound I-0010 (15 mg, yield 10.4%).

$^1$H-NMR (CDCl$_3$) δ: 2.06 (s, 3H), 5.04 (s, 2H), 6.67 (d, J=6.8 Hz, 1H), 7.06-7.65 (m, 911).

Example 11

Synthesis of Compound I-0011

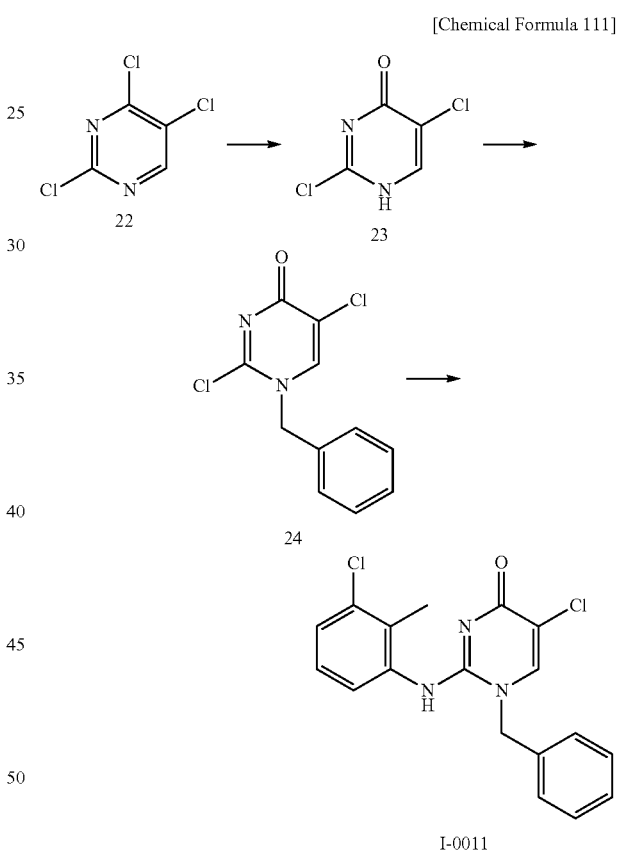

[Chemical Formula 111]

Step 1

The compound 22 (7.2 g, 39.3 mmol) was dissolved in tetrahydrofuran (28 mL). A 1 mol/L aqueous solution of sodium hydroxide (56 mL, 56 mmol) was added to the solution. The mixture was stirred at room temperature for 1.5 hours. A 2 mol/L hydrochloric acid solution (6 mL, 12 mmol) was added to the mixture. The mixture was extracted with ethyl acetate. The organic layer was washed by water and brine, and dried over anhydrous sodium sulfate. The solvent was evaporated under reduced pressure, Ethyl acetate-hexane was added to the obtained residue. The precipitated solids were filtered to give the compound 23 (3.4 g, yield 53%)

$^1$H-NMR (CDCl3) δ: 8.07 (s, 1H) .

Step 2

The compound 23 (3.0 g, 18.18 mmol) was dissolved in dichloromethane (30 mL). DIEA (4.76 mL, 27.30 mmol) was added to the solution. The mixture was stirred until dissolved. Then, benzyl bromide (2.34 mL, 20.00 mmol) was added to the mixture. The mixture was stirred at room temperature for 1.5 hours. After the mixture was left standing overnight, the reaction mixture was poured into water. The mixture was extracted with ethyl acetate. The organic layer was washed by 5% aqueous solution of citric acid and water, and dried over anhydrous sodium sulfate. The solvent was evaporated under reduced pressure. Ethyl ether was added to the obtained residue. The obtained solid was filtered to give the compound 24 (1.5 g, yield 32%).

$^1$H-NMR (CDCl3) δ: 5.22 (s, 2H), 7.20-7.30 (m, 2H), 7.40-7.50 (m, 3H), 7.58 (s, 1H)

Step 3

The compound 24 (100 mg, 0.39 mmol) was dissolved in dioxane (2 mL). 3-Chloro-2-methylaniline (83 mg, 0.59 mmol) was added to the solution. The mixture was stirred under microwave irradiation at 130° C. for 10 minutes. The solvent was evaporated under reduced pressure. The obtained residue was purified by silica-gel column chromatography (ethyl acetate-n-hexane) to give the compound I-0011 (73 mg, yield 52%).

$^1$H-NMR (CDCl3) δ: 2.04 (s, 3H), 5.08 (s, 2H), 6.66 (d, J=7.2 Hz, 1H), 7.05-7.14 (m, 2H), 7.30-7.44 (m, 6H), 7.57 (s, 1H)

Example 12

Synthesis of Compound I-0012

[Chemical Formula 112]

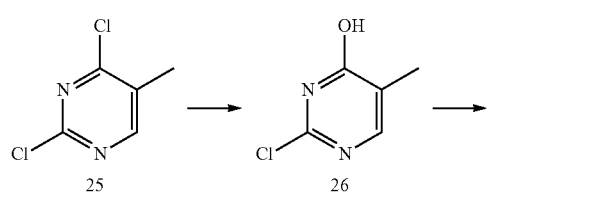

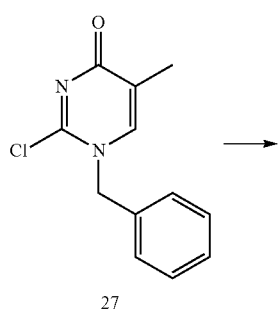

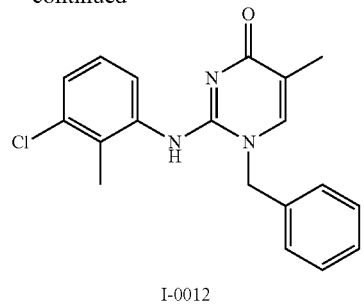

I-0012

Step 1

The compound 25 (5.0 g, 30.7 mmol) was dissolved in tetrahydrofuran (10 mL). A 1 mol/L aqueous solution of sodium hydroxide (46 mL, 46.0 mmol) was added to the solution. The mixture was stirred at room temperature for 24 hours. The reaction mixture was washed by diethyl ether. Under ice cooling, a 2 mol/L aqueous solution of hydrochloric acid was added to the mixture to adjust the pH to 3. The precipitated solids were filtered, and washed by cold water. The obtained solid was dried to give the compound 26 (1.9 g, yield 42.8%).

$^1$H-NMR (DMSO-$d_6$) δ: 1.96 (s, 3H), 7.94 (s, 1H), 12.80-13.80 (br, 1H).

Step 2

The compound 26 (500 mg, 3.46 mmol) was dissolved in dichloromethane (5 mL). DIEA (904 μL, 0.19 mmol) and benzyl bromide (494 μL, 4.16 mmol) were added to the solution. The mixture was stirred at room temperature for 1 day. A 2 mol/L aqueous solution of hydrochloric acid was added to the mixture. The mixture was extracted with chloroform. The organic layer was washed by brine, and dried over anhydrous sodium sulfate. The solvent was evaporated under reduced pressure. The obtained residue was purified by silica-gel column chromatography (chloroform-methanol) to give the compound 27 (416 mg, yield 51.2%). 41 NMR (CDCl$_3$) δ: 2.00 (s, 3H), 5.17 (s, 2H), 7.18-7.24 (m, 3H), 7.37-7.48 (m, 3H>.

Step 3

The compound 27 (50 mg, 0.213 mmol) was dissolved in dioxane (3 mL). 3-Chloro-2-methylaniline (151 mg, 1.07 mmol) was added to the solution. The mixture was stirred under microwave irradiation at 100° C. for 120 minutes. Insoluble materials were filtered off, and rinced by ethyl acetate. The filtrate was evaporated under reduced pressure. The obtained residue was purified by silica-gel column chromatography (hexane-ethyl acetate) to give the compound I-0012 (52 mg, yield 71.8%).

$^1$H-NMR (CDCl$_3$) δ: 1.86 (s, 3H), 2.04 (s, 3H), 5.05 (s, 2H), 6.67 (d, J=6.0 Hz, 1H), 7.02-7.12 (m, 3H), 7.32-7.43 (m, 5H), 7.46-7.52 (br, 1H).

Example 13

Synthesis of Compound I-0013

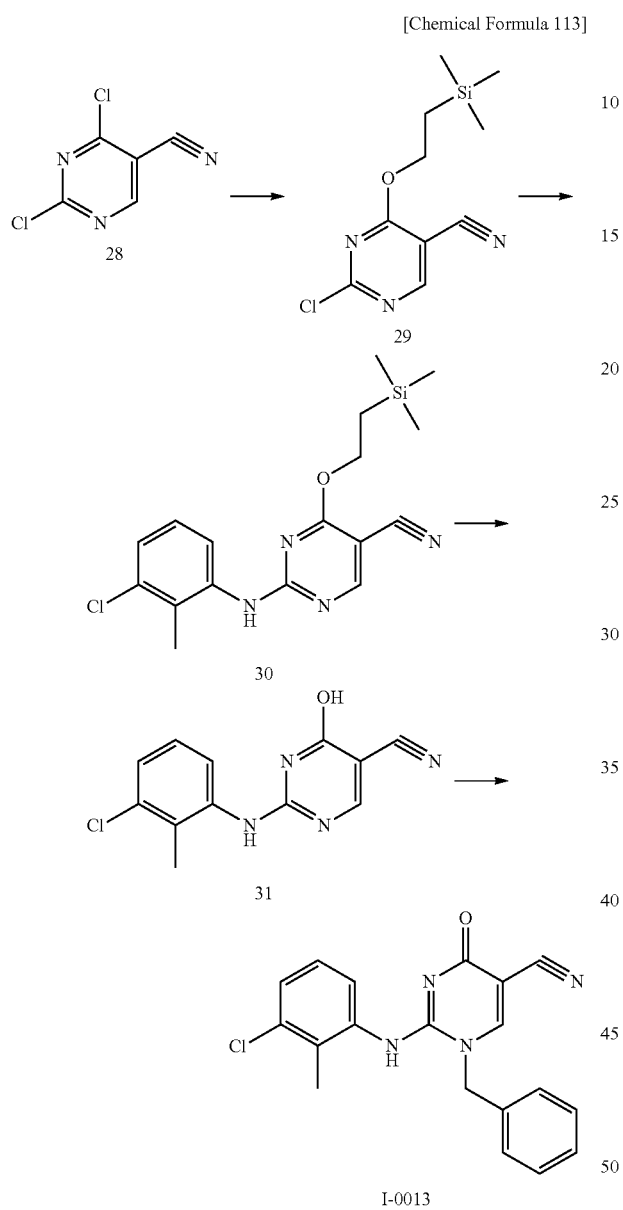

Step 1

Under nitrogen atmosphere, 2-(trimethylsilyl)ethanol (2.5 mL, 17.3 mmol) was dissolved in tetrahydrofuran (25 mL). Under ice cooling, sodium hydride (60% oil dispersion, 506 mg, 12.6 mmol) was added to the solution. The mixture was stirred at room temperature for 1 hour. Under ice cooling, the tetrahydrofuran solution (5 mL) of the compound 28 (2.0 g, 11.5 mmol) was added dropwise to the mixture. The mixture was stirred at room temperature for 5.5 hours. A 2 mol/L aqueous solution of hydrochloric acid was added to the mixture. The organic layer was washed by brine, and dried over anhydrous sodium sulfate. The solvent was evaporated under reduced pressure. The obtained residue was purified by silica-gel column chromatography (hexane-ethyl acetate) to give the compound 29<1.07 g, yield 36.4%).

$^1$H-NMR (CDCl$_3$) δ: 0.11 (s, 9H), 1.18-1.26 (m, 2H), 4.63-4.67 (m, 2H), 8.59 (s, 1H).

Step 2

The compound 29 (693 mg, 2.71 mmol) was dissolved in dioxane (10 mL). 3-Chloro-2-methylaniline (537 mg, 3.79 mmol), palladium acetate (61 mg, 0.271 mmol), Xantphos (235 mg, 0.406 mmol) and cesium carbonate (1.24 g, 3.81 mmol) were added to the solution. The mixture was stirred under reflux for 1.5 hours. A 2 mol/L aqueous solution of hydrochloric acid was added to the mixture. The mixture was extracted with ethyl acetate. The organic layer was washed by the saturated aqueous solution of sodium hydrogen carbonate and brine, and dried over anhydrous sodium sulfate. The solvent was evaporated under reduced pressure. The obtained residue was purified by silica-gel column chromatography (hexane-ethyl acetate) to give the compound 30 (153 mg, yield 15.6%).

$^1$H-NMR (CDCl$_3$) δ: 0.06 (s, 9H), 1.14 (t, J=8.4 Hz, 2H), 2.36 (s, 3H), 4.47 (t, J=8.4 Hz, 2H), 7.02-7.11 (br, 1H). 7.17 (t, J=8.0 Hz, 1H), 7.27 (d, J=8.0 Hz, 1H), 7.69 (d, J=8.0 Hz, 1H), 8.38 (s, 1H).

Step 3

The compound 30 (150 mg, 0.416 mmol) was dissolved in tetrahydrofuran (1 mL). Tetrabutyl ammonium fluoride (1 mol/L tetrahydrofuran solution, 831 µL, 0.831 mmol) was added to the solution. The mixture was stirred at room temperature for 1 day. The solvent was evaporated under reduced pressure. The obtained residue was purified by silica-gel column chromatography (chloroform-methanol) to give the compound 31 (92 mg, yield 84.9%).

$^1$H-NMR (DMSO-d$_6$) δ: 2.22 (s, 3H), 7.24 (t, J=8.0 Hz, 1H), 7.37 (d, J=8.0 Hz, 2H), 8.25 (s, 1H), 9.25-9.90 (br, 1H), 11.70-12.60 (br, 1H).

Step 4

The compound 31 (45 mg, 0.173 mmol) was dissolved in dichloromethane (3 mL). DIEA (90 µL, 0.518 mmol) and benzyl bromide (41 µL, 0.345 mmol) were added to the solution. The mixture was stirred at room temperature for 2 days. The solvent was evaporated under reduced pressure. The obtained residue was purified by silica-gel column chromatography (hexane-ethyl acetate) to give the compound I-0013 (14 mg, yield 23.1%).

$^1$H-NMR (CDCl$_3$) δ: 2.02 (s, 3H), 5.15 (s, 2H), 6.65 (d, J=8.0 Hz, 1H), 7.10-7.20 (m, 2H), 7.34-7.49 (m, 614), 7.55-7.61 (br, 1H), 7.79 (s, 1H).

Example 14

Synthesis of Compound I-0015

[Chemical Formula 114]

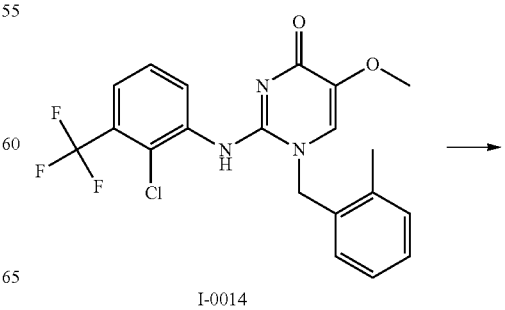

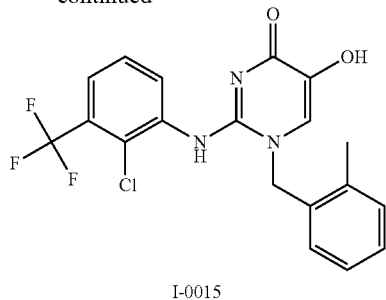

I-0015

Under nitrogen atmosphere, the compound I-0014 (15 mg, 0.037 mmol) obtained by the similar synthesis of Example 2 was dissolved in dichloromethane (2 mL). A 1 mol/L boron tribromide (8.33 μL, 0.088 mmol) was added to the solution. The mixture was stirred at room temperature for 3 hours. The saturated aqueous solution of sodium hydrogen carbonate was added to the mixture. The mixture was extracted with ethyl acetate. The organic layer was washed by brine, and dried over anhydrous magnesium sulfate. The solvent was evaporated under reduced pressure. The obtained residue was purified by silica-gel column chromatography (n-hexane-ethyl acetate) to give the compound I-0015 (8 mg, yield 55%). 1H-NMR (DMSO-D6) δ: 1.95 (3H, s). 4.80 (1H, d, J=15.8 Hz), 5.03 (1H, d, J=15.8 Hz), 6.82 (1H, d, J=7.5 Hz), 7.09-7.20 (3H, m), 7.64-7.61 (2H, m), 7.70 (1H, d, J=7.8 Hz), 7.97 (1H, d, J=7.8 Hz)

Example 15

Synthesis of Compound I-0016

[Chemical Formula 115]

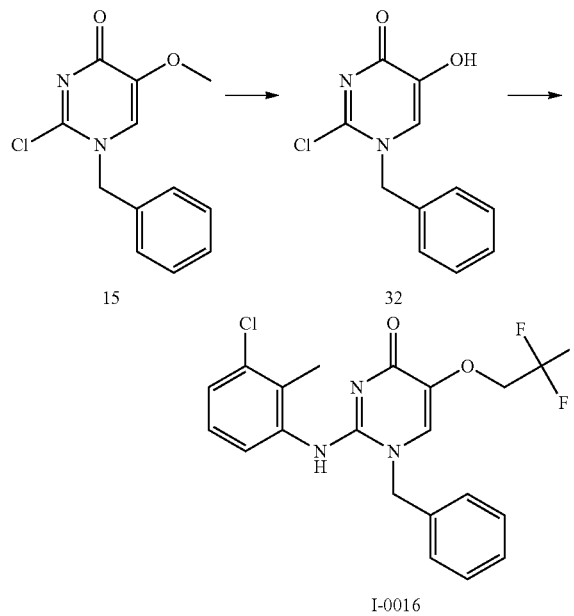

Step 1

The compound 15 (2.0 g, 7.98 mmol) was dissolved in dichloromethane (40 mL). The solution was cooled to 0° C. Boron tribromide (dichloromethane solution, 1 mol/L) was added to the solution. The mixture was stirred at 0° C. for 1 hour. The saturated aqueous solution of sodium hydrogen carbonate and chloroform were added to the reaction mixture. The mixture was stirred at room temperature for 15 minutes. A 2 mol/L hydrochloric acid solution was added to the reaction mixture. The mixture was extracted with chloroform. The organic layer was dried over anhydrous magnesium sulfate. The solvent was evaporated under reduced pressure. Ethyl acetate and hexane were added to the obtained residue. The resulting powder was filtered to give the compound 32 (2.0 g) as a crude product.

LC-MS (Condition [1]): RT=1.07, 236 [M+H]+

Step 2

The compound 32 (200 mg, 0.845 mmol) was dissolved in NMP (4.0 mL). 2,2,2-Trifluoroethyl trifluoromethanesulfonate (1960 mg, 8.45 mmol) and potassium carbonate (350 mg, 2.54 mmol) wore added to the solution. The mixture was stirred at 50° C. for 4 hours. Water was added to the reaction mixture. The mixture was extracted with chloroform. The organic layer was dried over anhydrous magnesium sulfate. The solvent was evaporated under reduced pressure.

The obtained crude product was dissolved in NMP (4.0 mL). 3-Chloro-2-methylaniline (0.200 mL, 1.69 mmol) was added to the solution. The mixture was stirred under microwave irradiation at 130° C. for 1.0 minutes. Water was added to the reaction mixture. The mixture was extracted with ethyl acetate. The organic layer was dried over anhydrous magnesium sulfate. The solvent was evaporated under reduced pressure. The obtained residue was purified by reverse-phase silica-gvl column chromatography (water-acetonitrile) to give the compound I-0016 (22 mg, yield 6%) as a white powder.

LC-MS (Condition [1]): RT=2.03, 424 [M+H]+

1H-NMR (DMSO-D6) δ: 1.82 (3H, s), 4.69 (2H, q, J=9.0 Hz), 5.22 (2H, s), 7.05-7.44 (8H, m), 7.74 (1H, s), 8.73 (1H, s).

Example 16

Synthesis of Compound I-0018

[Chemical Formula 116]

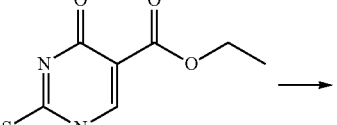

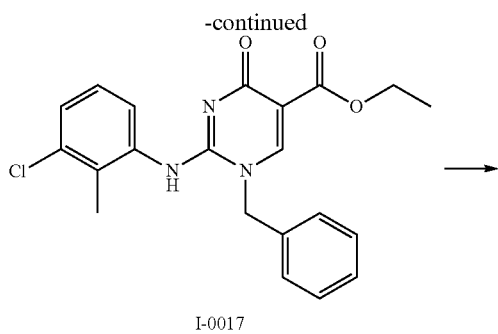

I-0017

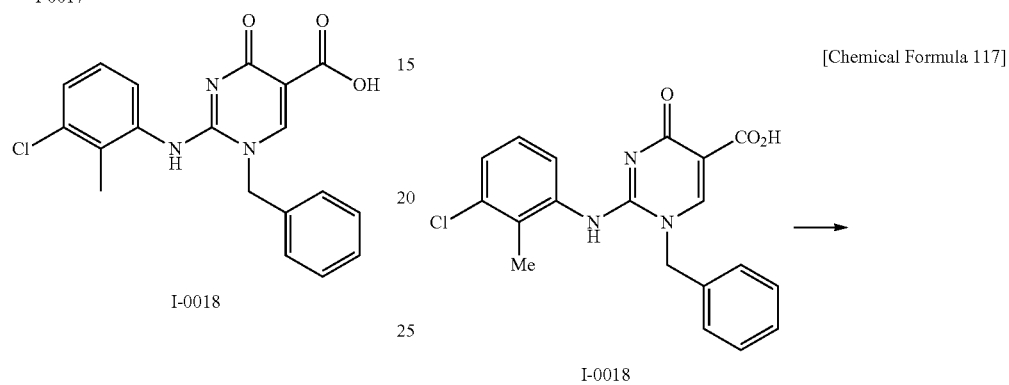

I-0018

Step 1

The compound 33 (1.0 g, 4.67 mmol) was dissolved in dichloromethane (10 mL). DIEA (1.22 mL, 7.00 mmol) and benzyl bromide (665 µL, 5.60 mmol) were added to the solution. The mixture was stirred at room temperature for 0.1 day. A 2 mol/L aqueous solution of hydrochloric acid was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (chloroform-methanol) to give the compound 34 (1.09 g, yield 76.7%). $^1$H-NMR (CDCl$_3$) δ: 1.34 (t, J=6.8 Hz, 3H), 2.61 (s, 3H), 4.33 (q, J=6.8 Hz, 2H), 5.09 (s, 2H), 7.21-7.26 (m, 2H>. 7.38-7.47 (m, 3H), 8.06 (s, 1H).

Step 2

The compound 34 (927 mg, 3.05 mmol) was dissolved in tert-butanol (18 mL). Acetic acid (2.6 mL, 45.7 mmol) and 3-chloro-2-methyl anilino (647 mg, 4.57 mmol) were added to the solution. The mixture was stirred under reflux for 96 hours. After cooled to room temperature, the mixture was diluted with ethyl acetate. The mixture was washed by the saturated aqueous solution of sodium hydrogen carbonate and brine. The mixture was dried over anhydrous sodium sulfate. The solvent was evaporated under reduced pressure. The obtained residue was purified by silica-gel column chromatography (hexane-ethyl acetate) to give the compound I-0017 (770 mg, yield 63.5%).

$^1$H-NMR (CDCl$_3$) δ: 1.33 (t, J=7.2 Hz, 3H), 1.96 (s, 3H), 4.31 (q, J=7.2 Hz, 2H), 5.16 (s, 2H), 6.64 (d, J=7.6 Hz, 1H), 7.06-7.17 (m, 2H), 7.35-7.47 (m, 6H), 8.32 (s, 1H).

Step 3

The compound I-0017 (757 mg, 1.90 mmol) was dissolved in a mixed solution of ethanol (5.7 mL) and tetrahydrofuran (5.7 mL). A 1 mol/L aqueous solution of lithium hydroxide (5.7 mL, 5.7 mmol) was added to the solution. The mixture was stirred at 50° C. for 2.5 hours. A 10% aqueous solution of citric acid was added to the mixture. The mixture was extracted with ethyl acetate. The organic layer was washed by brine, and dried over anhydrous sodium sulfate. The solvent was evaporated under reduced pressure. The obtained solids were washed by IPE to give the compound I-0018 (631 mg, yield 89.7%).

$^1$H-NMR (CDCl$_3$) δ: 1.99 (s, 3H), 5.19 (s, 2H), 6.66 (d, J=7.6 Hz, 1H), 7.10-7.21 (m, 2H), 7.35-7.49 (m, 511), 7.55-7.90 (br, 1H), 8.52 (s, 1H), 11.78-12.30 (br, 1H).

Example 17

Synthesis of Compound I-0019

[Chemical Formula 117]

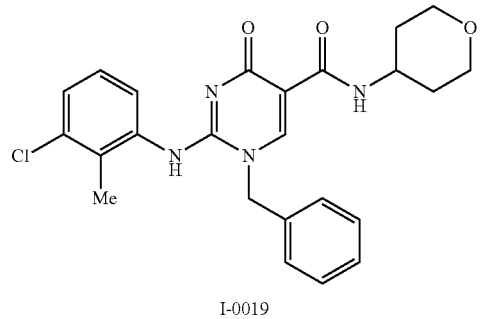

I-0018

I-0019

4-aminotetrahydro-2H-pyran hydrochloride (41 mg, 0.3 mmol), 1-hydroxybenzotriazole (41 mg, 0.3 mmol) and 1-ethyl-3-(3-dimethylaminopropyl)carbodiimide hydrochloride (58 mg, 0.3 mmol) were added to a mixed solution of the compound I-0018 (74 mg, 0.2 mmol) and DMF (2 mL). Then, triethylamine (0.042 mL, 0.3 mmol) was added to the mixture. The mixture was stirred at room temperature for 8 hours. Water was added to the reaction mixture. The mixture was extracted with ethyl acetate. The organic layer was washed by the saturated aqueous solution of sodium hydrogen carbonate and brine, and dried over anhydrous magnesium sulfate. The solvent was evaporated under reduced pressure. Ethyl acetate and hexane were added to the obtained residue. The resulting powder was filtered to give the compound I-0019 (0.08 g, yield 88%) as a white powder.

$^1$H-NMR, (DMSO-d6) δ: 1.40-1.46 (211, m), 1.78-1.83 (5H, m), 3.35-3.44 (2H, m), 3.77-3.81 (2H, m), 3.93 (1H, m), 5.26 (2H, brs), 6.68 (1H, brs), 7.10 (2H, brs), 7.34-7.39 (5H, m), 8.59 (1H, brs), 10.43 (1H, brs).

Example 18

Synthesis of Compound I-0020

[Chemical Formula 118]

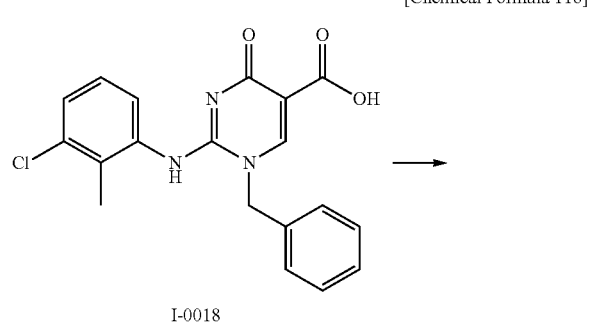

The compound I-0018 (50 mg, 0.135 mmol) was dissolved in toluene (5.0 mL). Methanol (55 μL, 1.35 mmol), triethylamine (22 μL, 0.162 mmol) and DPPA (32 μL, 0.149 mmol) were added to the solution. The mixture was stirred at 100° C. for 4 hours and then stirred under reflux for 1 hour. The saturated aqueous solution of sodium hydrogen carbonate was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (hexane-ethyl acetate) to give the compound I-0020 (20 mg, yield 37.1%).

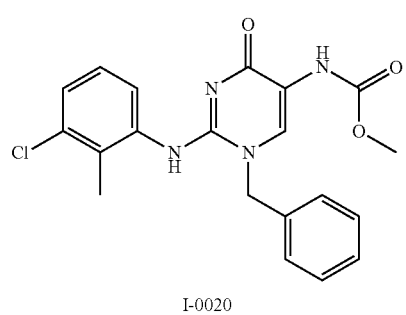

$^1$H-NMR (DMSO-$d_6$) δ: 1.88 (s, 3H), 3.61 (s, 3H), 5.15-5.34 (br, 2H), 6.93-7.51 (m, 8H), 7.95-8.20 (br, 1H), 8.01 (s, 1H), 8.72-9.00 (br, 1H).

Example 19

Synthesis of Compound I-0021

[Chemical Formula 119]

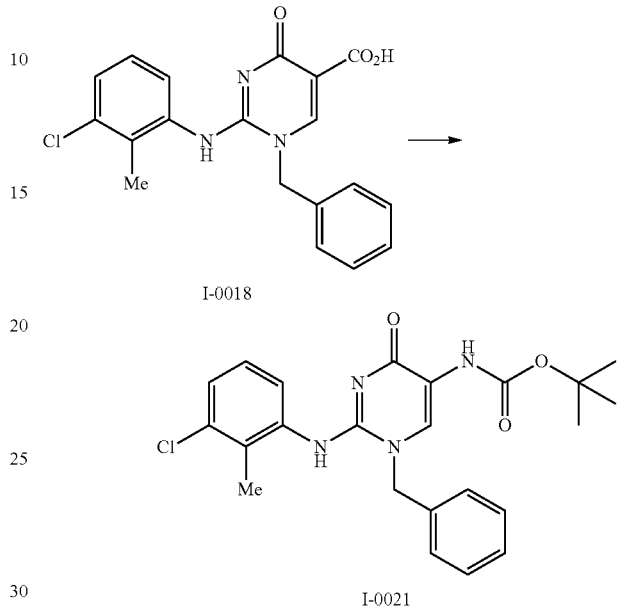

DPPA (0.103 mL. 0.48 mmol) and triethylamine (0.067 mL, 0.48 mmol) were added to a mixed solution of the compound I-0018 (148 mg, 0.4 mmol), dioxane (1 mL) and tert-butanol (0.5 mL). The mixture was stirred under reflux for 2 hours. Water was added to the reaction mixture. The mixture was extracted with ethyl acetate. The organic layer was washed by brine, and dried over anhydrous magnesium sulfate. The solvent was evaporated under reduced pressure. The obtained residue was purified by silica-gel column chromatography (ethyl acetate-hexane). Ethyl acetate and hexane were added to the obtained residue. The resulting powder was filtered to give the compound I-0021 (50 mg, yield 28%) as a white powder.

$^1$H-NMR (CDCl3) δ: 1.49 (1.51) (9H, s), 1.98 (1.75) (3H, s), 5.06 (5.03) (2H, a), 5.83-8.18 (10H, m).

Example 20

Synthesis of Compound I-0022

[Chemical Formula 120]

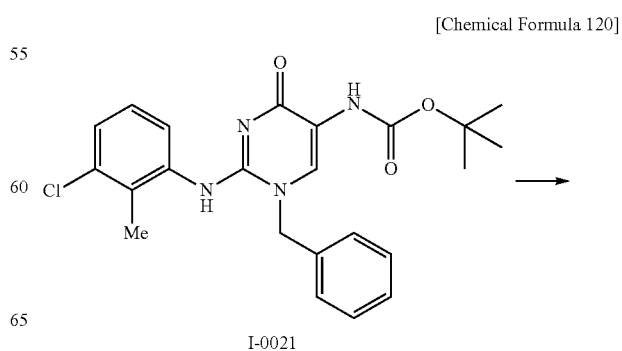

-continued

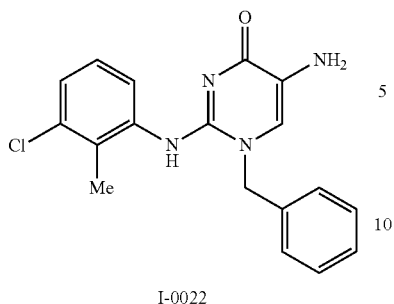

I-0022

-continued

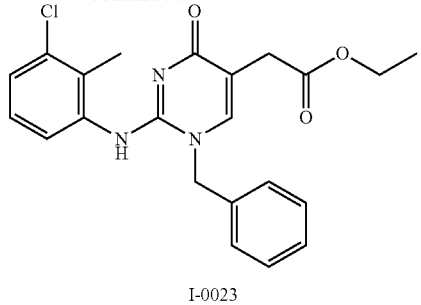

I-0023

A 4 mol/L hydrochloric acid-dioxane solution (0.10 mL, 0.4 mmol) was added to a mixed solution of the compound I-0021 (35 mg, 0.08 mmol) and dioxane (1 mL). The mixture was stirred at 50° C. for 2 hours. The saturated aqueous solution of sodium hydrogen carbonate (20 mL) was added to the reaction mixture. The mixture was extracted with ethyl acetate (50 mL). The organic layer was washed by brine, and dried over anhydrous magnesium sulfate. The solvent was evaporated under reduced pressure. The obtained residue was purified by silica-gel column chromatography (ethyl acetate-hexane) to give the compound I-0022 (23 mg, yield 84%) as a white powder.

1H-NMR (CDCl3) δ: 2.07 (2H, s), 3.24 (2H, brs), 5.01 (2H, s), 6.72 (2H, brs), 7.05-7.10 (2H, m), 7.34-7.42 (5H, m), 7.61 (1H, brs).

Example 21

Synthesis of Compound I-0023

[Chemical Formula 121]

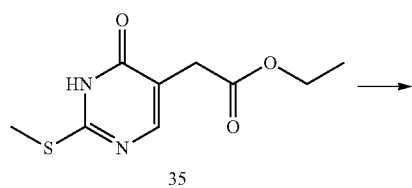

35

Step 1

DIEA (11.5 mL, 65.7 mmol) and benzyl bromide (6.2 mL, 52.6 mmol) were added to a suspension of the compound 35 (10 g, 43.8 mmol) in dichloromethane (10 mL). The mixture was stirred at room temperature for 20 hours. A 2 mol/L hydrochloric acul solution was added to the reaction mixture. The mixture was extracted with ethyl acetate. The organic layer was dried over anhydrous magnesium sulfate. The solvent was evaporated under reduced pressure. Hexane was added to the obtained residue. The resulting powder was filtered to give the compound 36 (12.3 g) as a crude product.

LC-MS (Condition [1]): RT=1.46, 319 [M+H]+

Step 2

3-chloro-2-methylaniline (100 mg, 0.707 mmol) was added to an acetic acid (0.40 mL, 7.07 mmol) solution of the compound 36 (0.15 g, 0.471 mmol). The mixture was stirred under reflux for 4 hours. Water was added to the reaction mixture. The mixture was extracted with ethyl acetate. The organic layer was dried over anhydrous magnesium sulfate. The solvent was evaporated under reduced pressure. The obtained residue was purified by reverse-phase silica-gel column chromatography (water-acetonitrile) to give the compound I-0023 (41.0 mg, yield 21%) as a white powder.

LC-MS (Condition [3]): RT=2.33, 412 [M+H]+

1H-NMR (DMSO-D6) δ: 1.17 (3H, t, J=7.2 Hz), 1.86 (3H, s), 3.20 (2H, s), 4.05 (2H, q, J=7.1 Hz), 5.06 (2H, br s), 6.55-7.45 (8H, m), 7.79 (1H, s), 9.93 (1H, s).

Example 22

Synthesis of Compound I-0024

[Chemical Formula 122]

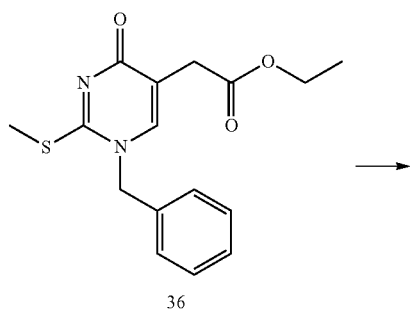

36

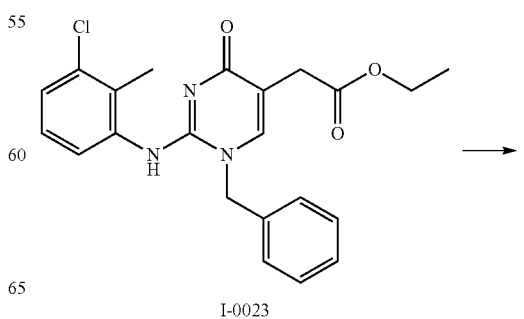

I-0023

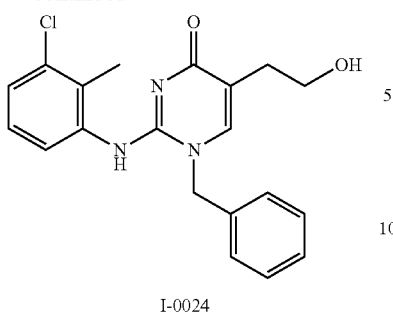

I-0024

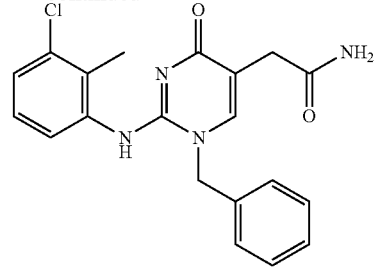

I-0026

Lithium borohydride (10.6 mg, 0.486 mmol) was added to a tetrahydrofuran (2.0 mL) solution of the compound I-0023 (1.00 mg, 0.243 mmol). The mixture was stirred at room temperature for 2 hours. Lithium borohydride (10.6 mg, 0.486 mmol) was further added to the mixture. The mixture was stirred at room temperature for 2 hours. The saturated aqueous solution of ammonium was added to the reaction mixture. The mixture was extracted with ethyl acetate. The organic layer was dried over anhydrous magnesium sulfate. The solvent was evaporated under reduced pressure. The obtained residue was purified by reverse-phase silica-gel column chromatography (water-acetonitrile) to give the compound I-0024 (72.9 mg, yield 99%) as a white powder.

LC-MS (Condition [3]): RT=1.87, 370 [M+H]$^+$

1H-NMR (DMSO-D6) δ: 1.85 (3H, s), 2.32 (2H, t, J=6.5 Hz), 3.46 (2H, q, J=6.1 Hz). 4.58 (1H, br s). 5.05 (2H, br s), 6.55-7.70 (9H, m), 9.66 (1H, s).

Example 23

Synthesis of Compound I-0026

[Chemical Formula 123]

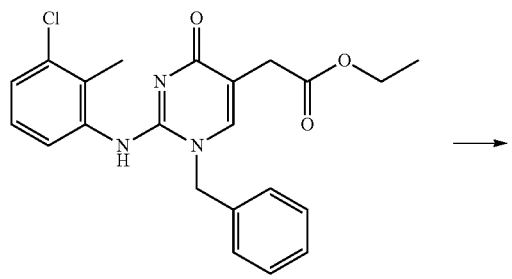

I-0023

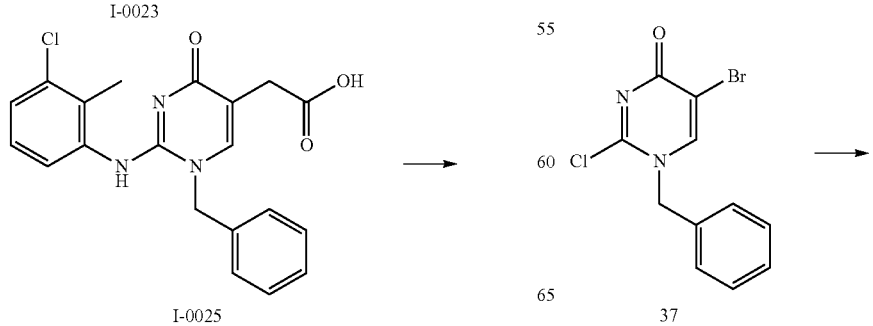

I-0025

Step 1

A 2 mol/L aqueous solution of sodium hydroxide (9.71 mL, 19.42 mmol) was added to a tetrahydrofuran (20 mL) and methanol (20 mL) solution of the compound I-0023 (2.0 g, 4.86 mmol). The mixture was stirred at room temperature for 0.1 hour. The solvent in the reaction mixture was evaporated under reduced pressure. A 2 mol/L hydrochloric acid solution was added to the mixture. The resulting powder was filtered to give the compound I-0025 (1.75 g, yield 94%) as a crude product.

LC-MS (Condition [3]): RT=1.79, 384 [M+H])$^+$ $^1$H-NMR (DMSO-D6) δ: 1.88 (3H, s), 3.17 (2H, s), 5.16 (2H, br s), 6.70-7.60 (8H, m), 7.83 (1H, s), 9.88 (1H, br s), 12.30 (1H, br s).

Step 2

HATU (149 mg, 0.391 mmol), ammonium chloride (20.9 mg, 0.391 mmol) and triethylamine (0.10 mL, 0.782 mmol) were added to a DMF (2.0 mL) solution of the compound I-0025 (100 mg, 0.261 mmol). The mixture was stirred at room temperature for 1.5 hours. The saturated aqueous solution of sodium hydrogen carbonate was added to the reaction mixture. The mixture was extracted with ethyl acetate. The organic layer was dried over anhydrous magnesium sulfate. The solvent, was evaporated under reduced pressure. The obtained residue was purified by reverse-phase silica-gel column chromatography (water-acetonitrile) to give the compound I-0026 (100.0 mg, yield 96%) as a white powder.

LC-MS (Condition [3]): RT=1.77, 383 [M+H]$_+$

1H-NMR (DMSO-D6) δ: 1.87<3H, s), 2.98 (2H, s), 5.08 (2H, s), 6.65-7.50 (10H, m), 7.69 (1H, s), 9.73 (1H, br s).

Example 24

Synthesis of Compound I-0028

[Chemical Formula 124]

37

Example 25

Synthesis of Compound I-0029

[Chemical Formula 125]

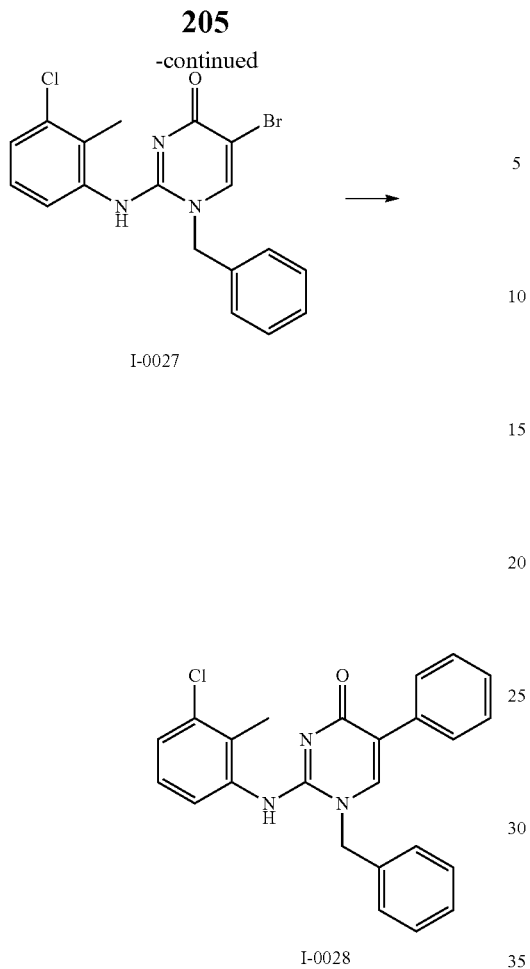

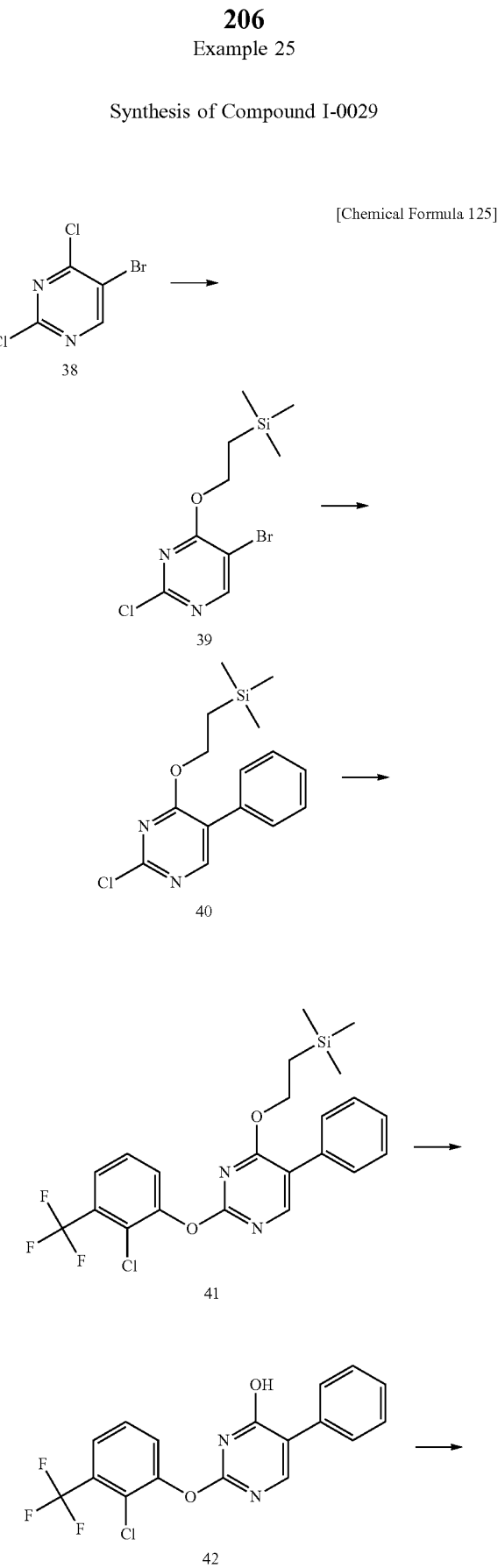

Step 1

3-Chloro-2-methylaniline (496 mg, 3.51 mmol) was added to a dioxane (15 mL) solution of the compound 37 (0.7 g, 2.33 mmol). The mixture was stirred under microwave irradiation at 1.30° C. for 1.0 minutes. The solvent in the reaction mixture was evaporated under reduced pressure. Ethyl acetate and hexane were added to the residue. The resulting powder was filtered to give the compound I-0027 (850 mg) as a crude product.

LC-MS (Condition [1]): RT=1.96, 405 [M+H]$^{30}$

Step 2

Phenylboronic acid (36.2 mg, 0.297 mmol). [1,1'-bis(di-tert-butylphosphino)ferrocene]palladium(II) dichloride (8.0 mg, 0.012 mmol) and sodium carbonate (0.49 mL, 0.988 mmol) were added to a DMF (15 mL) solution of the compound I-0027 (100 mg, 0.247 mmol). The mixture was stirred at 100° C. for 3 hours. Water was added to the reaction mixture. The mixture was extracted with ethyl acetate. The organic layer was dried over anhydrous magnesium sulfate. The solvent was evaporated under reduced pressure. The obtained residue was purified by reverse-phase silica-gel column chromatography (water-acetonitrile) to give the compound I-0028 (1.4.3 mg, yield 14%) as a white powder.

LC-MS (Condition [3]): RT=2.73, 402 [M+H]$^+$

1H-NMR (DMSO-D6) δ: 1.93 (311, s), 4.92 (2H, dd, J=46.8, 14.9 Hz), 7.01-7.33 (13H, m), 7.61 (1H, s), 9.84 (1H, s).

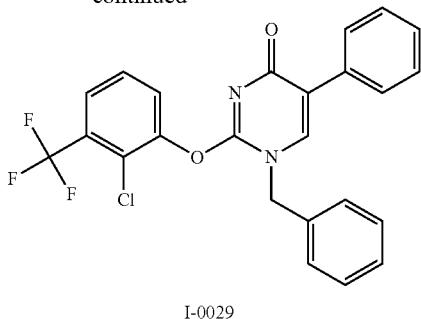

I-0029

Step 1

Under nitrogen atmosphere, 2-(trimethylsilyl)ethanol (2.85 mL, 19.8 mmol) was dissolved in tetrahydrofuran (30 mL). Sodium hydride (00% oil dispersion, 032 mg, 15.8 mmol) was added to the solution under ice cooling. The mixture was stirred at room temperature for 1 hour. A 15 mL of tetrahydrofuran solution of the compound 38 (3.0 g, 13.2 mmol) was added dropwise to the mixture under ice cooling. The mixture was stirred at room temperature for 2.5 hours. A 2 mol/L aqueous solution of hydrochloric acid was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (hexane-ethyl acetate) to give the compound 39 (3.81 g, yield 93.5%).

1H-NMR (CDCl$_3$) δ: 0.10 (s, 9H), 1.12 (t, J=8.0 Hz, 2H), 4.57 (t, J=8.0 Hz, 2H), 8.41 (s, 1H).

Step 2

Under nitrogen atmosphere, the compound 39 (500 mg, 1.62 mmol) was dissolved in dioxane (15 mL). Phenylboronic acid (276 mg, 2.26 mmol), [1,1'-bis(diphenylphosphino)ferrocene]palladium(II) dichloride dichloromethane adduct (132 mg, 0.161 mmol) and a 2 mol/L aqueous solution of sodium carbonate (2.4 mL, 4.8 mmol) were added to the solution. The mixture was stirred under reflux for 4 hours. After cooled to room temperature, water was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (hexane-ethyl acetate) to give the compound 40 (407 mg, yield 82.1%).

Step 3

The compound 40 (181 mg, 0.590 mmol) was dissolved in dioxane (4 mL). 2-Chloro-3-trifluoromethylphenol (1.51 mg, 0.767 mmol) and cesium carbonate (288 mg, 0.885 mmol) were added to the solution. The mixture was stirred under microwave irradiation at 100° C. for 4.5 hours. Water was added to the mixture. The mixture was washed by ethyl acetate. The organic layer was washed by brine, and dried over anhydrous sodium sulfate. The solvent was evaporated under reduced pressure. The obtained residue was purified by silica-gel column chromatography (hexane-ethyl acetate) to give the compound 41 (132 mg, yield 47.9%).

$^1$H-NMR (CDCl$_3$) δ: −0.05 (s, 9H), 1.06 (t, J=8.0 Hz, 2H), 4.38 (t, J=8.0 Hz, 2H), 7.20-7.52 (m, 7H), 7.64 (d, J=7.6 Hz, 1H), 8.26 (s, 1H).

Step 4

The compound 41 (127 mg, 0.272 mmol) was dissolved in tetrahydrofuran (0.5 mL). Tetrabutyl ammonium fluoride (1 mol/L tetrahydrofuran solution, 408 μL, 0.408 mmol) was added to the solution. The mixture was stirred at room temperature for 4 days. The solvent was evaporated under reduced pressure. The obtained residue was purified by silica-gel column chromatography (chloroform-methanol) to give the compound 42 (77 mg, yield 77.2%).

$^1$H-NMR (DMSO-d$_6$) δ: 7.30-7.43 (m, 3H), 7.58-7.72 (m, 3H), 7.82-8.06 (m, 3H), 13.20-13.65 (br, III).

Step 5

The compound 42 (75 mg, 0.205 mmol) was dissolved in dichloromethane (2 mL). DIEA (54 μL, 0.307 mmol) and benzyl bromide (32 μL, 0.266 mmol) were added to the solution. The mixture was stirred at room temperature for 1 day. A 2 mol/L aqueous solution of hydrochloric acid was added to the mixture. The mixture was extracted with chloroform. The organic layer was washed by brine, and dried over anhydrous sodium sulfate. The solvent was evaporated under reduced pressure. The obtained residue was purified by silica-gel column chromatography (chloroform-methanol) to give the compound I-0029 (78 mg, yield 83.5%).

$^1$H-NMR (DMSO-d$_6$) δ: 5.35 (s, 2H), 7.31-7.51 (m, 8H), 7.61-7.78 (m, 4H), 7.87 (d, J=8.0 Hz, 1H), 8.34 (s, 1H).

Example 26

Synthesis of Compound I-0030

[Chemical Formula 126]

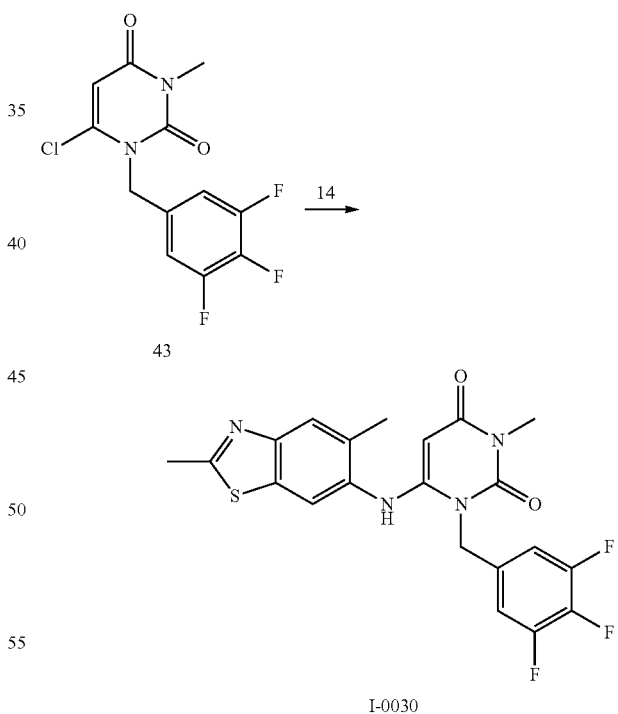

The compound 43 (200 mg, 0.66 mmol) obtained by the similar synthesis of Example 2 was dissolved in dioxane (6 mL). The compound 14 (117 mg, 0.66 mmol), palladium acetate (15 mg, 0.07 mmol), Xantphos (57 mg, 0.10 mmol) and cesium carbonate (209 mg, 0.92 mmol) were added to the solution. Under nitrogen atmosphere, the mixture was stirred under reflux for 1.5 hours. A 5% aqueous solution of citric acid was added to the mixture. The mixture was extracted with ethyl acetate. The organic layer was washed by the aqueous solution of sodium hydrogen carbonate, water and brine, and dried over anhydrous sodium sulfate. The solvent was evaporated under reduced pressure. The obtained residue was purified by silica-gel column chromatography (ethyl acetate-n-hexane) to give the compound I-0030 (70 mg, yield 24%).

$^1$H-NMR (CDCl3) δ: 2.01 (s, 3H), 2.83 (s, 3H), 3.35 (s, 3H), 4.65 (s, 1H), 5.30 (s, 2H), 5.87 (s, 1H), 6.95-7.05 (m, 2H>, 7.46 (s, 1H), 7.76 (s, 1H)

Example 27

Synthesis of Compound I-0031

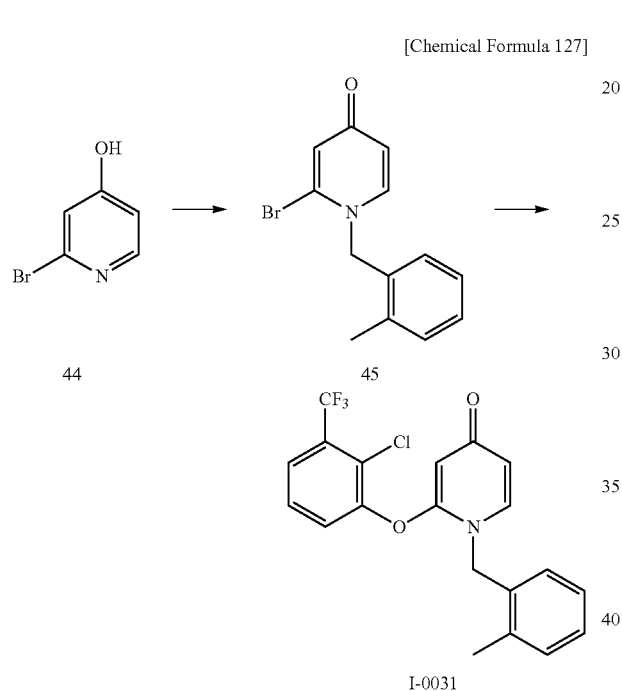

Step 1

The compound 44 (3 g, 17.24 mmol) was dissolved in DMF (20 mL). DIEA (3.61 mL, 20.69 mmol) and 2-methylbenzyl bromide (2.43 mL, 18.10 mmol) were added to the solution. The mixture was stirred at room temperature for 7 hours. After the mixture was left standing overnight, water was added to the mixture. The mixture was extracted with ethyl acetate. The organic layer was washed by brine, and dried over anhydrous sodium sulfate. The solvent was evaporated under reduced pressure. The obtained residue was solidified with ethyl acetate and IPE. The precipitated solids were filtered, and dried to give the compound 45 (812 mg, yield 15%).

LC-MS (Condition [2]): RT=1.40, 278 [M+H]$^{30}$

Step 2

The compound 45 (30 mg, 0.095 mmol) was dissolved in DMF (1 mL). Cesium carbonate (93 mg, 0.286 mmol) and 2-chloro-3-trifluoromethyl-phenol (19 µL, 0.143 mmol) were added to the solution. The mixture was stirred at 70° C. for 5 hours. Then, the mixture was stirred at 100° C. for 16 hours. Water was added to the reaction mixture. The mixture was extracted with chloroform-methanol (9/1). The solvent was evaporated under reduced pressure. The obtained residue was purified by a preparative high performance liquid chromatography to give the compound I-0031 (9.4 mg, yield 25%).

1H-NMR (CDCl3) δ: 2.31 (311, s), 5.08 (1H, s), 5.31 (2H, s), 6.08 (1H, d, J=7.6 Hz), 6.94 (1H, s), 7.23 (3H, s), 7.62-7.67 (2H, m), 7.73 (1H, d, J=7.6 Hz), 7.85 (1H, d, J=7.3 Hz)

Example 28

Synthesis of Compound I-0032

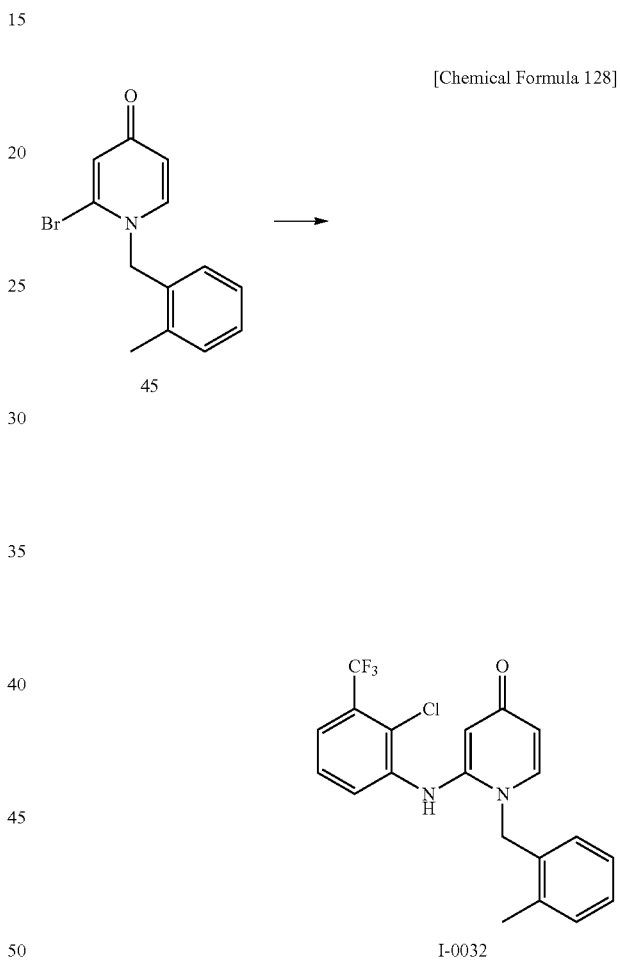

Under nitrogen atmosphere, the compound 45 (40 mg, 0.127 mmol) was dissolved in dioxane (1 mL). 3'Chloro-2-methylaniline (34.8 mg, 0.178 mmol), palladium acetate (2.85 mg, 0.013 mmol), Xantphos (11.04 mg, 0.019 mmol) and cesium carbonate (104 mg, 0.318 mmol) were added to the solution. The mixture was stirred under reflux for 5 hours. Water was added to the reaction mixture. The mixture was extracted with ethyl acetate. The organic layer was washed by brine, and dried over anhydrous sodium sulfate. The solvent was evaporated under reduced pressure. The obtained residue was purified by a preparative high performance liquid chromatography to give the compound I-0032 (9.4 mg, yield 19%).

LC-MS (Condition [2]): RT=1.99, 393 [M+H]$^+$

Example 29

Synthesis of Compound I-0033

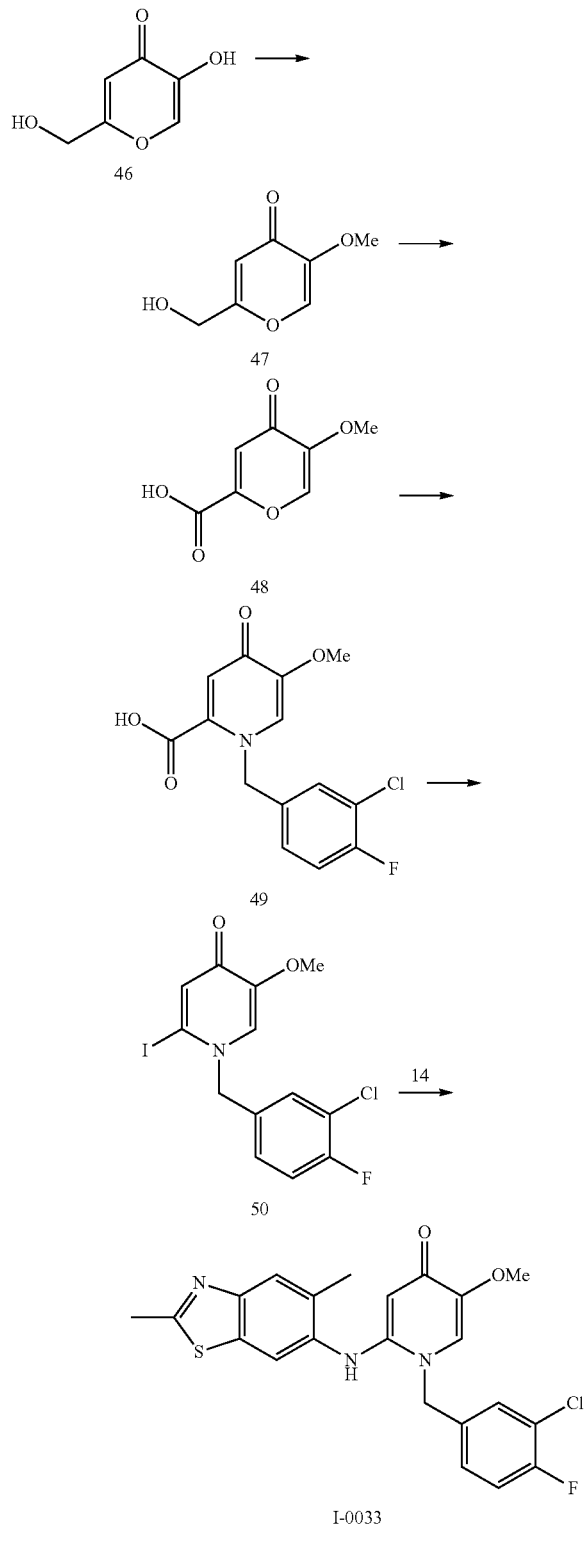

Step 1

Dimethylsulfone acid (1.06 mL, 1.11 mmol) was added dropwise to a 10% aqueous solution of potassium hydroxide (651 mL) of the compound 46 (150 g, 1.06 mmol) at 3° C. to 5° C. The mixture was stirred at 0° C. to 5° C. for 4 hours. The precipitates were filtered, and washed by IPE. The obtained solids were dried under reduced pressure to give the compound 47 (1.065 g, yield 65%).

Step 2

2,2,2,6-tetramethylpiperidine 1-oxyl (2.60 g, 16.7 mmol) and sodium hydrogen carbonate (14.0 g, 167 mmol) were added to a tetrahydrofuran solution (1.20 mL) of the compound 47 (52.0 g, 333 mmol) at 0° C. Then, a 5% aqueous solution of sodium hypochlorite (1.15 L, 833 mmol) was added dropwise to the mixture at 0° C. to 15° C. over 2.5 hours. The mixture was stirred at 5° C. for 45 minutes. Sodium sulfite (35 g) was added to the mixture. The reaction mixture was washed by ethyl acetate. Concentrated hydrochloric acid was added to the obtained aqueous layer. The white precipitated solids were filtered, and dried under reduced pressure to give the compound 48 (20.0 g, yield 35%).

Step 3

3-Chloro-4-fluorobenzylamine (20 g, 125 mmol) and a 2 mol/L aqueous solution of sodium hydroxide (80 mL, 160 mmol) were added to an ethanol (80 mL) solution of the compound 48 (19.4 g, 114 mmol) at room temperature. The mixture was stirred at 90° C. for 1 hour. The reaction mixture was concentrated under reduced pressure. Water was added to the residue. The mixture was washed by chloroform. A 2 mol/L hydrochloric acid solution was added to the obtained aqueous layer. The yellow precipitated solids were filtered, and dried under reduced pressure to give the compound 49 (18.6 g, yield 62%).

$^1$H NMR (d$_6$-DMSO) δ: 3.72 (s, 3H), 5.51 (s, 2H), 6.67 (s, 1H), 7.18 (ddd, J=8.5, 4.5, 1.8 Hz, 1H), 7.42 (dd, J=9.0, 8.5 Hz, 1H), 7.46 (dd, J=7.0, 1.8 Hz, 1H), 7.78 (s, 1H).

Step 4

Iodine (5.86 g, 23.1 mmol) was added to a dimethyl sulfoxide (40 mL) solution of the compound 49 (6.00 g, 1.14 mmol) at room temperature. The mixture was stirred at 120° C. for 3 hours. After cooled to room temperature, a 5% aqueous solution of sodium thiosulfate was added to the reaction mixture. The mixture was extracted with ethyl acetate. The organic layer was washed by brine, and dried over anhydrous magnesium sulfate. The solvent was evaporated under reduced pressure. The obtained residue was purified by silica-gel column chromatography (chloroform-methanol) to give the compound 50 (3.10 g, yield 39%) as colorless foam.

$^1$H-NMR (d$_6$-DMSO) δ: 3.65 (s, 3H), 5.36<s, 2H), 6.77 (s, 1H), 7.11 (ddd, J=8.5, 4.5, 2.3 Hz, 1H), 7.43 (dd, J=7.0, 2.3 Hz, 1H), 7.45 (dd, J=9.0, 8.5 Hz, 1H), 7.88 (s, 1H).

Step 5

The compound 14 (50 mg, 0.279 mmol), Xantphos (29 mg, 0.051 mmol), palladium acetate (8.6 mg, 0.038 mmol) and cesium carbonate (207 mg, 0.635 mmol) were added to a 1,4-dioxane (2 mL) solution of the compound 50 (100 mg, 0.254 mmol) at room temperature. The mixture was stirred at 80° C. for 5 hours. After cooled to room temperature, the reaction mixture was poured into brine. The mixture was extracted with ethyl acetate. The organic layer was washed by brine, and dried over anhydrous magnesium sulfate. The solvent was evaporated under reduced pressure. The obtained residue was purified by silica-gel column chromatography (chloroform-methanol) to give the compound I-0033 (60 mg, yield 53%) as colorless solids.

¹H-NMR (CDCl₃) δ: 2.05 (s, 3H), 2.80 (s, 3H), 3.79 (s, 3H), 6.04 (s, 2H), 5.37 (s, 1H), 5.83 (s, 1H), 6.81 (s, 1H), 7.05 (m, 1H), 7.20 (dd, J=8.5, 8.5 Hz, 1H), 7.25 (m, 1H), 7.29 (m, 1H), 7.72 (s, 1H).

Example 30

Synthesis of Compound I-1118

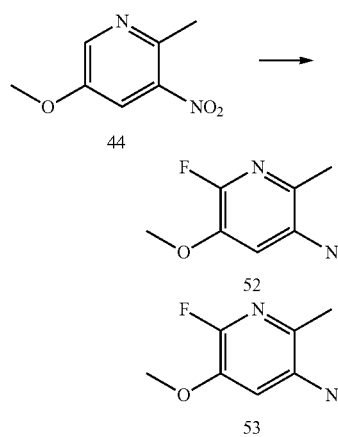

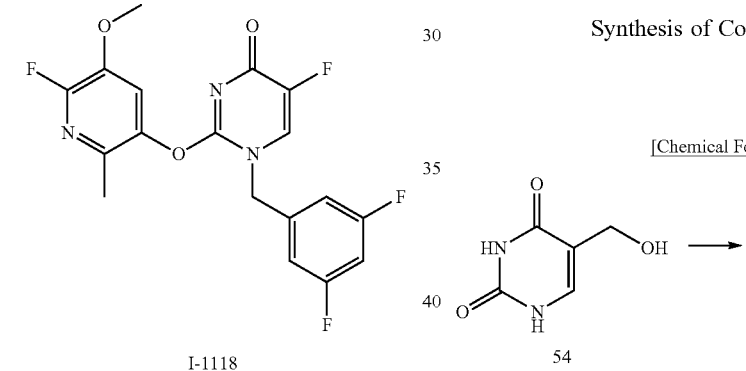

I-1118

Step 1

The compound 51 (900 mg, 5.35 mmol) was dissolved in acetonitrile (10 mL). Silver(II) fluoride (2.34 g, 16.06 mmol) was added to the solution. The mixture was vigorously stirred at room temperature for 1.5 hours. The reaction mixture was warmed to 50° C., and vigorously stirred for 3 hours. Silver(II) fluoride (1.56 g, 10.70 mmol) was further added to the mixture. The mixture was vigorously stirred at 50° C. for 2.5 hours. Silver(II) fluoride (0.78 g, 5.35 mmol) was further added to the mixture. The mixture was vigorously stirred at 50° C. for 2 hours. Under ice cooling, the saturated aqueous solution of sodium hydrogen carbonate was added to the reaction mixture. Insoluble materials were filtered off. The filtrate was extracted with ethyl acetate. The organic layer was washed by water and brine, and dried over anhydrous sodium sulfate. The solvent was evaporated under reduced pressure. The obtained residue was purified by silica-gel column chromatography (ethyl acetate/hexane) to give the compound 52 (374 mg, yield 38%).

LC-MS (Condition [3]): RT=1.60, 187 [M+H]⁺

Step 2

The compound 52 (370 mg, 1.98 mmol) was dissolved in methanol (3 mL). A 10% palladium-carbon (containing 50% water, 423 mg, 0.199 mmol) was added to the solution. The mixture was stirred under stream of 1 atm hydrogen at room temperature for 52 hours. The reaction mixture was filtered through Celite. The solvent was evaporated under reduced pressure to give the crude product of the compound 53 (267 mg, yield 77%).

1H-NMR (DMSO-D6) δ: 2.09 (s, 3H), 3.74 (s, 3H), 4.94 (s, 2H), 6.86 (d, 1H)

Step 3

The crude product of the compound 3 (50 mg, 0.32 mmol) was dissolved in dioxane (1 mL). 2-Chloro-1-(3,5-difluorobenzyl)-5-fluoropyrimidin-4(1H)-one (88 mg, 0.32 mmol) was added to the solution. The mixture was stirred under microwave irradiation at 130° C. for 15 minutes. Water was added to the reaction mixture. The precipitated solids were filtered. The crude was resolidized by EtOAc. The obtained precipitated solids were filtered, and then dried to give the compound I-1118 (43.1 mg, yield 34%).

LC-MS (Condition [2]): ET=1.47, 395 [M+H]⁺

1H-NMR (DMSO-D6) δ: 8.82 (10.70) (1H, s), 8.09 (1H, s), 7.45 (7.11) (1H, s), 7.24 (1H, brs), 7.11 (2H, d, J=5.0 Hz), 5.20 (2H, brs), 3.81 (3H, s), 1.90 (3H, s).

Example 31

Synthesis of Compound I-1138

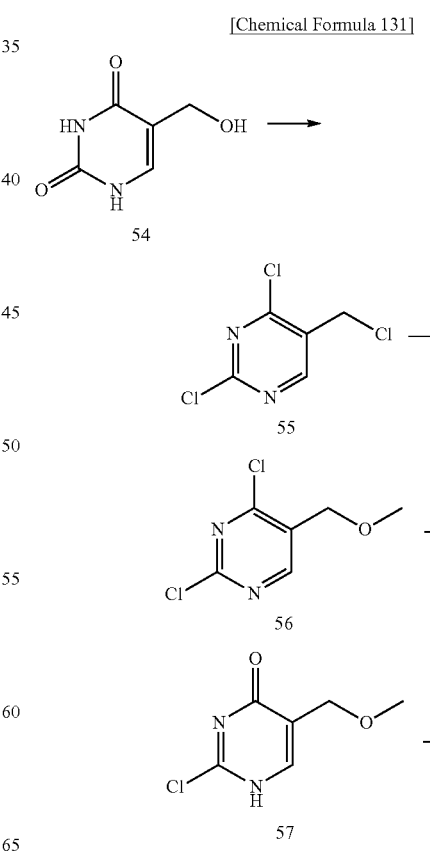

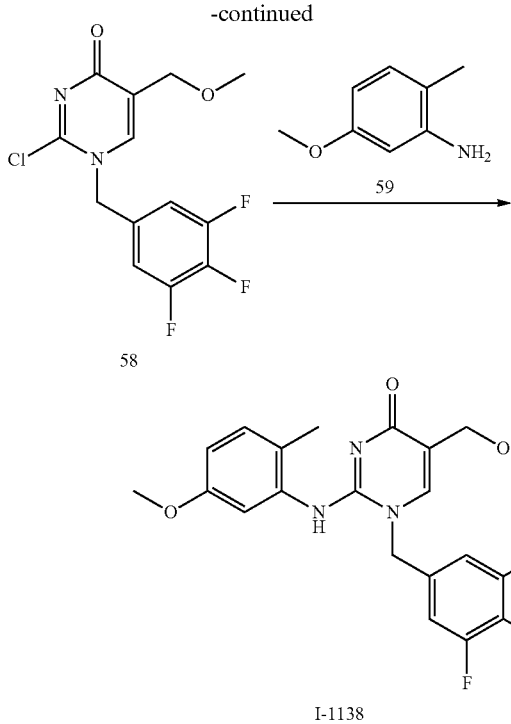

Step 1

The compound 54 (2 g, 14.1 mmol) was dissolved in phosphoryl chloride (2.62 mL, 28.1 mmol). Under ice cooling, DIEA (2.46 mL, 14.1 mmol) was added to the solution. The mixture was stirred at 125° C. for 5 hours. Under ice cooling, water was added to the reaction mixture. Water was added to the reaction mixture in an ice bath. The mixture was extracted with ethyl acetate. The organic layer was washed by brine, and dried over sodium sulfate. The solvent was evaporated under reduced pressure. The obtained residue was purified by silica-gel column chromatography (chloroform) to give the compound 55 (2.42 g, yield 87%).

$^1$H-NMR (CDCl$_3$) δ: 4.58 (s, 2H), 8.61 (s, 1H).

Step 2

The compound 55 (2.42 g, 12.3 mmol) was dissolved in methanol (24.2 mL). Under ice cooling, NaOMe (28% MeOH solution, 2.37 g, 12.26 mmol) was slowly added to the solution. The mixture was stirred for 5 hours. Under ice cooling, 10% citric acid was added to the reaction mixture to render the reaction mixture acidic. The mixture was extracted with ethyl acetate. The organic layer was washed by brine, and dried over sodium sulfate. The solvent was evaporated under reduced pressure. The obtained residue was purified by silica-gel column chromatography (ethyl acetate-n-hexane) to give the compound 56 (1.41 g, yield 59%).

Step 3

The compound 56 (1.41 g, 7.110 mmol) was dissolved in tetrahydrofuran (14.1 mL). A 2 mol/L aqueous solution of sodium hydroxide (7.30 mL, 14.6 mmol) was added to the solution. The mixture was stirred for 8 hours. Under ice cooling, a 2 mol/L aqueous solution of hydrochloric acid was added to the reaction mixture to render the reaction mixture acidic. NaCl was added to the mixture until saturated. The mixture was extracted with chloroform. The organic layer was washed by brine, and dried over sodium sulfate. The solvent was evaporated under reduced pressure. The obtained solids were washed by a solvent of ethyl acetate:n-hexane=1:1 to give the compound 57 (0.75 g, yield 58%).

Step 4

The compound 57 (0.75 g, 4.30 mmol) was dissolved in dichloromethane (7.50 mL). DIEA (1.05 mL, 6.01 mmol) was added to the solution. The mixture was stirred for 15 hours. Water was added to the reaction mixture. The mixture was extracted with ethyl acetate. The organic layer was washed by brine, and dried over sodium sulfate. The solvent was evaporated under reduced pressure. The obtained residue was purified by silica-gel column chromatography (ethyl acetate-n-hexane) to give the compound 58 (0.361 mg, yield 26%).

1H-NMR (DMSO-D6) δ: 3.34 (m, 3H), 4.16 (s, 2H), 5.31 (s, 2H), 7.34 (dd, J=6.8 Hz. 2H), 7.97 (s, 1H).

Step 5

The compound 58 (70.0 mg, 0.22 mmol) and the compound 59 (39.0 mg, 0.286 mmol) were dissolved in dioxane (2 mL). The solution was stirred at 80° C. for 1.5 hours. Water was added to the reaction mixture. The mixture was extracted with ethyl acetate. The organic layer was washed by brine, and dried over sodium sulfate. The solvent was evaporated under reduced pressure. The obtained residue was purified by silica-gel column chromatography (ethyl acetate-n-hexane) to give the compound I-1138 (25.1 mg, yield 27%).

$^1$H-NMR (DMSO-D6) δ: 1.90 (s, 3H), 3.42 (s, 3H), 3.77 (s, 3H), 4.16 (s, 2H), 4.99 (s, 2H), 6.29 (s, 1H), 6.58 (d, J=8.4 Hz, 1H), 7.05 (dd, J=6.8 Hz, 2H), 7.10 (d, J=8.4 Hz, 1H), 7.26 (s, 1H), 7.58 (s, 1H).

Example 32

Synthesis of Compound I-1153

[Chemical Formula 132]

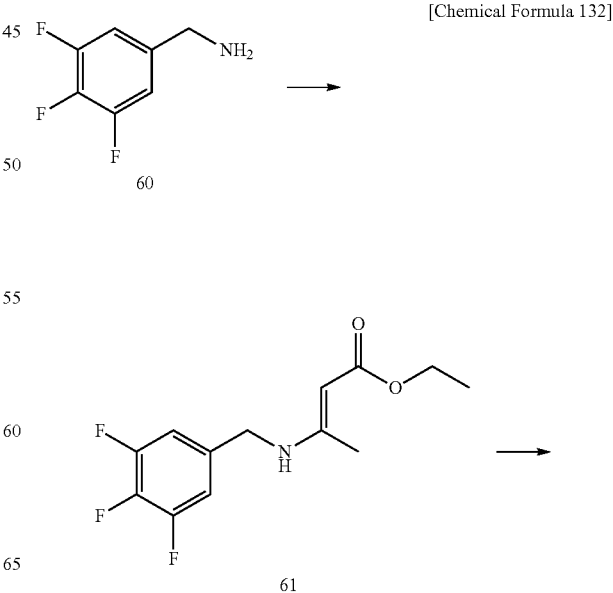

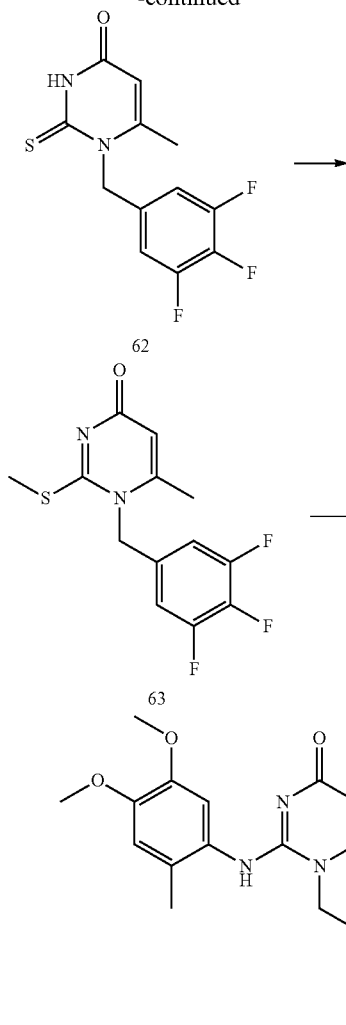

I-1153

¹H-NMR (DMSO-D₆) δ: 2.16 (s, 3H), 5.67 (s, 2H), 5.96 (s, 1H), 7.18-7.25 (m, 2H), 12.72 (s, 1H).

Step 3

The compound 62 (1.00 g, 3.49 mmol) was dissolved in acetonitrile (10 mL). DIEA (1.22 mL, 6.99 mmol) and methyl iodide (1.09 mL, 17.47 mmol) were added to the solution. The mixture was stirred at 50° C. for 1.5 hours. The reaction mixture was poured into ice water, and rendered the reaction mixture acidic with a 5% aqueous solution of citric acid. The mixture was extracted with ethyl acetate. The organic layer was washed by the aqueous solution of sodium hydrogen carbonato and water, and dried over anhydrous sodium sulfate. The solvent was evaporated under reduced pressure. The obtained solid was solidified with hexane-ethyl acetate to give the compound 63 (0.66 g, yield 63%).

¹H-NMR (DMSO-D₆) δ: 2.15 (s, 3H), 2.45 (s, 3H), 5.25 (s, 2H), 5.90 (s, 1H), 7.12-7.20 (m, 2H).

Step 4

The compound 63 (100 mg, 0.33 mmol) was dissolved in propionic acid (1 mL). 4,5-dimethoxy-2-methylaniline (223 mg, 1.33 mmol) was added to the solution. The mixture was stirred at 150° C. for 30 minutes. The reaction mixture was poured into ice water, and neutralized with the aqueous solution of sodium hydrogen carbonate. The mixture was extracted with ethyl acetate. The organic layer was washed by water and brine, and dried over anhydrous sodium sulfate. The solvent was evaporated under reduced pressure. The obtained oil was purified by silica-gel column chromatography (hexane-ethyl acetate). The obtained residue was solidified with ethyl acetate-hexane to give the compound 5 (66 mg, yield 47%).

¹H-NMR (CDCl₃) R: 1.91 (s, 3H), 2.20 (s, 3H), 3.81 (s, 3H), 3.85 (s, 3H), 5.24 (br s, 2H), 5.38 (s, 1H), 6.26 (s, 1H), 6.70 (s, 1H), 6.50-6.85<m, 2H), 7.52 (br s, 1H).

Example 33

Synthesis of Compound I-1248

[Chemical Formula 133]

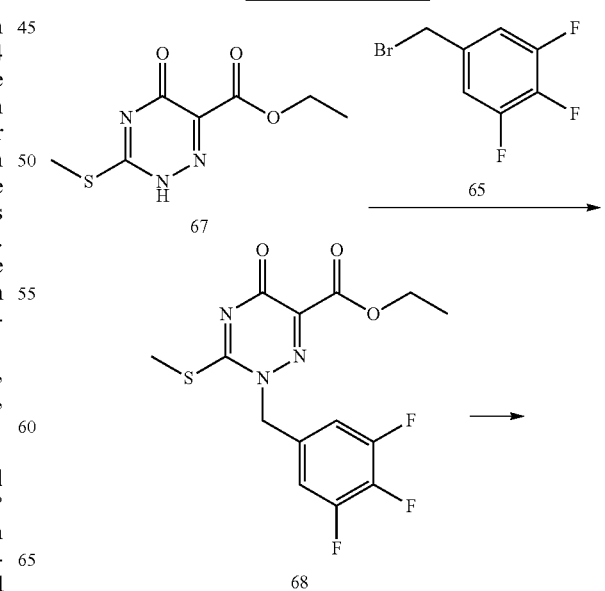

Step 1

The compound 60 (2.00 g, 12.4 mmol) was dissolved in ethanol (20 mL). Acetoacetic acid ethyl eater (1.60 mL, 12.4 mmol) and p-toluenesulfonic acid (0.24 g, 0.12 mmol) were added to the solution. The mixture was stirred at room temperature for 3.5 hours. The solvent was evaporated under reduced pressure. Water and the aqueous solution of sodium hydrogen carbonate were added to the residue. The mixture was extracted with ethyl acetate. The organic layer was washed by water, and dried over anhydrous sodium sulfate. The solvent was evaporated under reduced pressure. The obtained light brown oil was purified by silica-gel column chromatography (hexane-ethyl acetate) to give the compound 61. (2.00 g, yield 59%).

¹H-NMR (CDCl₃) δ: 1.27 (t, J=5.4 Hz, 3H), 1.87 (s, 3H), 4.12 (q, J=5.4 Hz, 2H), 4.36 (d, J=5.1 Hz, 2H), 4.59 (s, 1H), 6.89 (m, 2H), 8.95 (br s, 1H).

Step 2

The compound 61 (2.00 g, 7.32 mmol) and trimethylsilyl isothiocyanato (10.32 mL, 73.20 mmol) wore stirred at 150° C. for 1.5 hours. The reaction mixture was cooled to room temperature. Diethyl ether (10 mL) was added to the mixture. The obtained solids were filtered to give the compound 62 (1.53 g, yield 73%).

-continued

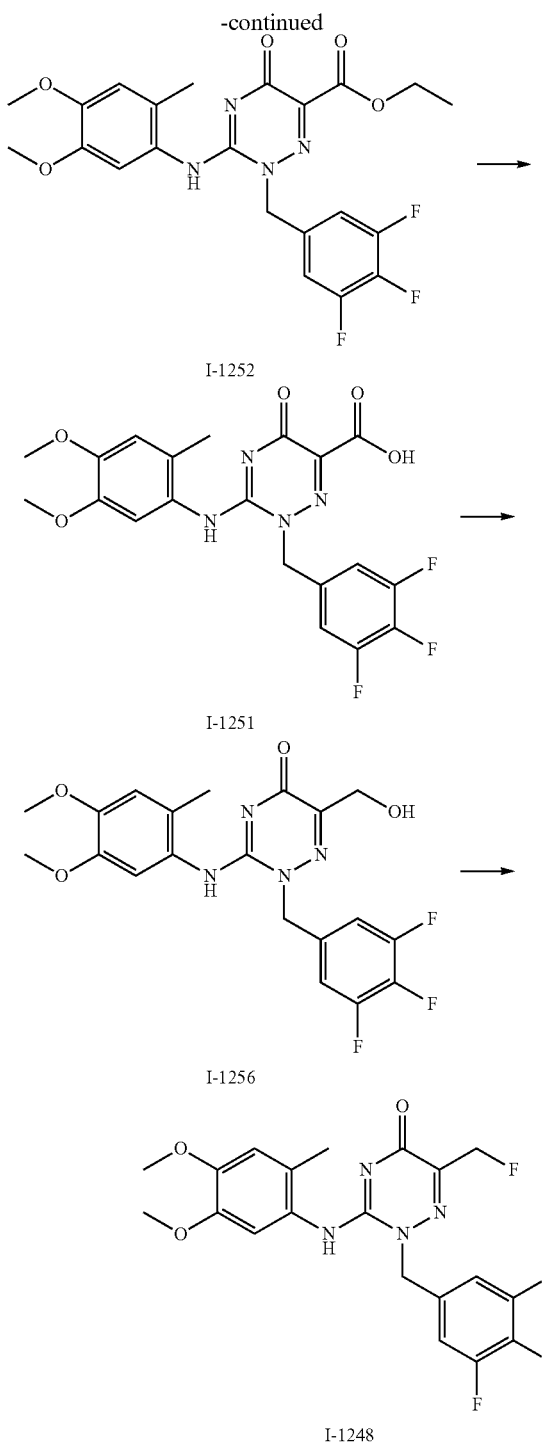

Step 1

The compound 67 (100 mg, 0.465 mmol) was dissolved in dichloromethane (0.5 mL). The compound 65 (0.082 mL, 0.604 mmol) and DIEA (0.105 mL, 0.604 mmol) were added to the solution. The mixture was stirred for 4 hours. Water was added to the reaction mixture. The mixture was extracted with ethyl acetate. The organic layer was washed by brine, and dried over sodium sulfate. The solvent was evaporated under reduced pressure. The obtained residue was solidified with ethyl acetate to give the compound 68 (113 mg, yield 67%).

1H-NMR (DMSO-D6) δ: 1.40 (t, J=6.8 Hz, 3H), 2.61 (m, 3H), 4.44 (q, J=5.6, 13.6 Hz, 2H), 5.17 (s, 2H), 7.01 (dd, J=6.8 Hz, 2H), 7.27 (s, 1H).

Step 2

The compound 68 (150 mg, 0.415 mmol) was dissolved in acetic acid (0.75 mL). 4,5-dimethoxy-2-methylaniline (84 mg, 0.501 mmol) was added to the solution. The mixture was stirred at 100° C. for 3 hours. Water was added to the reaction mixture. The mixture was extracted with ethyl acetate. The organic layer was washed by brine, and dried over sodium sulfate. The solvent was evaporated under reduced pressure. The obtained residue was purified by silica-gel column chromatography (ethyl acetate-n-hexane) to give the compound I-252 (112 mg, yield 56%). 1H-NMR (DMSO-D6) δ: 1.24 (t, J=7.2 Hz, 3H), 1.98 (s, 3H), 3.69 (s, 3H), 3.74 (s, 3H), 4.26 (q, J=6.8, 14.0 Hz, 2H), 5.37 (s, 2H), 6.76 (s, 1H), 6.83 (s, 1H), 7.36 (dd, J=6.8 Hz, 2H), 9.05 (s, 1H).

Step 3

The compound I-1252 (200 mg, 0.418 mmol) was dissolved in tetrahydrofuran (1 mL). A 4 mol/L aqueous solution of lithium hydroxide (146 mL, 0.585 mmol) was added to the solution. The mixture was stirred for 30 minutes. The reaction mixture was washed by Diethyl ether. A 5% citric acid was added to the aqueous layer to render the aqueous layer acidic. The aqueous layer was extracted with ethyl acetate. The organic layer was washed by brine, and dried over sodium sulfate. The solvent was evaporated under reduced pressure. The obtained residue was washed by ethyl acetate to give the compound I-1251 (169 mg, yield 89%).

1H-NMR (DMSO-D6) δ: 1.89 (s, 3H), 3.69 (s, 3H), 3.75 (s, 3H), 5.50 (s, 2H), 6.75 (s, 1H), 6.85 (s, 1H), 7.39 (dd, J=7.6 Hz, 2H), 9.41 (br, 1H), 14.9 (br, 1H).

Step 4

The compound I-1251 (650 mg, 1.44 mmol) was dissolved in tetrahydrofuran (6.5 mL). Triethylamine (0.30 mL, 2.17 mmol) and ethyl chloroformate (0.206 mL, 2.17 mmol) were added to the solution. The mixture was stirred at room temperature for 30 minutes. Insoluble materials were filtered off. Under ice cooling, the filtrate was added to the aqueous solution of sodium borohydride (mixture of sodium borohydride (82 rag, 2.17 mmol) and water (6.5 mL)). The mixture was stirred for 1 hour. Water was added to the reaction mixture. The mixture was extracted with ethyl acetate. The organic layer was washed by brine, and dried over sodium sulfate. The solvent was evaporated under reduced pressure. The obtained residue was purified by silica-gel column chromatography (ethyl acetate-n-hexane) to give the compound I-1256 (332 mg, yield 52%).

1H-NMR (DMSO-D6) δ: 1.88 (s, 3H), 3.69 (s, 3H), 3.75 (s, 3H), 4.03 (d, J=6.4 Hz, 2H), 4.98 (t, J=6.0 Hz, 1H), 5.33 (s, 2H), 6.73 (s, 1H), 6.82 (s, 1H), 7.34 (dd, 0.1=7.2 Hz, 2H), 8.74 (s, 1H).

Step 5

The compound I-1256 (51 mg, 0.117 mmol) was dissolved in dichloromethane (0.510 mL). N,N-diethylaminosulfur trifluoride (18.5 μL, 0.14 mmol) was added to the solution. The mixture was stirred at room temperature for 30 minutes. Under ice cooling, the saturated aqueous solution of sodium hydrogen carbonate was added to the mixture. The mixture was extracted with ethyl acetate. The organic layer was washed by brine, and dried over sodium sulfate. The solvent was evaporated under reduced pressure. The obtained residue was purified by silica-gel column chromatography (ethyl acetate-n-hexane) to afford the compound I-1248 (17 mg, yield 33%).

1H-NMR (DMSO-D6) δ: 1.90 (s, 3H), 3.70 (s, 3H), 3.75 (s, 3H), 5.33 (s, 2H), 6.75 (s, 1H), 6.83 (s, 1H), 7.33 (dd, J=8.0 Hz, 2H), 7.40 (s, 1H), 8.83 (s, 1H).

Example 34

Synthesis of Compound I-1204

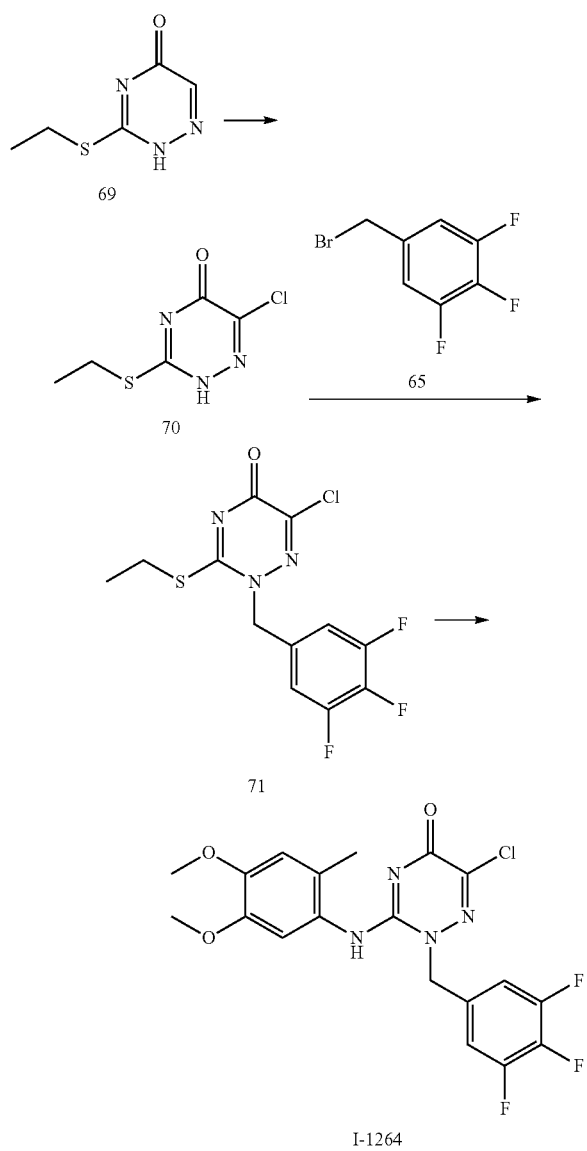

[Chemical Formula 134]

Step 1

The compound 09 (300 mg, 1.91 mmol) was dissolved in DMF (6 mL). N-chlorosuccinimide (255 mg, 1.91 mmol) was added to the solution. The mixture was stirred for 3 hours. Water was added to the reaction mixture. The mixture was extracted with ethyl acetate. The organic layer was washed by brine, and dried over sodium sulfate. The solvent was evaporated under reduced pressure. The obtained residue was solidified with ethyl acetate to give the compound 70 (321 mg, yield 87%).

Step 2

The compound 70 (100 mg, 0.522 mmol) was dissolved in dichloromethane (0.5 mL). The compound 65 (132 mg, 0.574 mmol) and DIEA (0.109 mL, 0.626 mmol) were added to the solution. The mixture was stirred for 3 hours. Water was added to the reaction mixture. The mixture was extracted with ethyl acetate. The organic layer was washed by brine, and dried over sodium sulfate. The solvent was evaporated under reduced pressure. The obtained residue was purified by silica-gel column chromatography (ethyl acetate-n-hexane) to give the compound 71 (98 mg, yield 55%).

1H-NMR (DMSO-D6) δ: 1.40 (t, J=7.2 Hz, 3H), 3.23 (q, J=7.2, 14.8 Hz, 2H), 5.07 (s, 2H), 6.99 (dd, J=6.8 Hz, 2H).

Step 3

The compound 71 (75 mg, 0.223 mmol) was dissolved in acetic acid (0.375 mL). 4,5-Dimethoxy-2-methylaniline (374 mg, 2.23 mmol) was added to the solution. The mixture was stirred at 100° C. for 3 hours. Water was added to the reaction mixture. The mixture was extracted with ethyl acetate. The organic layer was washed by brine, and dried over sodium sulfate. The solvent was evaporated under reduced pressure. The obtained residue was purified by silica-gel column chromatography (ethyl acetate-n-hexane) to give the compound I-1264 (19.3 mg, yield 19%).

1H-NMR (DMSO-D6) δ: 1.92 (s, 3H), 3.68 (s, 3H), 3.74 (s, 3H), 5.31 (s, 2H), 6.74 (s, 1H), 6.81 (s, 1H), 7.36 (dd, J=7.2 Hz, 2H), 9.05 (br, 1H).

Example 35

Synthesis of Compound I-1281

[Chemical Formula 135]

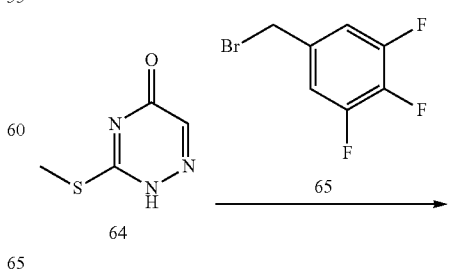

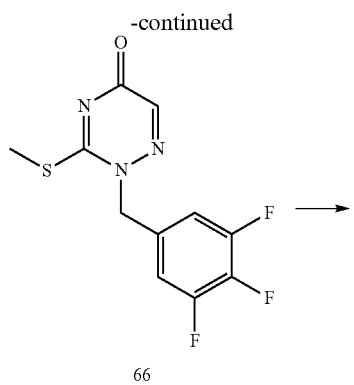

66

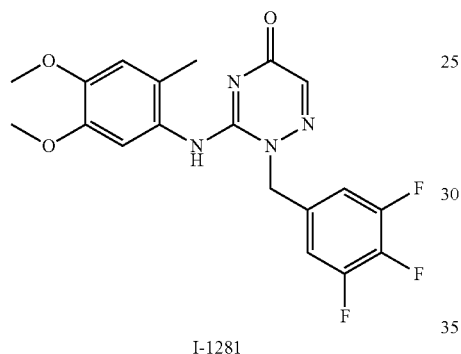

I-1281

Step 1

The compound 64 (231 mg, 1.61 mmol) was dissolved in dichloromethane (2.31 mL). The compound 65 (0.255 mL, 1.94 mmol) and DIEA (0.423 mL, 2.42 mmol) were added to the solution. The mixture was stirred for 3 hours. Water was added to the reaction mixture. The mixture was extracted with ethyl acetate. The organic layer was washed by brine, and dried over sodium sulfate. The solvent was evaporated under reduced pressure. The obtained residue was solidified with ethyl acetate to give the compound 66 (104 mg, yield 22%).

1H-NMR (DMSO-6) δ: 2.60 fin, 3H), 5.12 (s, 2H), 7.00 (dd, J=6.8 Hz, 2H), 7.62 (s, 1H).

Step 2

The compound 66 (830 mg, 2.75 mmol) was dissolved in acetic acid (6.64 mL). 4,5-dimethoxy-2-methylaniline (2.30 g, 13.7 mmol) was added to the solution. The mixture was stirred at 100° C. for 3 hours. Water was added to the reaction mixture. The mixture was extracted with ethyl acetate. The organic layer was washed by brine, and dried over sodium sulfate. The solvent was evaporated under reduced pressure. The obtained residue was solidified with ethyl acetate to give the compound I-1281 (450 mg, yield 40%).

¹H-NMR (DMSO-D6) δ: 1.90 (s, 3H), 3.70 (s, 3H), 3.75<s, 310, 5.33 (s, 2H), 6.75 (s, 1H), 6.83 (s, 1H), 7.33 (dd, J=8.0 Hz, 2H), 7.40 (s, 1H), 8.83 (s, 1H).

Example 36

Synthesis of Compound I-1286

[Chemical Formula 136]

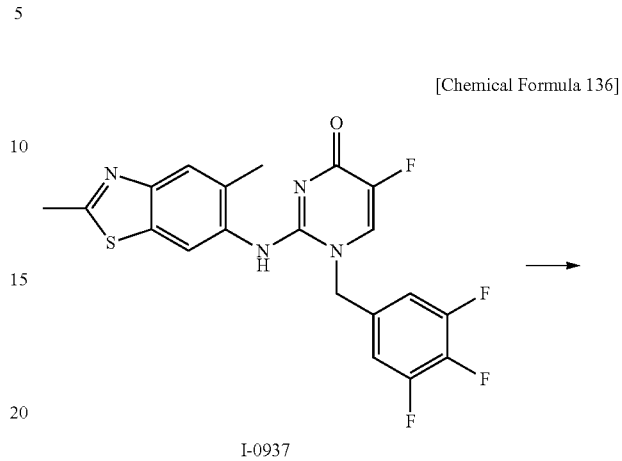

I-0937

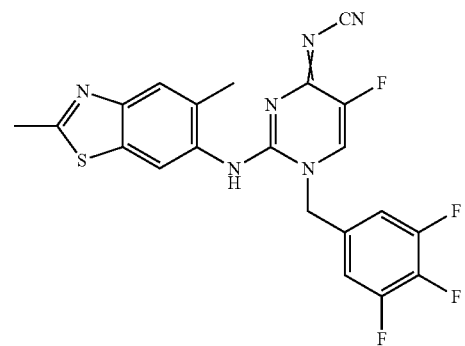

I-1286

The compound I-0937 (100 mg, 0.342 mmol) was dissolved in dioxane (2 mL). A Lawesson's reagent (180 mg, 0.444 mmol) was added to the solution. The mixture was stirred at 100° C. for 1 hour. Pyridine (541 mg, 6.85 mmol) and cyanamide (71.8 mg, 1.709 mmol) were added to the reaction mixture. The mixture was stirred at 60° C. for 1 hour. Ethyl acetate and 1 mol/L hydrochloric acid solution were added to the reaction mixture. The mixture was extracted with ethyl acetate. The organic layer was dried over sodium sulfate, and filtered. The Solvent, was evaporated under reduced pressure The obtained residue was purified by silica-gel column chromatography (ethyl acetate-n-hexane) to give the compound I-1286 (25.5 mg, yield 16%).

¹H-NMR (DMSO-D6) δ: 2.06 (s, 3H>, 2.77 (s, 3H), 5.26 (s, 3H), 7.41 (m, 2H), 7.75 (s, 1H), 7.91 (s, 1H), 8.19 (s, 1H), 9.16 (s, 1H).

The following compounds were synthesised according to the general synthetic procedures and the procedures described in Examples. Their chemical structural formulas and physical properties (LC/MS data or NMR spectrum) are shown below.

TABLE 1

| Compound No. | Chemical structure | NMR | [M + H] | Retention time (min) | LC/MS condition |
|---|---|---|---|---|---|
| I-0001 | 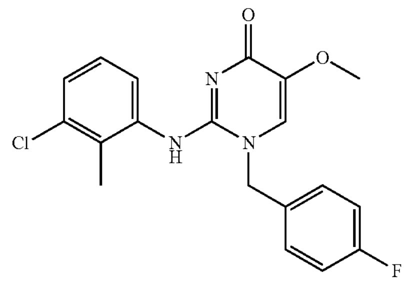 [SMILES: COc1cn(Cc2ccc(F)cc2)c(Nc2cccc(Cl)c2C)nc1=O] | 1H-NMR (CDCl3) δ: 2.06 (s, 3H), 3.71 (s, 3H), 5.01 (s, 2H), 6.66 (d, J = 6.4 Hz, 1H), 6.80 (s, 1H), 7.04-7.15 (m, 4H), 7.32-7.40 (m, 2H), 7.53-7.61 (br, 1H). | 374 | 1.72 | [1] |
| I-0002 | 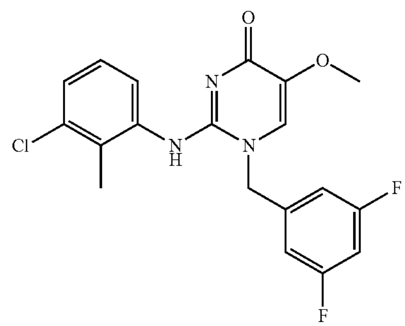 [SMILES: COc1cn(Cc2cc(F)cc(F)c2)c(Nc2cccc(Cl)c2C)nc1=O] | 1H-NMR (CDCl3) δ: 2.05 (s, 3H), 3.73 (s, 3H), 5.01 (s, 2H), 6.65 (m, 1H), 6.75-6.95 (m, 4H), 7.05-7.15 (m, 2H), 7.59 (s, 1H) | 392 | 1.77 | [1] |
| I-0003 | 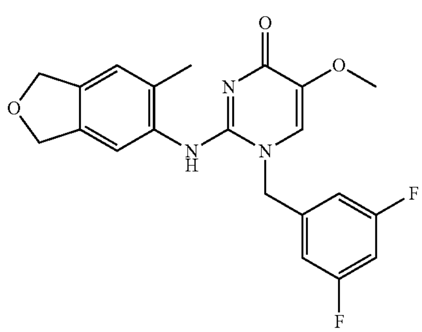 [SMILES: COc1cn(Cc2cc(F)cc(F)c2)c(Nc2cc3c(cc2C)COC3)nc1=O] | 1H-NMR (DMSO-D6) δ: 3.59 (s, 3H), 4.94 (s, 4H), 5.20 (s, 2H), 7.01-7.03 (m, 3H), 7.11 (s, 1H), 7.24 (t, J = 9.0 Hz, 1H), 7.34 (s, 1H), 8.36 (s, 1H). | 400 | 1.44 | [3] |
| I-0004 | 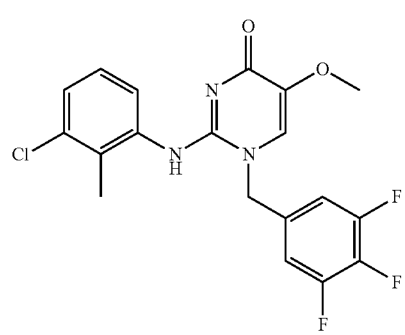 [SMILES: COc1cn(Cc2cc(F)c(F)c(F)c2)c(Nc2cccc(Cl)c2C)nc1=O] | 1H-NMR (DMSO-d6) δ: 1.90 (s, 3H), 3.61 (s, 3H), 5.14 (brs, 2H), 6.90-7.60 (m, 7H) | 409 | 1.88 | [1] |

TABLE 1-continued

| Compound No. | Chemical structure | NMR | [M + H] | Retention time (min) | LC/MS condition |
|---|---|---|---|---|---|
| I-0005 | 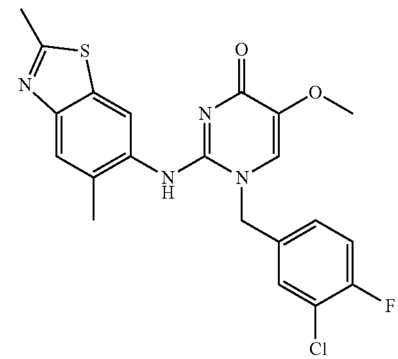 [SMILES: COc1cn(Cc2ccc(F)c(Cl)c2)c(Nc2cc3sc(C)nc3cc2C)nc1=O] | 1H-NMR (DMSO-D6) δ: 1.95 (s, 3H), 2.77 (s, 3H), 3.60 (s, 5H), 5.20 (s, 2H), 7.37 (s, 3H), 7.48 (s, 1H), 7.58 (s, 1H), 7.74 (s, 1H), 8.49 (s, 1H). | 445 | 1.6 | [3] |

TABLE 2

| Compound No. | Chemical structure | NMR | [M + H] | Retention time (min) | LC/MS condition |
|---|---|---|---|---|---|
| I-0006 | 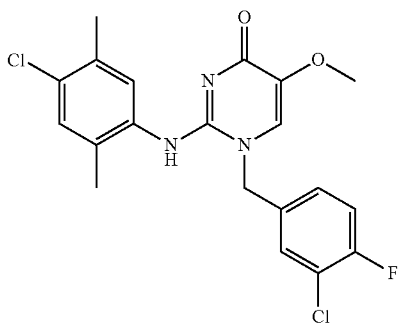 [SMILES: COc1cn(Cc2ccc(F)c(Cl)c2)c(Nc2cc(C)c(Cl)cc2C)nc1=O] | 1H-NMR (DMSO-D6) δ: 1.79 (3H, s), 2.26 (3H, s), 3.60 (3H, s), 5.17 (2H, br s), 6.95-7.55 (6H, m), 8.38 (1H, s). | 422 | 2.07 | [3] |
| I-0007 | 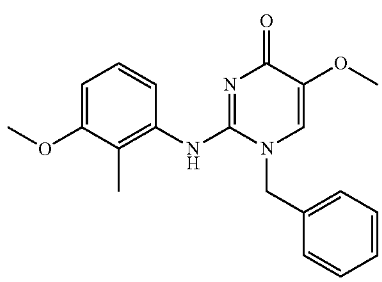 | 1H-NMR (DMSO-D6) δ: 1.67 (s, 3H), 3.62 (s, 3H), 3.74 (s, 3H), 5.21 (s, 2H), 6.68 (1H, d, J = 7.8 Hz), 6.84 (1H, d, J = 8.3 Hz), 7.33-7.44 (m, 7H), 8.37 (s, 1H). | 352 | 1.53 | [3] |
| I-0008 | 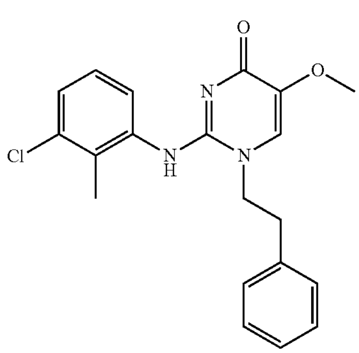 [SMILES: COc1cn(CCc2ccccc2)c(Nc2cccc(Cl)c2C)nc1=O] | 1H-NMR (CDCl3) δ: 3.12 (t, 2H), 2.22 (s, 3H), 3.48 (s, 3H), 4.07 (t, 2H), 6.30 (s, 1H), 6.67-6.69 (d, 2H), 7.09-7.12 (m, 2H), 7.21-7.23 (m, 2H), 7.26-7.28 (m, 1H), 7.28-7.35 (m, 2H), 7.53 (m, 1H) | 370 | 1.71 | [1] |

TABLE 2-continued
| I-0009 | 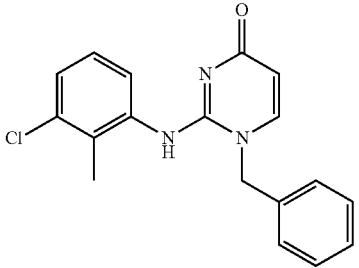 [SMILES: Cc1c(Cl)cccc1Nc1nc(=O)ccn1Cc1ccccc1] | 1H-NMR (CDCl3) δ: 2.03 (s, 3H), 5.07 (s, 2H), 5.43 (d, J = 7.6 Hz, 1H), 6.68 (d, J = 6.8 Hz, 1H), 7.05-7.13 (m, 2H), 7.20 (d, J = 7.6 Hz, 1H), 7.32-7.49 (m, 6H). | 326 | 2 | [1] |
| --- | --- | --- | --- | --- | --- |
| I-0010 | 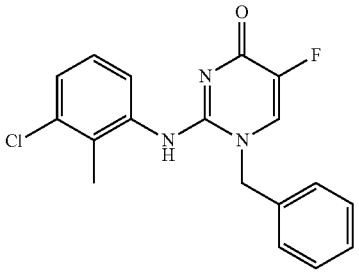 [SMILES: Cc1c(Cl)cccc1Nc1nc(=O)c(F)cn1Cc1ccccc1] | 1H-NMR (CDCl3) δ: 2.06 (s, 3H), 5.04 (s, 2H), 6.67 (d, J = 6.8 Hz, 1H), 7.06-7.65 (m, 9H). | 344 | 1.72 | [1] |
| I-0011 | 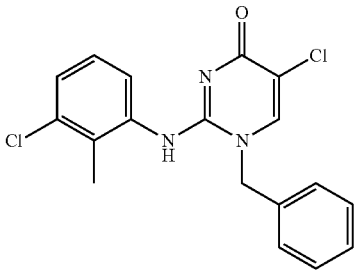 [SMILES: Cc1c(Cl)cccc1Nc1nc(=O)c(Cl)cn1Cc1ccccc1] | 1H-NMR (CDCl3) δ: 2.04 (s, 3H), 5.08 (s, 2H), 6.66 (d, J = 7.2 Hz, 1H), 7.05-7.14 (m, 2H), 7.30-7.44 (m, 6H), 7.57 (s, 1H) | 359 | 1.89 | [1] |
TABLE 3
| I-0012 | 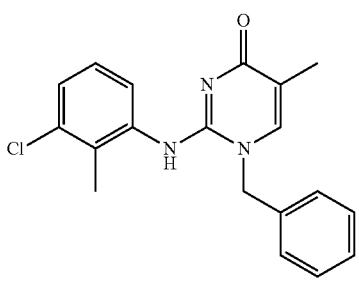 [SMILES: Cc1c(Cl)cccc1Nc1nc(=O)c(C)cn1Cc1ccccc1] | 1H-NMR (CDCl3) δ: 1.86 (s, 3H), 2.04 (s, 3H), 5.05 (s, 2H), 6.67 (d, J = 6.0 Hz, 1H), 7.02-7.12 (m, 3H), 7.32-7.43 (m, 5H), 7.46-7.52 (br, 1H). | 340 | 2.03 | [1] |
| --- | --- | --- | --- | --- | --- |
| I-0013 | 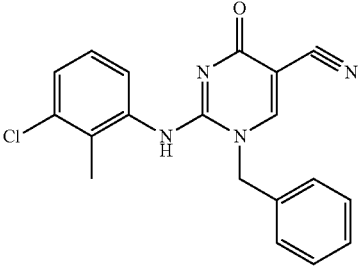 [SMILES: Cc1c(Cl)cccc1Nc1nc(=O)c(C#N)cn1Cc1ccccc1] | 1H-NMR (CDCl3) δ: 2.02 (s, 3H), 5.15 (s, 2H), 6.65 (d, J = 8.0 HZ, 1H), 7.10-7.20 (m, 2H), 7.34-7.49 (m, 5H), 7.55-7.61 (br, 1H), 7.79 (s, 1H). | 351 | 2.11 | [1] |

TABLE 3-continued
| I-0014 | 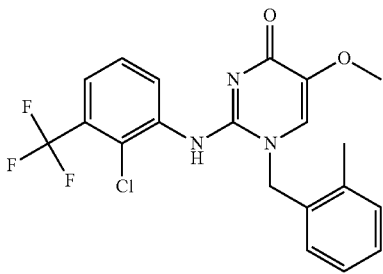 [SMILES: COc1cn(Cc2ccccc2C)c(Nc2cccc(C(F)(F)F)c2Cl)nc1=O] | | 409 | 1.79 | [1] |
|---|---|---|---|---|---|
| I-0015 | 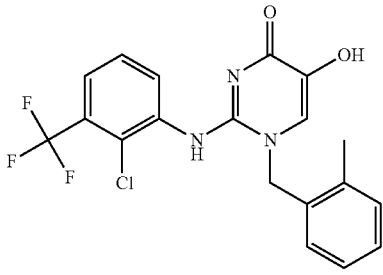 [SMILES: Cc1ccccc1Cn1cc(O)c(=O)nc1Nc1cccc(C(F)(F)F)c1Cl] | 1H-NMR (DMSO-D6) δ: 1.95 (3H, s), 4.80 (1H, d, J = 15.8 Hz), 5.03 (1H, d, J = 15.8 Hz), 6.82 (1H, d, J = 7.5 Hz), 7.09-7.20 (3H, m), 7.54-7.61 (2H, m), 7.70 (1H, d, J = 7.8 Hz), 7.97 (1H, d, J = 7.8 Hz). | 395 | 1.81 | [1] |
| I-0016 | 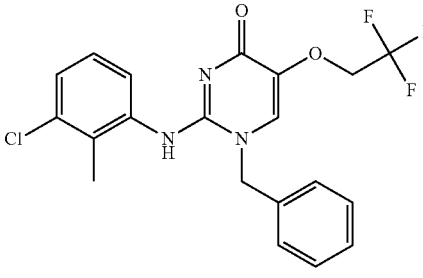 | 1H-NMR (DMSO-D6) δ: 1.82 (3H, s), 4.59 (2H, q, J = 9.0 Hz), 5.22 (2H, s), 7.05-7.44 (8H, m), 7.74 (1H, s), 8.73 (1H, s). | 424 | 2.03 | [1] |
| I-0017 | 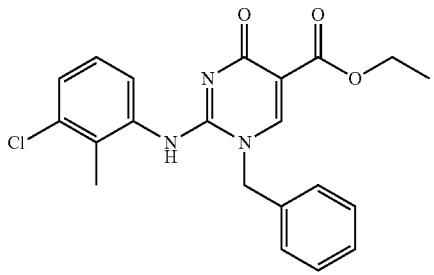 [SMILES: CCOC(=O)c1cn(Cc2ccccc2)c(Nc2cccc(Cl)c2C)nc1=O] | 1H-NMR (CDCl3) δ: 1.33 (t, J = 7.2 Hz, 3H), 1.96 (s, 3H), 4.31 (q, J = 7.2 Hz, 2H), 5.16 (s, 2H), 6.64 (d, J = 7.6 Hz, 1H), 7.06-7.17 (m, 2H), 7.35-7.47 (m, 6H), 8.32 (s, 1H) | | | |
TABLE 4
| I-0018 | 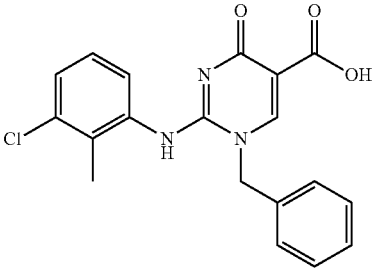 [SMILES: Cc1c(Cl)cccc1Nc1nc(=O)c(C(=O)O)cn1Cc1ccccc1] | 1H-NMR (CDCl3) δ: 1.99 (s, 3H), 5.19 (s, 2H), 6.66 (d, J = 7.6 Hz, 1H), 7.10-7.21 (m, 2H), 7.35-7.49 (m, 5H), 7.55-7.90 (br, 1H), 8.52 (s, 1H), 11.78-12.30 (br, 1H). | 370 | 1.96 | [1] |

TABLE 4-continued
| I-0019 | 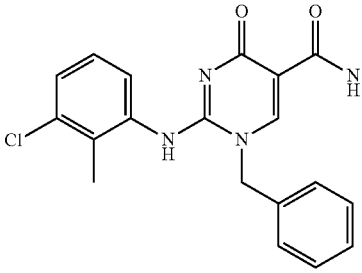 | 1H-NMR (DMSO-d6) δ: 1.40-1.46 (2H, m), 1.78-1.83 (5H, m), 3.35-3.44 (2H, m), 3.77-3.81 (2H, m), 3.93 (1H, m), 5.26 (2H, brs), 6.68 (1H, brs), 7.10 (2H, brs), 7.34-7.39 (5H, m), 8.59 (1H, brs), 10.43 (1H, brs). | 453 | 2.14 | [1] |
| --- | --- | --- | --- | --- | --- |
| I-0020 | 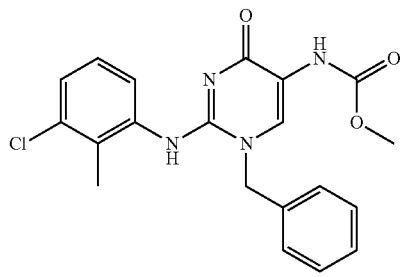 [SMILES: COC(=O)Nc1cn(Cc2ccccc2)c(Nc2cccc(Cl)c2C)nc1=O] | 1H-NMR (DMSO-d6) δ: 1.88 (s, 3H), 3.61 (s, 3H), 5.15-5.34 (br, 2H), 6.93-7.51 (m, 8H), 7.95-8.20 (br, 1H), 8.01 (s, 1H), 8.72-9.00 (br, 1H). | 399 | 1.83 | [1] |
| I-0021 | 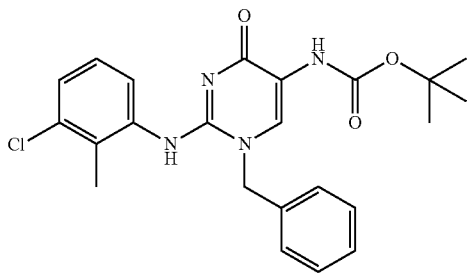 [SMILES: Cc1c(Cl)cccc1Nc1nc(=O)c(NC(=O)OC(C)(C)C)cn1Cc1ccccc1] | 1H-NMR (CDCl3) δ: 1.49 (1.51) (9H, s), 1.98 (1.75) (3H, s), 5.06 (5.03) (2H, s), 5.83-8.18 (10H, m). | 441 | 2.25 | [1] |
| I-0022 | 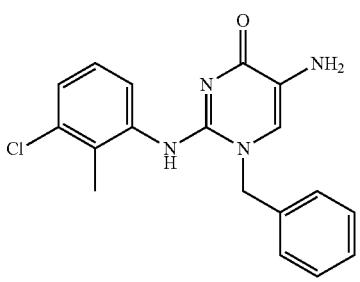 | 1H-NMR (CDCl3) δ: 2.07 (2H, s), 3.24 (2H, brs), 5.01 (2H, s), 6.72 (2H, brs), 7.05-7.10 (2H, m), 7.34-7.42 (5H, m), 7.61 (1H, brs). | 341 | 1.44 | [1] |
| I-0023 | 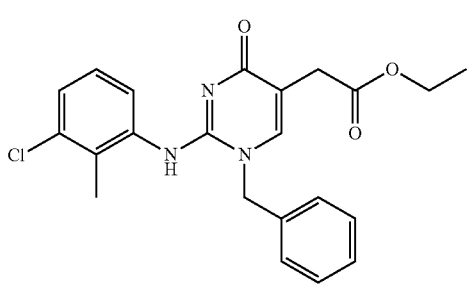 [SMILES: CCOC(=O)Cc1cn(Cc2ccccc2)c(Nc2cccc(Cl)c2C)nc1=O] | 1H-NMR (DMSO-D6) δ: 1.17 (3H, t, J = 7.2 Hz), 1.86 (3H, s), 3.20 (2H, s), 4.05 (2H, q, J = 7.1 Hz), 5.06 (2H, br s), 6.55-7.45 (8H, m), 7.79 (1H, s), 9.93 (1H, s). | 412 | 2.33 | [3] |

TABLE 5
| I-0024 | 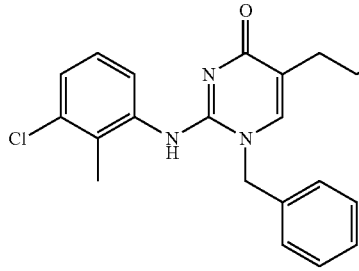 | 1H-NMR (DMSO-D6) δ: 1.85 (3H, s), 2.32 (2H, t, J = 6.5 Hz), 3.46 (2H, q, J = 6.1 Hz), 4.58 (1H, br s), 5.05 (2H, br s), 6.55-7.70 (9H, m), 9.66 (1H, s). | 370 | 1.87 | [3] |
| --- | --- | --- | --- | --- | --- |
| I-0025 | 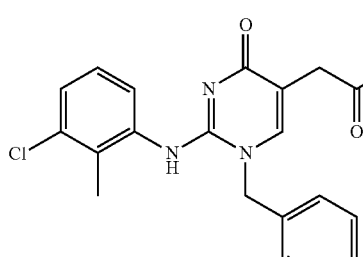 | 1H-NMR (DMSO-D6) δ: 1.88 (3H, s), 3.17 (2H, s), 5.16 (2H, br s), 6.70-7.60 (8H, m), 7.83 (1H, s), 9.88 (1H, br s), 12.30 (1H, br s). | 384 | 1.79 | [1] |
| I-0026 | 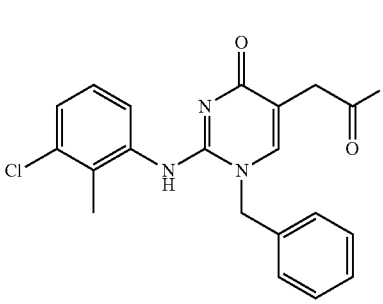 | 1H-NMR (DMSO-D6) δ: 1.87 (3H, s), 2.98 (2H, s), 5.08 (2H, s), 6.65-7.50 (10H, m), 7.69 (1H, s), 9.73 (1H, br s). | 383 | 1.77 | [3] |
| I-0027 | 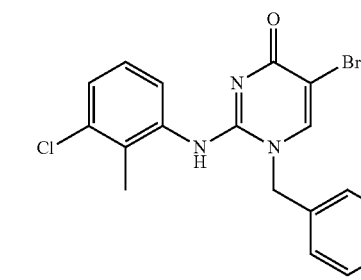 |  | 405 | 1.96 | [1] |
| I-0028 | 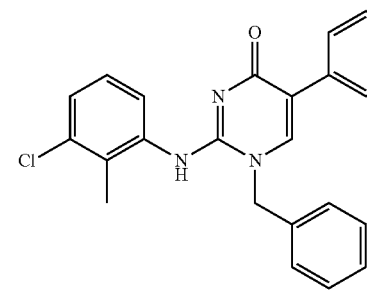 | 1H-NMR (DMSO-D6) δ: 1.93 (3H, s), 4.92 (2H, dd, J = 46.8, 14.9 Hz), 7.01-7.33 (13H, m), 7.61 (1H, s), 9.84 (1H, s). | 402 | 2.73 | [3] |

TABLE 5-continued
| I-0029 | 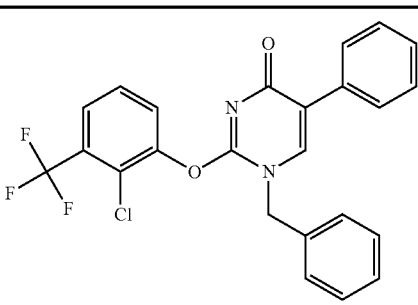 | 1H-NMR (DMSO-d6) δ: 5.35 (s, 2H), 7.31-7.51 (m, 8H), 7.61-7.78 (m, 4H), 7.87 (d, J = 8.0 Hz, 1H), 8.34 (s, 1H). | 457 | 2.41 | [1] |
TABLE 6
| I-0030 | 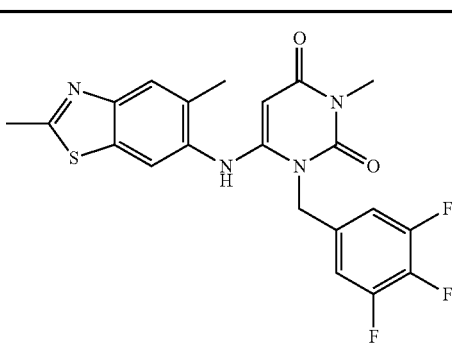 | 1H-NMR (CDCl3) δ: 2.04 (s, 3H), 2.83 (s, 3H), 3.35 (s, 3H), 4.65 (s, 1H), 5.30 (s, 2H), 5.87 (s, 1H), 6.95-7.05 (m, 2H), 7.46 (s, 1H), 7.76 (s, 1H) | 447 | 1.81 | [1] |
| I-0031 | 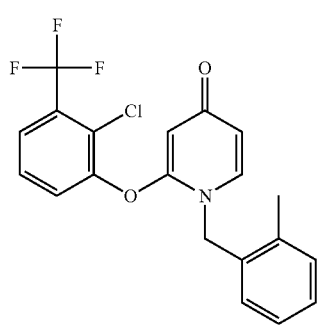 [SMILES: Cc1ccccc1Cn1ccc(=O)cc1Oc1cccc(C(F)(F)F)c1Cl] | 1H-NMR (CDCl3) δ: 2.31 (3H, s), 5.08 (1H, s), 5.31 (2H, s), 6.08 (1H, d, J = 7.6 Hz), 6.94 (1H, s), 7.23 (3H, s), 7.62-7.67 (2H, m), 7.73 (1H, d, J = 7.6 Hz), 7.85 (1H, d, J = 7.3 Hz) | 394 | 2.13 | [2] |
| I-0032 | 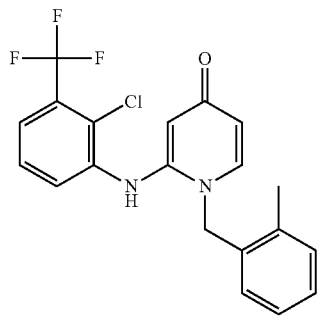 [SMILES: Cc1ccccc1Cn1ccc(=O)cc1Nc1cccc(C(F)(F)F)c1Cl] | | 393 | 1.99 | [2] |

TABLE 6-continued

| I-0033 | (structure) | 1H-NMR (CDCl3) δ: 2.05 (s, 3H), 2.80 (s, 3H), 3.79 (s, 3H), 5.04 (s, 2H), 5.37 (s, 1H), 5.83 (s, 1H), 6.81 (s, 1H), 7.05 (m, 1H), 7.20 (dd, J = 8.5, 8.5 Hz, 1H), 7.25 (m, 1H), 7.29 (m, 1H), 7.72 (s, 1H). | 444 | 1.47 | [1] |
|---|---|---|---|---|---|
| I-0034 | (structure) | | 411 | 2.01 | [1] |

TABLE 7

| I-0035 | (structure) | 424 | 1.8 | [1] |
|---|---|---|---|---|
| I-0036 | (structure) | 410 | 1.94 | [1] |
| I-0037 | (structure) | 428 | 1.61 | [1] |

TABLE 7-continued

| ID | Structure | MW | RT | Ref |
|---|---|---|---|---|
| I-0038 | 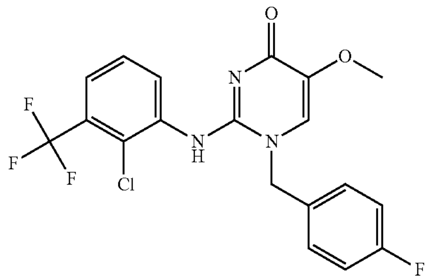 [SMILES: COc1cn(Cc2ccc(F)cc2)c(Nc2cccc(C(F)(F)F)c2Cl)nc1=O] | 428 | 1.94 | [1] |
| I-0039 | 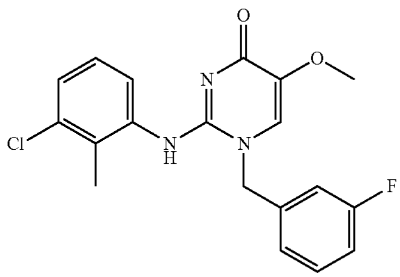 [SMILES: COc1cn(Cc2cccc(F)c2)c(Nc2cccc(Cl)c2C)nc1=O] | 374 | 1.72 | [1] |
| I-0040 | 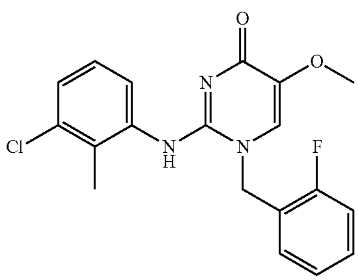 [SMILES: COc1cn(Cc2ccccc2F)c(Nc2cccc(Cl)c2C)nc1=O] | 374 | 1.73 | [1] |

TABLE 8

| ID | Structure | MW | RT | Ref |
|---|---|---|---|---|
| I-0041 | 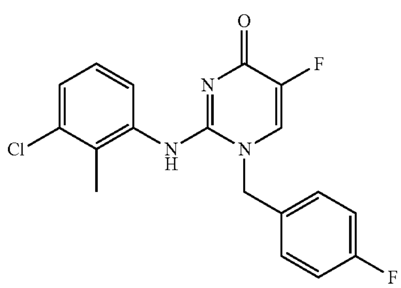 [SMILES: Cc1c(Cl)cccc1Nc1nc(=O)c(F)cn1Cc1ccc(F)cc1] | 362 | 1.73 | [1] |
| I-0042 | 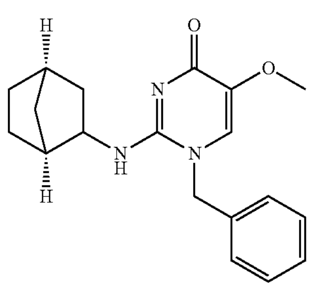 [SMILES: COc1cn(Cc2ccccc2)c(NC2C[C@@H]3CC[C@H]2C3)nc1=O] | 326 | 1.64 | [3] |

TABLE 8-continued

| | | | | |
|---|---|---|---|---|
| I-0043 | (structure) | 371 | 1.8 | [1] |
| I-0044 | (structure) | 371 | 1.81 | [1] |
| I-0045 | (structure) | 371 | 1.81 | [1] |
| I-0046 | (structure) | 381 | 1.64 | [1] |

TABLE 9

| | | | | |
|---|---|---|---|---|
| I-0047 | (structure) | 381 | 1.55 | [1] |

TABLE 9-continued
| | | | | |
|---|---|---|---|---|
| I-0048 | 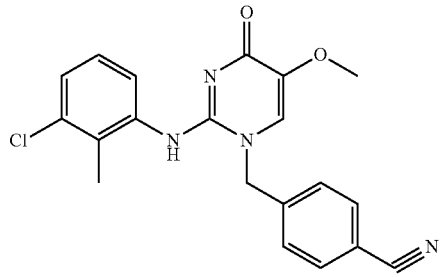 [SMILES: COc1cn(Cc2ccc(C#N)cc2)c(Nc2cccc(Cl)c2C)nc1=O] | 381 | 1.54 | [1] |
| I-0049 | 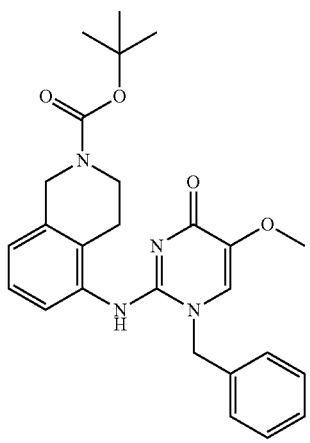 [SMILES: COc1cn(Cc2ccccc2)c(Nc2cccc3c2CCN(C(=O)OC(C)(C)C)C3)nc1=O] | 463 | 1.86 | [3] |
| I-0050 | 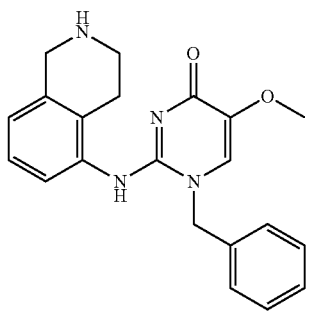 [SMILES: COc1cn(Cc2ccccc2)c(Nc2cccc3c2CCNC3)nc1=O] | 363 | 0.87 | [3] |
| I-0051 | 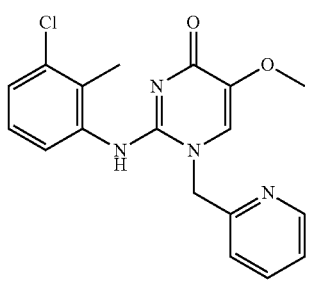 [SMILES: COc1cn(Cc2ccccn2)c(Nc2cccc(Cl)c2C)nc1=O] | 357 | 1.44 | [1] |
| I-0052 | 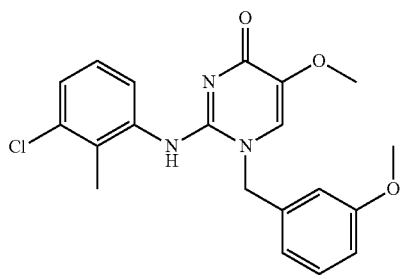 [SMILES: COc1cccc(Cn2cc(OC)c(=O)nc2Nc2cccc(Cl)c2C)c1] | 386 | 1.64 | [1] |

TABLE 10

| ID | Structure | MW | RT | Ref |
|---|---|---|---|---|
| I-0053 | 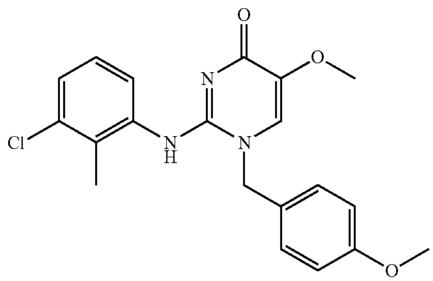 [SMILES: COc1ccc(Cn2cc(OC)c(=O)nc2Nc2cccc(Cl)c2C)cc1] | 386 | 1.62 | [1] |
| I-0054 | 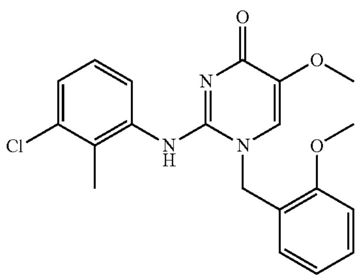 [SMILES: COc1ccccc1Cn1cc(OC)c(=O)nc1Nc1cccc(Cl)c1C] | 386 | 1.69 | [1] |
| I-0055 | 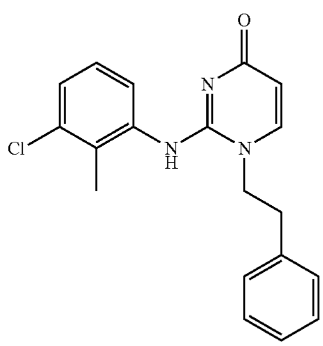 [SMILES: Cc1c(Cl)cccc1Nc1nc(=O)ccn1CCc1ccccc1] | 340 | 2.09 | [1] |
| I-0056 | 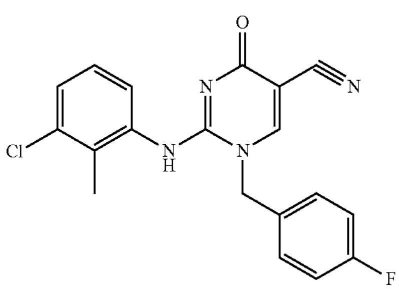 [SMILES: Cc1c(Cl)cccc1Nc1nc(=O)c(C#N)cn1Cc1ccc(F)cc1] | 369 | 2.15 | [1] |
| I-0057 | 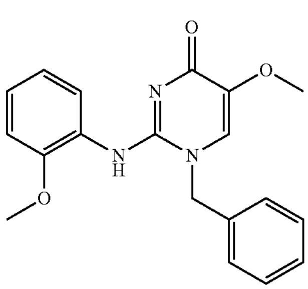 [SMILES: COc1ccccc1Nc1nc(=O)c(OC)cn1Cc1ccccc1] | 338 | 1.51 | [3] |

TABLE 10-continued

| | | | | |
|---|---|---|---|---|
| I-0058 | | 384 | 1.7 | [3] |

TABLE 11

| | | | | |
|---|---|---|---|---|
| I-0059 | | 326 | 1.32 | [3] |
| I-0060 | | 342 | 1.48 | [3] |
| I-0061 | | 322 | 1.45 | [3] |
| I-0062 | | 348 | 1.56 | [3] |

TABLE 11-continued

| ID | Structure | m/z | RT | Method |
|---|---|---|---|---|
| I-0063 | (2-phenoxyphenyl)NH-, 1-benzyl-5-methoxypyrimidin-4(1H)-one | 400 | 1.81 | [3] |
| I-0064 | (2-fluorobenzyl)NH-, 1-benzyl-5-methoxypyrimidin-4(1H)-one | 340 | 1.52 | [3] |

TABLE 12

| ID | Structure | m/z | RT | Method |
|---|---|---|---|---|
| I-0065 | (2-(trifluoromethyl)benzyl)NH-, 1-benzyl-5-methoxypyrimidin-4(1H)-one | 390 | 1.75 | [3] |
| I-0066 | (2-(p-tolyloxy)benzyl)NH-, 1-benzyl-5-methoxypyrimidin-4(1H)-one | 428 | 2.11 | [3] |
| I-0067 | (2-(dimethylamino)benzyl)NH-, 1-benzyl-5-methoxypyrimidin-4(1H)-one | 365 | 1.06 | [3] |
| I-0068 | (2,5-dimethylphenyl)NH-, 1-benzyl-5-methoxypyrimidin-4(1H)-one | 336 | 1.59 | [3] |
| I-0069 | 3-((1-benzyl-5-methoxy-4-oxo-1,4-dihydropyrimidin-2-yl)amino)-4-methylbenzamide | 365 | 1.2 | [3] |
| I-0070 | 1-benzyl-2-((5-(1,1-dioxidoisothiazolidin-2-yl)-2-methylphenyl)amino)-5-methoxypyrimidin-4(1H)-one | 441 | 1.45 | [3] |

TABLE 13
I-0071 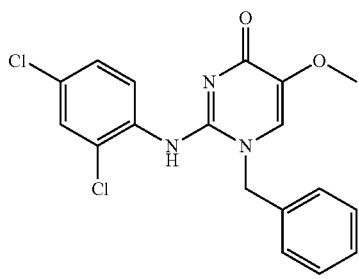 [SMILES: COc1cn(Cc2ccccc2)c(Nc2ccc(Cl)cc2Cl)nc1=O] 376 1.87 [3]
I-0072 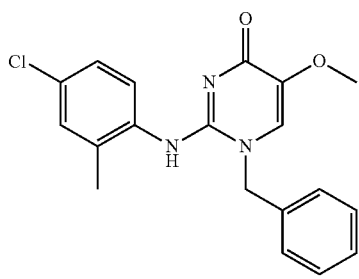 [SMILES: COc1cn(Cc2ccccc2)c(Nc2ccc(Cl)cc2C)nc1=O] 356 1.69 [3]
I-0073 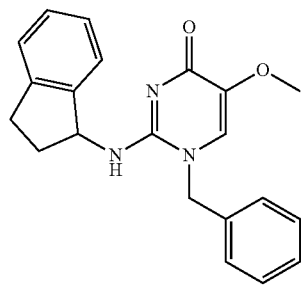 [SMILES: COc1cn(Cc2ccccc2)c(NC2CCc3ccccc32)nc1=O] 348 1.67 [3]
I-0074 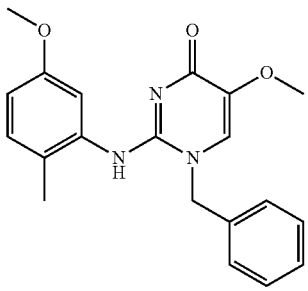 352 1.51 [3]
I-0075 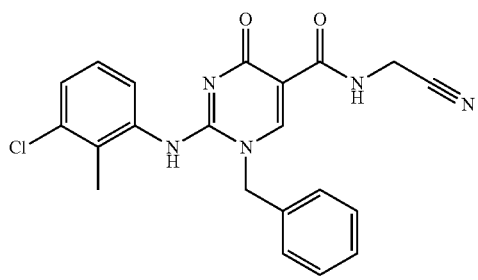 [SMILES: Cc1c(Cl)cccc1Nc1nc(=O)c(C(=O)NCC#N)cn1Cc1ccccc1] 408 2.1 [1]

TABLE 13-continued

| I-0076 | (structure) | 427 | 2.12 | [1] |

TABLE 14

| I-0077 | (structure) | 475 | 1.99 | [1] |
| I-0078 | (structure) | 397 | 2.22 | [1] |
| I-0079 | (structure) | 350 | 1.61 | [1] |
| I-0080 | (structure) | 376 | 1.79 | [1] |

TABLE 14-continued
| I-0081 | 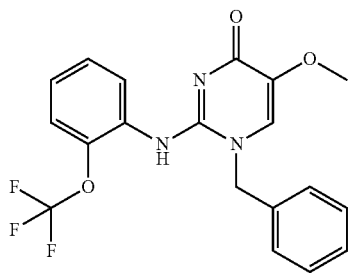 [SMILES: COc1cn(Cc2ccccc2)c(Nc2ccccc2OC(F)(F)F)nc1=O] | 392 | 1.67 | [1] |
| I-0082 | 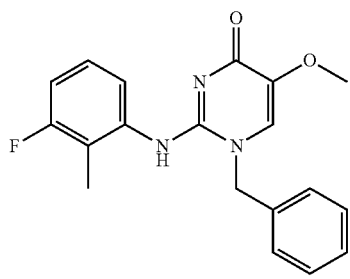 [SMILES: COc1cn(Cc2ccccc2)c(Nc2cccc(F)c2C)nc1=O] | 340 | 1.47 | [1] |
TABLE 15
| I-0083 | 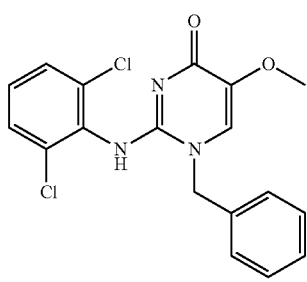 [SMILES: COc1cn(Cc2ccccc2)c(Nc2c(Cl)cccc2Cl)nc1=O] | 376 | 1.79 | [1] |
| I-0084 | 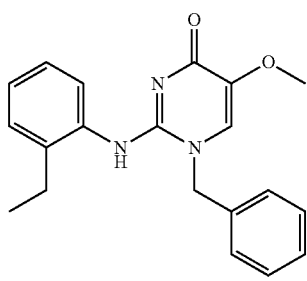 | 336 | 1.6 | [3] |
| I-0085 | 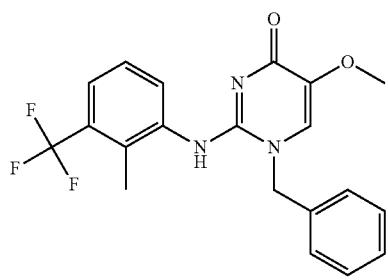 [SMILES: COc1cn(Cc2ccccc2)c(Nc2cccc(C(F)(F)F)c2C)nc1=O] | 390 | 1.74 | [1] |

TABLE 15-continued

| ID | Structure | | | |
|---|---|---|---|---|
| I-0086 | (structure) | 388 | 1.7 | [1] |
| I-0087 | (structure) | 352 | 1.31 | [1] |
| I-0088 | (structure) | 380 | 1.42 | [1] |

TABLE 16

| ID | Structure | | | |
|---|---|---|---|---|
| I-0089 | (structure) | 376 | 1.71 | [1] |
| I-0090 | (structure) | 340 | 1.47 | [1] |

TABLE 16-continued
| | | | | |
|---|---|---|---|---|
| I-0091 | 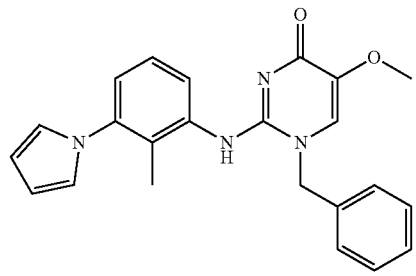 [SMILES: COc1cn(Cc2ccccc2)c(Nc2cccc(-n3cccc3)c2C)nc1=O] | 387 | 1.7 | [1] |
| I-0092 | 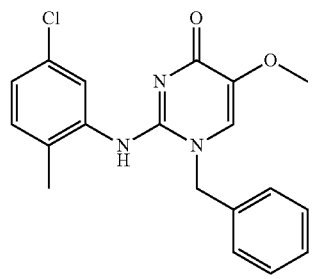 [SMILES: COc1cn(Cc2ccccc2)c(Nc2cc(Cl)ccc2C)nc1=O] | 356 | 1.65 | [1] |
| I-0093 | 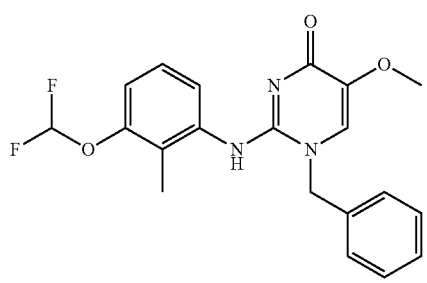 | 388 | 1.6 | [1] |
| I-0094 | 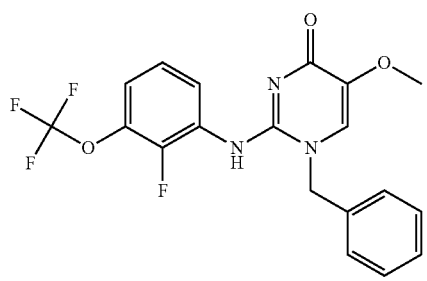 [SMILES: COc1cn(Cc2ccccc2)c(Nc2cccc(OC(F)(F)F)c2F)nc1=O] | 410 | 1.78 | [1] |
TABLE 17
| | | | | |
|---|---|---|---|---|
| I-0095 | 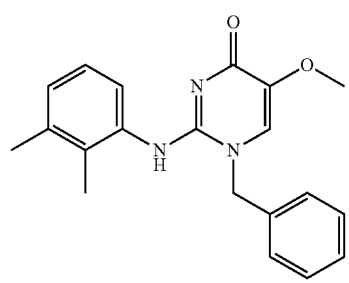 [SMILES: COc1cn(Cc2ccccc2)c(Nc2cccc(C)c2C)nc1=O] | 336 | 1.47 | [1] |

TABLE 17-continued
| I-0096 | 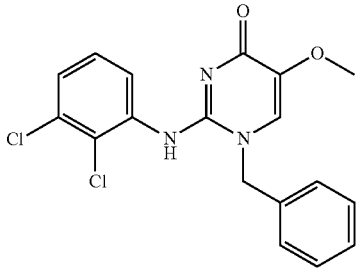 [SMILES: COc1cn(Cc2ccccc2)c(Nc2cccc(Cl)c2Cl)nc1=O] | 376 | 1.77 | [1] |
| I-0097 | 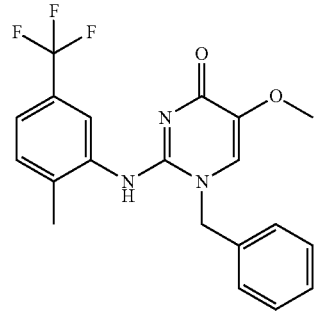 [SMILES: COc1cn(Cc2ccccc2)c(Nc2cc(C(F)(F)F)ccc2C)nc1=O] | 390 | 1.72 | [1] |
| I-0098 | 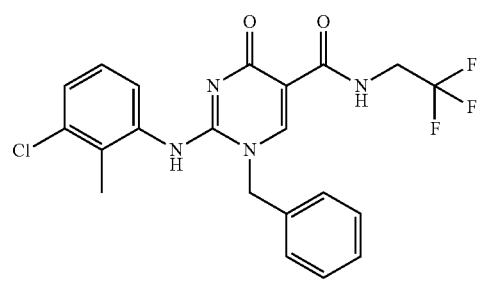 [SMILES: Cc1c(Cl)cccc1Nc1nc(=O)c(C(=O)NCC(F)(F)F)cn1Cc1ccccc1] | 451 | 2.37 | [1] |
| I-0099 | 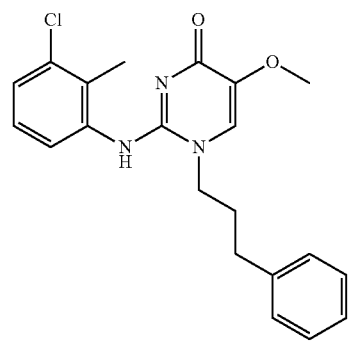 [SMILES: COc1cn(CCCc2ccccc2)c(Nc2cccc(Cl)c2C)nc1=O] | 384 | 1.83 | [1] |
| I-0100 | 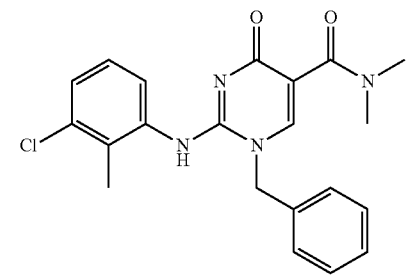 [SMILES: Cc1c(Cl)cccc1Nc1nc(=O)c(C(=O)N(C)C)cn1Cc1ccccc1] | 397 | 1.82 | [1] |

TABLE 18
| | | | | |
|---|---|---|---|---|
| I-0101 | 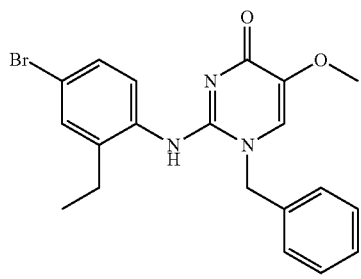 [SMILES: CCc1cc(Br)ccc1Nc1nc(=O)c(OC)cn1Cc1ccccc1] | 414 | 1.78 | [1] |
| I-0102 | 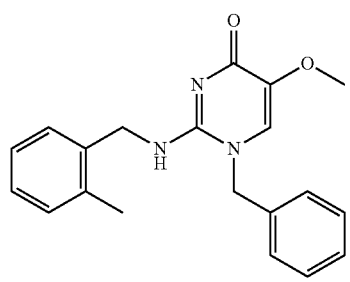 [SMILES: COc1cn(Cc2ccccc2)c(NCc2ccccc2C)nc1=O] | 336 | 1.48 | [1] |
| I-0103 | 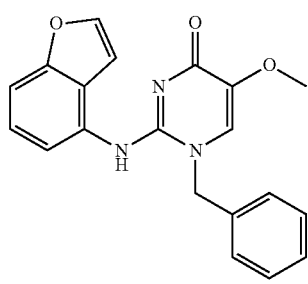 [SMILES: COc1cn(Cc2ccccc2)c(Nc2cccc3sccc23)nc1=O] | 348 | 1.41 | [1] |
| I-0104 | 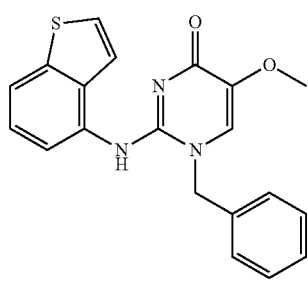 | 364 | 1.52 | [1] |
| I-0105 | 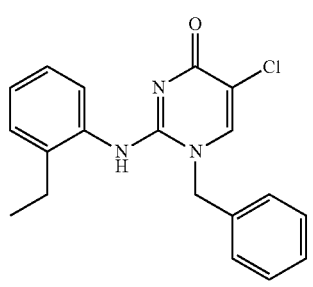 | 340 | 1.72 | [1] |

TABLE 18-continued
| | | | | |
|---|---|---|---|---|
| I-0106 | 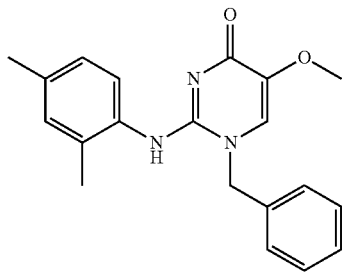 | 336 | 1.61 | [3] |
TABLE 19
| | | | | |
|---|---|---|---|---|
| I-0107 | 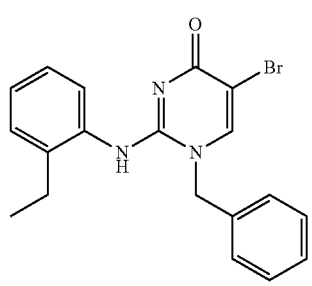 [SMILES: CCc1ccccc1Nc1nc(=O)c(Br)cn1Cc1ccccc1] | 384 | 1.78 | [1] |
| I-0108 | 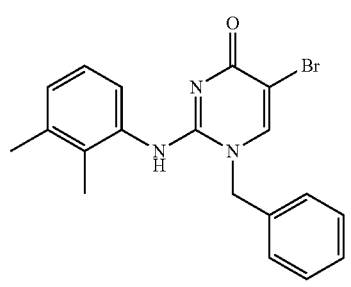 [SMILES: Cc1cccc(Nc2nc(=O)c(Br)cn2Cc2ccccc2)c1C] | 384 | 1.74 | [1] |
| I-0109 | 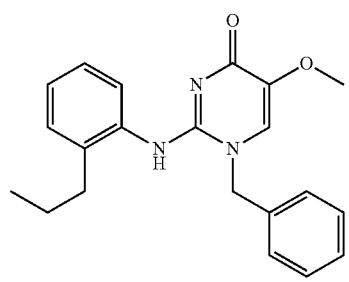 [SMILES: CCCc1ccccc1Nc1nc(=O)c(OC)cn1Cc1ccccc1] | 350 | 1.63 | [1] |
| I-0110 | 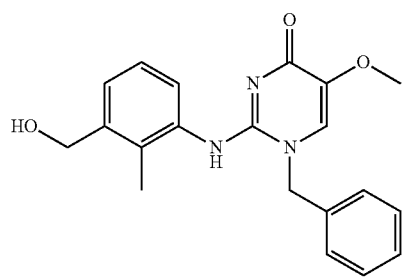 [SMILES: COc1cn(Cc2ccccc2)c(Nc2cccc(CO)c2C)nc1=O] | 352 | 1.1 | [1] |

TABLE 19-continued

| I-0111 | | 426 | 2.5 | [1] |
|---|---|---|---|---|
| I-0112 | | 356 | 1.64 | [1] |

TABLE 20

| I-0113 | | 352 | 1.44 | [1] |
|---|---|---|---|---|
| I-0114 | | 350 | 1.6 | [1] |
| I-0115 | | 372 | 1.51 | [1] |

TABLE 20-continued

| ID | Structure | | | |
|---|---|---|---|---|
| I-0116 | (indane-ethyl aryl)-NH-pyrimidinone-OMe, N-benzyl | 376 | 1.78 | [1] |
| I-0117 | (1-methylindol-4-yl)-NH-pyrimidinone-OMe, N-benzyl | 361 | 1.3 | [1] |
| I-0118 | (2-benzylphenyl)-NH-pyrimidinone-OMe, N-benzyl | 393 | 1.77 | [1] |

TABLE 21

| ID | Structure | | | |
|---|---|---|---|---|
| I-0119 | (benzothiazol-4-yl)-NH-pyrimidinone-OMe, N-benzyl | 365 | 1.58 | [3] |
| I-0120 | (2,3-dihydrobenzofuran-4-yl)-NH-pyrimidinone-OMe, N-benzyl | 350 | 1.42 | [3] |
| I-0121 | (3-chloro-2-methylbenzyl)-NH-pyrimidinone-OMe, N-benzyl | 370 | 1.79 | [3] |
| I-0122 | (2,3-dihydro-1,4-benzodioxin-5-yl)-NH-pyrimidinone-OMe, N-benzyl | 366 | 1.45 | [3] |

TABLE 21-continued
| | | | | |
|---|---|---|---|---|
| I-0123 | 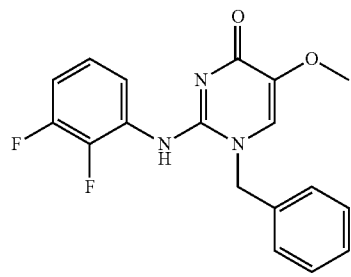 [SMILES: COc1cn(Cc2ccccc2)c(Nc2cccc(F)c2F)nc1=O] | 344 | 1.47 | [1] |
| I-0124 | 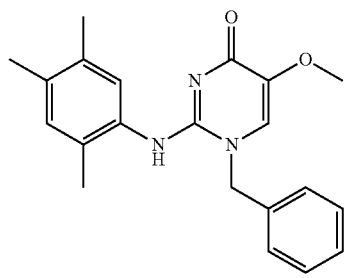 [SMILES: COc1cn(Cc2ccccc2)c(Nc2cc(C)c(C)cc2C)nc1=O] | 350 | 1.6 | [1] |
TABLE 22
| | | | | |
|---|---|---|---|---|
| I-0125 | 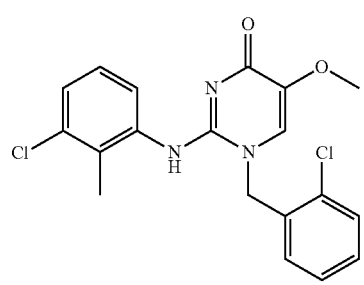 | 390 | 1.81 | [1] |
| I-0126 | 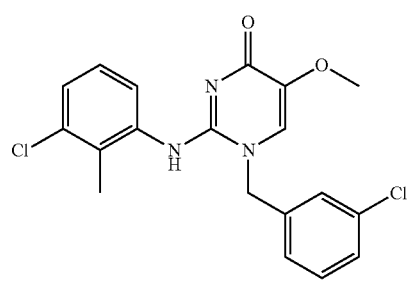 [SMILES: COc1cn(Cc2cccc(Cl)c2)c(Nc2cccc(Cl)c2C)nc1=O] | 390 | 1.82 | [1] |
| I-0127 | 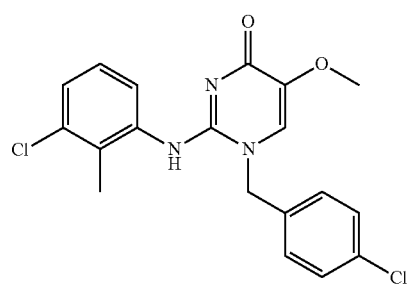 [SMILES: COc1cn(Cc2ccc(Cl)cc2)c(Nc2cccc(Cl)c2C)nc1=O] | 390 | 1.82 | [1] |
| I-0128 | 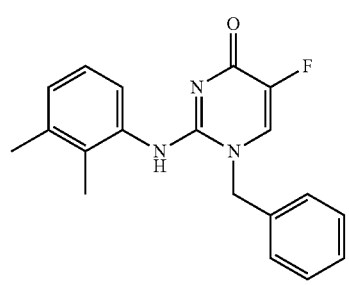 | 324 | 1.55 | [1] |

TABLE 22-continued

| ID | Structure | | | |
|---|---|---|---|---|
| I-0129 | (3-isopropoxy-2-methylphenyl)amino substituted 1-benzyl-5-methoxypyrimidin-4(1H)-one | 380 | 1.7 | [1] |
| I-0130 | (2-methoxy-3-methylphenyl)amino substituted 1-benzyl-5-methoxypyrimidin-4(1H)-one | 352 | 1.53 | [1] |

TABLE 23

| ID | Structure | | | |
|---|---|---|---|---|
| I-0131 | (2,6-dimethylbenzyl)amino substituted 1-benzyl-5-methoxypyrimidin-4(1H)-one | 350 | 1.61 | [1] |
| I-0132 | (2,3,4-trichlorophenyl)amino substituted 1-benzyl-5-methoxypyrimidin-4(1H)-one | 410 | 2.03 | [1] |
| I-0133 | (2-chloro-3-(difluoromethoxy)phenyl)amino substituted 1-benzyl-5-methoxypyrimidin-4(1H)-one | 408 | 1.72 | [1] |

TABLE 23-continued
| I-0134 | 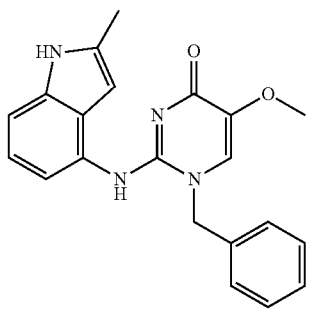 [SMILES: COc1cn(Cc2ccccc2)c(Nc2cccc3[nH]c(C)cc23)nc1=O] | 361 | 1.3 | [1] |
| I-0135 | 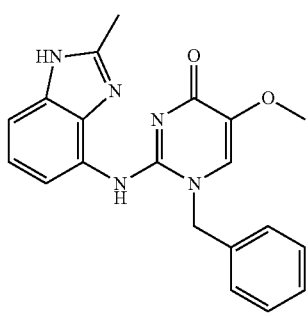 [SMILES: COc1cn(Cc2ccccc2)c(Nc2cccc3[nH]c(C)nc23)nc1=O] | 362 | 0.80 | [1] |
| I-0136 | 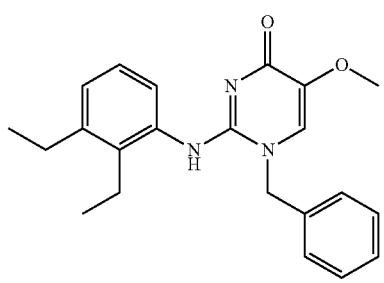 [SMILES: CCc1cccc(Nc2nc(=O)c(OC)cn2Cc2ccccc2)c1CC] | 364 | 1.75 | [1] |
TABLE 24
| I-0137 | 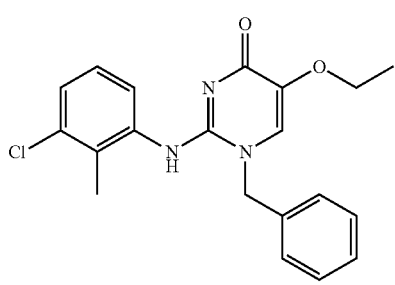 [SMILES: CCOc1cn(Cc2ccccc2)c(Nc2cccc(Cl)c2C)nc1=O] | 370 | 1.86 | [1] |
| I-0138 | 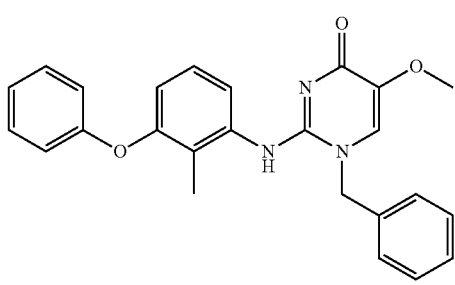 [SMILES: COc1cn(Cc2ccccc2)c(Nc2cccc(Oc3ccccc3)c2C)nc1=O] | 414 | 1.92 | [1] |

TABLE 24-continued
| | | | | |
|---|---|---|---|---|
| I-0139 | 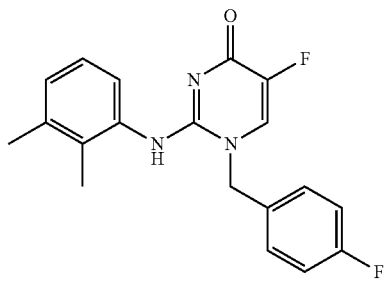 [SMILES: Cc1cccc(Nc2nc(=O)c(F)cn2Cc2ccc(F)cc2)c1C] | 342 | 1.59 | [1] |
| I-0140 | 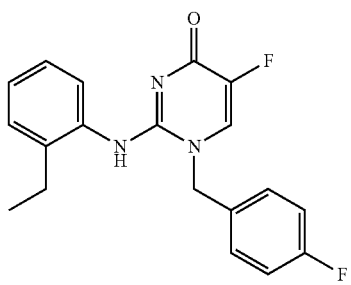 [SMILES: CCc1ccccc1Nc1nc(=O)c(F)cn1Cc1ccc(F)cc1] | 342 | 1.6 | [1] |
| I-0141 | 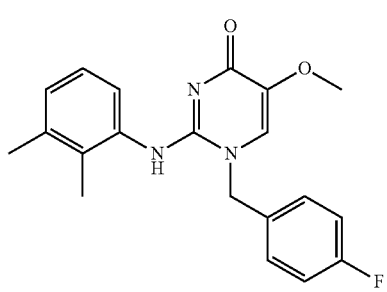 [SMILES: COc1cn(Cc2ccc(F)cc2)c(Nc2cccc(C)c2C)nc1=O] | 354 | 1.52 | [1] |
| I-0142 | 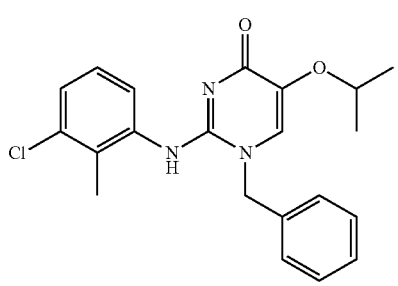 [SMILES: Cc1c(Cl)cccc1Nc1nc(=O)c(OC(C)C)cn1Cc1ccccc1] | 384 | 1.9 | [1] |
TABLE 25
| | | | | |
|---|---|---|---|---|
| I-0143 | 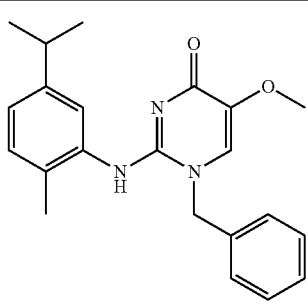 | 364 | 1.76 | [1] |
| I-0144 | 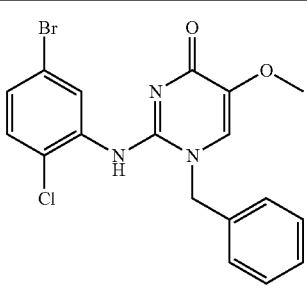 | 420 | 1.84 | [1] |

TABLE 25-continued
| | | | | |
|---|---|---|---|---|
| I-0145 | 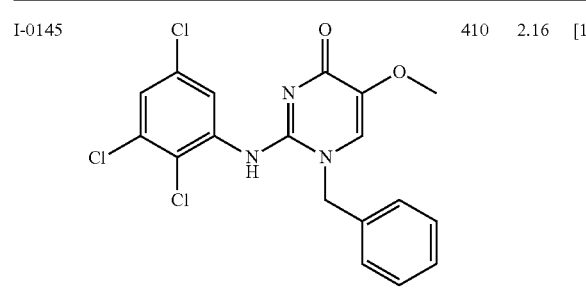 | 410 | 2.16 | [1] |
| I-0146 | 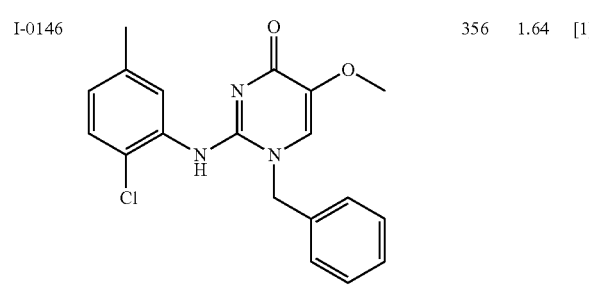 | 356 | 1.64 | [1] |
TABLE 25-continued
| | | | | |
|---|---|---|---|---|
| I-0147 | | 352 | 1.36 | [1] |
| I-0148 | | 429 | 1.39 | [1] |
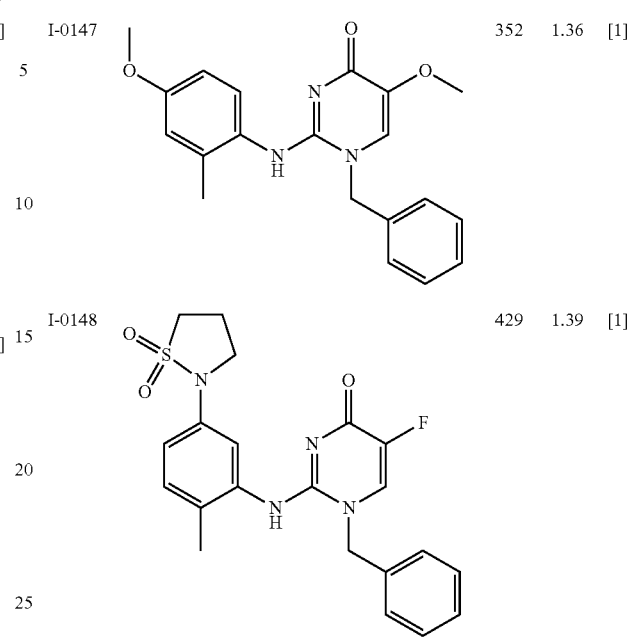
TABLE 26
| | | | | |
|---|---|---|---|---|
| I-0149 | | 432 | 2.06 | [1] |
| I-0150 | | 380 | 1.57 | [3] |
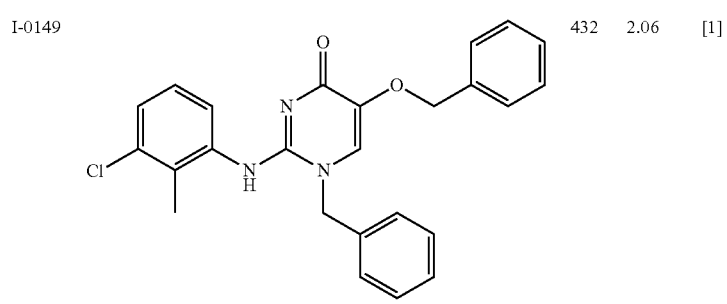
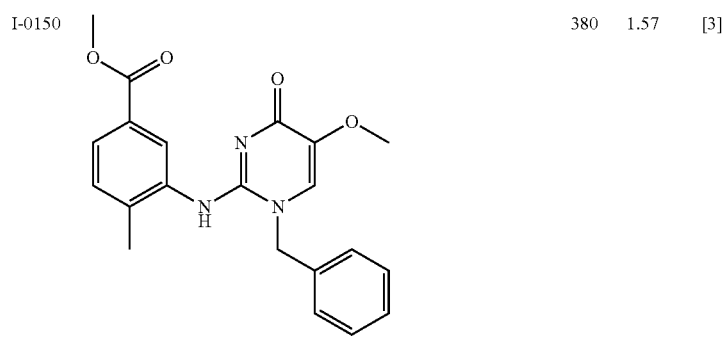

TABLE 26-continued
| | | | | |
|---|---|---|---|---|
| I-0151 | 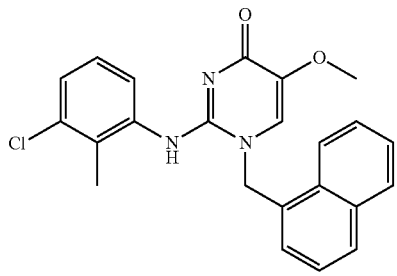 [SMILES: COc1cn(Cc2cccc3ccccc23)c(Nc2cccc(Cl)c2C)nc1=O] | 406 | 2.05 | [3] |
| I-0152 | 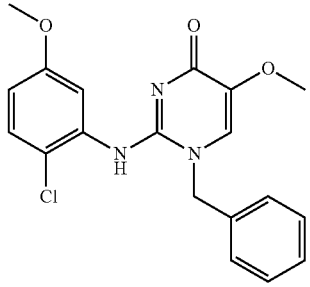 [SMILES: COc1ccc(Cl)c(Nc2nc(=O)c(OC)cn2Cc2ccccc2)c1] | 372 | 1.71 | [3] |
| I-0153 | 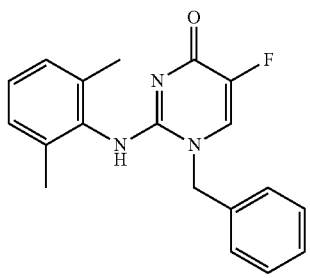 [SMILES: Cc1cccc(C)c1Nc1nc(=O)c(F)cn1Cc1ccccc1] | 324 | 1.51 | [1] |
| I-0154 | 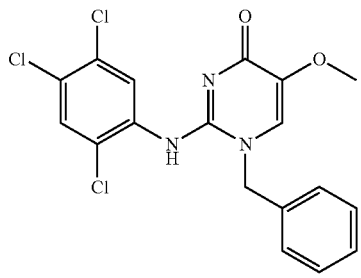 | 410 | 2.09 | [1] |
TABLE 27
| | | | | |
|---|---|---|---|---|
| I-0155 | 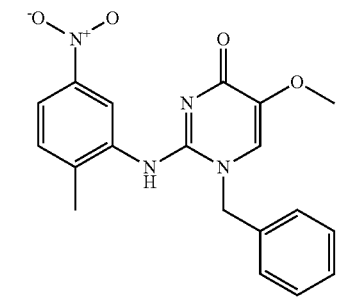 | 367 | 1.62 | [3] |
| I-0156 | 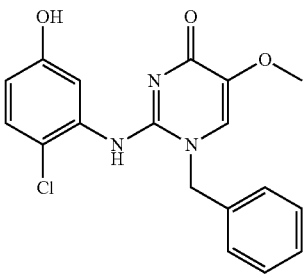 [SMILES: COc1cn(Cc2ccccc2)c(Nc2cc(O)ccc2Cl)nc1=O] | 358 | 1.53 | [3] |

TABLE 27-continued

| ID | Structure | MW | RT | Ref |
|---|---|---|---|---|
| I-0157 | 2-(2-ethylphenylamino)-1-benzyl-5-fluoropyrimidin-4(1H)-one | 324 | 1.57 | [1] |
| I-0158 | 2-(2,3-dimethylphenylamino)-1-benzyl-5-chloropyrimidin-4(1H)-one | 340 | 1.69 | [1] |
| I-0159 | 2-(2-methylbenzo[d]oxazol-7-ylamino)-1-benzyl-5-methoxypyrimidin-4(1H)-one | 363 | 1.23 | [1] |
| I-0160 | 2-(2-hydroxy-2-methyl-2,3-dihydrobenzo[d]oxazol-7-ylamino)-1-benzyl-5-methoxypyrimidin-4(1H)-one | 381 | 1.2 | [1] |

TABLE 28

| ID | Structure | MW | RT | Ref |
|---|---|---|---|---|
| I-0161 | | 370 | 1.73 | [1] |
| I-0162 | 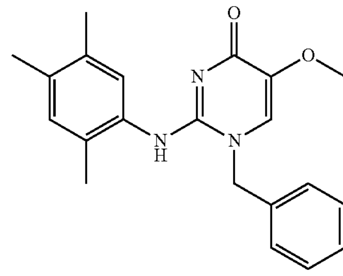 | 368 | 1.64 | [1] |
| I-0163 | 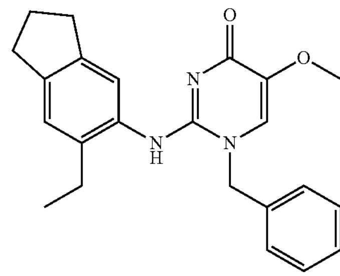 | 394 | 1.81 | [1] |
| I-0164 | 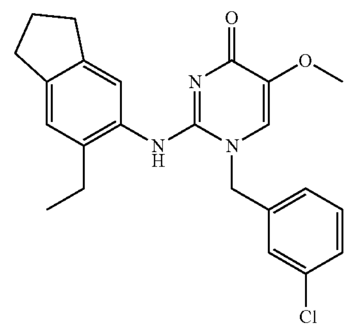 [SMILES: CCc1cc2c(cc1Nc1nc(=O)c(OC)cn1Cc1cccc(Cl)c1)CCC2] | 410 | 1.93 | [1] |
| I-0165 | 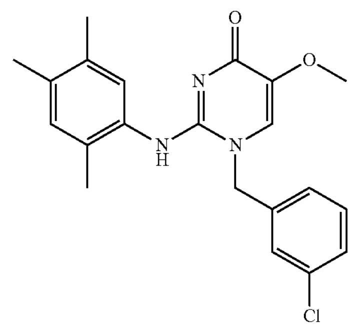 [SMILES: COc1cn(Cc2cccc(Cl)c2)c(Nc2cc(C)c(C)cc2C)nc1=O] | 384 | 1.73 | [1] |
| I-0166 | 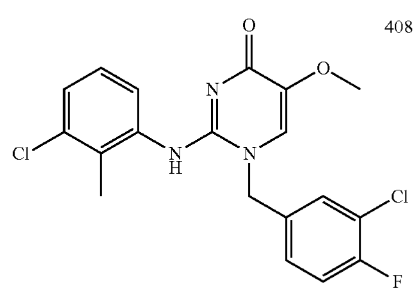 | 408 | 1.99 | [3] |

TABLE 29

| | | | | |
|---|---|---|---|---|
| I-0167 | ![structure] | 383 | 1.89 | [3] |
| I-0168 | ![structure] | 388 | 1.89 | [3] |
| I-0169 | ![structure] | 388 | 1.76 | [1] |
| I-0170 | ![structure] | 404 | 2.03 | [3] |
| I-0171 | ![structure] | 404 | 2.05 | [3] |

TABLE 30

| | | | | |
|---|---|---|---|---|
| I-0172 | [structure] | 404 | 2.03 | [3] |
| I-0173 | [structure] | 362 | 1.78 | [3] |
| I-0174 | [structure] | 362 | 1.78 | [3] |
| I-0175 | [structure] | 370 | 1.75 | [1] |
| I-0176 | [structure] | 368 | 1.64 | [1] |

TABLE 31

| | | | | |
|---|---|---|---|---|
| I-0177 | [structure] | 368 | 163 | [1] |
| I-0178 | [structure] | 394 | 1.8 | [1] |
| I-0179 | [structure] | 394 | 1.82 | [1] |
| I-0180 | [structure] | 352 | 1.29 | [3] |
| I-0181 | [structure] | 385 | 1.36 | [3] |

TABLE 31-continued
| | | | |
|---|---|---|---|
| I-0182 | 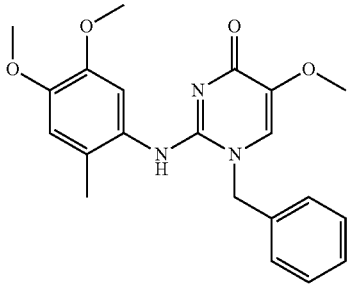 [SMILES: COc1cc(C)c(Nc2nc(=O)c(OC)cn2Cc2ccccc2)cc1OC] | 582 | 1.29 [1] |
TABLE 32
| | | | |
|---|---|---|---|
| I-0183 | 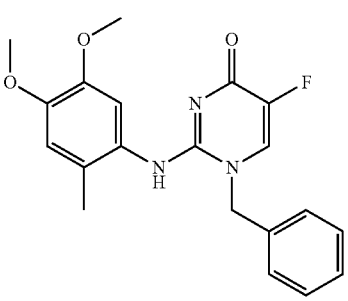 [SMILES: COc1cc(C)c(Nc2nc(=O)c(F)cn2Cc2ccccc2)cc1OC] | 370 | 1.37 [1] |
| I-0184 | 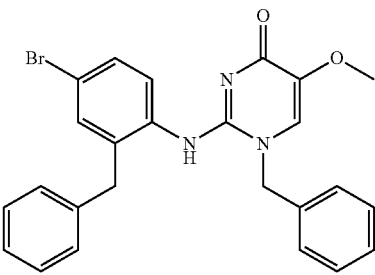 [SMILES: COc1cn(Cc2ccccc2)c(Nc2ccc(Br)cc2Cc2ccccc2)nc1=O] | 476 | 2.05 [1] |
| I-0185 | 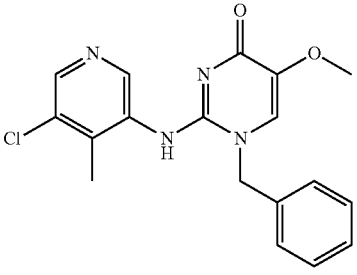 [SMILES: COc1cn(Cc2ccccc2)c(Nc2cncc(Cl)c2C)nc1=O] | 337 | 1.35 [1] |
| I-0186 | 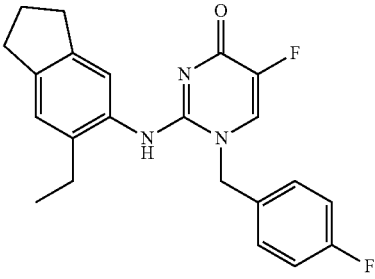 [SMILES: CCc1cc2c(cc1Nc1nc(=O)c(F)cn1Cc1ccc(F)cc1)CCC2] | 382 | 1.93 [1] |

TABLE 32-continued
| | | | | |
|---|---|---|---|---|
| I-0187 | 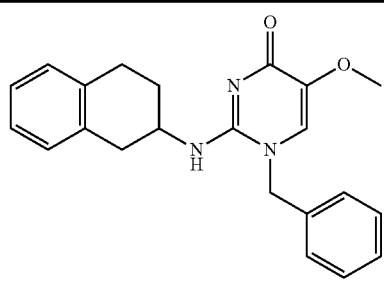 | 362 | 1.8. | [3] |
| I-0188 | 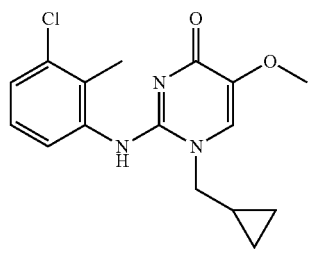 [SMILES: COc1cn(CC2CC2)c(Nc2cccc(Cl)c2C)nc1=O] | 320 | 1.46 | [3] |
TABLE 33
| | | | | |
|---|---|---|---|---|
| I-0189 | 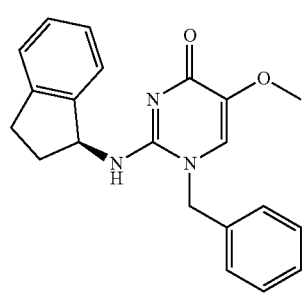 [SMILES: COc1cn(Cc2ccccc2)c(N[C@H]2CCc3ccccc32)nc1=O] | 348 | 1.69 | [3] |
| I-0190 | 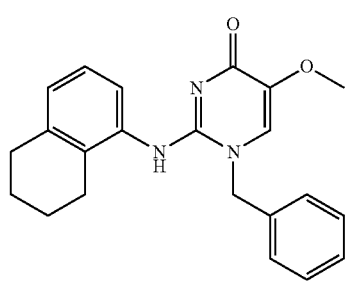 [SMILES: COc1cn(Cc2ccccc2)c(Nc2cccc3c2CCCC3)nc1=O] | 362 | 1.65 | [1] |
| I-0191 | 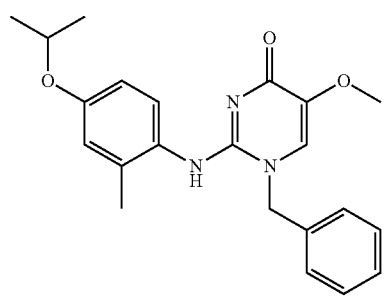 [SMILES: COc1cn(Cc2ccccc2)c(Nc2ccc(OC(C)C)cc2C)nc1=O] | 380 | 1.81 | [1] |

TABLE 33-continued
| I-0192 | 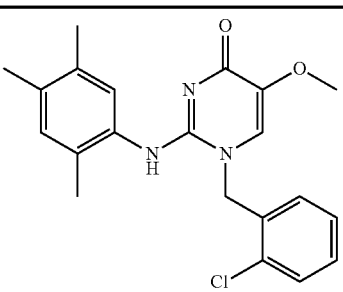 | 384 | 1.77 | [1] |
| I-0193 | 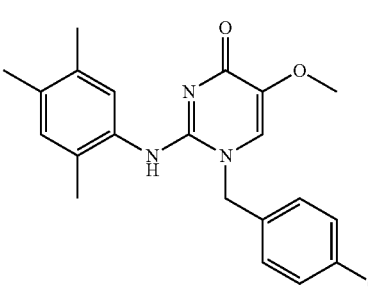 | 384 | 1.78 | [1] |
| I-0194 | 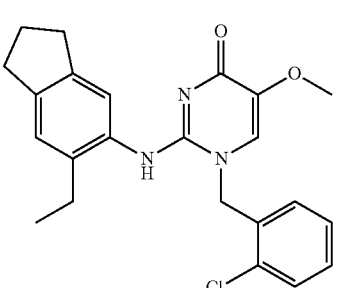 | 410 | 1.99 | [1] |
TABLE 34
| I-0195 | 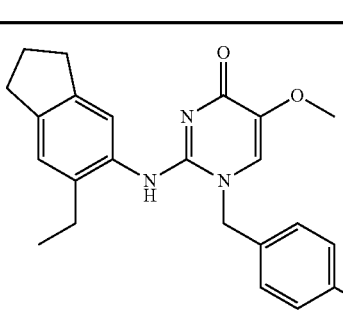 | 410 | 1.98 | [1] |
| I-0196 | 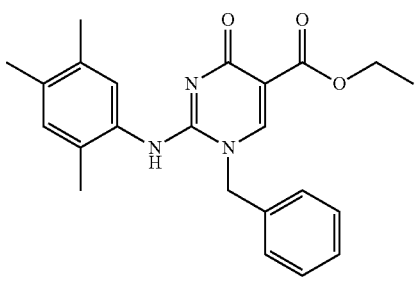 [SMILES: CCOC(=O)c1cn(Cc2ccccc2)c(Nc2cc(C)c(C)cc2C)nc1=O] | 392 | 2.22 | [1] |

TABLE 34-continued

| | | | | |
|---|---|---|---|---|
| I-0197 | (structure) | 325 | 1.91 | [1] |
| I-0198 | (structure) | 415 | 1.54 | [1] |
| I-0199 | (structure) | 337 | 1.8 | [1] |
| I-0200 | (structure) | 354 | 1.54 | [1] |

TABLE 35

| | | | | |
|---|---|---|---|---|
| I-0201 | (structure) | 348 | 1.56 | [1] |

TABLE 35-continued

| ID | Structure | MW | RT | Ref |
|---|---|---|---|---|
| I-0202 | 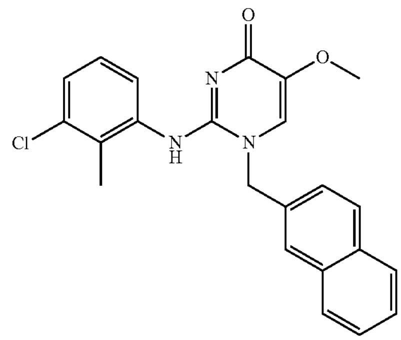 [SMILES: COc1cn(Cc2ccc3ccccc3c2)c(Nc2cccc(Cl)c2C)nc1=O] | 406 | 1.88 | [1] |
| I-0203 | 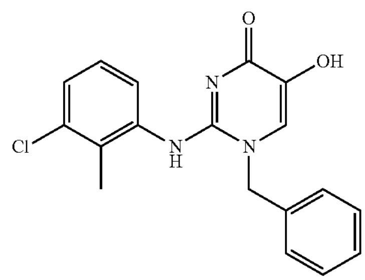 | 342 | 1.59 | [1] |
| I-0204 | 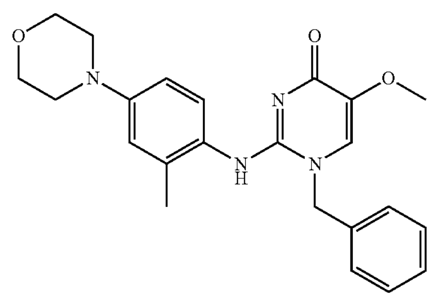 [SMILES: COc1cn(Cc2ccccc2)c(Nc2ccc(N3CCOCC3)cc2C)nc1=O] | 407 | 1.25 | [1] |
| I-0205 | 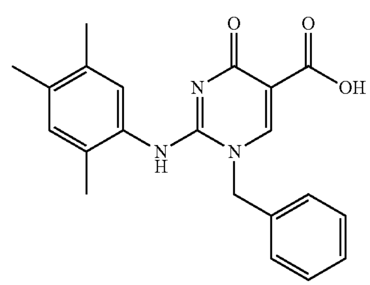 [SMILES: Cc1cc(C)c(Nc2nc(=O)c(C(=O)O)cn2Cc2ccccc2)cc1C] | 364 | 1.89 | [1] |
| I-0206 | 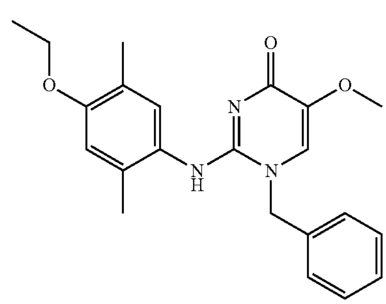 [SMILES: CCOc1cc(C)c(Nc2nc(=O)c(OC)cn2Cc2ccccc2)cc1C] | 380 | 1.65 | [1] |

TABLE 36

| | | | | |
|---|---|---|---|---|
| I-0207 | (structure) | 447 | 1.43 | [1] |
| I-0208 | (structure) | 416 | 1.46 | [1] |
| I-0209 | (structure) | 388 | 1.41 | [1] |
| I-0210 | (structure) | 364 | 1.76 | [1] |
| I-0211 | (structure) | 364 | 1.76 | [1] |

TABLE 37

| | | | | |
|---|---|---|---|---|
| I-0212 | (structure) | 366 | 1.57 | [1] |
| I-0213 | (structure) | 384 | 1.61 | [1] |
| I-0214 | (structure) | 400 | 1.78 | [1] |
| I-0215 | (structure) | 370 | 1.78 | [1] |
| I-0216 | (structure) | 394 | 2.49 | [3] |

TABLE 37-continued
| | | | | |
|---|---|---|---|---|
| I-0217 | 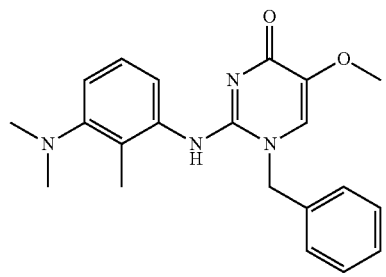 [SMILES: COc1cn(Cc2ccccc2)c(Nc2cccc(N(C)C)c2C)nc1=O] | 365 | 0.81 | [1] |
TABLE 38
| | | | | |
|---|---|---|---|---|
| I-0218 | 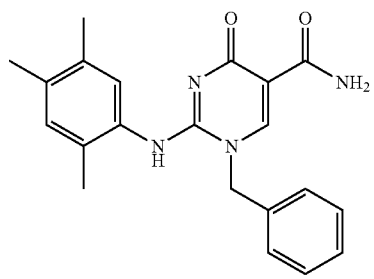 [SMILES: Cc1cc(C)c(Nc2nc(=O)c(C(N)=O)cn2Cc2ccccc2)cc1C] | 363 | 1.86 | [1] |
| I-0219 | 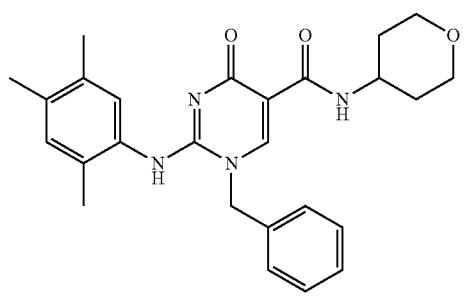 [SMILES: Cc1cc(C)c(Nc2nc(=O)c(C(=O)NC3CCOCC3)cn2Cc2ccccc2)cc1C] | 447 | 2.02 | [1] |
| I-0220 | 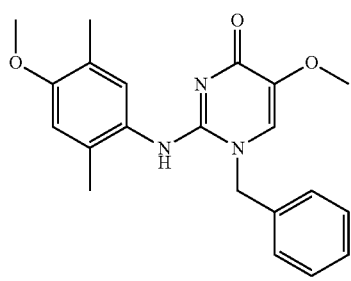 [SMILES: COc1cc(C)c(Nc2nc(=O)c(OC)cn2Cc2ccccc2)cc1C] | 366 | 1.49 | [1] |
| I-0221 | 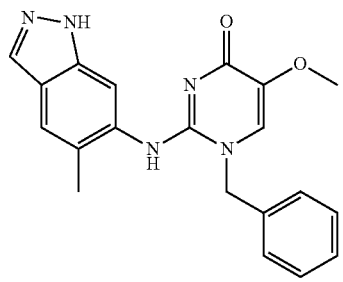 [SMILES: COc1cn(Cc2ccccc2)c(Nc2cc3[nH]ncc3cc2C)nc1=O] | 362 | 1.36 | [3] |

TABLE 38-continued
| I-0222 | 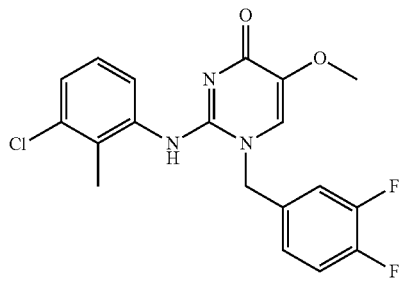 [SMILES: COc1cn(Cc2ccc(F)c(F)c2)c(Nc2cccc(Cl)c2C)nc1=O] | 392 | 1.87 | [3] |
| I-0223 | 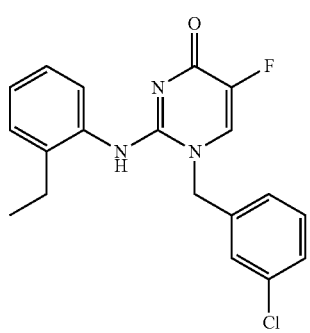 [SMILES: CCc1ccccc1Nc1nc(=O)c(F)cn1Cc1cccc(Cl)c1] | 358 | 1.73 | [1] |
TABLE 39
| I-0224 | 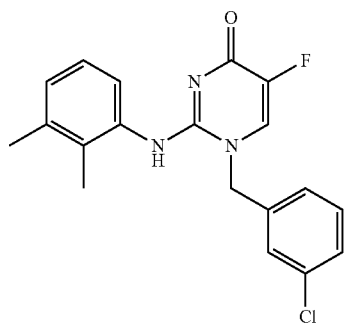 [SMILES: Cc1cccc(Nc2nc(=O)c(F)cn2Cc2cccc(Cl)c2)c1C] | 358 | 1.72 | [1] |
| I-0225 | 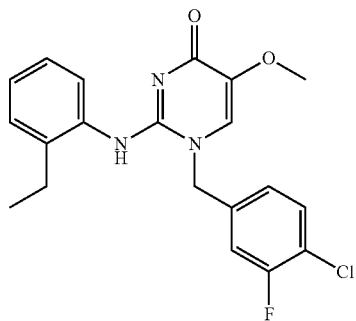 [SMILES: CCc1ccccc1Nc1nc(=O)c(OC)cn1Cc1ccc(Cl)c(F)c1] | 288 | 1.72 | [1] |

TABLE 39-continued
| | | | | |
|---|---|---|---|---|
| I-0226 | 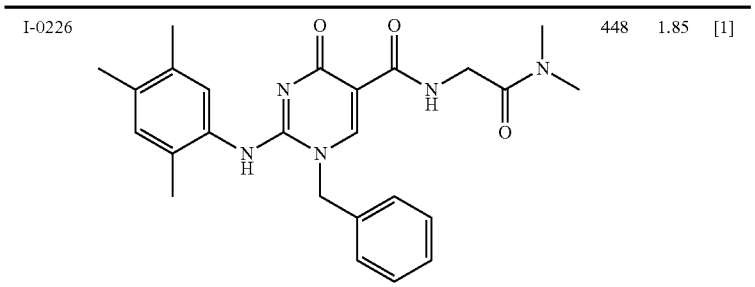 | 448 | 1.85 | [1] |
| I-0227 | 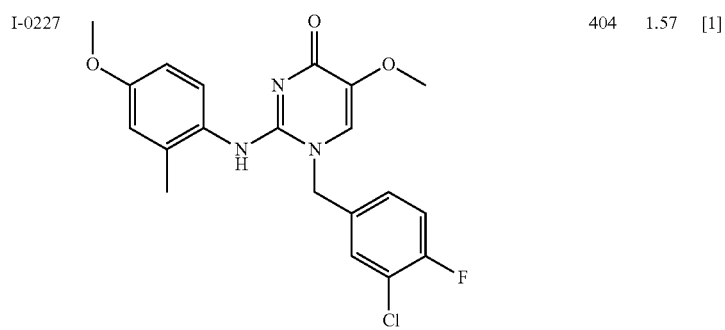 | 404 | 1.57 | [1] |
| I-0228 | 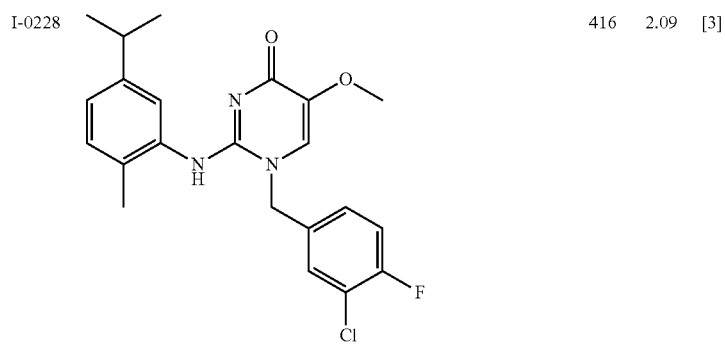 | 416 | 2.09 | [3] |
TABLE 40
| | | | | |
|---|---|---|---|---|
| I-0229 | 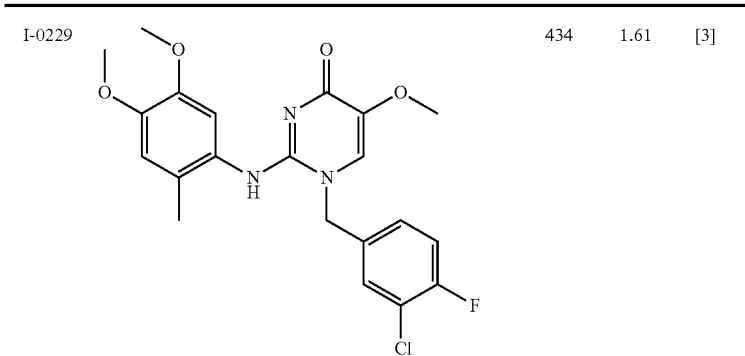 | 434 | 1.61 | [3] |

TABLE 40-continued
| | | | | |
|---|---|---|---|---|
| I-0230 | 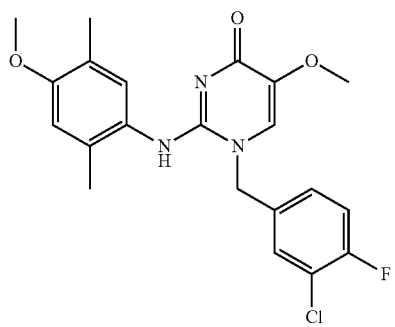 [SMILES: COc1cc(C)c(Nc2nc(=O)c(OC)cn2Cc2ccc(F)c(Cl)c2)cc1C] | 418 | 1.82 | [3] |
| I-0231 | 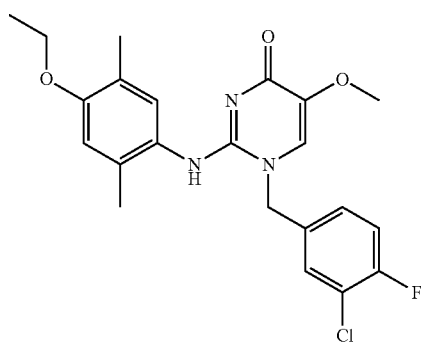 [SMILES: CCOc1cc(C)c(Nc2nc(=O)c(OC)cn2Cc2ccc(F)c(Cl)c2)cc1C] | 432 | 1.98 | [3] |
| I-0232 | 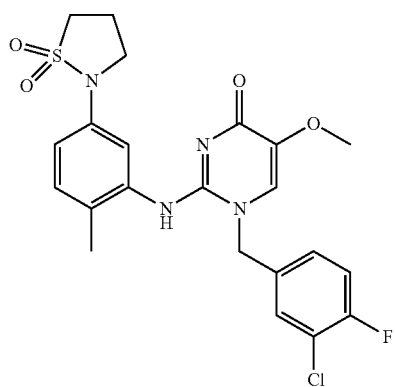 [SMILES: COc1cn(Cc2ccc(F)c(Cl)c2)c(Nc2cc(N3CCCS3(=O)=O)ccc2C)nc1=O] | 493 | 1.68 | [3] |
| I-0233 | 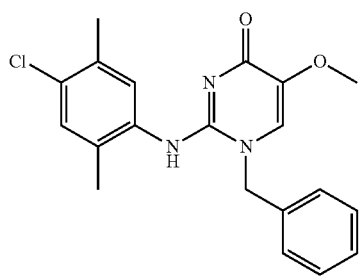 | 370 | 1.4 | [1] |

TABLE 41
| | | | | |
|---|---|---|---|---|
| I-0234 | 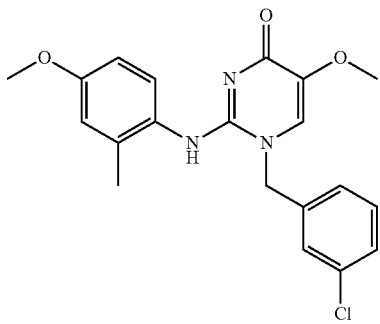 [SMILES: COc1ccc(Nc2nc(=O)c(OC)cn2Cc2cccc(Cl)c2)c(C)c1] | 386 | 1.53 | [1] |
| I-0235 | 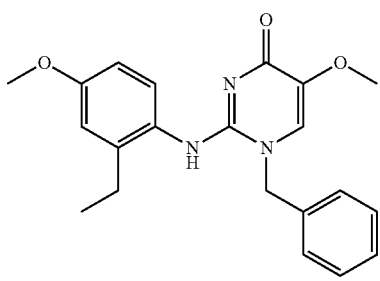 [SMILES: CCc1cc(OC)ccc1Nc1nc(=O)c(OC)cn1Cc1ccccc1] | 369 | 1.48 | [1] |
| I-0236 | 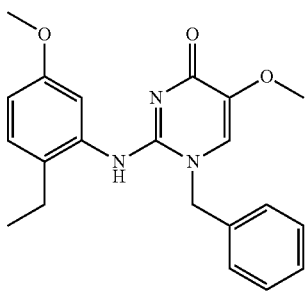 [SMILES: CCc1ccc(OC)cc1Nc1nc(=O)c(OC)cn1Cc1ccccc1] | 366 | 1.56 | [1] |
| I-0237 | 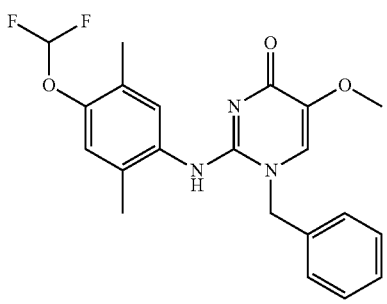 [SMILES: COc1cn(Cc2ccccc2)c(Nc2cc(C)c(OC(F)F)cc2C)nc1=O] | 402 | 1.67 | [1] |
| I-0238 | 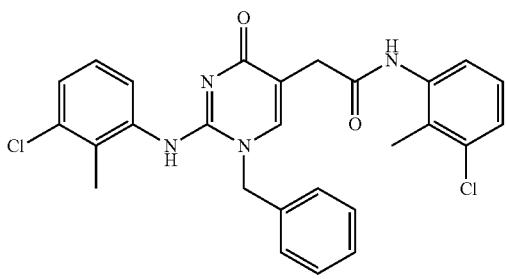 [SMILES: Cc1c(Cl)cccc1NC(=O)Cc1cn(Cc2ccccc2)c(Nc2cccc(Cl)c2C)nc1=O] | 507 | 2.4 | [1] |

TABLE 42

| ID | Structure | | | |
|---|---|---|---|---|
| I-0239 | 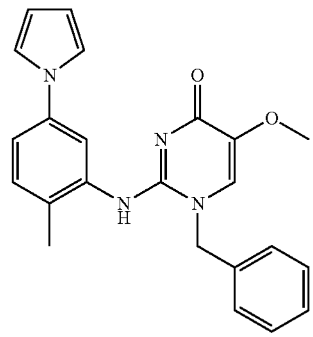 [SMILES: COc1cn(Cc2ccccc2)c(Nc2cc(-n3cccc3)ccc2C)nc1=O] | 387 | 1.71 | [1] |
| I-0240 | 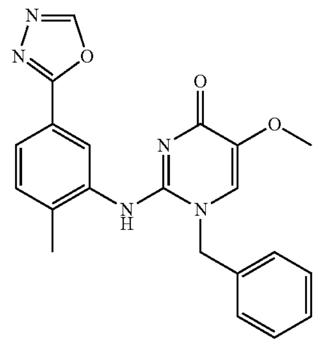 [SMILES: COc1cn(Cc2ccccc2)c(Nc2cc(-c3nnco3)ccc2C)nc1=O] | 390 | 1.28 | [1] |
| I-0241 | 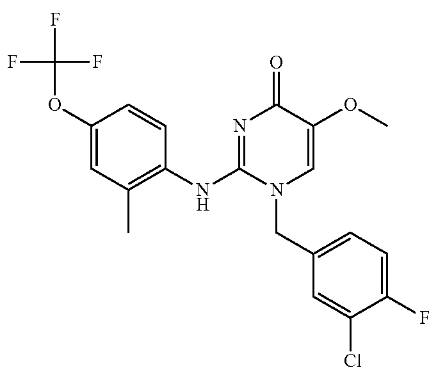 [SMILES: COc1cn(Cc2ccc(F)c(Cl)c2)c(Nc2ccc(OC(F)(F)F)cc2C)nc1=O] | 458 | 2.13 | [3] |
| I-0242 | 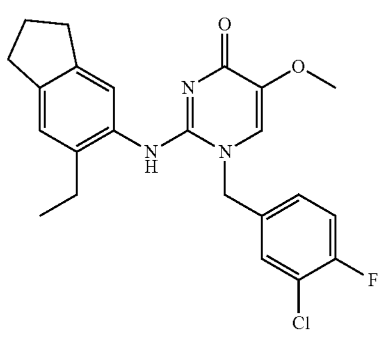 [SMILES: CCc1cc2c(cc1Nc1nc(=O)c(OC)cn1Cc1ccc(F)c(Cl)c1)CCC2] | 428 | 2.11 | [3] |

| | | | | |
|---|---|---|---|---|
| I-0243 | 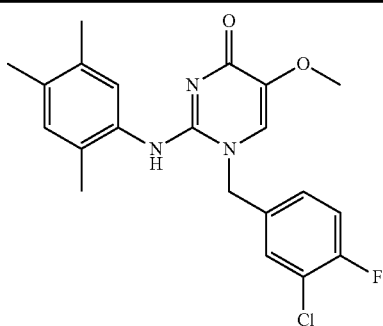 | 402 | 1.93 | [3] |
TABLE 43
| | | | | |
|---|---|---|---|---|
| I-0244 | 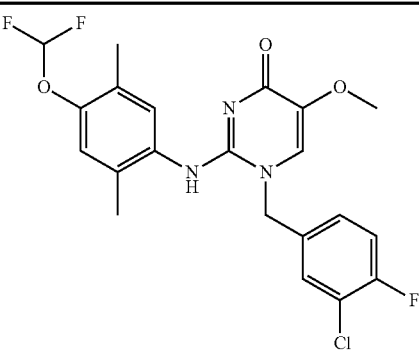 | 454 | 2.01 | [3] |
| I-0245 | 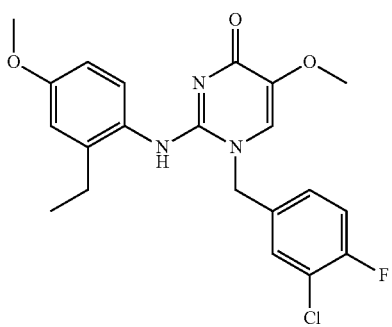 [SMILES: CCc1cc(OC)ccc1Nc1nc(=O)c(OC)cn1Cc1ccc(F)c(Cl)c1] | 418 | 1.8 | [3] |
| I-0246 | 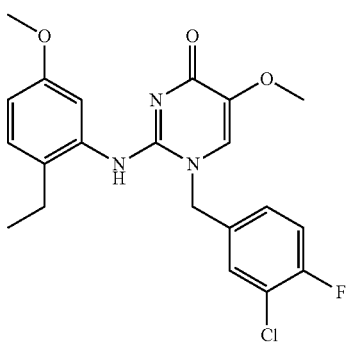 [SMILES: CCc1ccc(OC)cc1Nc1nc(=O)c(OC)cn1Cc1ccc(F)c(Cl)c1] | 418 | 1.89 | [3] |

TABLE 43-continued

| ID | Structure | MW | RT | Method |
|---|---|---|---|---|
| I-0247 | (structure) | 418 | 1.62 | [3] |
| I-0248 | (structure) | 417 | 1.24 | [3] |

TABLE 44

| ID | Structure | MW | RT | Method |
|---|---|---|---|---|
| I-0249 | (structure) | 384 | 1.53 | [1] |
| I-0250 | (structure) | 400 | 1.65 | [1] |

TABLE 44-continued

| ID | Structure | MW | RT | Method |
|---|---|---|---|---|
| I-0251 | (structure) | 384 | 1.59 | [1] |
| I-0252 | (structure) | 388 | 1.78 | [1] |

TABLE 44-continued
| | | | | |
|---|---|---|---|---|
| I-0253 | 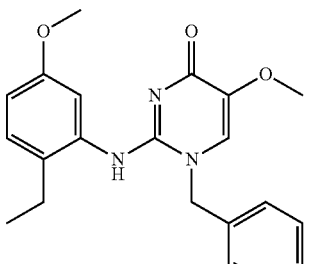 | 384 | 1.59 | [1] |
TABLE 45
| | | | | |
|---|---|---|---|---|
| I-0254 | 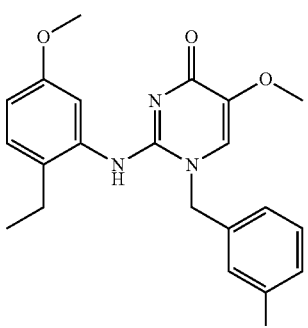 | 400 | 1.72 | [1] |
| I-0255 | 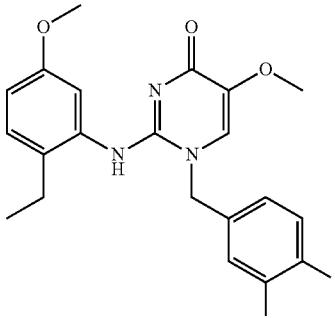 | 402 | 1.66 | [1] |
| I-0256 | 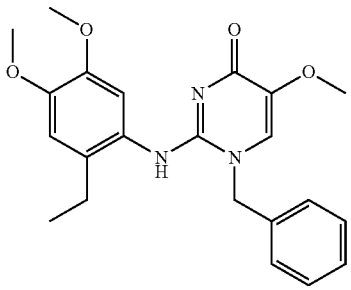 [SMILES: CCc1cc(OC)c(OC)cc1Nc1nc(=O)c(OC)cn1Cc1ccccc1] | 396 | 1.41 | [1] |

TABLE 45-continued

| I-0257 | [structure] | 398 | 1.81 | [3] |
| I-0258 | [structure] | 398 | 1.82 | [3] |

TABLE 46

| I-0259 | [structure] | 414 | 1.94 | [3] |
| I-0260 | [structure] | 416 | 1.88 | [3] |

TABLE 46-continued
| I-0261 | 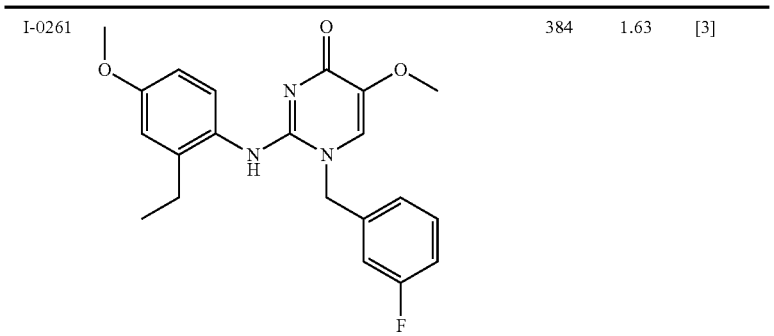 | 384 | 1.63 | [3] |
|---|---|---|---|---|
| I-0262 | 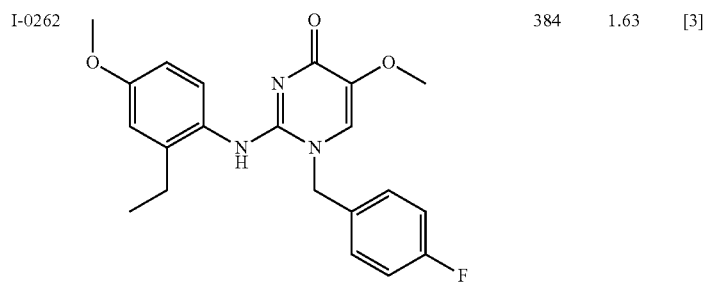 | 384 | 1.63 | [3] |
| I-0263 | 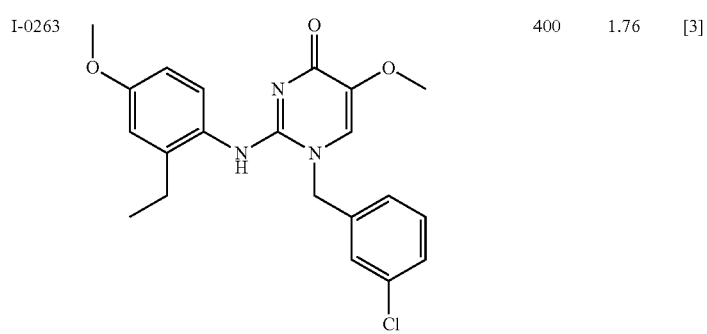 | 400 | 1.76 | [3] |
TABLE 47
| I-0264 | 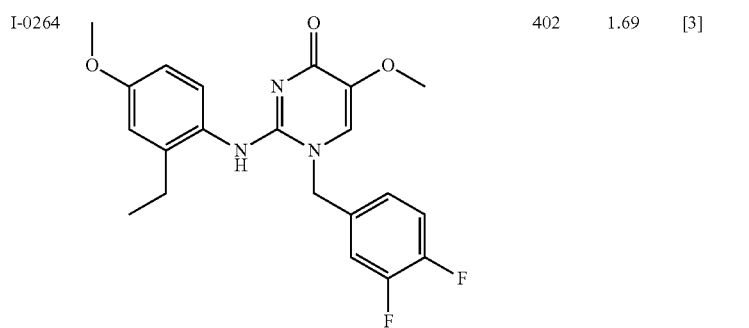 | 402 | 1.69 | [3] |
|---|---|---|---|---|

TABLE 47-continued
| | | | | |
|---|---|---|---|---|
| I-0265 | 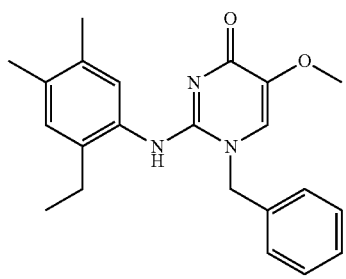 | 364 | 172 | [1] |
| I-0266 | 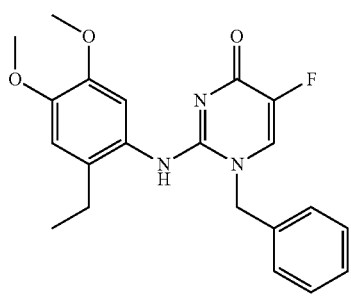 [SMILES: CCc1cc(OC)c(OC)cc1Nc1nc(=O)c(F)cn1Cc1ccccc1] | 384 | 1.49 | [1] |
| I-0267 | 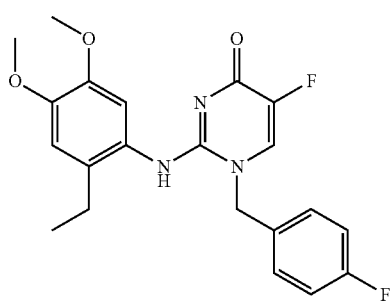 [SMILES: CCc1cc(OC)c(OC)cc1Nc1nc(=O)c(F)cn1Cc1ccc(F)cc1] | 402 | 1.52 | [1] |
| I-0268 | 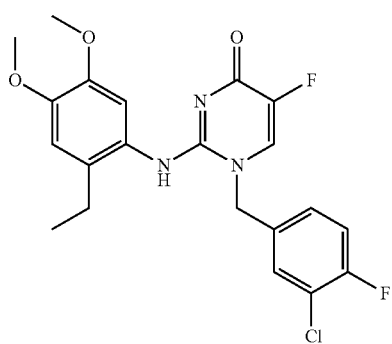 [SMILES: CCc1cc(OC)c(OC)cc1Nc1nc(=O)c(F)cn1Cc1ccc(F)c(Cl)c1] | 436 | 1.67 | [1] |

TABLE 48
| I-0269 | 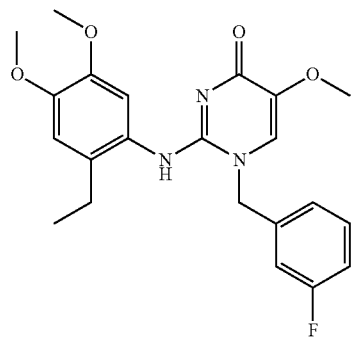 [SMILES: CCc1cc(OC)c(OC)cc1Nc1nc(=O)c(OC)cn1Cc1cccc(F)c1] | 414 | 1.54 | [3] |
| I-0270 | 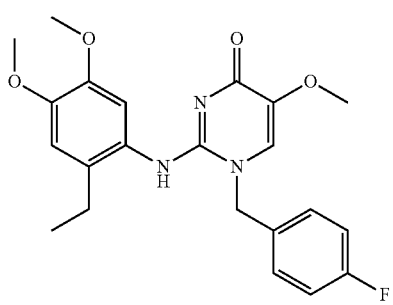 [SMILES: CCc1cc(OC)c(OC)cc1Nc1nc(=O)c(OC)cn1Cc1ccc(F)cc1] | 414 | 1.56 | [3] |
| I-0271 | 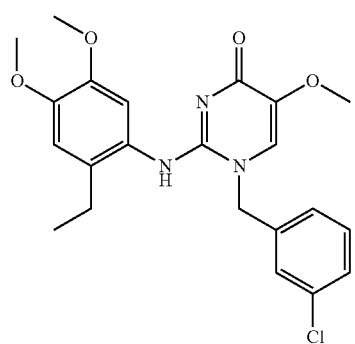 [SMILES: CCc1cc(OC)c(OC)cc1Nc1nc(=O)c(OC)cn1Cc1cccc(Cl)c1] | 430 | 1.68 | [3] |
| I-0272 | 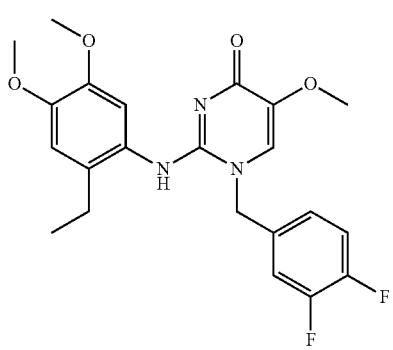 [SMILES: CCc1cc(OC)c(OC)cc1Nc1nc(=O)c(OC)cn1Cc1ccc(F)c(Cl)c1] | 432 | 1.61 | [3] |

TABLE 48-continued

| I-0273 | [structure] | 448 | 1.72 | [3] |

TABLE 49

| I-0274 | [structure] | 400 | 1.42 | [3] |
| I-0275 | [structure] | 400 | 1.43 | [3] |
| I-0276 | [structure] | 418 | 1.5 | [3] |

TABLE 49-continued
| I-0277 | 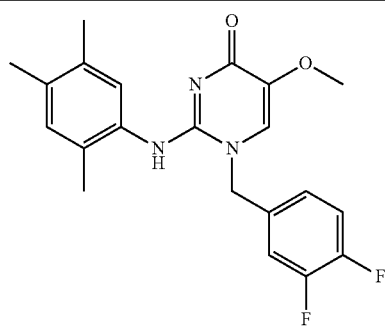 | 386 | 1.82 | [3] |
| I-0278 | 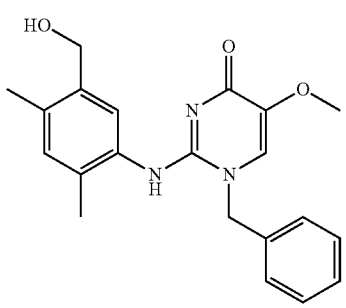 | 366 | 1.4 | [3] |
TABLE 50
| I-0279 | 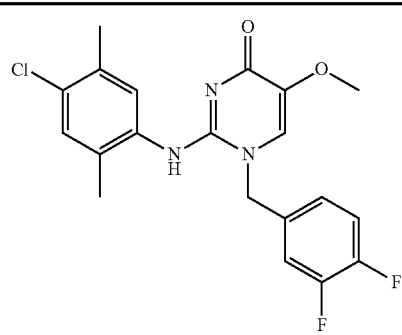 | 406 | 1.96 | [3] |
| I-0280 | 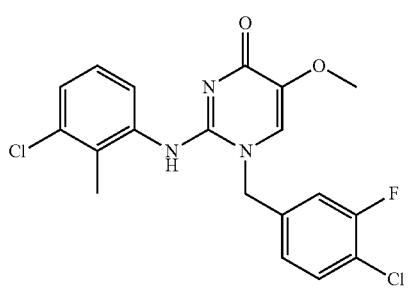 [SMILES: COc1cn(Cc2ccc(Cl)c(F)c2)c(Nc2cccc(Cl)c2C)nc1=O] | 408 | 1.89 | [1] |
| I-0281 | 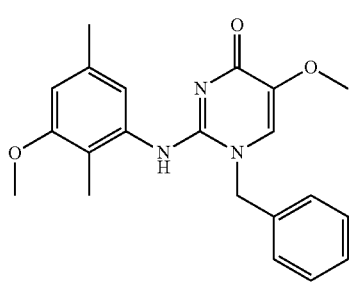 [SMILES: COc1cc(C)cc(Nc2nc(=O)c(OC)cn2Cc2ccccc2)c1C] | 366 | 1.62 | [1] |

TABLE 50-continued
| I-0282 | 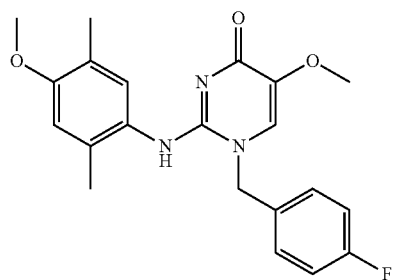 [SMILES: COc1cc(C)c(Nc2nc(=O)c(OC)cn2Cc2ccc(F)cc2)cc1C] | 384 | 1.54 | [1] |
| I-0283 | 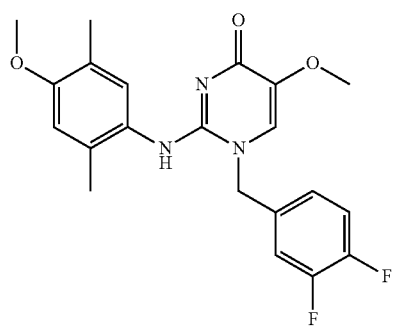 [SMILES: COc1cc(C)c(Nc2nc(=O)c(OC)cn2Cc2ccc(F)c(F)c2)cc1C] | 402 | 1.59 | [1] |
TABLE 51
| I-0284 | 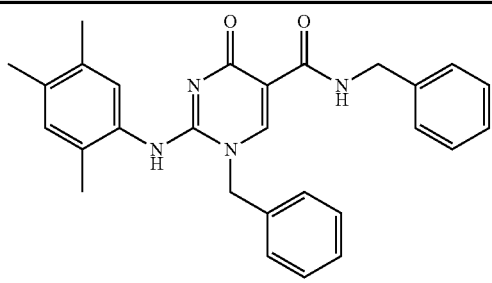 | 453 | 2.29 | [1] |
| I-0285 | 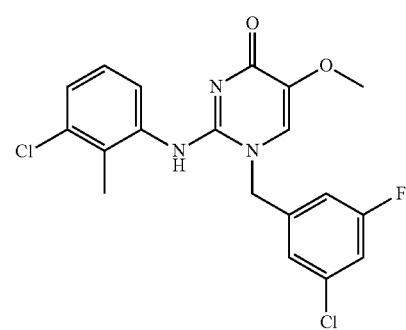 | 408 | 1.92 | [1] |
| I-0286 | 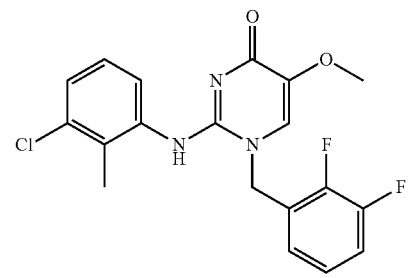 | 392 | 1.77 | [1] |

TABLE 51-continued
| I-0287 | 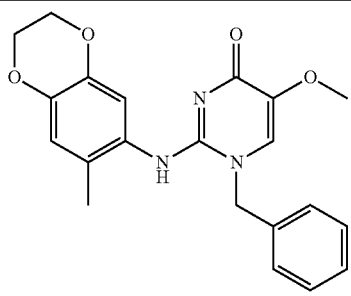 | 380 | 1.48 | [3] |
| I-0288 | 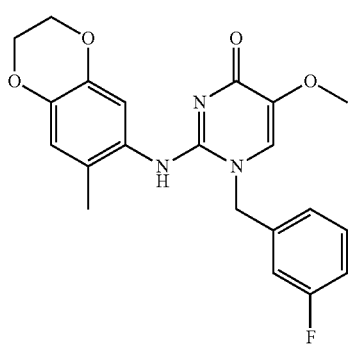 [SMILES: COc1cn(Cc2cccc(F)c2)c(Nc2cc3c(cc2C)OCCO3)nc1=O] | 398 | 1.52 | [3] |
TABLE 52
| I-0289 | 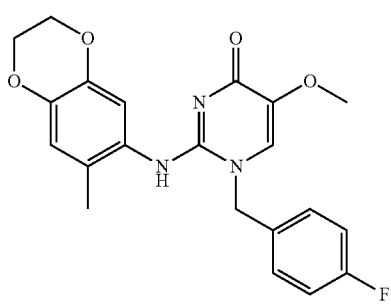 [SMILES: COc1cn(Cc2ccc(F)cc2)c(Nc2cc3c(cc2C)OCCO3)nc1=O] | 398 | 1.2 | [3] |
| I-0290 | 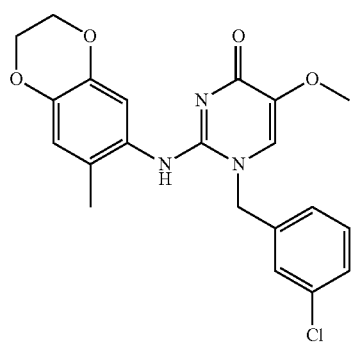 [SMILES: COc1cn(Cc2cccc(Cl)c2)c(Nc2cc3c(cc2C)OCCO3)nc1=O] | 414 | 1.66 | [3] |

TABLE 52-continued
| | | | | |
|---|---|---|---|---|
| I-0291 | 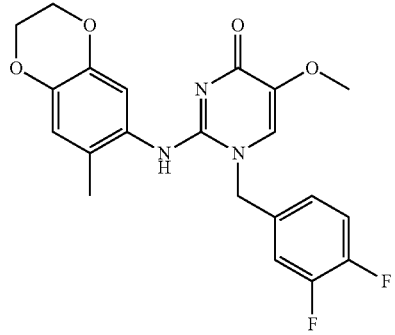 [SMILES: COc1cn(Cc2ccc(F)c(F)c2)c(Nc2cc3c(cc2C)OCCO3)nc1=O] | 416 | 1.59 | [3] |
| I-0292 | 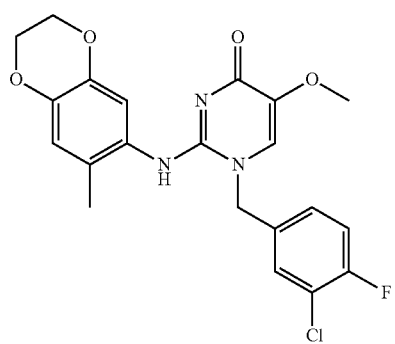 [SMILES: COc1cn(Cc2ccc(F)c(Cl)c2)c(Nc2cc3c(cc2C)OCCO3)nc1=O] | 432 | 1.7 | [3] |
| I-0293 | 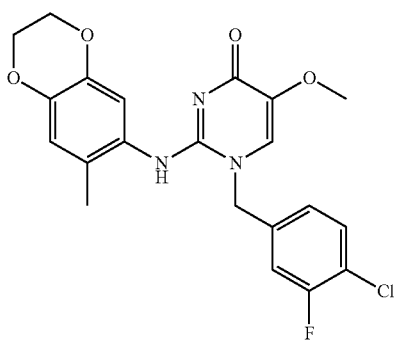 [SMILES: COc1cn(Cc2ccc(Cl)c(F)c2)c(Nc2cc3c(cc2C)OCCO3)nc1=O] | 432 | 1.72 | [3] |
TABLE 53
| | | | | |
|---|---|---|---|---|
| I-0294 | 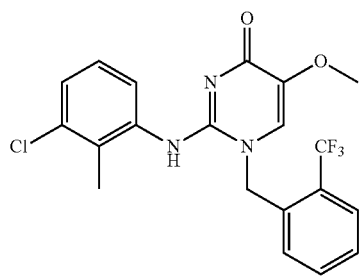 [SMILES: COc1cn(Cc2ccccc2C(F)(F)F)c(Nc2cccc(Cl)c2C)nc1=O] | 424 | 2.11 | [3] |

TABLE 53-continued
| I-0295 | 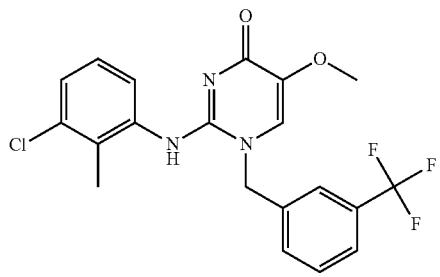 [SMILES: COc1cn(Cc2cccc(C(F)(F)F)c2)c(Nc2cccc(Cl)c2C)nc1=O] | 424 | 2.04 | [3] |
| I-0296 | 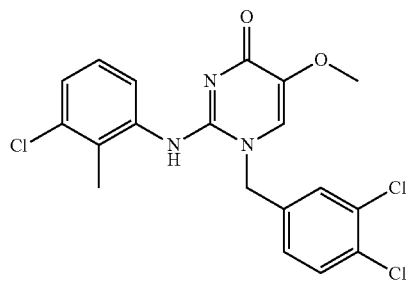 | 424 | 2.14 | [3] |
| I-0297 | 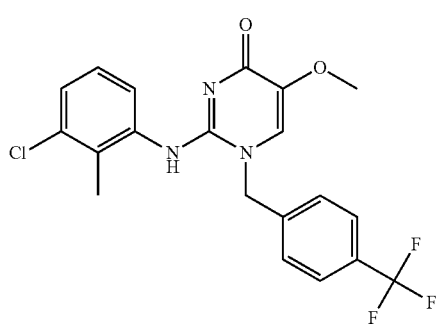 [SMILES: COc1cn(Cc2ccc(C(F)(F)F)cc2)c(Nc2cccc(Cl)c2C)nc1=O] | 424 | 1.92 | [1] |
| I-0298 | 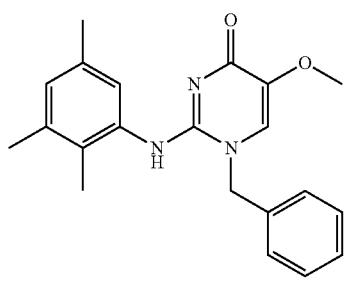 [SMILES: COc1cn(Cc2ccccc2)c(Nc2cc(C)cc(C)c2C)nc1=O] | 350 | 1.64 | [1] |
TABLE 54
| I-0299 | 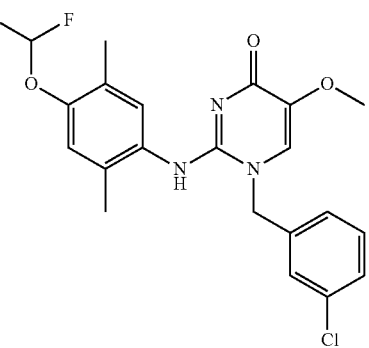 | 436 | 1.83 | [1] |

TABLE 54-continued
| I-0300 | 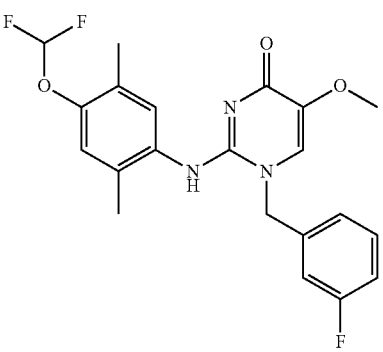 [SMILES: COc1cn(Cc2cccc(F)c2)c(Nc2cc(C)c(OC(F)F)cc2C)nc1=O] | 420 | 1.71 | [1] |
| I-0301 | 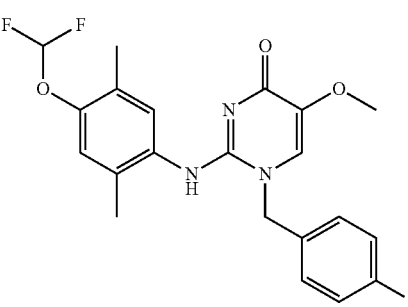 | 420 | 1.71 | [1] |
| I-0302 | 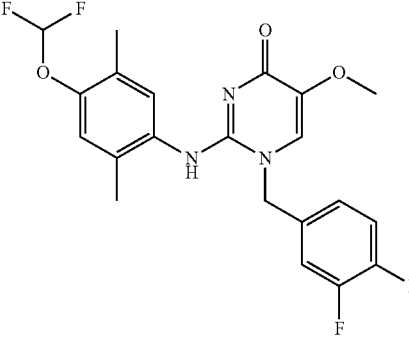 | 438 | 1.77 | [1] |
| I-0303 | 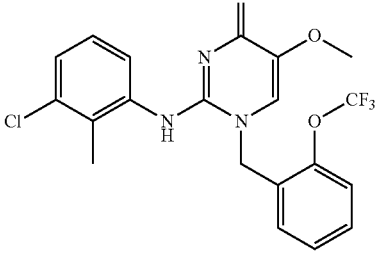 | 440 | 1.99 | [1] |

TABLE 55
| | | | | |
|---|---|---|---|---|
| I-0304 | 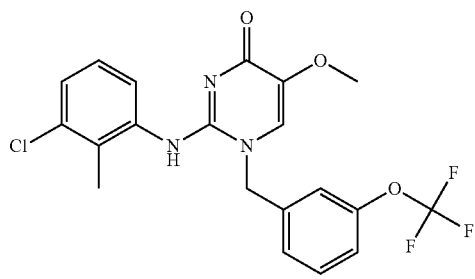 [SMILES: COc1cn(Cc2cccc(OC(F)(F)F)c2)c(Nc2cccc(Cl)c2C)nc1=O] | 440 | 1.99 | [1] |
| I-0305 | 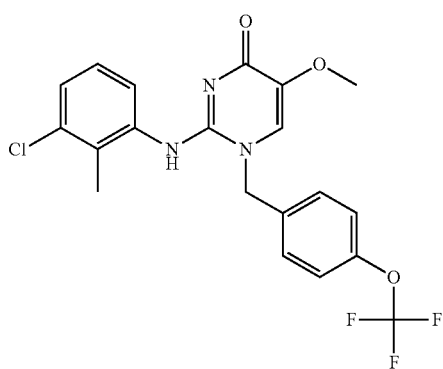 [SMILES: COc1cn(Cc2ccc(OC(F)(F)F)cc2)c(Nc2cccc(Cl)c2C)nc1=O] | 440 | 1.97 | [1] |
| I-0306 | 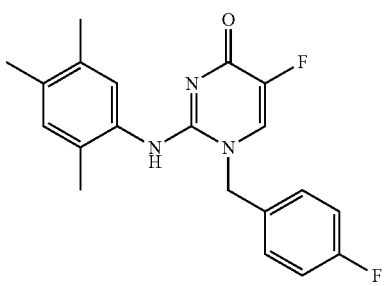 [SMILES: Cc1cc(C)c(Nc2nc(=O)c(F)cn2Cc2ccc(F)cc2)cc1C] | 356 | 1.73 | [1] |
| I-0307 | 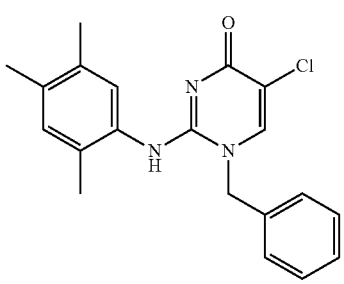 [SMILES: Cc1cc(C)c(Nc2nc(=O)c(Cl)cn2Cc2ccccc2)cc1C] | 354 | 1.81 | [1] |
| I-0308 | 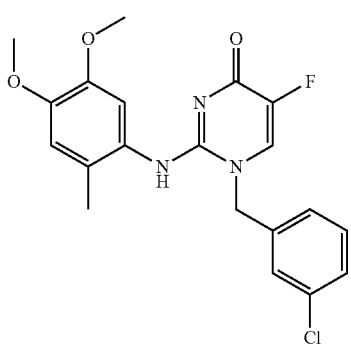 [SMILES: COc1cc(C)c(Nc2nc(=O)c(F)cn2Cc2cccc(Cl)c2)cc1OC] | 404 | 1.53 | [1] |

TABLE 56

| ID | Structure | | | |
|---|---|---|---|---|
| I-0309 | (structure) | 422 | 1.58 | [1] |
| I-0310 | (structure) | 386 | 1.47 | [1] |
| I-0311 | (structure) | 392 | 1.71 | [1] |
| I-0312 | (structure) | 370 | 1.65 | [1] |
| I-0313 | (structure) | 445 | 1.52 | [1] |

TABLE 57

| | | | | |
|---|---|---|---|---|
| I-0314 | (structure) | 402 | 1.8 | [1] |
| I-0315 | (structure) | 418 | 1.87 | [1] |
| I-0316 | (structure) | 436 | 1.97 | [1] |
| I-0317 | (structure) | 424 | 2.08 | [1] |
| I-0318 | (structure) | 354 | 1.59 | [1] |

TABLE 58

| ID | Structure | | | |
|---|---|---|---|---|
| I-0319 | (structure) | 372 | 1.63 | [1] |
| I-0320 | (structure) | 380 | 1.66 | [1] |
| I-0321 | (structure) | 432 | 1.87 | [1] |
| I-0322 | (structure) | 370 | 1.67 | [1] |
| I-0323 | (structure) | 354 | 1.52 | [1] |

TABLE 59

| ID | Structure | MW | RT | Ref |
|---|---|---|---|---|
| I-0324 | (2,3-dimethylphenyl)NH-pyrimidinone, 5-OMe, N1-(3,4-difluorobenzyl) | 372 | 1.59 | [1] |
| I-0325 | (2,3-dimethylphenyl)NH-pyrimidinone, 5-OMe, N1-(3-chloro-4-fluorobenzyl) | 388 | 1.7 | [1] |
| I-0326 | (2,3-dimethylphenyl)NH-pyrimidinone, 5-OMe, N1-(3,5-difluorobenzyl) | 372 | 1.59 | [1] |
| I-0327 | (2-ethylphenyl)NH-pyrimidinone, 5-OMe, N1-(3,5-difluorobenzyl) | 372 | 1.61 | [1] |
| I-0328 | (3-chloro-2-methylphenyl)NH-pyrimidinone, 5-OMe, N1-(2,5-difluorobenzyl) | 392 | 1.75 | [1] |

TABLE 60
| | | | | |
|---|---|---|---|---|
| I-0329 | 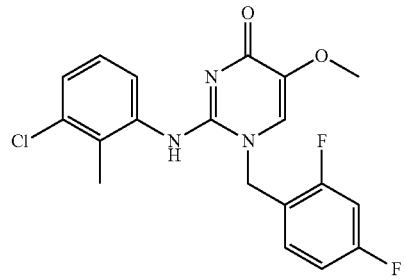 [SMILES: COc1cn(Cc2ccc(F)cc2F)c(Nc2cccc(Cl)c2C)nc1=O] | 392 | 176 | [1] |
| I-0330 | 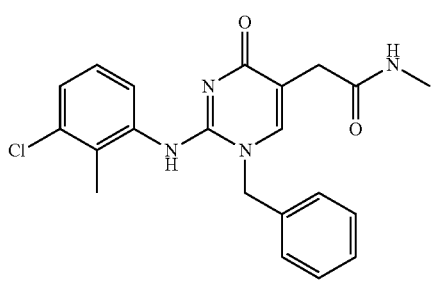 [SMILES: CNC(=O)Cc1cn(Cc2ccccc2)c(Nc2cccc(Cl)c2C)nc1=O] | 397 | 1.84 | [3] |
| I-0331 | 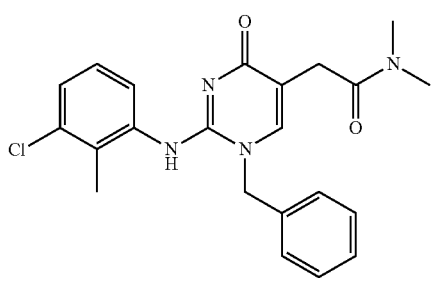 [SMILES: Cc1c(Cl)cccc1Nc1nc(=O)c(CC(=O)N(C)C)cn1Cc1ccccc1] | 411 | 1.89 | [3] |
| I-0332 | 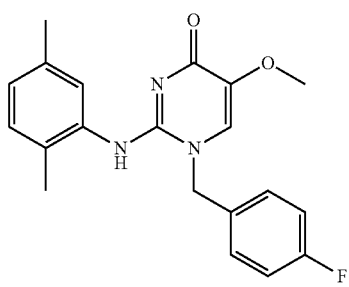 [SMILES: COc1cn(Cc2ccc(F)cc2)c(Nc2cc(C)ccc2C)nc1=O] | 354 | 1.65 | [3] |
| I-0333 | 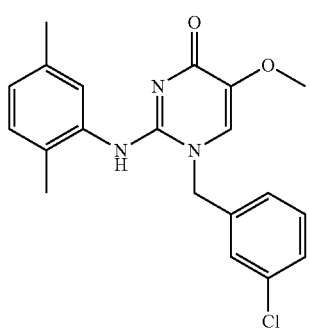 [SMILES: COc1cn(Cc2cccc(Cl)c2)c(Nc2cc(C)ccc2C)nc1=O] | 370 | 1.79 | [3] |

TABLE 61
| | | | | |
|---|---|---|---|---|
| I-0334 | 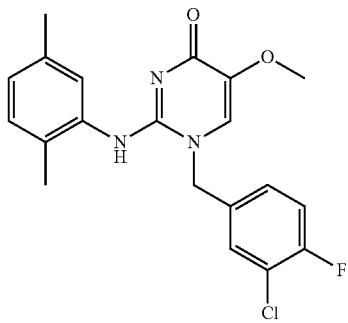 | 388 | 1.84 | [3] |
| I-0335 | 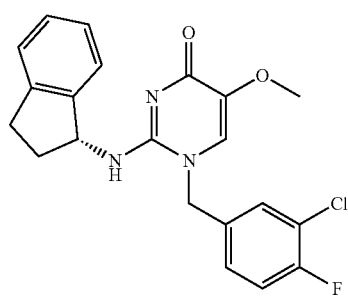 [SMILES: COc1cn(Cc2ccc(F)c(Cl)c2)c(N[C@@H]2CCc3ccccc32)nc1=O] | 400 | 1.87 | [3] |
| I-0336 | 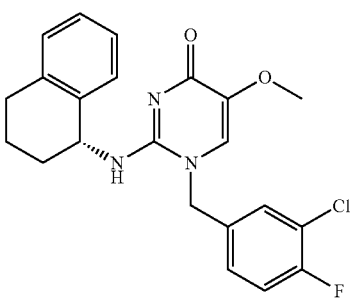 [SMILES: COc1cn(Cc2ccc(F)c(Cl)c2)c(N[C@@H]2CCCc3ccccc32)nc1=O] | 414 | 1.95 | [3] |
| I-0337 | 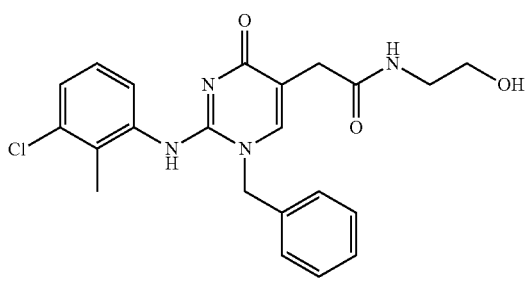 [SMILES: Cc1c(Cl)cccc1Nc1nc(=O)c(CC(=O)NCCO)cn1Cc1ccccc1] | 427 | 1.72 | [3] |
| I-0338 | 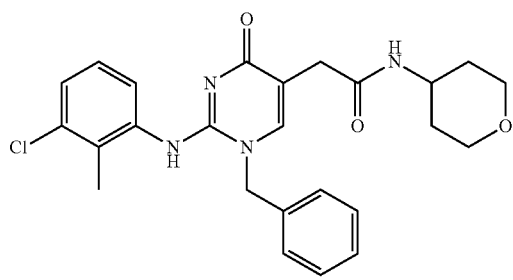 [SMILES: Cc1c(Cl)cccc1Nc1nc(=O)c(CC(=O)NC2CCOCC2)cn1Cc1ccccc1] | 467 | 1.9 | [3] |

TABLE 62
| | | | | |
|---|---|---|---|---|
| I-0339 | 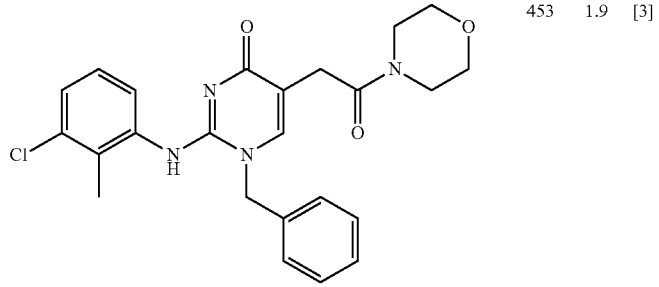 | 453 | 1.9 | [3] |
| I-0340 | 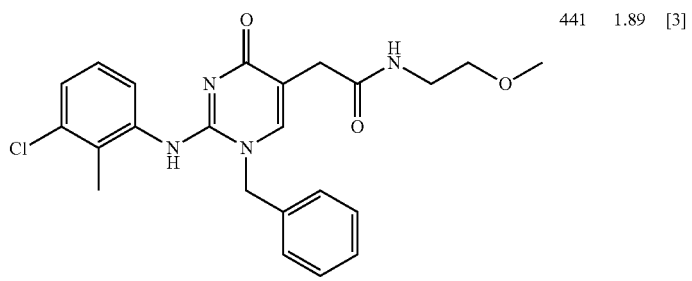 | 441 | 1.89 | [3] |
| I-0341 | 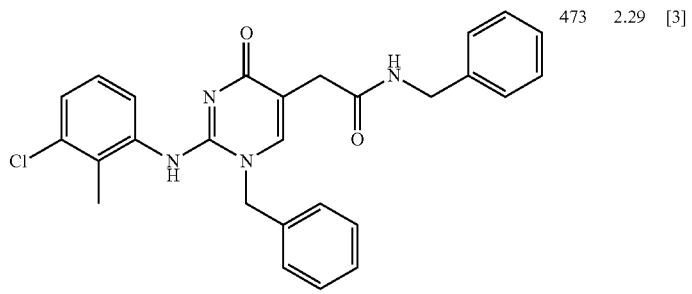 | 473 | 2.29 | [3] |
| I-0342 | 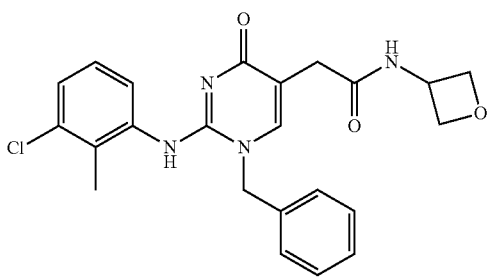 [SMILES: Cc1c(Cl)cccc1Nc1nc(=O)c(CC(=O)NC2COC2)cn1Cc1ccccc1] | 439 | 2.28 | [3] |
| I-0343 | 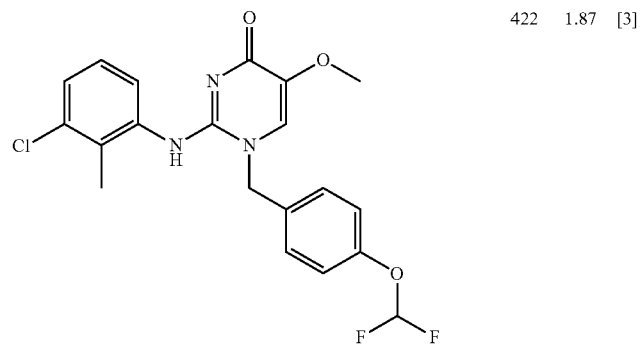 | 422 | 1.87 | [3] |

TABLE 63

| ID | Structure | | | |
|---|---|---|---|---|
| I-0344 | (structure) | 422 | 1.81 | [1] |
| I-0345 | (structure) | 436 | 1.7 | [1] |
| I-0346 | (structure) | 420 | 1.65 | [1] |
| I-0347 | (structure) | 409 | 1.85 | [1] |
| I-0348 | (structure) | 388 | 1.75 | [1] |

TABLE 64
| | | | | |
|---|---|---|---|---|
| I-0349 | 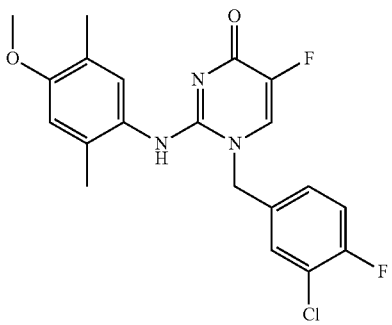 [SMILES: COc1cc(C)c(Nc2nc(=O)c(F)cn2Cc2ccc(F)c(Cl)c2)cc1C] | 406 | 1.78 | [1] |
| I-0350 | 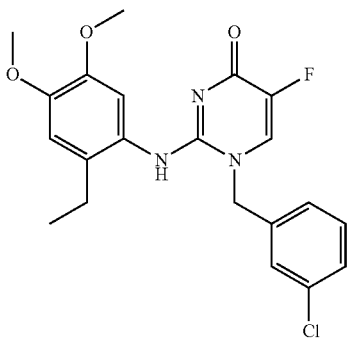 [SMILES: CCc1cc(OC)c(OC)cc1Nc1nc(=O)c(F)cn1Cc1cccc(Cl)c1] | 418 | 1.64 | [1] |
| I-0351 | 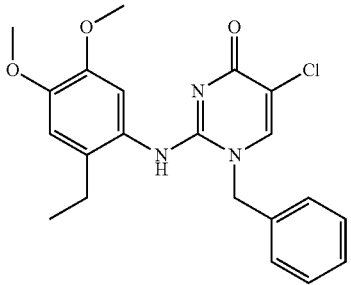 | 400 | 1.61 | [1] |
| I-0352 | 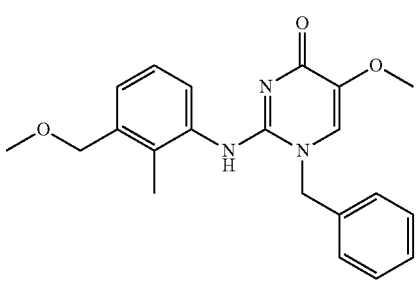 | 366 | 1.37 | [1] |
| I-0353 | 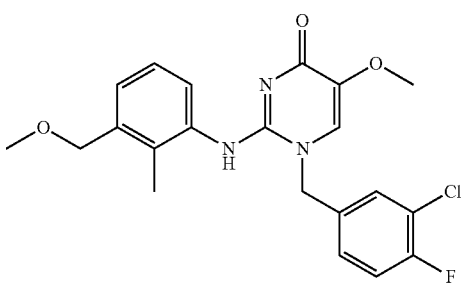 [SMILES: COCc1cccc(Nc2nc(=O)c(OC)cn2Cc2ccc(F)c(Cl)c2)c1C] | 418 | 1.59 | [1] |

TABLE 65

| ID | Structure | NMR | MS | RT | Method |
|---|---|---|---|---|---|
| I-0354 | 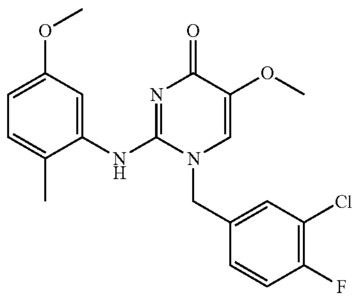 [SMILES: COc1ccc(C)c(Nc2nc(=O)c(OC)cn2Cc2ccc(F)c(Cl)c2)c1] | 1H-NMR (DMSO-D6) δ: 1.74 (s, 3H), 3.60 (s, 3H), 3.70 (s, 3H), 5.17 (s, 2H), 6.65 (s, 1H), 6.72 (d, J = 6.4 Hz, 1H), 7.06 (d, J = 8.0 Hz, 2H), 7.30-7.40 (m, 2H), 7.47 (t, J = 9.6 Hz, 1H), 7.54 (d, J = 6.8 Hz, 1H), 8.32 (s, 1H). | 404 | 1.74 | [1] |
| I-0355 | 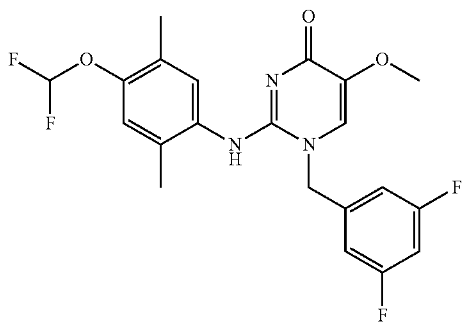 [SMILES: COc1cn(Cc2cc(F)cc(F)c2)c(Nc2cc(C)c(OC(F)F)cc2C)nc1=O] | | 438 | 1.78 | [1] |
| I-0356 | 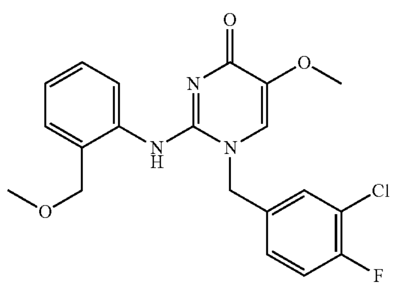 [SMILES: COCc1ccccc1Nc1nc(=O)c(OC)cn1Cc1ccc(F)c(Cl)c1] | | 404 | 1.64 | [1] |
| I-0357 | 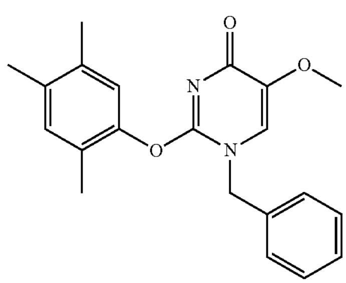 [SMILES: COc1cn(Cc2ccccc2)c(Oc2cc(C)c(C)cc2C)nc1=O] | | 351 | 1.99 | [1] |
| I-0358 | 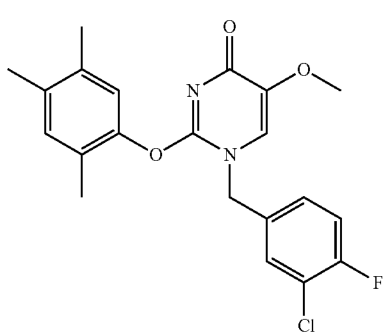 [SMILES: COc1cn(Cc2ccc(F)c(Cl)c2)c(Oc2cc(C)c(C)cc2C)nc1=O] | | 403 | 2.34 | [3] |

TABLE 66
| | | | | |
|---|---|---|---|---|
| I-0359 | 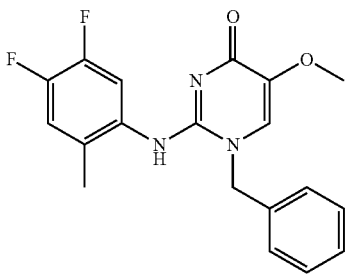 [SMILES: COc1cn(Cc2ccccc2)c(Nc2cc(F)c(F)cc2C)nc1=O] | 358 | 1.63 | [3] |
| I-0360 | 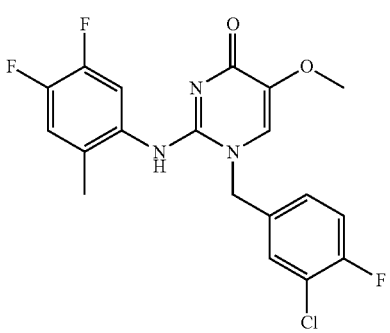 [SMILES: COc1cn(Cc2ccc(F)c(Cl)c2)c(Nc2cc(F)c(F)cc2C)nc1=O] | 410 | 1.77 | [1] |
| I-0361 | 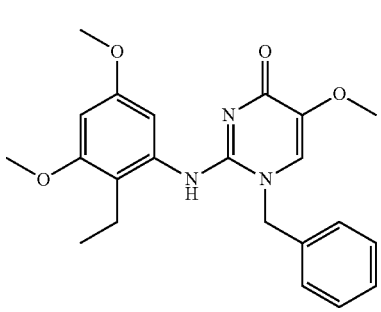 [SMILES: CCc1c(Nc2nc(=O)c(OC)cn2Cc2ccccc2)cc(OC)cc1OC] | 396 | 1.77 | [3] |
| I-0362 | 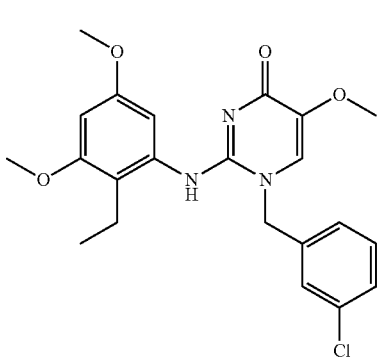 [SMILES: CCc1c(Nc2nc(=O)c(OC)cn2Cc2cccc(Cl)c2)cc(OC)cc1OC] | 430 | 1.94 | [3] |
| I-0363 | 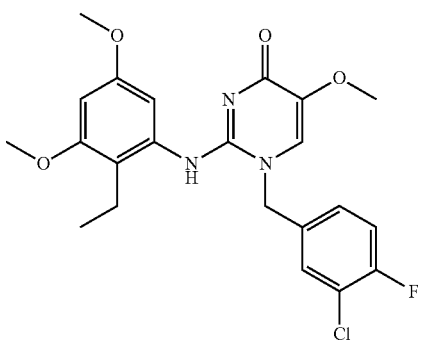 [SMILES: CCc1c(Nc2nc(=O)c(OC)cn2Cc2ccc(F)c(Cl)c2)cc(OC)cc1OC] | 448 | 1.98 | [3] |

TABLE 67

| ID | Structure | NMR | MS | RT | Ref |
|---|---|---|---|---|---|
| I-0364 | 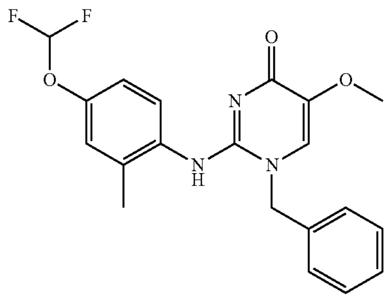 [SMILES: COc1cn(Cc2ccccc2)c(Nc2ccc(OC(F)F)cc2C)nc1=O] | | 388 | 1.7 | [3] |
| I-0365 | 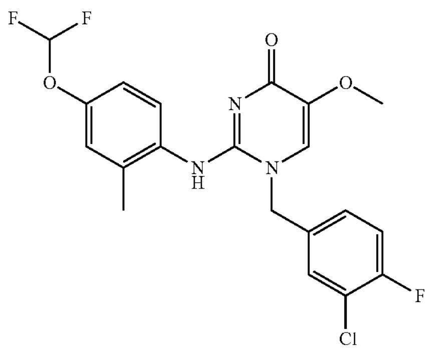 [SMILES: COc1cn(Cc2ccc(F)c(Cl)c2)c(Nc2ccc(OC(F)F)cc2C)nc1=O] | 1H-NMR (DMSO-D6) δ: 1.84 (s, 3H), 3.60 (s, 3H), 5.17 (br s, 2H), 6.88-7.20 (m, 4H), 7.25-7.40 (m, 2H), 7.48 (m, 1H), 7.56 (m, 1H), 8.38 (br s, 1H). | 440 | 1.92 | [1] |
| I-0366 | 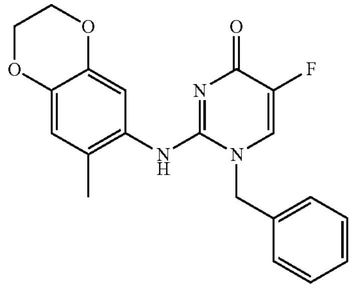 [SMILES: Cc1cc2c(cc1Nc1nc(=O)c(F)cn1Cc1ccccc1)OCCO2] | | 368 | 1.57 | [3] |
| I-0367 | 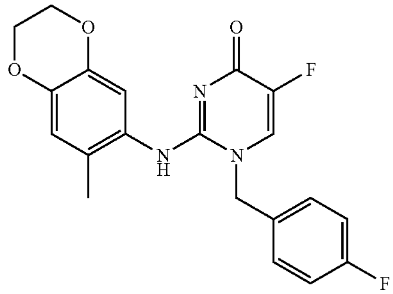 [SMILES: Cc1cc2c(cc1Nc1nc(=O)c(F)cn1Cc1ccc(F)cc1)OCCO2] | | 386 | 1.61 | [3] |
| I-0368 | 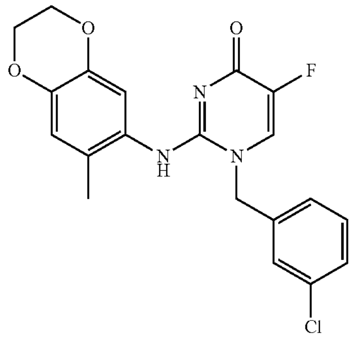 [SMILES: Cc1cc2c(cc1Nc1nc(=O)c(F)cn1Cc1cccc(Cl)c1)OCCO2] | | 402 | 1.75 | [3] |

TABLE 68

| ID | Structure | MS | RT | Method |
|---|---|---|---|---|
| I-0369 | | 420 | 1.79 | [3] |
| I-0370 | | 384 | 1.68 | [3] |
| I-0371 | | 402 | 1.71 | [3] |
| I-0372 | | 1H-NMR (DMSO-D6) δ: 1.83 (s, 3H), 2.08 (s, 3H), 3.59 (s, 3H), 3.75 (s, 3H), 5.19 (s, 2H), 6.74-6.79 (m, 2H), 6.97-7.02 (m, 2H), 7.24 (m, 1H), 7.30 (s, 1H), 8.18 (s, 1H). 402 | 1.59 | [1] |
| I-0373 | | 352 | 1.41 | [1] |

TABLE 69
| | | | | |
|---|---|---|---|---|
| I-0374 | 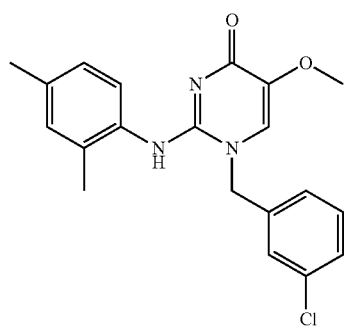 [SMILES: COc1cn(Cc2cccc(Cl)c2)c(Nc2ccc(C)cc2C)nc1=O] | 370 | 1.67 | [1] |
| I-0375 | 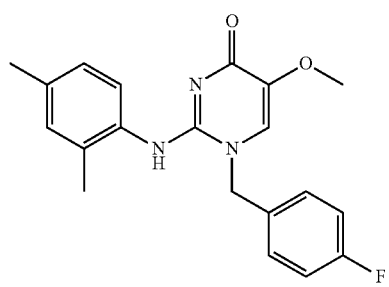 [SMILES: COc1cn(Cc2ccc(F)cc2)c(Nc2ccc(C)cc2C)nc1=O] | 354 | 1.59 | [1] |
| I-0376 | 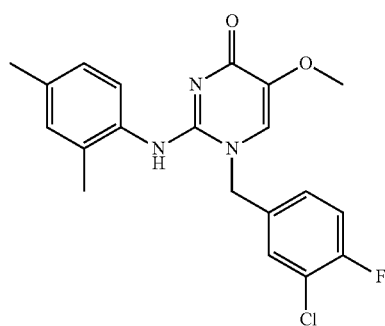 | 388 | 1.76 | [1] |
| I-0377 | 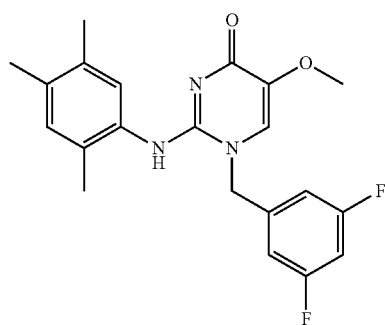 | 386 | 1.7 | [1] |
| I-0378 | 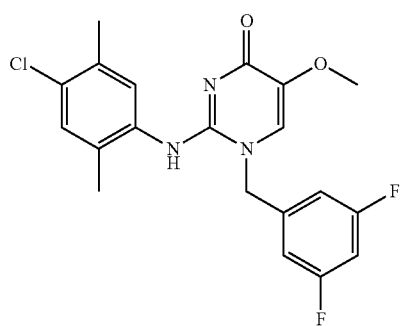 [SMILES: COc1cn(Cc2cc(F)cc(F)c2)c(Nc2cc(C)c(Cl)cc2C)nc1=O] | 406 | 1.84 | [1] |

TABLE 70
| | | | | |
|---|---|---|---|---|
| I-0379 | 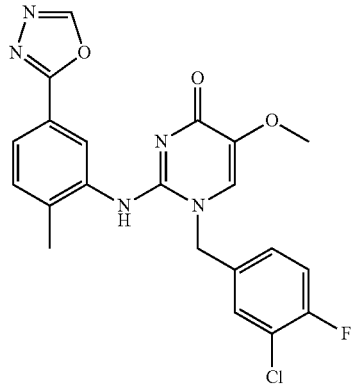 [SMILES: COc1cn(Cc2ccc(F)c(Cl)c2)c(Nc2cc(-c3nnco3)ccc2C)nc1=O] | 442 | 1.57 | [1] |
| I-0380 | 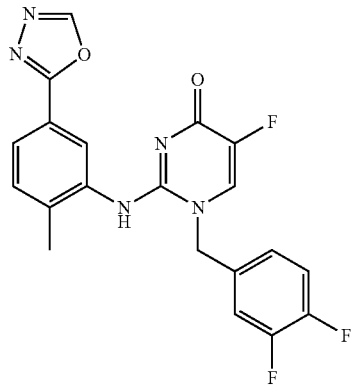 [SMILES: Cc1ccc(-c2nnco2)cc1Nc1nc(=O)c(F)cn1Cc1ccc(F)c(F)c1] | 354 | 1.55 | [1] |
| I-0381 | 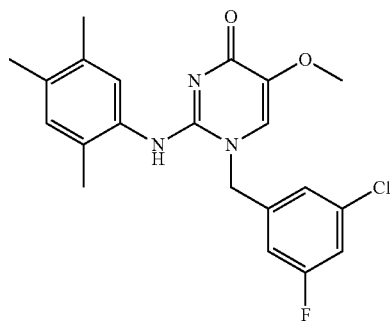 [SMILES: COc1cn(Cc2cc(F)cc(Cl)c2)c(Nc2cc(C)c(C)cc2C)nc1=O] | 402 | 1.83 | [1] |
| I-0382 | 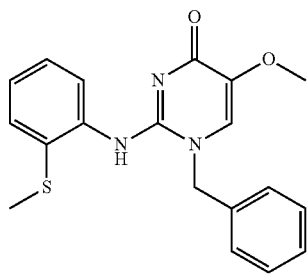 [SMILES: COc1cn(Cc2ccccc2)c(Nc2ccccc2SC)nc1=O] | 354 | 1.52 | [1] |

TABLE 70-continued

| I-0383 | [structure] | 416 | 1.75 | [1] |

TABLE 71

| I-0384 | [structure] | 432 | 1.86 | [1] |
| I-0385 | [structure] | 422 | 2.11 | [3] |
| I-0386 | [structure] | 400 | 1.76 | [3] |

TABLE 71-continued
| | | | | |
|---|---|---|---|---|
| I-0387 | 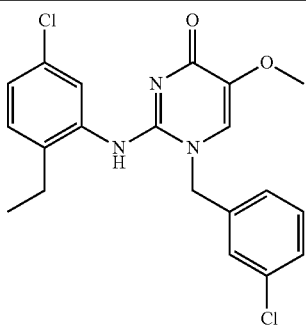 | 405 | 2.01 | [1] |
| I-0388 | 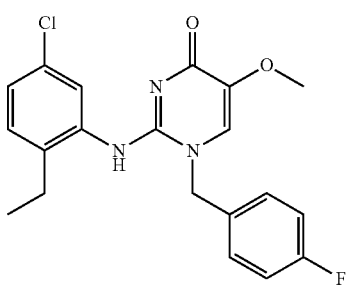 [SMILES: CCc1ccc(Cl)cc1Nc1nc(=O)c(OC)cn1Cc1ccc(F)cc1] | 525 | 1.87 | [1] |
TABLE 72
| | | | | |
|---|---|---|---|---|
| I-0389 | 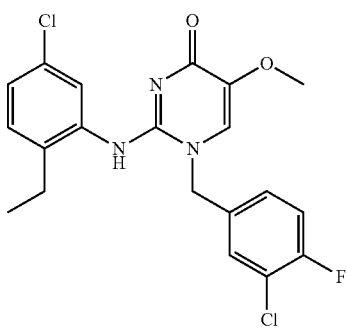 [SMILES: CCc1ccc(Cl)cc1Nc1nc(=O)c(OC)cn1Cc1ccc(F)c(Cl)c1] | 422 | 2.06 | [1] |
| I-0390 | 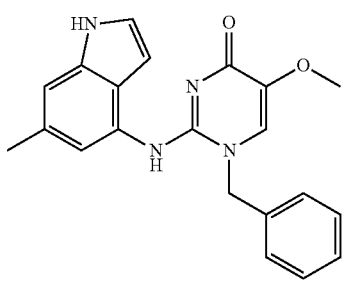 [SMILES: COc1cn(Cc2ccccc2)c(Nc2cc(C)cc3[nH]ccc23)nc1=O] | 361 | 1.37 | [3] |
| I-0391 | 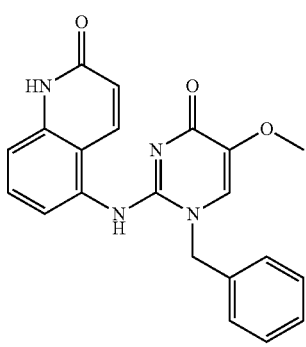 [SMILES: COc1cn(Cc2ccccc2)c(Nc2cccc3[nH]c(=O)ccc23)nc1=O] | 375 | 1.07 | [1] |
| I-0392 | 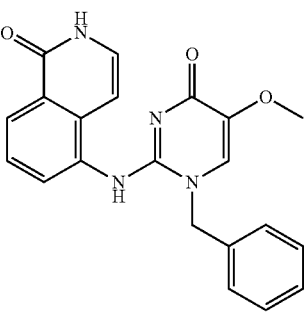 [SMILES: COc1cn(Cc2ccccc2)c(Nc2cccc3c(=O)[nH]ccc23)nc1=O] | 375 | 1.05 | [1] |
| I-0393 | 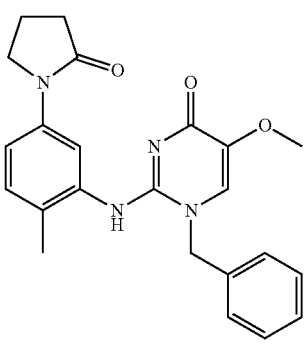 [SMILES: COc1cn(Cc2ccccc2)c(Nc2cc(N3CCCC3=O)ccc2C)nc1=O] | 405 | 1.36 | [1] |

TABLE 73

| | | | | |
|---|---|---|---|---|
| I-0394 | | 418 | 1.71 | [3] |
| I-0395 | | 418 | 1.81 | [1] |
| I-0396 | | 413 | 1.54 | [3] |
| I-0397 | | 427 | 1.33 | [1] |
| I-0398 | | 427 | 1.35 | [1] |

TABLE 74
| | | | |
|---|---|---|---|
| I-0399 | 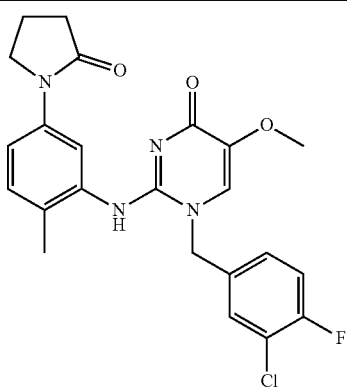 | 457 1.52 | [1] |
| I-0400 | 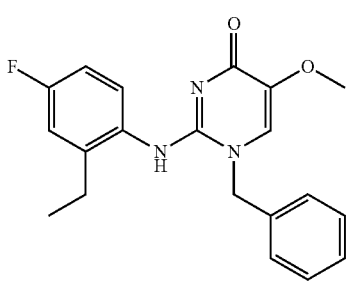 [SMILES: CCc1cc(F)ccc1Nc1nc(=O)c(OC)cn1Cc1ccccc1] | 354 1.55 | [1] |
| I-0401 | 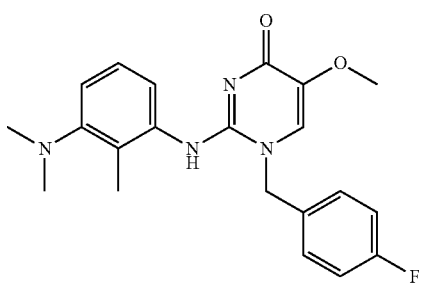 [SMILES: COc1cn(Cc2ccc(F)cc2)c(Nc2cccc(N(C)C)c2C)nc1=O] | 383 0.87 | [1] |
| I-0402 | 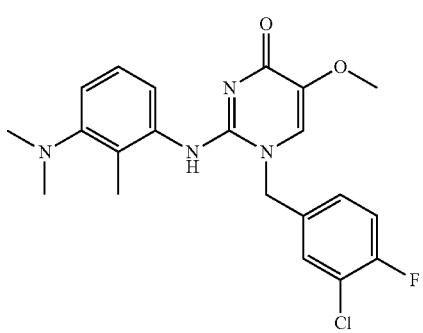 [SMILES: COc1cn(Cc2ccc(F)c(Cl)c2)c(Nc2cccc(N(C)C)c2C)nc1=O] | 417 1.11 | [1] |
| I-0403 | 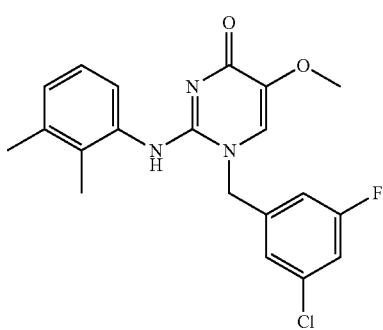 [SMILES: COc1cn(Cc2cc(F)cc(Cl)c2)c(Nc2cccc(C)c2C)nc1=O] | 388 1.73 | [1] |

TABLE 75

| ID | Structure | | | |
|---|---|---|---|---|
| I-0404 | (2,5-dimethyl-3-methoxyphenyl)NH–[5-methoxy-1-(3,4-difluorobenzyl)pyrimidin-4(1H)-one-2-yl] | 402 | 1.68 | [1] |
| I-0405 | (2,5-dimethyl-3-methoxyphenyl)NH–[5-methoxy-1-(3-fluorobenzyl)pyrimidin-4(1H)-one-2-yl] | 384 | 1.61 | [1] |
| I-0406 | (4,5-dimethoxy-2-methylphenyl)NH–[5-chloro-1-(4-fluorobenzyl)pyrimidin-4(1H)-one-2-yl] | 403 | 1.52 | [1] |
| I-0407 | (5-methoxy-2-methylphenyl)NH–[5-methoxy-1-(3,4-difluorobenzyl)pyrimidin-4(1H)-one-2-yl] | 388 | 1.54 | [1] |
| I-0408 | (5-methoxy-2-methylphenyl)NH–[5-methoxy-1-(3,5-difluorobenzyl)pyrimidin-4(1H)-one-2-yl] | 388 | 1.64 | [3] |

TABLE 76
| | | | |
|---|---|---|---|
| I-0409 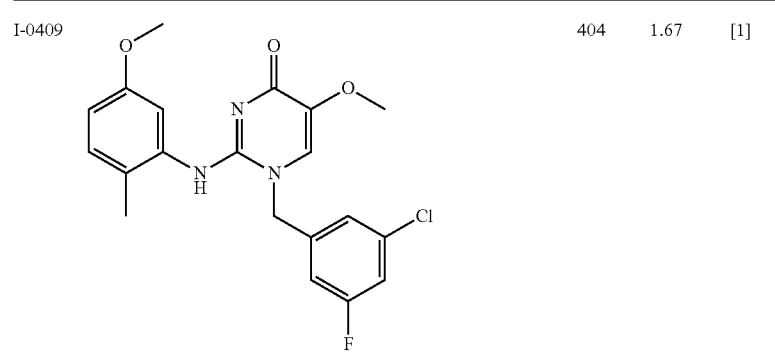 | 404 | 1.67 | [1] |
| I-0410 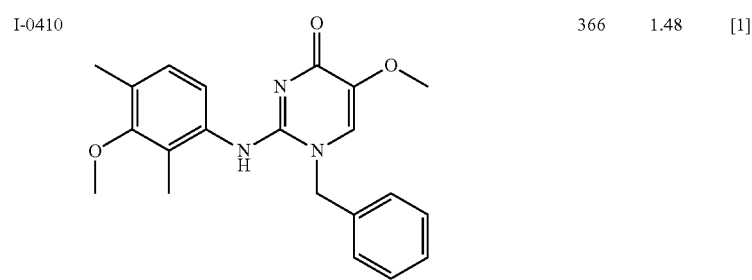 | 366 | 1.48 | [1] |
| I-0411 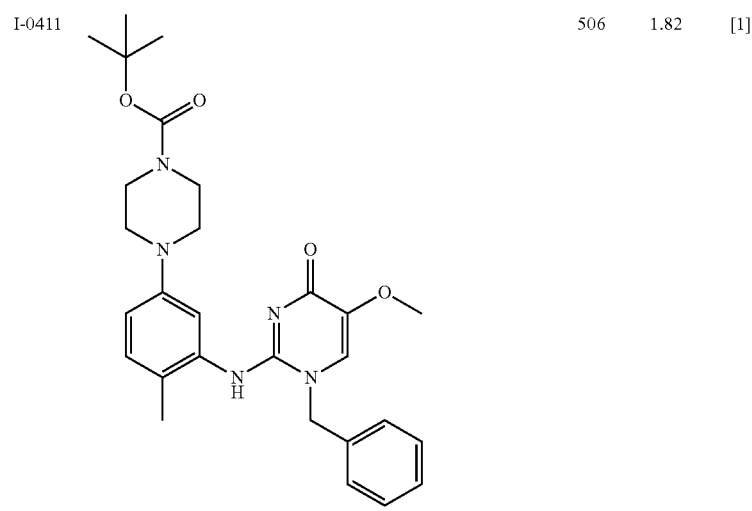 | 506 | 1.82 | [1] |

TABLE 76-continued
| | | | | |
|---|---|---|---|---|
| I-0412 | 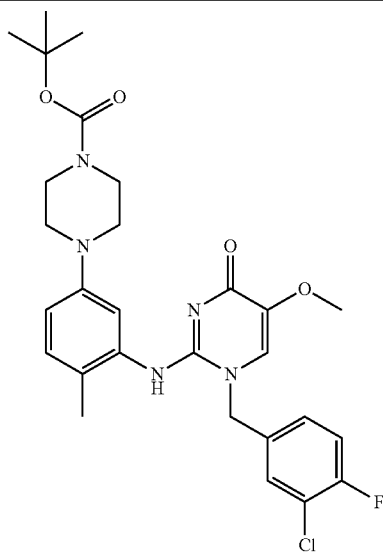 | 558 | 2.06 | [1] |
TABLE 77
| | | | | |
|---|---|---|---|---|
| I-0413 | 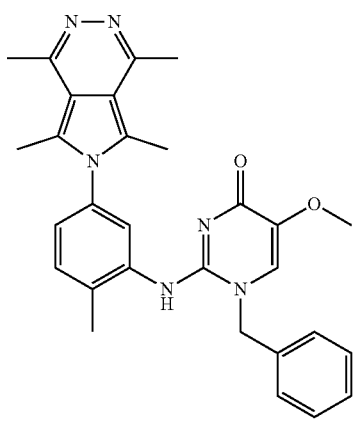 | 495 | 1.29 | [1] |
| I-0414 | 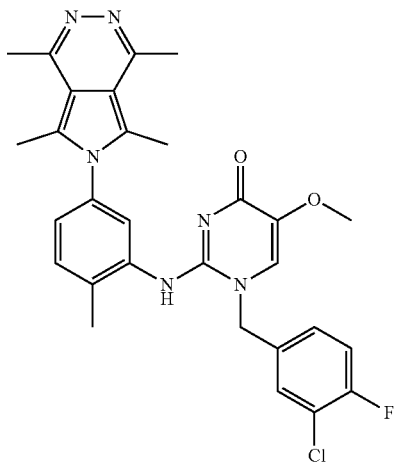 [SMILES: COc1cn(Cc2ccc(F)c(Cl)c2)c(Nc2cc(-n3c(C)c4c(C)nnc(C)c4c3C)ccc2C)nc1=O] | 547 | 1.41 | [1] |

TABLE 77-continued
| I-0415 | 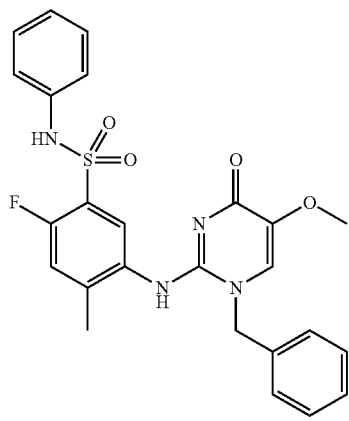 [SMILES: COc1cn(Cc2ccccc2)c(Nc2cc(S(=O)(=O)Nc3ccccc3)c(F)cc2C)nc1=O] | 495 | 1.67 | [1] |
| I-0416 | 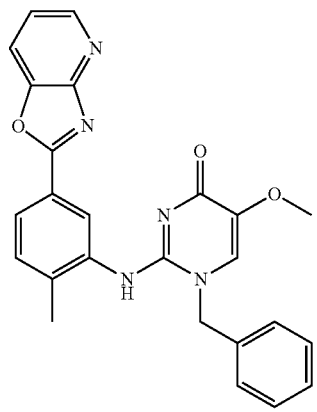 [SMILES: COc1cn(Cc2ccccc2)c(Nc2cc(-c3nc4ncccc4o3)ccc2C)nc1=O] | 440 | 1.49 | [1] |
TABLE 78
| I-0417 | 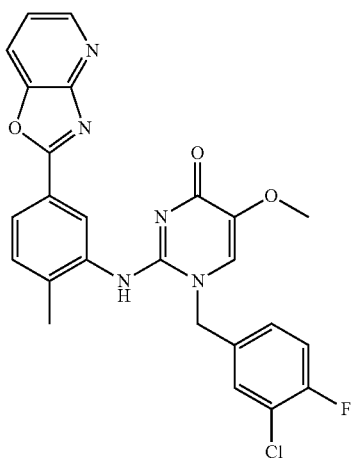 [SMILES: COc1cn(Cc2ccc(F)c(Cl)c2)c(Nc2cc(-c3nc4ncccc4o3)ccc2C)nc1=O] | 492 | 1.44 | [1] |
| I-0418 | 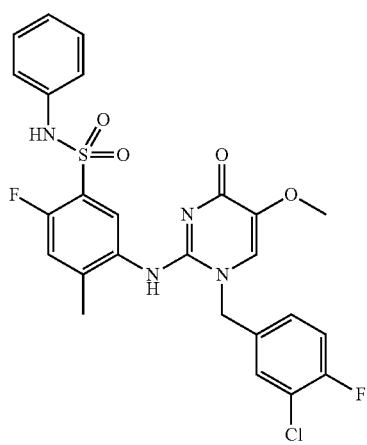 [SMILES: COc1cn(Cc2ccc(F)c(Cl)c2)c(Nc2cc(S(=O)(=O)Nc3ccccc3)c(F)cc2C)nc1=O] | 547 | 1.94 | [1] |

TABLE 78-continued

| ID | Structure | MW | RT | [M] |
|---|---|---|---|---|
| I-0419 | (2,4-dimethyl-3-methoxyphenyl)amino / 5-methoxy pyrimidinone / 3-chloro-4-fluorobenzyl | 418 | 1.7 | [1] |
| I-0420 | (4-fluoro-2-ethylphenyl)amino / 5-methoxy pyrimidinone / 3-chloro-4-fluorobenzyl | 406 | 1.79 | [1] |

TABLE 79

| ID | Structure | MW | RT | [M] |
|---|---|---|---|---|
| I-0421 | (3-chloro-2-methylphenyl)amino / 5-methoxy pyrimidinone / 2-(difluoromethoxy)benzyl | 422 | 1.95 | [3] |
| I-0422 | (3-chloro-2-methylphenyl)amino / 5-methoxy pyrimidinone / 3-(difluoromethoxy)benzyl | 422 | 1.93 | [3] |
| I-0423 | (4,5-dichloro-2-methylphenyl)amino / 5-methoxy pyrimidinone / benzyl | 390 | 2 | [3] |

TABLE 79-continued

| ID | Structure | MW | RT | [M] |
|---|---|---|---|---|
| I-0424 | (3-methoxy-5-methyl-2-methylphenyl)amino / 5-methoxy pyrimidinone / 3-chloro-4-fluorobenzyl | 418 | 1.77 | [1] |
| I-0425 | (3-chloro-2-methylphenyl)amino / 5-methoxy pyrimidinone / 3-fluoro-5-methylbenzyl | 388 | 1.81 | [1] |

TABLE 80

| ID | Structure | MW | RT | [M] |
|---|---|---|---|---|
| I-0426 | (4,5-dichloro-2-methylphenyl)amino / 5-methoxy pyrimidinone / 3-chloro-4-fluorobenzyl | 442 | 2.1 | [3] |
| I-0427 | (3-chloro-2-methylphenyl)amino / 5-methoxy pyrimidinone / 3-fluoro-5-methoxybenzyl | 404 | 1.72 | [1] |
| I-0428 | (3-methoxy-2,5-dimethylphenyl)amino / 5-methoxy pyrimidinone / 3-chlorobenzyl | 400 | 1.73 | [1] |

TABLE 80-continued
| I-0429 | 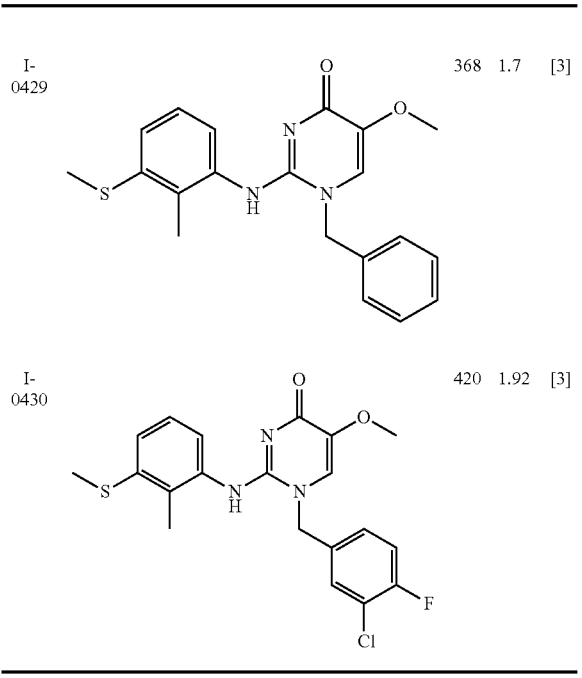 | 368 | 1.7 | [3] |
| I-0430 | | 420 | 1.92 | [3] |
TABLE 81
| I-0431 | 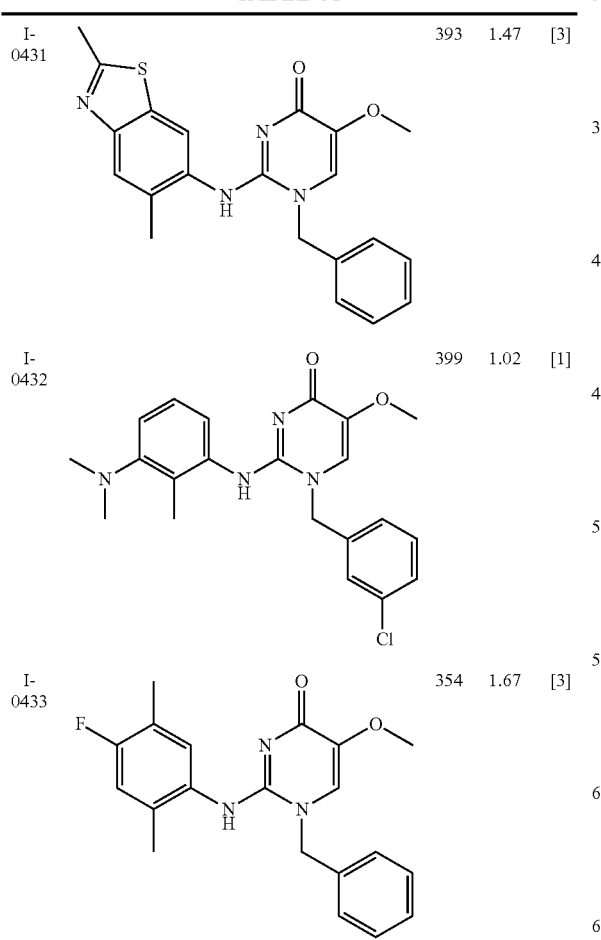 | 393 | 1.47 | [3] |
| I-0432 | | 399 | 1.02 | [1] |
| I-0433 | | 354 | 1.67 | [3] |
TABLE 81-continued
| I-0434 | 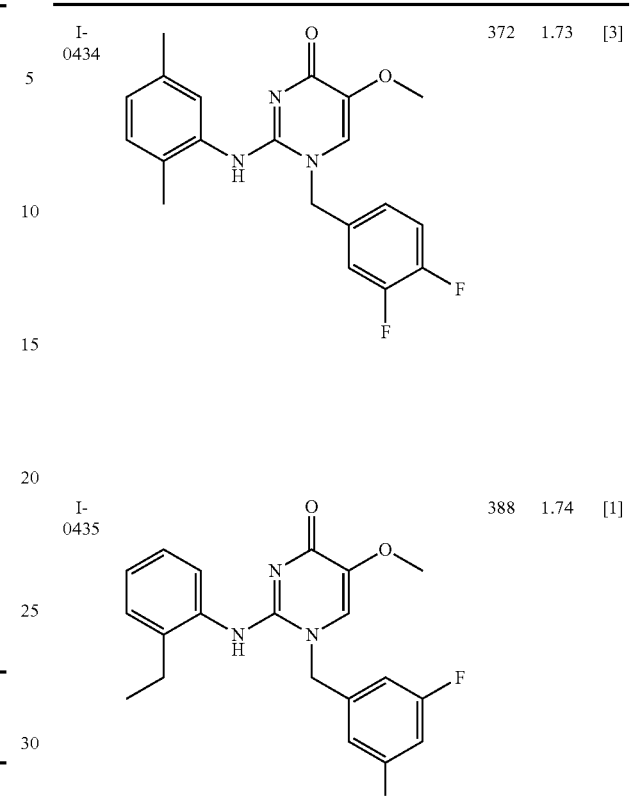 | 372 | 1.73 | [3] |
| I-0435 | | 388 | 1.74 | [1] |
TABLE 82
| I-0436 | 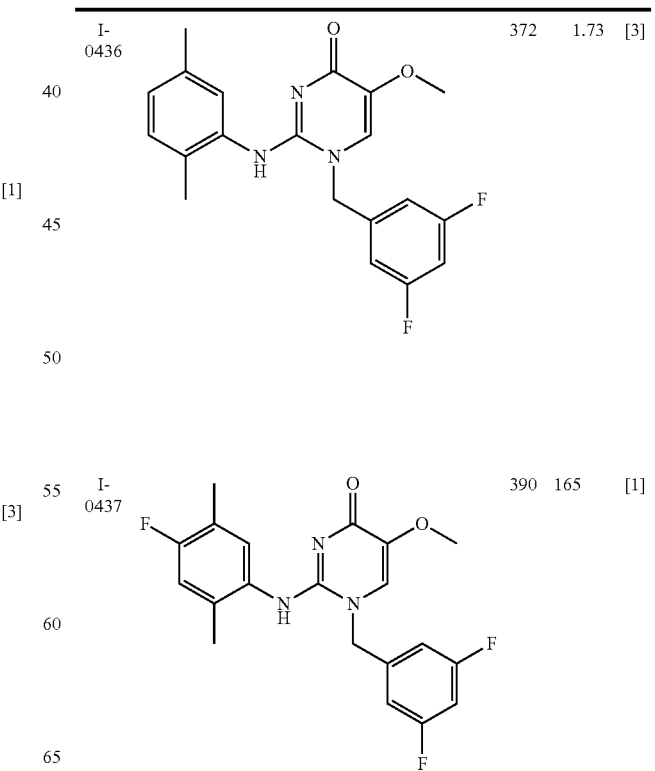 | 372 | 1.73 | [3] |
| I-0437 | | 390 | 165 | [1] |

TABLE 82-continued

| ID | Structure | MW | RT | Method |
|---|---|---|---|---|
| I-0438 | (3-methoxy-2-methylphenyl)amino; 5-methoxy; 1-(3,5-difluorobenzyl)pyrimidin-4(1H)-one | 388 | 1.67 | [3] |
| I-0439 | (4,5-dimethoxy-2-methylphenyl)amino; 5-methoxy; 1-(3,5-difluorobenzyl)pyrimidin-4(1H)-one | 418 | 1.52 | [3] |
| I-0440 | (2-ethyl-4-methoxyphenyl)amino; 5-methoxy; 1-(3,5-difluorobenzyl)pyrimidin-4(1H)-one | 402 | 1.7 | [3] |

TABLE 83

| ID | Structure | MW | RT | Method |
|---|---|---|---|---|
| I-0441 | benzo[b]thiophen-4-ylamino; 5-methoxy; 1-(3,5-difluorobenzyl)pyrimidin-4(1H)-one | 400 | 1.86 | [3] |
| I-0442 | (4-fluoro-2,5-dimethylphenyl)amino; 5-methoxy; 1-(3-fluorobenzyl)pyrimidin-4(1H)-one | 372 | 1.71 | [3] |
| I-0443 | (4-fluoro-2,5-dimethylphenyl)amino; 5-methoxy; 1-(4-fluorobenzyl)pyrimidin-4(1H)-one | 372 | 1.71 | [3] |
| I-0444 | (5-(1,3,4-oxadiazol-2-yl)-2-methylphenyl)amino; 5-methoxy; 1-(3-chlorobenzyl)pyrimidin-4(1H)-one | 424 | 1.58 | [3] |
| I-0445 | (2,5-dimethylphenyl)amino; 5-methoxy; 1-(3-chloro-5-fluorobenzyl)pyrimidin-4(1H)-one | 388 | 1.87 | [3] |

TABLE 84

| ID | Structure | MW | RT | Method |
|---|---|---|---|---|
| I-0446 | (4-methoxy-2,5-dimethylphenyl)amino; 5-methoxy; 1-(3-chloro-5-fluorobenzyl)pyrimidin-4(1H)-one | 418 | 1.85 | [3] |

TABLE 84-continued
| I-0447 | 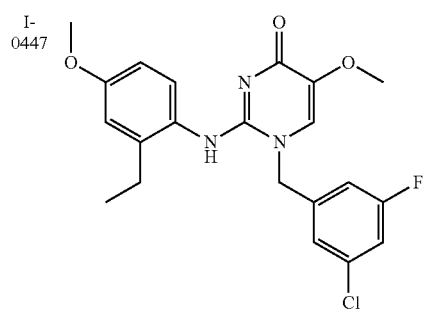 | 418 | 1.85 | [3] |
| I-0448 | 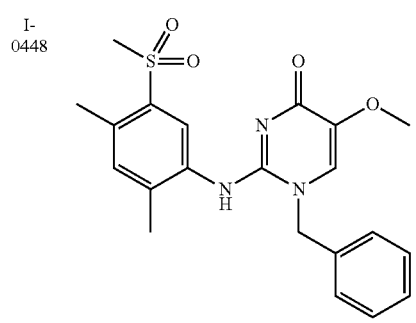 | 414 | 1.48 | [3] |
| I-0449 | 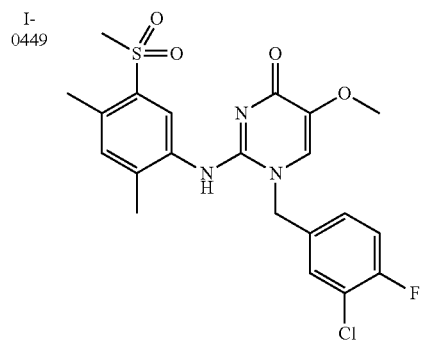 | 466 | 1.71 | [3] |
| I-0450 | 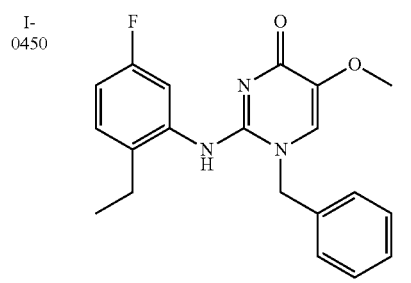 | 354 | 1.62 | [1] |
| I-0451 | 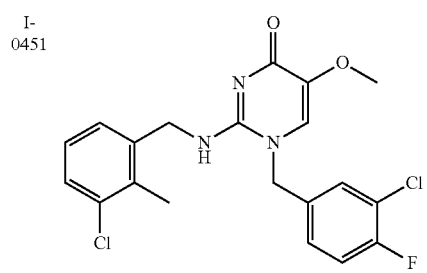 | 422 | 1.95 | [3] |
TABLE 85
| I-0452 | 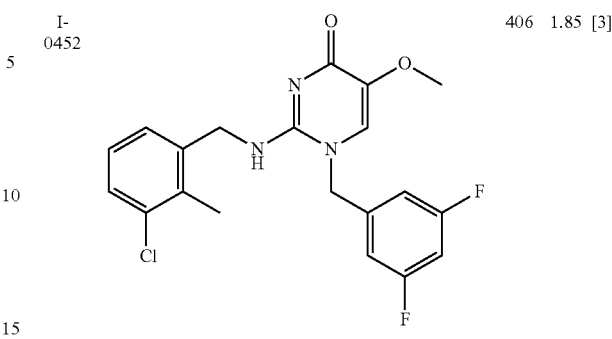 | 406 | 1.85 | [3] |
| I-0453 | 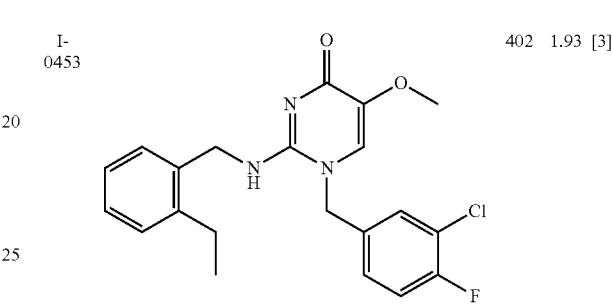 | 402 | 1.93 | [3] |
| I-0454 | 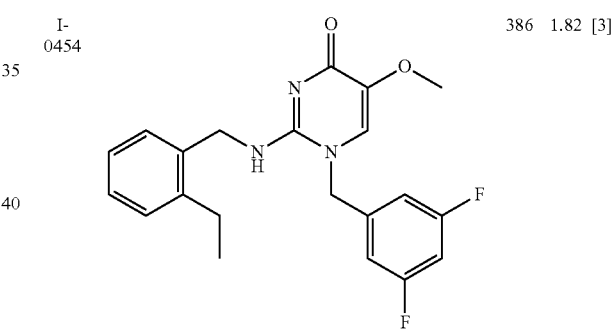 | 386 | 1.82 | [3] |
| I-0455 | 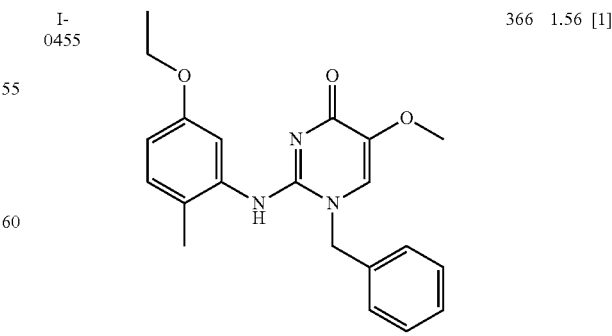 | 366 | 1.56 | [1] |

TABLE 85-continued
| | | | |
|---|---|---|---|
| I-0456 | 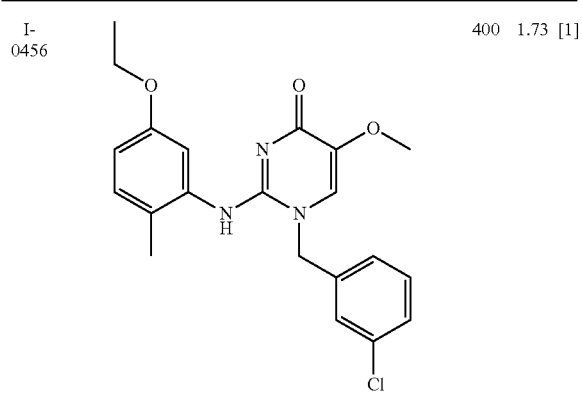 | 400 | 1.73 [1] |
TABLE 86
| | | | |
|---|---|---|---|
| I-0457 | 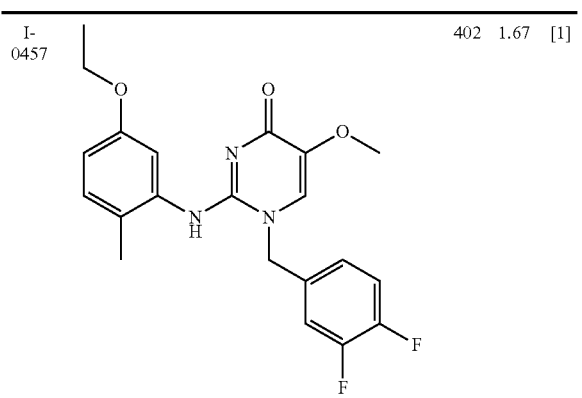 | 402 | 1.67 [1] |
| I-0458 | 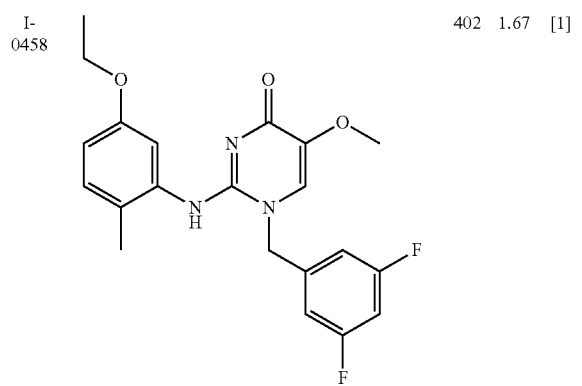 | 402 | 1.67 [1] |
| I-0459 | 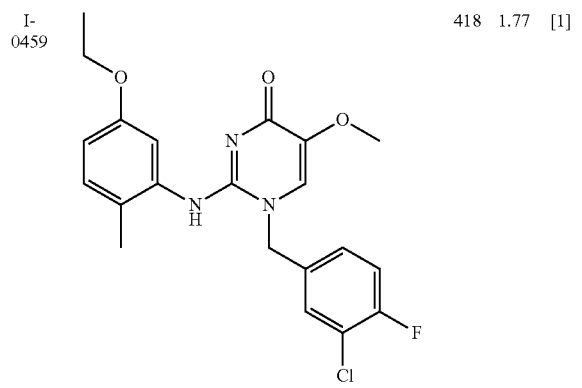 | 418 | 1.77 [1] |
TABLE 86-continued
| | | | |
|---|---|---|---|
| I-0460 | 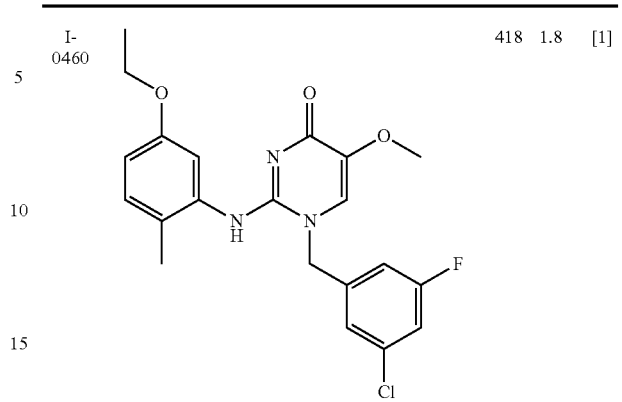 | 418 | 1.8 [1] |
| I-0461 | 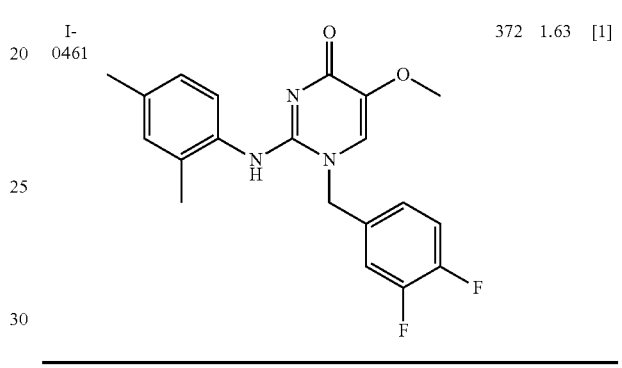 | 372 | 1.63 [1] |
TABLE 87
| | | | |
|---|---|---|---|
| I-0462 | 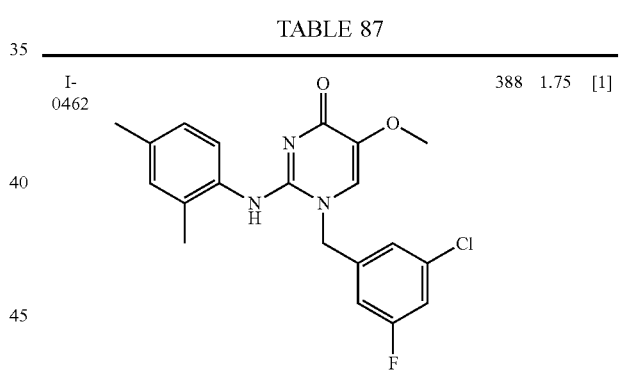 | 388 | 1.75 [1] |
| I-0463 | 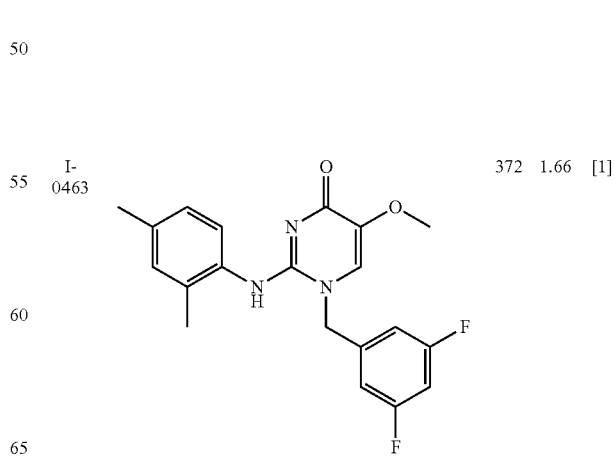 | 372 | 1.66 [1] |

TABLE 87-continued

| ID | Structure | MW | RT | Method |
|---|---|---|---|---|
| I-0464 | 5-chloro-4-methoxy-2-methylphenyl / 1-benzyl / 5-methoxy pyrimidinone | 386 | 1.57 | [1] |
| I-0465 | 5-chloro-4-methoxy-2-methylphenyl / 1-(3-chloro-4-fluorobenzyl) / 5-methoxy pyrimidinone | 438 | 1.75 | [1] |
| I-0466 | 2-methyl-3-(trifluoromethyl)phenyl / 1-(3-chlorobenzyl) / 5-methoxy pyrimidinone | 424 | 2.07 | [3] |
| I-0467 | 2-methyl-3-(trifluoromethyl)phenyl / 1-(3,4-difluorobenzyl) / 5-methoxy pyrimidinone | 426 | 2 | [3] |

TABLE 88

| ID | Structure | MW | RT | Method |
|---|---|---|---|---|
| I-0468 | 2-methyl-3-(trifluoromethyl)phenyl / 1-(3-chloro-4-fluorobenzyl) / 5-methoxy pyrimidinone | 442 | 2.12 | [3] |
| I-0469 | 4,5-dimethoxy-2-methylphenyl / 1-(3-chloro-5-fluorobenzyl) / 5-methoxy pyrimidinone | 434 | 1.64 | [3] |
| I-0470 | 2-methyl-3-(trifluoromethyl)phenyl / 1-(3,5-difluorobenzyl) / 5-methoxy pyrimidinone | 426 | 2.03 | [3] |
| I-0471 | 3-chloro-2-methylphenyl / 1-(3,4-difluorobenzyl) / 5-fluoro pyrimidinone | 380 | 1.94 | [3] |
| I-0472 | 3-chloro-2-methylphenyl / 1-(3,4-difluorobenzyl) / 5-chloro pyrimidinone | 396 | 2.2 | [3] |
| I-0473 | 4-chloro-5-methoxy-2-methylphenyl / 1-benzyl / 5-methoxy pyrimidinone | 386 | 1.77 | [3] |

TABLE 89
| ID | Structure | MW | RT | Method |
|---|---|---|---|---|
| I-0474 | 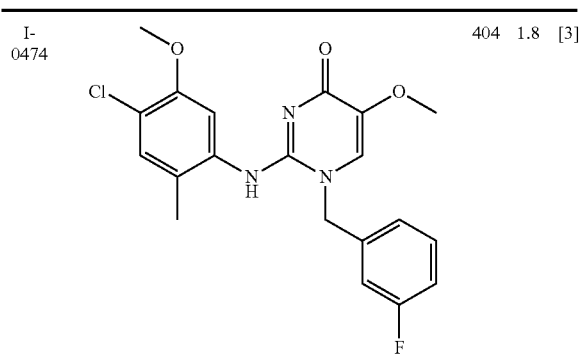 | 404 | 1.8 | [3] |
| I-0475 | 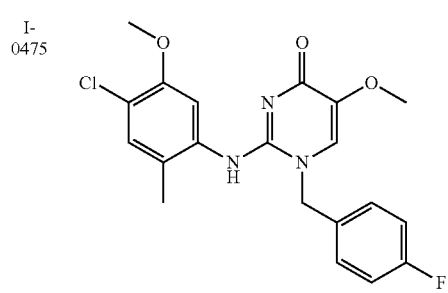 | 404 | 1.8 | [3] |
| I-0476 | 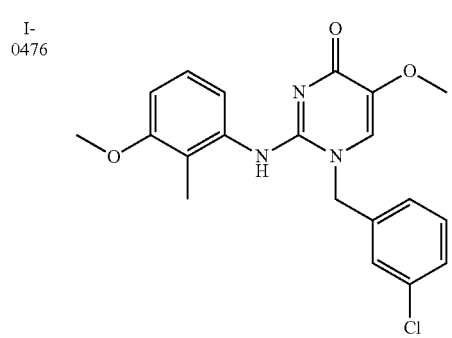 | 386 | 1.75 | [3] |
| I-0477 | 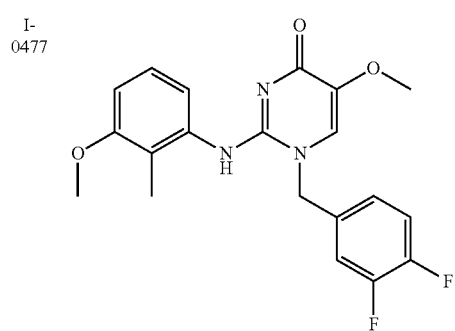 | 388 | 1.67 | [3] |
| I-0478 | 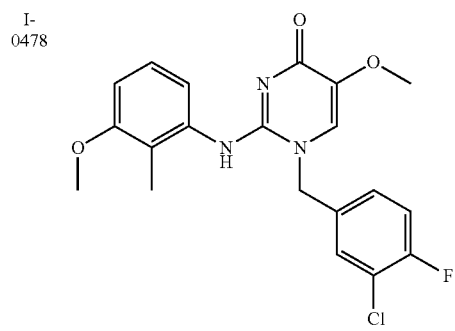 | 404 | 1.79 | [3] |
TABLE 90
| ID | Structure | MW | RT | Method |
|---|---|---|---|---|
| I-0479 | 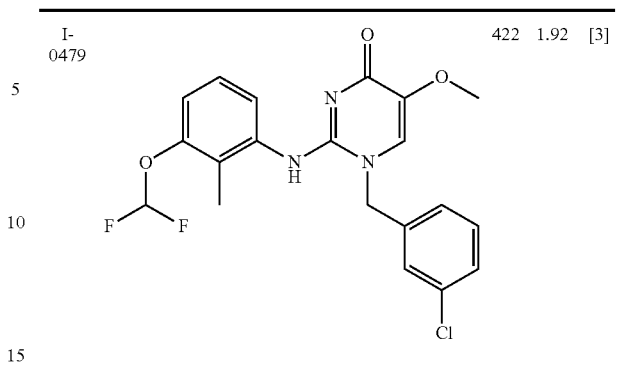 | 422 | 1.92 | [3] |
| I-0480 | 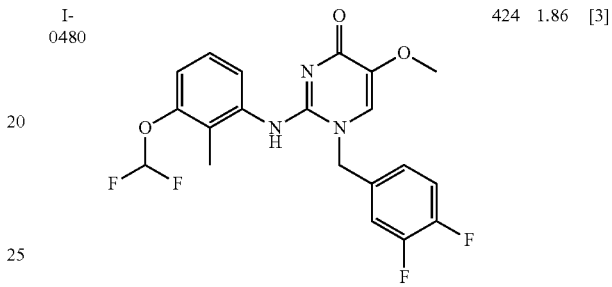 | 424 | 1.86 | [3] |
| I-0481 | 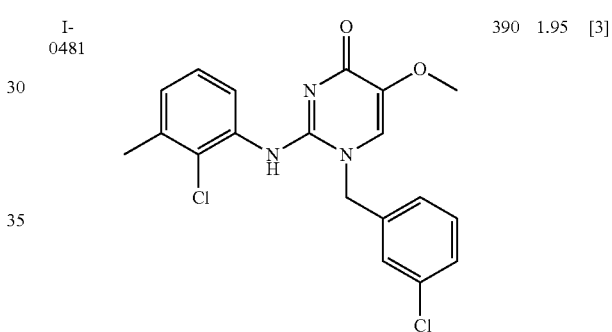 | 390 | 1.95 | [3] |
| I-0482 | 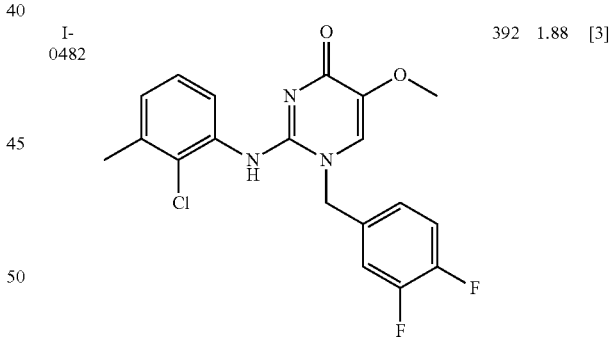 | 392 | 1.88 | [3] |
| I-0483 | 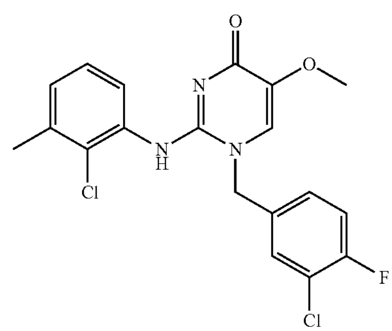 [SMILES: COc1cn(Cc2ccc(F)c(Cl)c2)c(Nc2cccc(C)c2Cl)nc1=O] | 408 | 2 | [3] |

TABLE 91
| I-0484 | 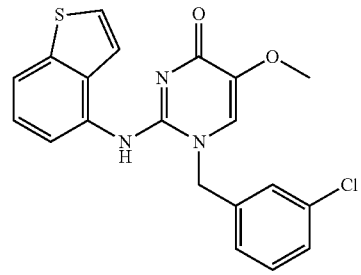 [SMILES: COc1cn(Cc2cccc(Cl)c2)c(Nc2cccc3sccc23)nc1=O] | 398 | 1.86 | [3] |
| I-0485 | 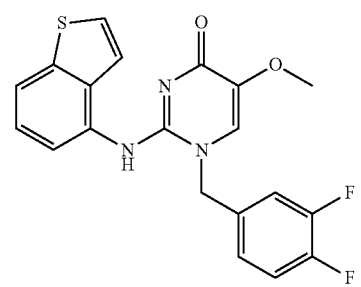 | 400 | 1.79 | [3] |
| I-0486 | 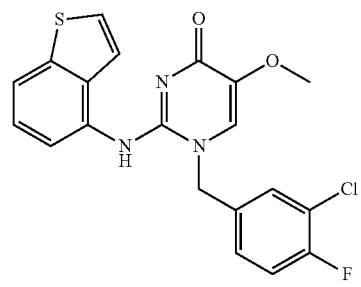 | 416 | 1.91 | [3] |
| I-0487 | 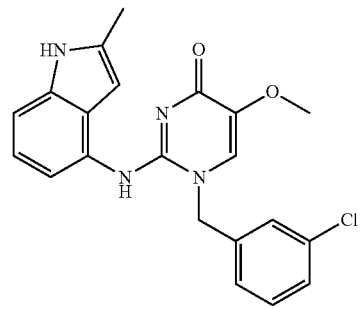 [SMILES: COc1cn(Cc2cccc(Cl)c2)c(Nc2cccc3[nH]c(C)cc23)nc1=O] | 395 | 1.59 | [3] |
| I-0488 | 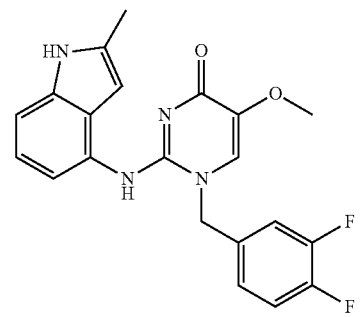 [SMILES: COc1cn(Cc2ccc(F)c(F)c2)c(Nc2cccc3[nH]c(C)cc23)nc1=O] | 397 | 1.53 | [3] |
TABLE 91-continued
| I-0489 | 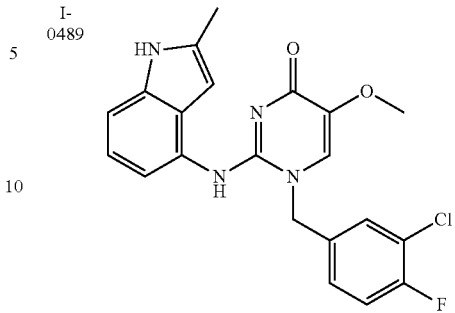 | 413 | 1.64 | [3] |
TABLE 92
| I-0490 | 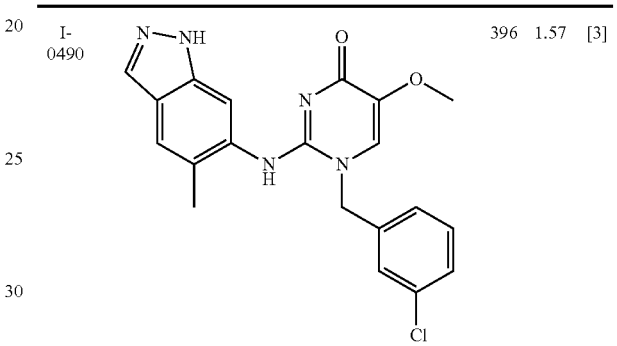 | 396 | 1.57 | [3] |
| I-0491 | 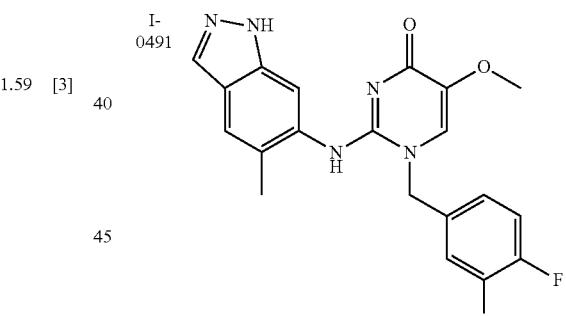 | 398 | 1.49 | [3] |
| I-0492 | 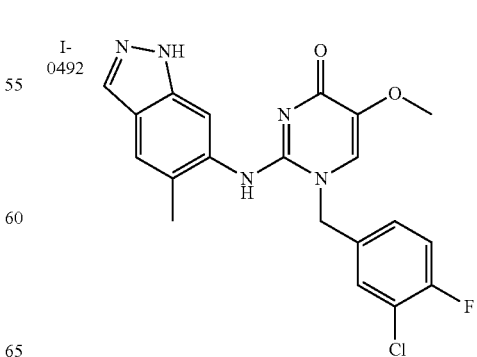 | 414 | 1.6 | [3] |

TABLE 92-continued
| | | | | |
|---|---|---|---|---|
| I-0493 | 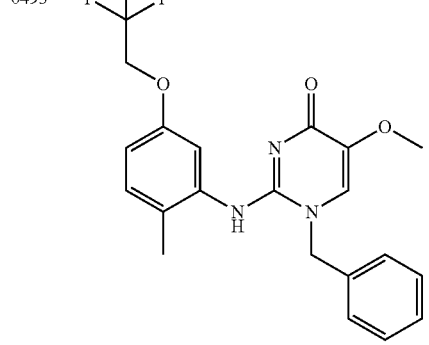 | 420 | 1.73 | [1] |
| I-0494 | 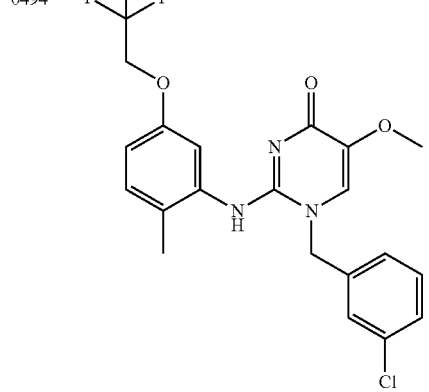 | 454 | 1.88 | [1] |
TABLE 93
| | | | | |
|---|---|---|---|---|
| I-0495 | 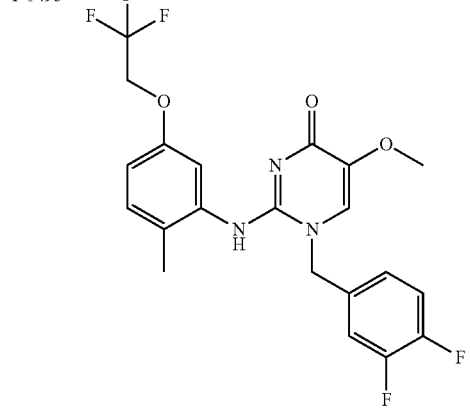 | 456 | 1.83 | [1] |

TABLE 93-continued
| | | | | |
|---|---|---|---|---|
| 1-0496 | 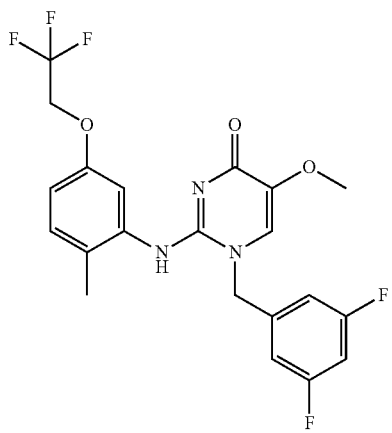 [SMILES: COc1cn(Cc2cc(F)cc(F)c2)c(Nc2cc(OCC(F)(F)F)ccc2C)nc1=O] | 456 | 1.83 | [1] |
| 1-0497 | 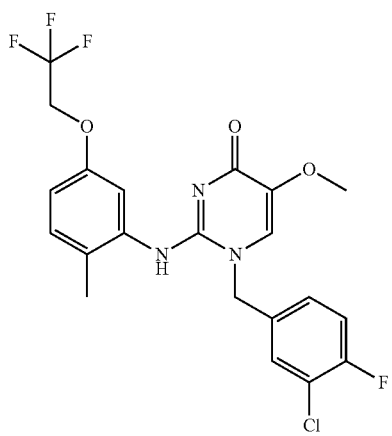 [SMILES: COc1cn(Cc2ccc(F)c(Cl)c2)c(Nc2cc(OCC(F)(F)F)ccc2C)nc1=O] | 472 | 1.92 | [1] |
| 1-0498 | 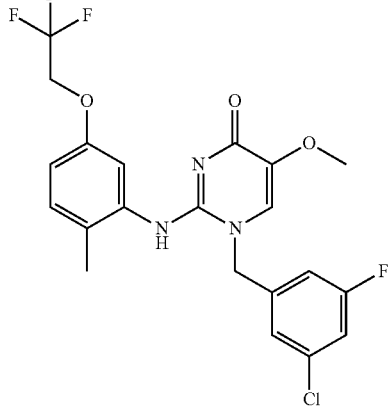 | 472 | 1.96 | [1] |
TABLE 94
| | | | | |
|---|---|---|---|---|
| I-0499 | 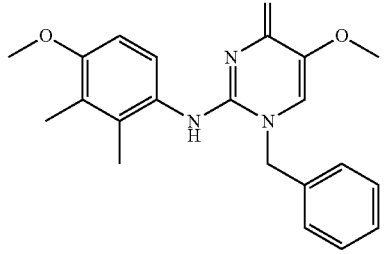 | 366 | 1.5 | [3] |

TABLE 94-continued
| | | | | |
|---|---|---|---|---|
| I-0500 | 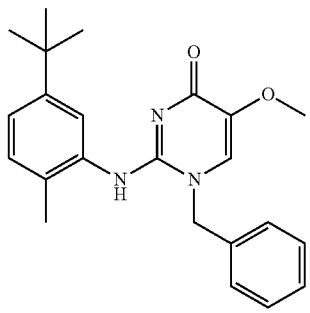 [SMILES: COc1cn(Cc2ccccc2)c(Nc2cc(C(C)(C)C)ccc2C)nc1=O] | 378 | 1.88 | [3] |
| I-0501 | 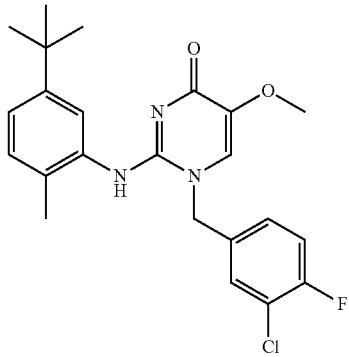 [SMILES: COc1cn(Cc2ccc(F)c(Cl)c2)c(Nc2cc(C(C)(C)C)ccc2C)nc1=O] | 430 | 2.04 | [3] |
| I-0502 | 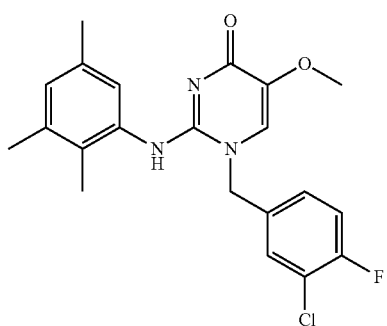 [SMILES: COc1cn(Cc2ccc(F)c(Cl)c2)c(Nc2cc(C)cc(C)c2C)nc1=O] | 402 | 1.39 | [3] |
| I-0503 | 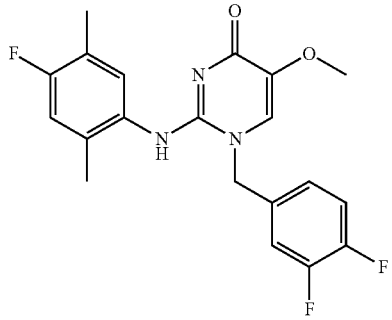 [SMILES: COc1cn(Cc2ccc(F)c(F)c2)c(Nc2cc(C)c(F)cc2C)nc1=O] | 390 | 1.79 | [3] |

TABLE 95

| | | | | |
|---|---|---|---|---|
| I-0504 | (structure) | 424 | 1.86 | [3] |
| I-0505 | (structure) | 392 | 1.89 | [3] |
| I-0506 | (structure) | 388 | 1.83 | [3] |
| I-0507 | (structure) | 406 | 1.9 | [3] |
| I-0508 | (structure) | 406 | 1.92 | [3] |

TABLE 96
| | | | | |
|---|---|---|---|---|
| I-0509 | 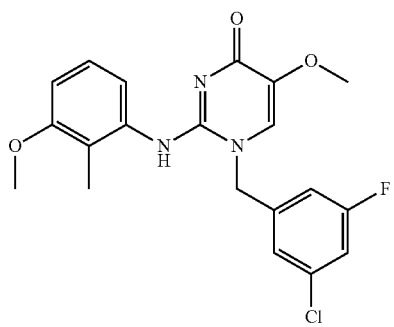 [SMILES: COc1cccc(Nc2nc(=O)c(OC)cn2Cc2cc(F)cc(Cl)c2)c1C] | 404 | 1.82 | [3] |
| I-0510 | 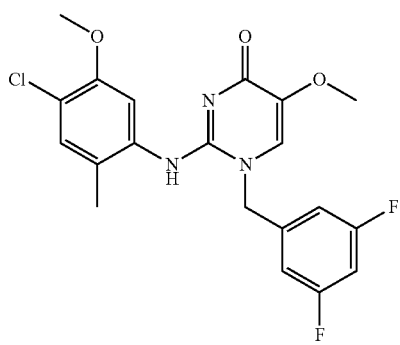 | 422 | 1.88 | [3] |
| I-0511 | 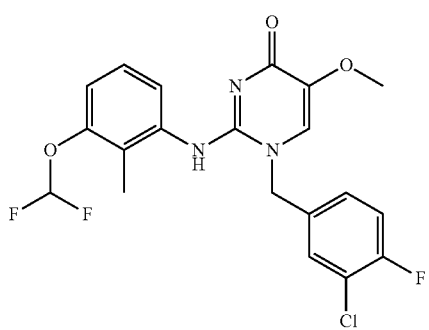 [SMILES: COc1cn(Cc2ccc(F)c(Cl)c2)c(Nc2cccc(OC(F)F)c2C)nc1=O] | 440 | 1.97 | [3] |
| I-0512 | 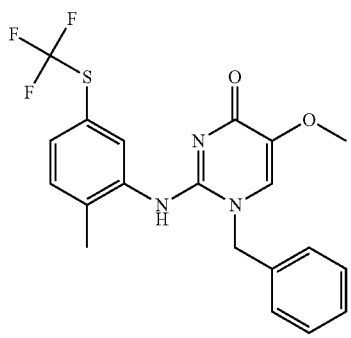 [SMILES: COc1cn(Cc2ccccc2)c(Nc2cc(SC(F)(F)F)ccc2C)nc1=O] | 422 | 2.04 | [3] |

TABLE 96-continued
| | | | | |
|---|---|---|---|---|
| I-0513 |  | 400 | 1.39 | [3] |
TABLE 97
| | | | | |
|---|---|---|---|---|
| I-0514 | (structure) | 416 | 1.82 | [1] |
| I-0515 | (structure) | 432 | 1.92 | [1] |
| I-0516 | (structure) | 424 | 1.72 | [3] |

TABLE 97-continued
| I-0517 | 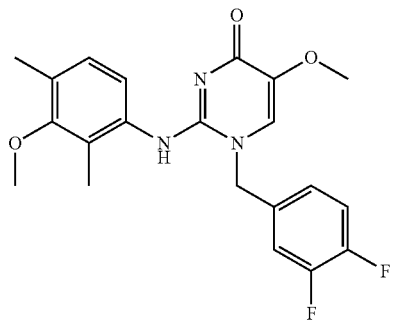 [SMILES: COc1c(C)ccc(Nc2nc(=O)c(OC)cn2Cc2ccc(F)c(F)c2)c1C] | 402 | 1.72 | [3] |
| I-0518 | 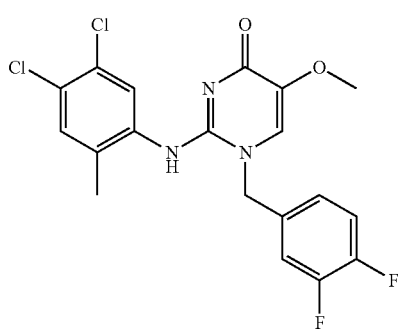 | 426 | 2.13 | [3] |
TABLE 98
| I-0519 | 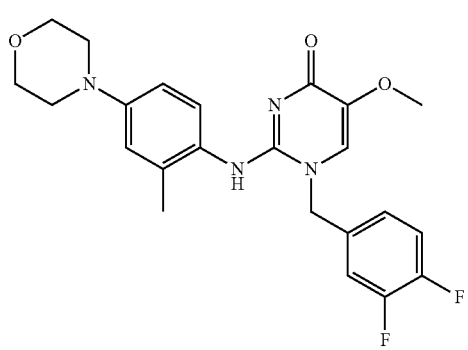 | 443 | 1.47 | [3] |
| I-0520 | 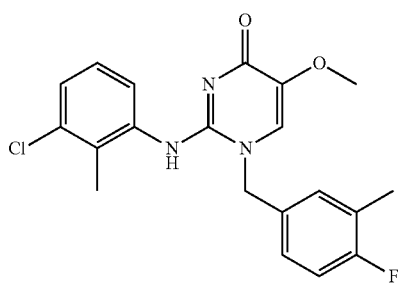 | 388 | 1.81 | [1] |

TABLE 98-continued
| I-0521 | 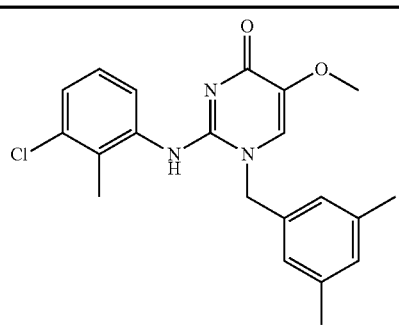 | 384 | 1.91 | [1] |
| --- | --- | --- | --- | --- |
| I-0522 | 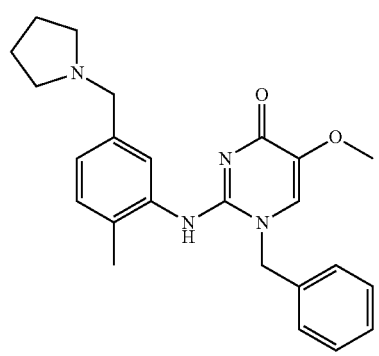 [SMILES: COc1cn(Cc2ccccc2)c(Nc2cc(CN3CCCC3)ccc2C)nc1=O] | 405 | 1.09 | [1] |
| I-0523 | 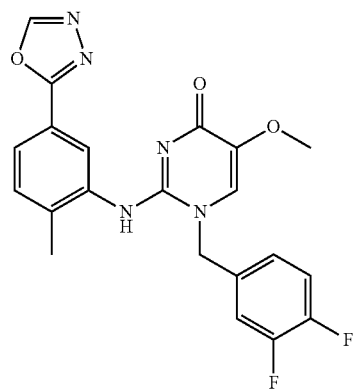 [SMILES: COc1cn(Cc2ccc(F)c(F)c2)c(Nc2cc(-c3nnco3)ccc2C)nc1=O] | 426 | 1.41 | [1] |
TABLE 99
| I-0524 | 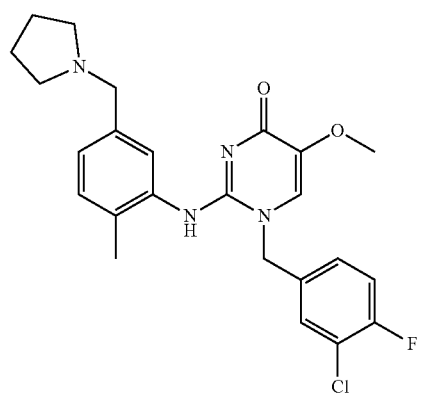 [SMILES: COc1cn(Cc2ccc(F)c(Cl)c2)c(Nc2cc(CN3CCCC3)ccc2C)nc1=O] | 457 | 1.41 | [1] |
| --- | --- | --- | --- | --- |

TABLE 99-continued
| | | | | |
|---|---|---|---|---|
| I-0525 | 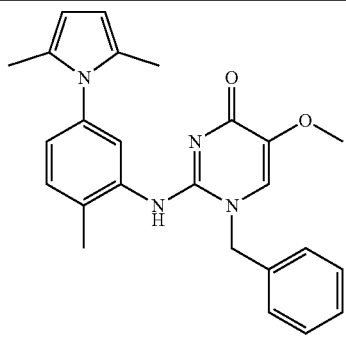 | 415 | 1.92 | [1] |
| I-0526 | 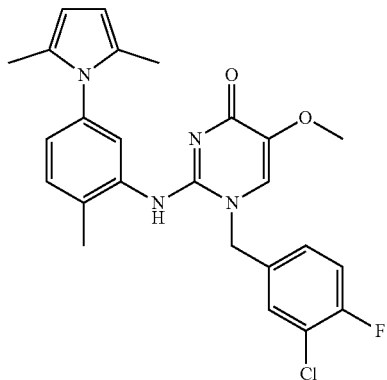 [SMILES: COc1cn(Cc2ccc(F)c(Cl)c2)c(Nc2cc(-n3c(C)ccc3C)ccc2C)nc1=O] | 467 | 2.13 | [1] |
| I-0527 | 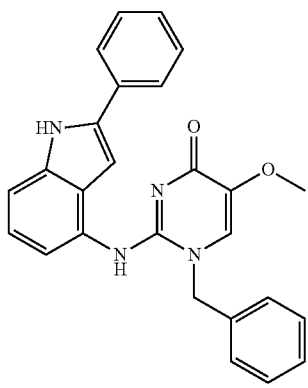 [SMILES: COc1cn(Cc2ccccc2)c(Nc2cccc3[nH]c(-c4ccccc4)cc23)nc1=O] | 423 | 1.67 | [1] |
TABLE 100
| | | | | |
|---|---|---|---|---|
| I-0528 | 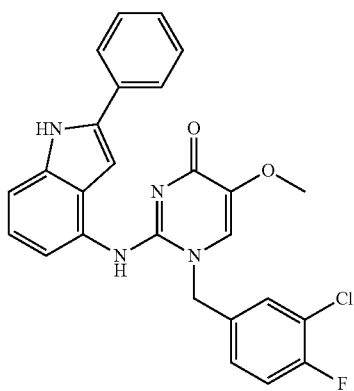 [SMILES: COc1cn(Cc2ccc(F)c(Cl)c2)c(Nc2cccc3[nH]c(-c4ccccc4)cc23)nc1=O] | 476 | 1.81 | [1] |

TABLE 100-continued
| I-0529 | 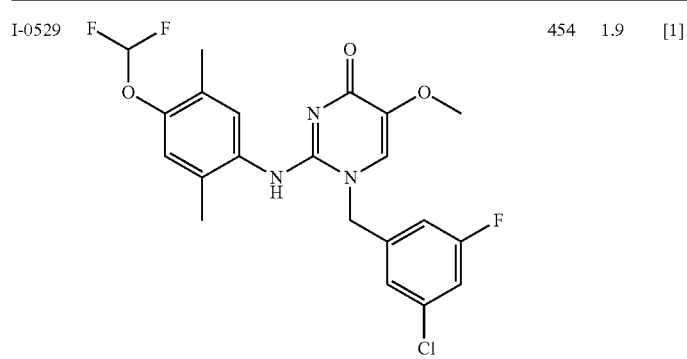 | 454 | 1.9 | [1] |
| I-0530 | 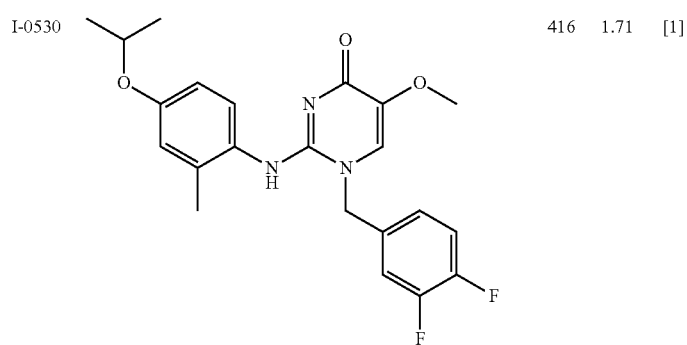 | 416 | 1.71 | [1] |
| I-0531 | 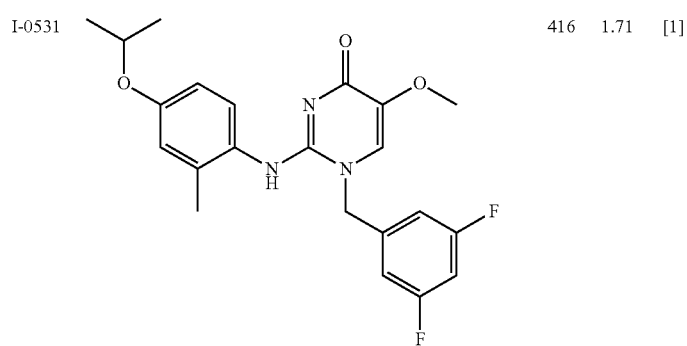 | 416 | 1.71 | [1] |
| I-0532 | 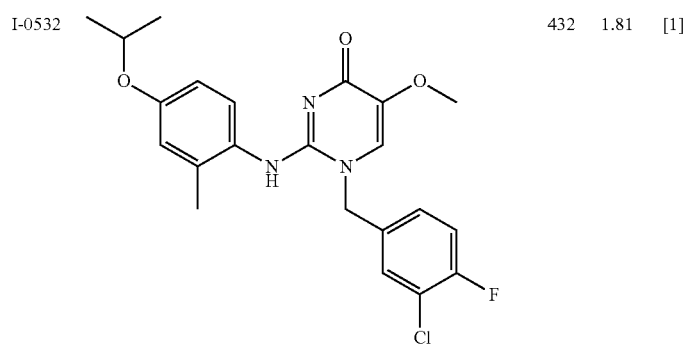 | 432 | 1.81 | [1] |

TABLE 101

| | | | |
|---|---|---|---|
| I-0533 | [structure] | 426 | 2.13 [3] |
| I-0534 | [structure] | 420 | 2.01 [3] |
| I-0535 | [structure] | 422 | 1.95 [3] |
| I-0536 | [structure] | 438 | 2.06 [3] |

TABLE 101-continued

| ID | Structure | MW | RT | Method |
|---|---|---|---|---|
| I-0537 | 4-chloro-5-methoxy-2-methylphenyl / 1-(3-chloro-5-fluorobenzyl)-5-methoxypyrimidin-4(1H)-one | 438 | 2.1 | [3] |

TABLE 102

| ID | Structure | MW | RT | Method |
|---|---|---|---|---|
| I-0538 | 4-methoxy-2-methylphenyl / 1-(3,5-difluorobenzyl)-5-methoxypyrimidin-4(1H)-one | 388 | 1.74 | [3] |
| I-0539 | 4-(difluoromethoxy)-2-methylphenyl / 1-(3,5-difluorobenzyl)-5-methoxypyrimidin-4(1H)-one | 424 | 1.97 | [3] |
| I-0540 | 3-methoxy-2,4-dimethylphenyl / 1-(3,5-difluorobenzyl)-5-methoxypyrimidin-4(1H)-one | 402 | 1.85 | [3] |

TABLE 102-continued
| | | | | |
|---|---|---|---|---|
| I-0541 | 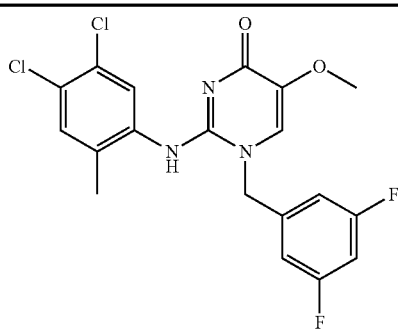 | 426 | 2.28 | [3] |
| I-0542 | 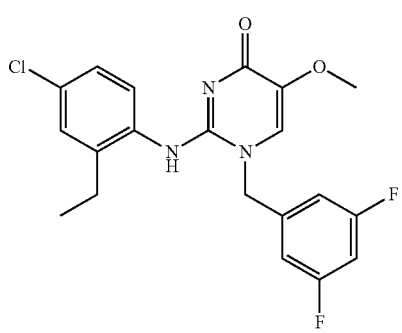 [SMILES: CCc1cc(Cl)ccc1Nc1nc(=O)c(OC)cn1Cc1cc(F)cc(F)c1] | 406 | 2.13 | [3] |
TABLE 103
| | | | | |
|---|---|---|---|---|
| I-0543 | 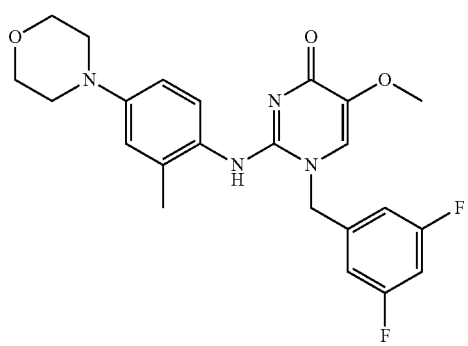 [SMILES: COc1cn(Cc2cc(F)cc(F)c2)c(Nc2ccc(N3CCOCC3)cc2C)nc1=O] | 408 | 1.98 | [3] |
| I-0544 | 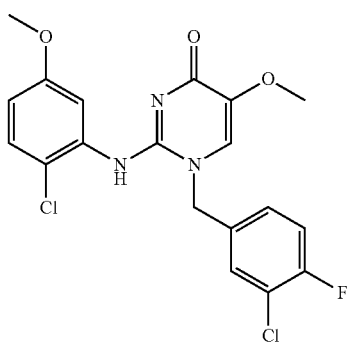 [SMILES: COc1ccc(Cl)c(Nc2nc(=O)c(OC)cn2Cc2ccc(F)c(Cl)c2)c1] | 424 | 1.95 | [3] |

TABLE 103-continued
| I-0545 | 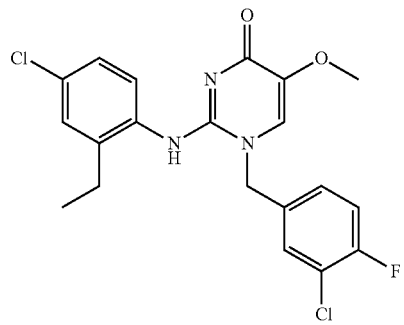 [SMILES: CCc1cc(Cl)ccc1Nc1nc(=O)c(OC)cn1Cc1ccc(F)c(Cl)c1] | 422 | 2.08 | [3] |
| I-0546 | 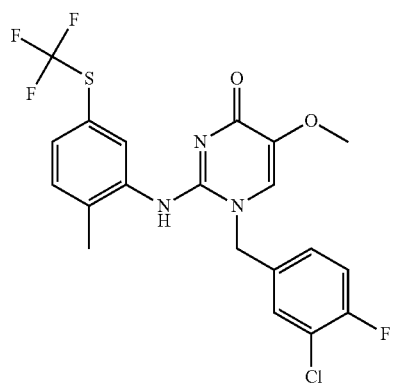 [SMILES: COc1cn(Cc2ccc(F)c(Cl)c2)c(Nc2cc(SC(F)(F)F)ccc2C)nc1=O] | 474 | 2.25 | [3] |
| I-0547 | 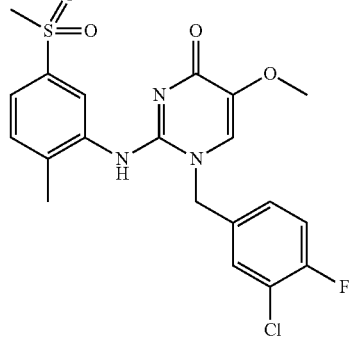 | 452 | 1.62 | [3] |
TABLE 104
| I-0548 | 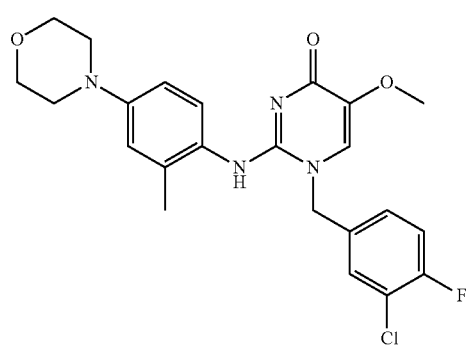 [SMILES: COc1cn(Cc2ccc(F)c(Cl)c2)c(Nc2ccc(N3CCOCC3)cc2C)nc1=O] | 459 | 1.56 | [3] |

TABLE 104-continued
| | | | | |
|---|---|---|---|---|
| I-0549 | 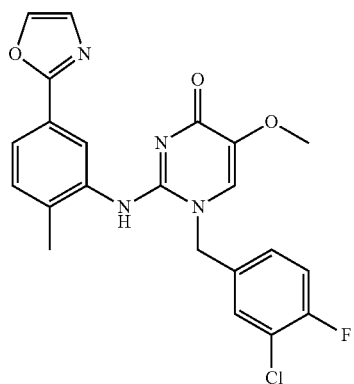 [SMILES: COc1cn(Cc2ccc(F)c(Cl)c2)c(Nc2cc(-c3ncco3)ccc2C)nc1=O] | 441 | 1.76 | [3] |
| I-0550 | 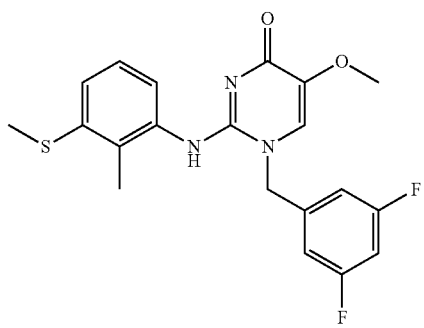 [SMILES: COc1cn(Cc2cc(F)cc(F)c2)c(Nc2cccc(SC)c2C)nc1=O] | 404 | 1.8 | [3] |
| I-0551 | 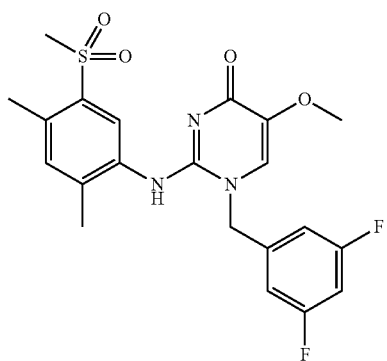 [SMILES: COc1cn(Cc2cc(F)cc(F)c2)c(Nc2cc(S(C)(=O)=O)c(C)cc2C)nc1=O] | 450 | 1.58 | [3] |
| I-0552 | 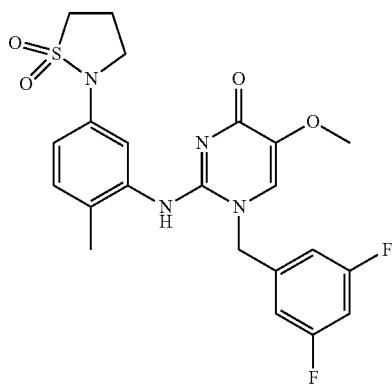 [SMILES: COc1cn(Cc2cc(F)cc(F)c2)c(Nc2cc(N3CCCS3(=O)=O)ccc2C)nc1=O] | 477 | 1.57 | [3] |

TABLE 105
| | | | |
|---|---|---|---|
| I-0553 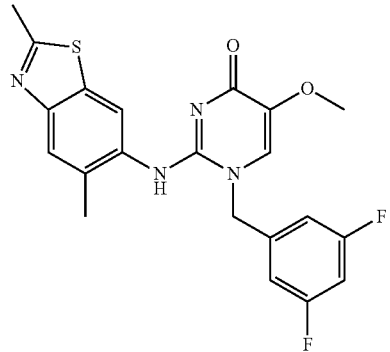 [SMILES: COc1cn(Cc2cc(F)cc(F)c2)c(Nc2cc3sc(C)nc3cc2C)nc1=O] | 429 | 1.56 | [3] |
| I-0554 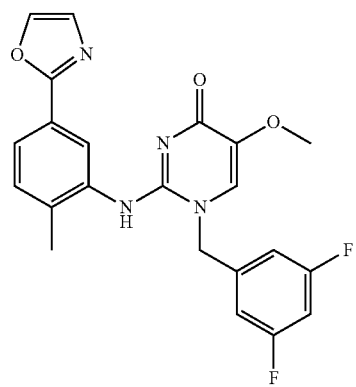 [SMILES: COc1cn(Cc2cc(F)cc(F)c2)c(Nc2cc(-c3ncco3)ccc2C)nc1=O] | 425 | 1.55 | [1] |
| I-0555 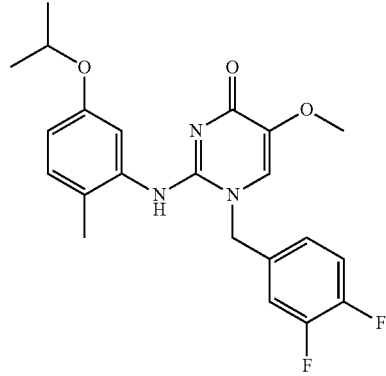 [SMILES: COc1cn(Cc2ccc(F)c(F)c2)c(Nc2cc(OC(C)C)ccc2C)nc1=O] | 416 | 1.77 | [1] |
| I-0556 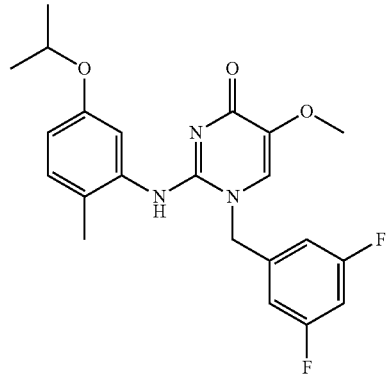 [SMILES: COc1cn(Cc2cc(F)cc(F)c2)c(Nc2cc(OC(C)C)ccc2C)nc1=O] | 416 | 1.77 | [1] |

TABLE 105-continued

| | | | | |
|---|---|---|---|---|
| I-0557 | [structure] | 432 | 1.91 | [1] |

TABLE 106

| | | | | |
|---|---|---|---|---|
| I-0558 | [structure] | 389 | 1.45 | [1] |
| I-0559 | [structure] | 411 | 1.49 | [3] |
| I-0560 | [structure] | 384 | 1.73 | [3] |

TABLE 106-continued
| I-0561 | 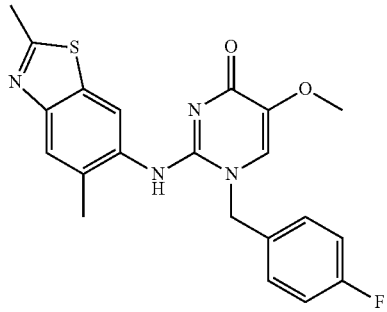 [SMILES: COc1cn(Cc2ccc(F)cc2)c(Nc2cc3sc(C)nc3cc2C)nc1=O] | 411 | 1.5 | [3] |
| I-0562 | 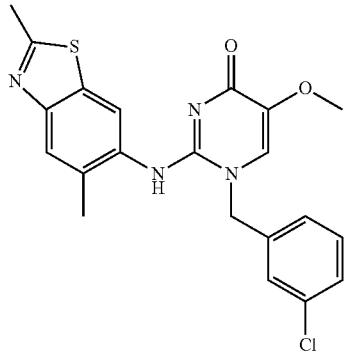 [SMILES: COc1cn(Cc2cccc(Cl)c2)c(Nc2cc3sc(C)nc3cc2C)nc1=O] | 427 | 1.63 | [3] |
TABLE 107
| I-0563 | 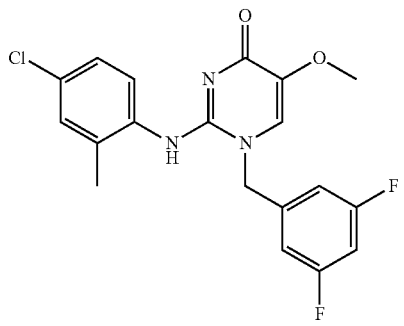 [SMILES: COc1cn(Cc2cc(F)cc(F)c2)c(Nc2ccc(Cl)cc2C)nc1=O] | 392 | 1.72 | [1] |
| I-0564 | 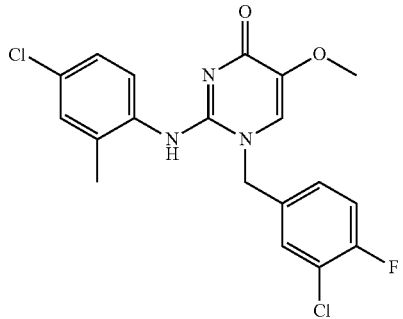 [SMILES: COc1cn(Cc2ccc(F)c(Cl)c2)c(Nc2ccc(Cl)cc2C)nc1=O] | 408 | 1.82 | [1] |

TABLE 107-continued
| | | | | |
|---|---|---|---|---|
| I-0565 | 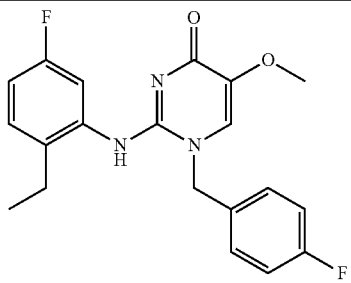 | 372 | 1.66 | [1] |
| I-0566 | 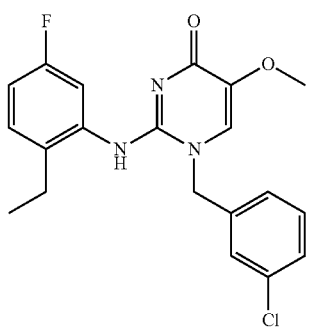 | 388 | 1.81 | [1] |
| I-0567 | 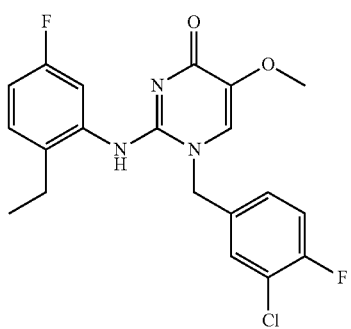 | 406 | 1.86 | [1] |
TABLE 108
| | | | | |
|---|---|---|---|---|
| I-0568 | 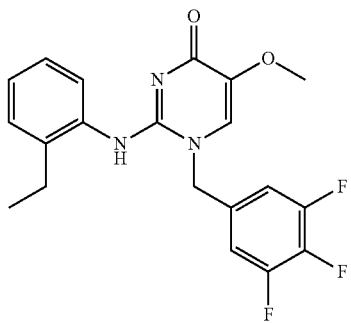 [SMILES: CCc1ccccc1Nc1nc(=O)c(OC)cn1Cc1cc(F)c(F)c(F)c1] | 390 | 1.71 | [1] |

TABLE 108-continued
| | | | | |
|---|---|---|---|---|
| I-0569 | 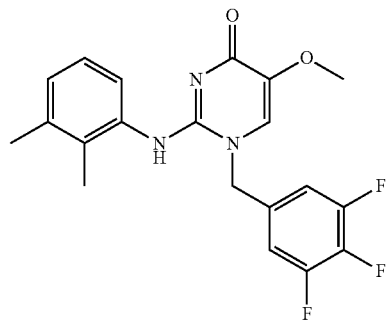 [SMILES: COc1cn(Cc2cc(F)c(F)c(F)c2)c(Nc2cccc(C)c2C)nc1=O] | 390 | 1.69 | [1] |
| I-0570 | 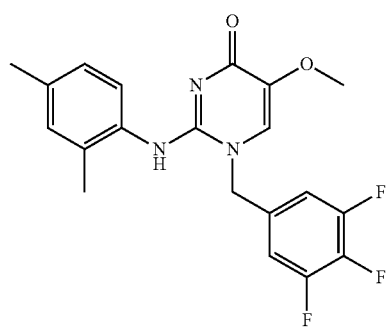 [SMILES: COc1cn(Cc2cc(F)c(F)c(F)c2)c(Nc2ccc(C)cc2C)nc1=O] | 390 | 1.69 | [1] |
| I-0571 | 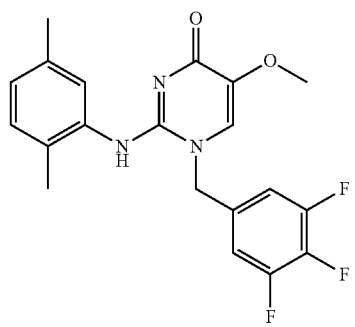 [SMILES: COc1cn(Cc2cc(F)c(F)c(F)c2)c(Nc2cc(C)ccc2C)nc1=O] | 390 | 1.71 | [1] |
| I-0572 | 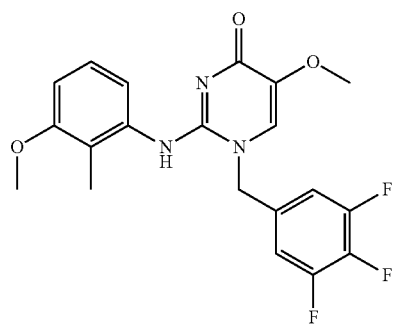 [SMILES: COc1cccc(Nc2nc(=O)c(OC)cn2Cc2cc(F)c(F)c(F)c2)c1C] | 406 | 1.65 | [1] |

TABLE 109

| | | | | |
|---|---|---|---|---|
| I-0573 | (structure) | 420 | 1.66 | [1] |
| I-0574 | (structure) | 404 | 1.79 | [1] |
| I-0575 | (structure) | 424 | 1.94 | [1] |
| I-0576 | (structure) | 440 | 1.98 | [3] |
| I-0577 | (structure) | 408 | 2.01 | [3] |

TABLE 110
| | | | | |
|---|---|---|---|---|
| I-0578 | 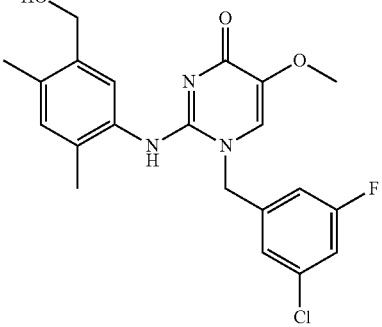 | 418 | 1.63 | [3] |
| I-0579 | 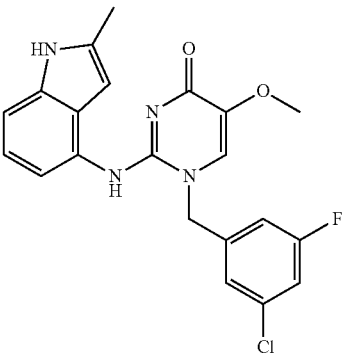 [SMILES: COc1cn(Cc2cc(F)cc(Cl)c2)c(Nc2cccc3[nH]c(C)cc23)nc1=O] | 413 | 1.63 | [3] |
| I-0580 | 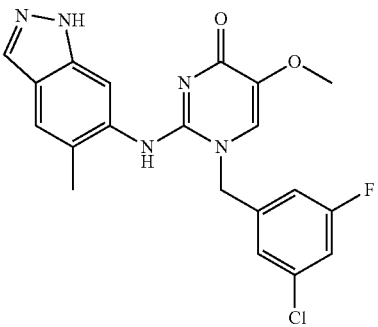 [SMILES: COc1cn(Cc2cc(F)cc(Cl)c2)c(Nc2cc3[nH]ncc3cc2C)nc1=O] | 414 | 1.6 | [3] |
| I-0581 | 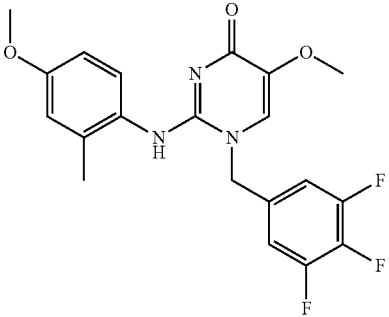 [SMILES: COc1ccc(Nc2nc(=O)c(OC)cn2Cc2cc(F)c(F)c(F)c2)c(C)c1] | 406 | 1.56 | [1] |

TABLE 110-continued
| I-0582 | 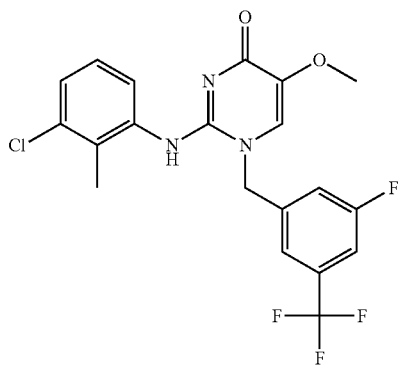 [SMILES: COc1cn(Cc2cc(F)cc(C(F)(F)F)c2)c(Nc2cccc(Cl)c2C)nc1=O] | 442 | 2.01 | [1] |
TABLE 111
| I-0583 | 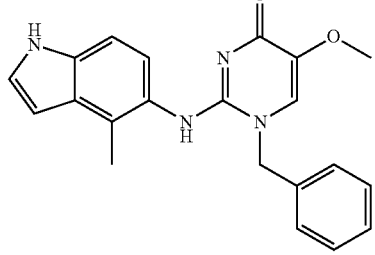 | 361 | 1.3 | [1] |
| I-0584 | 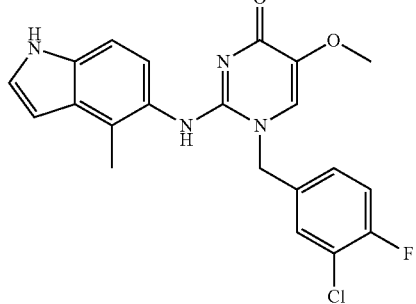 | 413 | 1.5 | [1] |
| I-0585 | 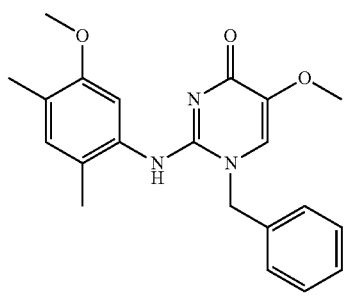 [SMILES: COc1cc(Nc2nc(=O)c(OC)cn2Cc2ccccc2)c(C)cc1C] | 366 | 1.57 | [1] |

TABLE 111-continued
| | | | | |
|---|---|---|---|---|
| I-0586 | 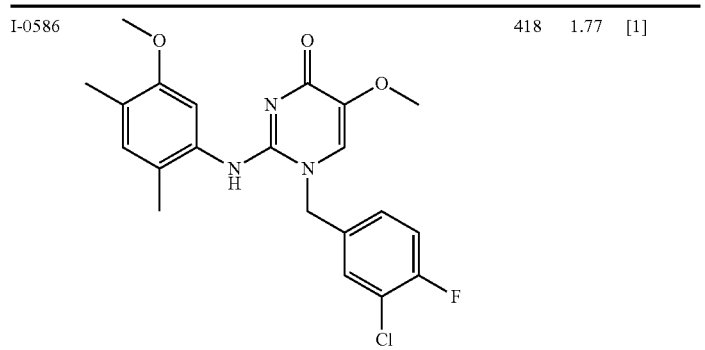 | 418 | 1.77 | [1] |
| I-0587 | 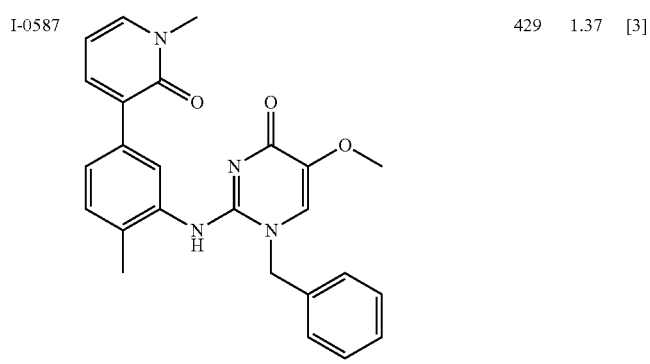 | 429 | 1.37 | [3] |
TABLE 112
| | | | | |
|---|---|---|---|---|
| I-0588 | 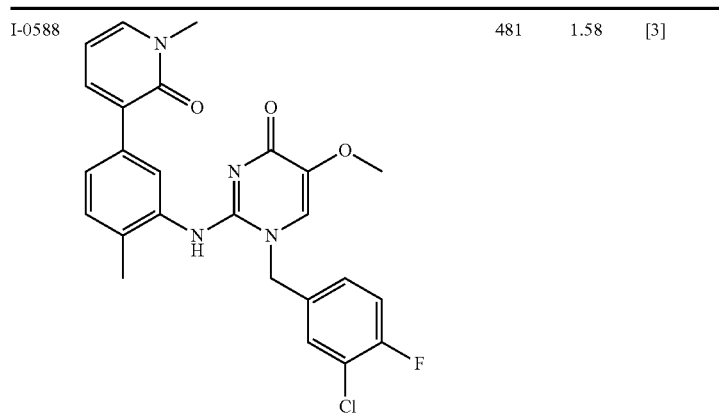 | 481 | 1.58 | [3] |
| I-0589 | 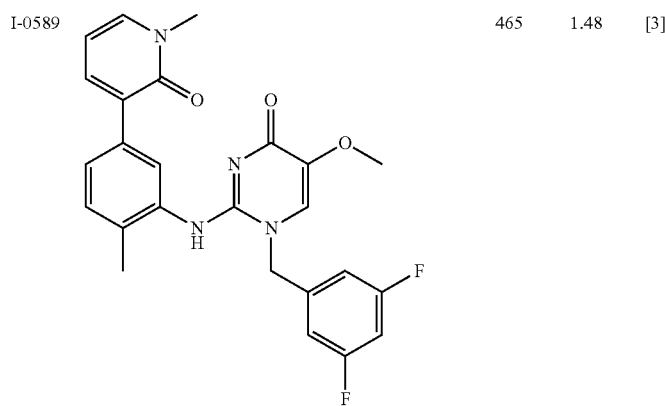 | 465 | 1.48 | [3] |

TABLE 112-continued

| I-0590 | (structure) | 447 | 1.37 | [3] |
| I-0591 | (structure) | 499 | 1.59 | [3] |

TABLE 113

| I-0592 | (structure) | 483 | 1.48 | [3] |
| I-0593 | (structure) | 392 | 1.75 | [1] |

TABLE 113-continued
| | | | | |
|---|---|---|---|---|
| I-0594 | 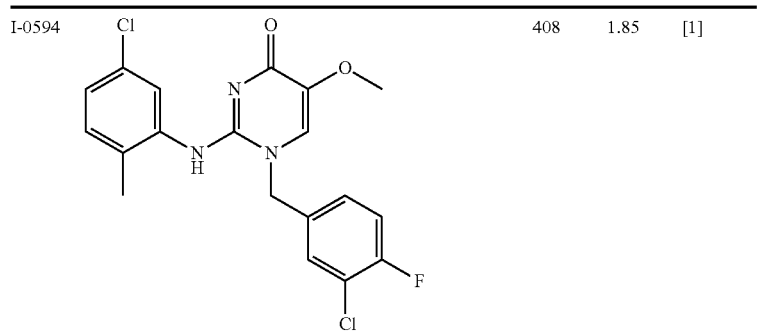 | 408 | 1.85 | [1] |
| I-0595 | 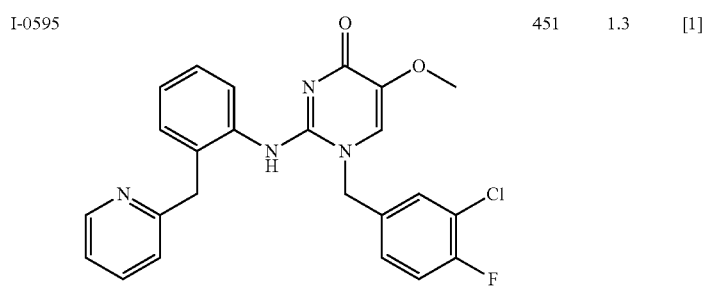 | 451 | 1.3 | [1] |
| I-0596 | 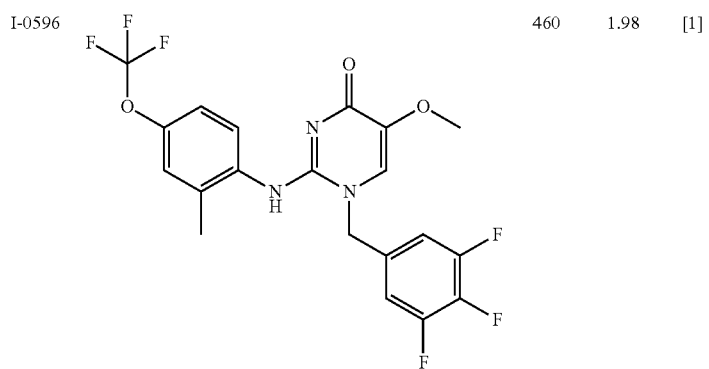 | 460 | 1.98 | [1] |
TABLE 114
| | | | | |
|---|---|---|---|---|
| I-0597 | 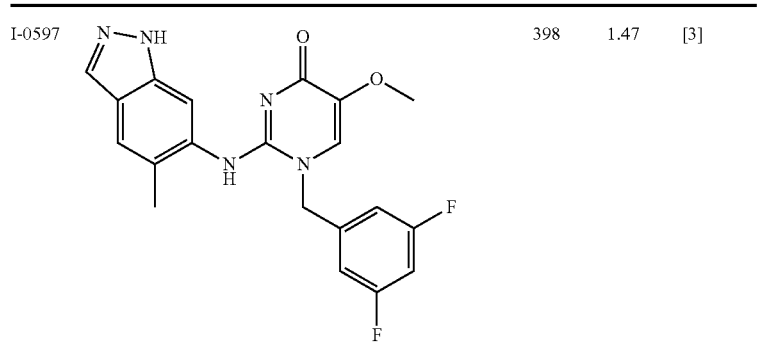 | 398 | 1.47 | [3] |

TABLE 114-continued
| | | | | |
|---|---|---|---|---|
| I-0598 | 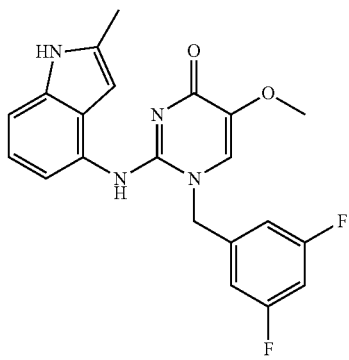 [SMILES: COc1cn(Cc2cc(F)cc(F)c2)c(Nc2cccc3[nH]c(C)cc23)nc1=O] | 397 | 1.39 | [1] |
| I-0599 | 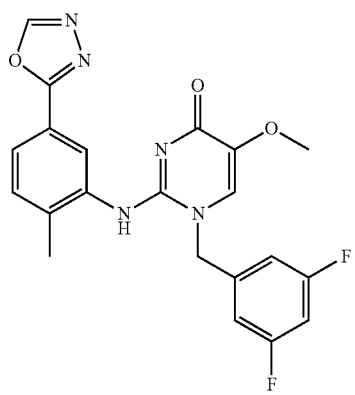 [SMILES: COc1cn(Cc2cc(F)cc(F)c2)c(Nc2cc(-c3nnco3)ccc2C)nc1=O] | 426 | 1.49 | [3] |
| I-0600 | 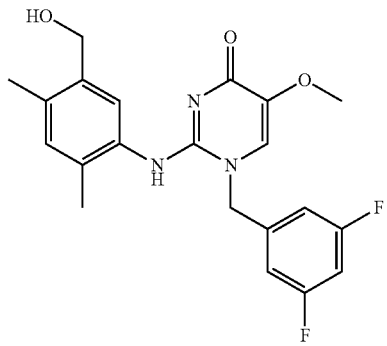 [SMILES: COc1cn(Cc2cc(F)cc(F)c2)c(Nc2cc(CO)c(C)cc2C)nc1=O] | 402 | 1.5 | [3] |
| I-0601 | 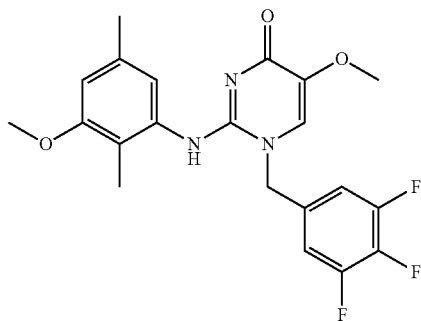 [SMILES: COc1cc(C)cc(Nc2nc(=O)c(OC)cn2Cc2cc(F)c(F)c(F)c2)c1C] | 420 | 1.76 | [1] |

TABLE 115
| | | | | |
|---|---|---|---|---|
| I-0602 | 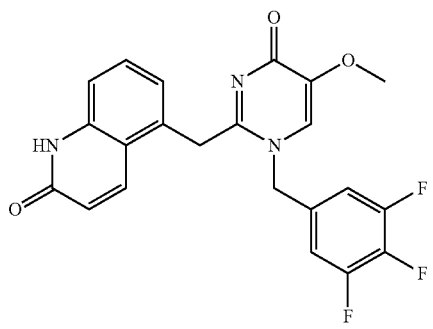 [SMILES: COc1cn(Cc2cc(F)c(F)c(F)c2)c(Cc2cccc3[nH]c(=O)ccc23)nc1=O] | 429 | 1.33 | [1] |
| I-0603 | 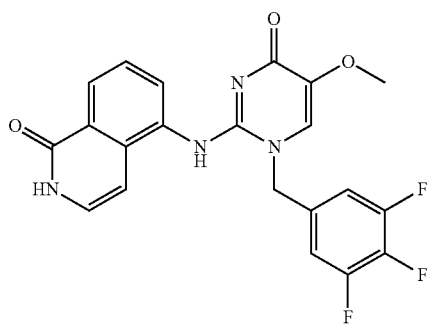 [SMILES: COc1cn(Cc2cc(F)c(F)c(F)c2)c(Nc2cccc3c(=O)[nH]ccc23)nc1=O] | 429 | 1.29 | [1] |
| I-0604 | 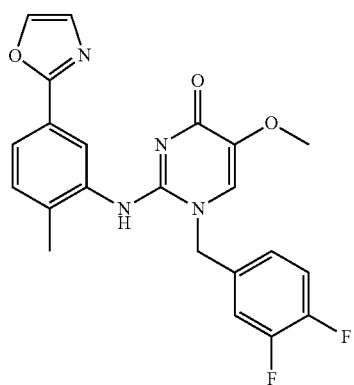 | 425 | 1.63 | [3] |
| I-0605 | 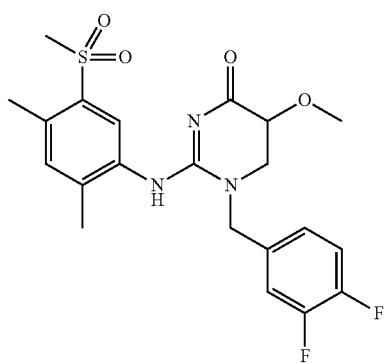 [SMILES: COC1CN(Cc2ccc(F)c(F)c2)C(Nc2cc(S(C)(=O)=O)c(C)cc2C)=NC1=O] | 450 | 1.56 | [3] |

TABLE 115-continued
| | | | | |
|---|---|---|---|---|
| I-0606 | 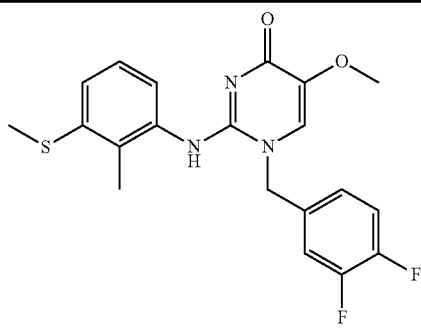 | 404 | 1.79 | [3] |
TABLE 116
| | | | | |
|---|---|---|---|---|
| I-0607 | 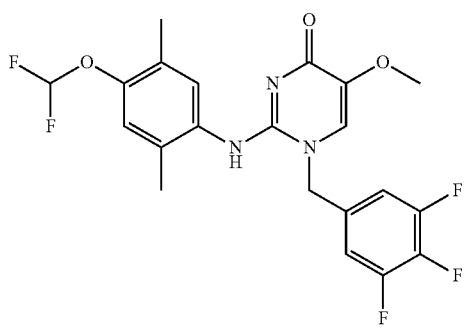 [SMILES: COc1cn(Cc2cc(F)c(F)c(F)c2)c(Nc2cc(C)c(OC(F)F)cc2C)nc1=O] | 456 | 1.86 | [1] |
| I-0608 | 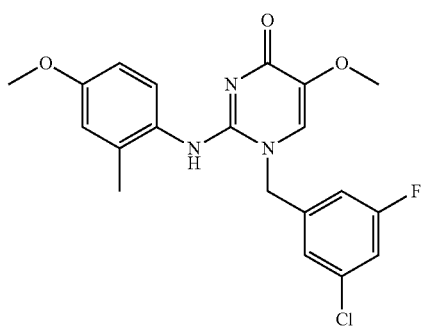 [SMILES: COc1ccc(Nc2nc(=O)c(OC)cn2Cc2cc(F)cc(Cl)c2)c(C)c1] | 404 | 1.71 | [3] |
| I-0609 | 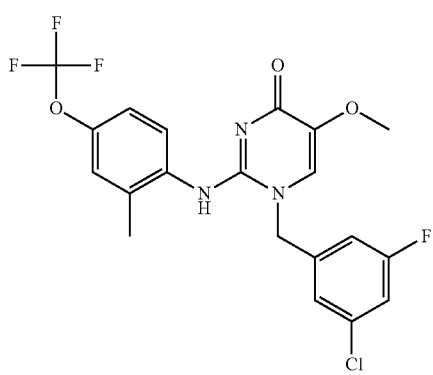 [SMILES: COc1cn(Cc2cc(F)cc(Cl)c2)c(Nc2ccc(OC(F)(F)F)cc2C)nc1=O] | 458 | 2.16 | [3] |

TABLE 116-continued
| 1-0610 | 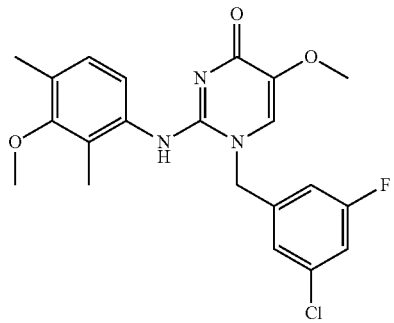 [SMILES: COc1c(C)ccc(Nc2nc(=O)c(OC)cn2Cc2cc(F)cc(Cl)c2)c1C] | 418 | 1.83 | [3] |
| 1-0611 | 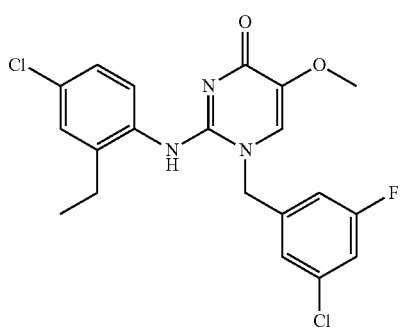 | 422 | 2.13 | [3] |
TABLE 117
| I-0612 | 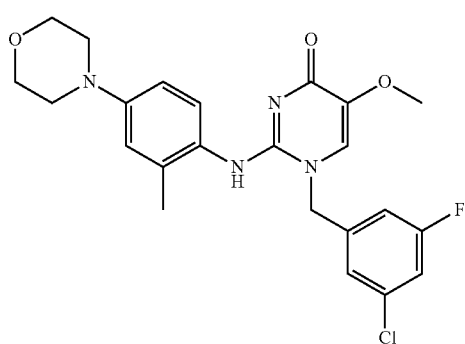 [SMILES: COc1cn(Cc2cc(F)cc(Cl)c2)c(Nc2ccc(N3CCOCC3)cc2C)nc1=O] | 459 | 1.57 | [3] |
| I-0613 | 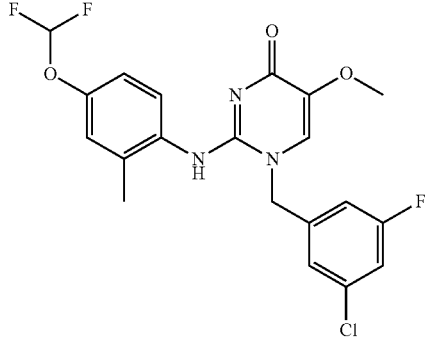 | 440 | 1.93 | [3] |

TABLE 117-continued
| I-0614 | 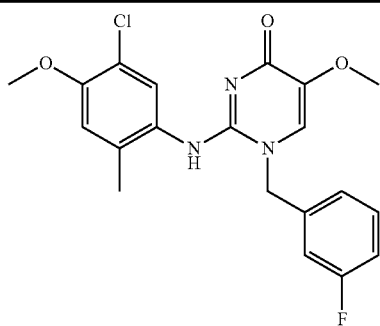 | 404 | 1.67 | [3] |
| I-0615 | 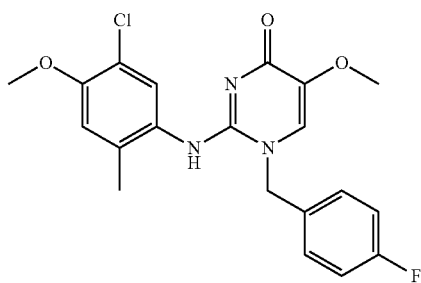 [SMILES: COc1cc(C)c(Nc2nc(=O)c(OC)cn2Cc2ccc(F)cc2)cc1Cl] | 404 | 1.68 | [3] |
| I-0616 | 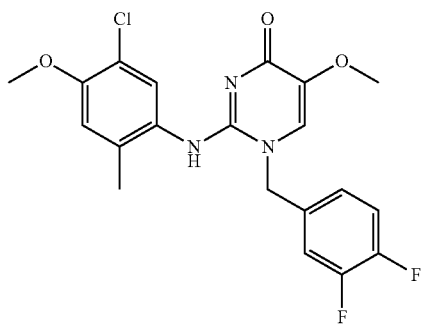 [SMILES: COc1cc(C)c(Nc2nc(=O)c(OC)cn2Cc2ccc(F)c(F)c2)cc1Cl] | 422 | 1.74 | [3] |
TABLE 118
| I-0617 | 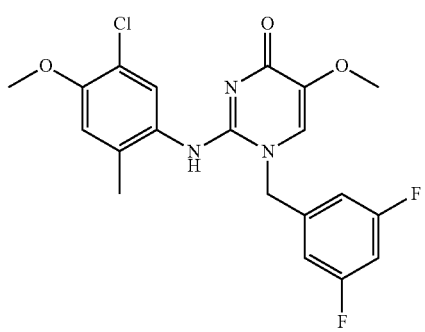 [SMILES: COc1cc(C)c(Nc2nc(=O)c(OC)cn2Cc2cc(F)cc(F)c2)cc1Cl] | 422 | 1.74 | [3] |

TABLE 118-continued

| ID | Structure | MW | RT | Ref |
|---|---|---|---|---|
| I-0618 | 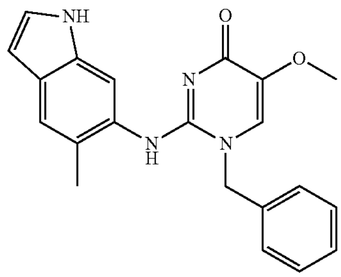 [SMILES: COc1cn(Cc2ccccc2)c(Nc2cc3[nH]ccc3cc2C)nc1=O] | 361 | 1.52 | [3] |
| I-0619 | 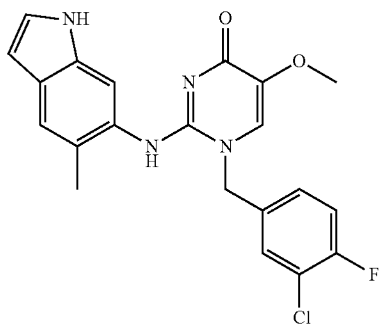 [SMILES: COc1cn(Cc2ccc(F)c(Cl)c2)c(Nc2cc3[nH]ccc3cc2C)nc1=O] | 413 | 1.74 | [3] |
| I-0620 | 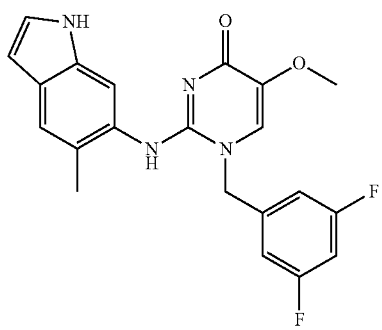 [SMILES: COc1cn(Cc2cc(F)cc(F)c2)c(Nc2cc3[nH]ccc3cc2C)nc1=O] | 397 | 1.63 | [3] |
| I-0621 | 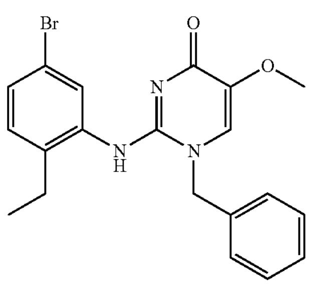 | 414 | 1.91 | [3] |
| I-0622 | 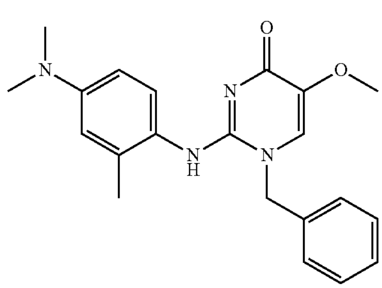 [SMILES: COc1cn(Cc2ccccc2)c(Nc2ccc(N(C)C)cc2C)nc1=O] | 365 | 0.94 | [1] |

TABLE 119
| | | | | |
|---|---|---|---|---|
| I-0623 | 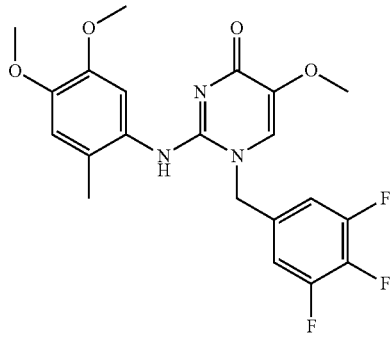 [SMILES: COc1cc(C)c(Nc2nc(=O)c(OC)cn2Cc2cc(F)c(F)c(F)c2)cc1OC] | 436 | 1.49 | [1] |
| I-0624 | 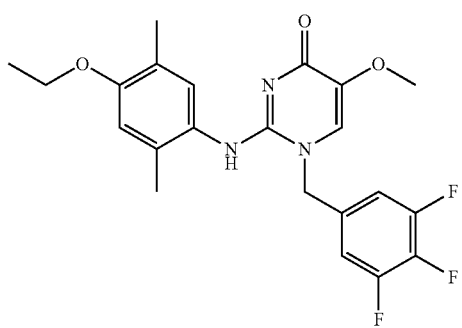 [SMILES: CCOc1cc(C)c(Nc2nc(=O)c(OC)cn2Cc2cc(F)c(F)c(F)c2)cc1C] | 434 | 1.83 | [1] |
| I-0625 | 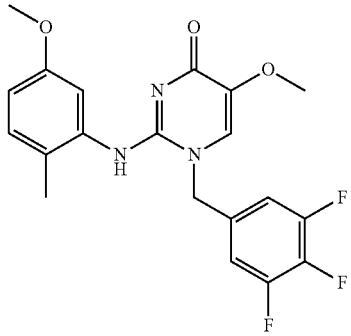 [SMILES: COc1ccc(C)c(Nc2nc(=O)c(OC)cn2Cc2cc(F)c(F)c(F)c2)c1] | 406 | 1.64 | [1] |
| I-0626 | 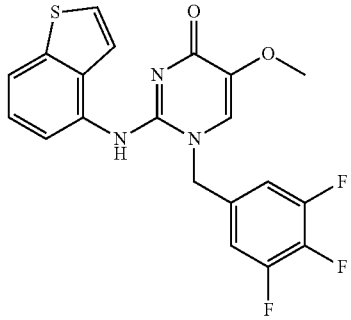 [SMILES: COc1cn(Cc2cc(F)c(F)c(F)c2)c(Nc2cccc3sccc23)nc1=O] | 418 | 1.78 | [1] |

TABLE 119-continued
| I-0627 | 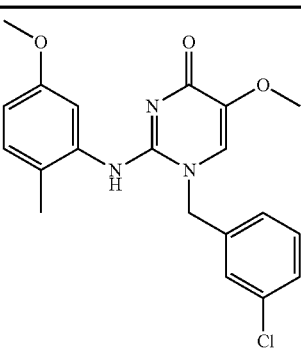 | 386 | 1.59 | [1] |
TABLE 120
| I-0628 | 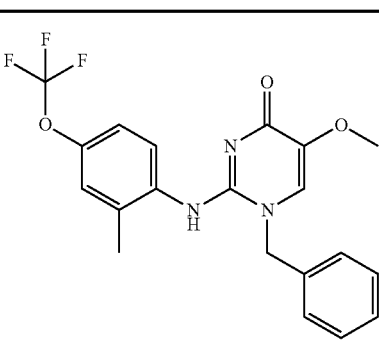 | 406 | 1.78 | [1] |
| I-0629 | 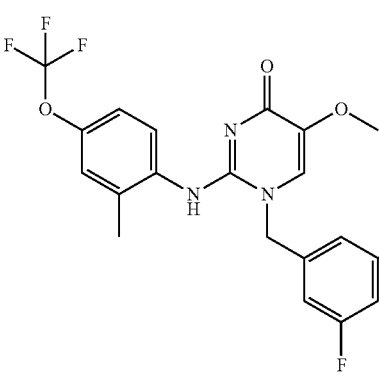 | 442 | 1.89 | [1] |
| I-0630 | 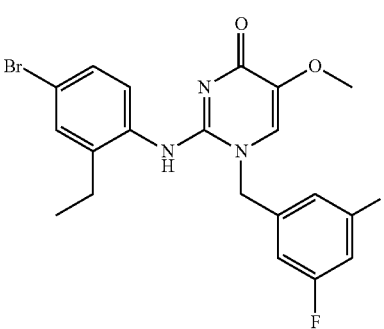 | 452 | 2.02 | [1] |

TABLE 120-continued

| I-0631 | [structure] | 468 | 2.1 | [1] |

| I-0632 | [structure] | 420 | 1.67 | [1] |

TABLE 121

| I-0633 | [structure] | 434 | 1.86 | [1] |

| I-0634 | [structure] | 442 | 1.99 | [1] |

TABLE 121-continued
| | | | | |
|---|---|---|---|---|
| I-0635 | 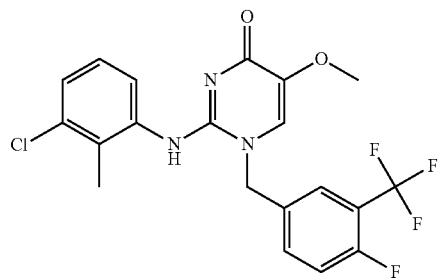 [SMILES: COc1cn(Cc2ccc(F)c(C(F)(F)F)c2)c(Nc2cccc(Cl)c2C)nc1=O] | 442 | 1.97 | [1] |
| I-0636 | 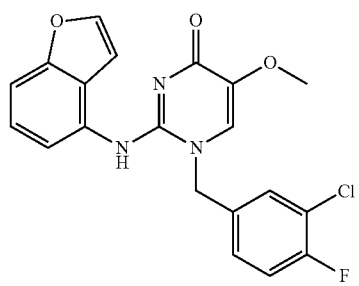 [SMILES: COc1cn(Cc2ccc(F)c(Cl)c2)c(Nc2cccc3occc23)nc1=O] | 400 | 1.65 | [1] |
| I-0637 | 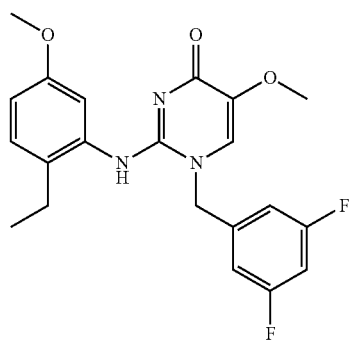 [SMILES: CCc1ccc(OC)cc1Nc1nc(=O)c(OC)cn1Cc1cc(F)cc(F)c1] | 402 | 1.78 | [3] |
TABLE 122
| | | | | |
|---|---|---|---|---|
| I-0638 | 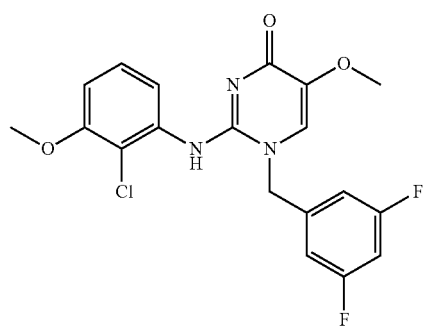 [SMILES: COc1cccc(Nc2nc(=O)c(OC)cn2Cc2cc(F)cc(F)c2)c1Cl] | 408 | 1.73 | [3] |

TABLE 122-continued
| | | | | |
|---|---|---|---|---|
| I-0639 | 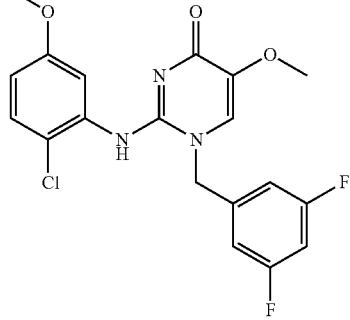 | 408 | 1.88 | [3] |
| I-0640 | 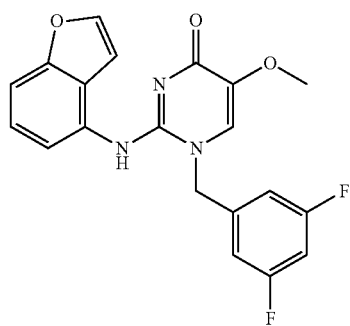 [SMILES: COc1cn(Cc2cc(F)cc(F)c2)c(Nc2cccc3occc23)nc1=O] | 384 | 1.64 | [3] |
| I-0641 | 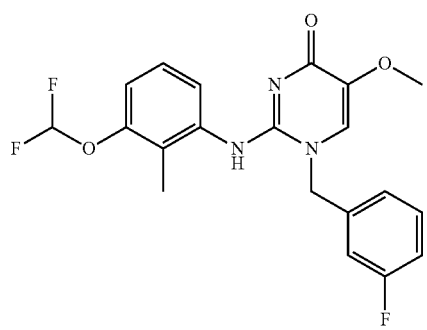 [SMILES: COc1cn(Cc2cccc(F)c2)c(Nc2cccc(OC(F)F)c2C)nc1=O] | 406 | 1.76 | [3] |
| I-0642 | 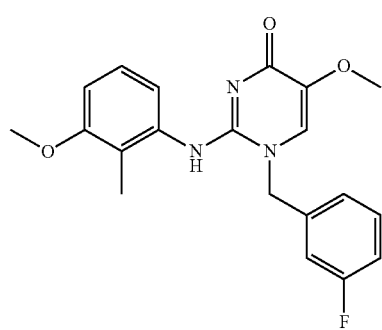 | 370 | 1.58 | [3] |

TABLE 123
I-0643 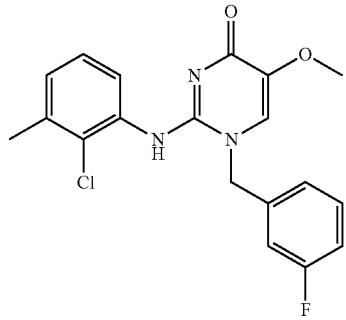 [SMILES: COc1cn(Cc2cccc(F)c2)c(Nc2cccc(C)c2Cl)nc1=O] 374 1.78 [3]
I-0644 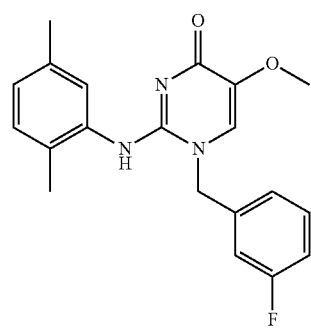 [SMILES: COc1cn(Cc2cccc(F)c2)c(Nc2cc(C)ccc2C)nc1=O] 354 1.64 [3]
I-0645 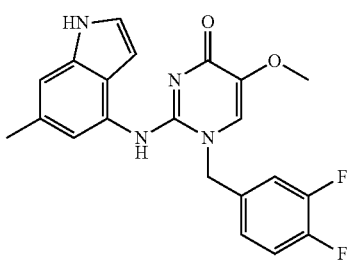 [SMILES: COc1cn(Cc2ccc(F)c(F)c2)c(Nc2cc(C)cc3[nH]ccc23)nc1=O] 397 1.44 [1]
I-0646 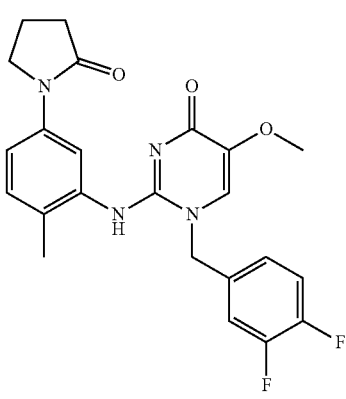 441 1.49 [1]
TABLE 123-continued
I-0647 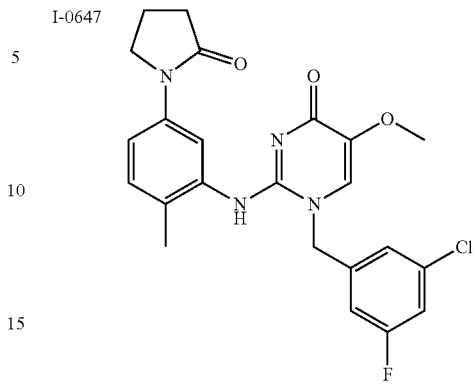 457 1.61 [1]
TABLE 124
I-0648 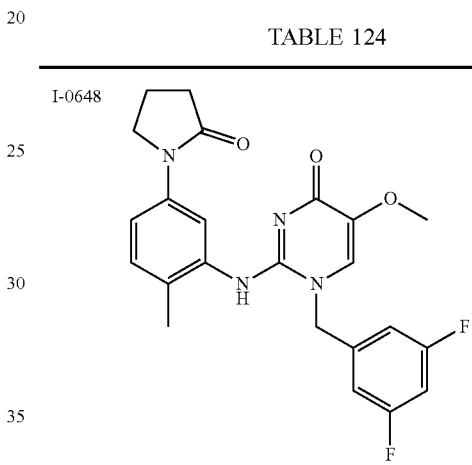 441 1.48 [1]
I-0649 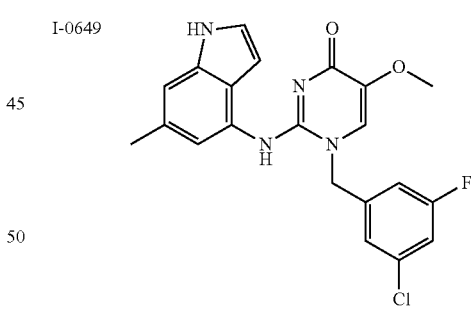 413 1.55 [1]
I-0650 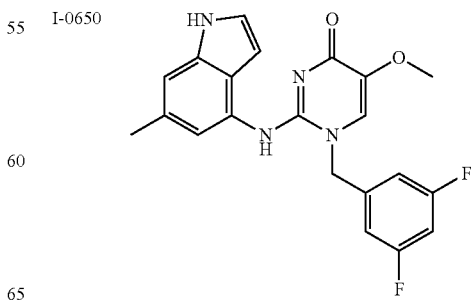 397 1.43 [1]

TABLE 124-continued

| ID | Structure | MW | RT | Ref |
|---|---|---|---|---|
| I-0651 | (1-oxo-1,2-dihydroisoquinolin-5-yl)amino pyrimidinone with 3-chloro-5-fluorobenzyl | 427 | 1.31 | [1] |
| I-0652 | (1-oxo-1,2-dihydroisoquinolin-5-yl)amino pyrimidinone with 3,5-difluorobenzyl | 411 | 1.18 | [1] |

TABLE 125

| ID | Structure | MW | RT | Ref |
|---|---|---|---|---|
| I-0653 | 5-(1H-pyrrol-1-yl)-2-methylphenylamino pyrimidinone with 3,4-difluorobenzyl | 423 | 1.88 | [1] |
| I-0654 | 5-(1H-pyrrol-1-yl)-2-methylphenylamino pyrimidinone with 3-chloro-5-fluorobenzyl | 439 | 2.03 | [1] |

TABLE 125-continued

| ID | Structure | MW | RT | Ref |
|---|---|---|---|---|
| I-0655 | 5-(1H-pyrrol-1-yl)-2-methylphenylamino pyrimidinone with 3,5-difluorobenzyl | 423 | 1.88 | [1] |
| I-0656 | 4-bromo-2-ethylphenylamino pyrimidinone with 3-chloro-5-fluorobenzyl | 468 | 2.26 | [1] |
| I-0657 | 5-methoxy-2-ethylphenylamino pyrimidinone with 3-chloro-5-fluorobenzyl | 418 | 2.03 | [1] |

TABLE 126

| ID | Structure | MW | RT | Ref |
|---|---|---|---|---|
| I-0658 | 5-(5-methylfuran-2-yl)-2-methylphenylamino pyrimidinone with benzyl | 402 | 1.89 | [1] |

TABLE 126-continued

| ID | MW | RT | Ref |
|---|---|---|---|
| I-0659 | 454 | 2.08 | [1] |
| I-0660 | 406 | 1.76 | [3] |
| I-0661 | 370 | 1.58 | [3] |
| I-0662 | 374 | 1.79 | [3] |

TABLE 127

| ID | MW | RT | Ref |
|---|---|---|---|
| I-0663 | 400 | 1.46 | [3] |
| I-0664 | 452 | 1.68 | [3] |
| I-0665 | 429 | 1.56 | [3] |
| I-0666 | 442 | 2.28 | [3] |
| I-0667 | 442 | 1.64 | [3] |

TABLE 128
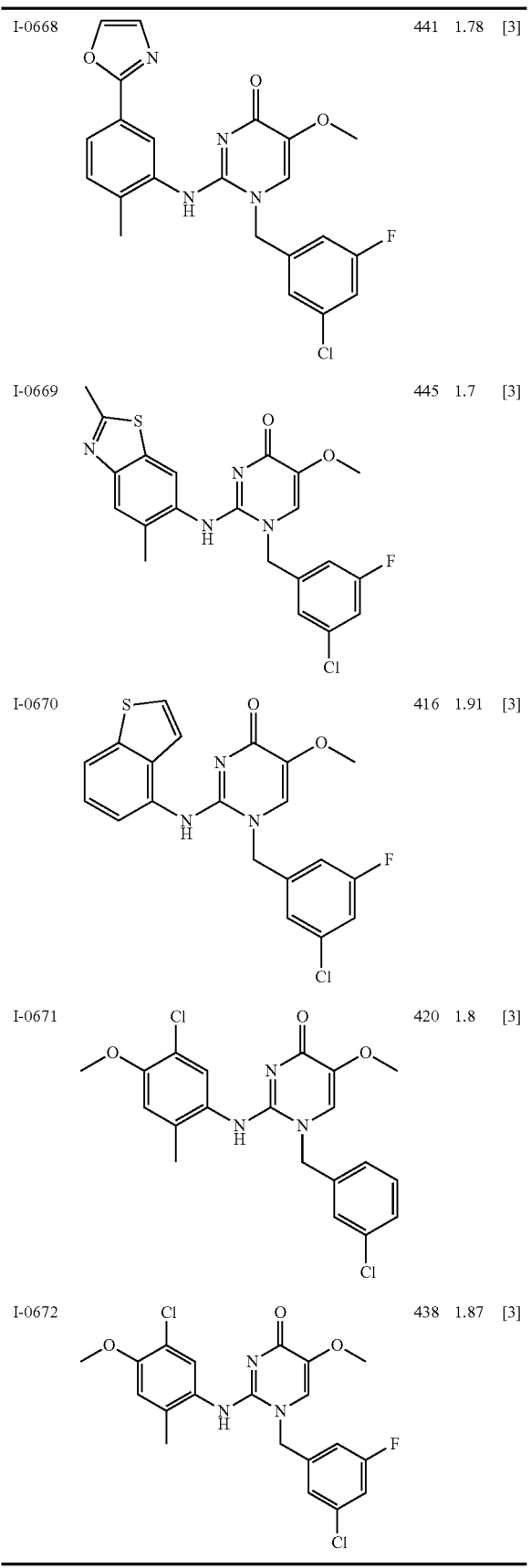
TABLE 129
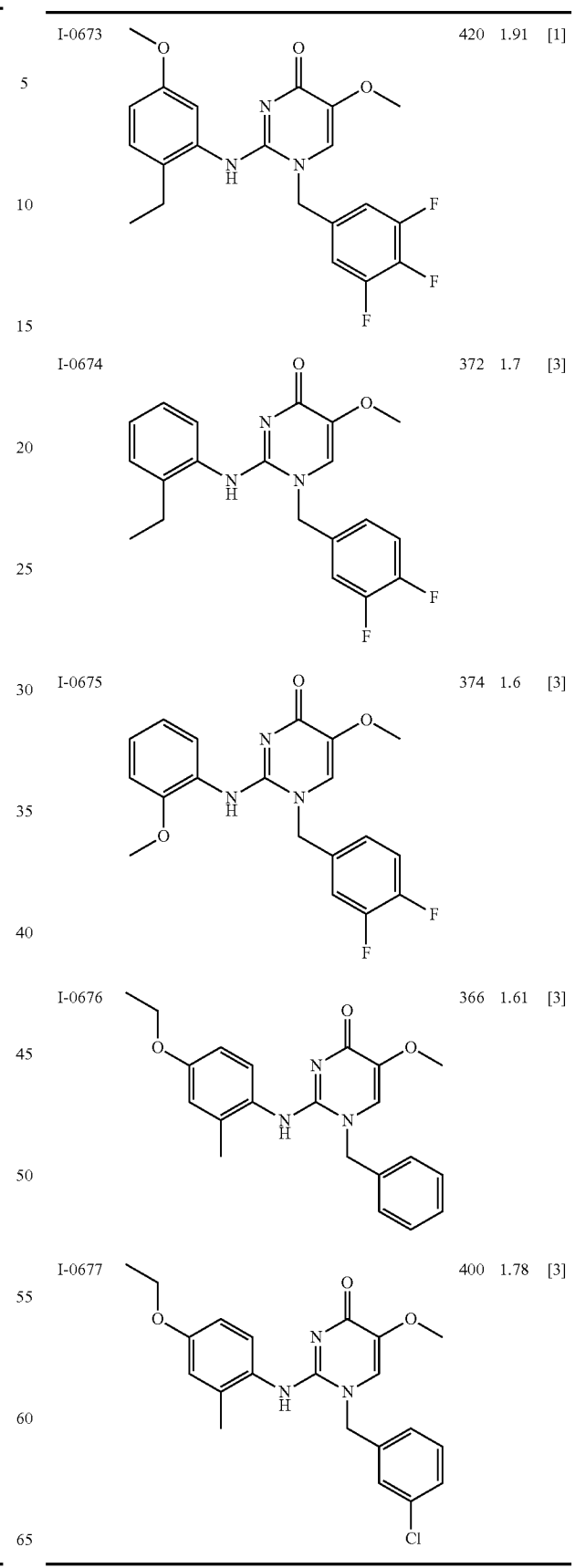

TABLE 130
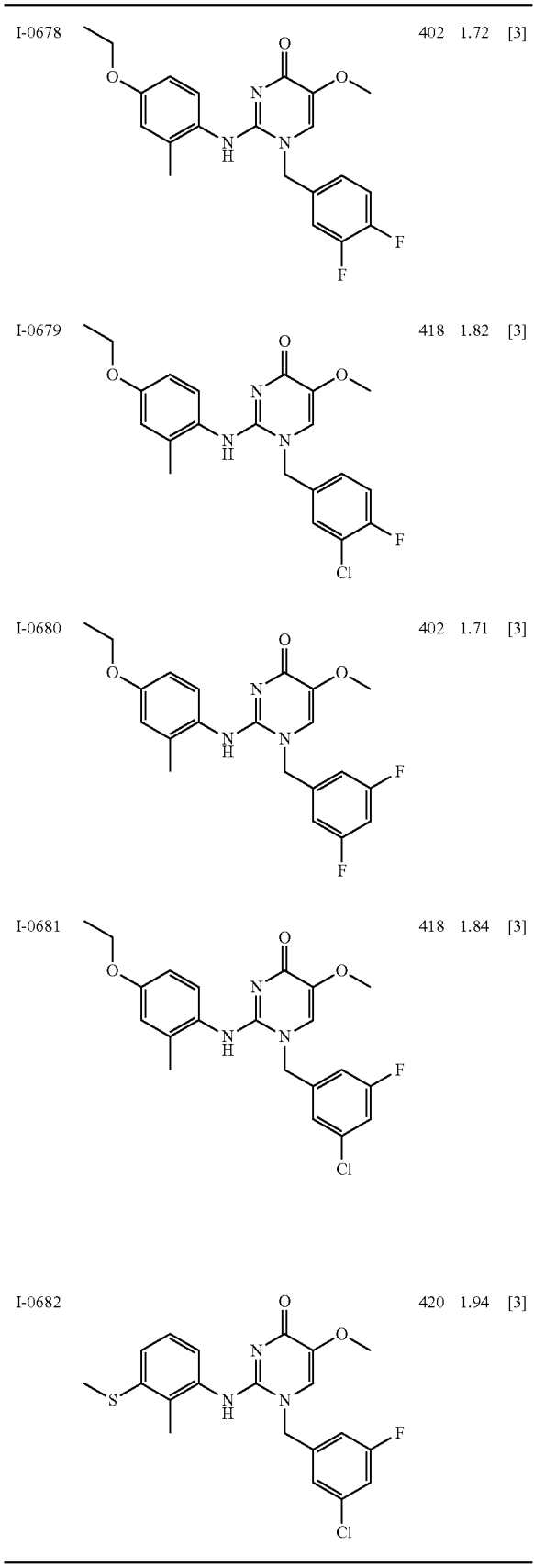
| ID | MW | RT | [M] |
|---|---|---|---|
| I-0678 | 402 | 1.72 | [3] |
| I-0679 | 418 | 1.82 | [3] |
| I-0680 | 402 | 1.71 | [3] |
| I-0681 | 418 | 1.84 | [3] |
| I-0682 | 420 | 1.94 | [3] |
TABLE 131
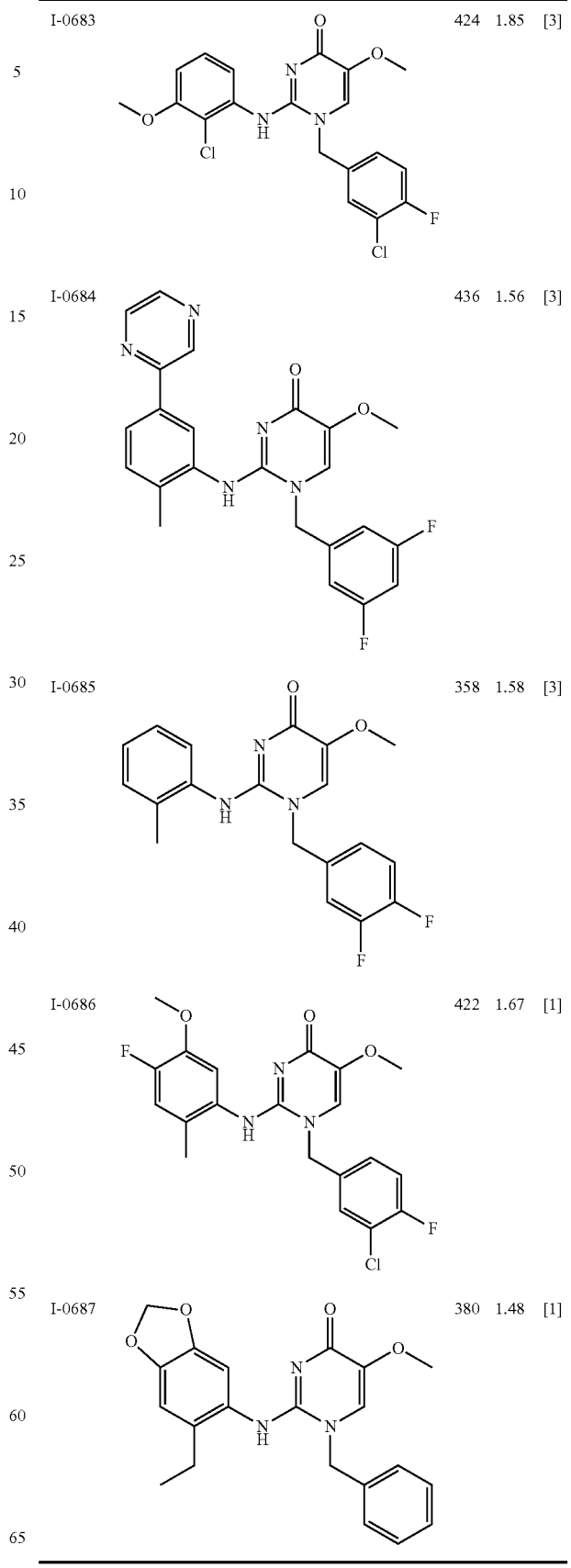
| ID | MW | RT | [M] |
|---|---|---|---|
| I-0683 | 424 | 1.85 | [3] |
| I-0684 | 436 | 1.56 | [3] |
| I-0685 | 358 | 1.58 | [3] |
| I-0686 | 422 | 1.67 | [1] |
| I-0687 | 380 | 1.48 | [1] |

TABLE 132
I-0688     432   1.67   [1]
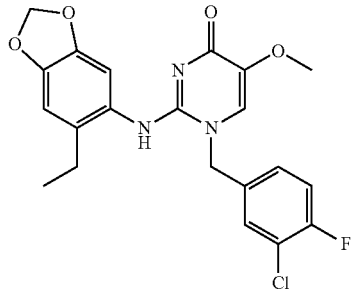 [SMILES: CCc1cc2c(cc1Nc1nc(=O)c(OC)cn1Cc1ccc(F)c(Cl)c1)OCO2]
I-0689     411   1.19   [1]
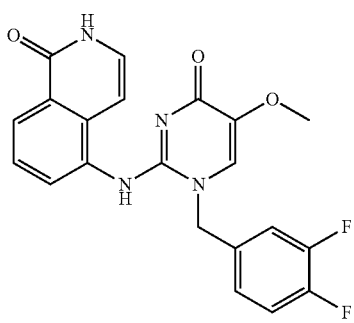 [SMILES: COc1cn(Cc2ccc(F)c(F)c2)c(Nc2cccc3c(=O)[nH]ccc23)nc1=O]
I-0690     399   1.09   [3]
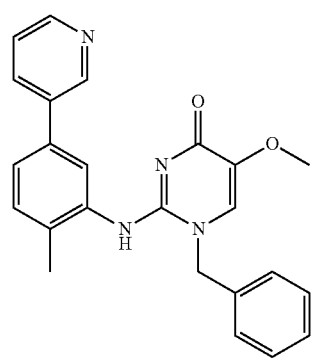 [SMILES: COc1cn(Cc2ccccc2)c(Nc2cc(-c3cccnc3)ccc2C)nc1=O]
I-0691     406   1.91   [3]
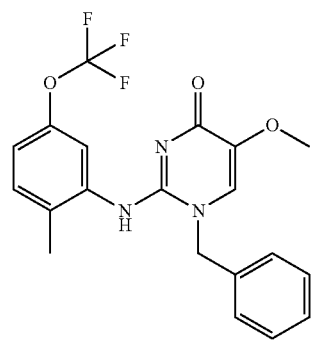 [SMILES: COc1cn(Cc2ccccc2)c(Nc2cc(OC(F)(F)F)ccc2C)nc1=O]
TABLE 132-continued
I-0692     458   2.15   [3]
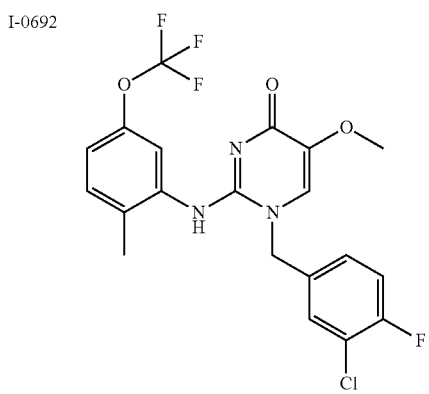
TABLE 133
I-0693     442   2.03   [3]
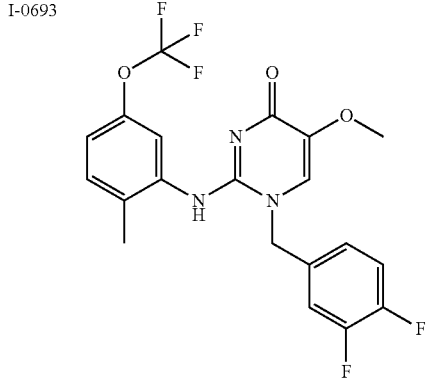
I-0694     458   2.2   [3]
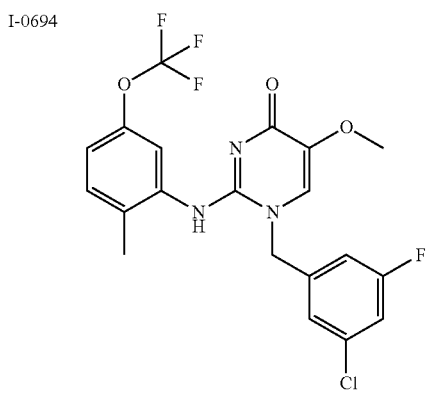
I-0695     442   2.05   [3]
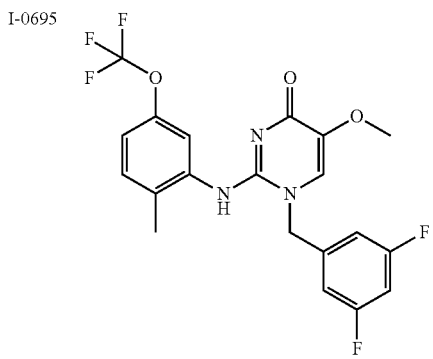

TABLE 133-continued
| | | | | |
|---|---|---|---|---|
| I-0696 | 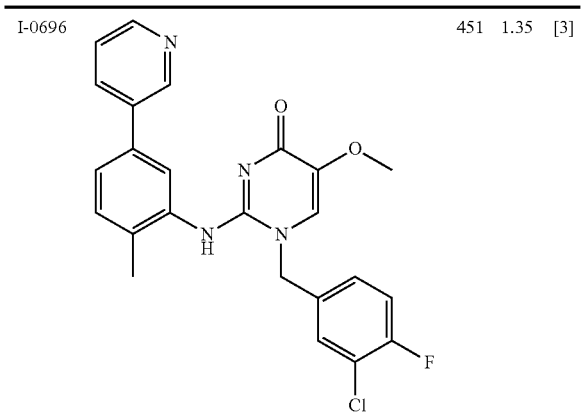 | 451 | 1.35 | [3] |
TABLE 133-continued
| | | | | |
|---|---|---|---|---|
| I-0697 | 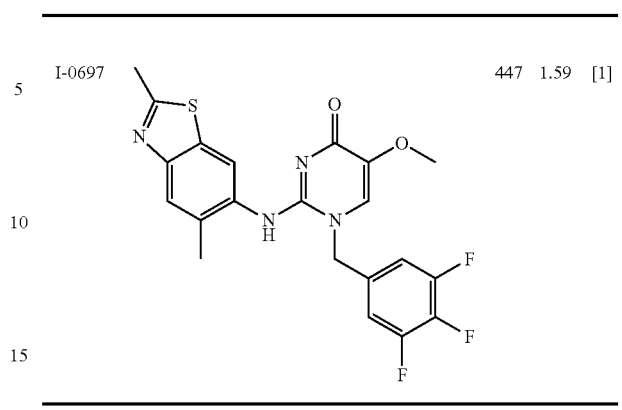 | 447 | 1.59 | [1] |
TABLE 134
| | | | | |
|---|---|---|---|---|
| I-0698 | 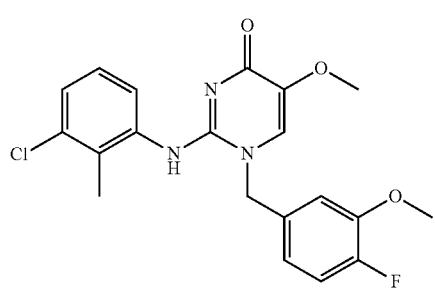 [SMILES: COc1cc(Cn2cc(OC)c(=O)nc2Nc2cccc(Cl)c2C)ccc1F] | 404 | 1.67 | [1] |
| I-0699 | 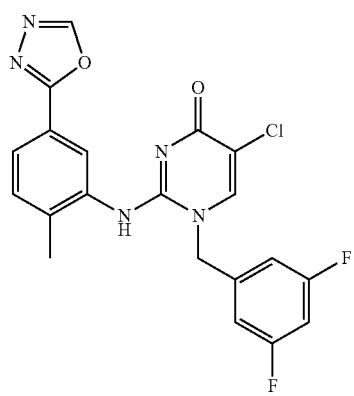 [SMILES: Cc1ccc(-c2nnco2)cc1Nc1nc(=O)c(Cl)cn1Cc1cc(F)cc(F)c1] | 430 | 1.68 | [3] |
| I-0700 | 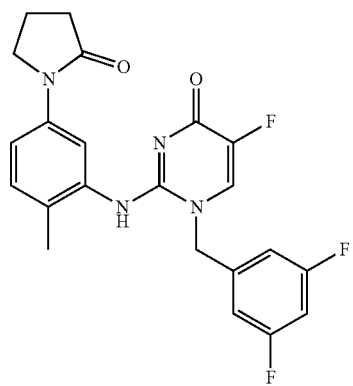 [SMILES: Cc1ccc(N2CCCC2=O)cc1Nc1nc(=O)c(F)cn1Cc1cc(F)cc(F)c1] | 429 | 1.5 | [3] |

TABLE 134-continued
| I-0701 | 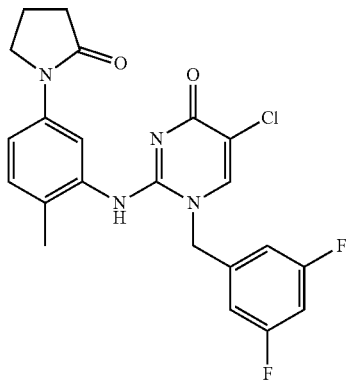 [SMILES: Cc1ccc(N2CCCC2=O)cc1Nc1nc(=O)c(Cl)cn1Cc1cc(F)cc(F)c1] | | 445 | 1.66 | [3] |
| I-0702 | 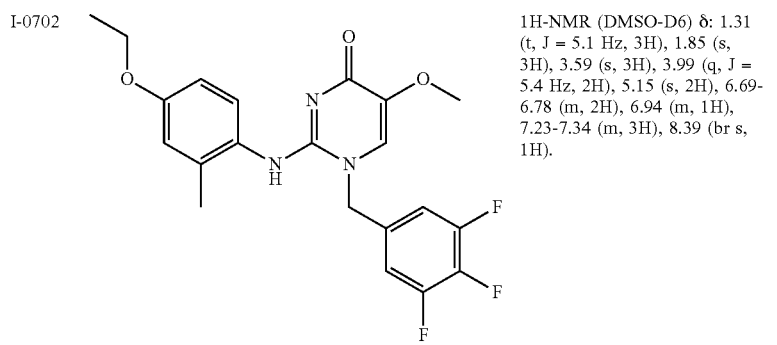 | 1H-NMR (DMSO-D6) δ: 1.31 (t, J = 5.1 Hz, 3H), 1.85 (s, 3H), 3.59 (s, 3H), 3.99 (q, J = 5.4 Hz, 2H), 5.15 (s, 2H), 6.69-6.78 (m, 2H), 6.94 (m, 1H), 7.23-7.34 (m, 3H), 8.39 (br s, 1H). | 420 | 1.68 | [1] |
TABLE 135
| I-0703 | 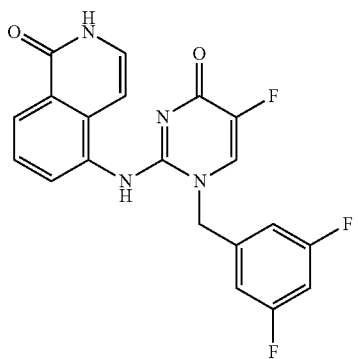 [SMILES: O=c1nc(Nc2cccc3c(=O)[nH]ccc23)n(Cc2cc(F)cc(F)c2)cc1F] | 399 | 1.22 | [3] |
| I-0704 | 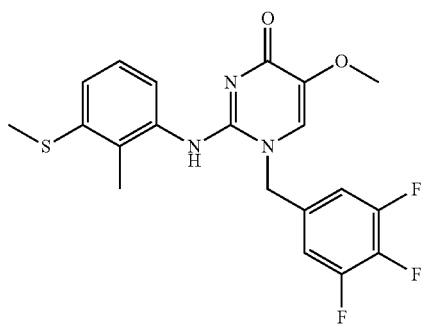 | 422 | 1.78 | [1] |

TABLE 135-continued

| | | | | | |
|---|---|---|---|---|---|
| I-0705 | (structure) | | 385 | 1.57 | [3] |
| I-0706 | (structure) | | 401 | 1.78 | [3] |
| I-0707 | (structure) | 1H-NMR (DMSO-D6) δ: 1.88 (s, 3H), 3.60 (s, 3H), 5.17 (br s, 2H), 6.88-7.40 (m, 7H), 8.35 (br s, 1H). | 442 | 1.76 | [1] |

TABLE 136

| | | | | |
|---|---|---|---|---|
| I-0708 | (structure) | 434 | 1.56 | [1] |

TABLE 136-continued
| I-0709 | 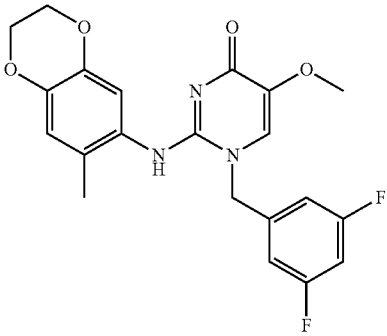 | 1H-NMR (DMSO-D6) δ: 1.72 (s, 3H), 3.59 (s, 3H), 4.20 (s, 4H), 5.18 (s, 2H), 6.55 (s, 1H), 6.66 (s, 1H), 6.99 (d, J = 6.9 Hz, 2H), 7.24 (t, J = 9.7 Hz, 1H), 7.30 (s, 1H), 8.16 (s, 1H). | 416 | 1.38 | [3] |
|---|---|---|---|---|---|
| I-0710 | 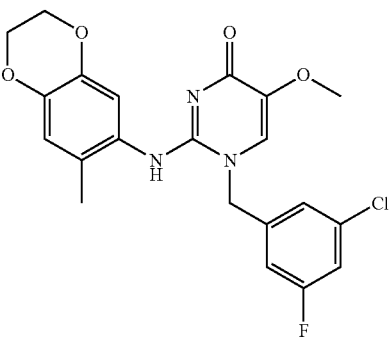 [SMILES: COc1cn(Cc2cc(F)cc(Cl)c2)c(Nc2cc3c(cc2C)OCCO3)nc1=O] | 1H-NMR (DMSO-D6) δ: 1.73 (s, 3H), 3.59 (s, 3H), 4.20 (s, 4H), 5.17 (s, 2H), 6.54 (s, 1H), 6.67 (s, 1H), 7.11 (d, J = 9.3 Hz, 1H), 7.18 (s, 1H), 7.31 (s, 1H), 7.44 (d, J = 8.4 Hz, 1H), 8.17 (s, 1H). | 432 | 1.67 | [3] |
| I-0711 | 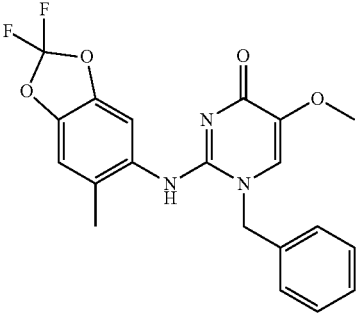 [SMILES: COc1cn(Cc2ccccc2)c(Nc2cc3c(cc2C)OC(F)(F)O3)nc1=O] | 1H-NMR (CDCl3) δ: 1.97 (s, 3H), 3.69 (s, 3H), 5.04 (s, 2H), 6.51 (s, 1H), 6.81 (s, 1H), 6.90 (s, 1H), 7.37-7.39 (m, 5H), 7.52 (s, 1H). | 402 | 1.78 | [3] |
| I-0712 | 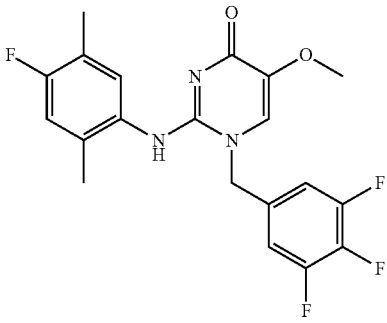 [SMILES: COc1cn(Cc2cc(F)c(F)c(F)c2)c(Nc2cc(C)c(F)cc2C)nc1=O] | | 408 | 1.75 | [1] |

TABLE 137
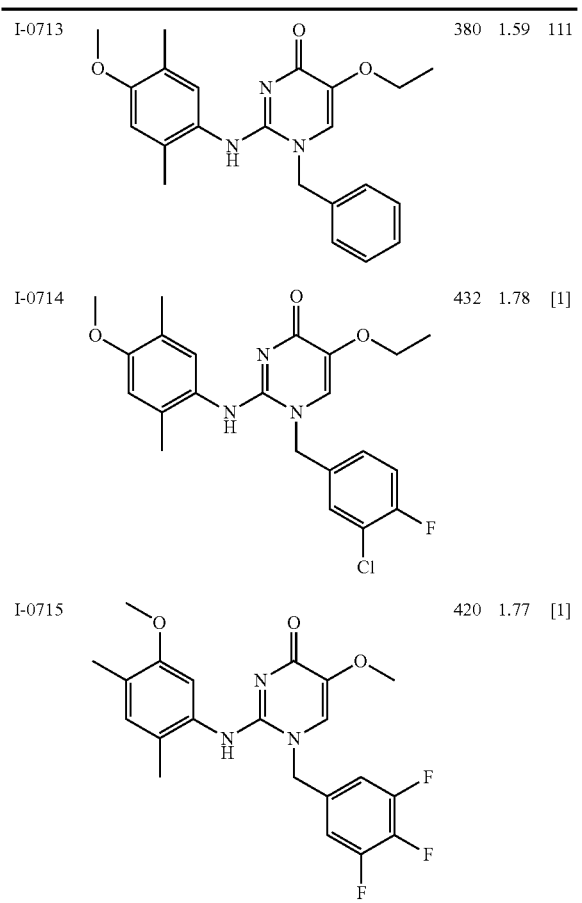
| ID | MW | RT | [M] |
|---|---|---|---|
| I-0713 | 380 | 1.59 | 111 |
| I-0714 | 432 | 1.78 | [1] |
| I-0715 | 420 | 1.77 | [1] |
TABLE 137-continued
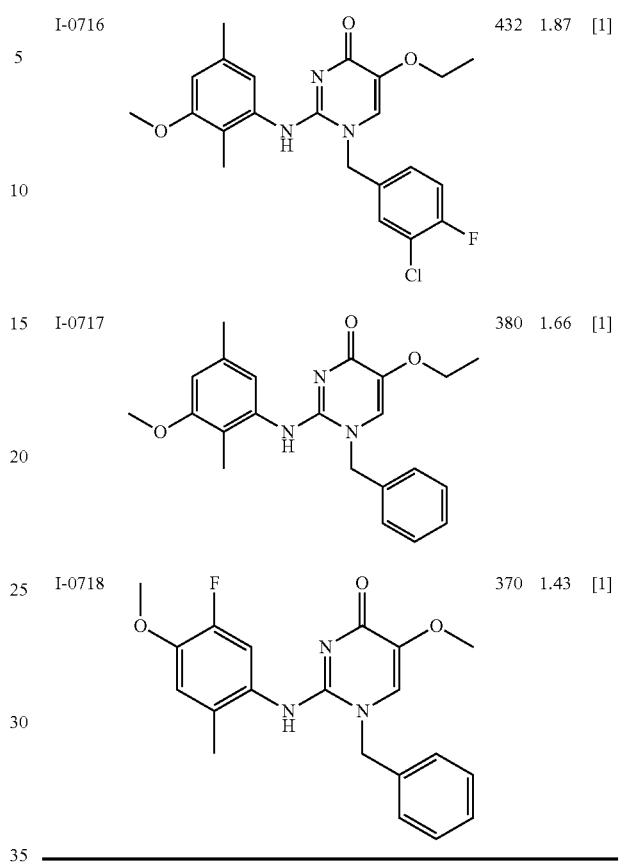
| ID | MW | RT | [M] |
|---|---|---|---|
| I-0716 | 432 | 1.87 | [1] |
| I-0717 | 380 | 1.66 | [1] |
| I-0718 | 370 | 1.43 | [1] |
TABLE 138
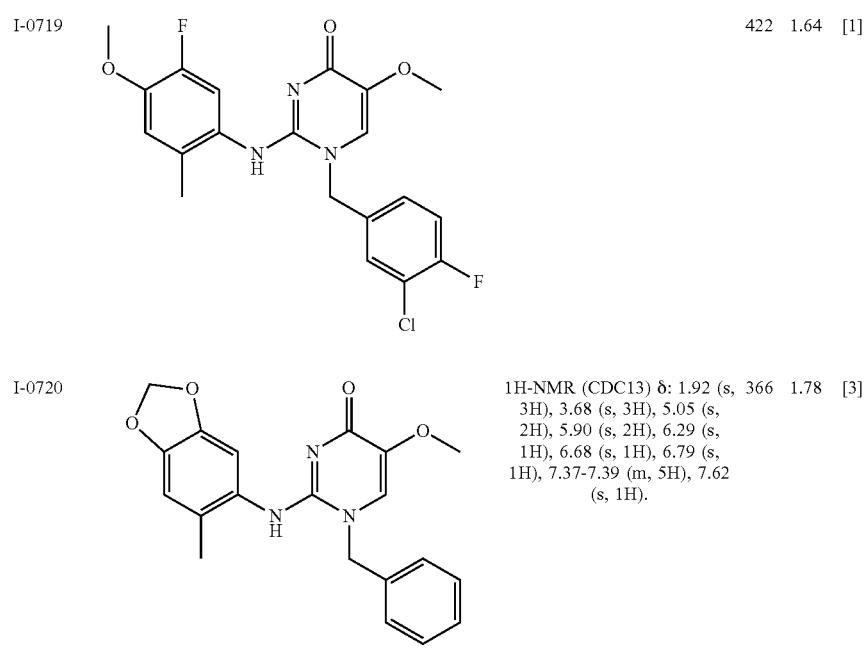
| ID | NMR | MW | RT | [M] |
|---|---|---|---|---|
| I-0719 | | 422 | 1.64 | [1] |
| I-0720 | 1H-NMR (CDCl3) δ: 1.92 (s, 3H), 3.68 (s, 3H), 5.05 (s, 2H), 5.90 (s, 2H), 6.29 (s, 1H), 6.68 (s, 1H), 6.79 (s, 1H), 7.37-7.39 (m, 5H), 7.62 (s, 1H). | 366 | 1.78 | [3] |

TABLE 138-continued
| I-0721 | 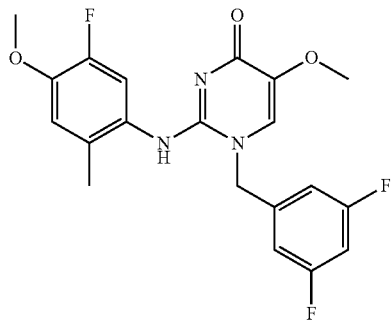 | 406 | 1.53 | [1] |
| I-0722 | 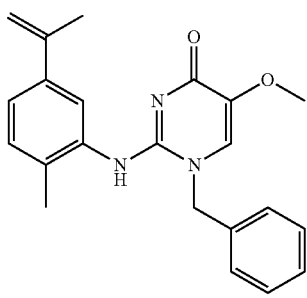 | 362 | 1.8 | [3] |
| I-0723 | 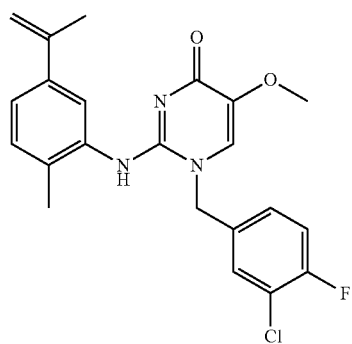 | 414 | 203 | [3] |
| I-0724 | 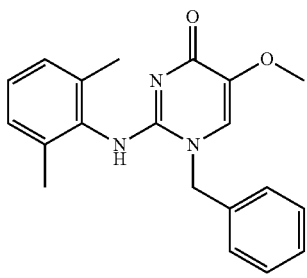 | 336 | 1.49 | [3] |

TABLE 139

| | | | | | |
|---|---|---|---|---|---|
| I-0726 | | 1H-NMR (CDCl3) δ: 3.73 (s, 3H), 4.86 (s, 2H), 6.62 (s, 1H), 6.79-6.82 (m, 4H), 6.91 (s, 1H), 8.28 (s, 1H). | 438 | 1.9 | [3] |
| I-0727 | | 1H-NMR (CDCl3) δ: 3.73 (s, 3H), 4.97 (s, 2H), 6.79 (s, 1H), 6.91 (s, 1H), 7.15-7.19 (m, 2H), 7.36 (d, J = 6.8 Hz, 1H), 7.45 (d, J = 7.3 Hz, 1H), 7.53 (s, 1H). | 454 | 2 | [3] |
| I-0728 | | 1H-NMR (CDCl3) δ: 0.99 (t, J = 7.5 Hz, 3H), 2.30 (q, J = 7.5 Hz, 2H), 3.70 (s, 3H), 5.04 (s, 2H), 6.50 (s, 1H), 6.82 (s, 1H), 6.91 (s, 1H), 7.30-7.42 (m, 5H), 7.58 (s, 1H). | 416 | 1.91 | [3] |
| I-0729 | | 1H-NMR (CDCl3) δ: 0.98 (t, J = 7.5 Hz, 3H), 2.27 (q, J = 7.5 Hz, 2H), 3.74 (s, 3H), 5.00 (s, 2H), 6.48 (s, 1H), 6.78 (s, 1H), 6.81 (dd, J = 8.9, 2.3 Hz, 1H), 6.87 (d, J = 5.9 Hz, 2H), 6.92 (s, 1H), 7.60 (s, 1H). | 452 | 2.02 | [3] |

TABLE 139-continued

| | | | | |
|---|---|---|---|---|
| I-0730 | (structure) | 1H-NMR (CDCl3) δ: 1.00 (t, J = 7.5 Hz, 3H), 2.29 (q, J = 7.5 Hz, 2H), 3.73 (s, 3H), 4.97 (s, 2H), 6.48 (s, 1H), 6.80 (s, 1H), 6.93 (s, 1H), 7.17 (t, J = 8.5 Hz, 1H), 7.22 (dd, J = 4.4, 2.0 Hz, 1H), 7.43 (dd, J = 6.8, 1.9 Hz, 1H), 7.58 (s, 1H). | 468 | 2.14 [3] |

TABLE 140

| | | | | |
|---|---|---|---|---|
| I-0731 | (structure) | | 380 | 1.46 [3] |
| I-0732 | (structure) | | 416 | 1.56 [3] |
| I-0733 | (structure) | | 454 | 1.73 [3] |
| I-0734 | (structure) | | 454 | 1.75 [3] |
| I-0735 | (structure) | | 459 | 1.61 [3] |

TABLE 141
| | | | | |
|---|---|---|---|---|
| I-0736 | 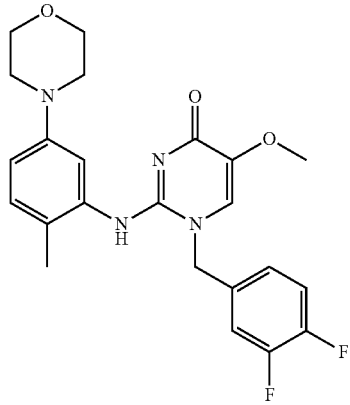 | 443 | 1.49 | [3] |
| I-0737 | 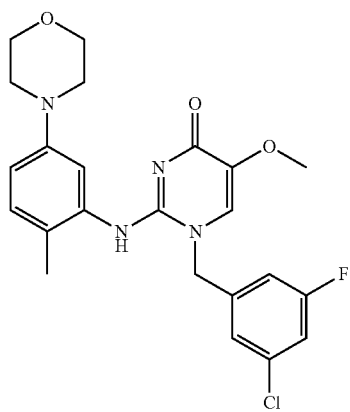 | 459 | 1.63 | [3] |
| I-0738 | 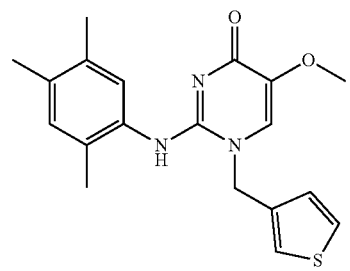 | 356 | 1.54 | [1] |
| I-0739 | 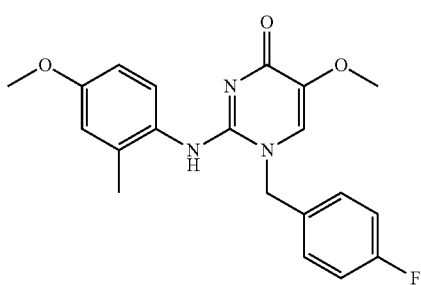 | 370 | 1.4 | [1] |

TABLE 141-continued
| I-0740 | 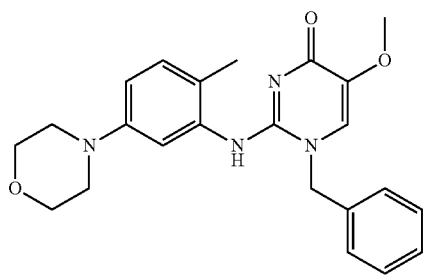 | 407 | 1.37 | [3] |
TABLE 142
| I-0741 | 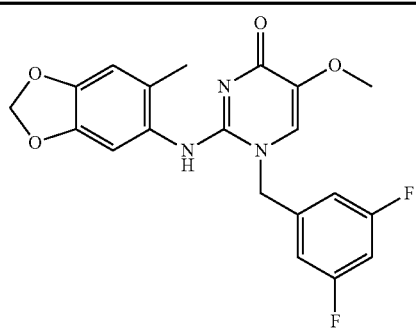 | 402 | 1.51 | [3] |
| I-0742 | 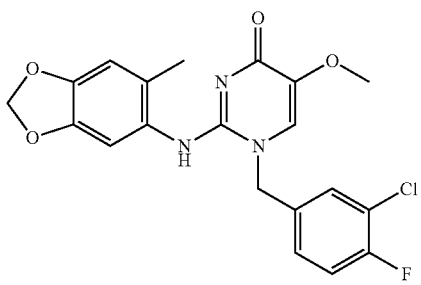 | 418 | 1.64 | [3] |
| I-0743 | 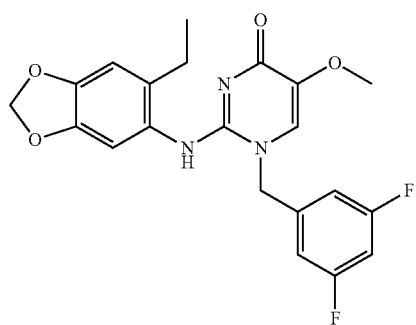 | 416 | 1.64 | [3] |
| I-0744 | 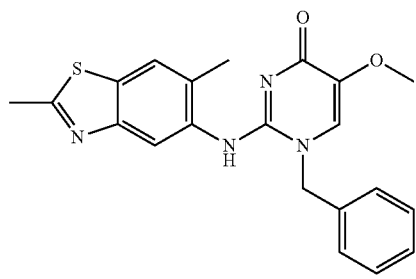 | 393 | 1.49 | [3] |

TABLE 142-continued
| I-0745 | 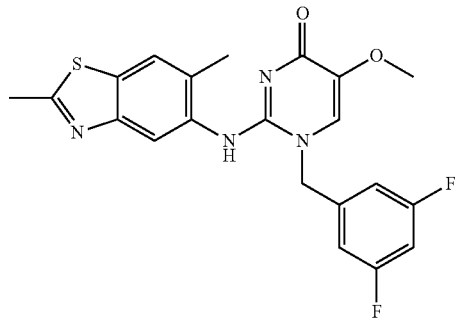 | 429 | 1.59 | [3] |
| I-0746 | 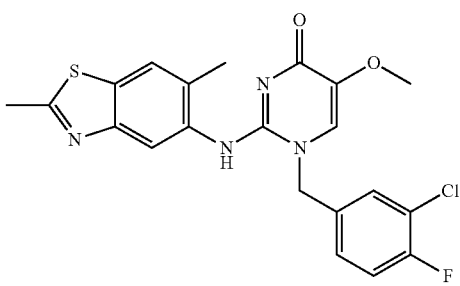 | 445 | 1.71 | [3] |
TABLE 143
| I-0747 | 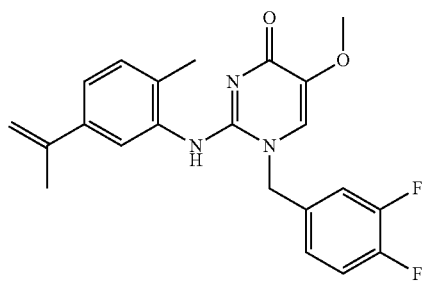 | 398 | 1.59 | [3] |
| I-0748 | 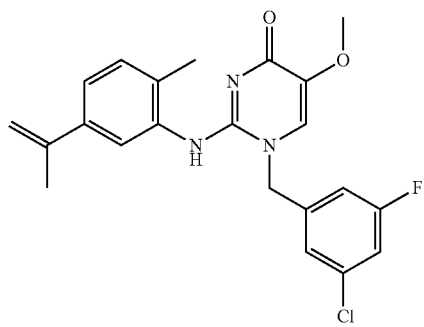 | 414 | 2.02 | [3] |

TABLE 143-continued
| | | | | |
|---|---|---|---|---|
| I-0749 | 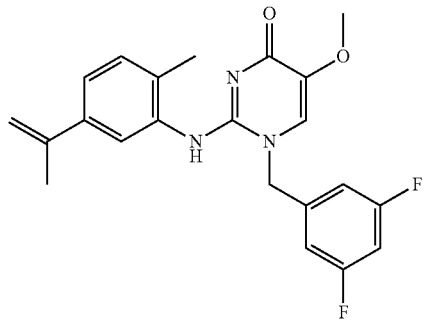 [SMILES: C=C(C)c1ccc(C)c(Nc2nc(=O)c(OC)cn2Cc2cc(F)cc(F)c2)c1] | 398 | 1.87 | [3] |
| I-0750 | 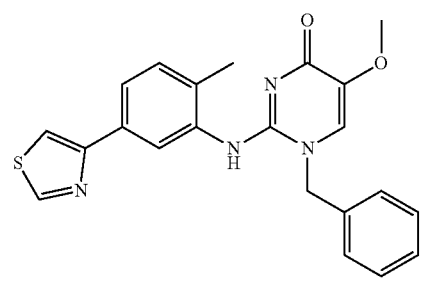 [SMILES: COc1cn(Cc2ccccc2)c(Nc2cc(-c3cscn3)ccc2C)nc1=O] | 405 | 1.54 | [3] |
| I-0751 | 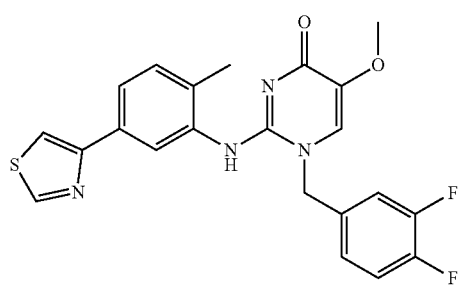 [SMILES: COc1cn(Cc2ccc(F)c(F)c2)c(Nc2cc(-c3cscn3)ccc2C)nc1=O] | 441 | 1.64 | [3] |
| I-0752 | 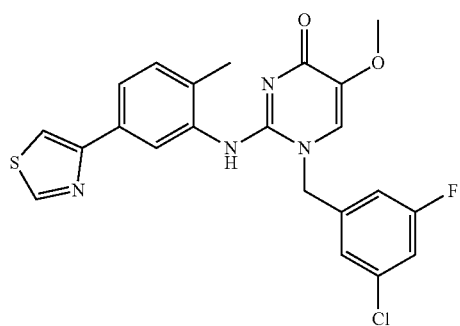 | 458 | 1.76 | [3] |

TABLE 144
| | | | | |
|---|---|---|---|---|
| I-0753 | 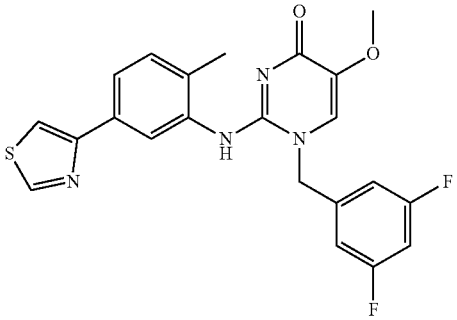 [SMILES: COc1cn(Cc2cc(F)cc(F)c2)c(Nc2cc(-c3cscn3)ccc2C)nc1=O] | 441 | 1.64 | [3] |
| I-0754 | 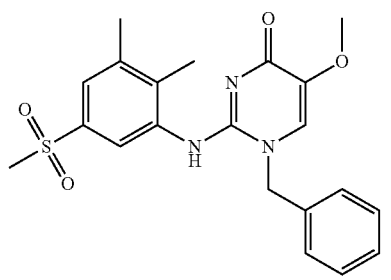 [SMILES: COc1cn(Cc2ccccc2)c(Nc2cc(S(C)(=O)=O)cc(C)c2C)nc1=O] | 414 | 1.47 | [3] |
| I-0755 | 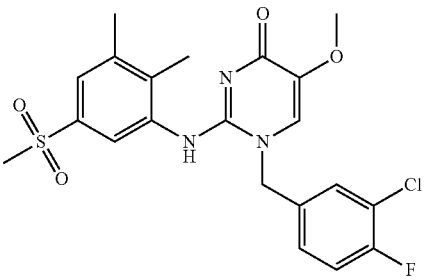 [SMILES: COc1cn(Cc2ccc(F)c(Cl)c2)c(Nc2cc(S(C)(=O)=O)cc(C)c2C)nc1=O] | 467 | 1.66 | [3] |
| I-0756 | 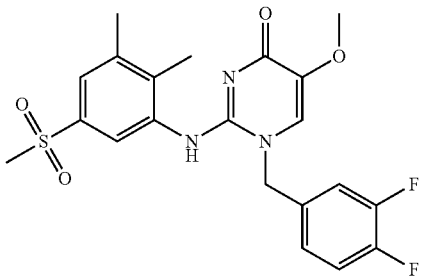 [SMILES: COc1cn(Cc2ccc(F)c(F)c2)c(Nc2cc(S(C)(=O)=O)cc(C)c2C)nc1=O] | 450 | 1.55 | [3] |
| I-0757 | 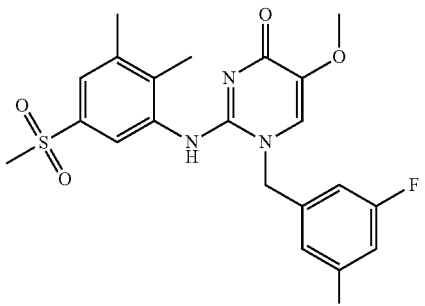 | 467 | 1.69 | [3] |

TABLE 144-continued
| | | | | |
|---|---|---|---|---|
| I-0758 | 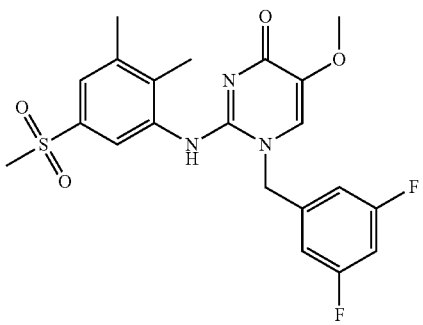 [SMILES: COc1cn(Cc2cc(F)cc(F)c2)c(Nc2cc(S(C)(=O)=O)cc(C)c2C)nc1=O] | 450 | 1.55 | [3] |
TABLE 145
| | | | | |
|---|---|---|---|---|
| I-0759 | 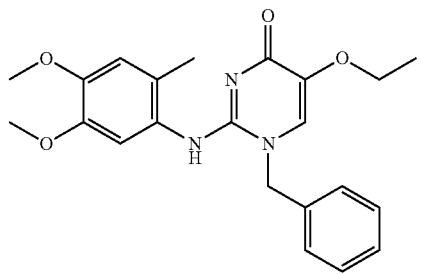 [SMILES: CCOc1cn(Cc2ccccc2)c(Nc2cc(OC)c(OC)cc2C)nc1=O] | 396 | 1.4 | [1] |
| I-0760 | 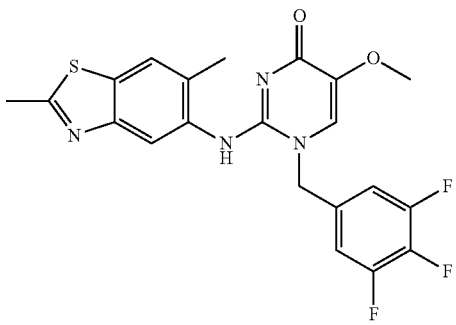 [SMILES: COc1cn(Cc2cc(F)c(F)c(F)c2)c(Nc2cc3nc(C)sc3cc2C)nc1=O] | 447 | 1.66 | [1] |
| I-0761 | 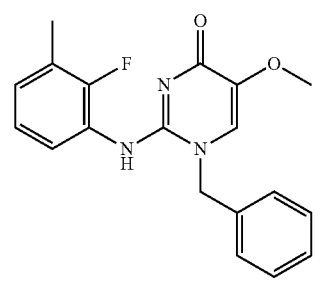 [SMILES: COc1cn(Cc2ccccc2)c(Nc2cccc(C)c2F)nc1=O] | 340 | 1.5 | [1] |
| I-0762 | 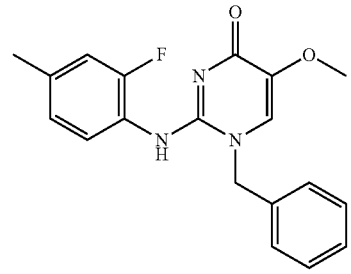 [SMILES: COc1cn(Cc2ccccc2)c(Nc2ccc(C)cc2F)nc1=O] | 340 | 1.49 | [1] |

TABLE 145-continued
| | | | | |
|---|---|---|---|---|
| I-0763 | 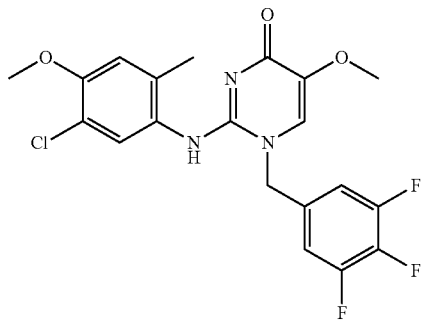 | 440 | 1.72 | [1] |
| I-0764 | 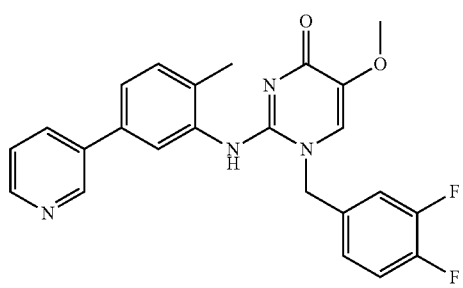 [SMILES: COc1cn(Cc2ccc(F)c(F)c2)c(Nc2cc(-c3cccnc3)ccc2C)nc1=O] | 435 | 1.21 | [3] |
TABLE 146
| | | | | |
|---|---|---|---|---|
| I-0765 | 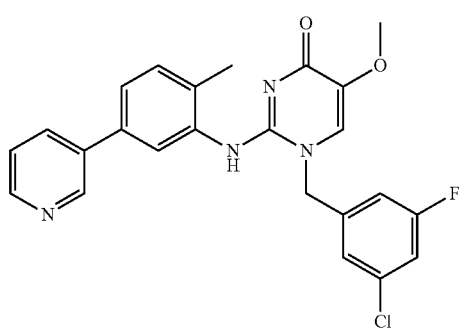 [SMILES: COc1cn(Cc2cc(F)cc(Cl)c2)c(Nc2cc(-c3cccnc3)ccc2C)nc1=O] | 451 | 1.49 | [3] |
| I-0766 | 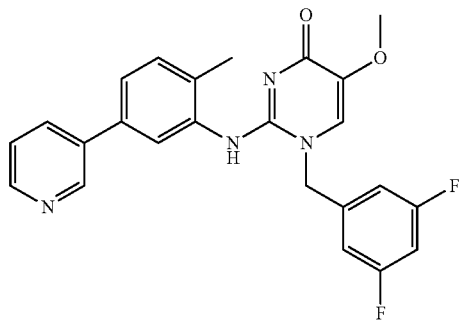 [SMILES: COc1cn(Cc2cc(F)cc(F)c2)c(Nc2cc(-c3cccnc3)ccc2C)nc1=O] | 435 | 1.38 | [3] |

TABLE 146-continued
| I-0767 | 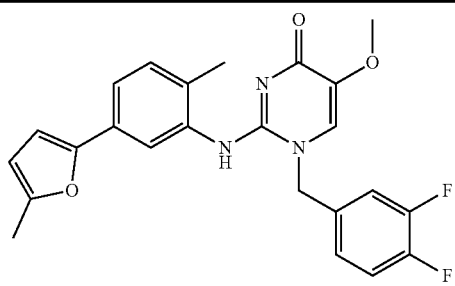 | 438 | 2.05 | [3] |
| I-0768 | 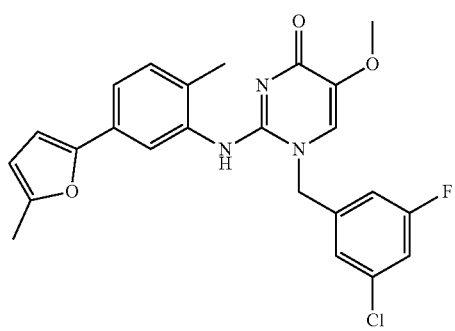 [SMILES: COc1cn(Cc2cc(F)cc(Cl)c2)c(Nc2cc(-c3ccc(C)o3)ccc2C)nc1=O] | 454 | 2.19 | [3] |
| I-0769 | 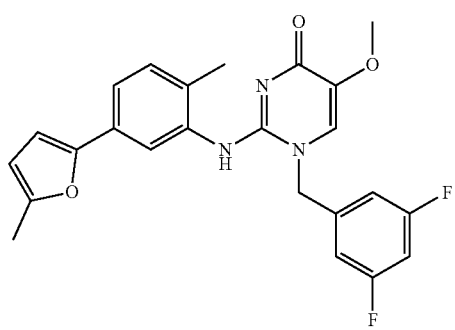 [SMILES: COc1cn(Cc2cc(F)cc(F)c2)c(Nc2cc(-c3ccc(C)o3)ccc2C)nc1=O] | 438 | 2.03 | [3] |
| I-0770 | 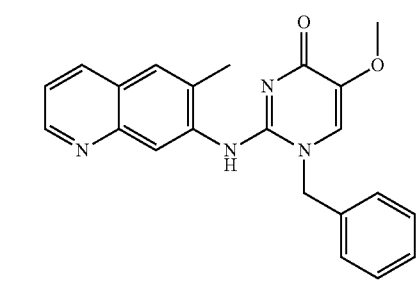 [SMILES: COc1cn(Cc2ccccc2)c(Nc2cc3ncccc3cc2C)nc1=O] | 373 | 1.12 | [3] |
TABLE 147
| I-0771 | 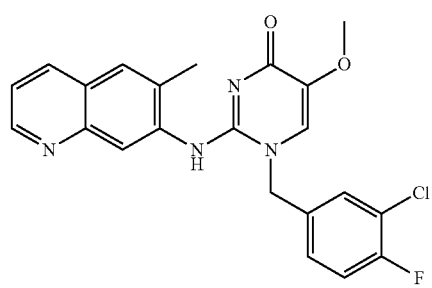 [SMILES: COc1cn(Cc2ccc(F)c(Cl)c2)c(Nc2cc3ncccc3cc2C)nc1=O] | 425 | 1.4 | [3] |

TABLE 147-continued

| | | | | |
|---|---|---|---|---|
| I-0772 | | 409 | 1.27 | [3] |
| I-0773 | | 425 | 1.43 | [3] |
| I-0774 | | 409 | 1.29 | [3] |
| I-0775 | | 432 | 1.67 | [3] |
| I-0776 | | 432 | 1.68 | [3] |

TABLE 148

| | | | | |
|---|---|---|---|---|
| I-0777 | (structure) | 434 | 1.91 | [1] |
| I-0778 | (structure) | 433 | 1.68 | [3] |
| I-0779 | (structure) | 406 | 1.66 | [3] |
| I-0780 | (structure) | 422 | 1.8 | [3] |
| I-0781 | (structure) | 406 | 1.66 | [3] |

TABLE 148-continued
| | | | | |
|---|---|---|---|---|
| I-0782 | 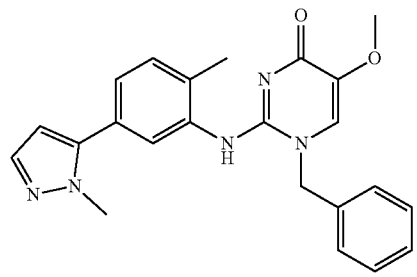 [SMILES: COc1cn(Cc2ccccc2)c(Nc2cc(-c3ccnn3C)ccc2C)nc1=O] | 402 | 1.53 | [3] |
TABLE 149
| | | | | |
|---|---|---|---|---|
| I-0783 | 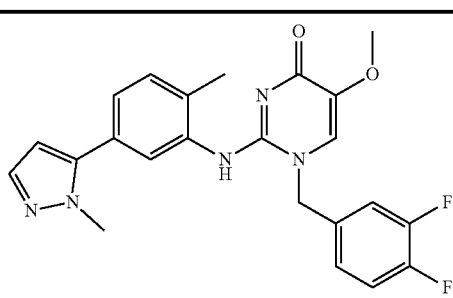 | 438 | 1.63 | [3] |
| I-0784 | 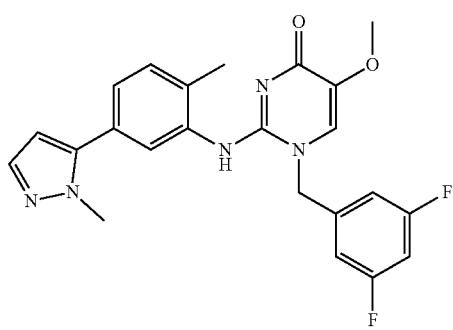 [SMILES: COc1cn(Cc2cc(F)cc(F)c2)c(Nc2cc(-c3ccnn3C)ccc2C)nc1=O] | 438 | 1.62 | [3] |
| I-0785 | 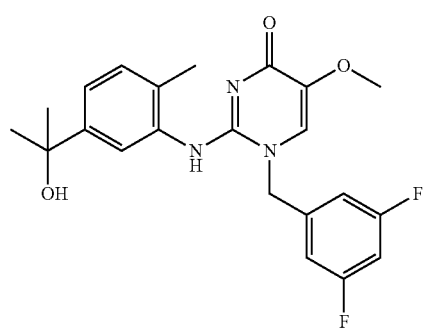 [SMILES: COc1cn(Cc2cc(F)cc(F)c2)c(Nc2cc(C(C)(C)O)ccc2C)nc1=O] | 416 | 1.55 | [3] |
| I-0786 | 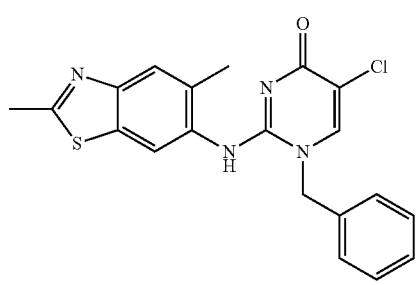 [SMILES: Cc1nc2cc(C)c(Nc3nc(=O)c(Cl)cn3Cc3ccccc3)cc2s1] | 397 | 1.61 | [3] |

TABLE 149-continued
| I-0787 | 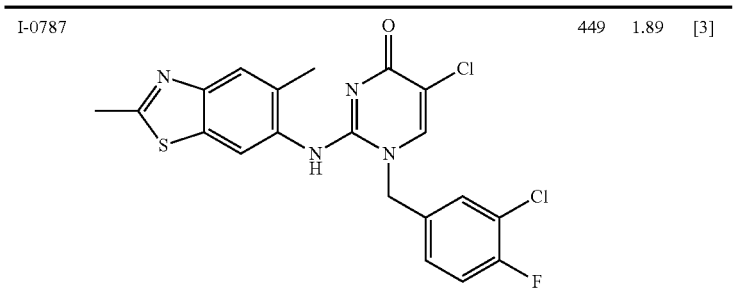 | 449 | 1.89 | [3] |
| I-0788 | 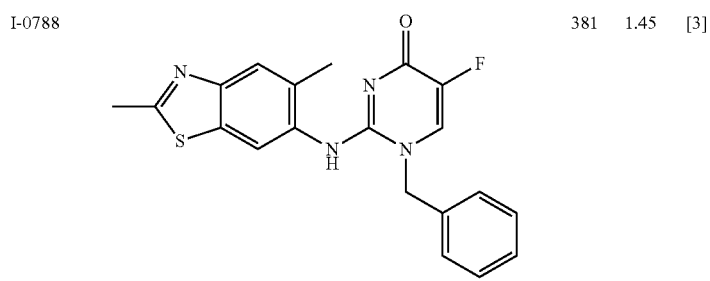 | 381 | 1.45 | [3] |
TABLE 150
| I-0789 | 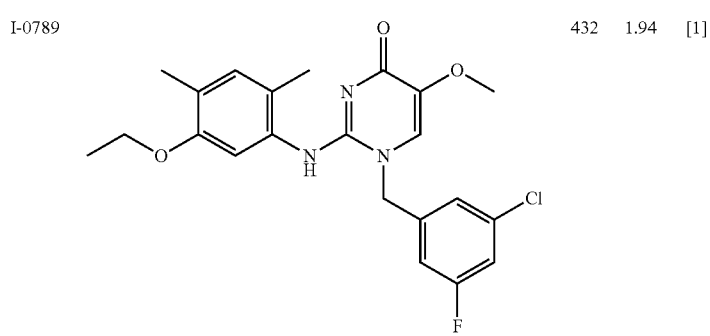 | 432 | 1.94 | [1] |
| I-0790 | 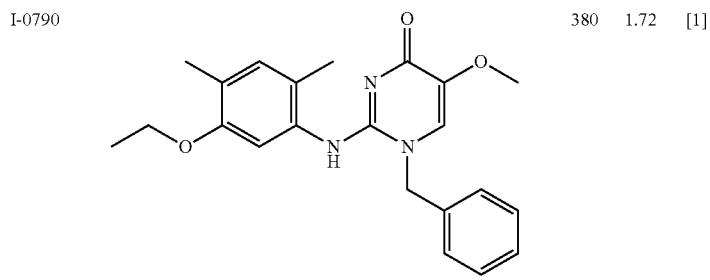 | 380 | 1.72 | [1] |
| I-0791 | 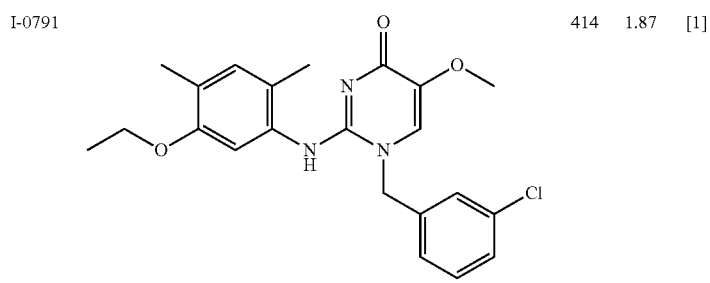 | 414 | 1.87 | [1] |

TABLE 150-continued
| I-0792 | 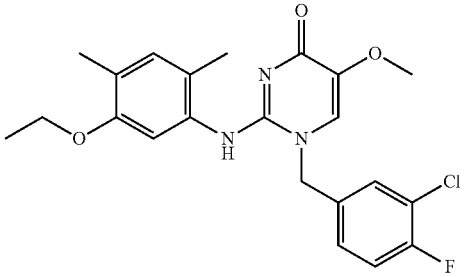 [SMILES: CCOc1cc(Nc2nc(=O)c(OC)cn2Cc2ccc(F)c(Cl)c2)c(C)cc1C] | 432 | 1.91 | [1] |
| I-0793 | 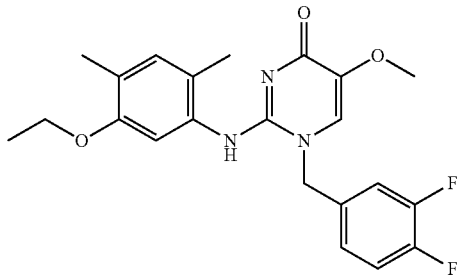 [SMILES: CCOc1cc(Nc2nc(=O)c(OC)cn2Cc2ccc(F)c(F)c2)c(C)cc1C] | 416 | 1.81 | [1] |
| I-0794 | 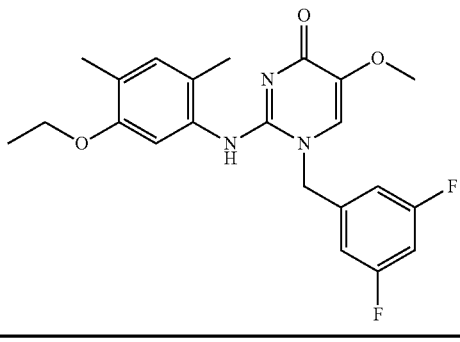 | 416 | 1.81 | [1] |
TABLE 151
| I-0795 | 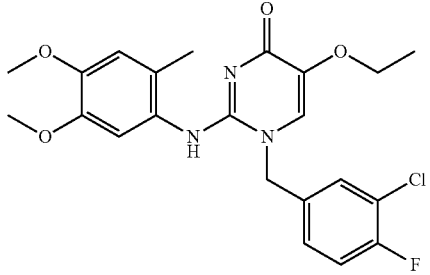 [SMILES: CCOc1cn(Cc2ccc(F)c(Cl)c2)c(Nc2cc(OC)c(OC)cc2C)nc1=O] | 448 | 1.6 | [1] |
| I-0796 | 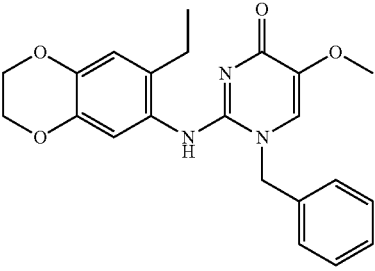 [SMILES: CCc1cc2c(cc1Nc1nc(=O)c(OC)cn1Cc1ccccc1)OCCO2] | 394 | 1.57 | [3] |

TABLE 151-continued

| ID | Structure | | | |
|---|---|---|---|---|
| I-0797 | 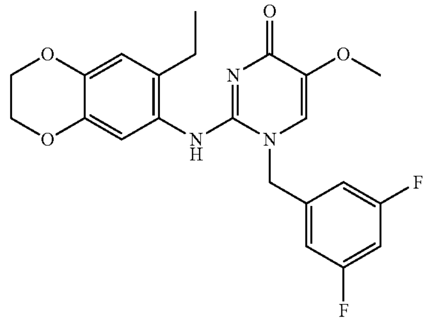 [SMILES: CCc1cc2c(cc1Nc1nc(=O)c(OC)cn1Cc1cc(F)cc(F)c1)OCCO2] | 430 | 1.56 | [3] |
| I-0798 | 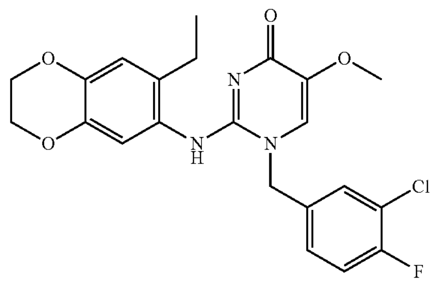 [SMILES: CCc1cc2c(cc1Nc1nc(=O)c(OC)cn1Cc1ccc(F)c(Cl)c1)OCCO2] | 446 | 1.77 | [3] |
| I-0799 | 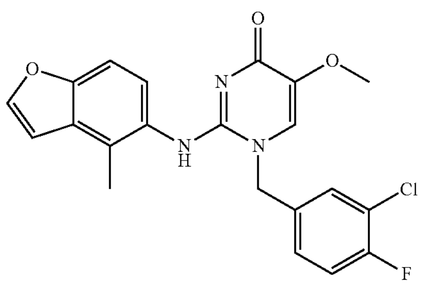 [SMILES: COc1cn(Cc2ccc(F)c(Cl)c2)c(Nc2ccc3occc3c2C)nc1=O] | 414 | 1.73 | [3] |
| I-0800 | 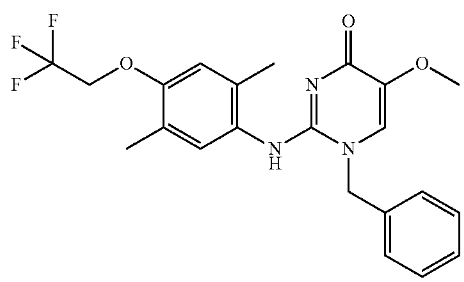 [SMILES: COc1cn(Cc2ccccc2)c(Nc2cc(C)c(OCC(F)(F)F)cc2C)nc1=O] | 434 | 1.79 | [1] |

TABLE 152

| ID | Structure | | | |
|---|---|---|---|---|
| I-0801 | 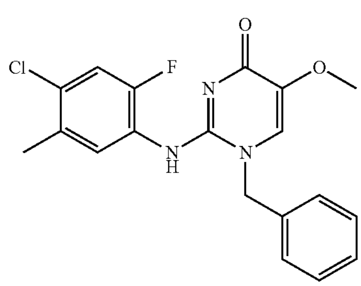 [SMILES: COc1cn(Cc2ccccc2)c(Nc2cc(C)c(Cl)cc2F)nc1=O] | 374 | 1.73 | [1] |

TABLE 152-continued
| I-0802 | 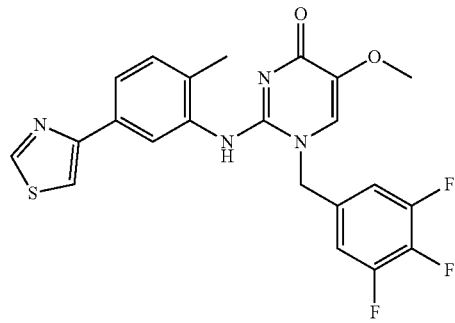 [SMILES: COc1cn(Cc2cc(F)c(F)c(F)c2)c(Nc2cc(-c3cscn3)ccc2C)nc1=O] | 459 | 1.69 | [1] |
| I-0803 | 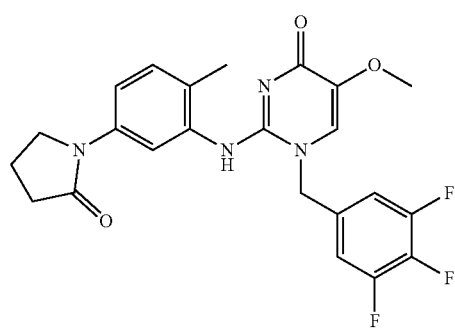 [SMILES: COc1cn(Cc2cc(F)c(F)c(F)c2)c(Nc2cc(N3CCCC3=O)ccc2C)nc1=O] | 459 | 1.52 | [1] |
| I-0804 | 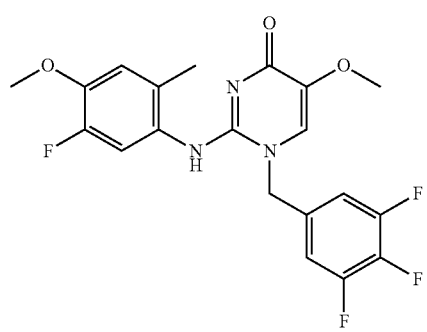 [SMILES: COc1cc(C)c(Nc2nc(=O)c(OC)cn2Cc2cc(F)c(F)c(F)c2)cc1F] | 424 | 1.63 | [1] |
| I-0805 | 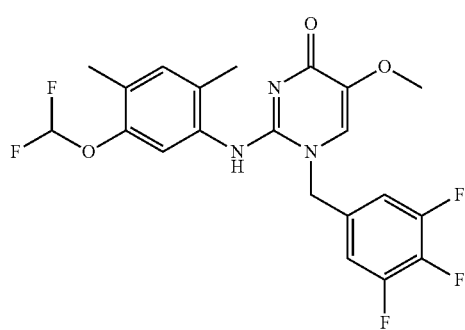 [SMILES: COc1cn(Cc2cc(F)c(F)c(F)c2)c(Nc2cc(OC(F)F)c(C)cc2C)nc1=O] | 456 | 1.91 | [1] |

TABLE 153
| | | | |
|---|---|---|---|
| I-0806 | 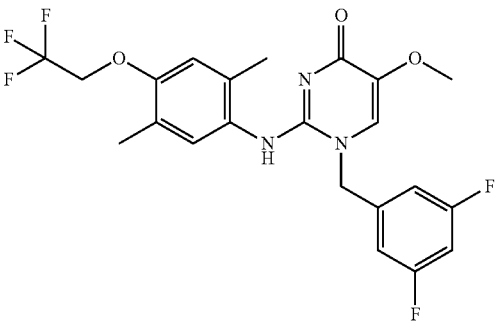 [SMILES: COc1cn(Cc2cc(F)cc(F)c2)c(Nc2cc(C)c(OCC(F)(F)F)cc2C)nc1=O] | 470 | 1.87 [1] |
| I-0807 | 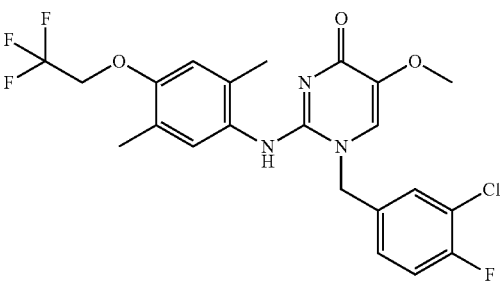 [SMILES: COc1cn(Cc2ccc(F)c(Cl)c2)c(Nc2cc(C)c(OCC(F)(F)F)cc2C)nc1=O] | 486 | 1.95 [1] |
| I-0808 | 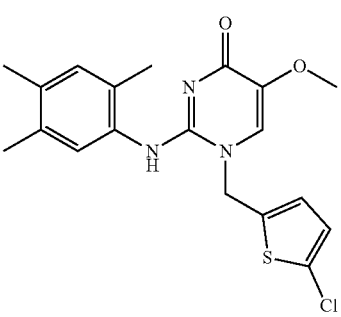 | 432 | 1.55 [1] |
| I-0809 | 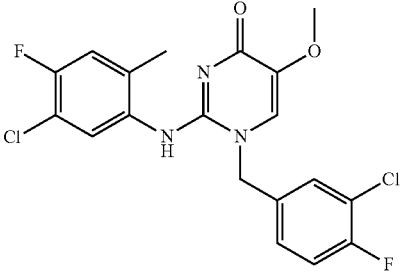 | 426 | 2.13 [3] |
| I-0810 | 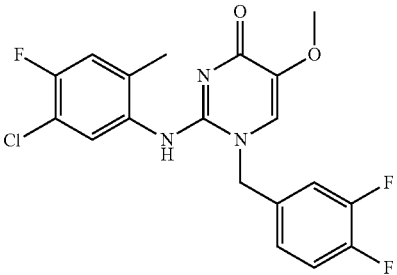 [SMILES: COc1cn(Cc2ccc(F)c(F)c2)c(Nc2cc(Cl)c(F)cc2C)nc1=O] | 410 | 2.02 [3] |

TABLE 153-continued
| I-0811 | 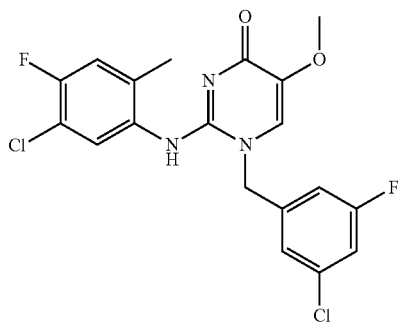 [SMILES: COc1cn(Cc2cc(F)cc(Cl)c2)c(Nc2cc(Cl)c(F)cc2C)nc1=O] | 426 | 2.04 | [3] |
TABLE 154
| I-0812 | 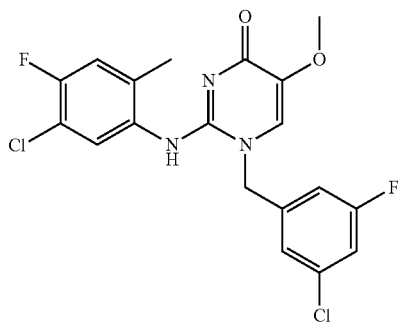 [SMILES: COc1cn(Cc2cc(F)cc(Cl)c2)c(Nc2cc(Cl)c(F)cc2C)nc1=O] | 410 | 1.88 | [3] |
| I-0813 | 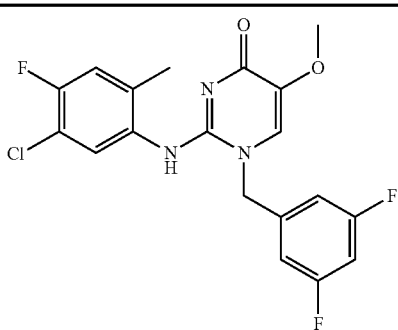 | 385 | 1.69 | [3] |
| I-0814 | 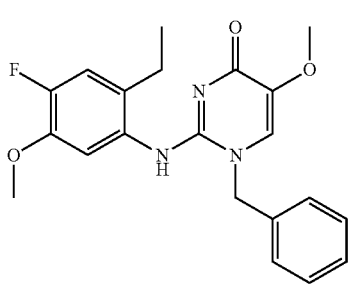 [SMILES: CCc1cc(F)c(OC)cc1Nc1nc(=O)c(OC)cn1Cc1ccccc1] | 436 | 1.91 | [3] |
| I-0815 | 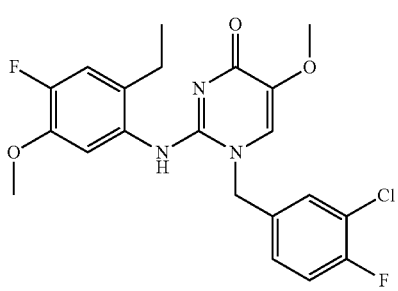 [SMILES: CCc1cc(F)c(OC)cc1Nc1nc(=O)c(OC)cn1Cc1ccc(F)c(Cl)c1] | 420 | 1.81 | [3] |

TABLE 154-continued

| ID | Structure | MS | RT | Method |
|---|---|---|---|---|
| I-0816 | 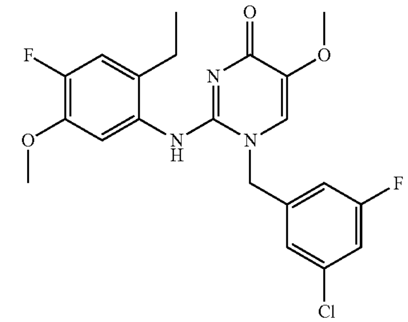 [SMILES: CCc1cc(F)c(OC)cc1Nc1nc(=O)c(OC)cn1Cc1cc(F)cc(Cl)c1] | 436 | 1.94 | [3] |
| I-0817 | 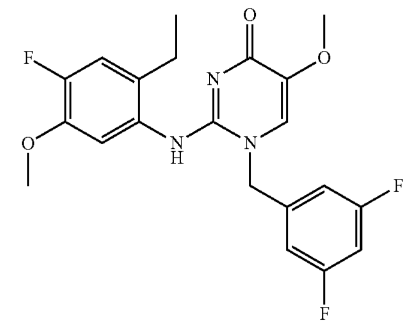 [SMILES: CCc1cc(F)c(OC)cc1Nc1nc(=O)c(OC)cn1Cc1cc(F)cc(F)c1] | 420 | 1.82 | [3] |

TABLE 155

| ID | Structure | MS | RT | Method |
|---|---|---|---|---|
| I-0818 | 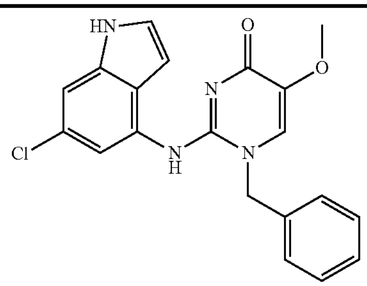 | 381 | 1.45 | [1] |
| I-0819 | 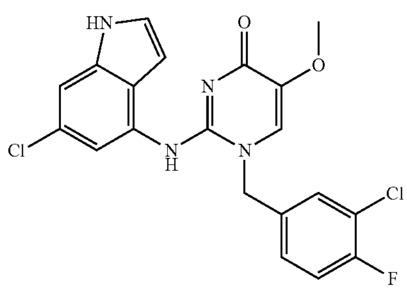 [SMILES: COc1cn(Cc2ccc(F)c(Cl)c2)c(Nc2cc(Cl)cc3[nH]ccc23)nc1=O] | 433 | 1.66 | [1] |
| I-0820 | 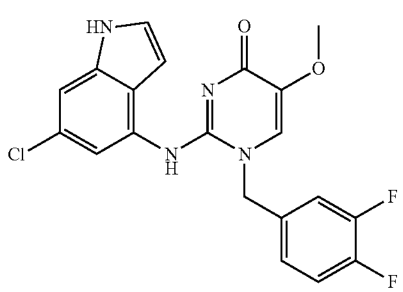 [SMILES: COc1cn(Cc2ccc(F)c(F)c2)c(Nc2cc(Cl)cc3[nH]ccc23)nc1=O] | 417 | 1.57 | [1] |

TABLE 155-continued
| I-0821 | 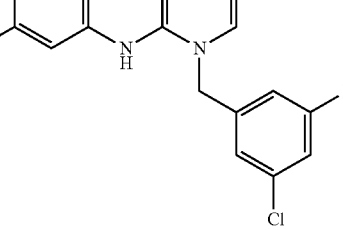 | 433 | 1.76 | [1] |
| I-0822 | 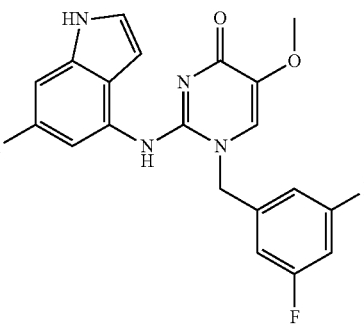 | 417 | 1.63 | [1] |
| I-0823 | 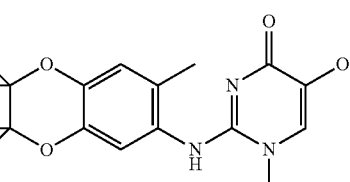 | 504 | 2.31 | [3] |
TABLE 156
| I-0824 | 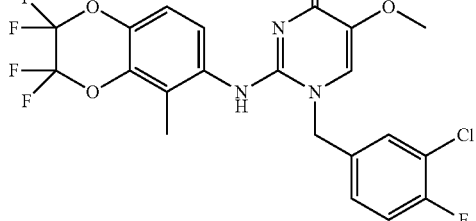 | 504 | 2.31 | [3] |
| I-0825 |  | 428 | 1.87 | [3] |

TABLE 156-continued
| I-0826 | 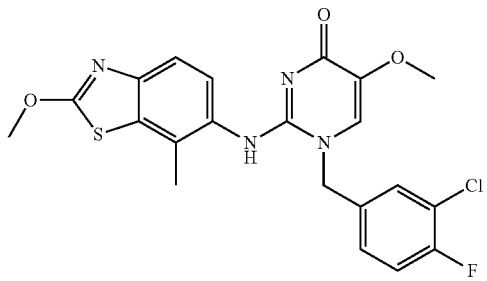 [SMILES: COc1nc2ccc(Nc3nc(=O)c(OC)cn3Cc3ccc(F)c(Cl)c3)c(C)c2s1] | 461 | 1.55 | [3] |
| I-0827 | 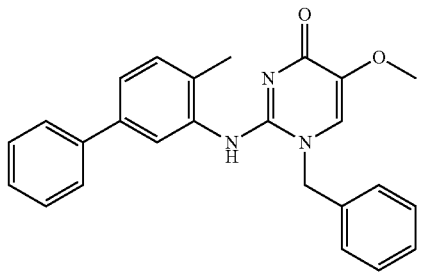 [SMILES: COc1cn(Cc2ccccc2)c(Nc2cc(-c3ccccc3)ccc2C)nc1=O] | 398 | 1.93 | [3] |
| I-0828 | 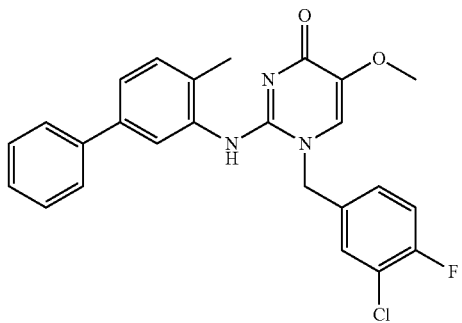 [SMILES: COc1cn(Cc2ccc(F)c(Cl)c2)c(Nc2cc(-c3ccccc3)ccc2C)nc1=O] | 450 | 2.12 | [3] |
| I-0829 | 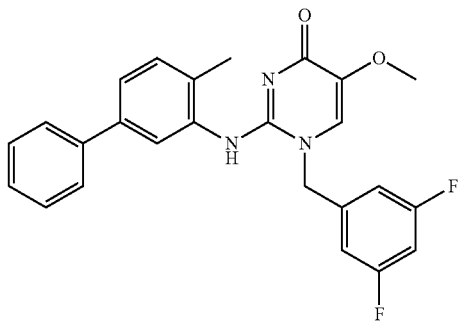 [SMILES: COc1cn(Cc2cc(F)cc(F)c2)c(Nc2cc(-c3ccccc3)ccc2C)nc1=O] | 434 | 2.02 | [3] |
TABLE 157
| I-0830 | 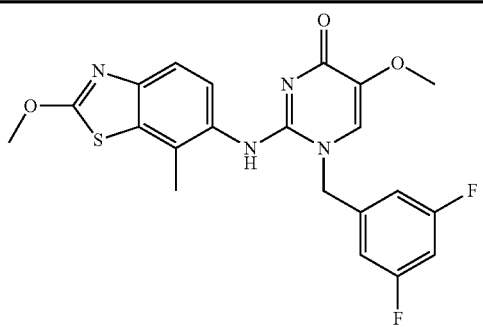 | 445 | 1.68 | [3] |

TABLE 157-continued
I-0831 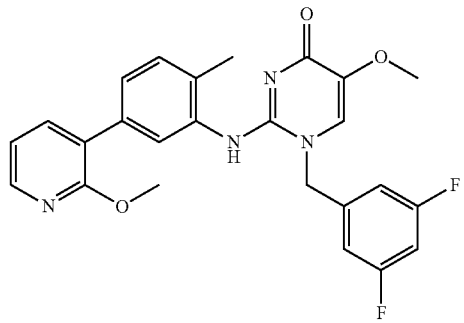 [SMILES: COc1ncccc1-c1ccc(C)c(Nc2nc(=O)c(OC)cn2Cc2cc(F)cc(F)c2)c1] 465 1.82 [3]
I-0832 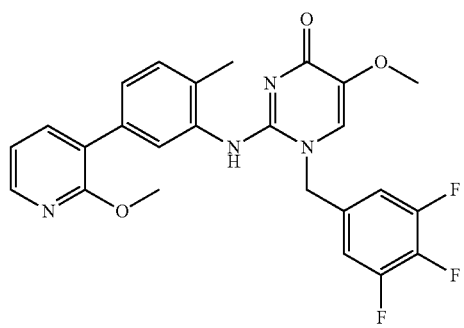 [SMILES: COc1ncccc1-c1ccc(C)c(Nc2nc(=O)c(OC)cn2Cc2cc(F)c(F)c(F)c2)c1] 483 1.91 [3]
I-0833 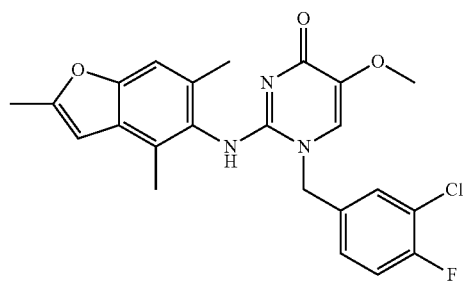 [SMILES: COc1cn(Cc2ccc(F)c(Cl)c2)c(Nc2c(C)cc3oc(C)cc3c2C)nc1=O] 442 1.87 [3]
I-0834 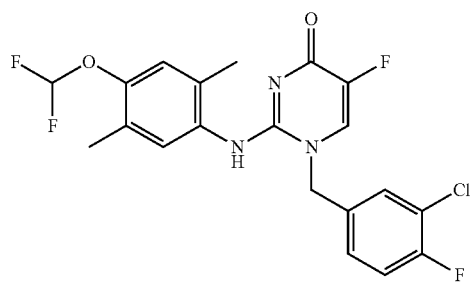 [SMILES: Cc1cc(OC(F)F)c(C)cc1Nc1nc(=O)c(F)cn1Cc1ccc(F)c(Cl)c1] 442 2.09 [3]
I-0835 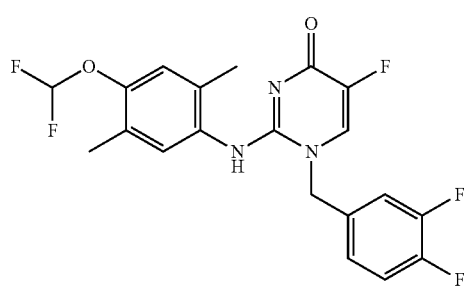 [SMILES: Cc1cc(OC(F)F)c(C)cc1Nc1nc(=O)c(F)cn1Cc1ccc(F)c(F)c1] 426 1.98 [3]

TABLE 158

| ID | Structure | MW | RT | Method |
|---|---|---|---|---|
| I-0836 | (2-(difluoromethoxy)-4,5-dimethylphenylamino)-1-(3,5-difluorobenzyl)-5-fluoropyrimidin-4(1H)-one | 426 | 1.98 | [3] |
| I-0837 | 5-chloro-2-(2-(difluoromethoxy)-4,5-dimethylphenylamino)-1-(3-chloro-4-fluorobenzyl)pyrimidin-4(1H)-one | 458 | 2.25 | [3] |
| I-0838 | 5-chloro-2-(2-(difluoromethoxy)-4,5-dimethylphenylamino)-1-(3,4-difluorobenzyl)pyrimidin-4(1H)-one | 442 | 2.13 | [3] |
| I-0839 | 5-chloro-2-(2-(difluoromethoxy)-4,5-dimethylphenylamino)-1-(3,5-difluorobenzyl)pyrimidin-4(1H)-one | 442 | 2.15 | [3] |
| I-0840 | 1-(3-chloro-4-fluorobenzyl)-5-fluoro-2-(4-methoxy-2-methylphenylamino)pyrimidin-4(1H)-one | 392 | 1.79 | [3] |

TABLE 158-continued

| I-0841 | [structure] | | 376 | 1.67 | [3] |

TABLE 159

| I-0842 | [structure] | 1H-NMR (DMSO-D6) δ: 1.84 (s, 3H), 3.73 (s, 3H), 5.19 (s, 2H), 6.73-6.79 (m, 2H), 6.96 (d, J = 8.4 Hz, 1H), 7.05 (d, J = 6.4 Hz, 2H), 7.25 (t, J = 9.6 Hz, 1H), 8.02 (d, J = 6.4 Hz, 1H), 8.47 (br, 1H). | 376 | 1.66 | [3] |
| I-0843 | [structure] | | 408 | 1.9 | [3] |
| I-0844 | [structure] | | 392 | 1.78 | [3] |
| I-0845 | [structure] | | 392 | 1.77 | [3] |

TABLE 159-continued
| I-0846 | 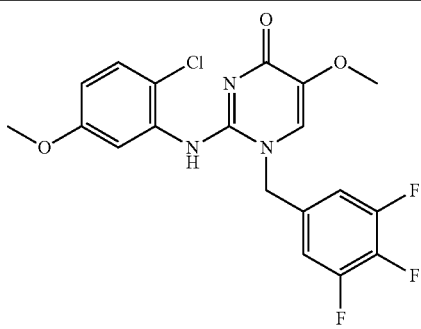 | 426 | 1.84 | [1] |
TABLE 160
| I-0847 | 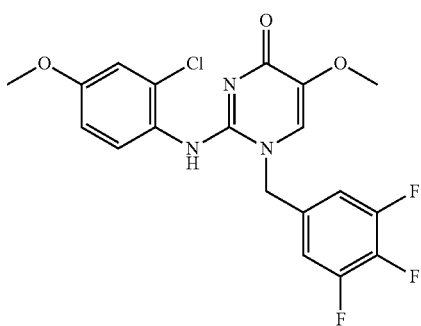 [SMILES: COc1ccc(Nc2nc(=O)c(OC)cn2Cc2cc(F)c(F)c(F)c2)c(Cl)c1] | 426 | 1.7 | [1] |
| I-0848 | 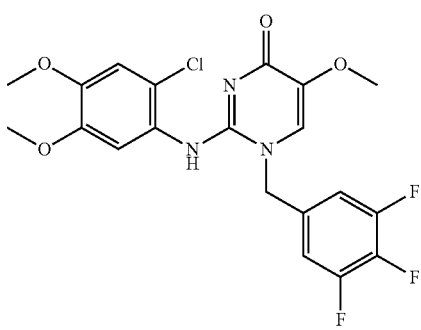 [SMILES: COc1cc(Cl)c(Nc2nc(=O)c(OC)cn2Cc2cc(F)c(F)c(F)c2)cc1OC] | 456 | 1.67 | [1] |
| I-0849 | 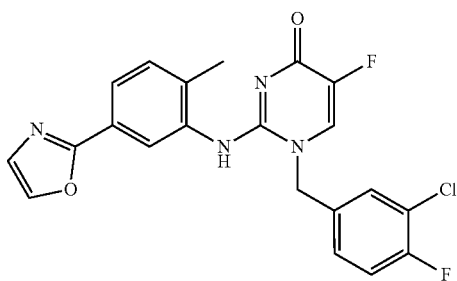 [SMILES: Cc1ccc(-c2ncco2)cc1Nc1nc(=O)c(F)cn1Cc1ccc(F)c(Cl)c1] | 429 | 1.99 | [1] |

TABLE 160-continued
| I-0850 | 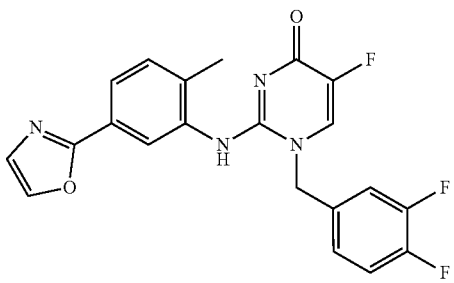 [SMILES: Cc1ccc(-c2ncco2)cc1Nc1nc(=O)c(F)cn1Cc1ccc(F)c(F)c1] | 413 | 1.87 | [1] |
| I-0851 | 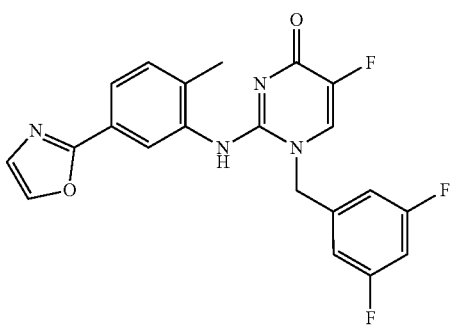 [SMILES: Cc1ccc(-c2ncco2)cc1Nc1nc(=O)c(F)cn1Cc1cc(F)cc(F)c1] | 413 | 1.87 | [1] |
| I-0852 | 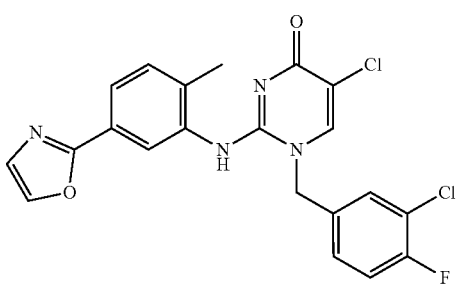 | 445 | 2.19 | [1] |
TABLE 161
| I-0853 | 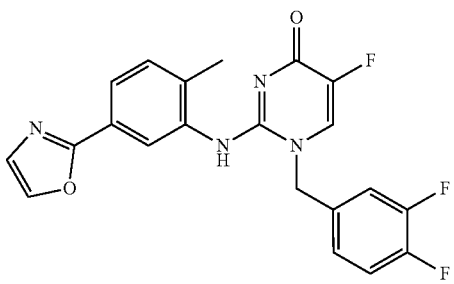 [SMILES: Cc1ccc(-c2ncco2)cc1Nc1nc(=O)c(F)cn1Cc1ccc(F)c(F)c1] | 429 | 2.05 | [1] |
| I-0854 | 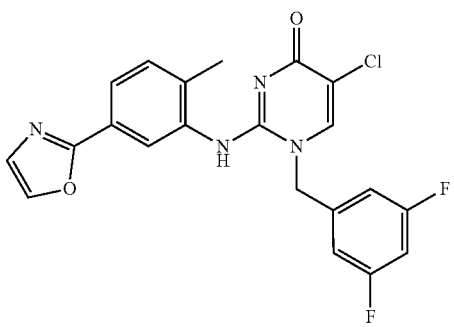 | 429 | 2.07 | [1] |

TABLE 161-continued

| | | | | |
|---|---|---|---|---|
| I-0855 | (structure) | 379 | 1.5 | [1] |
| I-0856 | (structure) | 431 | 1.75 | [1] |
| I-0857 | (structure) | 415 | 1.63 | [1] |
| I-0858 | (structure) | 393 | 1.63 | [1] |

TABLE 162

| | | | | |
|---|---|---|---|---|
| I-0859 | (structure) | 445 | 1.87 | [1] |

TABLE 162-continued
| | | | | |
|---|---|---|---|---|
| I-0860 | 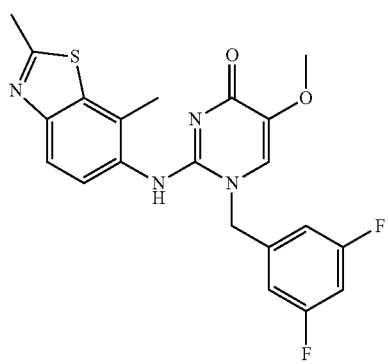 [SMILES: COc1cn(Cc2cc(F)cc(F)c2)c(Nc2ccc3nc(C)sc3c2C)nc1=O] | 429 | 1.76 | [1] |
| I-0861 | 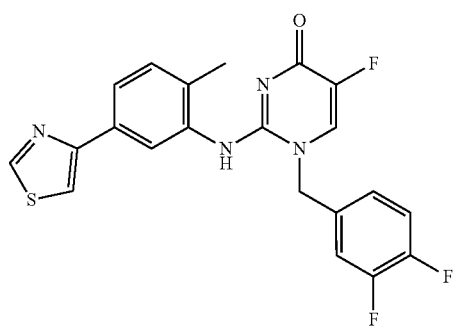 [SMILES: Cc1ccc(-c2cscn2)cc1Nc1nc(=O)c(F)cn1Cc1ccc(F)c(F)c1] | 429 | 1.71 | [3] |
| I-0862 | 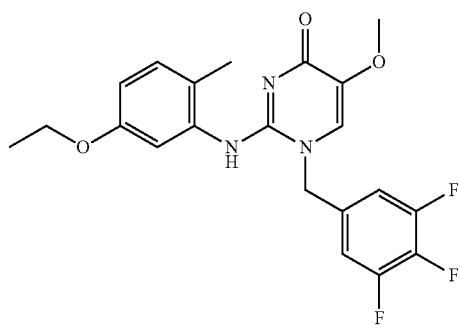 [SMILES: CCOc1ccc(C)c(Nc2nc(=O)c(OC)cn2Cc2cc(F)c(F)c(F)c2)c1] | 420 | 1.78 | [3] |
| I-0863 | 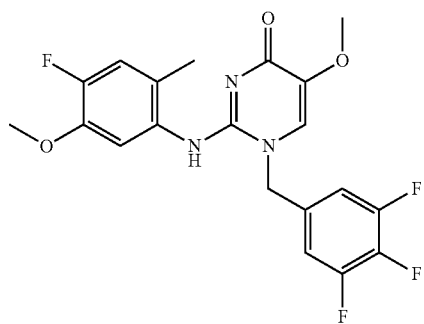 [SMILES: COc1cc(Nc2nc(=O)c(OC)cn2Cc2cc(F)c(F)c(F)c2)c(C)cc1F] | 424 | 1.67 | [3] |

TABLE 163
| I-0864 | 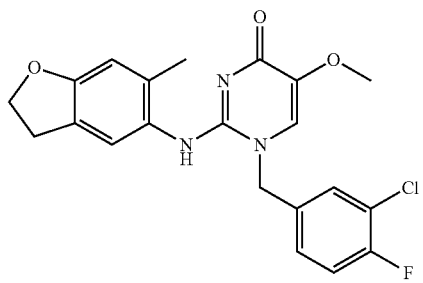 [SMILES: COc1cn(Cc2ccc(F)c(Cl)c2)c(Nc2cc3c(cc2C)OCC3)nc1=O] | 416 | 1.65 | [3] |
| I-0865 | 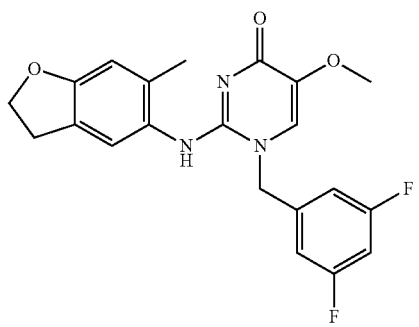 | 400 | 1.52 | [3] |
| I-0866 | 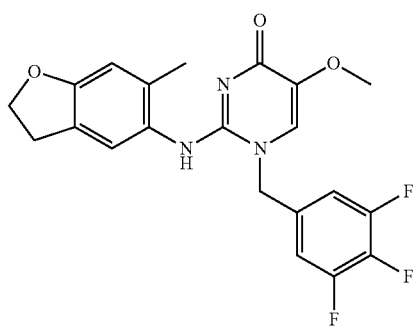 [SMILES: COc1cn(Cc2cc(F)c(F)c(F)c2)c(Nc2cc3c(cc2C)OCC3)nc1=O] | 418 | 1.62 | [3] |
| I-0867 | 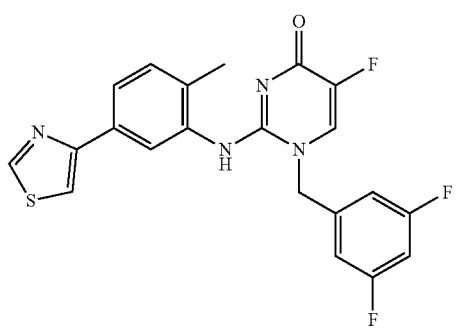 [SMILES: Cc1ccc(-c2cscn2)cc1Nc1nc(=O)c(F)cn1Cc1cc(F)cc(F)c1] | 429 | 1.7 | [3] |
| I-0868 | 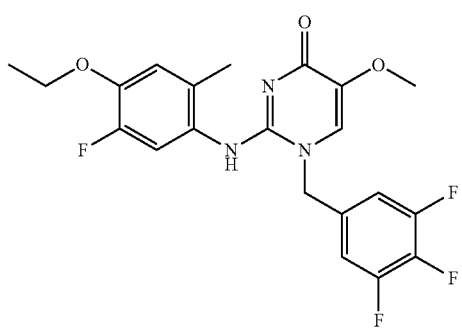 [SMILES: CCOc1cc(C)c(Nc2nc(=O)c(OC)cn2Cc2cc(F)c(F)c(F)c2)cc1F] | 438 | 1.77 | [1] |

TABLE 164
I-0869 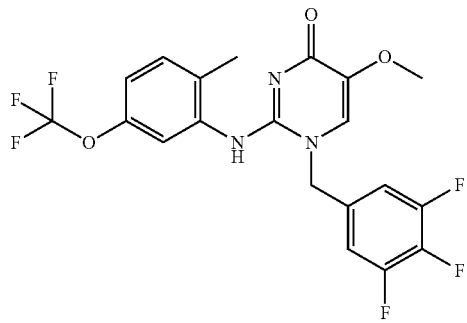 [SMILES: COc1cn(Cc2cc(F)c(F)c(F)c2)c(Nc2cc(OC(F)(F)F)ccc2C)nc1=O] 460 2.04 [1]
I-0870 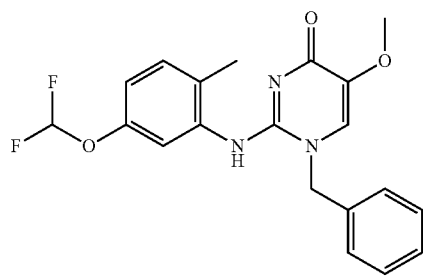 [SMILES: COc1cn(Cc2ccccc2)c(Nc2cc(OC(F)F)ccc2C)nc1=O] 388 1.83 [3]
I-0871 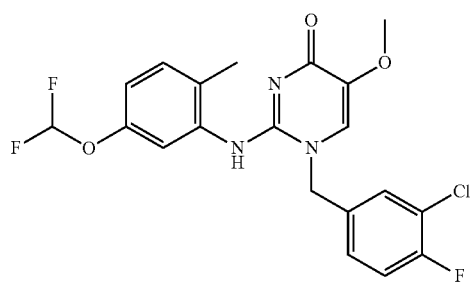 [SMILES: COc1cn(Cc2ccc(F)c(Cl)c2)c(Nc2cc(OC(F)F)ccc2C)nc1=O] 440 2.06 [3]
I-0872 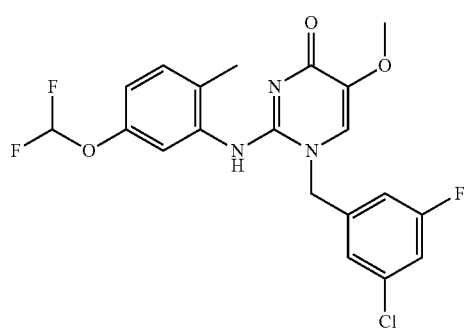 [SMILES: COc1cn(Cc2cc(F)cc(Cl)c2)c(Nc2cc(OC(F)F)ccc2C)nc1=O] 440 2.09 [3]
I-0873 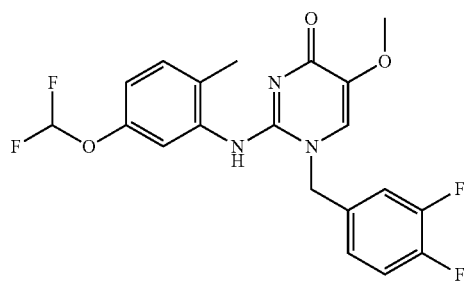 [SMILES: COc1cn(Cc2ccc(F)c(F)c2)c(Nc2cc(OC(F)F)ccc2C)nc1=O] 424 1.94 [3]

TABLE 164-continued
| I-0874 | 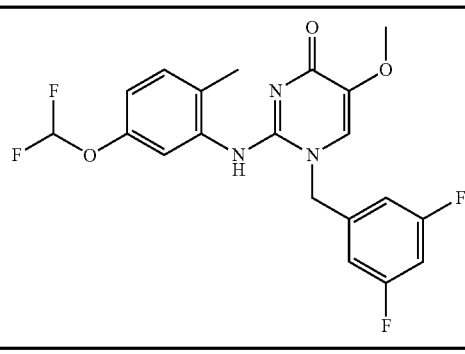 | 424 | 1.95 | [3] |
TABLE 165
| I-0875 | 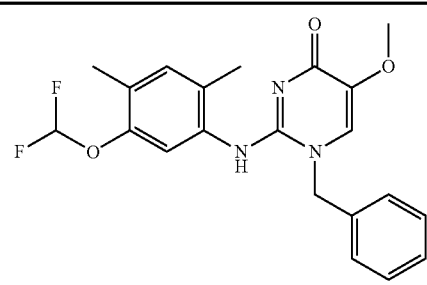 | 402 | 1.95 | [3] |
| I-0876 | 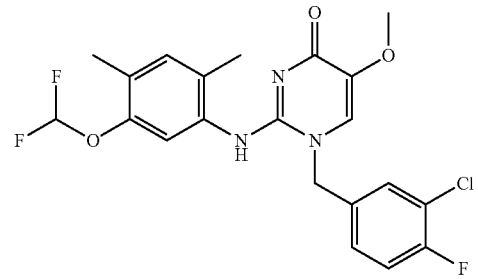 [SMILES: COc1cn(Cc2ccc(F)c(Cl)c2)c(Nc2cc(OC(F)F)c(C)cc2C)nc1=O] | 454 | 2.16 | [3] |
| I-0877 | 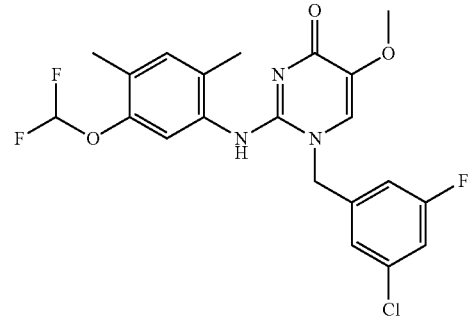 [SMILES: COc1cn(Cc2cc(F)cc(Cl)c2)c(Nc2cc(OC(F)F)c(C)cc2C)nc1=O] | 454 | 2.16 | [3] |
| I-0878 | 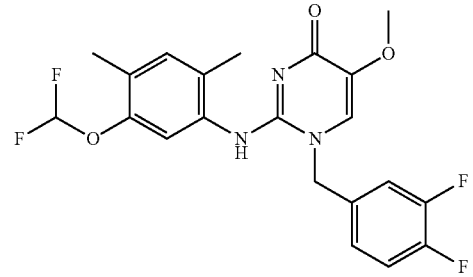 [SMILES: COc1cn(Cc2ccc(F)c(F)c2)c(Nc2cc(OC(F)F)c(C)cc2C)nc1=O] | 438 | 2.05 | [3] |

TABLE 165-continued
| I-0879 | 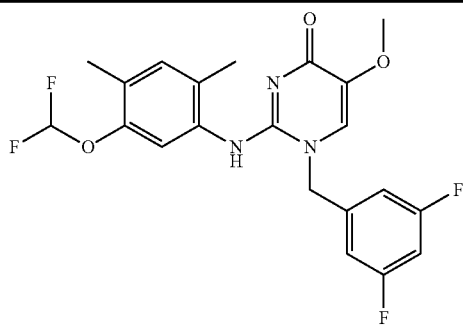 | 438 | 2.06 | [3] |
| I-0880 | 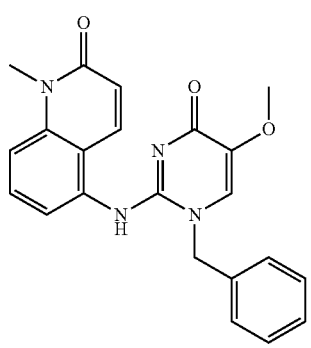 [SMILES: COc1cn(Cc2ccccc2)c(Nc2cccc3c2ccc(=O)n3C)nc1=O] | 389 | 1.25 | [3] |
TABLE 166
| I-0881 | 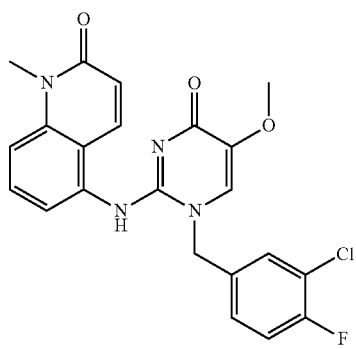 [SMILES: COc1cn(Cc2ccc(F)c(Cl)c2)c(Nc2cccc3c2ccc(=O)n3C)nc1=O] | 441 | 1.53 | [3] |
| I-0882 | 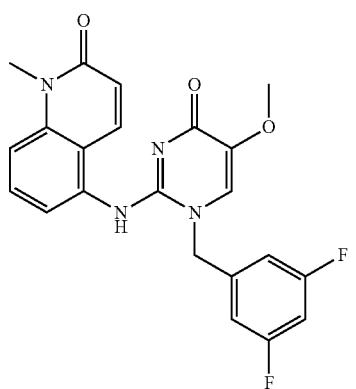 [SMILES: COc1cn(Cc2cc(F)cc(F)c2)c(Nc2cccc3c2ccc(=O)n3C)nc1=O] | 425 | 1.42 | [3] |

TABLE 166-continued
| | | | | |
|---|---|---|---|---|
| I-0883 | 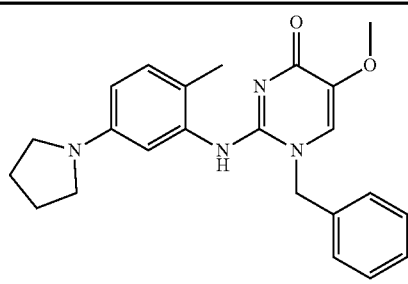 | 391 | 1.43 | [3] |
| I-0884 | 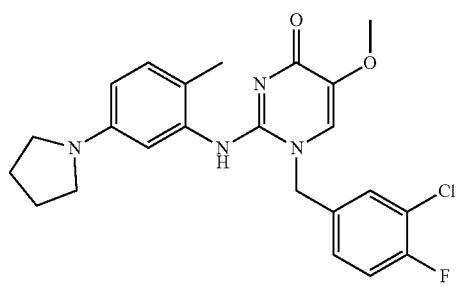 [SMILES: COc1cn(Cc2ccc(F)c(Cl)c2)c(Nc2cc(N3CCCC3)ccc2C)nc1=O] | 443 | 1.71 | [3] |
| I-0885 | 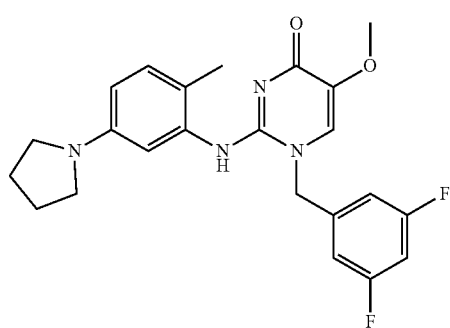 [SMILES: COc1cn(Cc2cc(F)cc(F)c2)c(Nc2cc(N3CCCC3)ccc2C)nc1=O] | 427 | 1.56 | [3] |
TABLE 167
| | | | | |
|---|---|---|---|---|
| I-0886 | 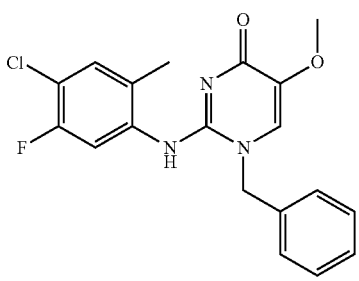 [SMILES: COc1cn(Cc2ccccc2)c(Nc2cc(F)c(Cl)cc2C)nc1=O] | 374 | 1.73 | [3] |
| I-0887 | 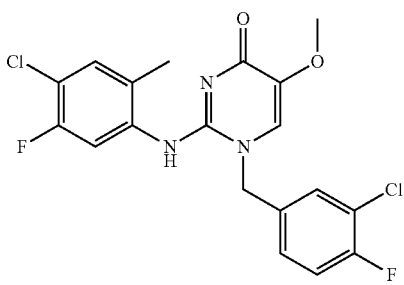 [SMILES: COc1cn(Cc2ccc(F)c(Cl)c2)c(Nc2cc(F)c(Cl)cc2C)nc1=O] | 426 | 1.99 | [3] |

TABLE 167-continued
| | | | | |
|---|---|---|---|---|
| I-0888 | 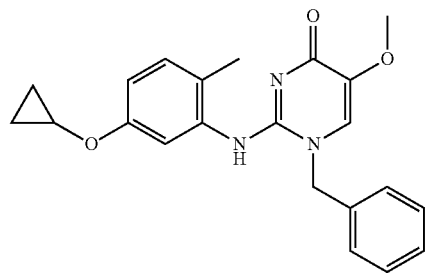 [SMILES: COc1cn(Cc2ccccc2)c(Nc2cc(OC3CC3)ccc2C)nc1=O] | 379 | 1.88 | [3] |
| I-0889 | 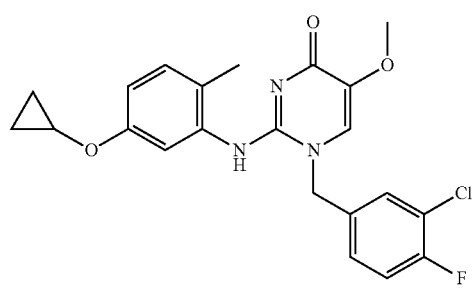 [SMILES: COc1cn(Cc2ccc(F)c(Cl)c2)c(Nc2cc(OC3CC3)ccc2C)nc1=O] | 430 | 2.1 | [3] |
| I-0890 | 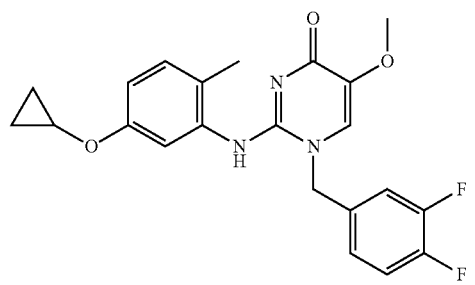 [SMILES: COc1cn(Cc2ccc(F)c(F)c2)c(Nc2cc(OC3CC3)ccc2C)nc1=O] | 414 | 1.84 | [3] |
| I-0891 | 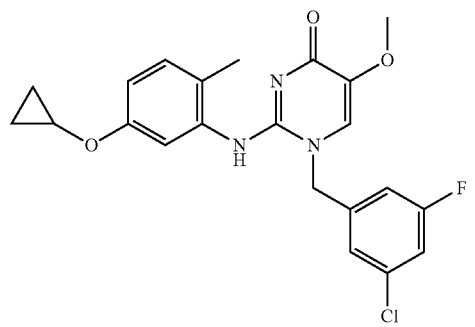 [SMILES: COc1cn(Cc2cc(F)cc(Cl)c2)c(Nc2cc(OC3CC3)ccc2C)nc1=O] | 430 | 2.12 | [3] |
TABLE 168
| | | | | |
|---|---|---|---|---|
| I-0892 | 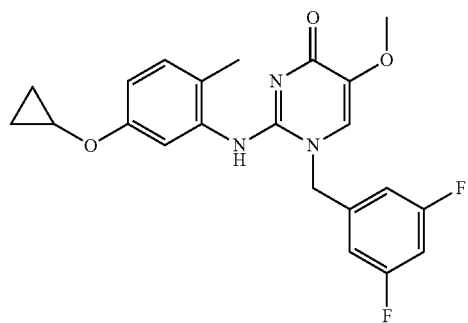 [SMILES: COc1cn(Cc2cc(F)cc(F)c2)c(Nc2cc(OC3CC3)ccc2C)nc1=O] | 415 | 1.98 | [3] |

| | | | |
|---|---|---|---|
| I-0893 | 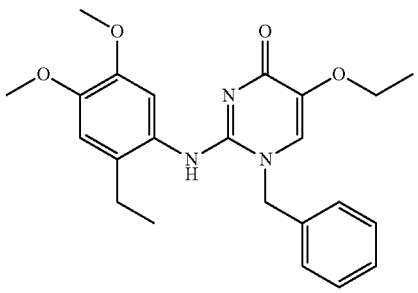 [SMILES: CCOc1cn(Cc2ccccc2)c(Nc2cc(OC)c(OC)cc2CC)nc1=O] | 410 1.52 | [1] |
| I-0894 | 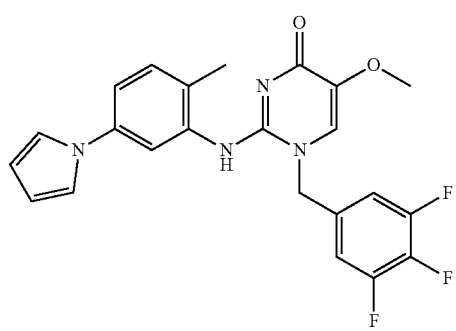 [SMILES: COc1cn(Cc2cc(F)c(F)c(F)c2)c(Nc2cc(-n3cccc3)ccc2C)nc1=O] | 441 1.92 | [1] |
| I-0895 | 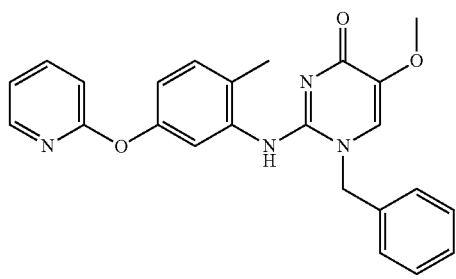 [SMILES: COc1cn(Cc2ccccc2)c(Nc2cc(Oc3ccccn3)ccc2C)nc1=O] | 415 1.65 | [3] |
| I-0896 | 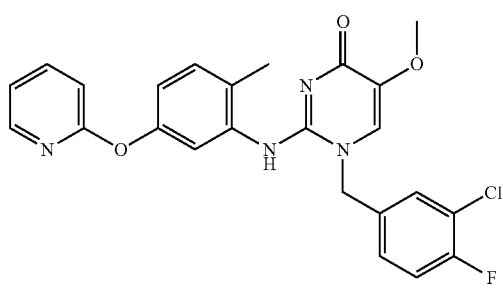 [SMILES: COc1cn(Cc2ccc(F)c(Cl)c2)c(Nc2cc(Oc3ccccn3)ccc2C)nc1=O] | 667 1.89 | [3] |
| I-0897 | 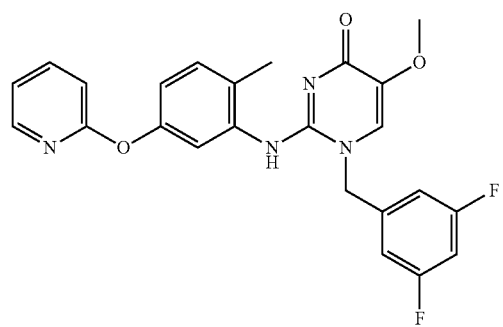 [SMILES: COc1cn(Cc2cc(F)cc(F)c2)c(Nc2cc(Oc3ccccn3)ccc2C)nc1=O] | 451 1.79 | [3] |

TABLE 169
| | | | | |
|---|---|---|---|---|
| I-0898 | 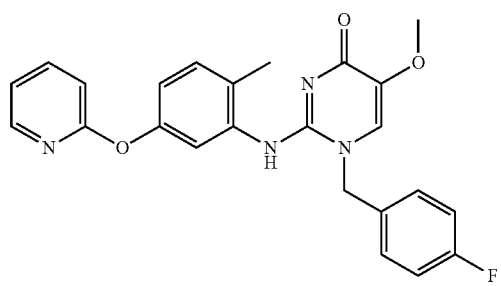 [SMILES: COc1cn(Cc2ccc(F)cc2)c(Nc2cc(Oc3ccccn3)ccc2C)nc1=O] | 433 | 1.7 | [3] |
| I-0899 | 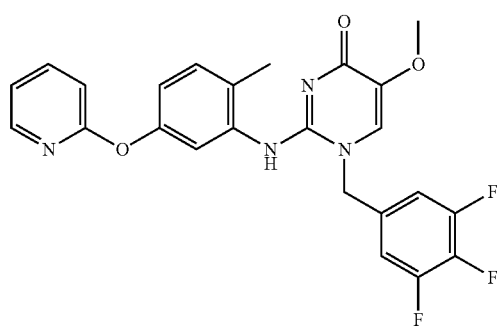 [SMILES: COc1cn(Cc2cc(F)c(F)c(F)c2)c(Nc2cc(Oc3ccccn3)ccc2C)nc1=O] | 469 | 1.89 | [3] |
| I-0900 | 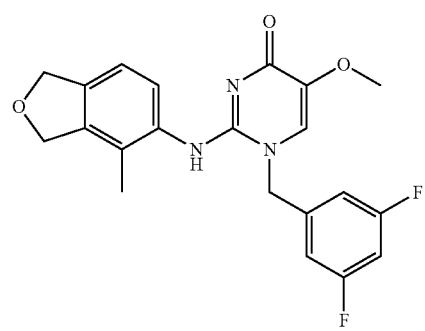 [SMILES: COc1cn(Cc2cc(F)cc(F)c2)c(Nc2ccc3c(c2C)COC3)nc1=O] | 400 | 1.41 | [3] |
| I-0901 | 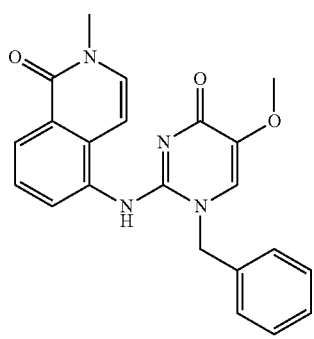 [SMILES: COc1cn(Cc2ccccc2)c(Nc2cccc3c(=O)n(C)ccc23)nc1=O] | 389 | 1.22 | [3] |
| I-0902 | 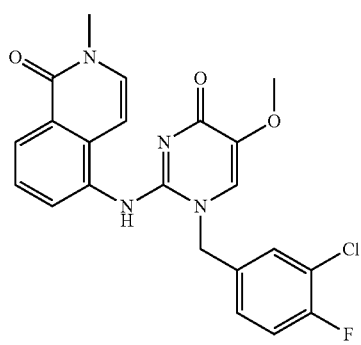 [SMILES: COc1cn(Cc2ccc(F)c(Cl)c2)c(Nc2cccc3c(=O)n(C)ccc23)nc1=O] | 441 | 1.48 | [3] |

TABLE 170
| | | | | |
|---|---|---|---|---|
| I-0903 | 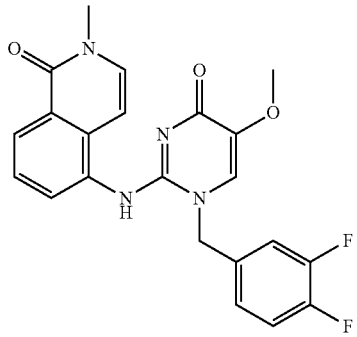 [SMILES: COc1cn(Cc2ccc(F)c(F)c2)c(Nc2cccc3c(=O)n(C)ccc23)nc1=O] | 425 | 1.36 | [3] |
| I-0904 | 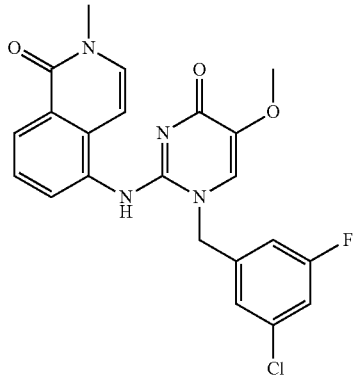 [SMILES: COc1cn(Cc2cc(F)cc(Cl)c2)c(Nc2cccc3c(=O)n(C)ccc23)nc1=O] | 441 | 1.64 | [3] |
| I-0905 | 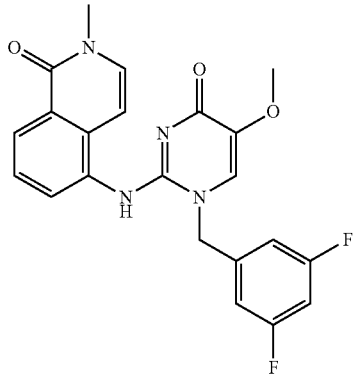 [SMILES: COc1cn(Cc2cc(F)cc(F)c2)c(Nc2cccc3c(=O)n(C)ccc23)nc1=O] | 425 | 1.51 | [3] |
| I-0906 | 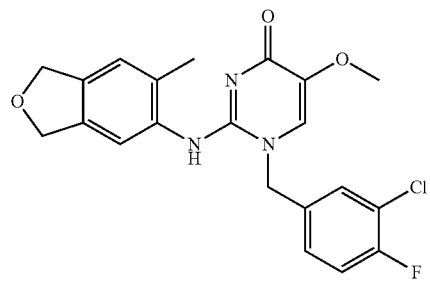 [SMILES: COc1cn(Cc2ccc(F)c(Cl)c2)c(Nc2cc3c(cc2C)COC3)nc1=O] | 416 | 1.57 | [3] |

TABLE 170-continued
| I-0907 | 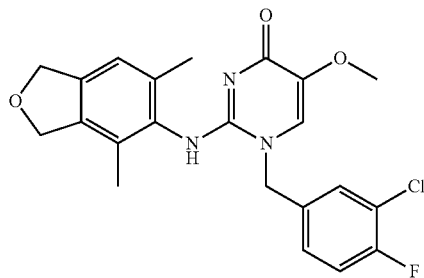 [SMILES: COc1cn(Cc2ccc(F)c(Cl)c2)c(Nc2c(C)cc3c(c2C)COC3)nc1=O] | 416 | 1.54 | [3] |
TABLE 171
| I-0908 | 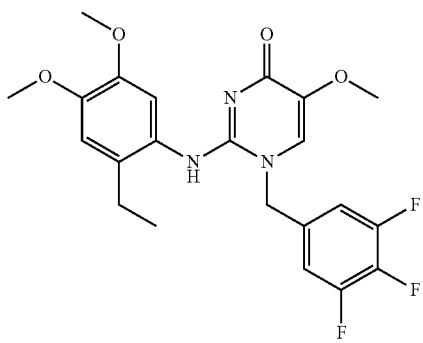 [SMILES: CCc1cc(OC)c(OC)cc1Nc1nc(=O)c(OC)cn1Cc1cc(F)c(F)c(F)c1] | | 450 | 1.61 | [1] |
| I-0909 | 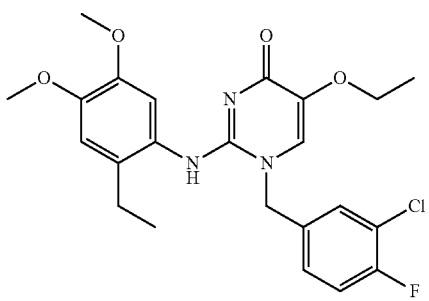 [SMILES: CCOc1cn(Cc2ccc(F)c(Cl)c2)c(Nc2cc(OC)c(OC)cc2CC)nc1=O] | | 462 | 1.71 | [1] |
| I-0910 | 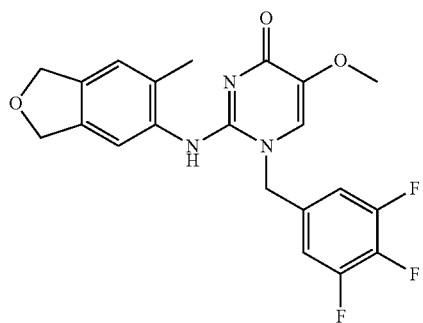 | 1H-NMR (DMSO-D6) δ 1.87 (s, 3H), 3.59 (s, 3H), 4.94 (s, 4H), 5.16 (s, 2H), 7.02 (s, 1H), 7,11 (s, 1H), 7.30-7.32 (m, 4H), 8.35 (s, 1H). | 418 | 1.54 | [3] |

TABLE 171-continued
| | | | | |
|---|---|---|---|---|
| I-0911 | 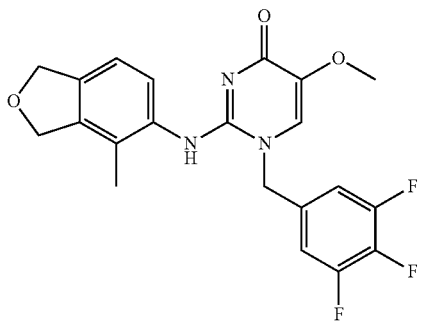 [SMILES: COc1cn(Cc2cc(F)c(F)c(F)c2)c(Nc2ccc3c(c2C)COC3)nc1=O] | 418 | 1.54 | [3] |
| I-0912 | 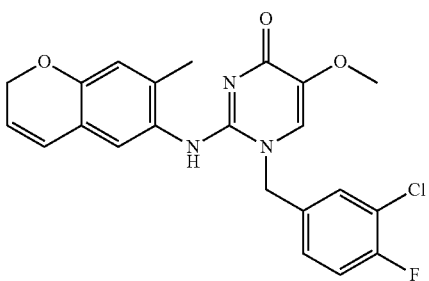 [SMILES: COc1cn(Cc2ccc(F)c(Cl)c2)c(Nc2cc3c(cc2C)OCC=C3)nc1=O] | 448 | 1.53 | [3] |
TABLE 172
| | | | | |
|---|---|---|---|---|
| I-0913 | 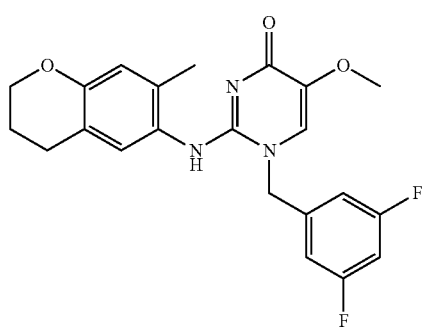 [SMILES: COc1cn(Cc2cc(F)cc(F)c2)c(Nc2cc3c(cc2C)OCCC3)nc1=O] | 414 | 1.63 | [3] |
| I-0914 | 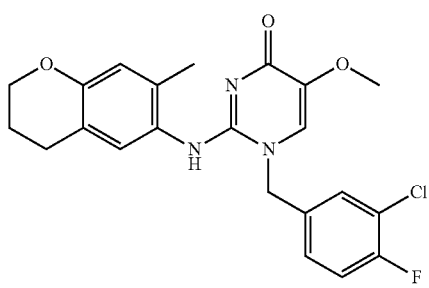 | 430 | 1.75 | [3] |

TABLE 172-continued
| | | | | |
|---|---|---|---|---|
| I-0915 | 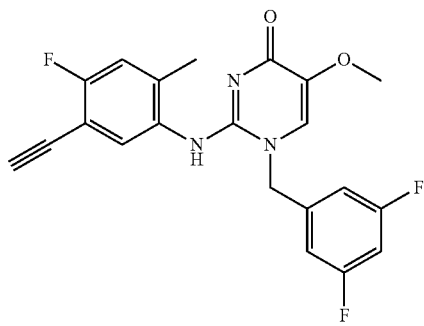 [SMILES: C#Cc1cc(Nc2nc(=O)c(OC)cn2Cc2cc(F)cc(F)c2)c(C)cc1F] | 400 | 1.75 | [3] |
| I-0916 | 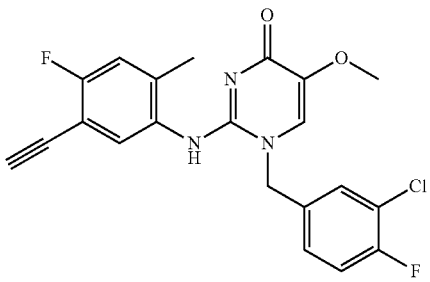 [SMILES: C#Cc1cc(Nc2nc(=O)c(OC)cn2Cc2ccc(F)c(Cl)c2)c(C)cc1F] | 416 | 1.86 | [3] |
| I-0917 | 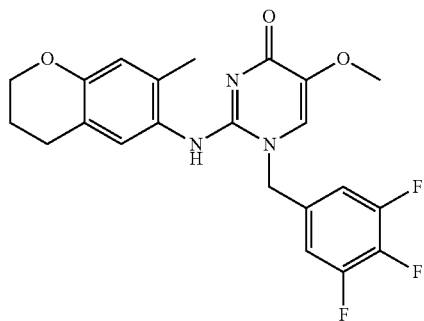 [SMILES: COc1cn(Cc2cc(F)c(F)c(F)c2)c(Nc2cc3c(cc2C)OCCC3)nc1=O] | 432 | 1.73 | [3] |
| I-0918 | 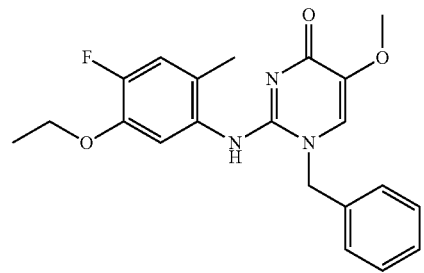 [SMILES: CCOc1cc(Nc2nc(=O)c(OC)cn2Cc2ccccc2)c(C)cc1F] | 384 | 1.8 | [3] |
TABLE 173
| | | | | |
|---|---|---|---|---|
| I-0919 | 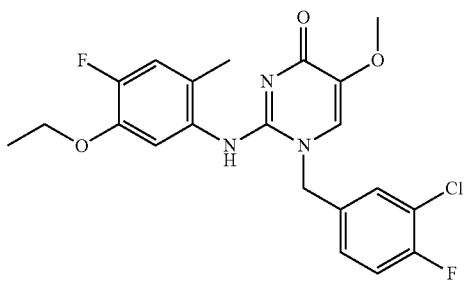 [SMILES: CCOc1cc(Nc2nc(=O)c(OC)cn2Cc2ccc(F)c(Cl)c2)c(C)cc1F] | 436 | 2.03 | [3] |

TABLE 173-continued
| I-0920 | 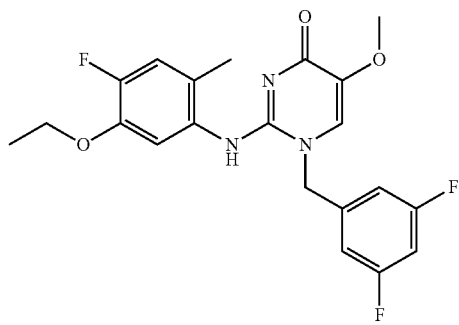 [SMILES: CCOc1cc(Nc2nc(=O)c(OC)cn2Cc2cc(F)cc(F)c2)c(C)cc1F] | 420 | 1.91 | [3] |
| I-0921 | 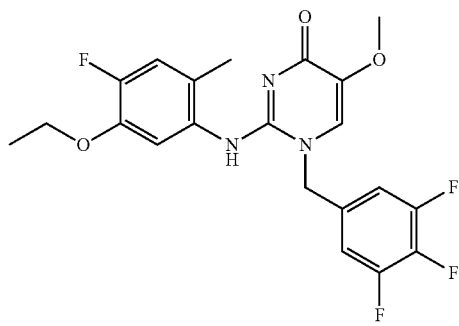 [SMILES: CCOc1cc(Nc2nc(=O)c(OC)cn2Cc2cc(F)c(F)c(F)c2)c(C)cc1F] | 438 | 2.01 | [3] |
| I-0922 | 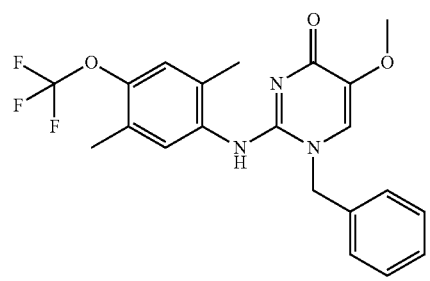 [SMILES: COc1cn(Cc2ccccc2)c(Nc2cc(C)c(OC(F)(F)F)cc2C)nc1=O] | 421 | 2.12 | [3] |
| I-0923 | 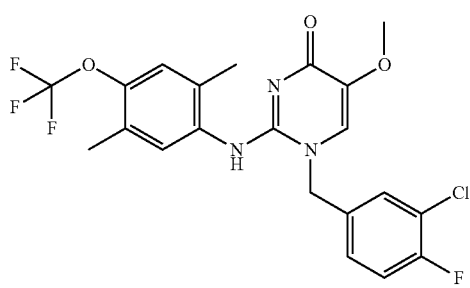 [SMILES: COc1cn(Cc2ccc(F)c(Cl)c2)c(Nc2cc(C)c(OC(F)(F)F)cc2C)nc1=O] | 472 | 2.33 | [3] |
| I-0924 | 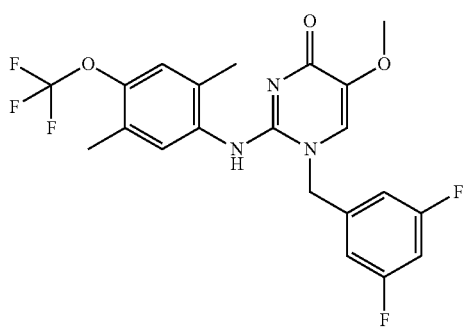 [SMILES: COc1cn(Cc2cc(F)cc(F)c2)c(Nc2cc(C)c(OC(F)(F)F)cc2C)nc1=O] | 456 | 2.23 | [3] |

TABLE 174
| | | | | |
|---|---|---|---|---|
| I-0925 | 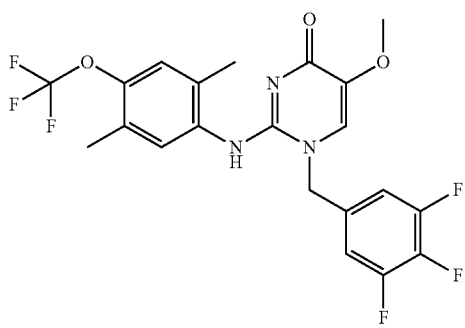 [SMILES: COc1cn(Cc2cc(F)c(F)c(F)c2)c(Nc2cc(C)c(OC(F)(F)F)cc2C)nc1=O] | 474 | 2.32 | [3] |
| I-0926 | 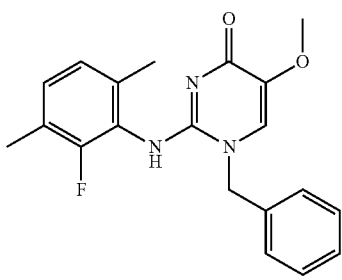 [SMILES: COc1cn(Cc2ccccc2)c(Nc2c(C)ccc(C)c2F)nc1=O] | 354 | 1.56 | [3] |
| I-0927 | 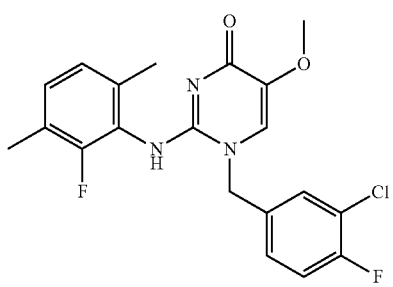 [SMILES: COc1cn(Cc2ccc(F)c(Cl)c2)c(Nc2c(C)ccc(C)c2F)nc1=O] | 407 | 1.79 | [3] |
| I-0928 | 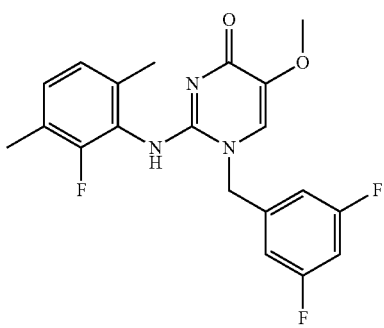 [SMILES: COc1cn(Cc2cc(F)cc(F)c2)c(Nc2c(C)ccc(C)c2F)nc1=O] | 390 | 1.67 | [3] |
| I-0929 | 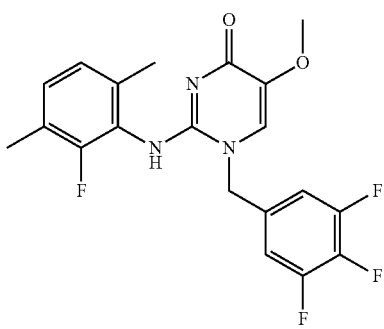 [SMILES: COc1cn(Cc2cc(F)c(F)c(F)c2)c(Nc2c(C)ccc(C)c2F)nc1=O] | 408 | 1.77 | [3] |

TABLE 174-continued
| | | | | |
|---|---|---|---|---|
| I-0930 | 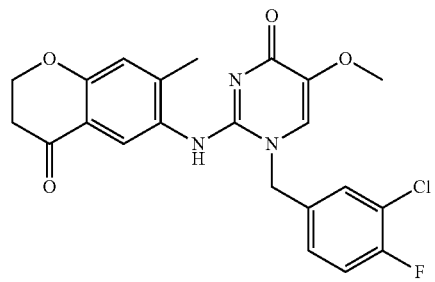 [SMILES: COc1cn(Cc2ccc(F)c(Cl)c2)c(Nc2cc3c(cc2C)OCCC3=O)nc1=O] | 444 | 1.61 | [3] |
TABLE 175
| | | | | |
|---|---|---|---|---|
| I-0931 | 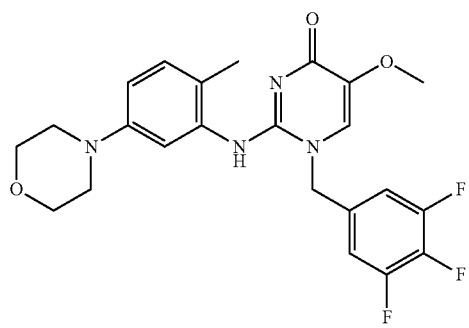 [SMILES: COc1cn(Cc2cc(F)c(F)c(F)c2)c(Nc2cc(N3CCOCC3)ccc2C)nc1=O] | 461 | 1.53 | [1] |
| I-0932 | 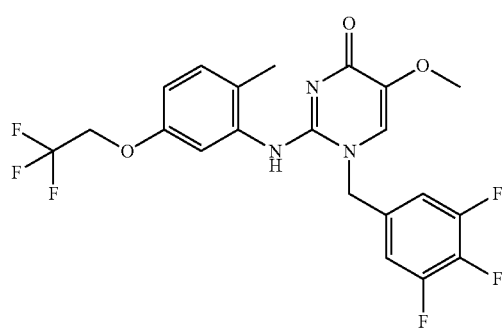 [SMILES: COc1cn(Cc2cc(F)c(F)c(F)c2)c(Nc2cc(OCC(F)(F)F)ccc2C)nc1=O] | 474 | 1.93 | [1] |
| I-0933 | 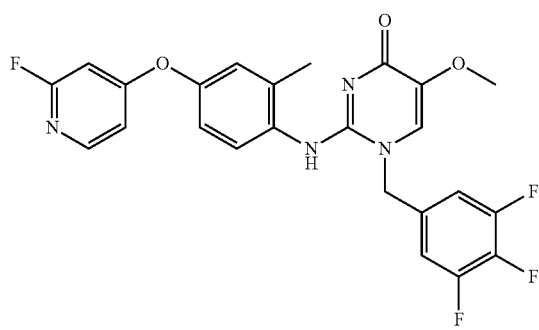 [SMILES: COc1cn(Cc2cc(F)c(F)c(F)c2)c(Nc2ccc(Oc3ccnc(F)c3)cc2C)nc1=O] | 487 | 1.8 | [1] |

TABLE 175-continued
| I-0934 | 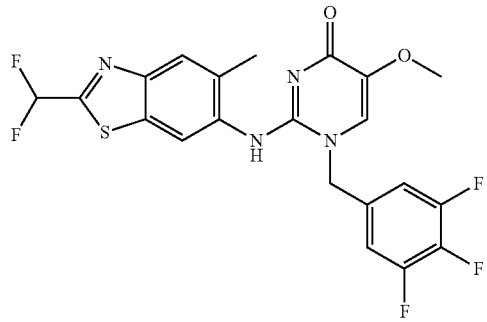 [SMILES: COc1cn(Cc2cc(F)c(F)c(F)c2)c(Nc2cc3sc(C(F)F)nc3cc2C)nc1=O] | 483 | 1.89 | [1] |
| I-0935 | 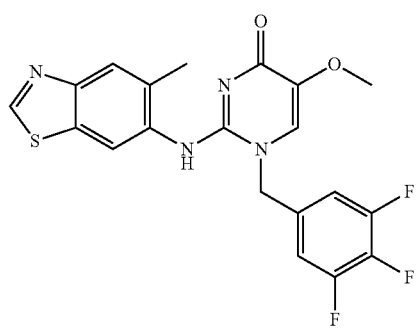 [SMILES: COc1cn(Cc2cc(F)c(F)c(F)c2)c(Nc2cc3scnc3cc2C)nc1=O] | 433 | 1.52 | [1] |
TABLE 176
| I-0936 | 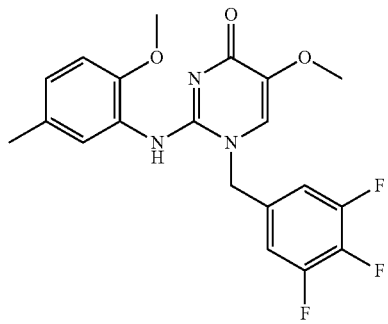 [SMILES: COc1ccc(C)cc1Nc1nc(=O)c(OC)cn1Cc1cc(F)c(F)c(F)c1] | 406 | 111 | [1] |
| I-0937 | 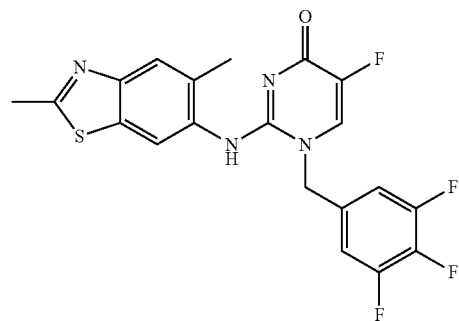 | 435 | 1.63 | [1] |

TABLE 176-continued
| | | | | |
|---|---|---|---|---|
| I-0938 | 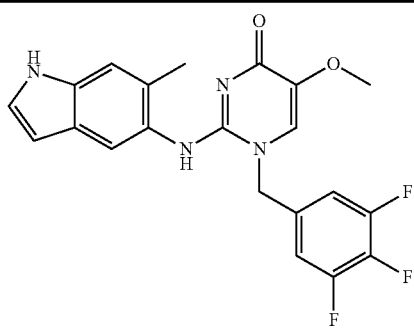 | 415 | 1.56 | [3] |
| I-0939 | 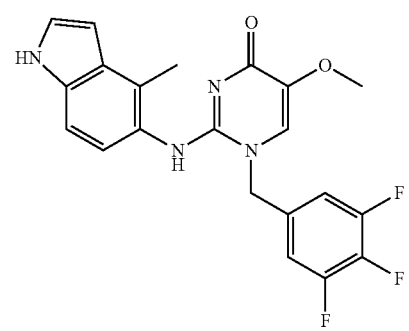 [SMILES: COc1cn(Cc2cc(F)c(F)c(F)c2)c(Nc2ccc3[nH]ccc3c2C)nc1=O] | 415 | 1.59 | [3] |
| I-0940 | 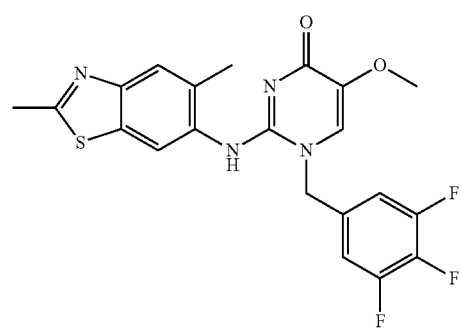 [SMILES: COc1cn(Cc2cc(F)c(F)c(F)c2)c(Nc2cc3sc(C)nc3cc2C)nc1=O] | 448 | 1.87 | [3] |
TABLE 177
| | | | | |
|---|---|---|---|---|
| I-0941 | 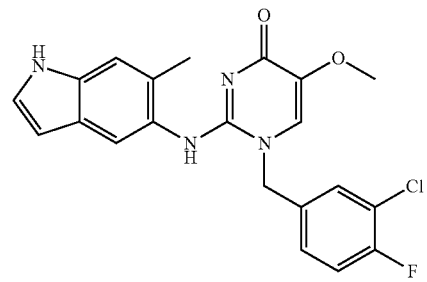 [SMILES: COc1cn(Cc2ccc(F)c(Cl)c2)c(Nc2cc3cc[nH]c3cc2C)nc1=O] | 413 | 1.6 | [3] |

TABLE 177-continued
| | | | | |
|---|---|---|---|---|
| I-0942 | 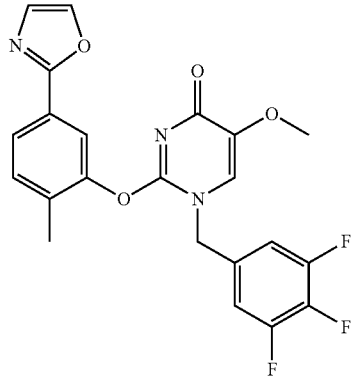 [SMILES: COc1cn(Cc2cc(F)c(F)c(F)c2)c(Oc2cc(-c3ncco3)ccc2C)nc1=O] | 444 | 1.92 | [3] |
| I-0943 | 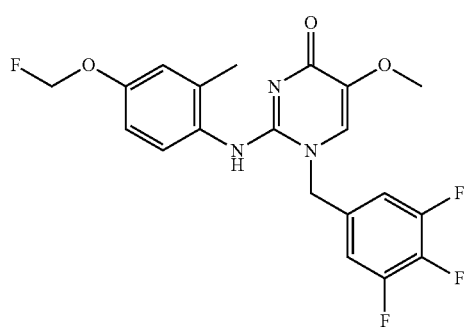 [SMILES: COc1cn(Cc2cc(F)c(F)c(F)c2)c(Nc2ccc(OCF)cc2C)nc1=O] | 424 | 1.63 | [1] |
| I-0944 | 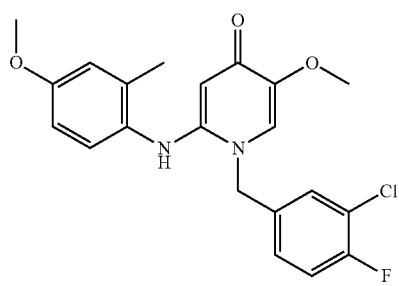 [SMILES: COc1ccc(Nc2cc(=O)c(OC)cn2Cc2ccc(F)c(Cl)c2)c(C)c1] | 403 | 1.47 | [1] |
| I-0945 | 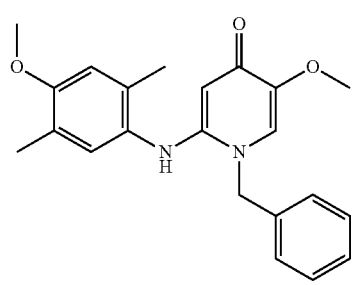 [SMILES: COc1cc(C)c(Nc2cc(=O)c(OC)cn2Cc2ccccc2)cc1C] | 365 | 1.42 | [1] |
| I-0946 | 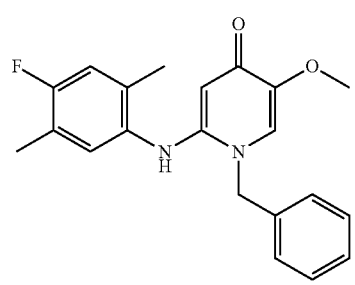 [SMILES: COc1cn(Cc2ccccc2)c(Nc2cc(C)c(F)cc2C)cc1=O] | 353 | 1.43 | [1] |

TABLE 178
| | | | | |
|---|---|---|---|---|
| I-0947 | 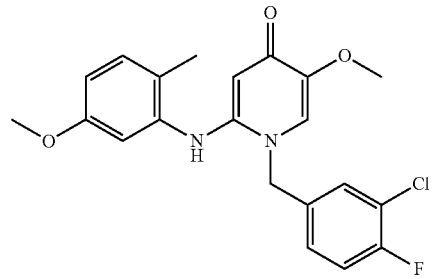 [SMILES: COc1ccc(C)c(Nc2cc(=O)c(OC)cn2Cc2ccc(F)c(Cl)c2)c1] | 403 | 1.51 | [1] |
| I-0948 | 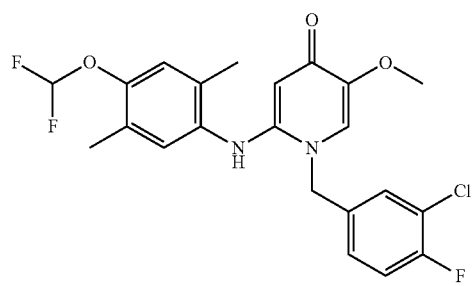 [SMILES: COc1cn(Cc2ccc(F)c(Cl)c2)c(Nc2cc(C)c(OC(F)F)cc2C)cc1=O] | 435 | 1.66 | [1] |
| I-0949 | 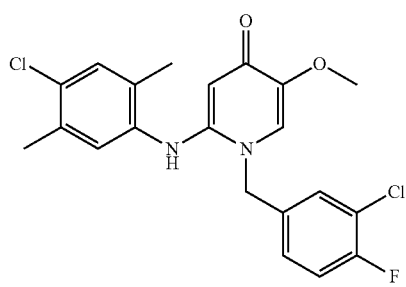 [SMILES: COc1cn(Cc2ccc(F)c(Cl)c2)c(Nc2cc(C)c(Cl)cc2C)cc1=O] | 421 | 1.74 | [1] |
| I-0950 | 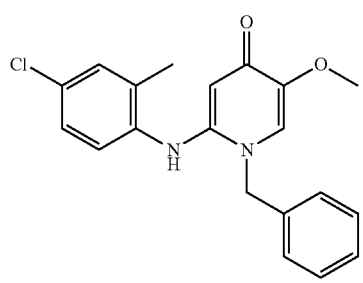 [SMILES: COc1cn(Cc2ccccc2)c(Nc2ccc(Cl)cc2C)cc1=O] | 355 | 1.43 | [1] |
| I-0951 | 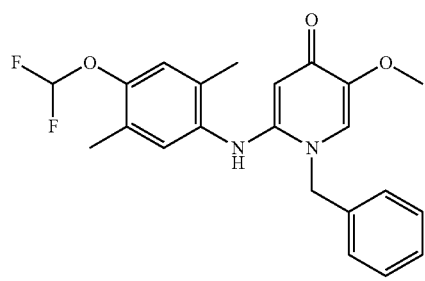 [SMILES: COc1cn(Cc2ccccc2)c(Nc2cc(C)c(OC(F)F)cc2C)cc1=O] | 401 | 1.5 | [1] |

TABLE 178-continued
| | | | | |
|---|---|---|---|---|
| I-0952 | 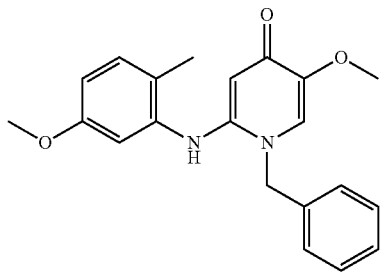 | 351 | 1.32 | [1] |
TABLE 179
| | | | | |
|---|---|---|---|---|
| I-0953 | 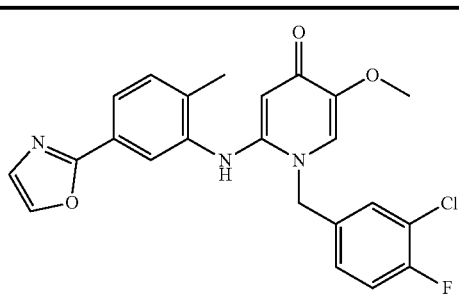 | 440 | 1.48 | [1] |
| I-0954 | 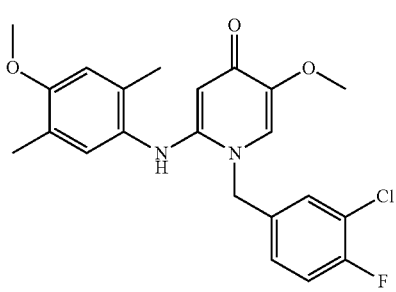 [SMILES: COc1cc(C)c(Nc2cc(=O)c(OC)cn2Cc2ccc(F)c(Cl)c2)cc1C] | 417 | 1.57 | [1] |
| I-0955 | 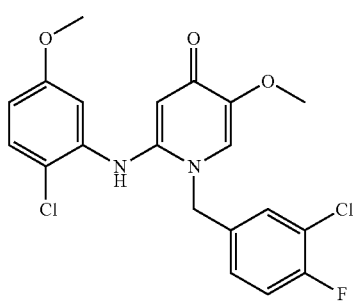 [SMILES: COc1ccc(Cl)c(Nc2cc(=O)c(OC)cn2Cc2ccc(F)c(Cl)c2)c1] | 423 | 1.62 | [1] |
| I-0956 | 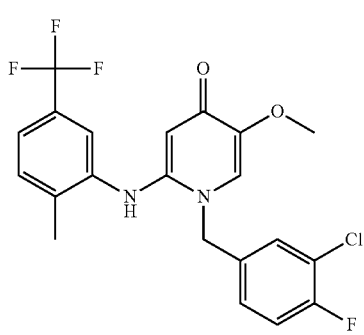 [SMILES: COc1cn(Cc2ccc(F)c(Cl)c2)c(Nc2cc(C(F)(F)F)ccc2C)cc1=O] | 441 | 1.71 | [1] |

TABLE 179-continued
| I-0957 | 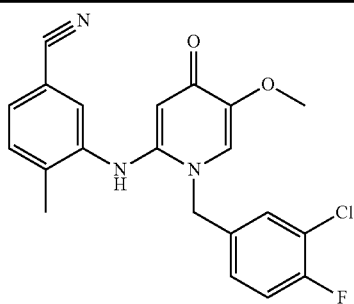 | 398 | 1.48 | [1] |
| I-0958 | 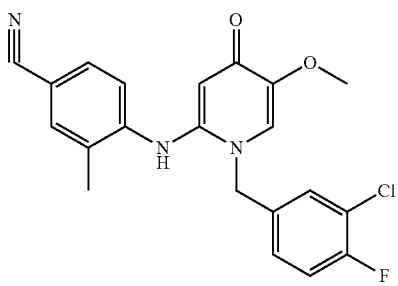 [SMILES: COc1cn(Cc2ccc(F)c(Cl)c2)c(Nc2ccc(C#N)cc2C)cc1=O] | 396 | 1.53 | [1] |
TABLE 180
| I-0959 | 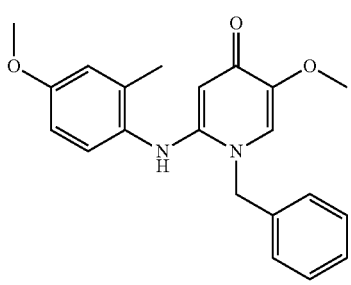 [SMILES: COc1ccc(Nc2cc(=O)c(OC)cn2Cc2ccccc2)c(C)c1] | 351 | 1.35 | [1] |
| I-0960 | 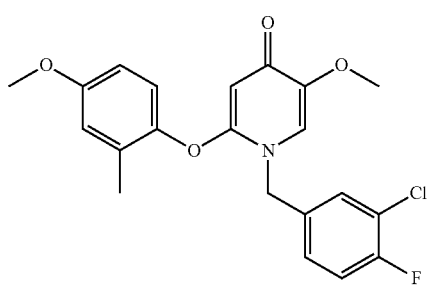 [SMILES: COc1ccc(Oc2cc(=O)c(OC)cn2Cc2ccc(F)c(Cl)c2)c(C)c1] | 403 | 1.85 | [1] |
| I-0961 | 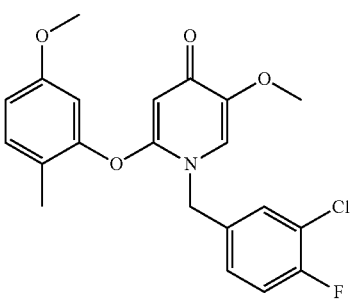 [SMILES: COc1ccc(C)c(Oc2cc(=O)c(OC)cn2Cc2ccc(F)c(Cl)c2)c1] | 404 | 1.87 | [1] |

TABLE 180-continued

| I-0962 | [structure] | 431 | 1.78 | [1] |
| I-0963 | [structure] | 431 | 1.83 | [1] |
| I-0964 | [structure] | 452 | 1.97 | [1] |

TABLE 181

| I-0965 | [structure] | 441 | 1.82 | [1] |
| I-0966 | [structure] | 445 | 1.8 | [1] |

TABLE 181-continued
| I-0967 | 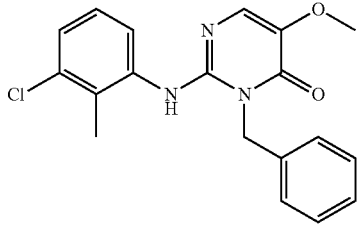 [SMILES: COc1cnc(Nc2cccc(Cl)c2C)n(Cc2ccccc2)c1=O] | 356 | 1.93 | [1] |
| I-0968 | 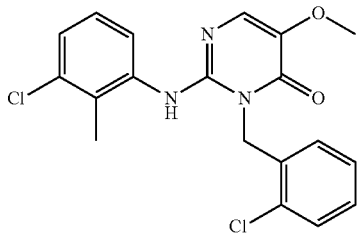 [SMILES: COc1cnc(Nc2cccc(Cl)c2C)n(Cc2ccccc2Cl)c1=O] | 390 | 2.11 | [1] |
| I-0969 | 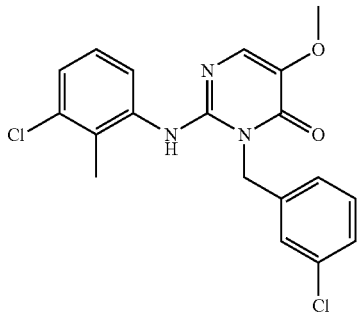 [SMILES: COc1cnc(Nc2cccc(Cl)c2C)n(Cc2cccc(Cl)c2)c1=O] | 390 | 2.32 | [3] |
| I-0970 | 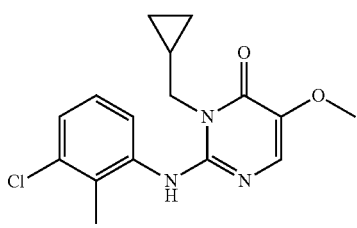 [SMILES: COc1cnc(Nc2cccc(Cl)c2C)n(CC2CC2)c1=O] | 320 | 1.77 | [3] |
TABLE 182
| I-0971 | 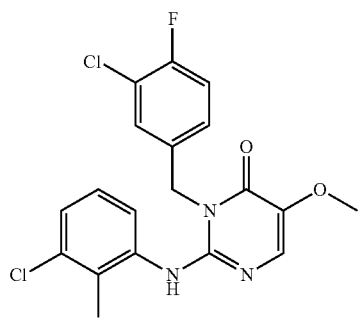 [SMILES: COc1cnc(Nc2cccc(Cl)c2C)n(Cc2ccc(F)c(Cl)c2)c1=O] | 408 | 2.37 | [3] |
| I-0972 | 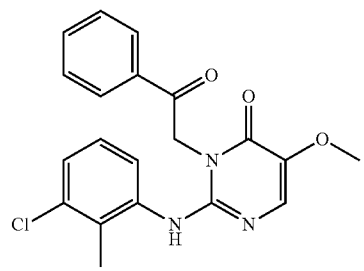 [SMILES: COc1cnc(Nc2cccc(Cl)c2C)n(CC(=O)c2ccccc2)c1=O] | 384 | 1.96 | [3] |

TABLE 182-continued
I-0973 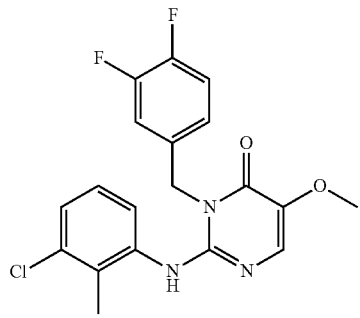 [SMILES: COc1cnc(Nc2cccc(Cl)c2C)n(Cc2ccc(F)c(F)c2)c1=O] 392 2.23 [3]
I-0974 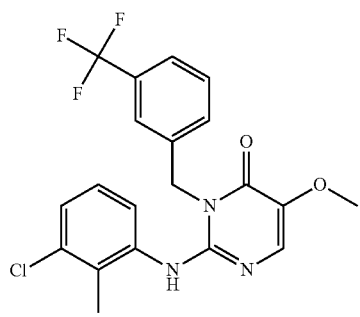 [SMILES: COc1cnc(Nc2cccc(Cl)c2C)n(Cc2cccc(C(F)(F)F)c2)c1=O] 424 2.4 [3]
I-0975 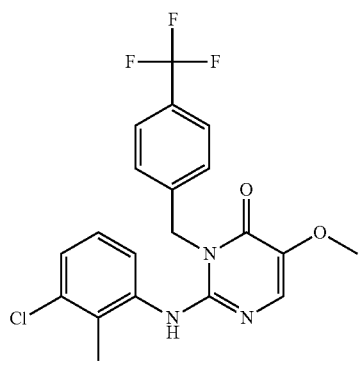 [SMILES: COc1cnc(Nc2cccc(Cl)c2C)n(Cc2ccc(C(F)(F)F)cc2)c1=O] 424 2.41 [3]
I-0976 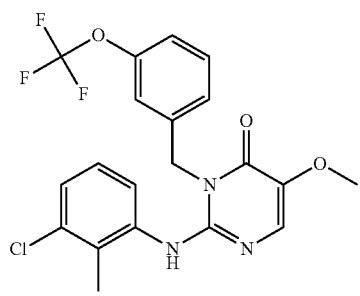 [SMILES: COc1cnc(Nc2cccc(Cl)c2C)n(Cc2cccc(OC(F)(F)F)c2)c1=O] 440 2.45 [3]
TABLE 183
I-0977 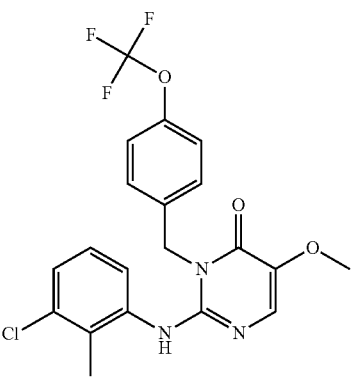 [SMILES: COc1cnc(Nc2cccc(Cl)c2C)n(Cc2ccc(OC(F)(F)F)cc2)c1=O] 440 2.47 [3]
I-0978 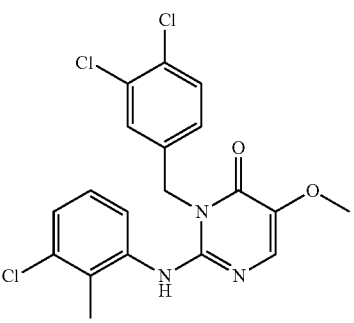 [SMILES: COc1cnc(Nc2cccc(Cl)c2C)n(Cc2ccc(Cl)c(Cl)c2)c1=O] 424 2.52 [3]
I-0979 422 2.3 [3]
I-0980 422 2.28 [3]
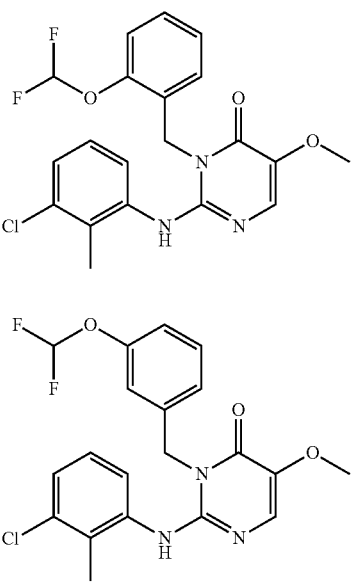
I-0981 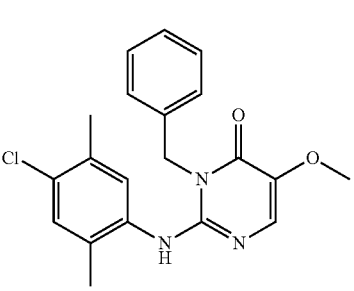 [SMILES: COc1cnc(Nc2cc(C)c(Cl)cc2C)n(Cc2ccccc2)c1=O] 370 2.24 [3]

TABLE 183-continued

| ID | Structure | | | |
|---|---|---|---|---|
| I-0982 | (3-benzyl-5-methoxy-2-(o-tolylamino)pyrimidin-4(3H)-one) | 322 | 1.74 | [3] |

TABLE 184

| ID | Structure | | | |
|---|---|---|---|---|
| I-0983 | (3-benzyl-2-((2-ethylphenyl)amino)-5-methoxypyrimidin-4(3H)-one) | 336 | 1.89 | [3] |
| I-0984 | (3-benzyl-5-methoxy-2-((2-methoxyphenyl)amino)pyrimidin-4(3H)-one) | 338 | 1.96 | [3] |
| I-0985 | (3-(3-chloro-4-fluorobenzyl)-2-((4-methoxy-2,5-dimethylphenyl)amino)-5-methoxypyrimidin-4(3H)-one) | 418 | 2.01 | [1] |
| I-0986 | (3-(3-chloro-4-fluorobenzyl)-5-methoxy-2-((2-methyl-5-(2-oxopyrrolidin-1-yl)phenyl)amino)pyrimidin-4(3H)-one) | 456 | 1.95 | [3] |

TABLE 184-continued

| ID | Structure | MW | RT | Ref |
|---|---|---|---|---|
| I-0987 | (2,6-dimethylbenzothiazol-5-yl)amino pyrimidinone with 5-methoxy, N-(3-chloro-4-fluorobenzyl) | 445 | 1.87 | [1] |
| I-0988 | [4-methyl-3-(1,3,4-thiadiazol-2-yl)phenyl]amino pyrimidinone with 5-methoxy, N-(3-chloro-4-fluorobenzyl) | 458 | 1.63 | [1] |
| I-0989 | (6-methyl-1H-indol-4-yl)amino pyrimidinone with 5-methoxy, N-(3-chloro-4-fluorobenzyl) | 413 | 1.8 | [3] |

TABLE 185

| ID | Structure | MW | RT | Ref |
|---|---|---|---|---|
| I-0990 | (3-chloro-2-methylphenyl)amino pyrimidine-2,4-dione, N-benzyl, N-methyl | 356 | 1.94 | [1] |
| I-0991 | (4-methoxy-2,5-dimethylphenyl)amino pyrimidine-2,4-dione, N-methyl, N-(3,4,5-trifluorobenzyl) | 420 | 2.01 | [1] |

TABLE 185-continued
| I-0993 | 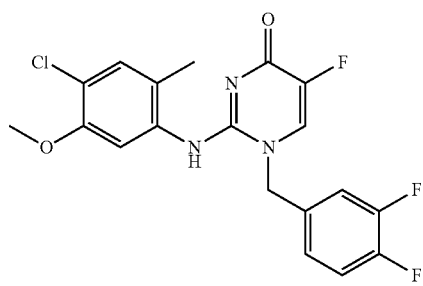 [SMILES: COc1cc(Nc2nc(=O)c(F)cn2Cc2ccc(F)c(F)c2)c(C)cc1Cl] | 410 | 1.78 | [1] |
| --- | --- | --- | --- | --- |
| I-0994 | 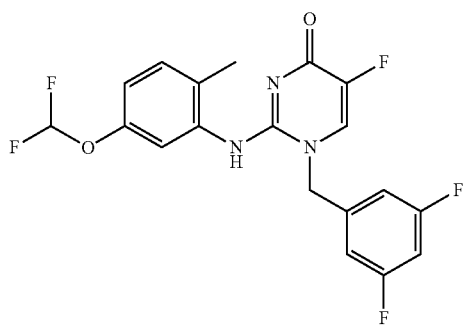 [SMILES: Cc1ccc(OC(F)F)cc1Nc1nc(=O)c(F)cn1Cc1cc(F)cc(F)c1] | 412 | 1.78 | [3] |
| I-0995 | 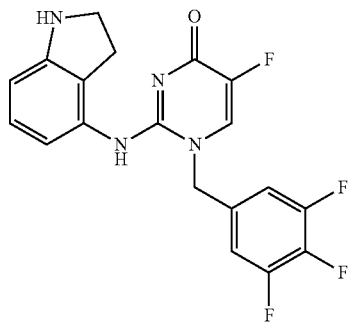 [SMILES: O=c1nc(Nc2cccc3c2CCN3)n(Cc2cc(F)c(F)c(F)c2)cc1F] | 391 | 1.4 | [3] |
| I-0996 | 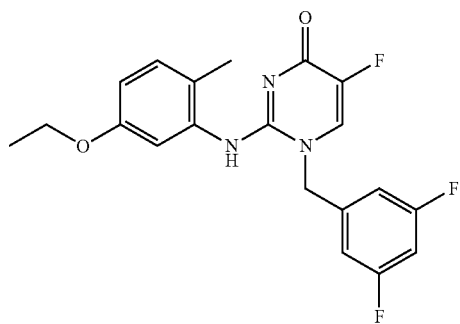 [SMILES: CCOc1ccc(C)c(Nc2nc(=O)c(F)cn2Cc2cc(F)cc(F)c2)c1] | 390 | 1.63 | [3] |

TABLE 186
| | | | | |
|---|---|---|---|---|
| I-0997 | 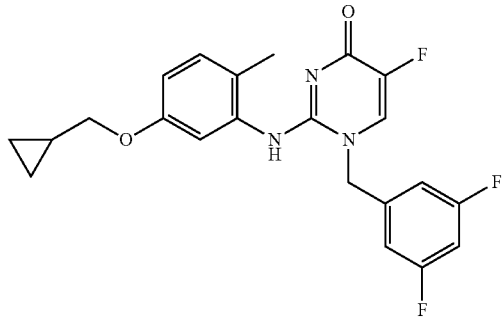 [SMILES: Cc1ccc(OCC2CC2)cc1Nc1nc(=O)c(F)cn1Cc1cc(F)cc(F)c1] | 416 | 1.97 | [3] |
| I-0998 | 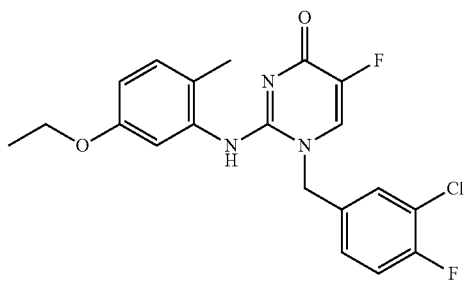 | 406 | 1.84 | [1] |
| I-0999 | 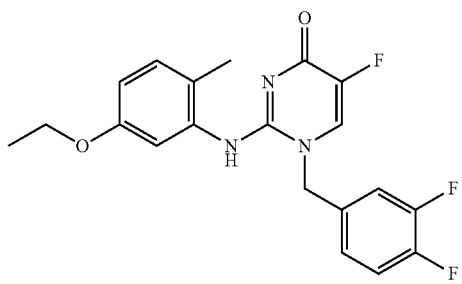 | 390 | 1.74 | [1] |
| I-1000 | 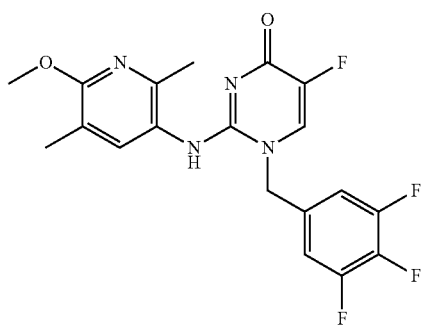 [SMILES: COc1nc(C)c(Nc2nc(=O)c(F)cn2Cc2cc(F)c(F)c(F)c2)cc1C] | 409 | 1.72 | [1] |
| I-1001 | 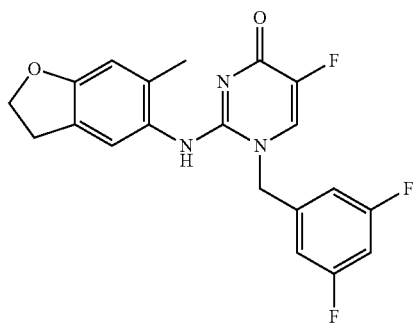 [SMILES: Cc1cc2c(cc1Nc1nc(=O)c(F)cn1Cc1cc(F)cc(F)c1)CCO2] | 388 | 1.56 | [3] |

TABLE 186-continued
| I-1002 | 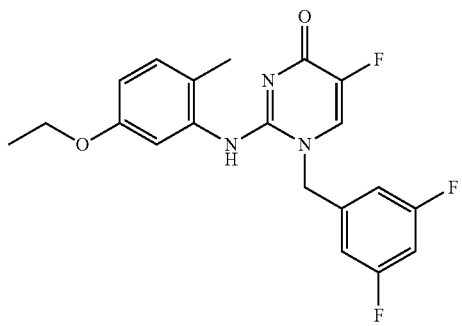 [SMILES: CCOc1ccc(C)c(Nc2nc(=O)c(F)cn2Cc2cc(F)cc(F)c2)c1] | 390 | 1.74 | [1] |
TABLE 187
| I-1003 | 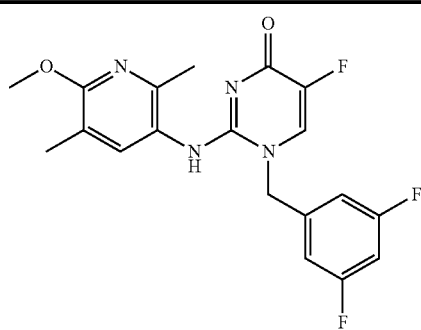 | 391 | 1.6 | [1] |
| I-1004 | 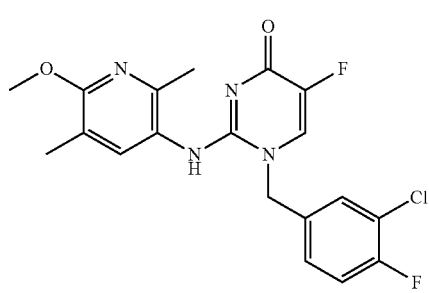 [SMILES: COc1nc(C)c(Nc2nc(=O)c(F)cn2Cc2ccc(F)c(Cl)c2)cc1C] | 407 | 1.72 | [1] |
| I-1005 | 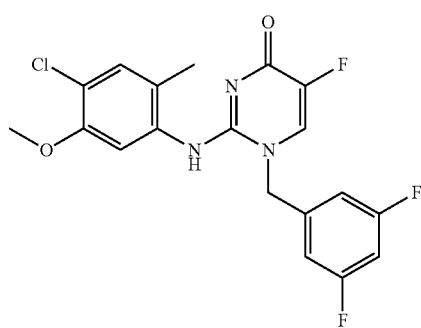 [SMILES: COc1cc(Nc2nc(=O)c(F)cn2Cc2cc(F)cc(F)c2)c(C)cc1Cl] | 410 | 1.72 | [1] |

TABLE 187-continued
| | | | | |
|---|---|---|---|---|
| I-1006 | 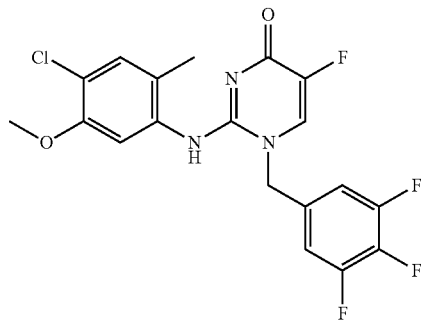 [SMILES: COc1cc(Nc2nc(=O)c(F)cn2Cc2cc(F)c(F)c(F)c2)c(C)cc1Cl] | 428 | 1.83 | [1] |
| I-1007 | 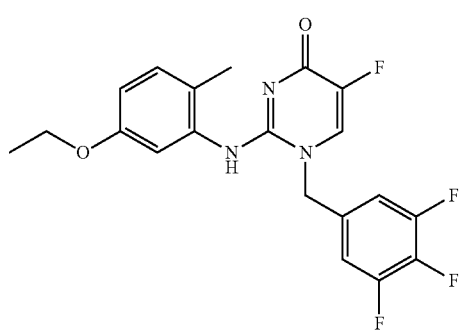 [SMILES: CCOc1ccc(C)c(Nc2nc(=O)c(F)cn2Cc2cc(F)c(F)c(F)c2)c1] | 409 | 1.82 | [1] |
TABLE 188
| | | | | |
|---|---|---|---|---|
| I-1008 | 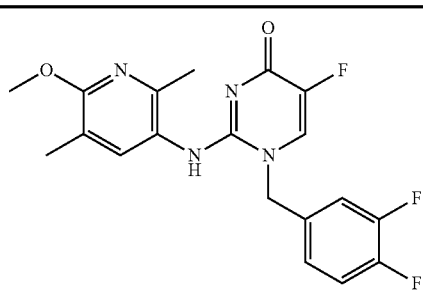 | 391 | 1.62 | [1] |
| I-1009 | 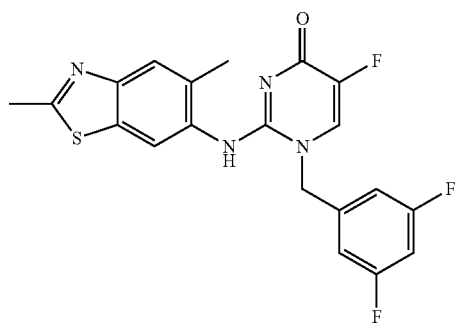 [SMILES: Cc1nc2cc(C)c(Nc3nc(=O)c(F)cn3Cc3cc(F)cc(F)c3)cc2s1] | 417 | 1.57 | [3] |

TABLE 188-continued

| ID | Structure | MS | RT | Method |
|---|---|---|---|---|
| I-1010 | 2-methylbenzothiazole-6-yl-NH-pyrimidinone with N-(3,4-difluorobenzyl), 5-F, 6-methyl | 417 | 1.57 | [3] |
| I-1011 | 2-methylbenzothiazole-6-yl-NH-pyrimidinone with N-(4-fluorobenzyl), 5-F, 6-methyl | 399 | 1.5 | [3] |
| I-1012 | 3-(hydroxymethyl)-6-methylphenyl-NH-pyrimidinone with N-(3,4-difluorobenzyl), 5-F | 376 | 1.4 | [3] |
| I-1013 | 3-(hydroxymethyl)-6-methylphenyl-NH-pyrimidinone with N-(3-chloro-4-fluorobenzyl), 5-F | 392 | 1.46 | [3] |

TABLE 189

| ID | Structure | MS | RT | Method |
|---|---|---|---|---|
| I-1014 | 3-(hydroxymethyl)-6-methylphenyl-NH-pyrimidinone with N-(3,5-difluorobenzyl), 5-F | 376 | 1.36 | [3] |

TABLE 189-continued
| | | | | |
|---|---|---|---|---|
| I-1015 | 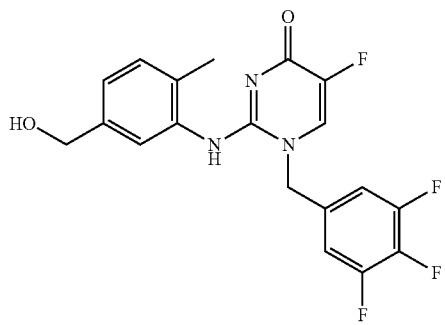 [SMILES: Cc1ccc(CO)cc1Nc1nc(=O)c(F)cn1Cc1cc(F)c(F)c(F)c1] | 394 | 1.47 | [3] |
| I-1016 | 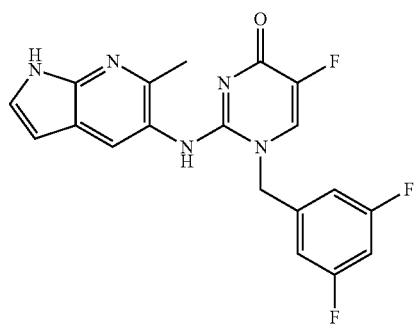 [SMILES: Cc1nc2[nH]ccc2cc1Nc1nc(=O)c(F)cn1Cc1cc(F)cc(F)c1] | 386 | 1.1 | [3] |
| I-1017 | 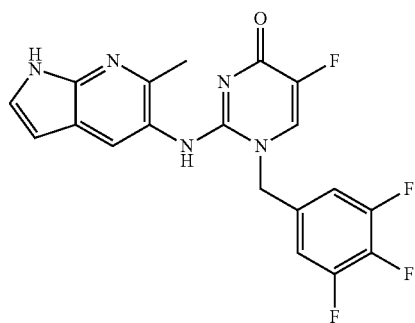 [SMILES: Cc1nc2[nH]ccc2cc1Nc1nc(=O)c(F)cn1Cc1cc(F)c(F)c(F)c1] | 404 | 1.21 | [3] |
| I-1018 | 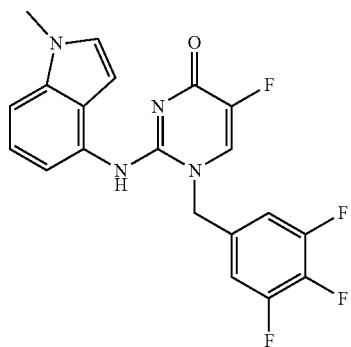 [SMILES: Cn1ccc2c(Nc3nc(=O)c(F)cn3Cc3cc(F)c(F)c(F)c3)cccc21] | 403 | 1.72 | [3] |

TABLE 190
| | | | | |
|---|---|---|---|---|
| I-1019 | 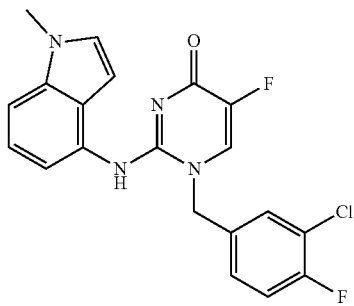 [SMILES: Cn1ccc2c(Nc3nc(=O)c(F)cn3Cc3ccc(F)c(Cl)c3)cccc21] | 401 | 1.73 | [3] |
| I-1020 | 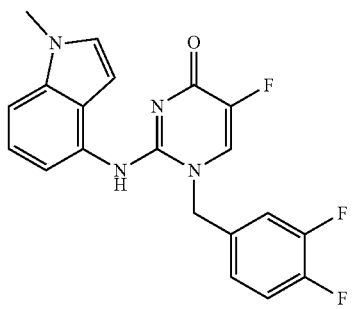 [SMILES: Cn1ccc2c(Nc3nc(=O)c(F)cn3Cc3ccc(F)c(F)c3)cccc21] | 385 | 1.64 | [3] |
| I-1021 | 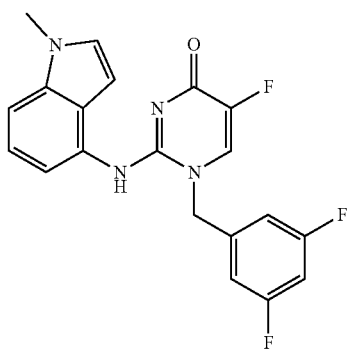 [SMILES: Cn1ccc2c(Nc3nc(=O)c(F)cn3Cc3cc(F)cc(F)c3)cccc21] | 385 | 1.64 | [3] |
TABLE 190-continued
| | | | | |
|---|---|---|---|---|
| I-1022 | 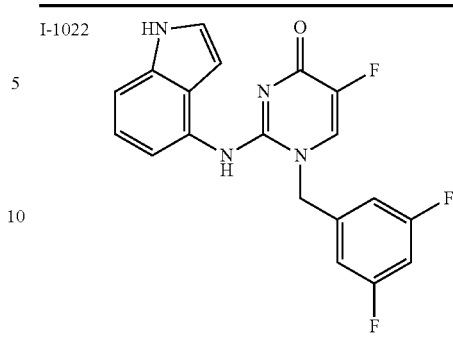 | 371 | 1.47 | [3] |
| I-1023 | 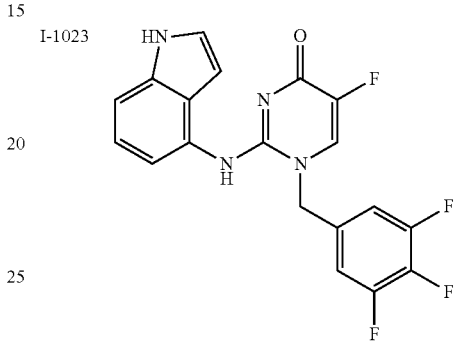 | 389 | 1.57 | [3] |
| I-1024 | 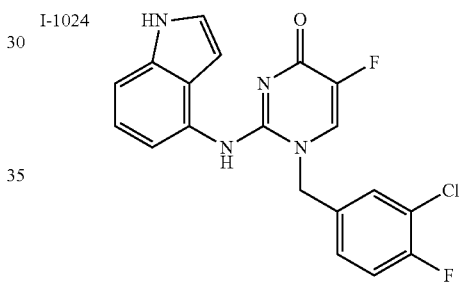 | 387 | 1.6 | [3] |
TABLE 191
| | | | | |
|---|---|---|---|---|
| I-1025 | 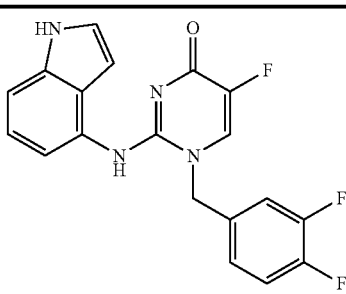 | 371 | 1.49 | [3] |
| I-1026 | 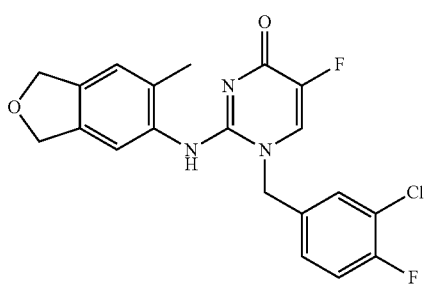 [SMILES: Cc1cc2c(cc1Nc1nc(=O)c(F)cn1Cc1ccc(F)c(Cl)c1)COC2] | 404 | 1.65 | [3] |

TABLE 191-continued
| | | | | |
|---|---|---|---|---|
| I-1027 | 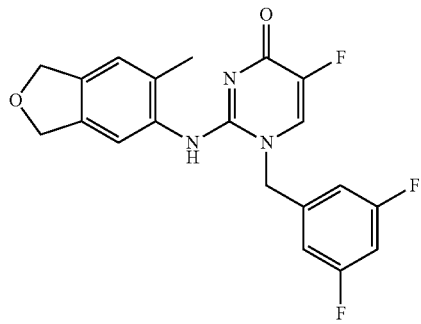 [SMILES: Cc1cc2c(cc1Nc1nc(=O)c(F)cn1Cc1cc(F)cc(F)c1)COC2] | 388 | 1.53 | [3] |
| I-1028 | 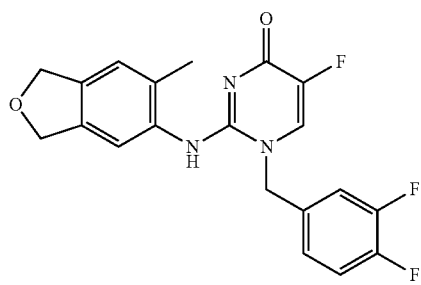 [SMILES: Cc1cc2c(cc1Nc1nc(=O)c(F)cn1Cc1ccc(F)c(F)c1)COC2] | 388 | 1.55 | [3] |
| I-1029 | 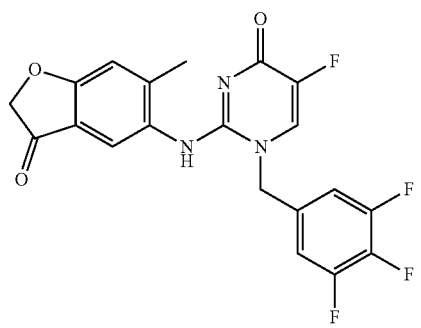 [SMILES: Cc1cc2c(cc1Nc1nc(=O)c(F)cn1Cc1cc(F)c(F)c(F)c1)C(=O)CO2] | 420 | 1.95 | [3] |
| I-1030 | 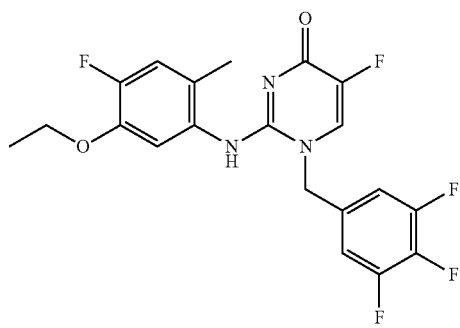 [SMILES: CCOc1cc(Nc2nc(=O)c(F)cn2Cc2cc(F)c(F)c(F)c2)c(C)cc1F] | 426 | 1.92 | [3] |
TABLE 192
| | | | | |
|---|---|---|---|---|
| I-1031 | 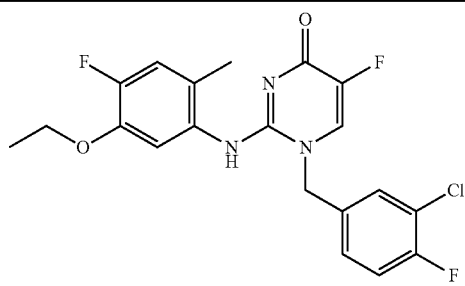 | 424 | 1.94 | [3] |

TABLE 192-continued
| | | | | |
|---|---|---|---|---|
| I-1032 | 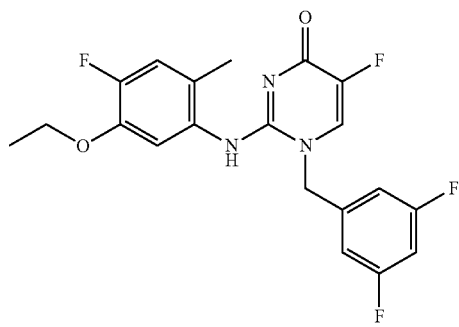 [SMILES: CCOc1cc(Nc2nc(=O)c(F)cn2Cc2cc(F)cc(F)c2)c(C)cc1F] | 408 | 1.83 | [3] |
| I-1033 | 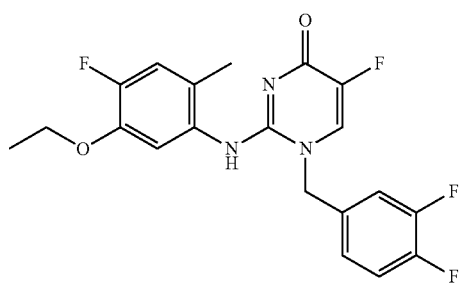 [SMILES: CCOc1cc(Nc2nc(=O)c(F)cn2Cc2ccc(F)c(F)c2)c(C)cc1F] | 408 | 1.83 | [3] |
| I-1034 | 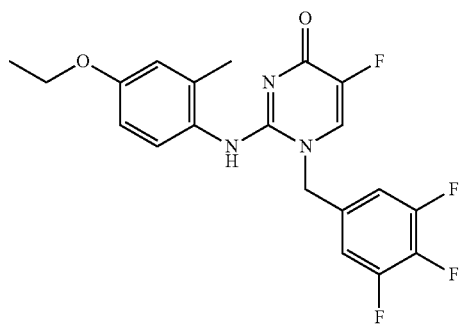 [SMILES: CCOc1ccc(Nc2nc(=O)c(F)cn2Cc2cc(F)c(F)c(F)c2)c(C)c1] | 408 | 1.86 | [3] |
| I-1035 | 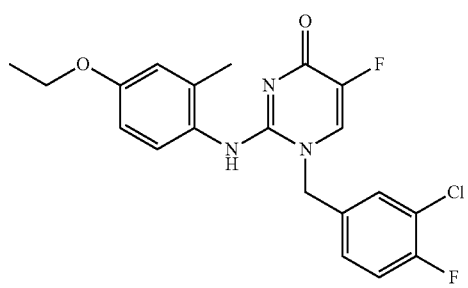 [SMILES: CCOc1ccc(Nc2nc(=O)c(F)cn2Cc2ccc(F)c(Cl)c2)c(C)c1] | 406 | 1.88 | [3] |
| I-1036 | 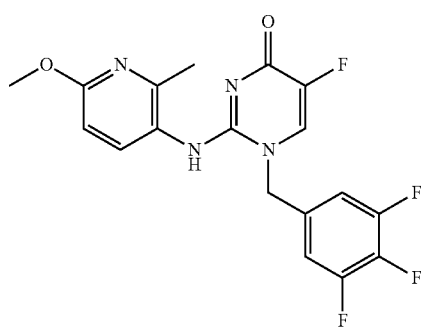 [SMILES: COc1ccc(Nc2nc(=O)c(F)cn2Cc2cc(F)c(F)c(F)c2)c(C)n1] | 395 | 1.45 | [1] |

TABLE 193
| | | | | | |
|---|---|---|---|---|---|
| I-1037 | 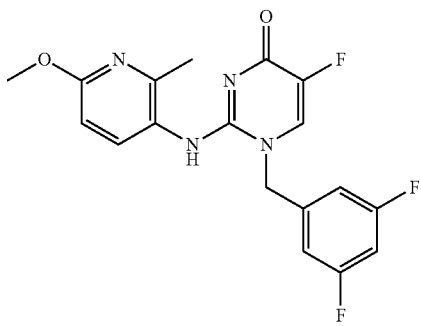 [SMILES: COc1ccc(Nc2nc(=O)c(F)cn2Cc2cc(F)cc(F)c2)c(C)n1] | | 377 | 1.34 | [1] |
| I-1038 | 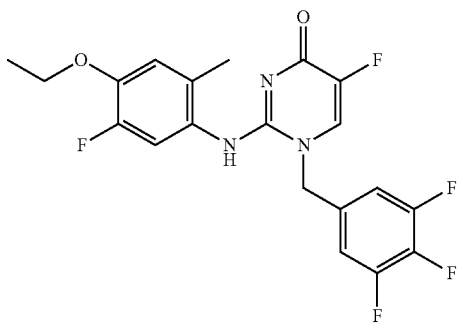 [SMILES: CCOc1cc(C)c(Nc2nc(=O)c(F)cn2Cc2cc(F)c(F)c(F)c2)cc1F] | | 426 | 1.92 | [3] |
| I-1039 | 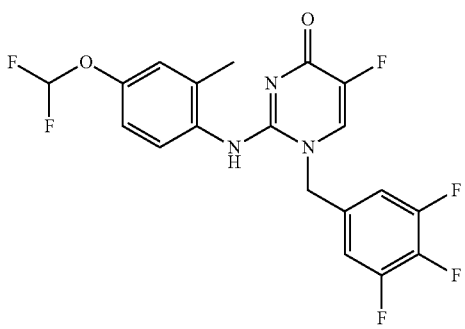 [SMILES: Cc1cc(OC(F)F)ccc1Nc1nc(=O)c(F)cn1Cc1cc(F)c(F)c(F)c1] | | 430 | 1.92 | [3] |
| I-1040 | 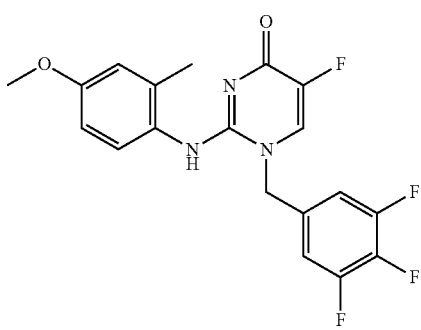 [SMILES: COc1ccc(Nc2nc(=O)c(F)cn2Cc2cc(F)c(F)c(F)c2)c(C)c1] | 1H-NMR (DMSO-D6) δ: 1.87 (s, 3H), 3.73 (s, 3H), 5.14 (s, 2H), 6.74-6.79 (m, 2H), 6.98 (d, J = 8.4 Hz, 1H), 7.33 (dd, J = 8.0 Hz, 2H), 7.99 (d, J = 4.8 Hz, 1H), 8.45 (s, 1H). | 394 | 1.62 | [1] |
| I-1041 | 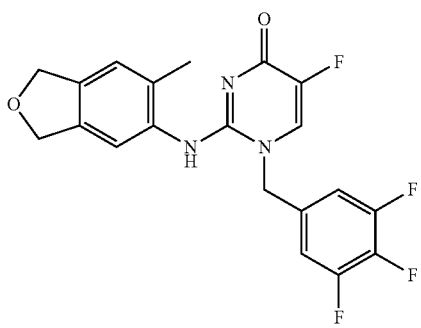 [SMILES: Cc1cc2c(cc1Nc1nc(=O)c(F)cn1Cc1cc(F)c(F)c(F)c1)COC2] | 1H-NMR (DMSO-D6) δ: 1.89 (s, 3H), 4.95 (s, 4H), 5.17 (s, 2H), 7.03 (s, 1H), 7.15 (s, 1H), 7.34 (t, J = 7.7 Hz, 2H), 8.02 (d, J = 5.5 Hz, 1H), 8.60 (s, 1H). | 406 | 1.77 | [3] |

TABLE 194
| I-1042 | 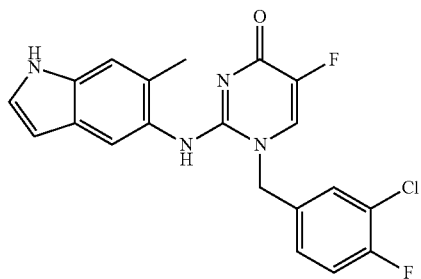 [SMILES: Cc1cc2[nH]ccc2cc1Nc1nc(=O)c(F)cn1Cc1ccc(F)c(Cl)c1] | 401 | 1.8 | [3] |
| I-1043 | 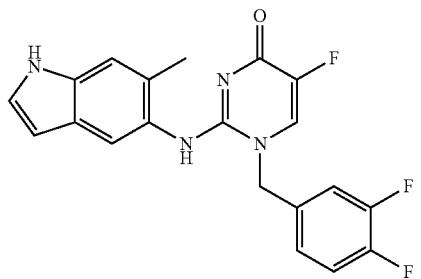 [SMILES: Cc1cc2[nH]ccc2cc1Nc1nc(=O)c(F)cn1Cc1ccc(F)c(F)c1] | 385 | 1.7 | [3] |
| I-1044 | 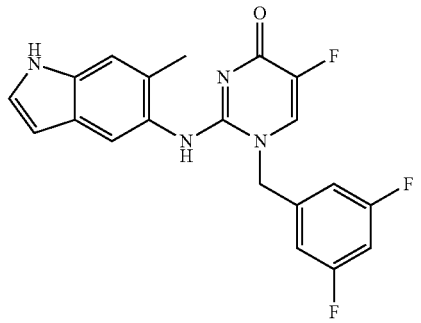 [SMILES: Cc1cc2[nH]ccc2cc1Nc1nc(=O)c(F)cn1Cc1cc(F)cc(F)c1] | 385 | 1.65 | [3] |
| I-1045 | 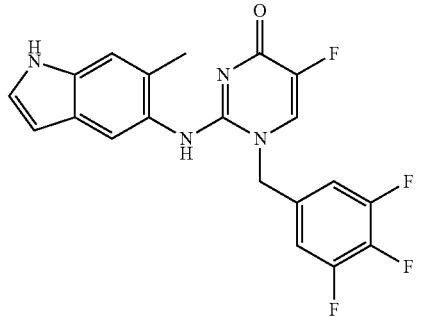 [SMILES: Cc1cc2[nH]ccc2cc1Nc1nc(=O)c(F)cn1Cc1cc(F)c(F)c(F)c1] | 403 | 1.77 | [3] |
| I-1046 | 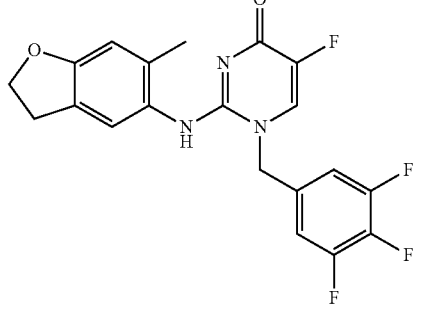 | 406 | 1.8 | [3] |

TABLE 194-continued
| ID | Structure | MS | RT | Method |
|---|---|---|---|---|
| I-1047 | 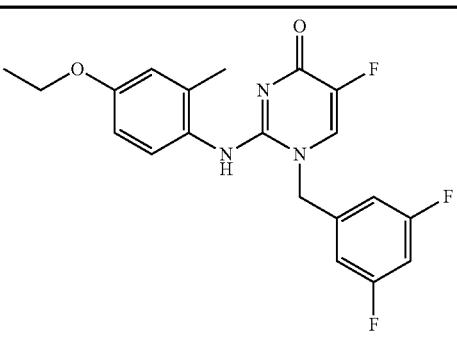 | 390 | 1.77 | [3] |
TABLE 195
| ID | Structure | NMR | MS | RT | Method |
|---|---|---|---|---|---|
| I-1048 | 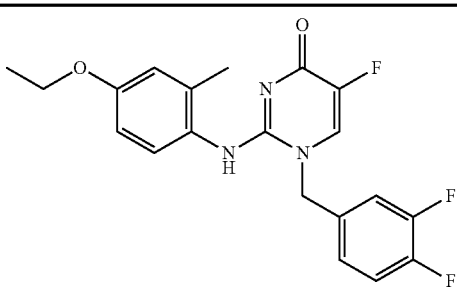 | | 390 | 1.83 | [3] |
| I-1049 | 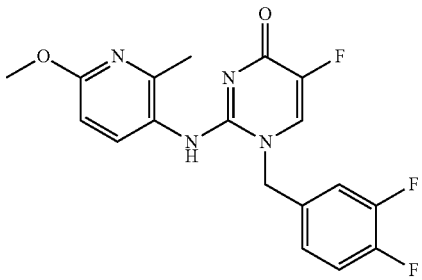 [SMILES: COc1ccc(Nc2nc(=O)c(F)cn2Cc2ccc(F)c(F)c2)c(C)n1] | | 377 | 1.37 | [1] |
| I-1050 | 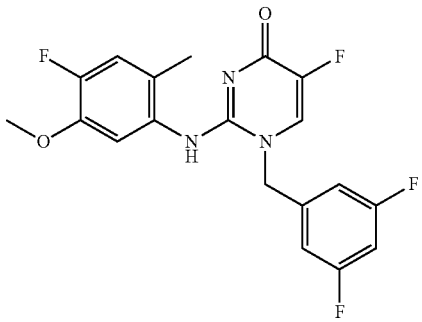 [SMILES: COc1cc(Nc2nc(=O)c(F)cn2Cc2cc(F)cc(F)c2)c(C)cc1F] | 1H-NMR (DMSO-D6) δ: 1.77 (s, 3H), 3.77 (s, 3H), 5.20 (br s, 2H), 6.89 (m, 1H), 7.20-7.15 (m, 3H), 7.26 (m, 1H), 8.05 (m, 1H), 8.63 (br s, 1H). | 394 | 1.61 | [1] |
| I-1051 | 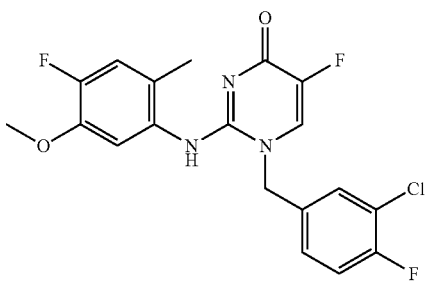 [SMILES: COc1cc(Nc2nc(=O)c(F)cn2Cc2ccc(F)c(Cl)c2)c(C)cc1F] | | 410 | 1.72 | [1] |

TABLE 195-continued
| I-1052 | 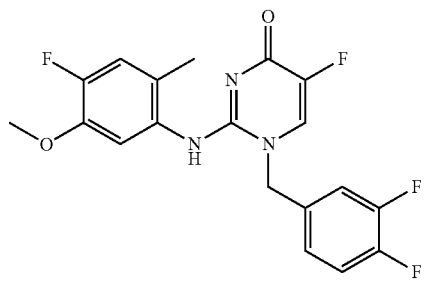 [SMILES: COc1cc(Nc2nc(=O)c(F)cn2Cc2ccc(F)c(F)c2)c(C)cc1F] | 394 | 1.61 | [1] |
| I-1053 | 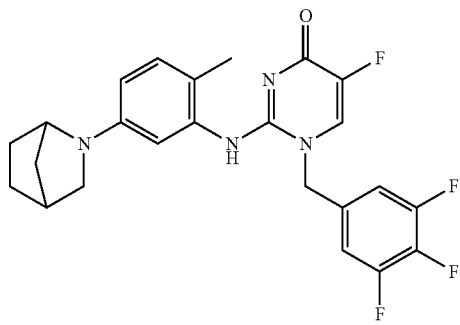 [SMILES: Cc1ccc(N2CC3CCC2C3)cc1Nc1nc(=O)c(F)cn1Cc1cc(F)c(F)c(F)c1] | 459 | 1.93 | [3] |
TABLE 196
| I-1054 | 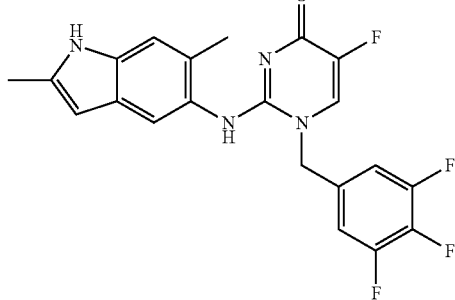 | 417 | 1.75 | [3] |
| I-1055 | 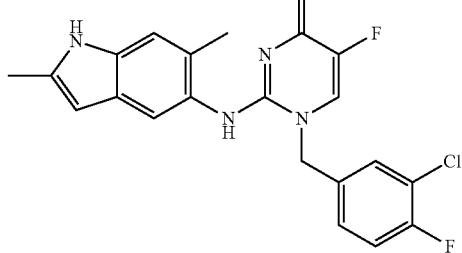 | 415 | 1.78 | [3] |
| I-1056 | 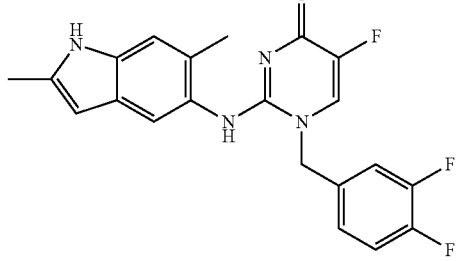 | 399 | 1.68 | [3] |

TABLE 196-continued
| | | | | |
|---|---|---|---|---|
| I-1057 | 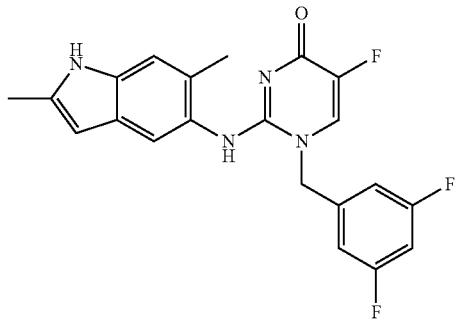 [SMILES: Cc1cc2cc(Nc3nc(=O)c(F)cn3Cc3cc(F)cc(F)c3)c(C)cc2[nH]1] | 399 | 1.58 | [3] |
| I-1058 | 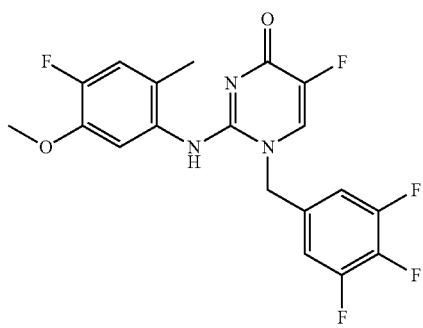 [SMILES: COc1cc(Nc2nc(=O)c(F)cn2Cc2cc(F)c(F)c(F)c2)c(C)cc1F] | 412 | 1.7 | [1] |
| I-1059 | 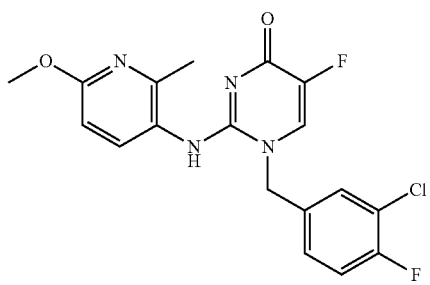 [SMILES: COc1ccc(Nc2nc(=O)c(F)cn2Cc2ccc(F)c(Cl)c2)c(C)n1] | 393 | 1.47 | [1] |
TABLE 197
| | | | | |
|---|---|---|---|---|
| I-1060 | 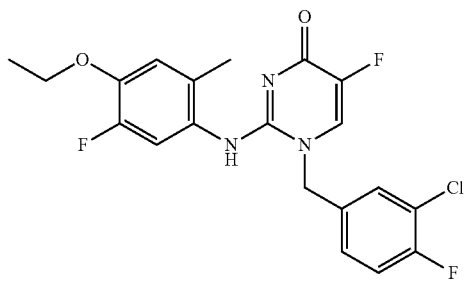 [SMILES: CCOc1cc(C)c(Nc2nc(=O)c(F)cn2Cc2ccc(F)c(Cl)c2)cc1F] | 424 | 1.93 | [3] |

TABLE 197-continued
| | | | | |
|---|---|---|---|---|
| I-1061 | 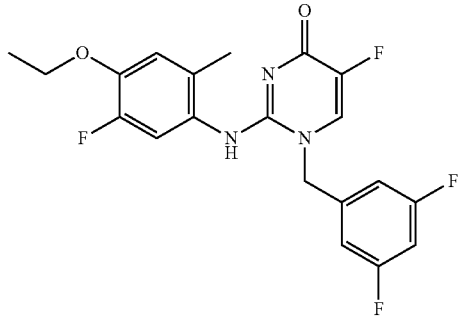 [SMILES: CCOc1cc(C)c(Nc2nc(=O)c(F)cn2Cc2cc(F)cc(F)c2)cc1F] | 408 | 1.81 | [3] |
| I-1062 | 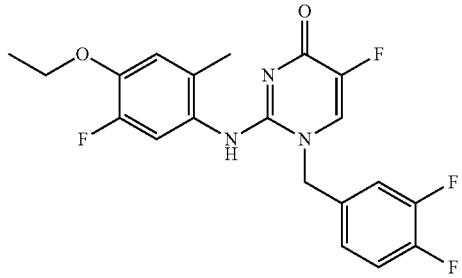 [SMILES: CCOc1cc(C)c(Nc2nc(=O)c(F)cn2Cc2ccc(F)c(F)c2)cc1F] | 408 | 1.81 | [3] |
| I-1063 | 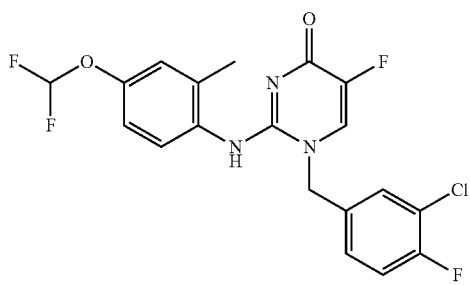 [SMILES: Cc1cc(OC(F)F)ccc1Nc1nc(=O)c(F)cn1Cc1ccc(F)c(Cl)c1] | 428 | 1.93 | [3] |
| I-1064 | 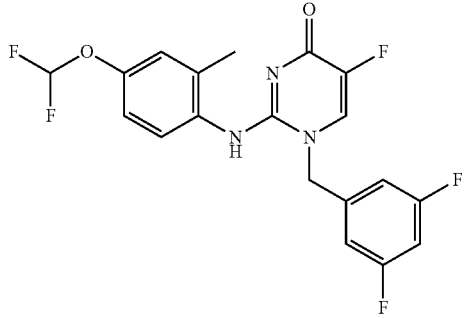 [SMILES: Cc1cc(OC(F)F)ccc1Nc1nc(=O)c(F)cn1Cc1cc(F)cc(F)c1] | 412 | 1.83 | [3] |
| I-1065 | 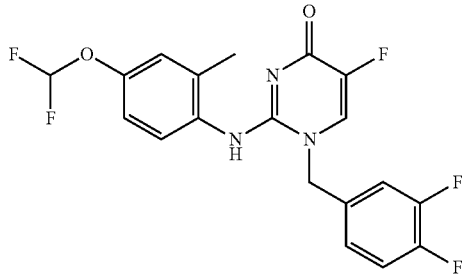 [SMILES: Cc1cc(OC(F)F)ccc1Nc1nc(=O)c(F)cn1Cc1ccc(F)c(F)c1] | 412 | 1.84 | [3] |

TABLE 198
| I-1066 | 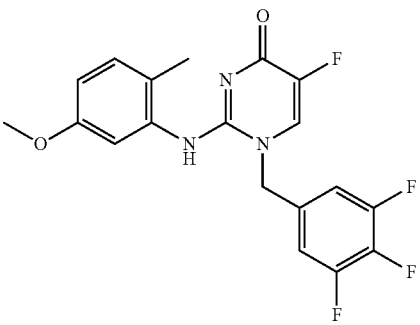 [SMILES: COc1ccc(C)c(Nc2nc(=O)c(F)cn2Cc2cc(F)c(F)c(F)c2)c1] | 1H-NMR (DMSO-D6) δ: 8.58 (1H, s), 8.03 (1H, d, J = 5.8 Hz), 7.35 (2H, t, J = 7.5 Hz), 7.10 (1H, d, J = 8.2 Hz), 6.77 (1H, d, J = 7.4 Hz), 6.69 (1H, s), 5.16 (2H, s), 3.71 (3H, s), 1.79 (3H, s). | 394 | 1.76 | [3] |
|---|---|---|---|---|---|
| I-1067 | 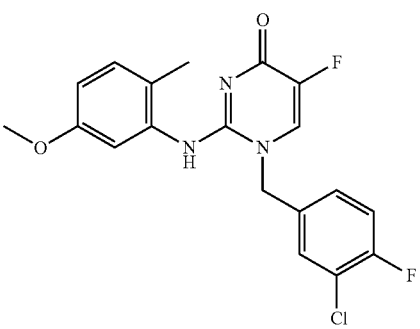 [SMILES: COc1ccc(C)c(Nc2nc(=O)c(F)cn2Cc2ccc(F)c(Cl)c2)c1] | | 392 | 1.77 | [3] |
| I-1068 | 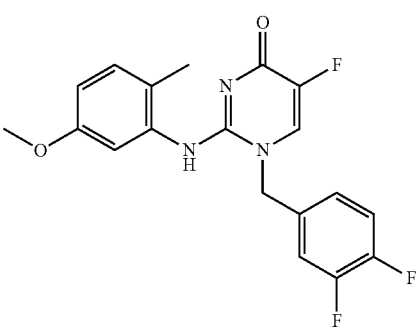 [SMILES: COc1ccc(C)c(Nc2nc(=O)c(F)cn2Cc2ccc(F)c(F)c2)c1] | | 376 | 1.65 | [3] |
| I-1069 | 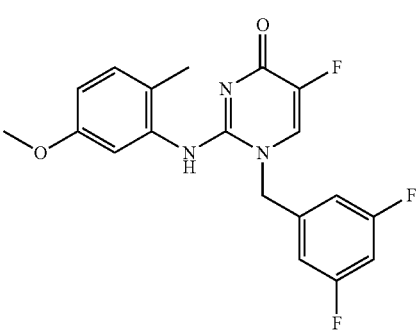 [SMILES: COc1ccc(C)c(Nc2nc(=O)c(F)cn2Cc2cc(F)cc(F)c2)c1] | | 376 | 1.64 | [3] |
| I-1070 | 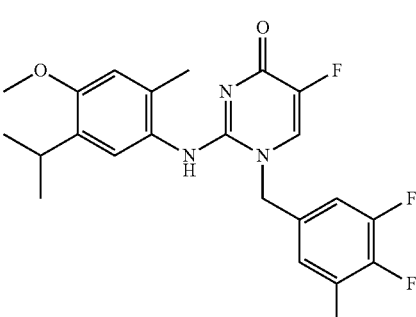 | | 436 | 2.11 | [3] |

TABLE 199
| I-1071 | 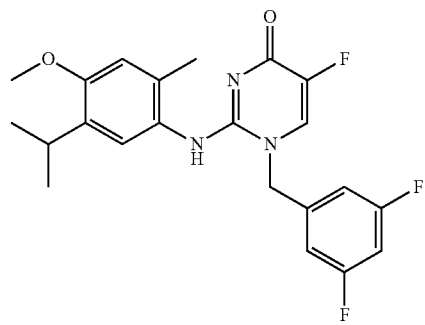 [SMILES: COc1cc(C)c(Nc2nc(=O)c(F)cn2Cc2cc(F)cc(F)c2)cc1C(C)C] | 418 | 2.19 | [3] |
| I-1072 | 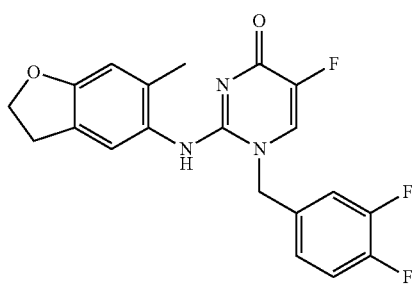 [SMILES: Cc1cc2c(cc1Nc1nc(=O)c(F)cn1Cc1ccc(F)c(F)c1)CCO2] | 388 | 1.59 | [3] |
| I-1073 | 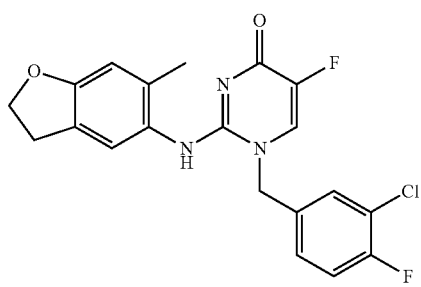 [SMILES: Cc1cc2c(cc1Nc1nc(=O)c(F)cn1Cc1ccc(F)c(Cl)c1)CCO2] | 404 | 111 | [3] |
| I-1074 | 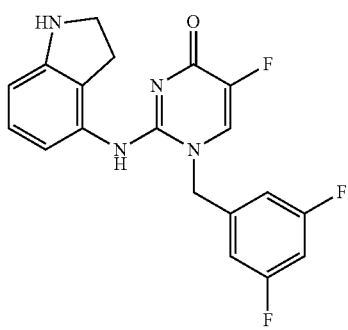 | 373 | 1.23 | [3] |
| I-1075 | 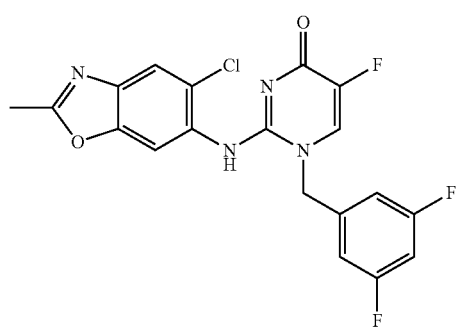 [SMILES: Cc1nc2cc(Cl)c(Nc3nc(=O)c(F)cn3Cc3cc(F)cc(F)c3)cc2o1] | 421 | 1.62 | [3] |

TABLE 199-continued
| I-1076 | 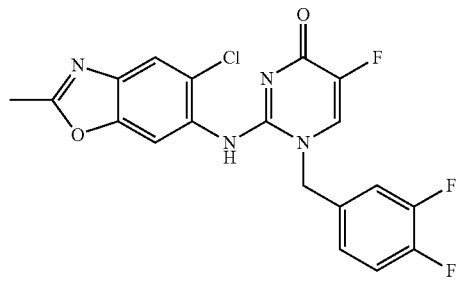 [SMILES: Cc1nc2cc(Cl)c(Nc3nc(=O)c(F)cn3Cc3ccc(F)c(F)c3)cc2o1] | 421 | 1.61 | [3] |
TABLE 200
| I-1077 | 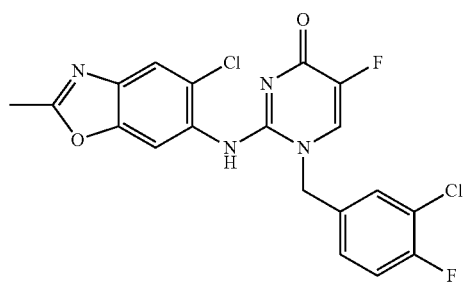 [SMILES: Cc1nc2cc(Cl)c(Nc3nc(=O)c(F)cn3Cc3ccc(F)c(Cl)c3)cc2o1] | 437 | 1.74 | [3] |
| I-1078 | 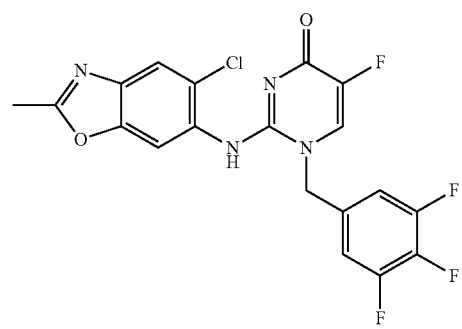 [SMILES: Cc1nc2cc(Cl)c(Nc3nc(=O)c(F)cn3Cc3cc(F)c(F)c(F)c3)cc2o1] | 439 | 1.73 | [3] |
| I-1079 | 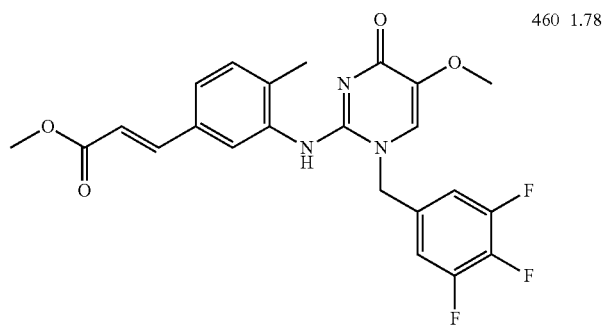 | 460 | 1.78 | [1] |

TABLE 200-continued
| I-1080 | 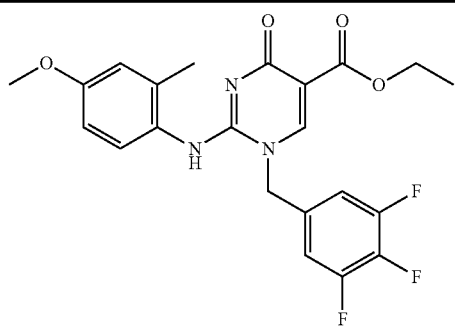 | 448 | 2.1 | [1] |
| I-1081 | 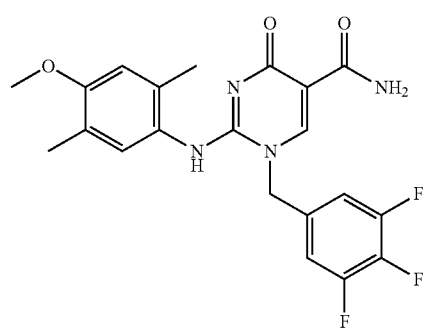 [SMILES: COc1cc(C)c(Nc2nc(=O)c(C(N)=O)cn2Cc2cc(F)c(F)c(F)c2)cc1C] | 433 | 1.94 | [1] |
TABLE 201
| I-1082 | 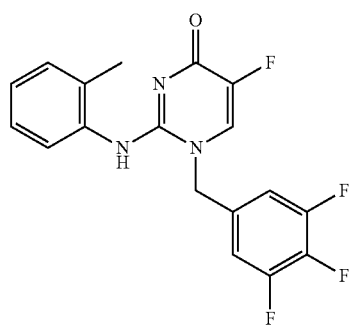 | 364 | 1.64 | [1] |
| I-1083 | 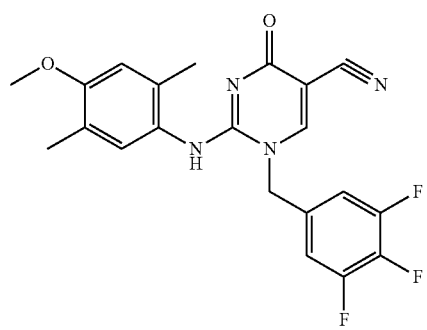 [SMILES: COc1cc(C)c(Nc2nc(=O)c(C#N)cn2Cc2cc(F)c(F)c(F)c2)cc1C] | 415 | 2.07 | [1] |

TABLE 201-continued
| I-1084 | 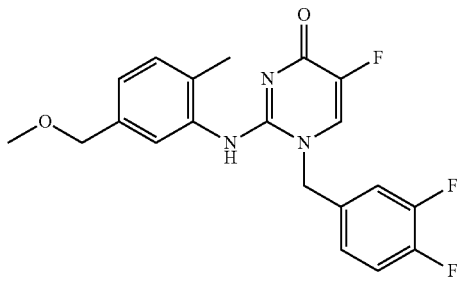 [SMILES: COCc1ccc(C)c(Nc2nc(=O)c(F)cn2Cc2ccc(F)c(F)c2)c1] | 390 | 1.62 | [3] |
| I-1085 | 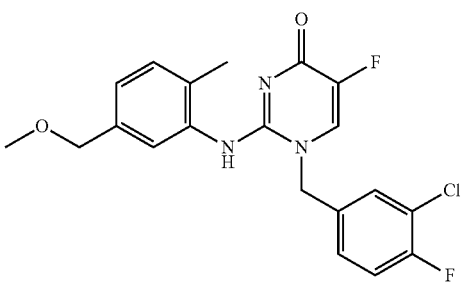 [SMILES: COCc1ccc(C)c(Nc2nc(=O)c(F)cn2Cc2ccc(F)c(Cl)c2)c1] | 406 | 1.75 | [3] |
| I-1086 | 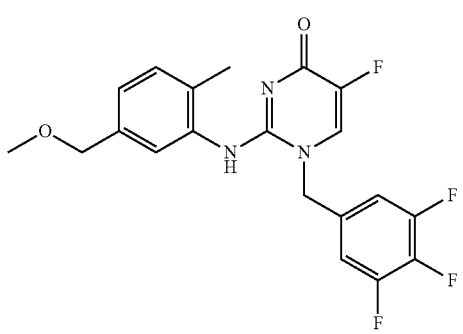 [SMILES: COCc1ccc(C)c(Nc2nc(=O)c(F)cn2Cc2cc(F)c(F)c(F)c2)c1] | 408 | 1.72 | [3] |
| I-1087 | 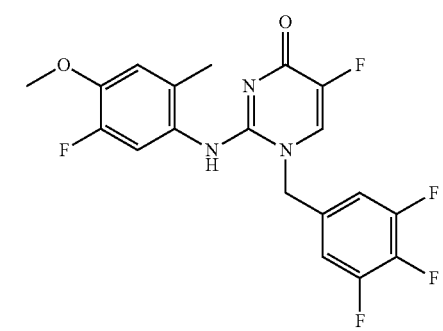 | 412 | 1.78 | [3] |
TABLE 202
| I-1088 | 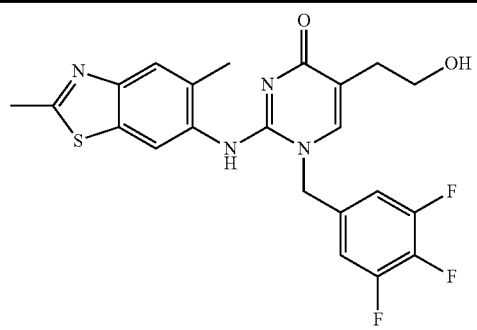 | 461 | 1.77 | [1] |

TABLE 202-continued
| I-1089 | 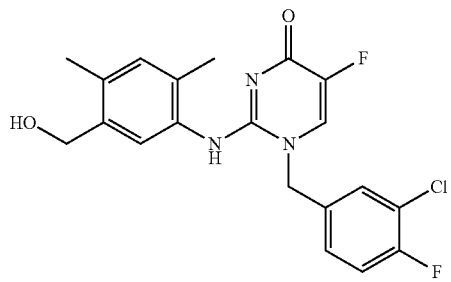 [SMILES: Cc1cc(C)c(Nc2nc(=O)c(F)cn2Cc2ccc(F)c(Cl)c2)cc1CO] | 406 | 1.56 | [1] |
| I-1090 | 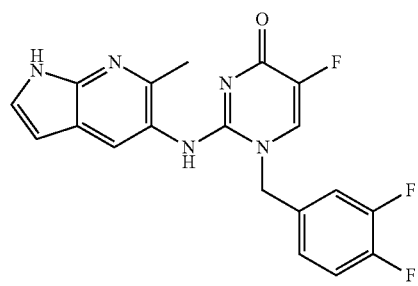 [SMILES: Cc1nc2[nH]ccc2cc1Nc1nc(=O)c(F)cn1Cc1ccc(F)c(F)c1] | 386 | 1.15 | [3] |
| I-1091 | 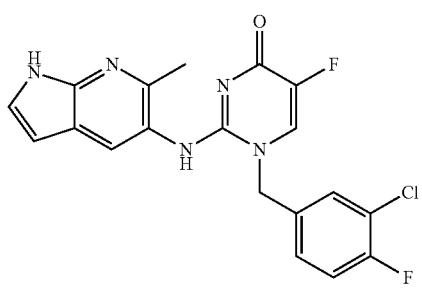 | 402 | 1.3 | [3] |
| I-1092 | 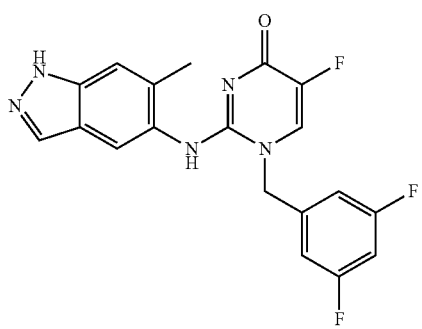 [SMILES: Cc1cc2[nH]ncc2cc1Nc1nc(=O)c(F)cn1Cc1cc(F)cc(F)c1] | 386 | 1.33 | [3] |
| I-1093 | 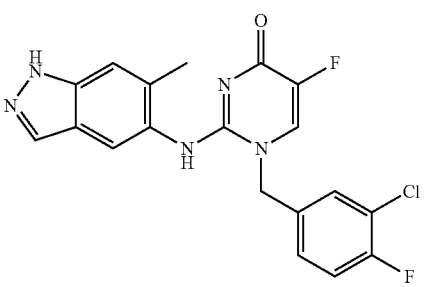 [SMILES: Cc1cc2[nH]ncc2cc1Nc1nc(=O)c(F)cn1Cc1ccc(F)c(Cl)c1] | 402 | 1.12 | [3] |

TABLE 203

| | | | | |
|---|---|---|---|---|
| I-1094 | (structure) | 404 | 1.43 | [3] |
| I-1095 | (structure) | 386 | 1.34 | [3] |
| I-1096 | (structure) | 401 | 1.23 | [3] |
| I-1097 | (structure) | 376 | 158 | [1] |
| I-1098 | (structure) | 360 | 1.89 | [1] |

TABLE 204
| | | | | |
|---|---|---|---|---|
| I-1099 | 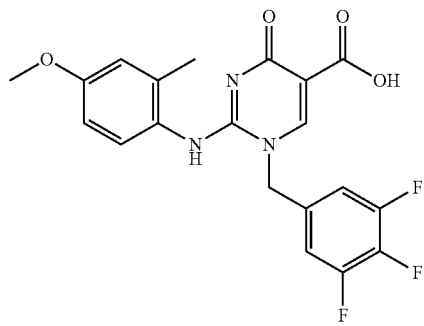 [SMILES: COc1ccc(Nc2nc(=O)c(C(=O)O)cn2Cc2cc(F)c(F)c(F)c2)c(C)c1] | 420 | 1.8 | [1] |
| I-1100 | 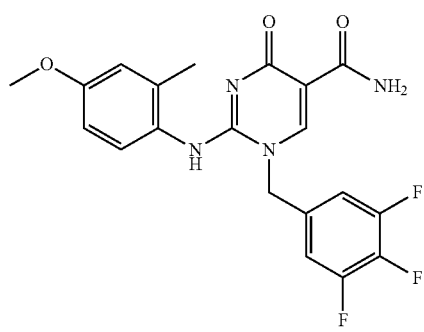 [SMILES: COc1ccc(Nc2nc(=O)c(C(N)=O)cn2Cc2cc(F)c(F)c(F)c2)c(C)c1] | 419 | 1.77 | [1] |
| I-1101 | 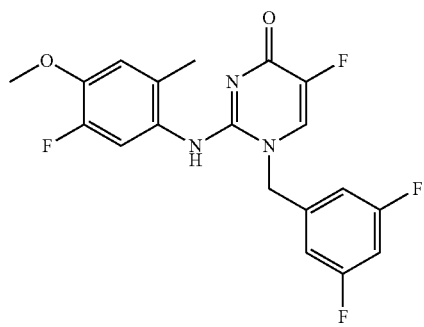 [SMILES: COc1cc(C)c(Nc2nc(=O)c(F)cn2Cc2cc(F)cc(F)c2)cc1F] | 394 | 1.69 | [3] |
| I-1102 | 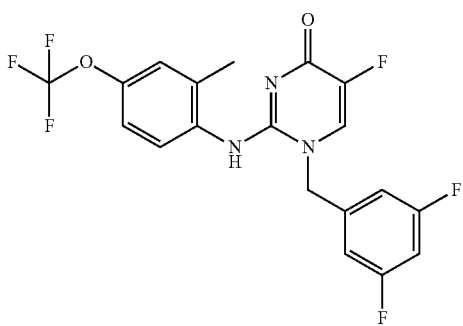 [SMILES: Cc1cc(OC(F)(F)F)ccc1Nc1nc(=O)c(F)cn1Cc1cc(F)cc(F)c1] | 430 | 2.04 | [3] |

TABLE 204-continued
| | | | | |
|---|---|---|---|---|
| I-1103 | 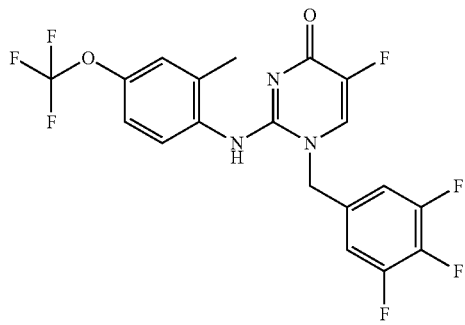 [SMILES: Cc1cc(OC(F)(F)F)ccc1Nc1nc(=O)c(F)cn1Cc1cc(F)c(F)c(F)c1] | 412 | 1.78 | [3] |
TABLE 205
| | | | | |
|---|---|---|---|---|
| I-1104 | 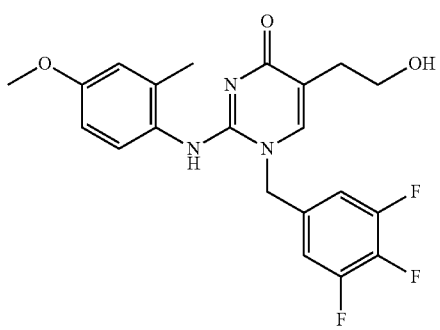 [SMILES: COc1ccc(Nc2nc(=O)c(CCO)cn2Cc2cc(F)c(F)c(F)c2)c(C)c1] | 420 | 1.51 | [1] |
| I-1105 | 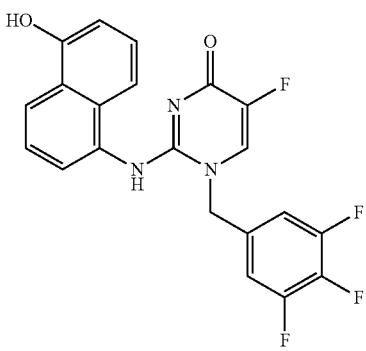 | 416 | 1.64 | [3] |
| I-1106 | 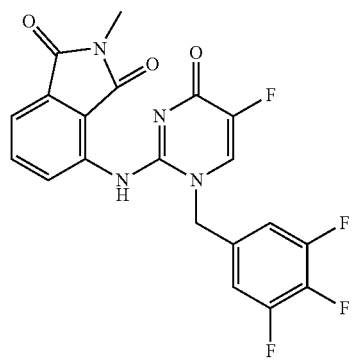 [SMILES: CN1C(=O)c2cccc(Nc3nc(=O)c(F)cn3Cc3cc(F)c(F)c(F)c3)c2C1=O] | 433 | 1.78 | [3] |

TABLE 205-continued
| I-1107 | 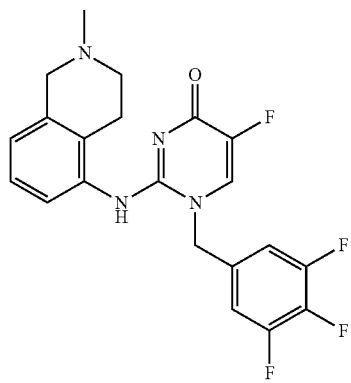 [SMILES: CN1CCc2c(cccc2Nc2nc(=O)c(F)cn2Cc2cc(F)c(F)c(F)c2)C1] | | 419 | 1.11 | [3] |
| I-1108 | 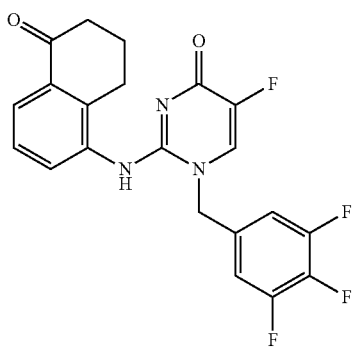 [SMILES: O=C1CCCc2c(Nc3nc(=O)c(F)cn3Cc3cc(F)c(F)c(F)c3)cccc21] | 1H-NMR (DMSO-D6) δ: 1.88 (t, J = 5.9 Hz, 2H), 2.45 (s, 2H), 2.56 (s, 2H), 5.19 (s, 2H), 7.39 (d, J = 7.8 Hz, 4H), 7.82 (s, 1H), 8.05 (s, 1H), 8.75 (s, 1H) | 418 | 1.62 | [3] |
TABLE 206
| I-1109 | 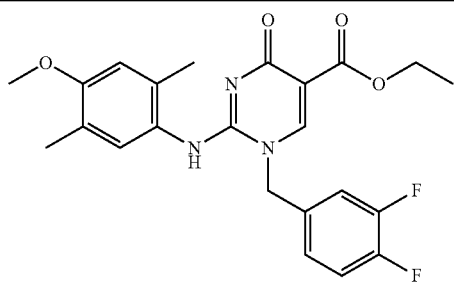 | | 444 | 2.15 | [1] |
| I-1110 | 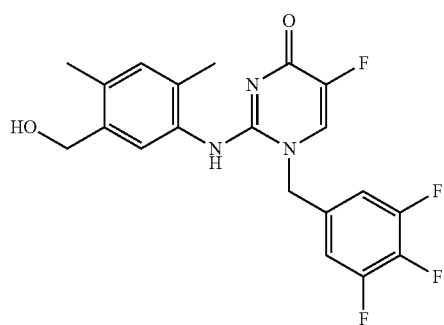 [SMILES: Cc1cc(C)c(Nc2nc(=O)c(F)cn2Cc2cc(F)c(F)c(F)c2)cc1CO] | | 408 | 1.53 | [1] |

TABLE 206-continued
I-1111 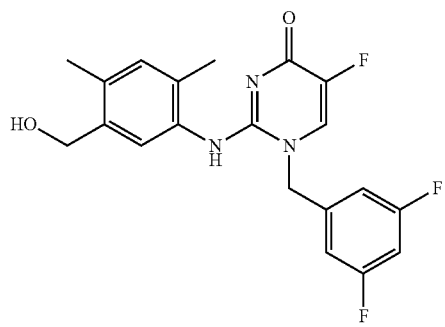 [SMILES: Cc1cc(C)c(Nc2nc(=O)c(F)cn2Cc2cc(F)cc(F)c2)cc1CO] 390 1.46 [1]
I-1112 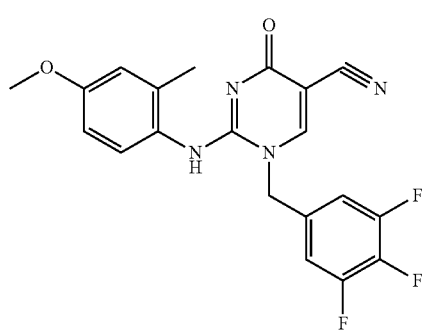 [SMILES: COc1ccc(Nc2nc(=O)c(C#N)cn2Cc2cc(F)c(F)c(F)c2)c(C)c1] 401 1.91 [1]
I-1113 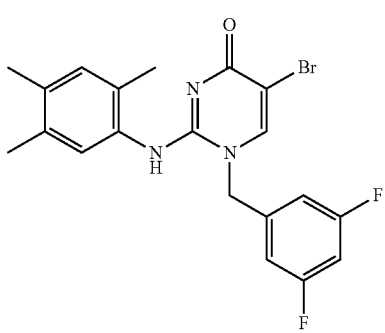 [SMILES: Cc1cc(C)c(Nc2nc(=O)c(Br)cn2Cc2cc(F)cc(F)c2)cc1C] 434 1.99 [1]
TABLE 207
I-1114 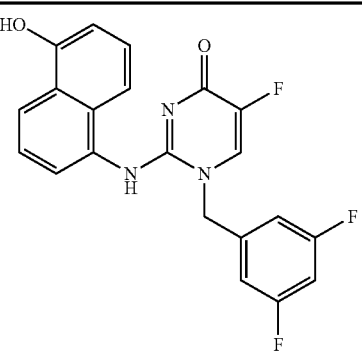 398 1.52 [3]

TABLE 207-continued
| I-1115 | 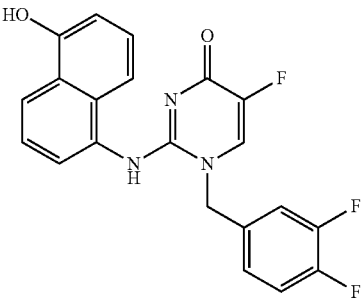 [SMILES: O=c1nc(Nc2cccc3c(O)cccc23)n(Cc2ccc(F)c(F)c2)cc1F] | | 398 | 1.54 | [3] |
| I-1116 | 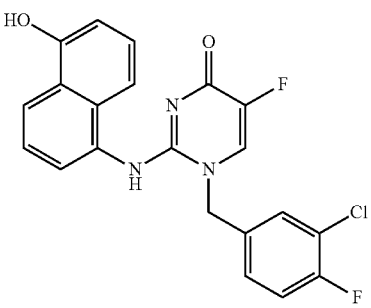 [SMILES: O=c1nc(Nc2cccc3c(O)cccc23)n(Cc2ccc(F)c(Cl)c2)cc1F] | | 414 | 1.64 | [3] |
| I-1117 | 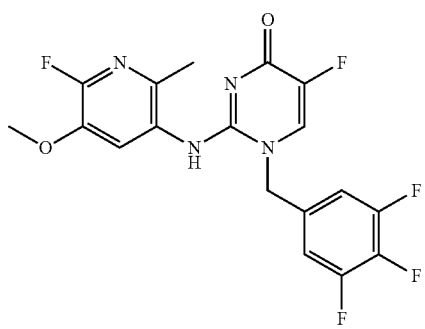 [SMILES: COc1cc(Nc2nc(=O)c(F)cn2Cc2cc(F)c(F)c(F)c2)c(C)nc1F] | | 413 | 1.58 | [2] |
| I-1118 | 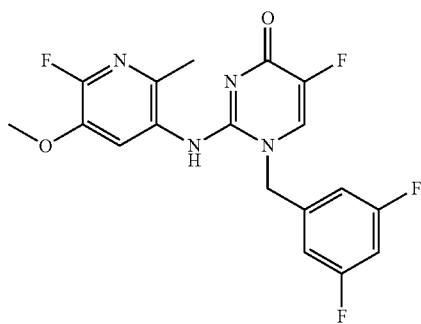 [SMILES: COc1cc(Nc2nc(=O)c(F)cn2Cc2cc(F)cc(F)c2)c(C)nc1F] | 1H-NMR (DMSO-D6): δ 8.82 (10.70) (1H, s), 8.09 (1H, s), 7.45 (7.11) (1H, s), 7.24 (1H, brs), 7.11 (2H, d, J = 5.0 Hz), 5.20 (2H, brs), 3.81 (3H, s), 1.90 (3H, s). | 395 | 1.47 | [2] |

TABLE 208
| | | | | |
|---|---|---|---|---|
| I-1119 | 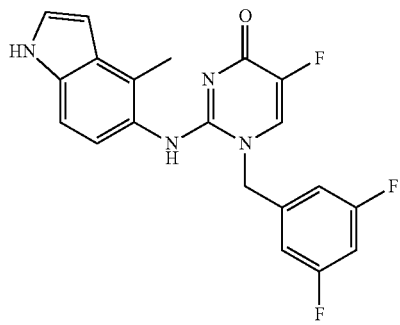 [SMILES: Cc1c(Nc2nc(=O)c(F)cn2Cc2cc(F)cc(F)c2)ccc2[nH]ccc12] | 385 | 1.6 | [2] |
| I-1120 | 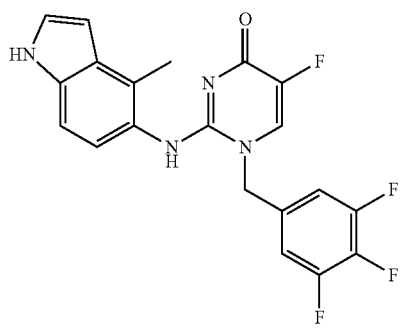 [SMILES: Cc1c(Nc2nc(=O)c(F)cn2Cc2cc(F)c(F)c(F)c2)ccc2[nH]ccc12] | 403 | 1.69 | [2] |
| I-1121 | 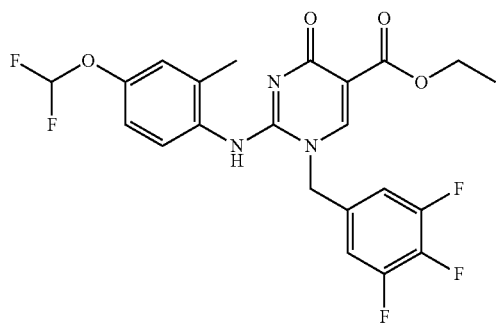 [SMILES: CCOC(=O)c1cn(Cc2cc(F)c(F)c(F)c2)c(Nc2ccc(OC(F)F)cc2C)nc1=O] | 484 | 2.31 | [2] |
| I-1122 | 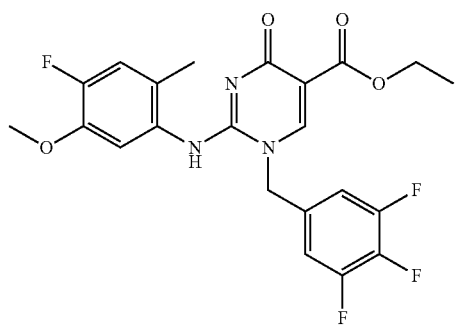 [SMILES: CCOC(=O)c1cn(Cc2cc(F)c(F)c(F)c2)c(Nc2cc(OC)c(F)cc2C)nc1=O] | 465 | 2.25 | [2] |

TABLE 208-continued
| I-1123 | 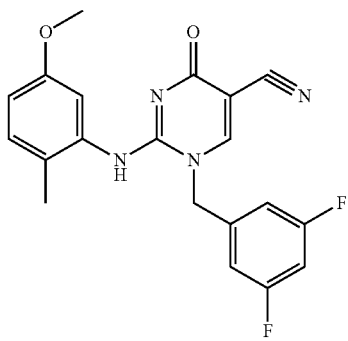 [SMILES: COc1ccc(C)c(Nc2nc(=O)c(C#N)cn2Cc2cc(F)cc(F)c2)c1] | 383 | 2.04 | [3] |
TABLE 209
| I-1124 | 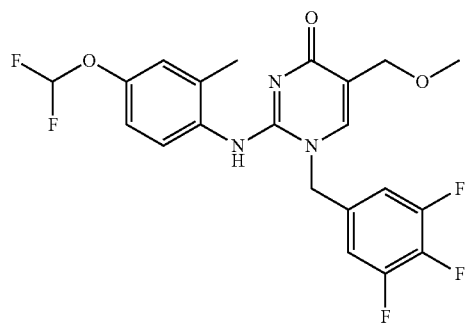 [SMILES: COCc1cn(Cc2cc(F)c(F)c(F)c2)c(Nc2ccc(OC(F)F)cc2C)nc1=O] | 456 | 2.2 | [3] |
| I-1125 | 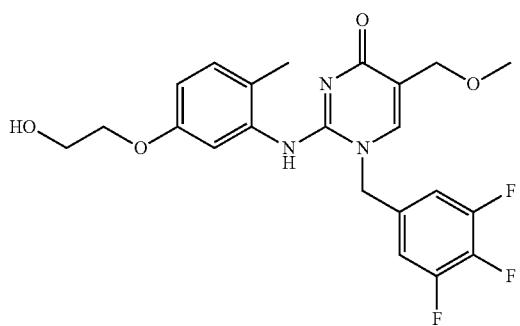 [SMILES: COCc1cn(Cc2cc(F)c(F)c(F)c2)c(Nc2cc(OCCO)ccc2C)nc1=O] | 450 | 1.74 | [3] |
| I-1126 | 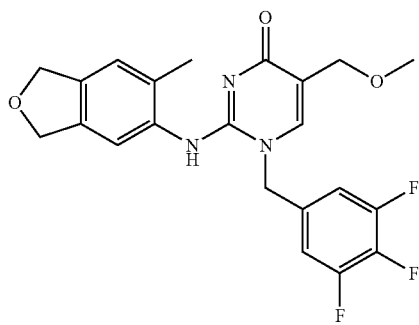 [SMILES: COCc1cn(Cc2cc(F)c(F)c(F)c2)c(Nc2cc3c(cc2C)COC3)nc1=O] | 432 | 1.86 | [3] |

TABLE 209-continued
| I-1127 | 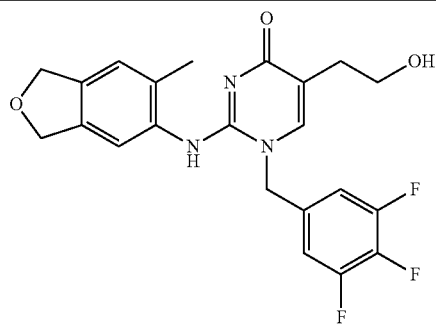 | 432 | 1.57 | [1] |
| I-1128 | 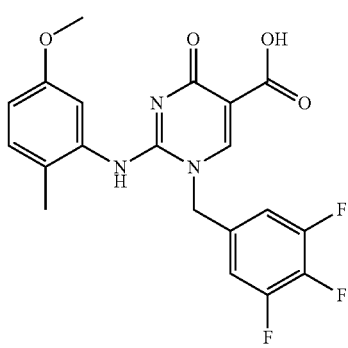 [SMILES: COc1ccc(C)c(Nc2nc(=O)c(C(=O)O)cn2Cc2cc(F)c(F)c(F)c2)c1] | 420 | 2.01 | [3] |
TABLE 210
| I-1129 | 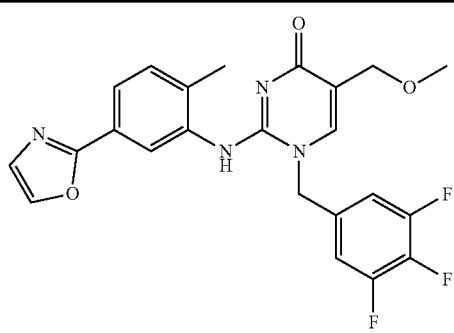 | 457 | 2.06 | [3] |
| I-1130 | 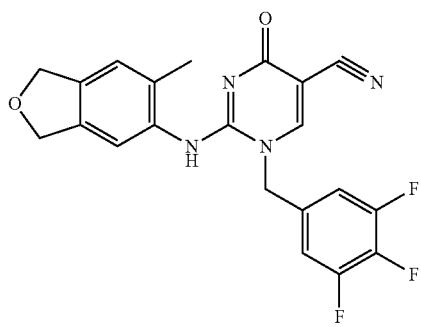 [SMILES: Cc1cc2c(cc1Nc1nc(=O)c(C#N)cn1Cc1cc(F)c(F)c(F)c1)COC2] | 413 | 1.95 | [3] |

TABLE 210-continued
| I-1131 | 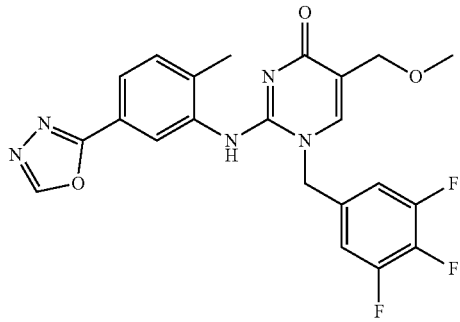 [SMILES: COCc1cn(Cc2cc(F)c(F)c(F)c2)c(Nc2cc(-c3nnco3)ccc2C)nc1=O] | 458 | 1.89 | [3] |
| I-1132 | 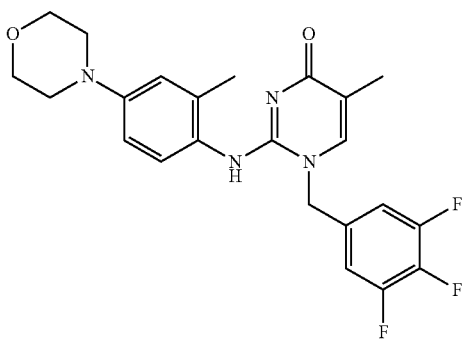 [SMILES: Cc1cc(N2CCOCC2)ccc1Nc1nc(=O)c(C)cn1Cc1cc(F)c(F)c(F)c1] | 445 | 1.6 | [3] |
| I-1133 | 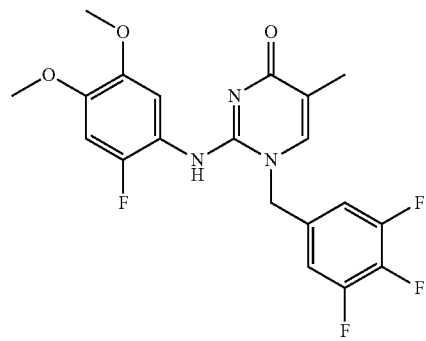 [SMILES: COc1cc(F)c(Nc2nc(=O)c(C)cn2Cc2cc(F)c(F)c(F)c2)cc1OC] | 424 | 1.83 | [1] |
TABLE 211
| I-1134 | 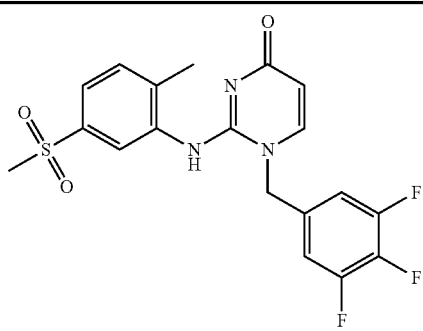 | 424 | 1.75 | [1] |

TABLE 211-continued

| ID | Structure | MS | RT | Method |
|---|---|---|---|---|
| I-1135 | | 416 | 1.58 | [1] |
| I-1136 | | 431 | 1.97 | [1] |
| I-1137 | | 471 | 1.84 | [3] |
| I-1138 | | 420 | 2.07 | [3] |

I-1138: 1H-NMR (DMSO-D6) δ: 1.90 (s, 3H), 3.42 (s, 3H), 3.77 (s, 3H), 4.16 (s, 2H), 4.99 (s, 2H), 6.29 (s, 1H) 6.58 (d, J = 8.4 Hz, 1H), 7.05 (dd, J = 6.8 Hz, 2H), 7.10 (d, J = 8.4 Hz, 1H), 7.26 (s, 1H), 7.58 (s, 1H),

TABLE 212
| I-1139 | 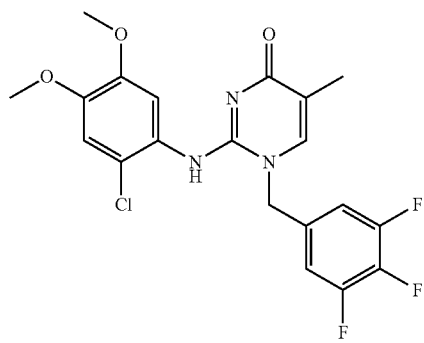 [SMILES: COc1cc(Cl)c(Nc2nc(=O)c(C)cn2Cc2cc(F)c(F)c(F)c2)cc1OC] | 440 | 202 | [1] |
| I-1140 | 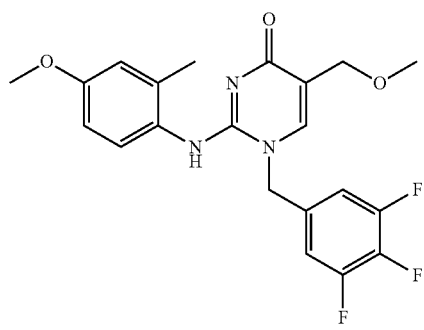 | 420 | 1.83 | [3] |
| I-1141 | 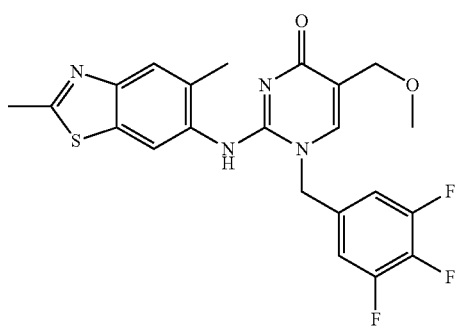 [SMILES: COCc1cn(Cc2cc(F)c(F)c(F)c2)c(Nc2cc3sc(C)nc3cc2C)nc1=O] | 461 | 1.99 | [1] |
| I-1142 | 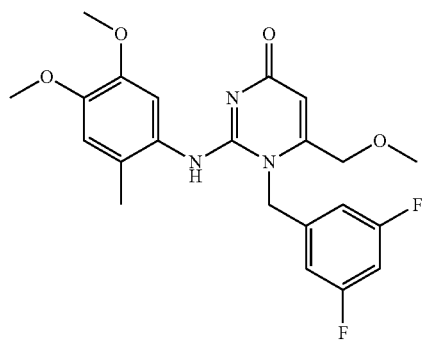 | 432 | 1.73 | [1] |

TABLE 212-continued
| I-1143 | 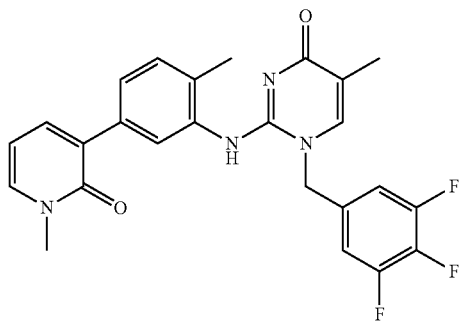 [SMILES: Cc1ccc(-c2cccn(C)c2=O)cc1Nc1nc(=O)c(C)cn1Cc1cc(F)c(F)c(F)c1] | 467 | 1.79 | [3] |
TABLE 213
| I-1144 | 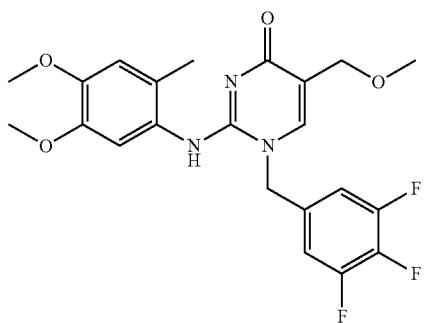 [SMILES: COCc1cn(Cc2cc(F)c(F)c(F)c2)c(Nc2cc(OC)c(OC)cc2C)nc1=O] | 450 | 1.76 | [3] |
| I-1145 | 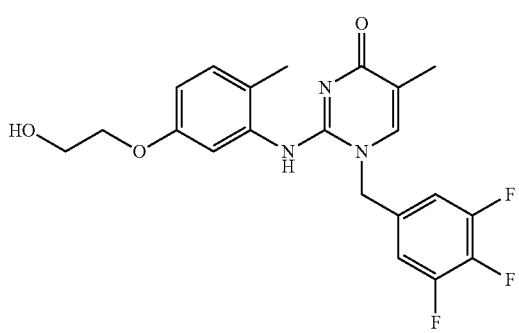 | 420 | 1.66 | [3] |
| I-1146 | 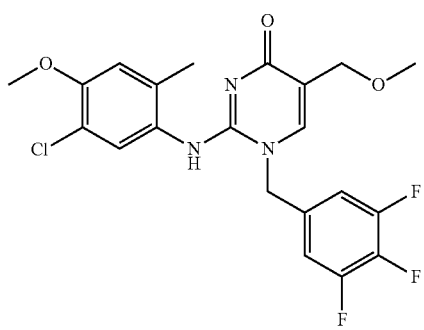 | 454 | 2.15 | [3] |

TABLE 213-continued
| | | | | |
|---|---|---|---|---|
| I-1147 | 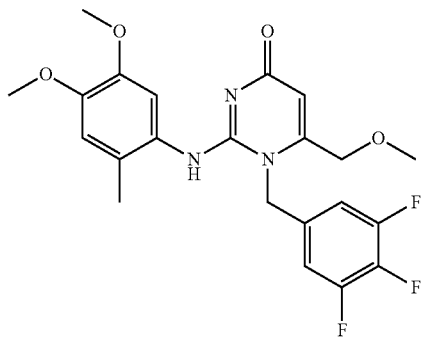 | 450 | 1.84 | [1] |
| I-1148 | 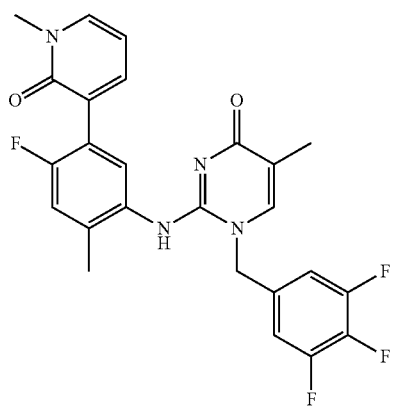 [SMILES: Cc1cc(F)c(-c2cccn(C)c2=O)cc1Nc1nc(=O)c(C)cn1Cc1cc(F)c(F)c(F)c1] | 485 | 1.83 | [3] |
TABLE 214
| | | | | |
|---|---|---|---|---|
| I-1149 | 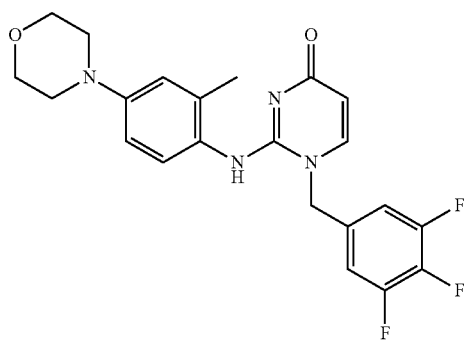 [SMILES: Cc1cc(N2CCOCC2)ccc1Nc1nc(=O)ccn1Cc1cc(F)c(F)c(F)c1] | 431 | 1.58 | [3] |
| I-1150 | 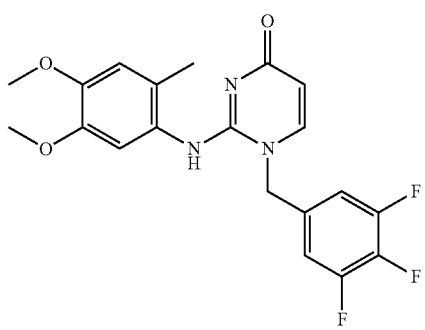 [SMILES: COc1cc(C)c(Nc2nc(=O)ccn2Cc2cc(F)c(F)c(F)c2)cc1OC] | 406 | 1.68 | [3] |

TABLE 214-continued
| I-1151 | 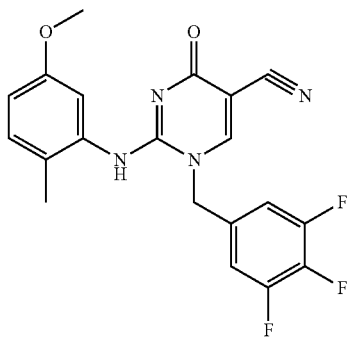 [SMILES: COc1ccc(C)c(Nc2nc(=O)c(C#N)cn2Cc2cc(F)c(F)c(F)c2)c1] | | 401 | 2.15 | [3] |
| I-1152 | 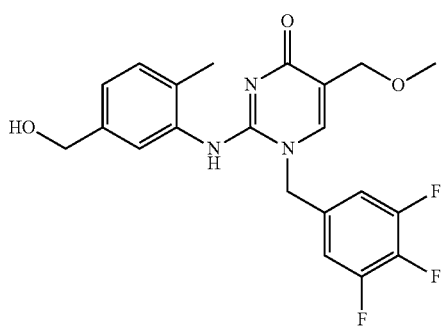 [SMILES: COCc1cn(Cc2cc(F)c(F)c(F)c2)c(Nc2cc(CO)ccc2C)nc1=O] | | 420 | 1.66 | [3] |
| I-1153 | 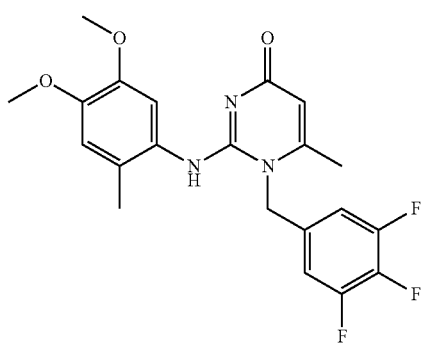 [SMILES: COc1cc(C)c(Nc2nc(=O)cc(C)n2Cc2cc(F)c(F)c(F)c2)cc1OC] | 1H-NMR (CDCl3) δ: 1.91 (s, 3H), 2.20 (s, 3H), 3.81 (s, 3H), 3.85 (s, 3H), 5.24 (br s, 2H), 5.38 (s, 1H), 6.26 (s, 1H), 6.70 (s, 1H), 6.50-6.85 (m, 2H), 7.52 (br s, 1H). | 420 | 1.76 | [1] |
TABLE 215
| I-1154 | 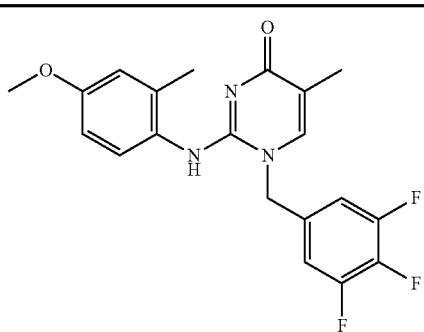 | | 390 | 1.69 | [3] |

TABLE 215-continued

| | | | | |
|---|---|---|---|---|
| I-1155 | | 429 | 1.88 | [3] |
| I-1156 | | 434 | 1.97 | [3] |
| I-1157 | | 448 | 1.77 | [3] |
| I-1158 | | 415 | 1.81 | [1] |

TABLE 216

| | | | | |
|---|---|---|---|---|
| I-1159 | | 404 | 1.66 | [1] |

TABLE 216-continued
| | | | | |
|---|---|---|---|---|
| I-1160 | 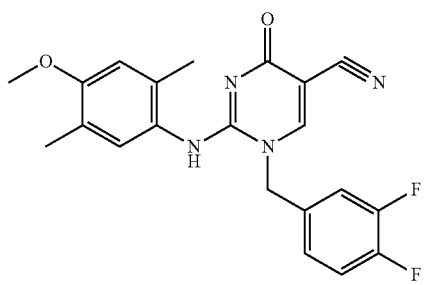 [SMILES: COc1cc(C)c(Nc2nc(=O)c(C#N)cn2Cc2ccc(F)c(F)c2)cc1C] | 397 | 1.97 | [1] |
| I-1161 | 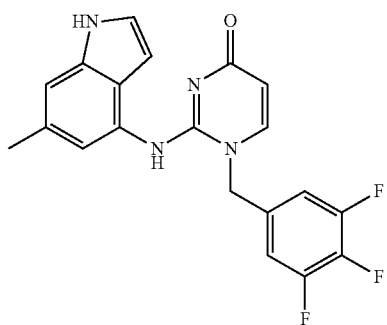 [SMILES: Cc1cc(Nc2nc(=O)ccn2Cc2cc(F)c(F)c(F)c2)c2cc[nH]c2c1] | 385 | 1.76 | [1] |
| I-1162 | 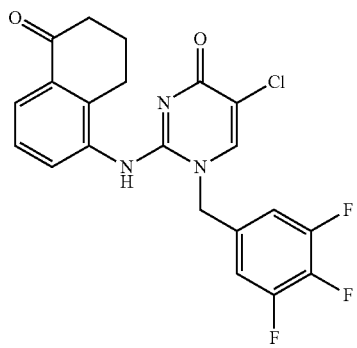 | 434 | 1.83 | [3] |
| I-1163 | 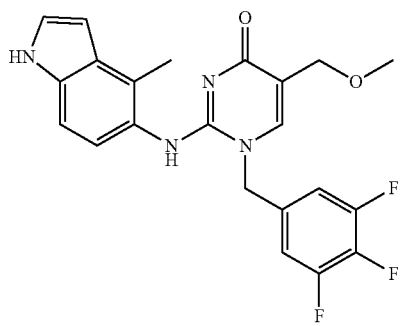 [SMILES: COCc1cn(Cc2cc(F)c(F)c(F)c2)c(Nc2ccc3[nH]ccc3c2C)nc1=O] | 429 | 1.63 | [3] |

TABLE 217

| | | | | |
|---|---|---|---|---|
| I-1164 | | 381 | 1.46 | [1] |
| I-1165 | | 399 | 1.55 | [3] |
| I-1166 | | 404 | 2.09 | [3] |
| I-1167 | | 390 | 1.82 | [1] |
| I-1168 | | 381 | 1.45 | [3] |

TABLE 217-continued
| | | | | |
|---|---|---|---|---|
| I-1169 | 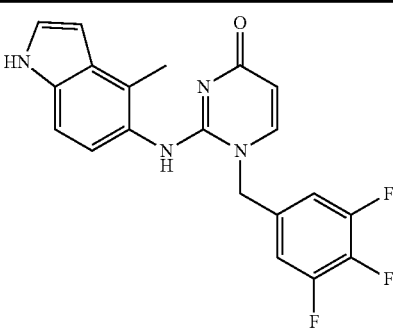 | 385 | 1.49 | [1] |
TABLE 218
| | | | | |
|---|---|---|---|---|
| I-1170 | 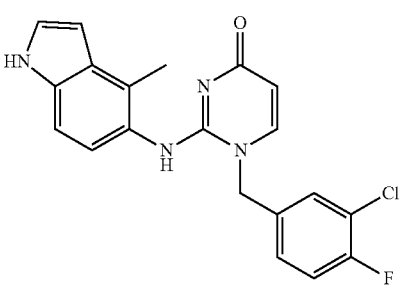 [SMILES: Cc1c(Nc2nc(=O)ccn2Cc2ccc(F)c(Cl)c2)ccc2[nH]ccc12] | 383 | 1.51 | [1] |
| I-1171 | 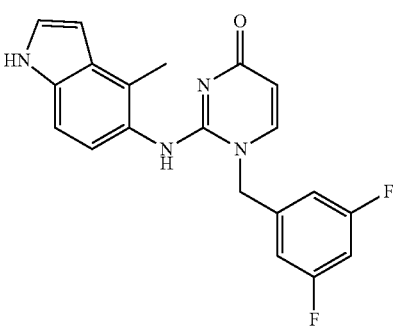 [SMILES: Cc1c(Nc2nc(=O)ccn2Cc2cc(F)cc(F)c2)ccc2[nH]ccc12] | 367 | 1.36 | [1] |
| I-1172 | 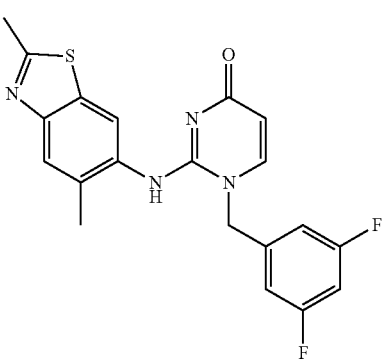 [SMILES: Cc1nc2cc(C)c(Nc3nc(=O)ccn3Cc3cc(F)cc(F)c3)cc2s1] | 399 | 1.79 | [1] |

TABLE 218-continued
| I-1173 | 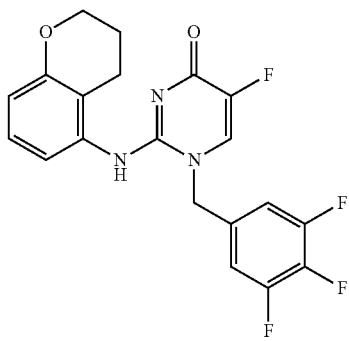 [SMILES: O=c1nc(Nc2cccc3c2CCCO3)n(Cc2cc(F)c(F)c(F)c2)cc1F] | 406 | 1.72 | [3] |
| I-1174 | 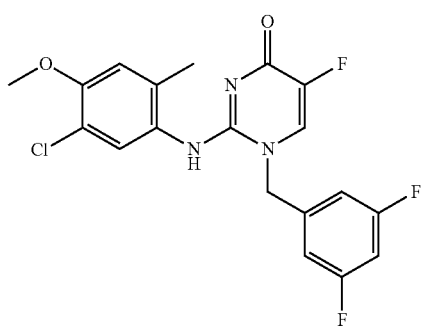 [SMILES: COc1cc(C)c(Nc2nc(=O)c(F)cn2Cc2cc(F)cc(F)c2)cc1Cl] | 410 | 1.77 | [3] |
TABLE 219
| I-1175 | 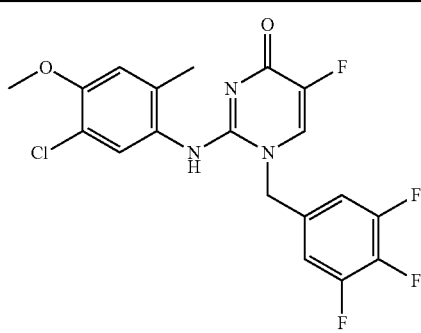 | 428 | 1.87 | [3] |
| I-1176 | 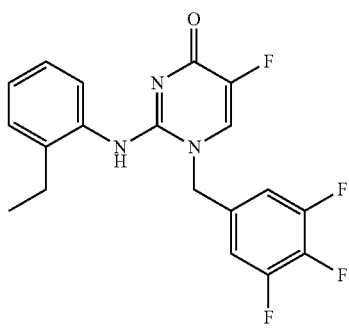 [SMILES: CCc1ccccc1Nc1nc(=O)c(F)cn1Cc1cc(F)c(F)c(F)c1] | 378 | 1.75 | [1] |

TABLE 219-continued
| I-1177 | 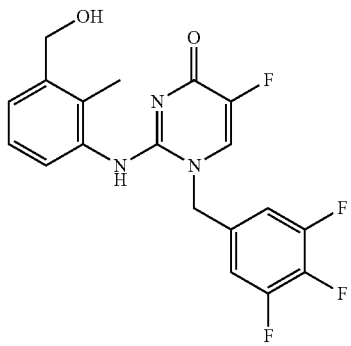 [SMILES: Cc1c(CO)cccc1Nc1nc(=O)c(F)cn1Cc1cc(F)c(F)c(F)c1] | 394 | 1.4 | [3] |
| I-1178 | 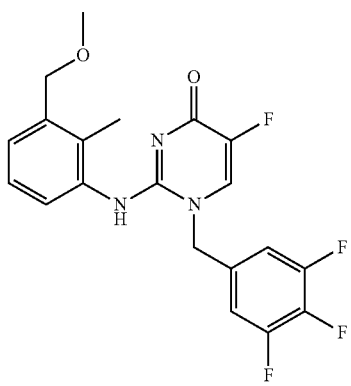 [SMILES: COCc1cccc(Nc2nc(=O)c(F)cn2Cc2cc(F)c(F)c(F)c2)c1C] | 408 | 1.65 | [3] |
| I-1179 | 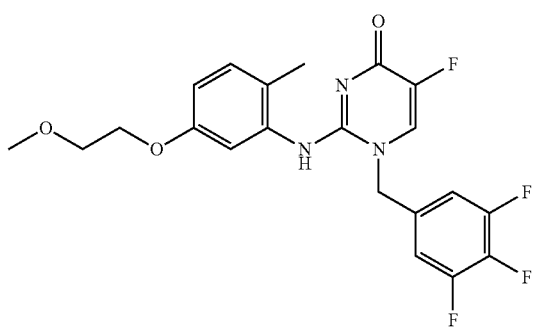 [SMILES: COCCOc1ccc(C)c(Nc2nc(=O)c(F)cn2Cc2cc(F)c(F)c(F)c2)c1] | 438 | 1.76 | [3] |
TABLE 220
| I-1180 | 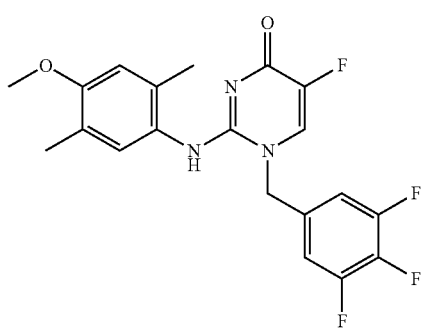 [SMILES: COc1cc(C)c(Nc2nc(=O)c(F)cn2Cc2cc(F)c(F)c(F)c2)cc1C] | 408 | 1.77 | [1] |

TABLE 220-continued
| | | | | |
|---|---|---|---|---|
| I-1181 | 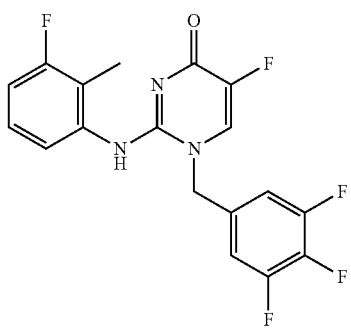 [SMILES: Cc1c(F)cccc1Nc1nc(=O)c(F)cn1Cc1cc(F)c(F)c(F)c1] | 382 | 1.76 | [1] |
| I-1182 | 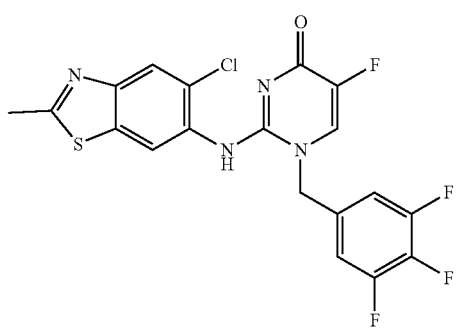 [SMILES: Cc1nc2cc(Cl)c(Nc3nc(=O)c(F)cn3Cc3cc(F)c(F)c(F)c3)cc2s1] | 455 | 1.82 | [1] |
| I-1183 | 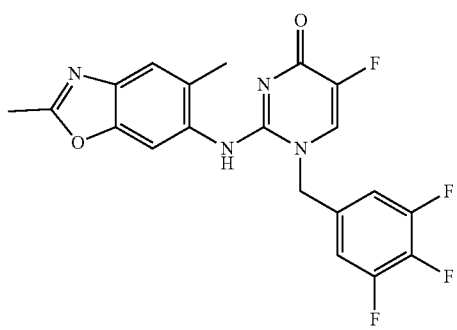 [SMILES: Cc1nc2cc(C)c(Nc3nc(=O)c(F)cn3Cc3cc(F)c(F)c(F)c3)cc2o1] | 419 | 1.57 | [3] |
| I-1184 | 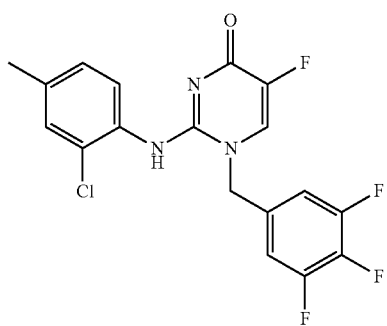 [SMILES: Cc1ccc(Nc2nc(=O)c(F)cn2Cc2cc(F)c(F)c(F)c2)c(Cl)c1] | 398 | 1.88 | [1] |

TABLE 221
| | | | | |
|---|---|---|---|---|
| I-1185 | 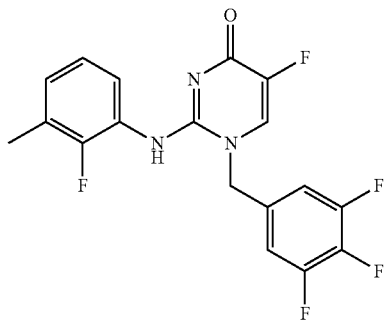 [SMILES: Cc1cccc(Nc2nc(=O)c(F)cn2Cc2cc(F)c(F)c(F)c2)c1F] | 382 | 1.76 | [1] |
| I-1186 | 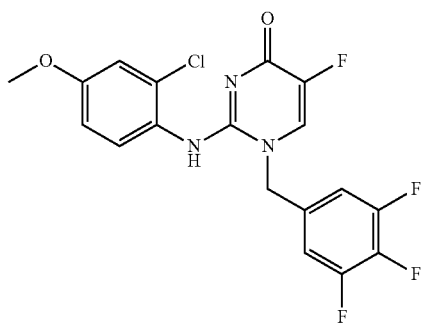 [SMILES: COc1ccc(Nc2nc(=O)c(F)cn2Cc2cc(F)c(F)c(F)c2)c(Cl)c1] | 414 | 1.82 | [3] |
| I-1187 | 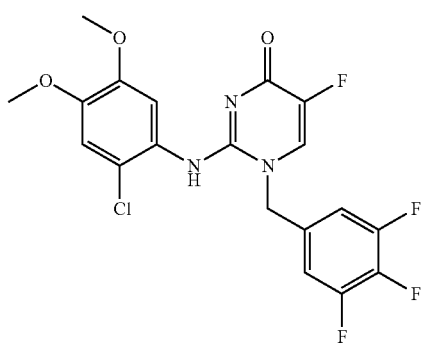 [SMILES: COc1cc(Cl)c(Nc2nc(=O)c(F)cn2Cc2cc(F)c(F)c(F)c2)cc1OC] | 444 | 1.7 | [1] |
| I-1188 | 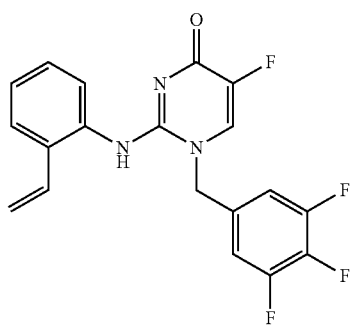 [SMILES: C=Cc1ccccc1Nc1nc(=O)c(F)cn1Cc1cc(F)c(F)c(F)c1] | 376 | 1.75 | [1] |

TABLE 221-continued
| I-1189 | 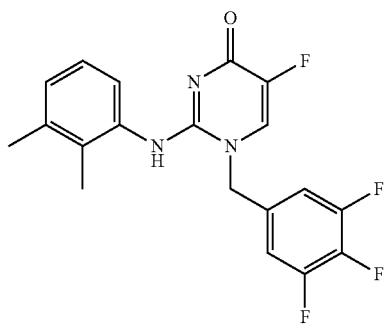 [SMILES: Cc1cccc(Nc2nc(=O)c(F)cn2Cc2cc(F)c(F)c(F)c2)c1C] | 378 | 1.76 | [1] |
TABLE 222
| I-1190 | 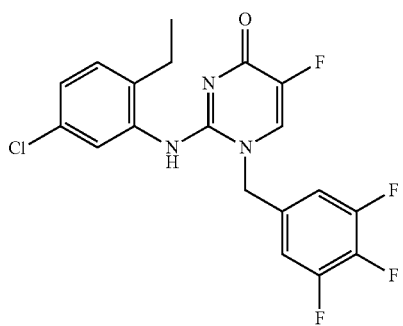 [SMILES: CCc1ccc(Cl)cc1Nc1nc(=O)c(F)cn1Cc1cc(F)c(F)c(F)c1] | 412 | 2.02 | [3] |
| I-1191 | 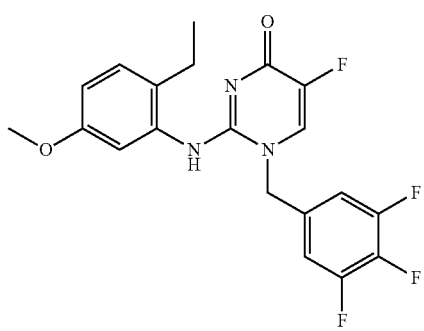 [SMILES: CCc1ccc(OC)cc1Nc1nc(=O)c(F)cn1Cc1cc(F)c(F)c(F)c1] | 408 | 1.88 | [3] |
| I-1192 | 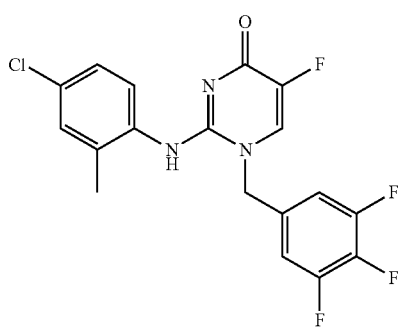 [SMILES: Cc1cc(Cl)ccc1Nc1nc(=O)c(F)cn1Cc1cc(F)c(F)c(F)c1] | 398 | 1.87 | [1] |

TABLE 222-continued
| I-1193 | 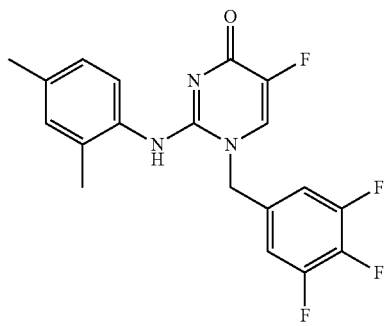 [SMILES: Cc1ccc(Nc2nc(=O)c(F)cn2Cc2cc(F)c(F)c(F)c2)c(C)c1] | 378 | 1.77 | [1] |
| I-1194 | 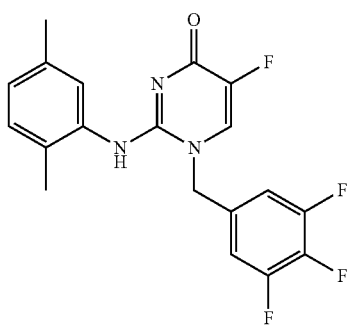 [SMILES: Cc1ccc(C)c(Nc2nc(=O)c(F)cn2Cc2cc(F)c(F)c(F)c2)c1] | 378 | 1.78 | [1] |
TABLE 223
| I-1195 | 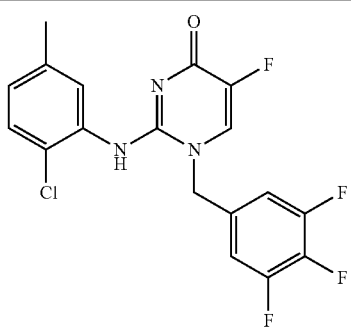 [SMILES: Cc1ccc(Cl)c(Nc2nc(=O)c(F)cn2Cc2cc(F)c(F)c(F)c2)c1] | 393 | 1.91 | [1] |
| I-1196 | 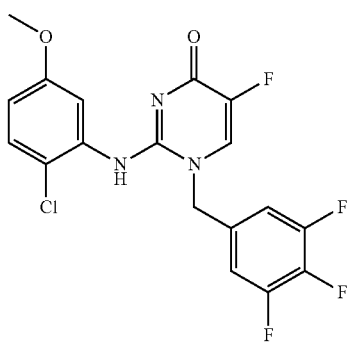 | 414 | 1.88 | [1] |

TABLE 223-continued
| | | | | |
|---|---|---|---|---|
| I-1197 | 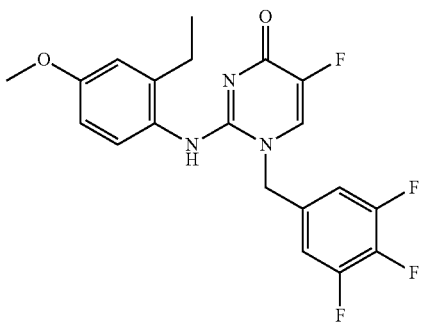 [SMILES: CCc1cc(OC)ccc1Nc1nc(=O)c(F)cn1Cc1cc(F)c(F)c(F)c1] | 408 | 1.8 | [3] |
| I-1198 | 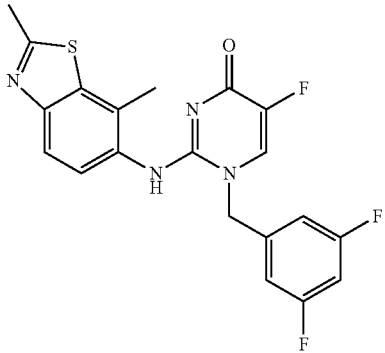 [SMILES: Cc1nc2ccc(Nc3nc(=O)c(F)cn3Cc3cc(F)cc(F)c3)c(C)c2s1] | 417 | 1.57 | [3] |
| I-1199 | 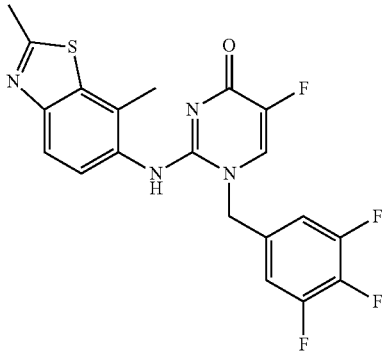 [SMILES: Cc1nc2ccc(Nc3nc(=O)c(F)cn3Cc3cc(F)c(F)c(F)c3)c(C)c2s1] | 435 | 1.71 | [3] |
TABLE 224
| | | | | |
|---|---|---|---|---|
| I-1200 | 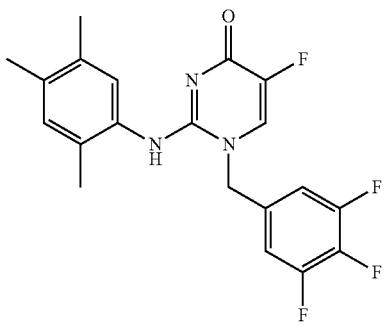 [SMILES: Cc1cc(C)c(Nc2nc(=O)c(F)cn2Cc2cc(F)c(F)c(F)c2)cc1C] | 392 | 1.87 | [1] |

TABLE 224-continued
| | | | | |
|---|---|---|---|---|
| I-1201 | 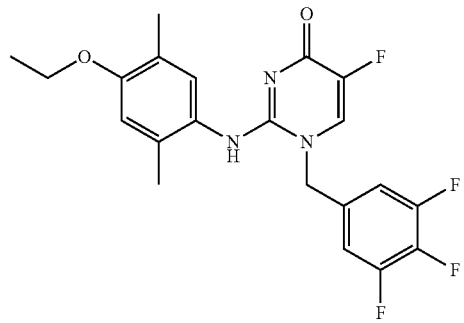 [SMILES: CCOc1cc(C)c(Nc2nc(=O)c(F)cn2Cc2cc(F)c(F)c(F)c2)cc1C] | 422 | 1.92 | [1] |
| I-1202 | 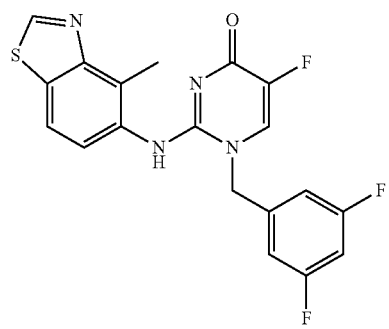 [SMILES: Cc1c(Nc2nc(=O)c(F)cn2Cc2cc(F)cc(F)c2)ccc2scnc12] | 403 | 1.49 | [3] |
| I-1203 | 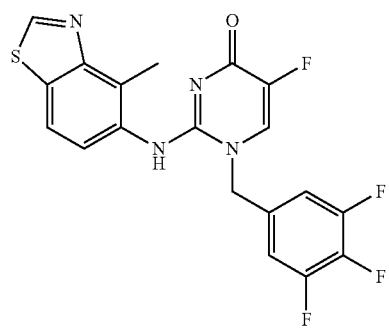 [SMILES: Cc1c(Nc2nc(=O)c(F)cn2Cc2cc(F)c(F)c(F)c2)ccc2scnc12] | 421 | 1.59 | [3] |
| I-1204 | 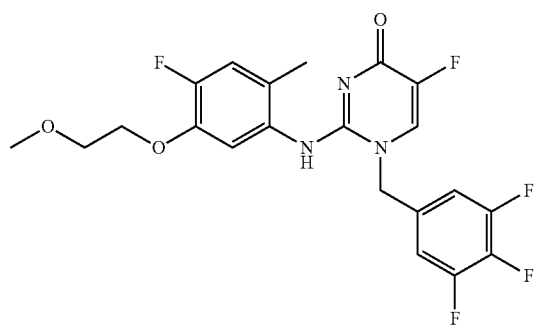 [SMILES: COCCOc1cc(Nc2nc(=O)c(F)cn2Cc2cc(F)c(F)c(F)c2)c(C)cc1F] | 456 | 1.79 | [3] |

TABLE 225
| | | | |
|---|---|---|---|
| I-1205 | 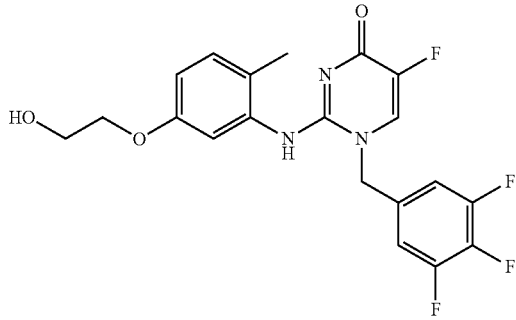 [SMILES: Cc1ccc(OCCO)cc1Nc1nc(=O)c(F)cn1Cc1cc(F)c(F)c(F)c1] | 424 1.53 | [3] |
| I-1206 | 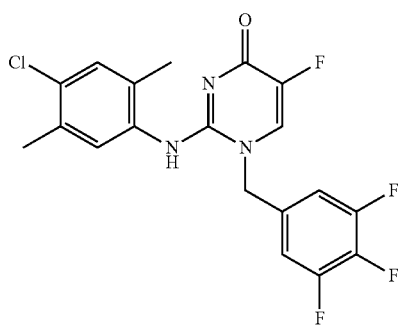 [SMILES: Cc1cc(Nc2nc(=O)c(F)cn2Cc2cc(F)c(F)c(F)c2)c(C)cc1Cl] | 394 1.95 | [3] |
| I-1207 | 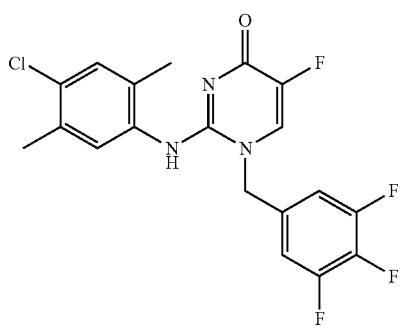 [SMILES: Cc1cc(Nc2nc(=O)c(F)cn2Cc2cc(F)c(F)c(F)c2)c(C)cc1Cl] | 412 2.05 | [3] |
| I-1208 | 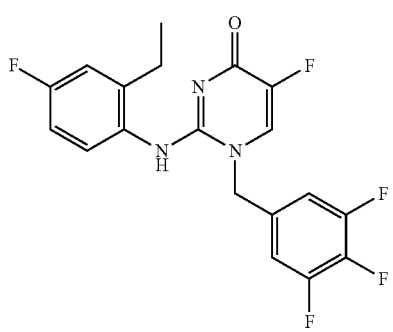 [SMILES: CCc1cc(F)ccc1Nc1nc(=O)c(F)cn1Cc1cc(F)c(F)c(F)c1] | 396 1.86 | [3] |
| I-1209 | 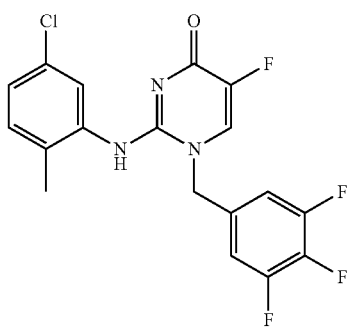 [SMILES: Cc1ccc(Cl)cc1Nc1nc(=O)c(F)cn1Cc1cc(F)c(F)c(F)c1] | 398 1.89 | [1] |

TABLE 226

| | | | |
|---|---|---|---|
| I-1210 | [structure] | 444 1.91 | [1] |
| I-1211 | [structure] | 426 1.89 | [3] |
| I-1212 | [structure] | 456 1.7 | [3] |
| I-1213 | [structure] | 380 1.77 | [1] |
| I-1214 | [structure] | 389 1.7 | [3] |

TABLE 227
| | | | |
|---|---|---|---|
| I-1215 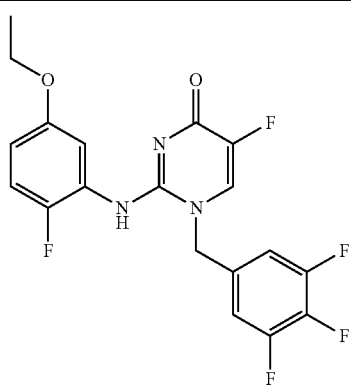 | 412 | 1.84 | [1] |
| I-1216 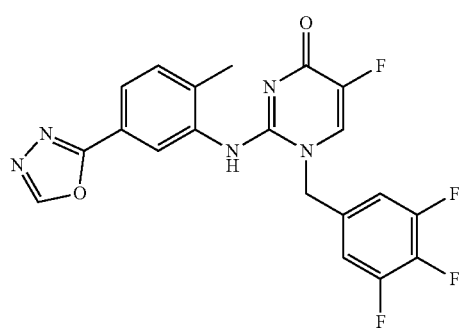 [SMILES: Cc1ccc(-c2nnco2)cc1Nc1nc(=O)c(F)cn1Cc1cc(F)c(F)c(F)c1] | 432 | 1.57 | [3] |
| I-1217 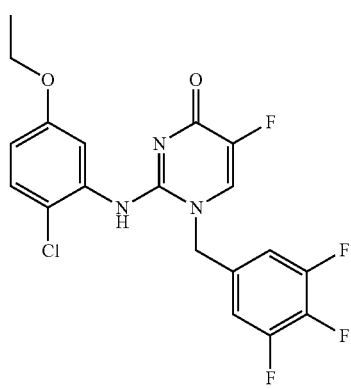 [SMILES: CCOc1ccc(Cl)c(Nc2nc(=O)c(F)cn2Cc2cc(F)c(F)c(F)c2)c1] | 428 | 2.01 | [1] |
| I-1218 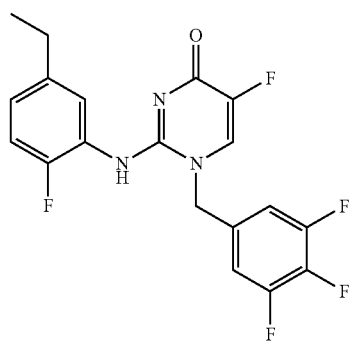 [SMILES: CCc1ccc(F)c(Nc2nc(=O)c(F)cn2Cc2cc(F)c(F)c(F)c2)c1] | 396 | 1.89 | [1] |

TABLE 227-continued
| I-1219 | 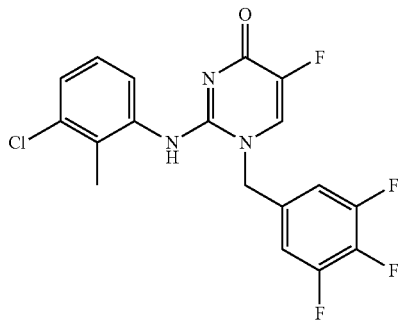 [SMILES: Cc1c(Cl)cccc1Nc1nc(=O)c(F)cn1Cc1cc(F)c(F)c(F)c1] | 398 | 1.89 | [1] |
TABLE 228
| 1-1220 | 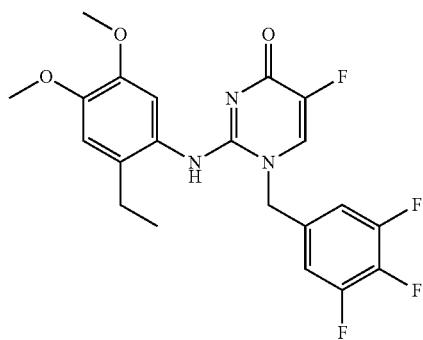 [SMILES: CCc1cc(OC)c(OC)cc1Nc1nc(=O)c(F)cn1Cc1cc(F)c(F)c(F)c1] | 438 | 1.67 | [1] |
| 1-1221 | 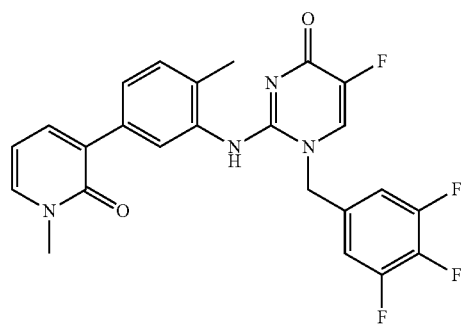 [SMILES: Cc1ccc(-c2cccn(C)c2=O)cc1Nc1nc(=O)c(F)cn1Cc1cc(F)c(F)c(F)c1] | 471 | 1.62 | [3] |
| 1-122.2 | 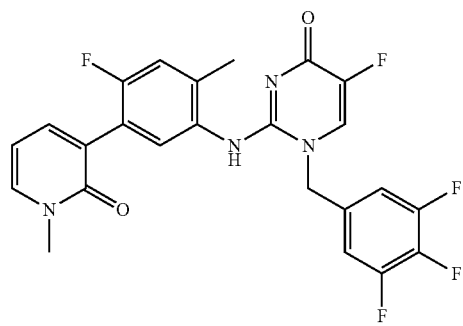 [SMILES: Cc1cc(F)c(-c2cccn(C)c2=O)cc1Nc1nc(=O)c(F)cn1Cc1cc(F)c(F)c(F)c1] | 489 | 1.62 | [3] |

TABLE 228-continued
| | | | | |
|---|---|---|---|---|
| 1-1223 | 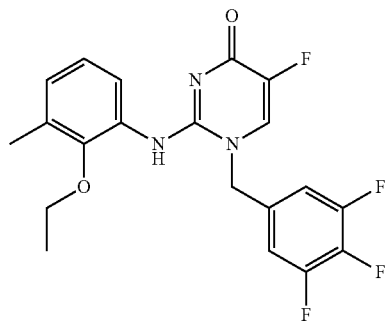 [SMILES: CCOc1c(C)cccc1Nc1nc(=O)c(F)cn1Cc1cc(F)c(F)c(F)c1] | 408 | 1.87 | [1] |
| 1-1224 | 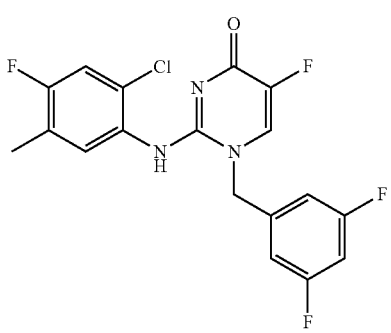 [SMILES: Cc1cc(Nc2nc(=O)c(F)cn2Cc2cc(F)cc(F)c2)c(Cl)cc1F] | 398 | 2.04 | [3] |
TABLE 229
| | | | | |
|---|---|---|---|---|
| I-1225 | 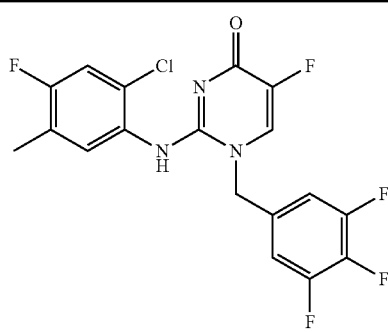 | 416 | 2.12 | [3] |
| I-1226 | 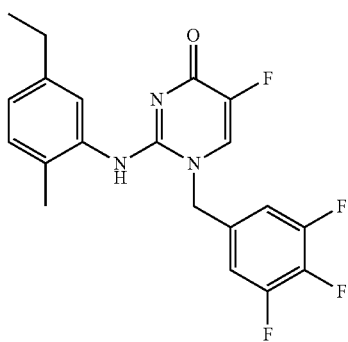 [SMILES: CCc1ccc(C)c(Nc2nc(=O)c(F)cn2Cc2cc(F)c(F)c(F)c2)c1] | 392 | 1.91 | [1] |

TABLE 229-continued
| ID | Structure | | | |
|---|---|---|---|---|
| I-1227 | 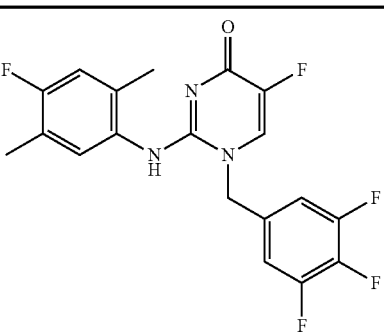 | 396 | 1.86 | [3] |
| I-1228 | 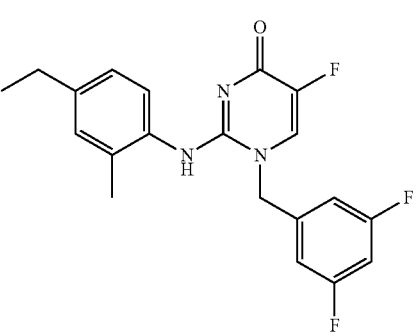 [SMILES: CCc1ccc(Nc2nc(=O)c(F)cn2Cc2cc(F)cc(F)c2)c(C)c1] | 374 | 1.82 | [1] |
| I-1229 | 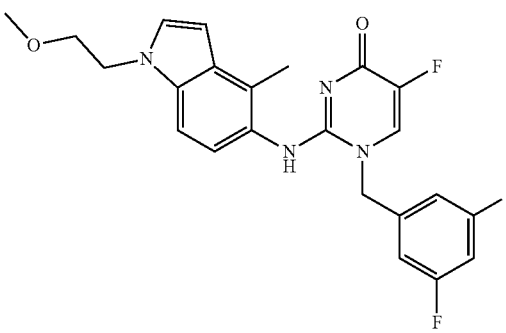 | 443 | 1.67 | [3] |
TABLE 230
| ID | Structure | | | |
|---|---|---|---|---|
| I-1230 | 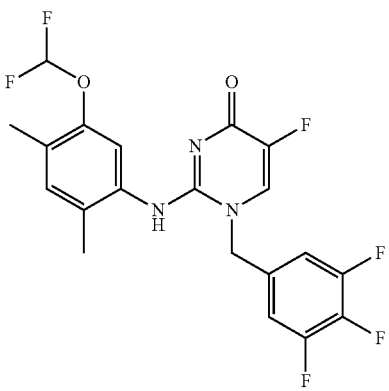 [SMILES: Cc1cc(C)c(OC(F)F)cc1Nc1nc(=O)c(F)cn1Cc1cc(F)c(F)c(F)c1] | 444 | 1.95 | [1] |

TABLE 230-continued
| | | | | | |
|---|---|---|---|---|---|
| I-1231 | 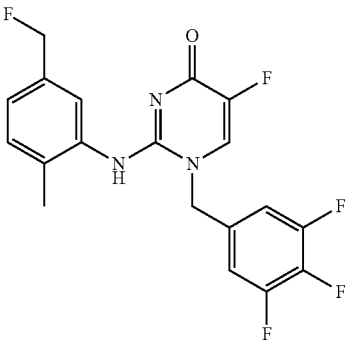 [SMILES: Cc1ccc(CF)cc1Nc1nc(=O)c(F)cn1Cc1cc(F)c(F)c(F)c1] | | 396 | 1.71 | [1] |
| I-1232 | 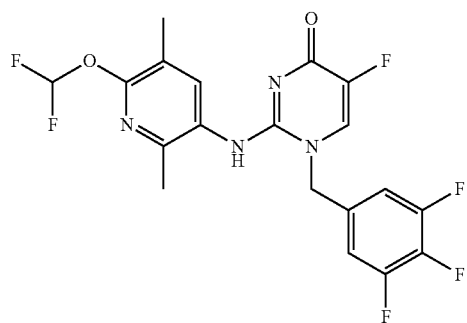 [SMILES: Cc1cc(Nc2nc(=O)c(F)cn2Cc2cc(F)c(F)c(F)c2)c(C)nc1OC(F)F] | 1H-NMR (DMSO-D6) δ: 2.02 (s, 3H), 2.16 (s, 3H), 5.15 (br s, 2H), 7.32-7.41 (m, 2H), 7.50 (m, 1H), 7.65 (m, 1 H), 8.04 (br s, 1H), 8.71 (br s, 1H) | 445 | 1.92 | [1] |
| I-1233 | 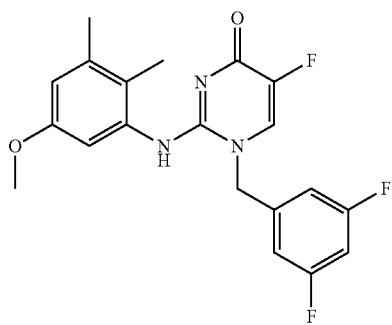 [SMILES: COc1cc(C)c(C)c(Nc2nc(=O)c(F)cn2Cc2cc(F)cc(F)c2)c1] | | 390 | 1.9 | [3] |
| I-1234 | 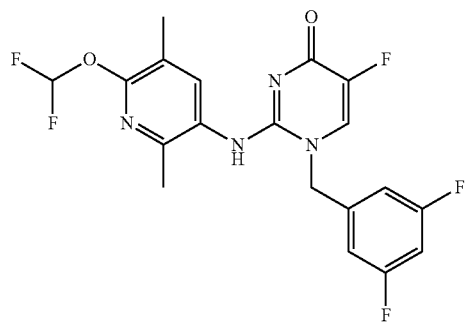 [SMILES: Cc1cc(Nc2nc(=O)c(F)cn2Cc2cc(F)cc(F)c2)c(C)nc1OC(F)F] | | 427 | 1.84 | [1] |

TABLE 231

| | | | | |
|---|---|---|---|---|
| I-1235 | (structure) | 426 | 1.55 | [1] |
| I-1236 | (structure) | 394 | 1.38 | [1] |
| I-1237 | (structure) | 414 | 1.72 | [1] |
| I-1238 | (structure) | 396 | 1.86 | [1] |
| I-1239 | (structure) | 432 | 1.84 | [1] |

TABLE 231-continued
| I-1240 | 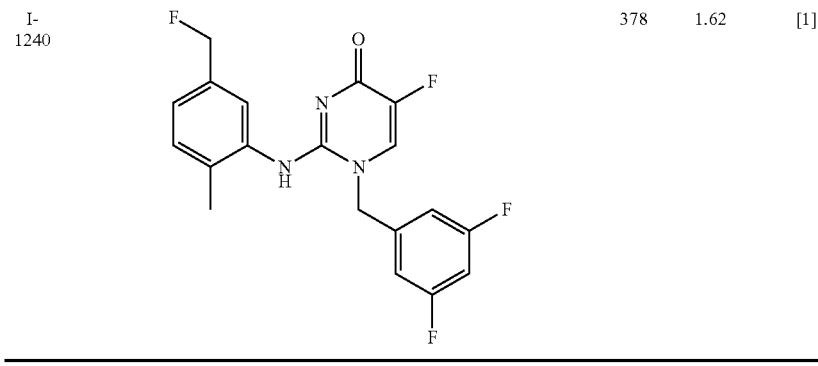 | 378 | 1.62 | [1] |
TABLE 232
| I-1241 | 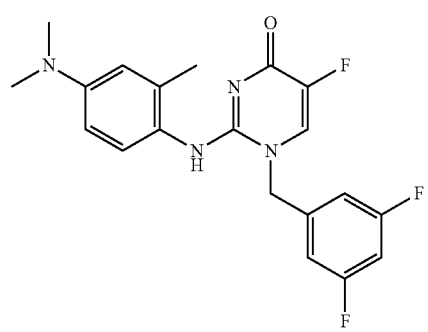 [SMILES: Cc1cc(N(C)C)ccc1Nc1nc(=O)c(F)cn1Cc1cc(F)cc(F)c1] | 389 | 1.19 | [1] |
| I-1242 | 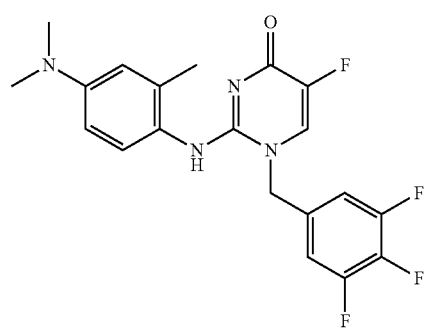 [SMILES: Cc1cc(N(C)C)ccc1Nc1nc(=O)c(F)cn1Cc1cc(F)c(F)c(F)c1] | 407 | 1.28 | [1] |
| I-1243 | 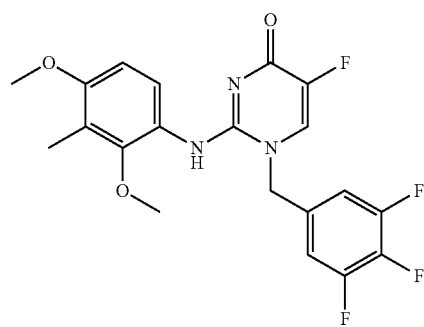 [SMILES: COc1ccc(Nc2nc(=O)c(F)cn2Cc2cc(F)c(F)c(F)c2)c(OC)c1C] | 424 | 1.78 | [1] |

TABLE 232-continued
| I-1244 | 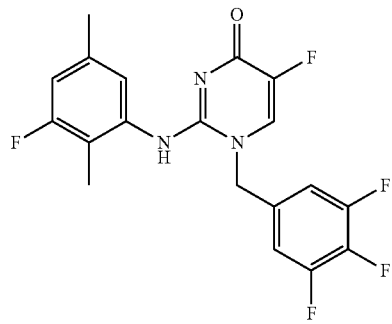 [SMILES: Cc1cc(F)c(C)c(Nc2nc(=O)c(F)cn2Cc2cc(F)c(F)c(F)c2)c1] | 396 | 1.89 | [1] |
| I-1245 | 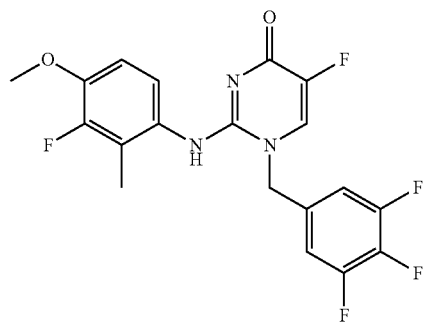 [SMILES: COc1ccc(Nc2nc(=O)c(F)cn2Cc2cc(F)c(F)c(F)c2)c(C)c1F] | 412 | 1.69 | [1] |
| I-1246 | 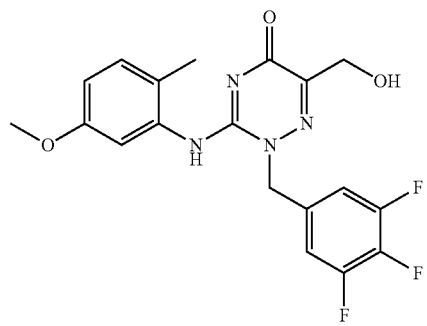 [SMILES: COc1ccc(C)c(Nc2nc(=O)c(CO)nn2Cc2cc(F)c(F)c(F)c2)c1] | 407 | 1.59 | [1] |
TABLE 233
| I-1247 | 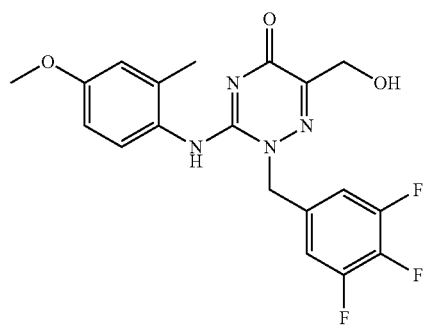 [SMILES: COc1ccc(Nc2nc(=O)c(CO)nn2Cc2cc(F)c(F)c(F)c2)c(C)c1] | 407 | 1.56 | [1] |

TABLE 233-continued
| | | | | | |
|---|---|---|---|---|---|
| I-1248 | 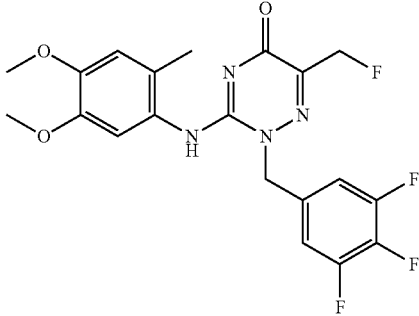 [SMILES: COc1cc(C)c(Nc2nc(=O)c(CF)nn2Cc2cc(F)c(F)c(F)c2)cc1OC] | 1H-NMR (DMSO-D6) δ: 1.92 (s, 3H), 3.82 (s, 3H), 3.86 (s, 3H), 5.21 (d, J = 47.2 Hz, 2H), 5.50 (s, 2H), 6.25 (s, 1H), 6.73 (s, 1H), 7.16 (dd, J = 7.2 Hz, 2H) 7.26 (m, 1H), 7.87 (s, 1H). | 439 | 1.81 | [1] |
| I-1249 | 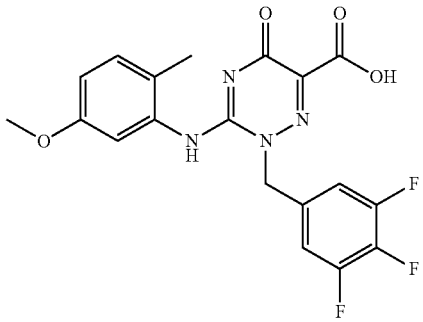 [SMILES: COc1ccc(C)c(Nc2nc(=O)c(C(=O)O)nn2Cc2cc(F)c(F)c(F)c2)c1] | | 421 | 2.03 | [1] |
| I-1250 | 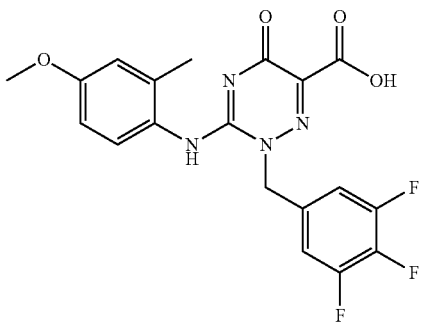 [SMILES: COc1ccc(Nc2nc(=O)c(C(=O)O)nn2Cc2cc(F)c(F)c(F)c2)c(C)c1] | | 421 | 2.01 | [1] |
| I-1251 | 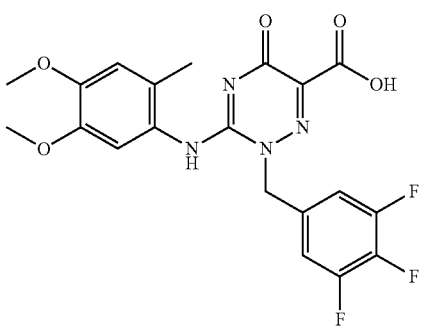 [SMILES: COc1cc(C)c(Nc2nc(=O)c(C(=O)O)nn2Cc2cc(F)c(F)c(F)c2)cc1OC] | 1H-NMR (DMSO-D6) δ: 1.89 (s, 3H), 3.69 (s, 3H), 3.75 (s, 3H), 5.50 (s, 2H), 6.75 (s, 1H), 6.85 (s, 1H), 7.39 (dd, J = 7.6 Hz, 2H), 9.41 (br, 1H), 14.9 (br, 1H). | 451 | 1.74 | [1] |

TABLE 234

| | | | | | |
|---|---|---|---|---|---|
| I-1252 | [structure] | 1H-NMR (DMSO-D6) δ: 1.24 (t, J = 7.2 Hz, 3H), 1.98 (s, 3H), 3.69 (s, 3H), 3.74 (s, 3H), 4.26 (q, J = 6.8, 14.0 Hz, 2H), 5.37 (s, 2H), 6.76 (s, 1H), 6.83 (s, 1H), 7.36 (dd, J = 6.8 Hz, 2H), 9.05 (s, 1H). | 479 | 1.89 | [1] |
| I-1253 | [structure] | | 395 | 1.64 | [1] |
| I-1254 | [structure] | | 391 | 1.72 | [1] |
| I-1255 | [structure] | | 377 | 1.62 | [1] |
| I-1256 | [structure] | 1H-NMR (DMSO-D6) δ: 1.88 (s, 3H), 3.69 (s, 3H), 3.75 (s, 3H), 4.03 (d, J = 6.4 Hz, 2H), 4.98 (t, J = 6.0 Hz, 1H), 5.33 (s, 2H), 6.73 (s, 1H), 6.82 (s, 1H), 7.34 (dd, J = 7.2 Hz, 2H), 8.74 (s, 1H). | 437 | 1.5 | [1] |

TABLE 235
| | | | | |
|---|---|---|---|---|
| I-1257 | 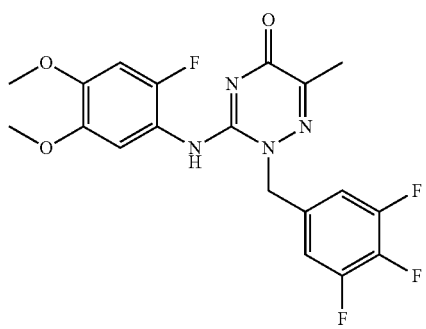 [SMILES: COc1cc(F)c(Nc2nc(=O)c(C)nn2Cc2cc(F)c(F)c(F)c2)cc1OC] | 424 | 1.86 | [1] |
| I-1258 | 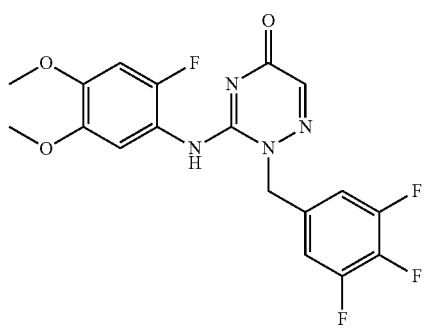 [SMILES: COc1cc(F)c(Nc2nc(=O)cnn2Cc2cc(F)c(F)c(F)c2)cc1OC] | 411 | 1.76 | [1] |
| I-1259 | 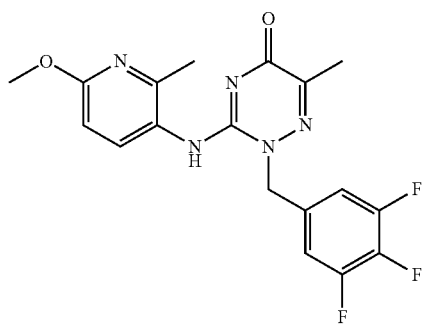 [SMILES: COc1ccc(Nc2nc(=O)c(C)nn2Cc2cc(F)c(F)c(F)c2)c(C)n1] | 392 | 1.88 | [3] |
| I-1260 | 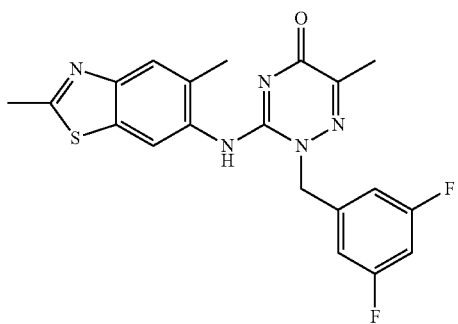 [SMILES: Cc1nc2cc(C)c(Nc3nc(=O)c(C)nn3Cc3cc(F)cc(F)c3)cc2s1] | 414 | 1.88 | [3] |

TABLE 235-continued
| | | | | | |
|---|---|---|---|---|---|
| I-1261 | 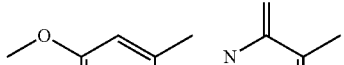 | 1H-NMR (DMSO-D6) δ: 1.87 (s, 3H), 2.05 (s, 3H), 3.69 (s, 3H), 3.74 (s, 3H), 5.33 (s, 2H), 6.70 (s, 1H), 6.81 (s, 1H), 7.04 (d, J = 6.4 Hz, 2H), 7.23 (t, J = 8,8 Hz, 1H), 8.68 (s, 1H). | 403 | 1.86 | [3] |
TABLE 236
| | | | | | |
|---|---|---|---|---|---|
| I-1262 | | | 400 | 2.01 | [3] |
| I-1263 | | | 386 | 1.78 | [3] |
| I-1264 | 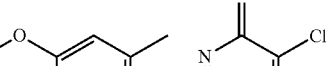 | 1H-NMR (DMSO-D6) δ: 1.92 (s, 3H), 3.68 (s, 3H), 3.74 (s, 3H), 5.31 (s, 2H), 6.74 (s, 1H), 6.81 (s, 1H), 7.36 (dd, J = 7.2 Hz, 2H), 9.05 (br, 1H). | 441 | 2.02 | [3] |

TABLE 236-continued

| I-1265 | [structure] | 411 | 2.04 | [3] |
| I-1266 | [structure] | 421 | 1.82 | [3] |

TABLE 237

| I-1267 | [structure] | 432 | 1.9 | [3] |
| I-1268 | [structure] | 375 | 1.85 | [3] |

TABLE 237-continued
| | | | | | |
|---|---|---|---|---|---|
| I-1269 | 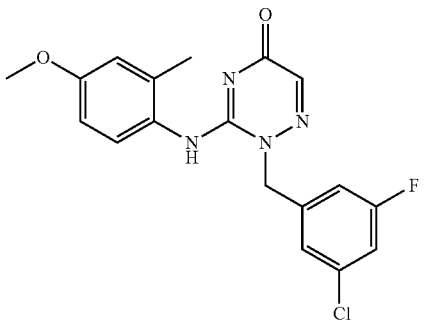 | 375 | 1.89 | [3] | |
| I-1270 | 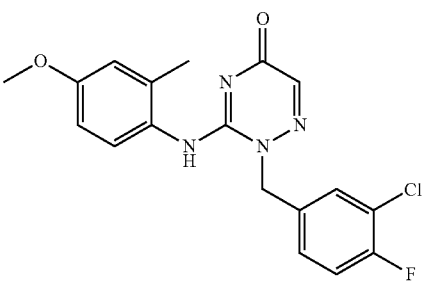 [SMILES: COc1ccc(Nc2nc(=O)cnn2Cc2ccc(F)c(Cl)c2)c(C)c1] | 375 | 1.83 | [2] | |
| I-1271 | 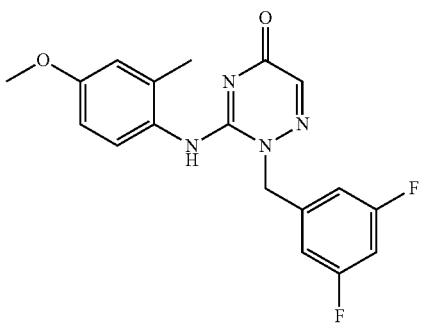 [SMILES: COc1ccc(Nc2nc(=O)cnn2Cc2cc(F)cc(F)c2)c(C)c1] | 360 | 1.7 | [3] | |
| I-1272 | 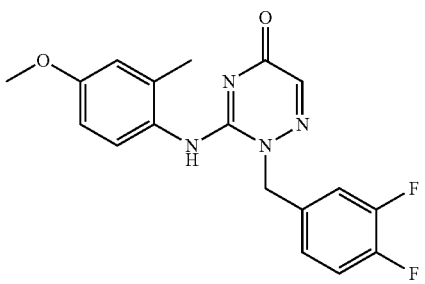 [SMILES: COc1ccc(Nc2nc(=O)cnn2Cc2ccc(F)c(F)c2)c(C)c1] | 360 | 1.71 | [3] | |
TABLE 238
| | | | | | |
|---|---|---|---|---|---|
| I-1273 | 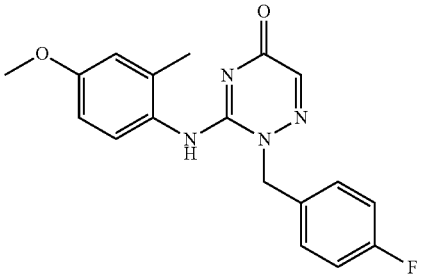 [SMILES: COc1ccc(Nc2nc(=O)cnn2Cc2ccc(F)cc2)c(C)c1] | 341 | 1.64 | [2] | |

TABLE 238-continued
| | | | | |
|---|---|---|---|---|
| I-1274 | 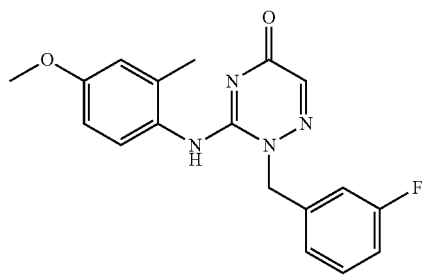 [SMILES: COc1ccc(Nc2nc(=O)cnn2Cc2cccc(F)c2)c(C)c1] | 341 | 1.64 | [3] |
| I-1275 | 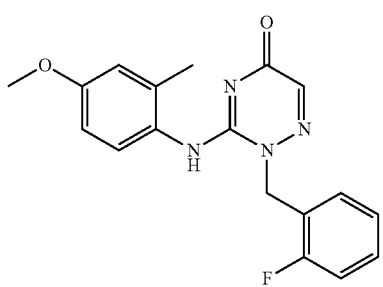 [SMILES: COc1ccc(Nc2nc(=O)cnn2Cc2ccccc2F)c(C)c1] | 341 | 1.62 | [3] |
| I-1276 | 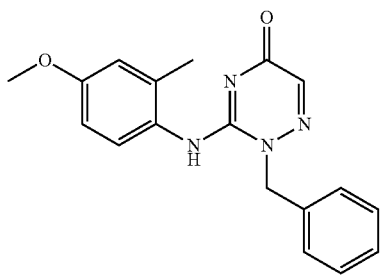 [SMILES: COc1ccc(Nc2nc(=O)cnn2Cc2ccccc2)c(C)c1] | 323 | 1.6 | [2] |
| I-1277 | 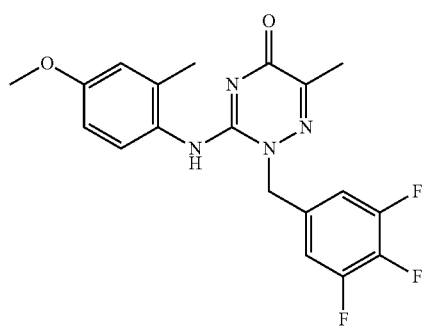 [SMILES: COc1ccc(Nc2nc(=O)c(C)nn2Cc2cc(F)c(F)c(F)c2)c(C)c1] | 391 | 1.94 | [3] |
| I-1278 | 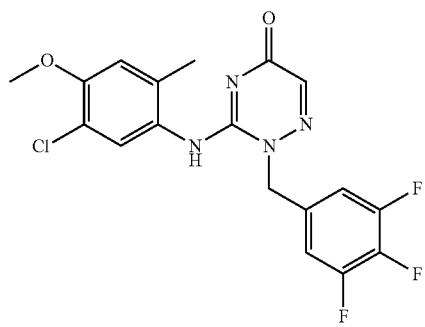 [SMILES: COc1cc(C)c(Nc2nc(=O)cnn2Cc2cc(F)c(F)c(F)c2)cc1Cl] | 411 | 1.95 | [3] |

TABLE 239
| I-1279 | 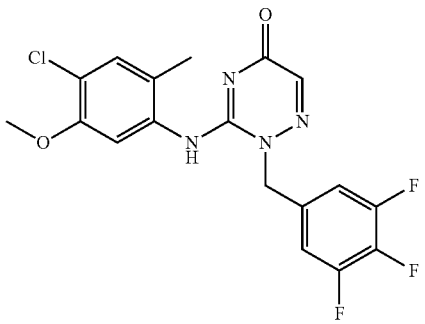 [SMILES: COc1cc(Nc2nc(=O)cnn2Cc2cc(F)c(F)c(F)c2)c(C)cc1Cl] | | 411 | 1.85 | [3] |
|---|---|---|---|---|---|
| I-1280 | 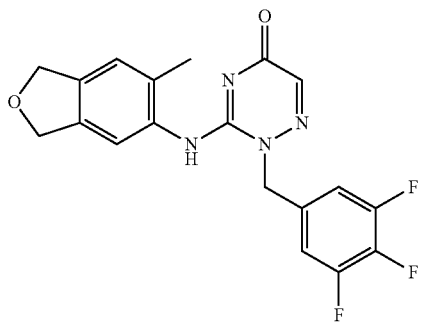 [SMILES: Cc1cc2c(cc1Nc1nc(=O)cnn1Cc1cc(F)c(F)c(F)c1)COC2] | | 389 | 1.67 | [1] |
| I-1281 | 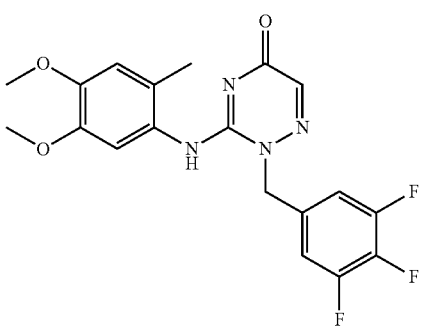 [SMILES: COc1cc(C)c(Nc2nc(=O)cnn2Cc2cc(F)c(F)c(F)c2)cc1OC] | 1H-NMR (DMSO-D6) δ: 1.90 (s, 3H), 3.70 (s, 3H), 3.75 (s, 3H), 5.33 (s, 2H), 6.75 (s, 1H), 6.83 (s, 1H), 7.33 (dd, J = 8.0 Hz, 2H), 7.40 (s, 1H), 8.83 (s, 1H). | 407 | 1.64 | [1] |
| I-1282 | 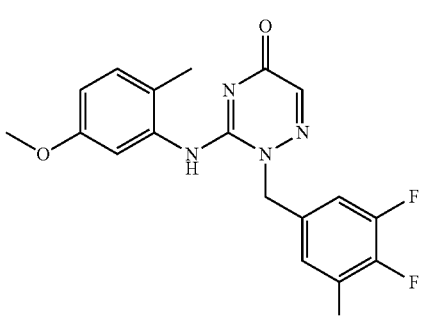 | | 377 | 1.77 | [3] |
| I-1283 | 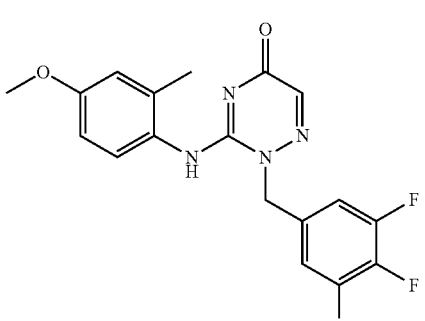 | | 377 | 1.75 | [1] |

TABLE 239-continued
| | | | | |
|---|---|---|---|---|
| I-1284 | 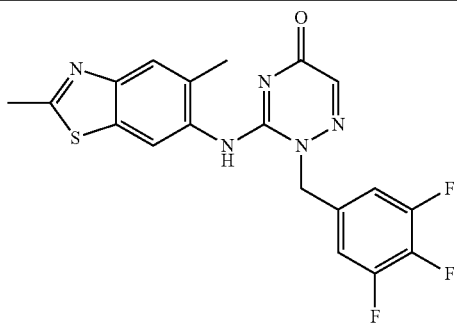 | | 418 | 1.71 [1] |
TABLE 240
| | | | | |
|---|---|---|---|---|
| I-1285 | 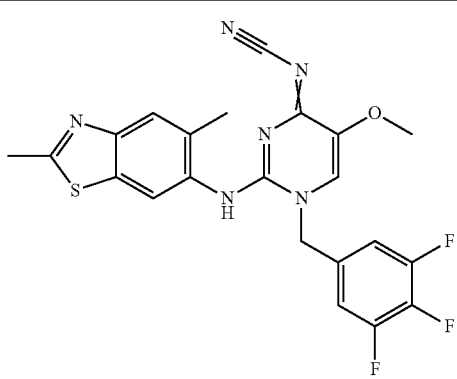 | | 471 | 1.77 [1] |
| I-1286 | 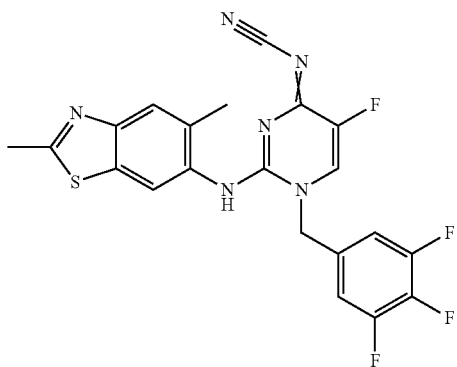 [SMILES: Cc1nc2cc(C)c(Nc3nc(=NC#N)c(F)cn3Cc3cc(F)c(F)c(F)c3)cc2s1] | 1H-NMR (DMSO-D6) δ: 2.06 (s, 3H), 2.77 (S, 3H), 5.26 (s, 3H), 7.41 (m, 2H), 7.75 (s, 1H), 7.91 (s, 1H), 8.19 (s, 1H), 9.16 (s, 1H). | 459 | 1.86 [1] |
| I-1287 | 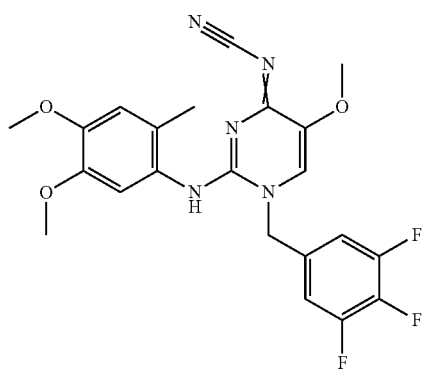 [SMILES: COc1cc(C)c(Nc2nc(=NC#N)c(OC)cn2Cc2cc(F)c(F)c(F)c2)cc1OC] | | 460 | 1.79 [1] |

TABLE 240-continued
| I-1288 | 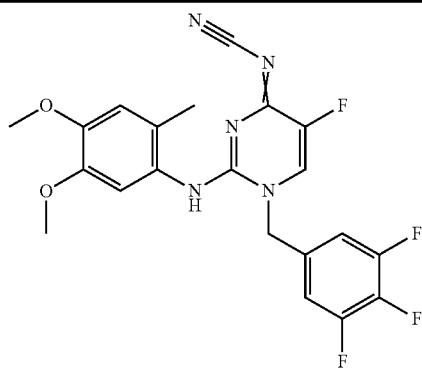 | 448 | 1.87 | [1] |
| --- | --- | --- | --- | --- |
| I-1289 | 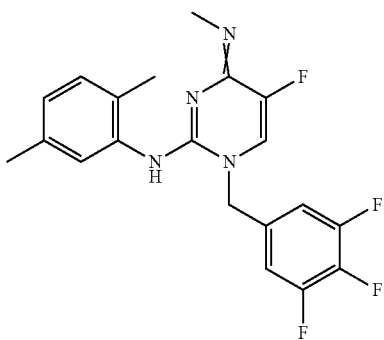 [SMILES: CN=c1nc(Nc2cc(C)ccc2C)n(Cc2cc(F)c(F)c(F)c2)cc1F] | 391 | 1.76 | [3] |
TABLE 241
| I-1290 | 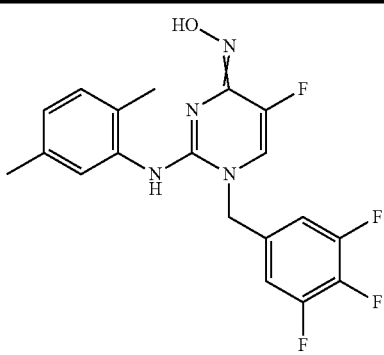 | 393 | 1.64 | [3] |
| --- | --- | --- | --- | --- |
| I-1291 | 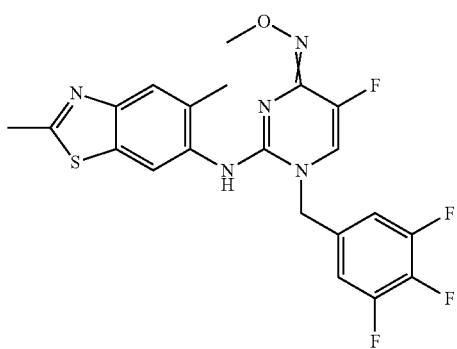 [SMILES: CON=c1nc(Nc2cc3sc(C)nc3cc2C)n(Cc2cc(F)c(F)c(F)c2)cc1F] | 464 | 1.76 | [3] |

TABLE 241-continued
| I-1292 | 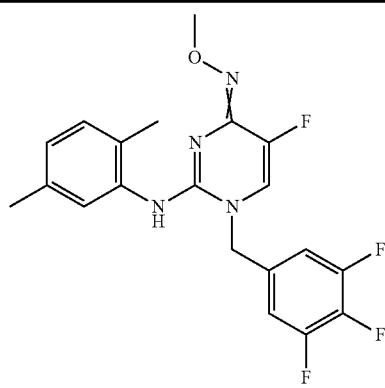 | 407 | 2.01 | [3] |
| I-1293 | 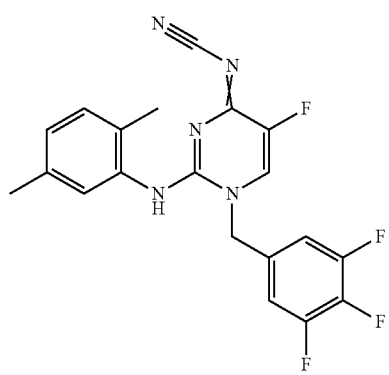 [SMILES: Cc1ccc(C)c(Nc2nc(=NC#N)c(F)cn2Cc2cc(F)c(F)c(F)c2)c1] | 402 | 2.07 | [3] |
| I-1294 | 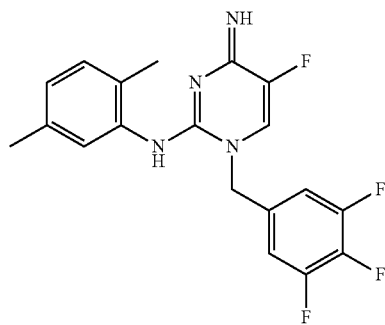 [SMILES: Cc1ccc(C)c(Nc2nc(=N)c(F)cn2Cc2cc(F)c(F)c(F)c2)c1] | 376 | 2.61 | [3] |
TABLE 242
| I-1295 | 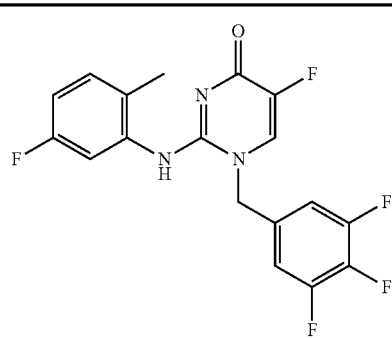 | 1H-NMR (DMSO-d6) δ: 1.85 (s, 3H), 5.17 (s, 2H), 6.98-7.10 (m, 2H), 7.23 (m, 1H), 7.30-7.40 (m, 2H), 7.26 (m, 1H), 8.04 (br s, 1H), 8.62 (br s, 1H). | 382 | 1.76 | [1] |

TABLE 242-continued

| | | | | | |
|---|---|---|---|---|---|
| I-1296 | [structure] | 1H-NMR (DMSO-d6) δ: 3.72 (s, 3H), 5.18 (s, 2H), 6.77-6.92 ((m, 2H), 7.16 (m, 1H), 7.23-7.40 (m, 2H), 8.03 (br s, 1H), 8.34 (br s, 1H). | 420 | 2.01 | [1] |
| I-1297 | [structure] | 1H-NMR (DMSO-d6) δ: 1.78 (s, 3H), 3.82 (s, 3H), 5.20 (s, 2H), 6.76 (m, 1H), 6.99 (m, 1H), 7.03-7.10 (m, 2H), 7.26 (m, 1H), 8.04 (m, 1H), 8.65 (br s, 1H). | 394 | 1.60 | [1] |

Biological test, examples for the compounds of the present invention are described below.

Test Example 1 Evaluation of a Human P2X7 Receptor Inhibitory Activity

Stably expressing cell line (1321N1 cell transfected with the human P2X7 receptor gene (GenBank accession number NM_002502.5 including T606C and G952A SNP)) was used. The cells were seeded in a 384-well microtiter plate at a concentration of 8000 cells/well and cultured in the medium (10% fetal bovine serum, 25 mM HEPES, 1% penicillin and streptomycin in DMEM) for one day at 37° C. under 5% carbon dioxide atmosphere. After replacing with 20 μL of the HBSS buffer (20 mM HEPES, 55.6 mM D-glucose, 1×HBSS(-), pH7.4-7.5). 16 μL of 17.3 μM Yo-Pro solution in the HBSS buffer was added. The plate was placed in high-throughput cellular screening system FLIPR TETRA (Molecullar Devices, LLC.) and 15 μL of 130 μM BzATP solution in the HBSS buffer was added. Measurement, of fluorescence intensity by FLIPR TETRA was started. After eight minutes, 15 μL of DMSO solutions containing different concentrations of the compound of the present invention as prepared by dilution with the HBSS buffer were dispensed to each well through the built-in automatic dispenser, and the measurement of fluorescence intensity was continued for 20 minutes. The maximum fluorescence intensity without the compound of the present invention is calculated as 0% inhibition and the maximum fluorescence intensity when the reference compound was added is calculated as 100% inhibition. Changing values of fluorescence intensity by the compound of the present invention were calculated by difference between maximum and minimum fluorescence intensity for 20 minutes. Inhibition ratios (%) were calculated from the following equation:

Inhibitation ratio:

$$\left[1 - \frac{\left(\begin{array}{c}\text{changing values by a} \\ \text{compound of present invention}- \\ \text{changing values by} \\ \text{reference compound}\end{array}\right)}{\left(\begin{array}{c}\text{changing values without} \\ \text{a compound} \\ \text{of the present invention}- \\ \text{changing values by} \\ \text{reference compound}\end{array}\right)}\right] \times 100 \ (\%)$$

$IC_{50}$ was calculated using Logistic approximation.

The antagonistic activity for the human P2X7 receptor of the compounds of the present invention is shown in the following table.

TABLE 243

| Compound No. | IC50 (nM) |
|---|---|
| I-0005 | 5 |
| I-0006 | 6 |
| I-0008 | 37 |
| I-0013 | 39 |
| I-0014 | 250 |
| I-0019 | 49 |
| I-0020 | 17 |
| I-0022 | 17 |
| I-0030 | 34 |
| I-0033 | 49 |
| I-0042 | 830 |
| I-0052 | 130 |
| I-0055 | 26 |
| I-0062 | 590 |
| I-0104 | 41 |
| I-0120 | 670 |

TABLE 243-continued

| Compound No. | IC50 (nM) |
|---|---|
| I-0121 | 280 |
| I-0149 | 26 |
| I-0176 | 13 |
| I-0178 | 21 |
| I-0185 | 270 |
| I-0186 | 2 |
| I-0187 | 230 |
| I-0190 | 71 |
| I-0193 | 18 |
| I-0195 | 26 |
| I-0196 | 13 |
| I-0203 | 18 |
| I-0205 | 91 |
| I-0207 | 9 |
| I-0218 | 19 |
| I-0242 | 12 |
| I-0289 | 27 |
| I-0294 | 250 |
| I-0295 | 170 |
| I-0297 | 250 |
| I-0335 | 170 |
| I-0336 | 120 |
| I-0347 | 20 |
| I-0354 | 3 |
| I-0358 | 160 |
| I-0365 | 18 |
| I-0366 | 35 |
| I-0367 | 13 |
| I-0370 | 47 |
| I-0372 | 5 |
| I-0382 | 350 |
| I-0384 | 10 |
| I-0397 | 67 |
| I-0405 | 2 |
| I-0407 | 6 |
| I-0425 | 19 |
| I-0437 | 8 |
| I-0452 | 110 |
| I-0453 | 73 |
| I-0480 | 4 |
| I-0487 | 25 |
| I-0520 | 9 |
| I-0550 | 2 |
| I-0561 | 19 |
| I-0597 | 20 |
| I-0618 | 7 |
| I-0626 | 4 |
| I-0636 | 50 |
| I-0652 | 34 |
| I-0670 | 20 |
| I-0675 | 190 |
| I-0698 | 100 |
| I-0702 | 11 |
| I-0703 | 16 |
| I-0706 | 15 |
| I-0707 | 14 |
| I-0738 | 3 |
| I-0742 | 16 |
| I-0744 | 180 |
| I-0755 | 12 |
| I-0771 | 43 |
| I-0774 | 110 |
| I-0786 | 25 |
| I-0788 | 12 |
| I-0792 | 9 |
| I-0817 | 4 |
| I-0821 | 5 |
| I-0825 | 9 |
| I-0833 | 39 |
| I-0836 | 2 |
| I-0842 | 5 |
| I-0849 | 3 |
| I-0857 | 26 |
| I-0858 | 10 |
| I-0865 | 8 |
| I-0900 | 12 |
| I-0910 | 14 |
| I-0912 | 22 |
| I-0914 | 22 |
| I-0924 | 17 |
| I-0928 | 10 |
| I-0935 | 6 |
| I-0939 | 4 |
| I-0940 | 240 |
| I-0941 | 12 |
| I-0942 | 230 |
| I-0945 | 170 |
| I-0953 | 25 |
| I-0957 | 110 |
| I-0961 | 410 |
| I-0965 | 440 |
| I-0966 | 480 |
| I-0967 | 450 |
| I-0985 | 65 |
| I-0986 | 24 |
| I-0987 | 110 |
| I-0989 | 300 |
| I-0990 | 320 |
| I-0991 | 29 |
| I-1019 | 4 |
| I-1040 | 6 |
| I-1041 | 9 |
| I-1050 | 10 |
| I-1059 | 11 |
| I-1066 | 3 |
| I-1071 | 15 |
| I-1108 | 4 |
| I-1188 | 4 |
| I-1216 | 6 |
| I-1232 | 6 |
| I-1267 | 10 |
| I-1261 | 16 |
| I-1263 | 3 |
| I-1281 | 4 |
| I-1285 | 27 |
| I-1290 | 21 |
| I-1295 | 13 |
| I-1296 | 11 |
| I-1297 | 16 |

The antagonistic activity for the human P2X7 receptor of the other compounds of the present invention is shown in the following table. As for $IC_{50}$ value, value from 0 nmol/L to below 10 nmol/L is represented as "A", value from 10 nmol/L to below 100 nmol/L is represented as "B", value from 100 nmol/L to below 500 nmol/L is represented as "C", and value from 500 nmol/L to below 1 pmoi/L is represented as "D".

TABLE 244

| Compound No. | IC50 |
|---|---|
| I-0001 | A |
| I-0002 | A |
| I-0003 | A |
| I-0004 | A |
| I-0007 | B |
| I-0009 | A |
| I-0010 | A |
| I-0011 | B |
| I-0012 | B |
| I-0015 | D |
| I-0016 | B |
| I-0018 | C |
| I-0021 | C |
| I-0023 | C |
| I-0024 | B |
| I-0025 | D |
| I-0026 | B |

TABLE 244-continued

| Compound No. | IC50 |
|---|---|
| I-0027 | B |
| I-0028 | D |
| I-0035 | C |
| I-0036 | C |
| I-0037 | A |
| I-0038 | B |
| I-0039 | B |
| I-0040 | B |
| I-0041 | A |
| I-0043 | C |
| I-0044 | B |
| I-0045 | D |
| I-0047 | D |
| I-0050 | D |
| I-0054 | C |
| I-0056 | B |
| I-0060 | D |
| I-0061 | D |
| I-0065 | D |
| I-0066 | D |
| I-0067 | D |
| I-0068 | B |
| I-0070 | B |
| I-0071 | C |
| I-0072 | B |
| I-0073 | D |
| I-0074 | B |
| I-0075 | C |
| I-0076 | C |
| I-0077 | B |
| I-0078 | C |
| I-0080 | C |
| I-0082 | C |
| I-0083 | D |
| I-0084 | B |
| I-0085 | B |
| I-0088 | C |
| I-0089 | D |
| I-0090 | C |
| I-0091 | C |
| I-0092 | C |
| I-0093 | B |
| I-0095 | B |
| I-0096 | B |
| I-0097 | C |
| I-0098 | D |
| I-0099 | C |
| I-0100 | C |
| I-0101 | B |
| I-0102 | C |
| I-0103 | C |
| I-0105 | C |
| I-0106 | B |
| I-0107 | C |
| I-0108 | B |
| I-0109 | D |
| I-0110 | C |
| I-0111 | C |
| I-0112 | B |
| I-0113 | D |
| I-0114 | C |
| I-0115 | B |
| I-0116 | A |
| I-0117 | B |
| I-0118 | B |
| I-0124 | A |
| I-0125 | B |
| I-0126 | B |
| I-0127 | B |
| I-0128 | B |
| I-0129 | C |
| I-0130 | C |
| I-0131 | C |
| I-0132 | C |
| I-0133 | C |
| I-0134 | B |
| I-0136 | A |
| I-0137 | B |
| I-0138 | D |
| I-0139 | A |
| I-0140 | B |
| I-0141 | B |
| I-0142 | B |
| I-0143 | B |
| I-0144 | C |
| I-0145 | B |
| I-0146 | B |
| I-0147 | B |
| I-0148 | B |
| I-0150 | C |
| I-0152 | C |
| I-0153 | B |
| I-0154 | C |
| I-0155 | D |
| I-0156 | C |
| I-0157 | B |
| I-0158 | B |
| I-0161 | B |
| I-0162 | A |
| I-0163 | A |
| I-0164 | A |
| I-0165 | A |
| I-0166 | A |
| I-0167 | B |
| I-0168 | A |
| I-0169 | A |
| I-0170 | C |
| I-0171 | B |
| I-0172 | B |
| I-0173 | C |
| I-0175 | B |
| I-0177 | A |
| I-0179 | A |
| I-0180 | B |
| I-0181 | D |
| I-0182 | A |
| I-0183 | B |
| I-0184 | C |
| I-0191 | C |
| I-0192 | B |
| I-0194 | B |
| I-0198 | C |
| I-0200 | B |
| I-0201 | D |
| I-0204 | C |
| I-0206 | B |
| I-0208 | A |
| I-0209 | A |
| I-0210 | B |
| I-0211 | A |
| I-0212 | A |
| I-0213 | A |
| I-0214 | A |
| I-0215 | A |
| I-0216 | C |
| I-0217 | B |
| I-0219 | B |
| I-0220 | A |
| I-0221 | B |
| I-0222 | A |
| I-0223 | B |
| I-0224 | A |
| I-0225 | C |

TABLE 245

| Compound No. | IC50 |
|---|---|
| I-0226 | B |
| I-0227 | B |

TABLE 245-continued

| Compound No. | IC50 |
|---|---|
| I-0228 | B |
| I-0229 | A |
| I-0230 | A |
| I-0231 | A |
| I-0232 | A |
| I-0233 | A |
| I-0234 | B |
| I-0235 | B |
| I-0236 | B |
| I-0237 | A |
| I-0238 | C |
| I-0239 | C |
| I-0240 | B |
| I-0241 | B |
| I-0243 | A |
| I-0244 | A |
| I-0245 | A |
| I-0246 | A |
| I-0247 | A |
| I-0248 | B |
| I-0249 | A |
| I-0250 | A |
| I-0251 | B |
| I-0252 | A |
| I-0253 | B |
| I-0254 | B |
| I-0255 | A |
| I-0256 | A |
| I-0257 | A |
| I-0258 | A |
| I-0259 | A |
| I-0260 | A |
| I-0261 | A |
| I-0262 | A |
| I-0263 | A |
| I-0264 | A |
| I-0265 | A |
| I-0266 | A |
| I-0267 | A |
| I-0268 | A |
| I-0269 | A |
| I-0270 | A |
| I-0271 | A |
| I-0272 | A |
| I-0273 | A |
| I-0274 | A |
| I-0275 | B |
| I-0276 | B |
| I-0277 | A |
| I-0278 | A |
| I-0279 | A |
| I-0280 | B |
| I-0281 | A |
| I-0282 | A |
| I-0283 | A |
| I-0284 | D |
| I-0285 | B |
| I-0286 | B |
| I-0287 | B |
| I-0288 | B |
| I-0290 | B |
| I-0291 | B |
| I-0292 | B |
| I-0293 | B |
| I-0296 | B |
| I-0298 | B |
| I-0299 | B |
| I-0300 | A |
| I-0301 | A |
| I-0302 | A |
| I-0303 | C |
| I-0304 | D |
| I-0306 | A |
| I-0307 | A |
| I-0308 | A |
| I-0309 | A |
| I-0310 | B |

TABLE 245-continued

| Compound No. | IC50 |
|---|---|
| I-0311 | C |
| I-0312 | B |
| I-0313 | B |
| I-0314 | A |
| I-0315 | A |
| I-0316 | A |
| I-0317 | C |
| I-0318 | A |
| I-0319 | A |
| I-0320 | C |
| I-0321 | B |
| I-0322 | B |
| I-0323 | A |
| I-0324 | A |
| I-0325 | A |
| I-0326 | A |
| I-0327 | B |
| I-0328 | B |
| I-0329 | B |
| I-0330 | C |
| I-0331 | C |
| I-0332 | B |
| I-0333 | B |
| I-0334 | A |
| I-0337 | C |
| I-0338 | C |
| I-0339 | C |
| I-0340 | C |
| I-0341 | C |
| I-0342 | C |
| I-0344 | C |
| I-0345 | A |
| I-0346 | A |
| I-0348 | A |
| I-0349 | A |
| I-0350 | A |
| I-0351 | A |
| I-0352 | C |
| I-0353 | B |
| I-0355 | A |
| I-0356 | C |
| I-0357 | D |
| I-0359 | D |
| I-0360 | B |
| I-0361 | A |
| I-0362 | A |
| I-0363 | A |
| I-0364 | C |
| I-0368 | B |
| I-0369 | A |
| I-0371 | A |
| I-0374 | B |
| I-0375 | B |
| I-0376 | A |
| I-0377 | A |
| I-0378 | A |
| I-0379 | A |
| I-0380 | B |
| I-0381 | A |
| I-0383 | A |
| I-0385 | B |
| I-0386 | B |
| I-0387 | B |
| I-0388 | B |
| I-0389 | A |
| I-0390 | B |
| I-0392 | B |
| I-0393 | B |
| I-0394 | A |
| I-0395 | A |
| I-0396 | A |
| I-0398 | B |
| I-0399 | A |
| I-0400 | C |
| I-0401 | B |
| I-0402 | A |
| I-0403 | B |

TABLE 245-continued

| Compound No. | IC50 |
|---|---|
| I-0404 | A |
| I-0406 | A |
| I-0408 | B |
| I-0409 | B |

TABLE 246

| Compound No. | IC50 |
|---|---|
| I-0410 | A |
| I-0411 | C |
| I-0412 | C |
| I-0415 | D |
| I-0416 | B |
| I-0417 | C |
| I-0419 | A |
| I-0420 | B |
| I-0421 | B |
| I-0422 | D |
| I-0423 | B |
| I-0424 | A |
| I-0426 | B |
| I-0427 | C |
| I-0428 | A |
| I-0429 | A |
| I-0430 | A |
| I-0431 | B |
| I-0432 | B |
| I-0433 | A |
| I-0434 | A |
| I-0435 | B |
| I-0436 | A |
| I-0438 | A |
| I-0439 | A |
| I-0440 | A |
| I-0441 | A |
| I-0442 | A |
| I-0443 | A |
| I-0444 | B |
| I-0445 | B |
| I-0446 | A |
| I-0447 | A |
| I-0448 | B |
| I-0449 | A |
| I-0450 | B |
| I-0451 | C |
| I-0454 | B |
| I-0455 | B |
| I-0456 | B |
| I-0457 | A |
| I-0458 | B |
| I-0459 | A |
| I-0460 | B |
| I-0461 | A |
| I-0462 | B |
| I-0463 | A |
| I-0464 | A |
| I-0465 | A |
| I-0466 | B |
| I-0467 | A |
| I-0468 | B |
| I-0469 | A |
| I-0470 | B |
| I-0471 | A |
| I-0472 | A |
| I-0473 | A |
| I-0474 | A |
| I-0475 | A |
| I-0476 | A |
| I-0477 | A |
| I-0478 | A |
| I-0479 | B |
| I-0481 | B |

TABLE 246-continued

| Compound No. | IC50 |
|---|---|
| I-0482 | A |
| I-0483 | A |
| I-0484 | B |
| I-0485 | A |
| I-0486 | A |
| I-0488 | B |
| I-0489 | A |
| I-0490 | A |
| I-0491 | A |
| I-0492 | A |
| I-0493 | B |
| I-0494 | B |
| I-0495 | B |
| I-0496 | B |
| I-0497 | B |
| I-0498 | C |
| I-0499 | B |
| I-0500 | B |
| I-0501 | B |
| I-0502 | B |
| I-0503 | A |
| I-0504 | A |
| I-0505 | B |
| I-0506 | A |
| I-0507 | A |
| I-0508 | B |
| I-0509 | A |
| I-0510 | A |
| I-0511 | A |
| I-0512 | C |
| I-0513 | C |
| I-0514 | B |
| I-0515 | B |
| I-0516 | B |
| I-0517 | A |
| I-0518 | B |
| I-0519 | B |
| I-0521 | D |
| I-0523 | B |
| I-0524 | C |
| I-0525 | C |
| I-0526 | B |
| I-0527 | D |
| I-0529 | B |
| I-0530 | B |
| I-0531 | B |
| I-0532 | B |
| I-0533 | A |
| I-0534 | A |
| I-0535 | A |
| I-0536 | A |
| I-0537 | A |
| I-0538 | B |
| I-0539 | B |
| I-0540 | A |
| I-0541 | B |
| I-0542 | B |
| I-0543 | B |
| I-0544 | B |
| I-0545 | A |
| I-0546 | B |
| I-0547 | B |
| I-0548 | B |
| I-0549 | A |
| I-0551 | B |
| I-0552 | B |
| I-0553 | B |
| I-0554 | B |
| I-0555 | B |
| I-0556 | B |
| I-0557 | B |
| I-0558 | B |
| I-0559 | B |
| I-0560 | A |
| I-0562 | B |
| I-0563 | B |
| I-0564 | B |

TABLE 246-continued

| Compound No. | IC50 |
|---|---|
| I-0565 | C |
| I-0566 | B |
| I-0567 | B |
| I-0568 | B |
| I-0569 | A |
| I-0570 | A |
| I-0571 | A |
| I-0572 | A |
| I-0573 | A |
| I-0574 | A |
| I-0575 | A |
| I-0576 | B |
| I-0577 | B |
| I-0578 | A |
| I-0579 | B |
| I-0580 | B |
| I-0581 | A |
| I-0582 | C |
| I-0583 | A |

TABLE 247

| Compound No. | IC50 |
|---|---|
| I-0584 | A |
| I-0585 | A |
| I-0586 | A |
| I-0587 | B |
| I-0588 | A |
| I-0589 | A |
| I-0590 | B |
| I-0591 | B |
| I-0592 | B |
| I-0593 | B |
| I-0594 | B |
| I-0595 | A |
| I-0596 | B |
| I-0598 | B |
| I-0599 | B |
| I-0600 | A |
| I-0601 | A |
| I-0602 | C |
| I-0603 | B |
| I-0604 | A |
| I-0605 | B |
| I-0606 | A |
| I-0607 | A |
| I-0608 | B |
| I-0609 | C |
| I-0610 | B |
| I-0611 | B |
| I-0612 | C |
| I-0613 | B |
| I-0614 | A |
| I-0615 | A |
| I-0616 | A |
| I-0617 | A |
| I-0619 | A |
| I-0620 | A |
| I-0621 | A |
| I-0622 | B |
| I-0623 | A |
| I-0624 | A |
| I-0625 | A |
| I-0627 | B |
| I-0628 | C |
| I-0629 | B |
| I-0630 | A |
| I-0631 | B |
| I-0632 | A |
| I-0633 | A |
| I-0634 | C |
| I-0635 | B |

TABLE 247-continued

| Compound No. | IC50 |
|---|---|
| I-0637 | A |
| I-0638 | A |
| I-0639 | B |
| I-0640 | B |
| I-0641 | B |
| I-0642 | A |
| I-0643 | B |
| I-0644 | B |
| I-0645 | B |
| I-0646 | B |
| I-0647 | B |
| I-0648 | B |
| I-0649 | B |
| I-0650 | B |
| I-0651 | B |
| I-0653 | A |
| I-0654 | B |
| I-0655 | B |
| I-0656 | B |
| I-0657 | B |
| I-0658 | B |
| I-0659 | B |
| I-0660 | B |
| I-0661 | A |
| I-0662 | B |
| I-0663 | B |
| I-0664 | A |
| I-0665 | A |
| I-0666 | C |
| I-0667 | B |
| I-0668 | B |
| I-0669 | B |
| I-0671 | A |
| I-0672 | A |
| I-0673 | A |
| I-0674 | B |
| I-0676 | C |
| I-0677 | B |
| I-0678 | A |
| I-0679 | A |
| I-0680 | B |
| I-0681 | B |
| I-0682 | B |
| I-0683 | A |
| I-0684 | B |
| I-0685 | B |
| I-0686 | A |
| I-0687 | B |
| I-0688 | A |
| I-0689 | B |
| I-0690 | B |
| I-0691 | C |
| I-0692 | B |
| I-0693 | B |
| I-0694 | C |
| I-0695 | B |
| I-0696 | A |
| I-0697 | A |
| I-0699 | A |
| I-0700 | A |
| I-0701 | A |
| I-0704 | A |
| I-0705 | A |
| I-0708 | A |
| I-0709 | A |
| I-0710 | B |
| I-0711 | C |
| I-0712 | A |
| I-0713 | A |
| I-0714 | A |
| I-0715 | A |
| I-0716 | A |
| I-0717 | A |
| I-0718 | B |
| I-0719 | A |
| I-0720 | B |
| I-0721 | A |

TABLE 247-continued

| Compound No. | IC50 |
|---|---|
| I-0722 | B |
| I-0723 | B |
| I-0724 | C |
| I-0725 | A |
| I-0726 | C |
| I-0727 | C |
| I-0728 | C |
| I-0729 | C |
| I-0730 | B |
| I-0731 | B |
| I-0732 | B |
| I-0733 | B |
| I-0734 | B |
| I-0735 | B |
| I-0736 | B |
| I-0737 | B |
| I-0739 | B |
| I-0740 | C |
| I-0741 | B |
| I-0743 | B |
| I-0745 | C |
| I-0746 | B |
| I-0747 | B |
| I-0748 | B |
| I-0749 | B |
| I-0750 | B |
| I-0751 | A |
| I-0752 | B |
| I-0753 | A |
| I-0754 | B |
| I-0756 | B |
| I-0757 | B |
| I-0758 | B |
| I-0759 | B |

TABLE 248

| Compound No. | IC50 |
|---|---|
| I-0760 | B |
| I-0761 | C |
| I-0762 | C |
| I-0763 | A |
| I-0764 | A |
| I-0765 | B |
| I-0766 | A |
| I-0767 | B |
| I-0768 | B |
| I-0769 | B |
| I-0770 | C |
| I-0772 | B |
| I-0773 | C |
| I-0775 | B |
| I-0776 | B |
| I-0777 | A |
| I-0778 | A |
| I-0779 | A |
| I-0780 | B |
| I-0781 | B |
| I-0782 | C |
| I-0783 | B |
| I-0784 | B |
| I-0785 | B |
| I-0787 | A |
| I-0789 | A |
| I-0790 | A |
| I-0791 | A |
| I-0793 | A |
| I-0794 | A |
| I-0795 | A |
| I-0796 | B |
| I-0797 | B |
| I-0798 | B |

TABLE 248-continued

| Compound No. | IC50 |
|---|---|
| I-0799 | A |
| I-0800 | B |
| I-0801 | C |
| I-0802 | A |
| I-0803 | B |
| I-0804 | A |
| I-0805 | A |
| I-0806 | B |
| I-0807 | B |
| I-0808 | A |
| I-0809 | B |
| I-0810 | B |
| I-0811 | B |
| I-0812 | B |
| I-0813 | A |
| I-0814 | A |
| I-0815 | A |
| I-0816 | A |
| I-0818 | B |
| I-0819 | B |
| I-0820 | B |
| I-0822 | B |
| I-0823 | C |
| I-0824 | B |
| I-0826 | B |
| I-0827 | B |
| I-0828 | B |
| I-0829 | B |
| I-0830 | B |
| I-0831 | A |
| I-0832 | A |
| I-0834 | A |
| I-0835 | A |
| I-0837 | A |
| I-0838 | A |
| I-0839 | A |
| I-0840 | A |
| I-0841 | A |
| I-0843 | B |
| I-0844 | A |
| I-0845 | B |
| I-0846 | A |
| I-0847 | A |
| I-0848 | A |
| I-0850 | A |
| I-0851 | A |
| I-0852 | A |
| I-0853 | A |
| I-0854 | A |
| I-0855 | B |
| I-0856 | B |
| I-0859 | B |
| I-0860 | B |
| I-0861 | A |
| I-0862 | A |
| I-0863 | A |
| I-0864 | A |
| I-0866 | A |
| I-0867 | A |
| I-0868 | B |
| I-0869 | B |
| I-0870 | B |
| I-0871 | B |
| I-0872 | B |
| I-0873 | B |
| I-0874 | B |
| I-0875 | B |
| I-0876 | A |
| I-0877 | B |
| I-0878 | A |
| I-0879 | A |
| I-0881 | C |
| I-0882 | D |
| I-0883 | B |
| I-0884 | B |
| I-0885 | B |
| I-0886 | B |

TABLE 248-continued

| Compound No. | IC50 |
|---|---|
| I-0887 | B |
| I-0888 | B |
| I-0889 | A |
| I-0890 | B |
| I-0891 | B |
| I-0892 | B |
| I-0893 | A |
| I-0894 | A |
| I-0895 | B |
| I-0896 | A |
| I-0897 | A |
| I-0898 | B |
| I-0899 | A |
| I-0901 | C |
| I-0902 | B |
| I-0903 | B |
| I-0904 | B |
| I-0905 | C |
| I-0906 | B |
| I-0907 | A |
| I-0908 | A |
| I-0909 | B |
| I-0911 | B |
| I-0913 | B |
| I-0915 | B |
| I-0916 | B |
| I-0917 | B |
| I-0918 | B |
| I-0919 | B |
| I-0920 | B |
| I-0921 | A |
| I-0922 | A |
| I-0923 | B |
| I-0925 | B |
| I-0926 | B |
| I-0927 | A |
| I-0929 | A |
| I-0930 | C |
| I-0931 | B |
| I-0932 | B |
| I-0933 | C |
| I-0934 | B |
| I-0936 | B |
| I-0937 | A |
| I-0938 | A |
| I-0943 | A |
| I-0944 | C |
| I-0946 | D |
| I-0947 | B |

TABLE 249

| Compound No. | IC50 |
|---|---|
| I-0948 | B |
| I-0949 | C |
| I-0950 | C |
| I-0951 | C |
| I-0952 | C |
| I-0954 | B |
| I-0955 | B |
| I-0956 | C |
| I-0958 | C |
| I-0959 | D |
| I-0964 | C |
| I-0969 | D |
| I-0971 | C |
| I-0973 | C |
| I-0981 | D |
| I-0993 | A |
| I-0994 | B |
| I-0995 | B |
| I-0996 | B |

TABLE 249-continued

| Compound No. | IC50 |
|---|---|
| I-0997 | B |
| I-0998 | A |
| I-0999 | A |
| I-1000 | A |
| I-1001 | A |
| I-1002 | B |
| I-1003 | A |
| I-1004 | A |
| I-1005 | A |
| I-1006 | A |
| I-1007 | A |
| I-1008 | A |
| I-1009 | A |
| I-1010 | A |
| I-1011 | A |
| I-1012 | A |
| I-1013 | A |
| I-1014 | A |
| I-1015 | A |
| I-1016 | B |
| I-1017 | B |
| I-1018 | A |
| I-1020 | A |
| I-1021 | A |
| I-1022 | A |
| I-1023 | A |
| I-1024 | A |
| I-1025 | A |
| I-1026 | A |
| I-1027 | B |
| I-1028 | A |
| I-1030 | A |
| I-1031 | A |
| I-1032 | B |
| I-1033 | A |
| I-1034 | A |
| I-1035 | B |
| I-1036 | B |
| I-1037 | B |
| I-1038 | B |
| I-1039 | B |
| I-1042 | A |
| I-1043 | A |
| I-1044 | A |
| I-1045 | A |
| I-1046 | A |
| I-1047 | B |
| I-1048 | B |
| I-1049 | B |
| I-1051 | A |
| I-1052 | A |
| I-1053 | B |
| I-1054 | A |
| I-1055 | B |
| I-1056 | B |
| I-1057 | B |
| I-1058 | A |
| I-1060 | B |
| I-1061 | B |
| I-1062 | B |
| I-1063 | B |
| I-1064 | B |
| I-1065 | B |
| I-1067 | A |
| I-1068 | A |
| I-1069 | B |
| I-1070 | B |
| I-1072 | A |
| I-1073 | A |
| I-1074 | B |
| I-1075 | A |
| I-1076 | A |
| I-1077 | A |
| I-1078 | A |
| I-1079 | B |
| I-1080 | B |
| I-1081 | B |

TABLE 249-continued

| Compound No. | IC50 |
|---|---|
| I-1082 | A |
| I-1083 | A |
| I-1084 | A |
| I-1085 | A |
| I-1086 | A |
| I-1087 | A |
| I-1088 | B |
| I-1089 | A |
| I-1090 | B |
| I-1091 | B |
| I-1092 | B |
| I-1093 | B |
| I-1094 | A |
| I-1095 | B |
| I-1096 | B |
| I-1097 | B |
| I-1098 | B |
| I-1099 | B |
| I-1100 | B |
| I-1101 | B |
| I-1102 | B |
| I-1103 | B |
| I-1104 | B |
| I-1105 | A |
| I-1107 | B |
| I-1109 | A |
| I-1110 | A |
| I-1111 | A |
| I-1112 | B |
| I-1113 | A |
| I-1114 | A |
| I-1115 | A |
| I-1116 | A |
| I-1117 | B |
| I-1118 | C |
| I-1119 | A |
| I-1120 | A |
| I-1121 | C |
| I-1122 | B |
| I-1123 | C |
| I-1124 | B |
| I-1125 | B |
| I-1126 | B |
| I-1127 | B |
| I-1128 | B |
| I-1129 | B |
| I-1130 | B |
| I-1131 | B |
| I-1132 | B |
| I-1133 | B |
| I-1134 | B |
| I-1135 | B |
| I-1136 | B |
| I-1137 | B |
| I-1138 | B |
| I-1139 | B |
| I-1140 | B |
| I-1141 | B |
| I-1142 | B |
| I-1143 | B |
| I-1144 | B |
| I-1145 | B |
| I-1146 | B |
| I-1147 | B |

TABLE 250

| Compound No. | IC50 |
|---|---|
| I-1148 | B |
| I-1149 | B |
| I-1150 | B |
| I-1151 | B |

TABLE 250-continued

| Compound No. | IC50 |
|---|---|
| I-1152 | A |
| I-1153 | A |
| I-1154 | A |
| I-1155 | A |
| I-1156 | A |
| I-1157 | A |
| I-1158 | A |
| I-1159 | A |
| I-1160 | A |
| I-1161 | A |
| I-1162 | A |
| I-1163 | A |
| I-1164 | A |
| I-1165 | A |
| I-1166 | A |
| I-1167 | A |
| I-1168 | A |
| I-1169 | A |
| I-1170 | A |
| I-1171 | A |
| I-1173 | A |
| I-1174 | A |
| I-1175 | A |
| I-1176 | A |
| I-1177 | A |
| I-1178 | A |
| I-1179 | A |
| I-1180 | A |
| I-1181 | A |
| I-1182 | A |
| I-1183 | A |
| I-1184 | A |
| I-1185 | A |
| I-1186 | A |
| I-1187 | A |
| I-1189 | A |
| I-1190 | A |
| I-1191 | A |
| I-1192 | A |
| I-1193 | A |
| I-1194 | A |
| I-1195 | A |
| I-1196 | A |
| I-1197 | A |
| I-1198 | A |
| I-1199 | A |
| I-1200 | A |
| I-1201 | A |
| I-1202 | A |
| I-1203 | A |
| I-1204 | A |
| I-1205 | A |
| I-1206 | A |
| I-1207 | A |
| I-1208 | A |
| I-1209 | A |
| I-1210 | A |
| I-1211 | A |
| I-1212 | A |
| I-1213 | A |
| I-1214 | A |
| I-1215 | A |
| I-1217 | A |
| I-1218 | A |
| I-1219 | A |
| I-1220 | A |
| I-1221 | A |
| I-1222 | A |
| I-1223 | A |
| I-1224 | A |
| I-1225 | A |
| I-1226 | A |
| I-1227 | A |
| I-1228 | A |
| I-1229 | A |
| I-1230 | A |
| I-1231 | A |

TABLE 250-continued

| Compound No. | IC50 |
|---|---|
| I-1233 | A |
| I-1234 | A |
| I-1235 | A |
| I-1236 | A |
| I-1237 | A |
| I-1238 | A |
| I-1239 | A |
| I-1240 | A |
| I-1241 | A |
| I-1242 | A |
| I-1243 | A |
| I-1244 | A |
| I-1245 | A |
| I-1246 | A |
| I-1247 | A |
| I-1248 | B |
| I-1249 | B |
| I-1250 | C |
| I-1251 | B |
| I-1252 | B |
| I-1253 | B |
| I-1254 | A |
| I-1255 | A |
| I-1256 | B |
| I-1257 | B |
| I-1258 | A |
| I-1259 | B |
| I-1260 | B |
| I-1262 | A |
| I-1264 | A |
| I-1265 | B |
| I-1266 | B |
| I-1268 | B |
| I-1269 | B |
| I-1270 | A |
| I-1271 | A |
| I-1272 | A |
| I-1273 | A |
| I-1274 | A |
| I-1275 | C |
| I-1276 | B |
| I-1277 | A |
| I-1278 | A |
| I-1279 | A |
| I-1280 | A |
| I-1282 | A |
| I-1283 | A |
| I-1284 | A |
| I-1286 | A |
| I-1287 | B |
| I-1288 | B |
| I-1289 | C |
| I-1291 | C |
| I-1292 | C |
| I-1293 | A |
| I-1294 | B |

Test Example 2 Evaluation of the Rat P2X7 Receptor Inhibitory Activity

Stably expressing cell line (1321N1 cell transfected with the rat P2X7 receptor gene (GenBank accession number NM_019256.1 including C586T and C652A SNP)) is used. The cells are seeded in a 384-well microtiter plate at a concentration of 10000 cells/well and cultured in the medium (10% fetal bovine serum, 2 mM ClutaMax-1, 1% penicillin and streptomycin in DMEM) for one day at 37° C. under 5% carbon dioxide atmosphere. After replacing with 20 μL of the HBSS buffer (20 mM HEPES, 55.6 mM D-glucose, 1×HBSS(+), pH7.4), 15 μL of 17.3 μM Yo-Pro solution in the HBSS buffer is added. The plate is placed in high-throughput cellular screening system FLIPR TETRA (Molecular Devices, LLC.) and 15 μL of 1083 μM BzATP solution in the HBSS buffer is added. Measurement of fluorescence intensity by FLIPR TETRA is started. Eight minutes after, 15 μL of DMSO solutions containing different concentrations of the compound of the present invention as prepared by dilution with the HBSS buffer are dispensed to each well through the built-in automatic dispenser, and the measurement of fluorescence intensity is continued for 20 minutes. The maximum fluorescence intensity without the compound of the present invention is calculated as 0% inhibition and the maximum fluorescence intensity when the reference compound is added is calculated as 100% inhibition. Changing values of fluorescence intensity by the compound of the present invention are calculated by difference between maximum and minimum fluorescence intensity for 20 minutes. Inhibition ratios (%) are calculated from the following equation:

Inhibitation ratio:

$$\left[1 - \frac{\left(\begin{array}{c}\text{changing values by a compound} \\ \text{of present invention} - \\ \text{changing values by} \\ \text{reference compound}\end{array}\right)}{\left(\begin{array}{c}\text{changing values without} \\ \text{a compound} \\ \text{of the present invention} - \\ \text{changing values by} \\ \text{reference compound}\end{array}\right)}\right] \times 100 \ (\%)$$

$IC_{50}$ is calculated using logistic approximation.

Test Example 3-1: Analgesic Effect in a Seltzer Model

Preparation of Partial Sciatic Nerve Ligation Model in Rats

Rats are anaesthetized using isoflurane/O2 inhalation anaesthesia. After induction of anesthesia, the left thigh is shaved. An incision was made in the skin just below the hip bone. The muscle was bluntly dissected to expose the sciatic nerve. About one half (½) of the sciatic nerve thickness is tightly ligated with a nylon thread and the wound is closed. The right thigh was used as a sham-operated control. The right thigh underwent an identical procedure with the left hind limb, however, the sciatic nerve was not manipulated or ligated.

Evaluation (1)

Two weeks after nerve ligation, the effect on mechanical allodynia was assessed using a series of von Frey filaments. For habituation, the rats were placed into a plastic cage on a wire mesh bottom. Von Frey filaments (0.4 to 26 g) were applied to the plantar surface of the rat hind paws from the wire mesh side, and the value of the filament pressure at which the paw was withdrawn was used as a pain threshold. The measurement of mechanical sensitivity of the right and left hind paws was performed to obtain prodose mechanical sensitivity. The rats showing the threshold change from 0.6 to 2 g (in nerve ligated side) and 8 to 1.5 g (in sham operated side) were used in the experiments. On the day before the experiment, the rata were evaluated with a series of von Frey filaments to familiarize them with the test procedure. The adopted animal was administrated with the compounds of the present invention. The compounds of the present invention were homogenized with mortar and pestle and suspended or diluted in 0.5% Methyl Cellulose to prepare 0.03-100 mg/2 mL/kg suspension and orally administered to rat using a syringe attached with a sonde. Post-dose mechanical sensitivities of the right and left hind paws were measured at approximately 1 to 7 hours after drug administration. Percent reversal of mechanical allodynia for each rat was calculated using the following formula. The analgesic effects of the compounds were compared.

$$\% \text{ Reversal} = 100 \times \frac{\text{Log}_{10}(\text{Postdose mechanical sensitivity in nerve ligated side}) - \text{Log}_{10}(\text{Predose mechanical sensitivity in nerve ligated side})}{\text{Log}_{10}(\text{Predose mechanical sensitivity in sham operated side}) - \text{Log}_{10}(\text{Predose mechanical sensitivty in nerve ligated side})}$$

The analgesic effects of the compounds of the present invention at 3 hours after the oral administration of 3 mg/kg in the above evaluation (1) are shown below as % reversal.
Compound I-0005: 45% reversal
Compound I-0006: 49% reversal
Compound I-0354: 51% reversal
Compound I-0372: 64% reversal
Compound I-1040: 49% reversal
Compound I-1295: 51% reversal
Compound I-1296: 59% reversal The analgesic effects of the compounds of the present invention at 5 hours after the oral administration of 3 mg/kg in the above evaluation (1) are shown below as % reversal.
Compound I-0365: 55% reversal
Compound I-0702: 58% reversal
Compound I-0842: 69% reversal
Compound I-0910: 45% reversal
Compound I-1041: 48% reversal
Compound I-1050: 46% reversal
Compound I-1066: 63% reversal
Compound I-1108: 42% reversal
Compound I-1232: 55% reversal
Compound I-1261: 54% reversal
Compound I-1281: 48% reversal
Compound I-1297: 49% reversal The analgesic effects of the compounds of the present invention at 7 hours after the oral administration of 3 mg/kg in the above evaluation (1) are shown below as % reversal.
Compound I-0707: 53% reversal Evaluation (2)

Mechanical hyperalgesia is evaluated using an analgesy meter (Randall Selitto). Two weeks after nerve ligation, the paw pressure test is performed using an analgesy meter (stimulus pressure increased 16 g per second) to obtain paw withdrawal thresholds (PWT). Measurements are made on both sides of the hind paw and to obtain pre-dose PWT. The rats showing the threshold change from 60 to 90 g (in nerve ligated side) and 100 to 175 g (in sham operated side) are used in the experiments. On the day before the experiment, the rats have their hind paws set on the apparatus to familiarize them with the test procedure. The adopted animal is administrated with the compound of the present invention. The compounds of the present invention are homogenized with mortar and pestle and suspended or diluted in 0.5% Methyl Cellulose to prepare 0.03-100 mg/2 mL/kg suspension and orally administered to rat using a syringe attached with a sonde. Post-dose PWT of the right and left hind paws are measured at approximately 1 to 5 hours after drug administration. Percent reversal of mechanical hyperalgesia for each rat is calculated using the following formula. The analgesic effects of the compounds are compared.

$$\% \text{ Reversal} = 100 \times \frac{\text{Postdose } PWT \text{ in nerve ligated side} - \text{Predose } PWT \text{ in nerve ligated side}}{\text{Predose } PWT \text{ in sham operated side} - \text{Predose } PWT \text{ in nerve ligated side}}$$

Test Example 3-2: Analgesic Effect in a Cauda Equina Nerve Compression Model

Preparation of Animal Model

In order to prepare animal models, an incision is made in the lumbar portions of the back of rats under anesthesia to expose the fourth, fifth, and sixth lumbar vertebras. An incision is made in the 4-5 and 5-6 lumbar vertebral joints. Silicon rubber is inserted into the fourth and sixth lumbar vertebral canals from the wounds of the vertebral joints, and indwelled. The wounds are closed.

In order to sham-operated animals, rats are operated by the above procedures except for the insertion and indwelling of silicon rubber.

Evaluation of Analgesic Effect

Two weeks after operation, the effect on mechanical allodynia is assessed using a series of von Frey filaments. For habituation, the rats are placed into a plastic cage on a wire mesh bottom. Von Frey filaments (0.4 to 26 g) were applied to the plantar surface of the vat hind paws from the wire mesh side, and the value of the filament pressure at which the paw was withdrawn was used as a pain threshold. The measurement of mechanical sensitivity of the right and left hind paws is performed to obtain predose mechanical sensitivity. The mechanical sensitivity of both hind paws is evaluated to obtain predose mechanical sensitivity in the animal models showing the threshold change from 0.4 to 1 g and a higher pain threshold. The rats showing the threshold change from 8 to 15 g (in sham-operated group) are used in the experiments. On the day before the experiment, the rats are evaluated with a series of von Frey filaments to familiarize them with the test, procedure. The adopted animal is administrated with the compounds of the present invention. The compounds of the present invention are homogenized with mortar and pestle and suspended or diluted in 0.5% Methyl Cellulose to prepare 0.03-1.00 mg/2 mL/kg suspension and orally administered to rat using a syringe attached with a sonde. Post-dose mechanical sensitivities of the right and left hind paws are measured at approximately 1 to 5 hours after drug administration. Percent reversal of mechanical allodynia for each rat is calculated using the following formula. The analgesic effects of the compounds are compared.

Test Example 3-3: Analgesic Effect in an EAE Model

Preparation of Rat Experimental Autoimmune Encephalomyelitis Model

Rats (Lewis rate, female) are anaesthetized using isoflurane. The backs at the tail bases are shaved. 1 g/L of an emulsion containing CFA (complete Freund's adjuvant) and the saline solution of MBP (myelin basic protein) mixed at 1:1 is prepared, and subcutaneously administered at 100 uL/animal to the backs at the rat tail bases for immunization. This is used as an operated group. An emulsion with CFA is prepared using MBP-free saline, and similar treatment is performed. This is used as a sham-operated group.

Evaluation

Three weeks after immunization, the effect, on mechanical allodynia is assessed using a series of von Frey filaments. For habituation, the rats are placed into a plastic cage on a wire mesh bottom. Von Frey filaments (0.4 to 26 g) were applied to the plantar surface of the rat hind paws from the wire mesh side, and the value of the filament pressure at which the paw was withdrawn was used as a pain threshold. The mechanical sensitivity of both hind paws is evaluated to obtain predose mechanical sensitivity in the animal models showing the threshold change from 4 g or less and a higher pain threshold from 0.6 to 2 g. The rata showing the threshold change from 6 to 15 g (in sham-operated group) are used in the experiments. On the day before the experiment, the rats are evaluated with a series of von Frey filaments to familiarize them with the test procedure. The adopted animal is administered with the compounds of the present invention. The compounds of the present invention are homogenized with mortar and pestle and suspended or diluted in 0.5% Methyl Cellulose to prepare 0.03-1.00 mg/2 mL/kg suspension and orally administered to rat using a syringe attached with a sonde. Post-dose mechanical sensitivities of the hind paws are measured at approximately 1 to 5 hours after drug administration. Percent reversal of mechanical allodynia for each rat is calculated using the Following formula. The analgesic effects of the compounds are compared. % Reversal=$\text{Log}_{10}$ (Postdose mechanical sensitivity in the operated group)–$\text{Log}_{10}$ (Predose mechanical sensitivity in the operated group)/$\text{Log}_{10}$ (Predose mechanical sensitivity in the sham-operated group)–$\text{Log}_{10}$ (Predose mechanical sensitivity in the operated group)

The antagonistic activity for the P2X7 receptor of the compounds of the present invention can be also evaluated by using the method described in British Journal of Pharmacology (2013) 170 624-640.

Test Example 4: CYP Inhibition Test

Using commercially available pooled human liver microsomes, an inhibitory degree of each metabolite production amount by the compound of the present invention is assessed as marker reactions of human main five CYP isoforms (CYP1A2, 2C9, 2C19, 2D6, and 3A4), 7-ethoxyresorufin O-deethylation (CYP1A2), tolbutamide methylhydroxylation (CYP2C9), mephenyloin dihydroxylation (CYP2C19), dextromethorphan O-demethylation (CYP2D6), and terfenadine hydroxylation.

The reaction conditions are as follows: substrate. 0.5 μmol/L ethoxyresorufin (CYP1A2), 100 μmol/L tolbutamide (CYP2C9), 50 μmol/L S mephenitoin (CYP2C19), 5 μmol/L dextromethorphan (CYP2D6), 1 μmol/L terfenadine (CYP3A4); reaction time, 15 minutes: reaction temperature, 37° C.; enzyme, pooled human liver microsomes 0.2 mg protein/mL: concentration of the compound of the present invention, 1.0, 5.0, 10, 20 μmol/L (four points).

Each five kinds of substrates, human liver microsomes, or the compound of the present invention in 50 mmol/L Hepes buffer are added to a 96-well plate at the composition as described above, and NADPH, as a cofactor is added to initiate metabolism reactions. After the incubation at 37° C. for 15 minutes, a methanol/acetonitrile=1/1 (V/V) solution is added to stop the reaction. After the centrifugation at 3000 rpm for 15 minutes, resorufin (CYP1A2 metabolite) in the supernatant is quantified by a fluorescent multilabel counter or LC/MS/MS and hydroxytolbutamide (CYP2C9 metabolite). 4' hydroxymephenytoin (CYP2C19 metabolite), dextromethorphan (CYP2D6 metabolite), and terfenadine alcohol metabolite (CYP3A4 metabolite) are quantified by LC/MS/MS.

The sample adding DMSO as a solvent to a reaction system instead of a solution dissolving a compound of the present invention is adopted as a control (100%). Remaining activity (%) is calculated at each concentration of the compound of the present invention compared to control, and $IC_{50}$ is calculated by reverse presumption by a logistic model using a concentration and an inhibition rate.

Test Example 5-1: CYP3A4 Fluorescent MBI Test

The CYP3A4 fluorescent MBI test is a test of investigating mechanism based inhibition (MBI) potential on CYP3A4 by the enhancement of inhibitory degree of metabolic reaction caused by the compound of the present invention. The test is performed using CYP3A4 enzyme expressed in *Escherichia coli*, as a marker reaction in which 7-benzyloxytrifluoromothylcoumarin (7-BFC) is debenzylated to produce a metabolite, 7-hydroxytrifluoromethyloou-marin (HFC) emitting fluorescent, light by CYP3A4 enzyme.

The reaction conditions are as follows: substrate, 5.6 μmol/L 7-BFC; pre-reaction time, 0 or 30 minutes; substrate reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 1.0-fold dilution); concentrations of the compound of the present invention. 0.625, 1.25, 2.5, 5, 10, 20 μmol/L (six points).

An enzyme and a solution of the compound of the present invention in K-Pi buffer (pH 7.4) as a pre-reaction solution are added to a 96-well plate at the composition of the pre-reaction as described above. A part of pre-reaction solution is transferred to another 96-well plate, and 1/10 diluted by a K-Pi buffer containing a substrate. NADPH as a co-factor is added to initiate a reaction as a marker reaction (without preincubation). After a predetermined time of a reaction, acetonitrile/0.5 mol/L Tris (trishydroxyaminomethane)=4/1 (V/V) is added to step the reaction. In addition, NADPH is added to a remaining pre-reaction solution to initiate a pre-reaction (with preincubation). After a predetermined time of a pre-reaction, a part is transferred to another plate, and 1/10 diluted by a K-Pi buffer containing a substrate to initiate a reaction as a marker reaction. After a predetermined time of a reaction, acetonitrile/0.5 mol/L Tris (trishydroxyaminomethane)=4/1 (V/V) is added to stop the reaction. For the plate on which each marker reaction has been performed, a fluorescent value of 7-HFC which is a metabolite is measured with a fluorescent plate reader. (Ex=420 nm, Em=636 nm).

The sample adding DMSO as a solvent to reaction system instead of a solution dissolving the compound of the present invention is adopted as a control (100%). Remaining activity (%) is calculated at each concentration of the compound of the present, invention compared to a control. $IC_{50}$ is calculated by reverse-presumption by a logistic model using a concentration and an inhibition rate. If a difference between $IC_{50}$ values with or without preincubation is 5 μmol/L or more, this is defined as (+). If the difference is 3 μmol/L or less, this is defined as (−).

Test Example 5-2: CYP3A4(MDZ)MBI Test

CYP3A4(MDZ) MBI test is a test of investigating MBI potential on CYP3A4 by the enhancement of inhibitory degree of a metabolic reaction caused by the compound of the present invention. CYP3A4 inhibition is evaluated using pooled human liver microsomes by 1-hydroxylation reaction of midazolam (MDZ) as a marker reaction.

The reaction conditions are as follows: substrate, 10 μmol/L MDZ; pre-reaction time, 0 or 30 minutest substrate reaction time, 2 minutest reaction temperature, 37° C.: protein content of pooled human liver microsomes, at pre-reaction time 0.5 mg/mL, at reaction time 0.05 pmg/mL (at 1.0-fold dilution); concentrations of the compound of the present invention, 1, 5, 10, 20 μmol/L (four points).

Pooled human liver microsomes and a solution of the compound of the present invention in K-Pi buffer (pH 7.4) as a pre-reaction solution are added to a 96-well plate at the composition of the pre-reaction. A part of pro-reaction solution is transferred to another 96-well plate, and 1/10 diluted by K-Pi buffer containing a substrate. NADPH as a co-factor is added to initiate a reaction as a marker reaction (without preincubation). After a predetermined time of a reaction, methanol/acetonitrile=1/1 (V/V) solution is added to stop the reaction. In addition, NADPH is added to a remaining pre-reaction solution to initiate a pre-reaction (with preincubation). After a predetermined time of a pre-reaction, a part is transferred to another 96-well plate, and 1/10 diluted by K-Pi buffer containing a substrate to initiate a reaction as a marker reaction. After a predetermined time of a reaction, methanol/acetonitrile=1/1 (V/V) solution is added to atop the reaction. After centrifuged at 3000 rpm for 15 minutes. 1-hydroxymidazolam in the supernatant is quantified by LC/MS/MS.

The sample adding DMSO to a reaction system instead of a solution dissolving the compound of the present invention is adopted as a control (100%). Remaining activity (%) is calculated at each concentration of the compound of the present invention compared to control, and IC value is calculated by reverse-presumption by a logistic model using a concentration and an inhibition rate. Shifted IC value is calculated as "IC of preincubation at 0 min/IC of preincubation at 30 min". When a shifted IC is 1.5 or more, this is defined as positive. When a shifted IC is 1.0 or less, this is defined as negative.

Test Example 6: BA Test

Materials and Methods for Experiments to Evaluate Oral Absorption
(1) Animals: The mice or rats are used
(2) Breeding conditions: The mice or rats are allowed to freely take solid food and sterilized tap water.
(3) Dose and grouping: orally or intravenously administered at a predetermined dose; grouping is as follows (Dose depends on the compound)
  Oral administration: 1~30 mg/kg (n=2~3)
  Intravenous administration: 0.5~10 mg/kg (n=2~3)
(4) Preparation of dosing solution: for oral administration, in a solution or a suspension state; for intravenous administration, in a solubilized state
(5) Administration method: in oral administration, forcedly administer into ventrical us with oral probe; in intravenous administration, administer from caudal vein with a needle-equipped syringe
(6) Evaluation items: blood is collected over time, and the plasma concentration of drug is measured by LC/MS/MS
(7) Statistical analysis: regarding the transition of the plasma concentration of the compound of the present invention, the area under the plasma concentration-time curve (AUC) is calculated by non-linear least squares program WinNonlin (Registered trade name), and the bioavailability (BA) is calculated from the AUCs of the oral administration group and intravenous administration group.

Test Example 7: Fluctuation Ames Test

Mutagenicity of the compound of the present invention is evaluated.

A 20 μL of freezing-stored *Salmonella typhimurium* (TA98 strain, TA100 strain) is inoculated on 10 mL of a liquid nutrient medium (2.5% Oxoid nutrient broth No. 2), and this is incubated at 37° C. for 10 hours under shaking. The 7.70 mL of TA98 culture medium is centrifuged (2000× g, 10 minutes) and TA98 is suspended in 7.70 mL Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4.7H_2O$: 0.1 g/L) after removing the culture medium. The TAOS suspension is mixed with 120 mL Exposure medium (Micro F buffer containing Biotin: 8 μg/mL, histidine: 0.2 μg/mL, glucose: 8 mg/mL). The 3.42 mL of TA100 culture medium strain is mixed with 130 mL Exposure medium. Each 12 μL of DMSO solution of the compound of the present invention (several stage dilution from maximum dose 50 mg/mL at 2 to 3 fold ratio), DMSO as a negative control, and 50 μg/mL of 4-nitroquinoline 1-oxide DMSO solution for the TA98 strain and 0.25 μg/mL of 2-(2-furyl)-3-(5-nitro-2-furyl)acrylamide DMSO solution for the TA100 strain in the assay without metabolic activation, 40 μg/mL of 2-aminoanthracene DMSO solution for the TA98 strain and 20 μg/mL of 2-aminoanthracene DMSO solution for the TA100 strain in the assay with metabolic activation as a positive control, and 588 μL of the test bacterial suspension (498 μL and 90 μL of S9 mixture in the case of metabolic activation assay) are mixed, and this is incubated at 37° C. for 90 minutes under shaking. A 460 μL of the mixture is mixed with 2300 μL of Indicator medium (Micro F buffer containing 8 μg/mL biotin, 0.2 μg/mL histidine, 8 mg/mL glucose, 37.5 μg/mL bromocresol purple), each 50 μL is dispensed to microplate 48 wells/dose, and this is incubated at 37° C. for 3 days. Since the wells containing the bacteria which gained growth ability by point mutation in amino acid (histidine) synthesizing enzyme gene turns from purple to yellow due to a pH change, the number of yellow wells in 48 wells is counted per dose, and is compared with the negative control group. (−) and (+) means negative and positive in mutagenicity respectively,

Test Example 8: hERG Test

For the purpose of assessing risk of an electrocardiogram QT interval prolongation of the compound of the present invention, effects of the compound of the present invention on delayed rectifier K+current ($I_{Kr}$), which plays an important role in the ventricular repolarization process, is studied using CHO cells expressing human ether-a-go-go related gene (hERG) channel.

After a cell is retained at a membrane potential of −80 mV by whole cell patch clamp method using an automated patch clamp system (QPatch; Sophion Bioscience A/S) and gave a leak potential of −50 mV, $I_{Kr}$ induced by depolarization pulse stimulation at +20 mV for 2 seconds and, further, repolarization pulse stimulation at −50 mV for 2 seconds, is recorded. After the generated current is stabilized, extracellular solution (NaCl: 145 mmol/L, KCl: 4 mmol/L, CaCl$_2$: 2 mmol/L, MgCl$_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration in the extracellular solution, is applied to the cell at room temperature for 10 minutes. From the recording $I_{Kr}$, an absolute value of the tail peak current is measured based on the current value at the resting membrane potential using analysis software (Falstor Patch; Sophion Bioscience A/S). Further, the % inhibition of tail peak current for the compound of the present invention relative to the tail peak current after application of the vehicle (0.1% dimethyl sulfoxide solution) is calculated to assess influence of the compound of the present invention on $I_{Kr}$.

Test Example 9: Solubility Test

The solubility of the compound of the present invention is determined under 1% DMSO addition conditions. 10 mmol/L solution of the compound is prepared with DMSO. 2 µL of the solution of the compound of the present invention is respectively added to 198 µL of JP-1 fluid or JP-2 fluid, or 6 µL of the solution of the compound of the present invention is respectively added to 594 µL of JP-1 fluid or JP-2 fluid. The mixture is left standing for 16 hours at 25° C. (condition 1) or shaking at room temperature for 1 hour (condition 2), and the mixture is vacuum-filtered. The filtrate is 10- or 100-fold diluted with methanol/water=1/1 (v/v) or acetonitrile/methanol/water=1/1/2 (v/v/v), and the compound concentration in the filtrate is measured with LC/MS or Solid-Phase Extraction (SPE)/MS by the absolute calibration method.

The composition of the JP-1 fluid is as below.
Water is added to 2.0 g of sodium chloride and 7.0 mL of hydrochloric acid to reach 1000 mL.
The composition of the JP-2 fluid is as below.
Composition 1. About 200 mL of 0.2 mol/L sodium hydroxide test, solution is added to 200 mL of 0.2 mol/L potassium dihydrogen phosphate test, solution to adjust the pH to 6.8, followed by addition of 600 mL of water.
Composition 2. 3.40 g of potassium dihydrogen phosphate and 3.55 g of anhydrous disodium hydrogen phosphate are dissolved in water to reach 1000 mL.
Composition 3. 1 volume of water is added to 1 volume of the solution in which 3.40 g of potassium dihydrogen phosphate and 3.55 g of anhydrous disodium hydrogen phosphate are dissolved in water to reach 1000 mL.

Test Example 10: Metabolism Stability Test

Using commercially available pooled human liver microsomes, the compound of the present invention is reacted for a constant time, a remaining rate is calculated by comparing a reacted sample and an unreacted sample, thereby, a degree of metabolism in liver is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction. 50 µL of the reaction solution is added to 100 µL of a methanol/acetonitrile=1/1 (v/v), mixed and centrifuged at 0.3000 rpm for 15 minutes. The compound of the present invention in the supernatant is quantified by LC/MS/MS or Solid-Phase Extraction (SPE)/MS, and a remaining amount of the compound of the present invention after the reaction is calculated, letting a compound amount at 0 minute reaction time to be 100%.

Test Example 11: Powder Solubility Test

Appropriate quantity of the compound of the present invention is put in suitable containers. 200 µL of JP-1 fluid (water is added to 2.0 g of sodium chloride and 7.0 mL of hydrochloric acid to reach 1000 mL), 200 µL of JP-2 fluid (1 volume of water is added to 1 volume of the solution which 3.40 g of potassium dihydrogen phosphate and 3.55 g of anhydrous disodium hydrogen phosphate dissolve in water to reach 1000 mL) or 20 mmol/L sodium taurocholate (TCA)/JP-2 fluid (JP-2 fluid is added to 1.08 g of TCA to reach 100 mL) is independently added to each container. When total amount is dissolved after adding the test reagent, the compound of the present invention is added appropriately. After sealing and shaking at 37° C. for 1 hour, solution is filtrated and 100 µL of methanol is added to 100 µL of each filtrate to dilute two-fold. The dilution rate is changed as necessary. After checking that there is no bubble and precipitate, the container is sealed and shaken. The compound of the present invention is measured using HPLC by absolute calibration curve method.

Test Example 12: Brain Distribution Test

The compound according to the present invention is intravenous administered at a dose of 0.5 mg/mL/kg to rats. After 30 minutes, the rats are killed by exsanguination through whole blood collection from the inferior vena cava under isoflurane anesthesia.

Then, the brain is excised, and 20 to 25% homogenate is prepared with distilled water.

The obtained blood is centrifuged, and plasma is then obtained. Then, control plasma and control brain are added to the brain sample and the plasma sample, respectively, at 1:1, and each sample is assayed using LC/MS/MS. The measured area ratio (blain/plasma) obtained is used as a brain Kp value.

Test Example 13: P-gp Substrate Test

The compound according to the present invention is added to one side of Transwell (registered trademark. CORNING) where human MDR1-expressing cells or parent cells have been monolayer-cultured. The cells are reacted for a constant time. The membrane permeability coefficients from the apical side toward the basolateral side (A→B) and from the basolateral side toward the apical side (B→A) are calculated for the MDR1-expressing cells or the parent cells, and the efflux ratio (ER: ratio of the membrane permeability coefficients of B→A and A→B) values of the MDR1-expressing cells and the parent cells are calculated. The efflux ratio (ER) values of the MDR1-expressing cells and the parent cells are compared to confirm whether or not the compound of the present invention would be a P-gp substrate.

Test Example 14: mdr1a (−/−) B6 Mouse P-Gp Substrate Test

Animal Used
mdr1a (−/−) B6 mice (knockout mice) or C57BL/6J mice (wild mice)

Method
1. The mice are allowed to freely take solid food and sterilized tap water.
2. The compound of the present invention is administered to 3 animals at each point in time. Blood and brain samples are collected at a predetermined point, in time (e.g., 15 minutes, 30 minutes, 1 hour, 2 hours, 4 hours, 6 hours, 8 hours or 24 hours) after administration. The blood (0.3-0.7 mL) is collected with a syringe containing anticoagulants (EDTA and heparin). The blood and brain samples are immediately cooled in ice.
3. The blood sample is centrifugated (1780× g, 10 minutes) for removal of cells to obtain plasma. Then, the plasma sample is transferred to a tube, and stored at −70° C.
4. The brain sample is homogenized at a tissue weight: distilled water weight ratio=1:3, transferred to a tube, and stored at −70® C.
5. The plasma and brain samples are deproteinized, and analyzed by LC/MS/MS. A calibration curve prepared from blank plasma or blank brain is used in measurement. A sample for quality control is used to confirm measurement trueness and accuracy.
6. Concentrations (ng/mL and ng/g) in the plasma and the brain are analyzed by an appropriate method for determining pharmacokinetic parameters, for example, Win-Nonlin (registered trademark) pharmacokinetic analysis software program.

Analysis

Kp: Brain/Blood Concentration Ratio

Kp ratio=knockout mouse(KO)Kp value/wild mouse (Wild)Kp value

KO/Wild ratio of brain AUC/plasma AUC=

{brain AUC/plasma AUC(KO)}/{brain AUC/plasma AUC(Wild)}

FORMULATION EXAMPLE

The following Formulation Example s are only exemplified and not intended to limit the scope of the invention.

FORMULATION EXAMPLE

Formulation Example 1: Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds of the present invention, lactose and calcium stearate are mixed uniformly to obtain powder medicines in the form of powders or fine granules. The powder medicines are filled into capsule containers to give capsules.

Formulation Example 3: Granules

The compounds of the present, invention, lactose and calcium stearate are mixed uniformly and the mixture is compressed and molded. Then, it is crushed, granulated and sieved to give suitable sizes of granules.

Formulation Example 4: Orally Dispersing Tablets

The compounds of the present invention and crystalline cellulose are mixed, granulated and tablets are made to give orally dispersing tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injections.

Formulation Example 7: Infusions

The compounds of the present invention and phosphate buffer are mixed to give infusions.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster or the like are mixed to give patches.

INDUSTRIAL APPLICABILITY

The compounds of the present invention have an antagonistic activity for the P2X7 receptor and are considered to be useful as a therapeutic and/or preventive agent for diseases or conditions associated with the P2X7 receptor.

The invention claimed is:

1. A method for treating a disease associated with the P2X7 receptor, comprising administering an effective amount of a compound selected from the group consisting of:

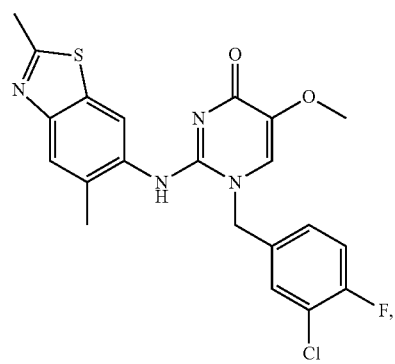

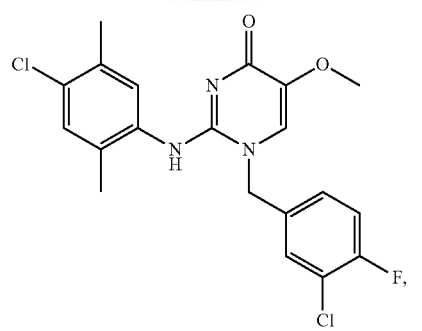
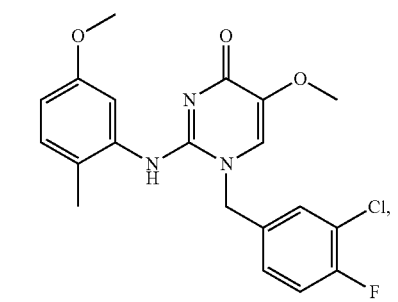
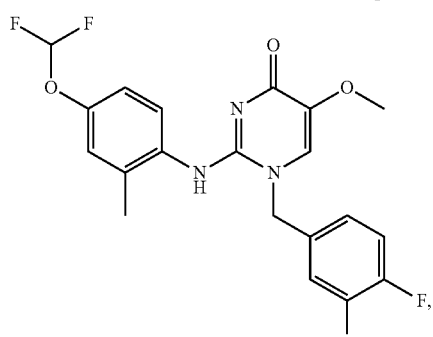
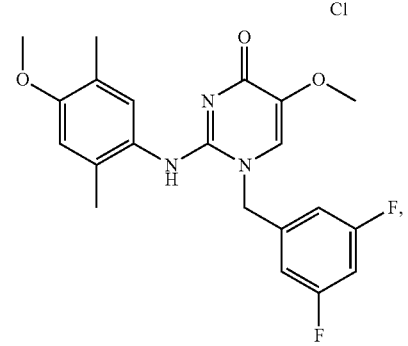
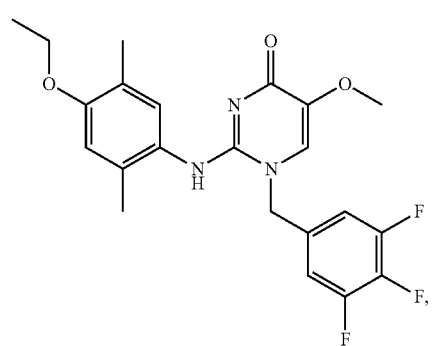
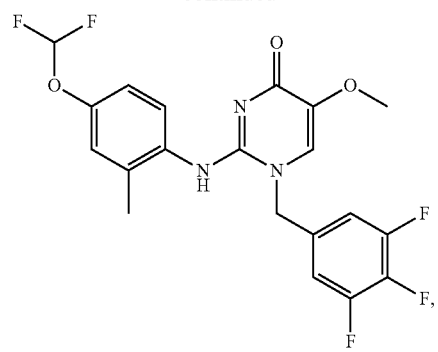
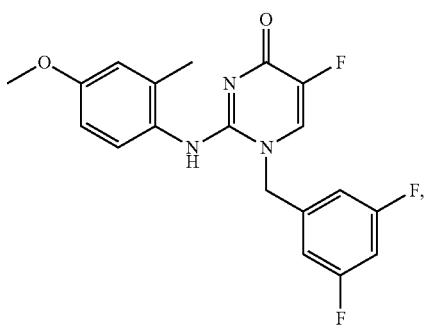
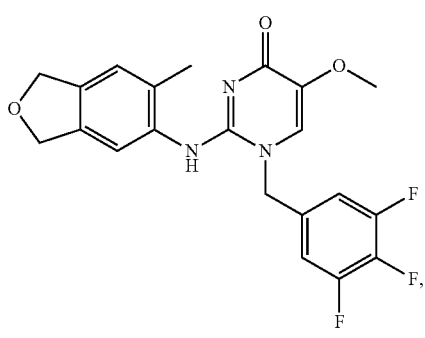
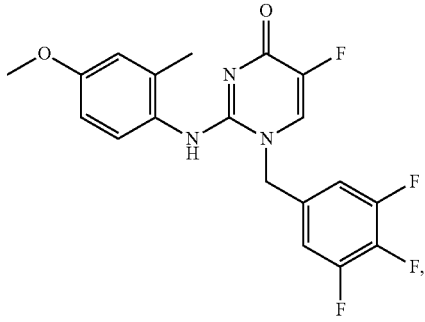
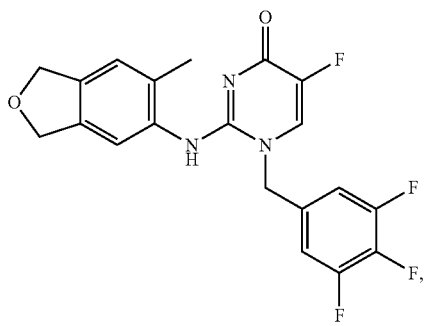

787
-continued
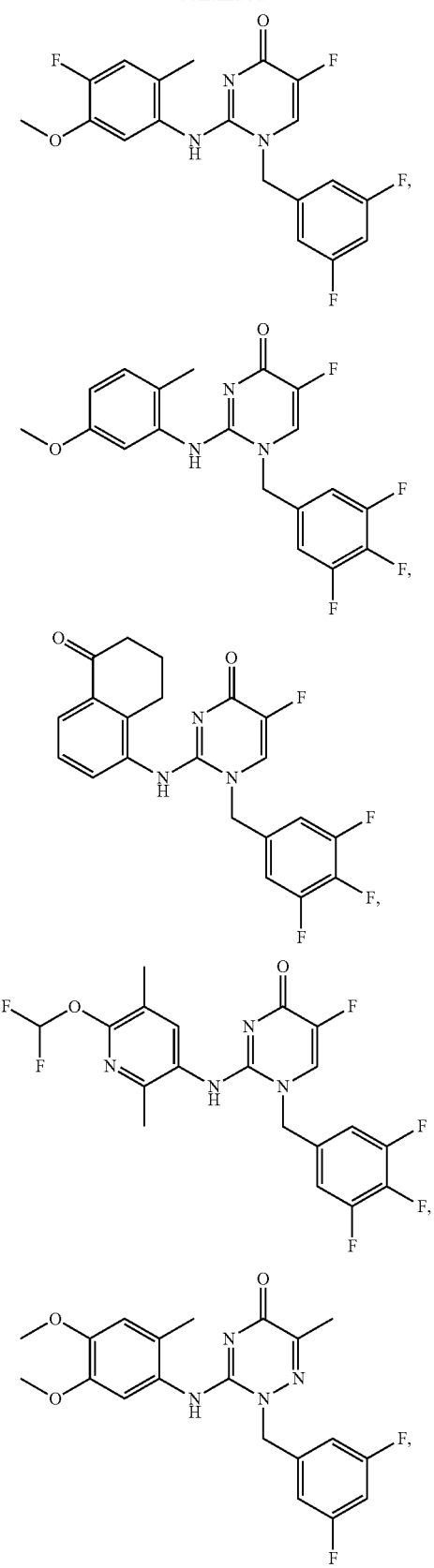
788
-continued
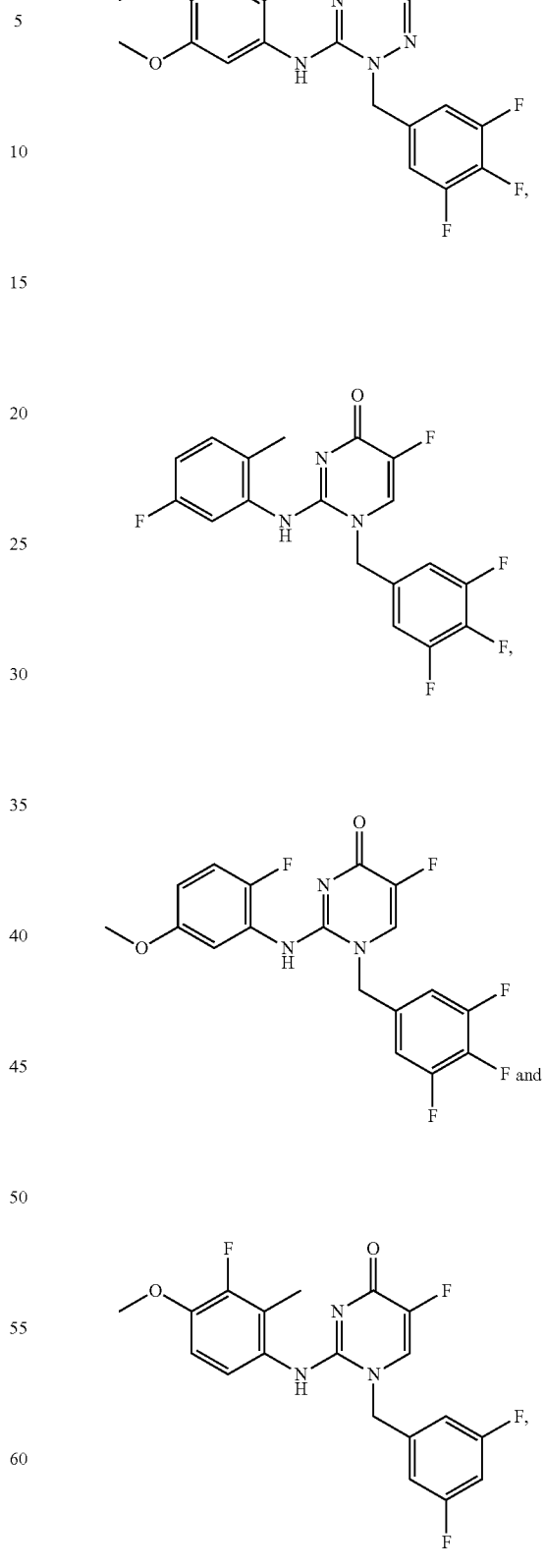
or a pharmaceutically acceptable salt thereof,
to a patient in need thereof.

2. The method according to claim 1, wherein the compound is

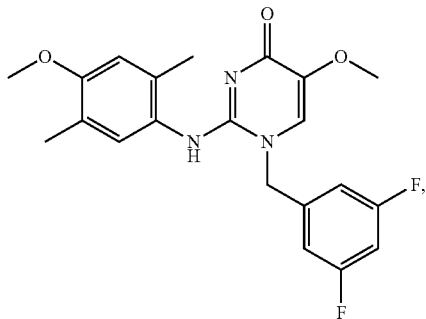 [SMILES: COc1cc(C)c(Nc2nc(=O)c(OC)cn2Cc2cc(F)cc(F)c2)cc1C]

or a pharmaceutically acceptable salt thereof.

3. The method according to claim 1, wherein the compound is

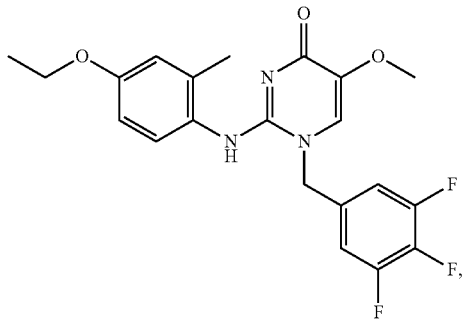 [SMILES: CCOc1ccc(Nc2nc(=O)c(OC)cn2Cc2cc(F)c(F)c(F)c2)c(C)c1]

or a pharmaceutically acceptable salt thereof.

4. The method according to claim 1, wherein the compound is

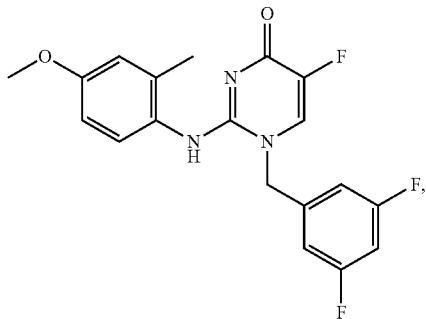 [SMILES: COc1ccc(Nc2nc(=O)c(F)cn2Cc2cc(F)cc(F)c2)c(C)c1]

or a pharmaceutically acceptable salt thereof.

5. The method according to claim 1, wherein the compound is

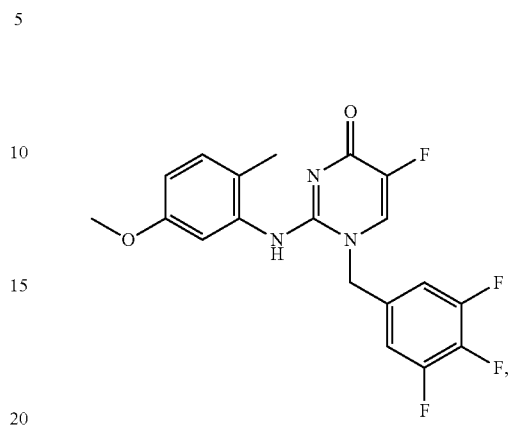

or a pharmaceutically acceptable salt thereof.

6. The method according to claim 1, wherein the compound is

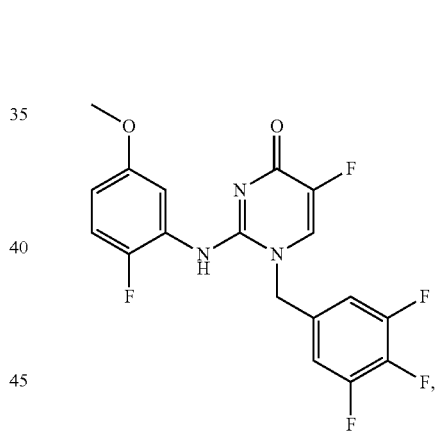

or a pharmaceutically acceptable salt thereof.

* * * * *